United States Patent
Chuang et al.

(10) Patent No.: US 12,065,436 B2
(45) Date of Patent: Aug. 20, 2024

(54) CARDIAC SARCOMERE INHIBITORS

(71) Applicant: Cytokinetics, Inc., South San Francisco, CA (US)

(72) Inventors: Chihyuan Chuang, Millbrae, CA (US); Bradley P. Morgan, Oakland, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

(21) Appl. No.: 17/823,910

(22) Filed: Aug. 31, 2022

(65) Prior Publication Data

US 2023/0119665 A1  Apr. 20, 2023

Related U.S. Application Data

(63) Continuation of application No. 17/013,472, filed on Sep. 4, 2020, now Pat. No. 11,472,796, which is a continuation of application No. 16/252,483, filed on Jan. 18, 2019, now Pat. No. 10,836,755.

(60) Provisional application No. 62/619,643, filed on Jan. 19, 2018, provisional application No. 62/745,724, filed on Oct. 15, 2018.

(51) Int. Cl.
| | |
|---|---|
| C07D 413/12 | (2006.01) |
| A61P 9/00 | (2006.01) |
| A61P 9/04 | (2006.01) |
| C07D 231/14 | (2006.01) |
| C07D 271/06 | (2006.01) |
| C07D 401/12 | (2006.01) |
| C07D 403/12 | (2006.01) |
| C07D 413/04 | (2006.01) |
| C07D 413/10 | (2006.01) |
| C07D 413/14 | (2006.01) |
| C07D 417/12 | (2006.01) |
| C07F 5/02 | (2006.01) |

(52) U.S. Cl.
CPC ............. *C07D 413/12* (2013.01); *A61P 9/00* (2018.01); *A61P 9/04* (2018.01); *C07D 231/14* (2013.01); *C07D 271/06* (2013.01); *C07D 401/12* (2013.01); *C07D 403/12* (2013.01); *C07D 413/04* (2013.01); *C07D 413/10* (2013.01); *C07D 413/14* (2013.01); *C07D 417/12* (2013.01); *C07F 5/027* (2013.01)

(58) Field of Classification Search
CPC .......................... C07D 413/12; C07D 271/06
USPC ....................................................... 548/131
See application file for complete search history.

(56) References Cited

U.S. PATENT DOCUMENTS

| | | | |
|---|---|---|---|
| 5,846,514 A | 12/1998 | Foster | |
| 5,919,785 A | 7/1999 | Dinsmore | |
| 6,334,997 B1 | 1/2002 | Foster | |
| 8,592,426 B2 | 11/2013 | Aebi et al. | |
| 9,181,203 B2 | 11/2015 | Oslob | |
| 9,199,945 B2 | 12/2015 | Oslob | |
| 9,663,516 B2 | 5/2017 | Oslob | |
| 9,925,177 B2 | 3/2018 | Oslob | |
| 10,836,755 B2 | 11/2020 | Chuang et al. | |
| 11,414,424 B2 | 8/2022 | Chuang et al. | |
| 11,472,796 B2 | 10/2022 | Chuang et al. | |
| 11,919,909 B2 | 3/2024 | Morgan | |
| 2005/0014749 A1 | 1/2005 | Chen et al. | |
| 2006/0173183 A1 | 8/2006 | Powers | |
| 2006/0241110 A1 | 10/2006 | Morgan | |
| 2007/0078126 A1 | 4/2007 | Morgan et al. | |
| 2009/0192168 A1 | 7/2009 | Muci et al. | |
| 2011/0275673 A1 | 11/2011 | Xiang et al. | |
| 2013/0018055 A1 | 1/2013 | Aebi et al. | |
| 2013/0296335 A1 | 11/2013 | Morgan et al. | |
| 2016/0176868 A1 | 6/2016 | Oslob et al. | |
| 2016/0289211 A1 | 10/2016 | Ashcraft | |

(Continued)

FOREIGN PATENT DOCUMENTS

| | | |
|---|---|---|
| CL | 2008001170 A1 | 5/2009 |
| CL | 2014001772 A1 | 10/2014 |

(Continued)

OTHER PUBLICATIONS

Chuang, C. et al.: Discovery of Aficamten (CK-274), a next generation cardiac myosin inhibitor for the treatment of hypertrophic cardiomyopathy. J. Med. Chem., vol. 64, pp. 14142-14152, 2021.*

(Continued)

*Primary Examiner* — Charanjit Aulakh

(74) *Attorney, Agent, or Firm* — MORRISON & FOERSTER LLP

(57) ABSTRACT

Provided are compounds of Formula (I):

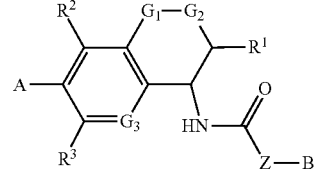

Formula (I)

or a pharmaceutically acceptable salt thereof, wherein A, Z, B, $R^1$, $R^2$, $R^3$, $G_1$, $G_2$, and $G_3$ are as defined herein.

Also provided is a pharmaceutically acceptable composition comprising a compound of Formula (I), or a pharmaceutically acceptable salt thereof.

Also provided are methods of using a compound of Formula (I), or a pharmaceutically acceptable salt thereof.

19 Claims, No Drawings

(56) References Cited

U.S. PATENT DOCUMENTS

| | | |
|---|---|---|
| 2019/0256504 A1 | 8/2019 | Chuang |
| 2019/0276435 A1 | 9/2019 | Shepard et al. |
| 2020/0000822 A1 | 1/2020 | Kruse |
| 2020/0048235 A1 | 2/2020 | Zhang et al. |
| 2020/0054636 A1 | 2/2020 | Semigran et al. |
| 2020/0109148 A1 | 4/2020 | Chuang |
| 2021/0147399 A1 | 5/2021 | Chuang et al. |
| 2021/0253563 A1 | 8/2021 | Morgan et al. |
| 2021/0276991 A1 | 9/2021 | Morgan et al. |
| 2021/0323913 A1 | 10/2021 | Martin et al. |
| 2022/0265612 A1 | 8/2022 | Qiao |
| 2022/0274969 A1 | 9/2022 | Tom et al. |
| 2022/0306642 A1 | 9/2022 | Morgan et al. |
| 2022/0315571 A1 | 10/2022 | Tom et al. |
| 2023/0045450 A1 | 2/2023 | Andersen et al. |
| 2023/0058927 A1 | 2/2023 | Malik et al. |
| 2023/0338378 A1 | 10/2023 | Perera et al. |

FOREIGN PATENT DOCUMENTS

| | | |
|---|---|---|
| CL | 2020002275 A1 | 9/2022 |
| EA | 020138 B1 | 8/2014 |
| WO | 2003059265 A2 | 7/2003 |
| WO | 2003059265 A3 | 6/2004 |
| WO | 2004064730 A2 | 8/2004 |
| WO | 2004064760 A2 | 8/2004 |
| WO | 2006009726 A2 | 1/2006 |
| WO | 2006116150 A1 | 11/2006 |
| WO | 2007078815 A2 | 7/2007 |
| WO | 2007117180 A1 | 10/2007 |
| WO | 2008130320 A2 | 10/2008 |
| WO | 2008130320 A3 | 12/2008 |
| WO | 2010033701 A2 | 3/2010 |
| WO | 2010130796 A1 | 11/2010 |
| WO | 2012101011 A2 | 8/2012 |
| WO | 2013048928 A1 | 4/2013 |
| WO | 2013108227 A1 | 7/2013 |
| WO | 2014205223 A1 | 12/2014 |
| WO | 2014205234 A1 | 12/2014 |
| WO | 2015089337 A1 | 6/2015 |
| WO | 2017055469 A1 | 4/2017 |
| WO | 2017103219 A1 | 6/2017 |
| WO | 2017103223 A1 | 6/2017 |
| WO | 2017222951 A1 | 12/2017 |
| WO | 2018063955 A1 | 4/2018 |
| WO | 2018089433 A1 | 5/2018 |
| WO | 2018117034 A1 | 6/2018 |
| WO | 2019144041 A1 | 7/2019 |
| WO | 2019182925 A1 | 9/2019 |
| WO | 2019226213 A2 | 11/2019 |
| WO | 2019226213 A3 | 1/2020 |
| WO | 2020005887 A1 | 1/2020 |
| WO | 2020005888 A1 | 1/2020 |
| WO | 2020047323 A1 | 3/2020 |
| WO | 2020047447 A1 | 3/2020 |
| WO | 2022047004 A1 | 3/2022 |

OTHER PUBLICATIONS

CAS Registry No. 1279871-13-4. (Apr. 14, 2011). "Carbamic acid, N-(3,4-dihydro-7-phenyl-2H-1-benzopyran-4-yl)-, 1, 1-dimethylethyl ester," 2 pages.

CAS Registry No. 1384080-08-3. (Jul. 23, 2012). "1,2,4-Oxadiazole-5-carboxylic acid, 3-[4-[(acetylamino)methyl] phenyl]-,methyl ester," 3 pages.

CAS Registry No. 1384080-74-3. (Jul. 23, 2012). "1,2,4-Oxadiazole-5-carboxylic acid, 3-[4-[(acetylamino)methyl] phenyl]-, ethyl ester," 2 Pages.

CAS Registry No. 1826330-24-8 (Dec. 10, 2015). "2-Pyridinamine, 5-Methyl-N-[[4-[3-(Trifluoromethyl)-1H-Pyrazol-1-yl] Phenyl] Methyl]-," 1 page.

CAS Registry No. 1826379-58-1 (Dec. 10, 2015). "2-Pyridinamine, 4-Methyl-N-[[4-[3-(Trifluoromethyl)-1H-Pyrazol-1-yl] Phenyl] Methyl]-," 1 page.

CAS Registry No. 1829209-70-2 (Dec. 14, 2015). "2-Pyridinamine, 3-Methyl-N-[[4-[3-(Trifluoromethyl)-1H-Pyrazol-1-yl] Phenyl] Methyl]-," 1 page.

CAS Registry No. 1829877-40-8. (Dec. 15, 2015). "2-Pyridinamine, 6-Methyl-N-[[4-[3-(Trifluoromethyl)-1H-Pyrazol-1-yl] Phenyl] Methyl]-," 1 page.

CAS Registry No. 2093706-41-1. (Apr. 30, 2017). "2-Pyrazinecarbonitrile, 5-[[[4-[3-(Trifluoromethyl)-1H-Pyrazol-1-yl] Phenyl]Methyl]Amino]-," 1 page.

CAS Registry No. 2649643-74-1. (Jul. 6, 2021). "1H-Pyrrole-3-carboxamide, N-[(1S)-2,3-dihydro-5-phenyl-1H-inden-1-yl]-1-ethyl-2,5-dihydro-4-hydroxy-5-oxo-," 3 pages.

Examination Report mailed on Aug. 17, 2023, For European Patent Application No. 19703917.5, 5 pages.

International Search Report and Written Opinion of the International Searching Authority mailed on May 17, 2022, for PCT Patent Application No. PCT/US2022/018725, filed on Mar. 3, 2022, 12 pages.

Martin, R. et al. (2009, e-pub. Sep. 8, 2009). "Total Synthesis Of Pentabromo- And Pentachloropseudilin, And Synthetic Analogues—Allosteric Inhibitors Of Myosin ATPase," Angew Chem. Int. Ed. 48(43):8042-8046.

U.S. Appl. No. 18/355,195, filed on Jul. 19, 2023, for Stephen B. Heitner et al.(U.S. Patent Application is not submitted herewith pursuant to the waiver of 37 C.F.R. § 1.98(a)(2)(iii) issued by the Office on Sep. 21, 2004.).

U.S. Appl. No. 18/365,038, filed Aug. 3, 2023, for Fady Malik et al.(U.S. Patent Application is not submitted herewith pursuant to the waiver of 37 C.F.R. § 1.98(a)(2)(iii) issued by the Office on Sep. 21, 2004.).

Anonymous (2022). "Empowering Muscle Empowering Lives: Sarcomere Directed Therapies," Cytokinetics, 57 pages.

Berge, S.M. et al. (Jan. 1977). "Pharmaceuticals Salts," J. Pharmaceutical Sciences 66(1):1-19.

Caputo, S. et al. (Nov. 28, 2017). "Diversity-Oriented Synthesis of Various Enantiopure Heterocycles by Coupling Organocatalysis with Multicomponent Reactions," European J. of Chem. 2017(45):6619-6628.

CAS (Dec. 5, 2011). "STN Registry Database Entry for CAS RN 1348860-91-2," accessed Feb. 13, 2021, 1 page.

CAS (Nov. 12, 2007). "STN Registry Database entry for CAS RN 953060-71-4," entry date of Nov. 12, 2007, accessed Jul. 15, 2021, 5 pages.

Dahl, L.K. et al. (Jun. 1, 1962). "Effects of Chronic Excess Salt Ingestion Evidence That Genetic Factors Play an Important Role in Susceptibility to Experimental Hypertension," J Exp Med. 115(6):1173-1190.

Database Registry (Jun. 18, 2008). RN-1028938-65-9 Emory MLSC database: "2, 5-Piperazinediones, 4-[(4-chlorophenyl)methyl]-3-(4-methoxyphenyl)-1-(2-phenylethyl)-," Chemical Abstracts Service, 1 page.

Database Registry (Jun. 24, 2008). RN-1030378-92-7 Emory MLSC database: "1-Piperazineacetamide, 3-(2-fluorophenyl)-N-(2-methylcyclohexyl)-4- [(4-methylphenyl)methyl]-2,5-dioxo," Chemical Abstracts Service, 1 page.

Database Registry (Nov. 4, 2011). RN-1340679-26-6 ChemDiv, Inc.: "2, 5-Piperazinedione, 1-(-3_methylbutyl)-4-(phenylmethyl)-3-(3-pyridinyl)," Chemical Abstracts Service, 3 pages.

Dean, D.C. (2000). "Recent Advances in the Synthesis and Applications of Radiolabeled Compounds for the Drug Discovery and Development," Curr. Pharm. Des. 6(10): Preface Only, 1 page.

Evans, A.E. (Mar. 1981, e-pub. Jan. 9, 2007). "Synthesis of Radiolabelled Compounds," J Radio Anal. Chem. 64(1-2):9-32.

Fillmore, N. et al. (2018). "Uncoupling of Glycolysis from Glucose Oxidation Accompanies the Development of Heart Failure with Preserved Ejection Fraction," Mol. Med. 24(3):1-12.

Geisterfer-Lowrance, A.A.T. et al. (May 3, 1996). "A Mouse Model of Familial Hypertrophic Cardiomyopathy," Science 272(5262):731-734.

(56) References Cited

OTHER PUBLICATIONS

Green, E. M. et al. (Feb. 5, 2016). "A Small-Molecule Inhibitor of Sarcomere Contractility Suppresses Hypertrophic Cardiomyopathy in Mice," Science 351(6273):617-621.
Guazzi, M. et al. (Sep. 26, 2017). "Cardiopulmonary Exercise Testing: What Is its Value?," J. Am. Coll. Cardiol. 70(13):1618-1636.
Hargrave, J.D. et al. (Nov. 21, 2010, e-pub. Sep. 8, 2010). "Rhodium-Catalysed Conjugate Addition of Arylboronic Acids to Enantiopure Dehydroamino Acid Derivatives," Org. Biomol. Chem. 8(22):5120-5125.
Hartung, A. et al. (Dec. 11, 2012). "One-Pot Ugi/Aza-Michael Synthesis of Highly Substituted 2,5-Diketopiperazines with Anti-Proliferative Properties," Molecules Online 17(12):14685-14699.
International Preliminary Report on Patentability mailed Jan. 27, 2022, for Patent Application No. PCT/US2020/042387, filed Jul. 16, 2020, 8 pages.
International Preliminary Report on Patentability mailed Jan. 27, 2022, for Patent Application No. PCT/US2020/042389, filed Jul. 16, 2020, 8 pages.
International Preliminary Report on Patentability mailed Jan. 27, 2022, for Patent Application No. PCT/US2020/042390, filed Jul. 16, 2020, 8 pages.
International Preliminary Report on Patentability mailed Jan. 7, 2021, for Patent Application No. PCT/US2019/038907, filed Jun. 25, 2019, 7 pages.
International Preliminary Report on Patentability mailed Jan. 7, 2021, for Patent Application No. PCT/US2019/038908, filed Jun. 25, 2019, 8 pages.
International Preliminary Report on Patentability mailed Jul. 30, 2020, for Patent Application No. PCT/US2019/014344. filed Jan. 18, 2019, 11 pages.
International Search Report and Written Opinion of the International Searching Authority mailed Aug. 28, 2019, for PCT Patent Application No. PCT/US2019/038907, filed Jun. 25, 2019, 19 pages.
International Search Report and Written Opinion of the International Searching Authority mailed Aug. 28, 2019, for PCT Patent Application No. PCT/US2019/038908, filed Jun. 25, 2019, 14 pages.
International Search Report and Written Opinion of the International Searching Authority mailed May 20, 2019, for PCT Patent Application No. PCT/US2019/014344, filed Jan. 18, 2019, 19 pages.
International Search Report and Written Opinion of the International Searching Authority mailed Nov. 10, 2020, for PCT Patent Application No. PCT/US2020/042387, filed Jul. 16, 2020, 13 pages.
International Search Report and Written Opinion of the International Searching Authority mailed Nov. 5, 2020, for PCT Patent Application No. PCT/US2020/042389, filed Jul. 16, 2020, 13 pages.
International Search Report and Written Opinion of the International Searching Authority mailed Nov. 6, 2020, for PCT Patent Application No. PCT/US2020/042390, filed Jul. 16, 2020, 14 pages.
Invitation to Pay Additional Fees mailed Mar. 28, 2019, for PCT Patent Application No. PCT/US2019/014344, filed Jan. 18, 2019, 14 pages.
Ito, N. (Jan. 2003). "A Medium-Term Rat Liver Bioassay For Rapid In Vivo Detection Of Carcinogenic Potential Of Chemicals," Cancer Science 94(1):3-8.
Jackson, P. et al. (Aug. 22, 2018). "Appendage and Scaffold Diverse Fully Functionalized Small-Molecule Probes via a Minimalist Terminal Alkyne-Aliphatic Diazirine Isocyanide," J. Org. Chem. 83(18):11245-11253.
Jiang, J. et al. (Oct. 4, 2013, e-pub. Jul. 14, 2014). "Allele-Specific Silencing of Mutant Myh6 Allele in Mice Suppresses Hypertrophic Cardiomyopathy," Science 342(6154):111-114, 11 pages.
Kabalka, G.W. et al. (1989). "The Synthesis of Radiolabeled Compounds via Organometallic Intermediates," Tetrahedron 45(21):6601-6621.
Kaim, L.E. et al. (2007, e-pub. Jan. 24, 2007). "New Indolizine Template from the Ugi Reaction," Synlett 2(1):227-230.
Kim-Mitsuyama, S. et al. (Oct. 2004). "Additive Beneficial Effects of the Combination of a Calcium Channel Blocker and an Angiotensin Blocker on a Hypertensive Rat-Heart Failure Model," Hypertens Res. 27(10):771-779.
Lee, M. et al. (May 25, 2016). "Convenient asymmetric synthesis of 1,3,4,6-tetrasubstituted 2,5-diketopiperazines," Arkivoc 2016(4):100-113.
Lee, M. et al. (May 19, 2016). "Stereoselective Nucleophilc Substitution of [alpha]-Bromo Tertiary Amides for Asymmetric Synthesis of Highly Substituted 2,5-Diketopiperazines," Bull. Korean Chem. Soc. 37(6):981-984.
Lesma, G. et al. (Jun. 18, 2014). "Asymmetric Ugi 3CR on isatin-derived ketimine: synthesis of chiral 3,3-disubstituted 3-aminooxindole derivatives," Beilstein Journal of Organic Chemistry 10:1383-1389.
Malhotra, R. et al. (Aug. 2016, e-pub. Jun. 8, 2016). "Cardiopulmonary Exercise Testing in Heart Failure," JACC Heart Fail 4(8):607-616.
Mamoun, O. et al. (1995, e-pub. Sep. 23, 2006). "Synthesis of Methyl 3-Amino-3-pyrrolidinecarboxylates: A Convenient Access to Cucurbitine and Analogues," Synthetic Communications 25(9):1295-1302.
Parker, M.F.L. et al. (Jan. 23, 2014). "Acceleration of an Aromatic Claisen Rearrangement Via a Designed Spiroligozyme Catalyst that Mimics the Ketosteroid Isomerase Catalytic Dyad," J. American Chem. Soc. 136(10):3817-3827.
Pettersson, M. et al. (Oct. 1, 2015). "Design, Synthesis and Evaluation of 2,5-Diketopiperazines as Inhibitors of the MDM2-p53 Interaction," PLOS One 10(10):e0137867, 19 pages.
Philipson, D. J. et al. (2017, e-pub. Aug. 31, 2017). "Emerging Pharmacologic and Structural Therapies For Hypertrophic Cardiomyopathy," Heart Fail Rev. 22(6):879-888.
Pyne, S.G. et al. (1993). "Asymmetric Synthesis of Chiral Cyclic Amino Acids by Diels-Alder Reactions of (2S)- and (2R)-4-Methyleneoxazolidin-5-ones," Aust. J Chem. 46(1):73-93.
Rowin, E.J. et al. (Nov. 2017). "Role of Exercise Testing in Hypertrophic Cardiomyopathy," JACC: Cariovasc Imaging. 10(11):1374-1386.
Sakata, Y. et al. (Jan. 2001). "Renin Angiotensin System-Dependent Hypertrophy as a Contributor to Heart Failure in Hypertensive Rats: Different Characteristics From Renin Angiotensin System-Independent Hypertrophy," J. Am. Coll. Cardiol. 37(1):293-299.
Santra, S. et al. (Apr. 1, 2011, e-pub. Feb. 25, 2011). "A Rapid, One-Pot, Microwave-Influenced Synthesis of Spiro-2,5-diketopiperazines via a Cascade Ugi/6-Exo-Trig Aza-Michael Reaction," Journal Of Organic Chemistry 76(7):2261-2264.
Taub, P.R. et al. (Oct. 1, 2013). "Perturbations in Skeletal Muscle Sarcomere Structure in Patients with Heart Failure and Type 2 Diabetes: Restorative Effects of (-)-epicatechin-rich Cocoa," Clinical Science 125(8):383-389.
U.S. Appl. No. 17/816,898, filed Aug. 2, 2022, for Denise Andersen et al. (U.S. Patent Application is not submitted herewith pursuant to the waiver of 37 C.F.R. § 1.98(a)(2)(iii) issued by the Office on Sep. 21, 2004.).
Walvoord, R.R. et al. (Nov. 4, 2014). "Quantification of Electrophilic Activation by Hydrogen-Bonding Organocatalysts", J. American Chem. Soc. 136(45):16055-16065.
Williams, R. et al. (Nov. 3, 1992). "Asymmetric synthesis of S-(-)-Cucurbitine," Tetrahedron Letters 33(45):6755-6758.
Williams, R.M. et al. (Nov. 1982). "A New and Efficient Cyclization Reaction to Construct the Bicyclomycin Ring System: Synthesis of N, N'-Dimethyl-4-desmethylenebicyclomycin," Journal Of The American Chemical Society 104(22):6092-6099.
Yates, P. et al. (Jan. 1, 1983). "Synthesis of Piperazine-2,5-diones Related to Bicyclomycin: 3-acetoxy-1,4-dibenzyl-3-[1-(2-methoxyethyl)-and 1-(2-hydroxyethyl)ethenyl]piperazine-2,5-dione. 1. Route Via Acyclic Intermediates," Canadian Journal Of Chemistry 61(3):519-528.
Yoshifuji, S. et al. (Aug. 1995). "Stereospecific Synthesis of (R)- and (S)-Baclofen and (R)- and (S)-PCPGABA [4-Amino-2-(4-

(56) References Cited

OTHER PUBLICATIONS chlorophenyl)butyric Acid] via (R)- and (S)-3-(4-Chlorophenyl)pyrrolidines," Chem Pharm Bull 42(8)1302-1306.

* cited by examiner

CARDIAC SARCOMERE INHIBITORS

CROSS REFERENCE TO RELATED APPLICATIONS

This application is a continuation of U.S. patent application Ser. No. 17/013,472, filed Sep. 4, 2020, now U.S. Pat. No. 11,472,796, which is a continuation of U.S. patent application Ser. No. 16/252,483, filed Jan. 18, 2019, now U.S. Pat. No. 10,836,755, which claims priority to U.S. Provisional Application No. 62/619,643, filed Jan. 19, 2018, entitled "CARDIAC SARCOMERE INHIBITORS" and U.S. Provisional Application No. 62/745,724, filed Oct. 15, 2018, entitled "CARDIAC SARCOMERE INHIBITORS," the contents of which are hereby incorporated by reference in their entirety for all purposes.

FIELD

Provided herein are heterocyclic compounds, pharmaceutical compositions comprising such compounds, and methods of treating various cardiac diseases and conditions with such compounds.

BACKGROUND

The disclosure relates to certain chemical entities that selectively modulate the cardiac sarcomere, and specifically to certain chemical entities, pharmaceutical compositions and methods for treating various cardiac diseases and conditions.

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic Ca++ and cyclic AMP concentrations in the inotropically stimulated myocardium. Given the limitations of current agents, new approaches are needed to improve cardiac function in HCM and HFpEF.

There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. The present disclosure provides such agents (particularly cardiac sarcomere inhibitors) and methods for their use. These agents are selective allosteric inhibitors of cardiac myosin that have little to no effect on smooth muscle myosin. Benefits of these compounds include a wider therapeutic index, less impact on cardiac relaxation, better pharmacokinetics, and better safety.

The present disclosure provides chemical entities, pharmaceutical compositions and methods for the treatment of heart failure including HCM and HFpEF. The compositions are inhibitors of the cardiac sarcomere, for example, inhibitors of cardiac myosin.

SUMMARY

In one aspect, provided is a compound of Formula (I), or a pharmaceutically acceptable salt thereof:

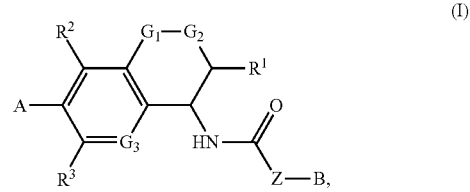

wherein:
G$_1$ is —CR$^4$R$^5$— or —O—;
G$_2$ is a bond or —CR$^6$R$^7$—;
G$_3$ is —CR$^8$— or —N—;
R$^1$, R$^3$, R$^4$, R$^5$, R$^6$, R$^7$, and R$^8$ are each independently H, C$_1$-C$_6$ alkyl, halo, or hydroxyl;
R$^2$ is H, C$_2$-C$_6$ alkyl, halo, or hydroxyl;
Z is selected from the group consisting of a bond, C$_1$-C$_6$ alkyl, —O—, —N(R$^9$)—, —R$^x$O—, —OR$^y$—, and —R$^z$S—;
R$^9$ is H, C$_1$-C$_6$ alkyl, or cycloalkyl;
A is selected from the group consisting of substituted C$_2$ alkynyl, unsubstituted C$_2$ alkynyl, substituted phenyl, unsubstituted phenyl, and 5- or 6-membered heteroaryl comprising at least one annular N atom, wherein the 5- or 6-membered heteroaryl is unsubstituted or substituted with one or more R$^{10}$ substituents;
each R$^{10}$ is independently selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, and —C(O)OR$^a$;
B is selected from the group consisting of H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents;
each R$^{11}$ is independently selected from the group consisting of substituted or unsubstituted heterocycloalkyl, substituted or unsubstituted heteroaryl, substituted or unsubstituted cycloalkyl, substituted or unsubstituted aryl, unsubstituted $C_1$-$C_6$ alkyl, $C_1$-$C_6$ alkyl substituted with one or more $R^{12}$ substituents, substituted or unsubstituted $C_2$-$C_6$ alkenyl, substituted or unsubstituted $C_2$-$C_6$ alkynyl, halo, —$OR^b$, —$C(O)R^c$, —$C(O)OR^d$, oxo, and —$NR^eR^f$;

each $R^{12}$ is independently selected from the group consisting of halo, —$OR^b$, —$C(O)R^g$, —$C(O)OR^h$, and —$C(O)NR^iR^j$;

each $R^a$, $R^b$, $R^c$, $R^d$, $R^e$, $R^f$, $R^g$, $R^h$, $R^i$, and $R^j$ is independently H or $C_1$-$C_6$ alkyl; and $R^x$, $R^y$, and $R^z$ are each $C_1$-$C_6$ alkyl, wherein when A is unsubstituted phenyl or 5-trifluoromethyl-1,2,4-oxadiazolyl, the —Z—B moiety is not —OC(CH$_3$)$_3$ or 1-ethyl-3-hydroxy-1,5-dihydro-2H-pyrrol-2-onyl. In some embodiments, the compound of Formula (I) is a compound of Formula (If):

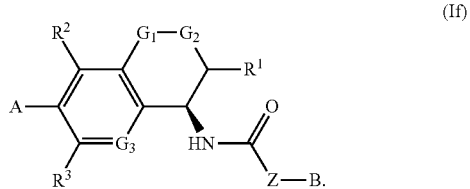

(If)

In some embodiments of Formula (I) or any variation thereof, such as Formula (Ia), (Ib), (Ic), (Id), (Ie), (If), (Ig), (Ih), (Ii), (Ij), or (Ik), or a pharmaceutically acceptable salt thereof, $R^1$, $R^2$, $R^3$, $R^4$, $R^5$, $R^6$, $R^7$, and $R^8$ are each H.

In some embodiments of Formula (I) or any variation thereof, $G_1$ is —$CR^4R^5$—. In some embodiments, $G_1$ is —$CH_2$—. In other embodiments, $G_1$ is —O—. In some embodiments, $G_2$ is a bond. In some embodiments, $G_2$ is —$CR^6R^7$—. In other embodiments, $G_2$ is —$CH_2$—. In some embodiments, $G_3$ is —$CR^8$—. In certain embodiments, $G_3$ is —CH—. In some embodiments, $G_3$ is —N—.

In some embodiments of Formula (I) or any variation thereof, $R^1$, $R^2$, and $R^3$ are each H. In some embodiments, Z is a bond. In some embodiments, Z is —O—. In other embodiments, Z is —N($R^9$)—.

In some embodiments of Formula (I) or any variation thereof, A is selected from the group consisting of substituted $C_2$ alkynyl, unsubstituted $C_2$ alkynyl, substituted phenyl, unsubstituted phenyl, and 5- or 6-membered heteroaryl comprising at least one annular N atom, wherein the 5- or 6-membered heteroaryl is unsubstituted or substituted with one or more $R^{10}$ substituents; wherein each $R^{10}$ is independently selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted 3- to 12-membered heterocycloalkyl, and —$C(O)OR^a$. In some embodiments, each $R^{10}$ is independently selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted 5- to 6-membered heterocycloalkyl, and —$C(O)OR^a$.

In some embodiments of Formula (I) or any variation thereof, A is selected from the group consisting of substituted phenyl, unsubstituted phenyl, and 5- or 6-membered heteroaryl comprising at least one annular N atom, wherein the 5- or 6-membered heteroaryl is unsubstituted or substituted with one or more $R^{10}$ substituents. In some embodiments, A is selected from the group consisting of phenyl, pyrazolyl, oxazolyl, oxadiazolyl, isoxazolyl, tetrazolyl, triazolyl, thiazolyl, pyrimidinyl, pyridinyl, pyrazinyl, and pyridazinyl, each of which is unsubstituted or substituted with one or more $R^{10}$ substituents. In some embodiments of Formula (I) or any variation thereof, or a pharmaceutically acceptable salt thereof, A is oxadiazolyl or isoxazolyl, each of which is unsubstituted or substituted with one or more $R^{10}$ substituents.

In some embodiments of Formula (I) or any variation thereof, A is selected from the group consisting of:

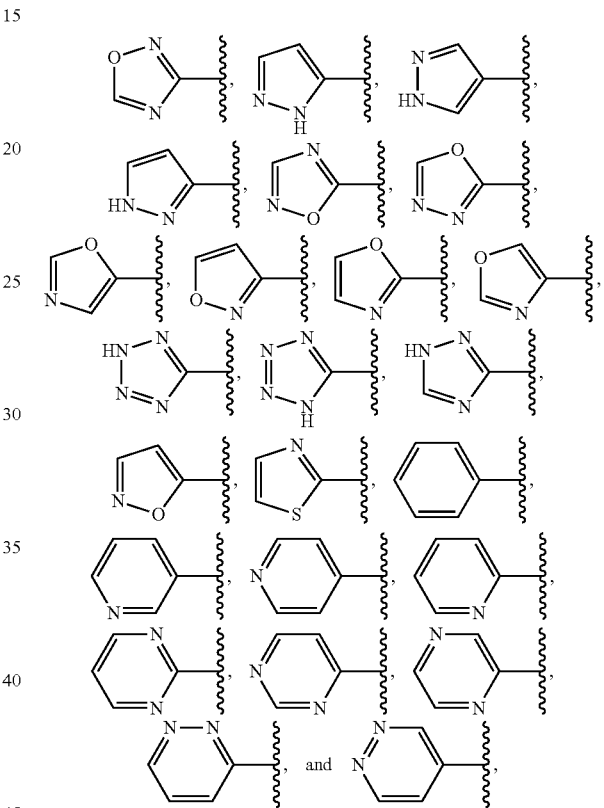

each of which is unsubstituted or substituted with one or more $R^{10}$ substituents. In some embodiments, each $C_1$-$C_6$ alkyl, cycloalkyl, or heterocycloalkyl of $R^{10}$ is independently unsubstituted or substituted with one more substituents independently selected from the group consisting of —$OR^k$ and —$OC(O)R^m$, wherein $R^k$ and $R^m$ are each independently H or $C_1$-$C_6$ alkyl. In some embodiments, each $R^{10}$ is independently selected from the group consisting of —$C(O)OCH_3$, methyl, ethyl, isopropyl, difluoromethyl, cyclopropyl, cyclobutyl, and oxetanyl, wherein each methyl, ethyl and isopropyl of $R^{10}$ is independently unsubstituted or substituted with one more substituents independently selected from the group consisting of —$OCH_3$, —OH, and —$OC(O)CH_3$.

In some embodiments of Formula (I) or any variation thereof, A is oxadiazolyl, which is unsubstituted or substituted with one substituent selected from the group consisting of methyl, methyl substituted with —$OCH_3$, —OH, or —$OC(O)CH_3$, ethyl, ethyl substituted with —$OCH_3$, —OH, or —$OC(O)CH_3$, isopropyl, isopropyl substituted with —$OCH_3$, —OH, or —$OC(O)CH_3$, difluoromethyl, cyclopropyl, cyclobutyl, oxetanyl, and —C(O)OCH₃. In some embodiments, A is oxadiazolyl, which is unsubstituted or substituted with one substituent selected from the group consisting of methyl, ethyl, isopropyl, difluoromethyl, cyclopropyl, and cyclobutyl.

In some embodiments of Formula (I) or any variation thereof, A is isoxazolyl, which is unsubstituted or substituted with one or more substituents selected from the group consisting of methyl, ethyl, and difluoromethyl. In some embodiments, A is isoxazolyl, which is unsubstituted or substituted with one substituent selected from the group consisting of methyl, ethyl, and difluoromethyl.

In some embodiments of Formula (I) or any variation thereof, A is selected from the group consisting of:

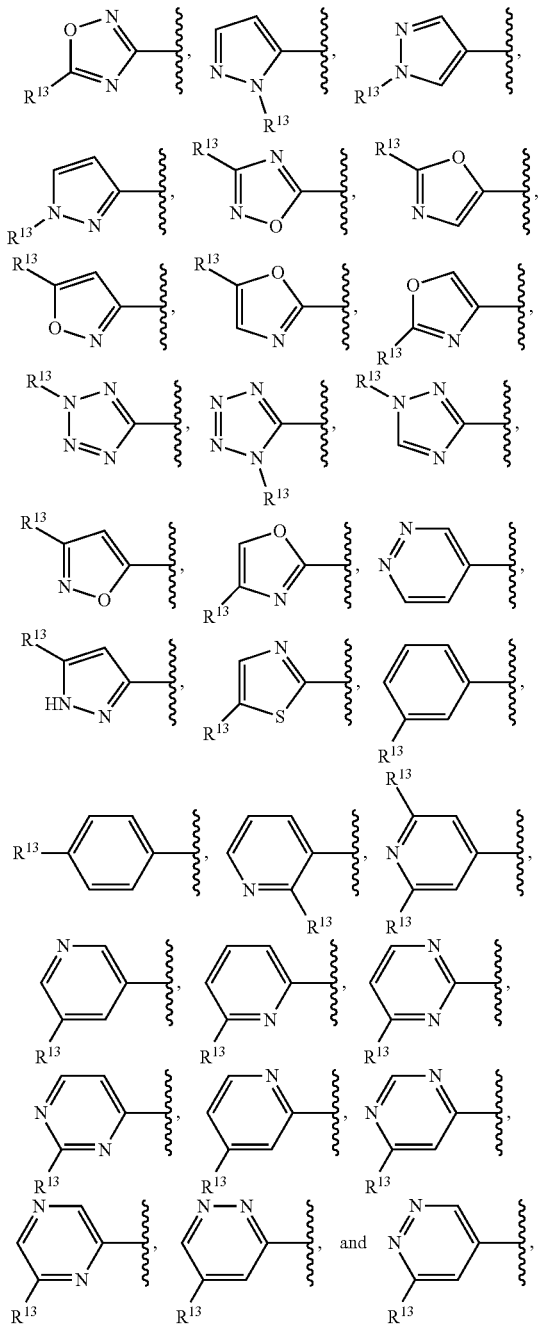

wherein each $R^{13}$ is independently selected from the group consisting of H, substituted or unsubstituted $C_1$-$C_6$ alkyl, substituted or unsubstituted cycloalkyl, substituted or unsubstituted heterocycloalkyl, and —C(O)OR$^a$; and R$^a$ is H or $C_1$-$C_6$ alkyl. In some embodiments, each $R^{13}$ is independently selected from the group consisting of H, —C(O)OCH₃, methyl, ethyl, isopropyl, difluoromethyl, cyclopropyl, cyclobutyl, and oxetanyl, wherein each methyl, ethyl and isopropyl of $R^{13}$ is independently unsubstituted or substituted with one more substituents independently selected from the group consisting of —OCH₃, —OH, and —OC(O)CH.

In some embodiments of Formula (I) or any variation thereof, B is selected from the group consisting of H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents; each $R^{11}$ is independently selected from the group consisting of heterocycloalkyl, heteroaryl, cycloalkyl, aryl, $C_1$-$C_6$ alkyl, halo, fluoroalkyl, —OR$^b$, —C(O)R$^c$, —C(O)OR$^d$, oxo, and —NR$^e$R$^f$, wherein each heterocycloalkyl and heteroaryl of $R^{11}$ is unsubstituted or substituted with one or more substituents selected from the group consisting of $C_1$-$C_6$ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or $C_1$-$C_6$ alkyl. In some embodiments of Formula (I) or any variation thereof, B is selected from the group consisting of H, $C_1$-$C_6$ alkyl, $C_3$-$C_8$ cycloalkyl, $C_6$-$C_{12}$ aryl, 3- to 12-membered heterocycloalkyl, and 5- to 10-membered heteroaryl, wherein the $C_1$-$C_6$ alkyl, $C_3$-$C_8$ cycloalkyl, $C_6$-$C_{12}$ aryl, 3- to 12-membered heterocycloalkyl, and 5- to 10-membered heteroaryl of B are each unsubstituted or substituted with one or more $R^{11}$ substituents. In some embodiments, B is unsubstituted or substituted with one or more $R^{11}$ substituents; wherein each $R^{11}$ is independently selected from the group consisting of substituted or unsubstituted 3- to 12-membered heterocycloalkyl, substituted or unsubstituted 5- to 10-membered heteroaryl, substituted or unsubstituted $C_3$-$C_8$ cycloalkyl, substituted or unsubstituted $C_6$-$C_{12}$ aryl, unsubstituted $C_1$-$C_6$ alkyl, $C_1$-$C_6$ alkyl substituted with one or more $R^{12}$ substituents, substituted or unsubstituted $C_2$-$C_6$ alkenyl, substituted or unsubstituted $C_2$-$C_6$ alkynyl, halo, —OR$^b$, —C(O)R$^c$, —C(O)OR$^d$, oxo, and —NR$^e$R$^f$. In some embodiments, B is unsubstituted or substituted with one or more $R^{11}$ substituents; wherein each $R^{11}$ is independently selected from the group consisting of 3- to 12-membered heterocycloalkyl, 5- to 10-membered heteroaryl, $C_3$-$C_8$ cycloalkyl, $C_6$-$C_{12}$ aryl, $C_1$-$C_6$ alkyl, halo, fluoroalkyl, —OR$^b$, —C(O)R$^c$, —C(O)OR$^d$, oxo, and —NR$^e$R$^f$, wherein each heterocycloalkyl and heteroaryl of $R^{11}$ is unsubstituted or substituted with one or more substituents selected from the group consisting of $C_1$-$C_6$ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or $C_1$-$C_6$ alkyl. In some embodiments, each heterocycloalkyl or heteroaryl of $R^{11}$ comprises 1, 2, 3, 4, or 5 heteroatoms selected from the group consisting of N, O, and S. In some embodiments of Formula (I) or any variation thereof, B is a phenyl, unsubstituted or substituted with one or more $R^{11}$ substituents. In some embodiments, B is a 5- to 6-membered heterocycloalkyl, unsubstituted or substituted with one or more $R^{11}$ substituents. In other embodiments, B is a 5- to 6-membered heteroaryl, unsubstituted or substituted with one or more $R^{11}$ substituents.

In some embodiments of Formula (I) or any variation thereof, B is selected from the group consisting of $C_1$-$C_4$ alkyl, $C_3$-$C_5$ cycloalkyl, 6- to 10-membered aryl (e.g., 6- to 9-membered aryl), 4- to 6-membered heterocycloalkyl containing at least one annular N or O atom, 5- or 6-membered monocyclic heteroaryl containing at least one annular N atom, and 8- or 9-membered bicyclic heteroaryl containing at least one annular N atom, each of which is substituted or unsubstituted. In some embodiments, B selected from the group consisting of $C_1$-$C_4$ alkyl, $C_3$-$C_5$ cycloalkyl, 6- to 10-membered aryl (e.g., 6- to 9-membered aryl), 4- to 6-membered heterocycloalkyl comprising at least one annular N or O atom, 5- or 6-membered monocyclic heteroaryl comprising at least one annular N atom, or 8- or 9-membered bicyclic heteroaryl comprising at least one annular N atom, each of which is unsubstituted or substituted with one or more $R^{11}$ substituents; each $R^{11}$ is independently selected from the group consisting of heterocycloalkyl, heteroaryl, cycloalkyl, aryl, $C_1$-$C_6$ alkyl, halo, fluoroalkyl, —$OR^b$, —$C(O)R^c$, —$C(O)OR^d$, oxo, and —$NR^eR^f$, wherein each heterocycloalkyl and heteroaryl of $R^{11}$ is unsubstituted or substituted with one or more substituents selected from the group consisting of $C_1$-$C_6$ alkyl, —$C(O)R^n$, —$C(O)OR^p$, and —$C(O)NR^qR^r$, and wherein each $C_1$-$C_6$ alkyl of $R^{11}$ is unsubstituted or substituted with —$OR^b$; and each $R^b$, $R^c$, $R^d$, $R^e$, $R^f$, $R^n$, $R^p$, $R^q$, and $R^r$ is independently H or $C_1$-$C_6$ alky.

In some embodiments of Formula (I) or any variation thereof, B is selected from the group consisting of methyl, ethyl, isopropyl, isobutyl, tert-butyl, cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl and benzoimidazolyl, each of which is unsubstituted or substituted with one or more $R^{11}$ substituents; each $R^{11}$ is independently selected from the group consisting of heterocycloalkyl, heteroaryl, cycloalkyl, aryl, $C_1$-$C_6$ alkyl, halo, fluoroalkyl, —$OR^b$, —$C(O)R^c$, —$C(O)OR^d$, oxo, and —$NR^eR^f$, wherein each heterocycloalkyl and heteroaryl of $R^{11}$ is unsubstituted or substituted with one or more substituents selected from the group consisting of $C_1$-$C_6$ alkyl, —$C(O)R^n$, —$C(O)OR^p$, and —$C(O)NR^qR^r$, and wherein each $C_1$-$C_6$ alkyl of $R^{11}$ is unsubstituted or substituted with —$OR^b$; and each $R^b$, $R^c$, $R^d$, $R^e$, $R^f$, $R^n$, $R^p$, $R^q$, and $R^r$ is independently H or $C_1$-$C_6$ alkyl. In some embodiments, each $R^{11}$ is independently selected from the group consisting of methyl, ethyl, isopropyl, cyclopropyl, difluoromethyl, trifluoromethyl, oxo, —$C(O)CH_3$, —$C(O)OtBu$, —$OCH_3$, —OH, —$NH_2$, —Cl, oxetanyl, oxadiazolyl, and azetidinyl, wherein each oxadiazolyl and azetidinyl of $R^{11}$ is unsubstituted or substituted with one or more substituents selected from the group consisting of ethyl, —$C(O)CH_3$, —$C(O)OtBu$, —$C(O)OCH_3$, —$C(O)NHCH_3$, —$C(O)NH_2$, and —$OCH_3$, and wherein each methyl, ethyl, and isopropyl of $R^{11}$ is unsubstituted or substituted with —OH.

In some embodiments of Formula (I) or any variation thereof, B is methyl, pyrazolyl, oxazolyl, tetrazolyl, isoxazolyl, thiazolyl, imidazolyl, or pyridinyl, each of which is unsubstituted or substituted with one or more $R^{11}$ substituents; each $R^{11}$ is independently selected from the group consisting of heterocycloalkyl, heteroaryl, halo, $C_1$-$C_6$ alkyl, $C_1$-$C_6$ alkyl substituted with one or two $R^{12}$ substituents, cycloalkyl, cycloalkyl substituted with one or two $R^{12}$ substituents, fluoroalkyl, —$OR^b$, —$C(O)R^c$, —$C(O)OR^d$, oxo, and —$NR^eR^f$; each $R^{12}$ is independently selected from the group consisting of halo, —$OR^b$, —$C(O)R^g$, —$C(O)OR^h$, and —$C(O)NR^iR^j$; and each $R^b$, $R^c$, $R^d$, $R^e$, and $R^f$, $R^g$, $R^h$, $R^i$, and $R^j$ is independently H or $C_1$-$C_6$ alkyl. In some embodiments, B is pyrazolyl, oxazolyl, tetrazolyl, isoxazolyl, thiazolyl, imidazolyl, or pyridinyl, each of which is unsubstituted or substituted with one or more $R^{11}$ substituents; each $R^{11}$ is independently selected from the group consisting of heterocycloalkyl, heteroaryl, halo, $C_1$-$C_6$ alkyl, $C_1$-$C_6$ alkyl substituted with one or two $R^{12}$ substituents, cycloalkyl, cycloalkyl substituted with one or two $R^{12}$ substituents, fluoroalkyl, —$OR^b$, oxo, and —$NR^eR^f$; each $R^{12}$ is independently selected from the group consisting of halo, —$OR^b$, and —$C(O)NR^1R^1$; and each $R^b$, $R^e$, $R^f$, $R^i$, and $R^j$ is independently H or $C_1$-$C_6$ alkyl. In some embodiments, $R^b$ is H.

In some embodiments of Formula (I) or any variation thereof, B is selected from the group consisting of:

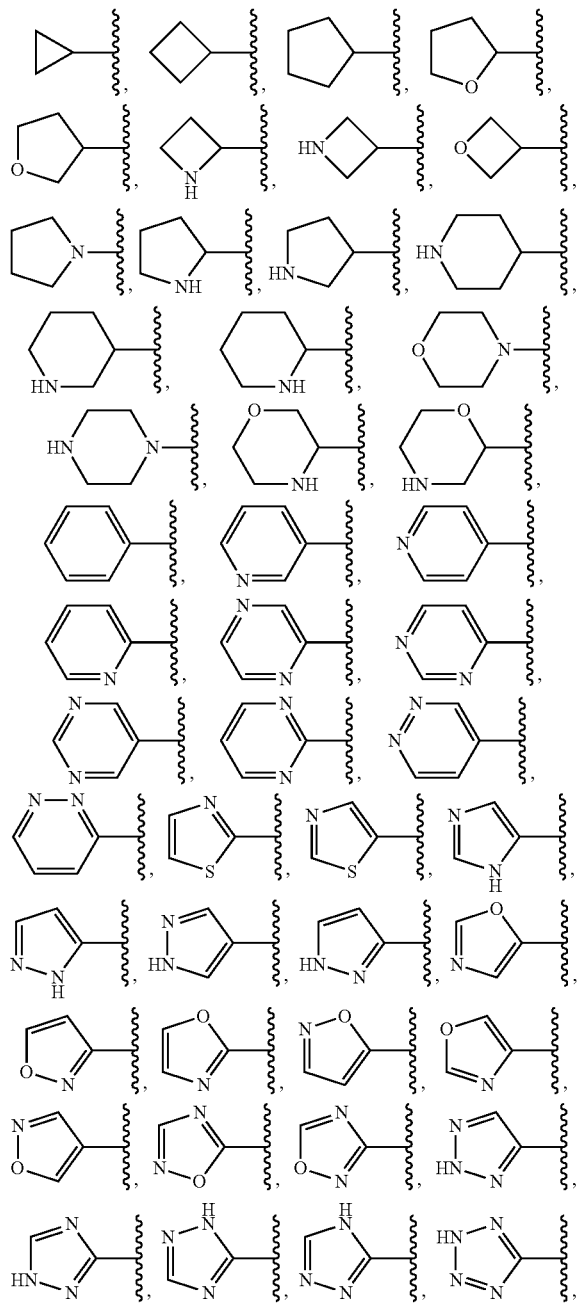

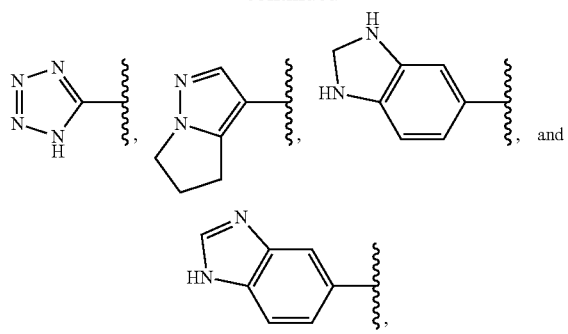

each of which is unsubstituted or substituted with one or more $R^{11}$ substituents; each $R^{11}$ is independently selected from the group consisting of heterocycloalkyl, heteroaryl, halo, $C_1$-$C_6$ alkyl, $C_1$-$C_6$ alkyl substituted with one or two $R^{12}$ substituents, cycloalkyl, cycloalkyl substituted with one or two $R^{12}$ substituents, fluoroalkyl, —$OR^b$, —$C(O)R^c$, —$C(O)OR^d$, oxo, and —$NR^eR^f$; each $R^{12}$ is independently selected from the group consisting of halo, —$OR^b$, —$C(O)R^g$, —$C(O)OR^h$, and —$C(O)NR^iR^j$; and each $R^b$, $R^c$, $R^d$, $R^e$, and $R^f$, $R^g$, $R^h$, $R^i$, and $R^j$ is independently H or $C_1$-$C_6$ alkyl.

In some embodiments of Formula (I) or any variation thereof, B is selected from the group consisting of:

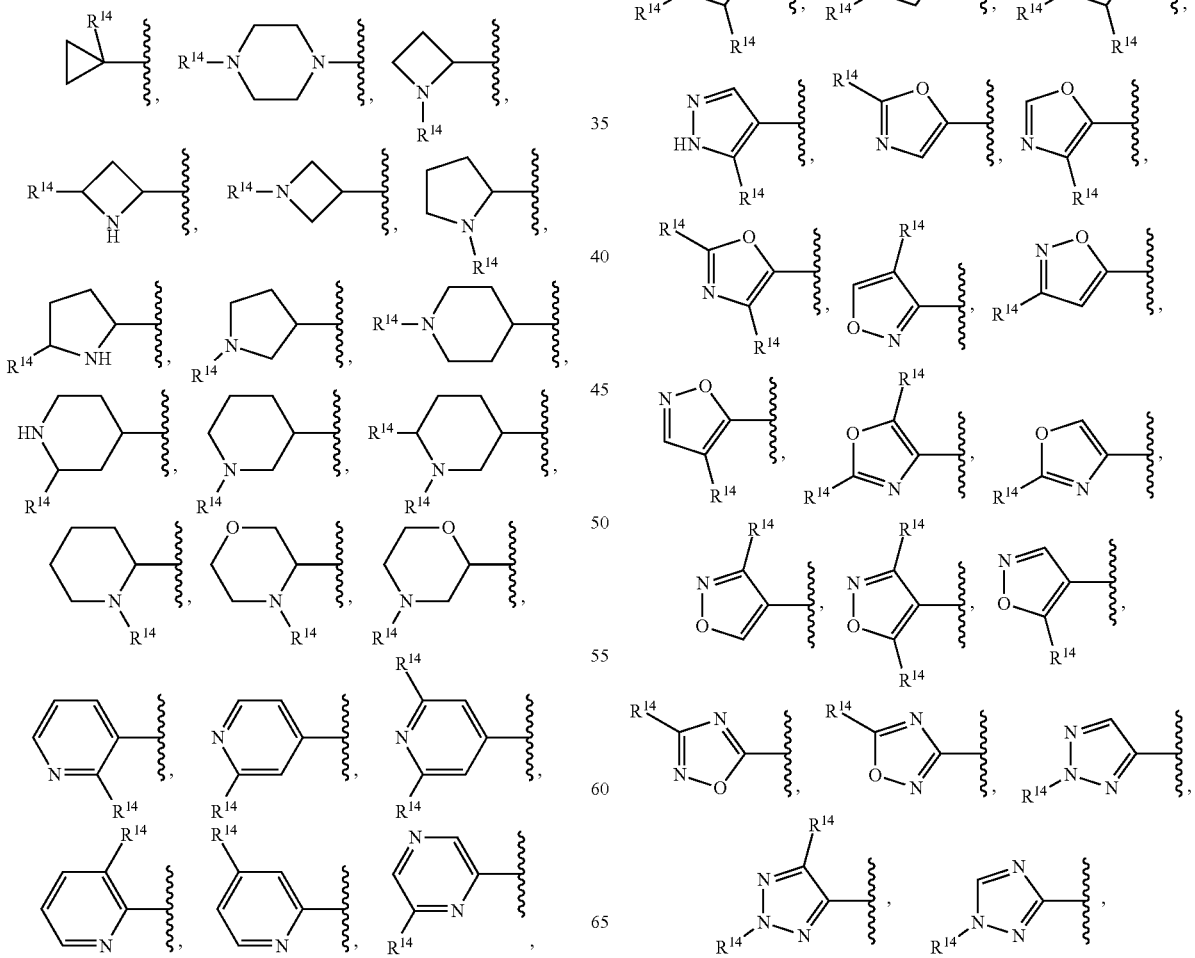

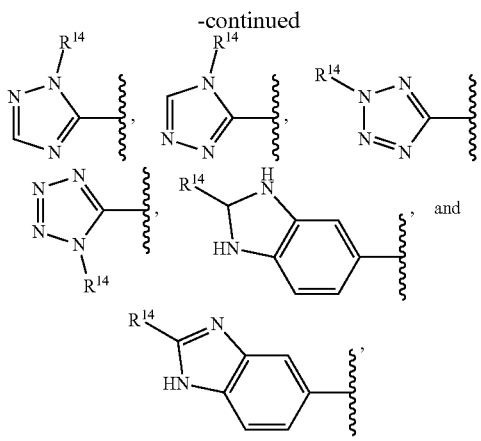

wherein each $R^{14}$ is independently selected from the group consisting of heterocycloalkyl, heteroaryl, cycloalkyl, aryl, $C_1$-$C_6$ alkyl, $C_1$-$C_6$ alkyl substituted with one or more $R^{12}$ substituents, halo, fluoroalkyl, —$OR^b$, —$C(O)R^c$, —$C(O)OR^d$, oxo, and —$NR^eR^f$, wherein each heterocycloalkyl and heteroaryl of $R^{14}$ is unsubstituted or substituted with one or more substituents selected from the group consisting of $C_1$-$C_6$ alkyl, —$C(O)R^n$, —$C(O)OR^p$, and —$C(O)NR^qR^r$; each $R^{12}$ is independently selected from the group consisting of halo, —OH, —$C(O)R^g$, —$C(O)OR^h$, and —$C(O)NR^1R^1$; and each $R^b$, $R^c$, $R^d$, $R^e$, $R^f$, $R^g$, $R^h$, $R^i$, and $R^j$, $R^n$, $R^p$, $R^q$, and $R^r$ is independently H or $C_1$-$C_6$ alkyl.

Provided in some embodiments are compounds selected from the group consisting of compounds of Table 1, or a pharmaceutically acceptable salt thereof.

Provided in some aspects is a pharmaceutical composition containing a compound of Formula (I) or any variation thereof, or a pharmaceutically acceptable salt thereof, and a pharmaceutically acceptable excipient.

Provided in some aspects are methods of treating heart disease in a subject in need thereof, the method including administering to the subject a compound of Formula (I) or any variation thereof, or a pharmaceutically acceptable salt thereof, or a pharmaceutical composition containing a compound of Formula (I) or any variation thereof. In some embodiments, the heart disease is hypertrophic cardiomyopathy (HCM). In some embodiments, the HCM is obstructive or nonobstructive or is caused by sarcomeric and/or non-sarcomeric mutations. In some embodiments, the heart disease is heart failure with preserved ejection fraction (HFpEF). In some embodiments, the heart disease is selected from the group consisting of diastolic dysfunction, primary or secondary restrictive cardiomyopathy, myocardial infarction and angina pectoris, and left ventricular outflow tract obstruction. In some embodiments, the heart disease is hypertensive heart disease, congenital heart disease, cardiac ischemia, coronary heart disease, diabetic heart disease, congestive heart failure, right heart failure, cardiorenal syndrome, or infiltrative cardiomyopathy. In some embodiments, the heart disease is a condition that is or is related to cardiac senescence and/or diastolic dysfunction due to aging. In some embodiments, the heart disease is a condition that is or is related to left ventricular hypertrophy and/or concentric left ventricular remodeling.

Provided in other aspects are methods of treating a disease or condition associated with HCM in a subject in need thereof, wherein the method involves administering to the subject a compound of Formula (I) or any variation thereof, or a pharmaceutically acceptable salt thereof, or a pharmaceutical composition containing a compound of Formula (I) or any variation thereof. In some embodiments, the disease or condition is selected from the group consisting of Fabry's Disease, Danon Disease, mitochondrial cardiomyopathies, and Noonan Syndrome.

Provided in some aspects are methods of treating a disease or condition that is associated with secondary left ventricular wall thickening in a subject in need thereof, wherein the method involves administering to the subject a compound of Formula (I) or any variation thereof, or a pharmaceutically acceptable salt thereof, or a pharmaceutical composition containing a compound of Formula (I) or any variation thereof. In some embodiments, the disease or condition is selected from the group consisting of hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, and Pompe disease.

Provided in other aspects are methods of treating a disease or condition that is associated with small left ventricular cavity and cavity obliteration, hyperdynamic left ventricular contraction, myocardial ischemia, or cardiac fibrosis. Also provided are methods of treating muscular dystrophies (e.g., Duchenne muscular dystrophy) or glycogen storage diseases.

Also provided are methods of inhibiting the cardiac sarcomere, wherein the method involves contacting the cardiac sarcomere with a compound of Formula (I) or any variation thereof, or a pharmaceutically acceptable salt thereof, or a pharmaceutical composition containing a compound of Formula (I) or any variation thereof.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (Ia), (Ib), (Ic), (Id), (Ie), (If), (Ig), (Ih), (Ii), (Ij), and (Ik), including all substructures, subgenera, preferences, embodiments, examples and particular compounds defined and/or described herein. References to a compound of Formula (I) and subgroups thereof, such as Formula (Ia), (Ib), (Ic), (Id), (Ie), (If), (Ig), (Ih), (Ii), (Ij), and (Ik), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (Ia), (Ib), (Ic), (Id), (Ie), (If), (Ig), (Ih), (Ii), (Ij), and (Ik), include polymorphs, solvates, co-crystals, isomers, tautomers and/or oxides thereof. In some embodiments, references to a compound of Formula (I) and subgroups thereof, such as Formula (Ia), (Ib), (Ic), (Id), (Ie), (If), (Ig), (Ih), (Ii), (Ij), and (Ik), include polymorphs, solvates, and/or co-crystals thereof. In some embodiments, references to a compound of Formula (I) and subgroups thereof, such as Formula (Ia), (Ib), (Ic), (Id), (Ie), (If), (Ig), (Ih), (Ii), (Ij), and (Ik), include isomers, tautomers and/or oxides thereof. In some embodiments, references to a compound of Formula (I) and subgroups thereof, such as Formula (Ia), (Ib), (Ic), (Id), (Ie), (If), (Ig), (Ih), (Ii), (Ij), and (Ik), include solvates thereof. Similarly, the term "salts" includes solvates of salts of compounds.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2$H, $^3$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate the cardiac sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

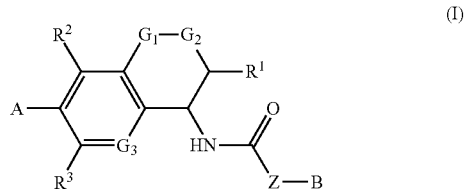

or a salt thereof, wherein $G_1$ is —$CR^4R^5$— or —O—;
$G_2$ is a bond or —$CR^6R^7$—;
$G_3$ is —$CR^8$— or —N—;
$R^1$, $R^3$, $R^4$, $R^5$, $R^6$, $R^7$, and $R^8$ are each independently H, $C_1$-$C_6$ alkyl, halo, or hydroxyl;
$R^2$ is H, $C_2$-$C_6$ alkyl, halo, or hydroxyl;
Z is selected from the group consisting of a bond, $C_1$-$C_6$ alkyl, —O—, —$N(R^9)$—, —$R^xO$—, —$OR^y$—, and —$R^zS$—;
$R^9$ is H, $C_1$-$C_6$ alkyl, or cycloalkyl;
A is selected from the group consisting of substituted $C_2$ alkynyl, unsubstituted $C_2$ alkynyl, substituted phenyl, unsubstituted phenyl, and 5- or 6-membered heteroaryl comprising at least one annular N atom, wherein the 5- or 6-membered heteroaryl is unsubstituted or substituted with one or more $R^{10}$ substituents;

each $R^{10}$ is independently selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocycloalkyl, and —C(O)OR$^a$;

B is selected from the group consisting of H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents;

each $R^{11}$ is independently selected from the group consisting of substituted or unsubstituted heterocycloalkyl, substituted or unsubstituted heteroaryl, substituted or unsubstituted cycloalkyl, substituted or unsubstituted aryl, unsubstituted $C_1$-$C_6$ alkyl, $C_1$-$C_6$ alkyl substituted with one or more $R^{12}$ substituents, substituted or unsubstituted $C_2$-$C_6$ alkenyl, substituted or unsubstituted $C_2$-$C_6$ alkynyl, halo, —OR$^b$, —C(O)R$^c$, —C(O)OR$^d$, oxo, and —NR$^e$R$^f$;

each $R^{12}$ is independently selected from the group consisting of halo, —OR$^b$, —C(O)R$^g$, —C(O)OR$^h$, and —C(O)NR$^i$R$^j$;

each R$^a$, R$^b$, R$^c$, R$^d$, R$^e$, R$^f$, R$^g$, R$^h$, R$^i$, and R$^j$ is independently H or $C_1$-$C_6$ alkyl; and R$^x$, R$^y$, and R$^z$ are each $C_1$-$C_6$ alkyl, wherein when A is unsubstituted phenyl or 5-trifluoromethyl-1,2,4-oxadiazolyl, the —Z—B moiety is not —OC(CH$_3$)$_3$ or 1-ethyl-3-hydroxy-1,5-dihydro-2H-pyrrol-2-onyl.

In some embodiments of Formula (I), $R^1$, $R^2$, $R^3$, $R^4$, $R^5$, $R^6$, $R^7$, and $R^8$ are each independently H. In some embodiments of Formula (I), at least one of $R^1$, $R^2$, $R^3$, $R^4$, $R^5$, $R^6$, $R^7$, and $R^8$ is not H.

In some variations of Formula (I) described herein, $G_1$ is —CR$^4$R$^5$—. In some embodiments, one of $R^4$ and $R^5$ is H, $C_1$-$C_6$ alkyl, halo, or hydroxyl and the other is $C_1$-$C_6$ alkyl, halo, or hydroxyl. In some embodiments, one of $R^4$ and $R^5$ is H, and the other is $C_1$-$C_6$ alkyl, halo, or hydroxyl. In some embodiments, both $R^4$ and $R^5$ are H, such that $G_1$ is —CH$_2$—. In some embodiments of Formula (I) described herein, $G_1$ is —O—.

In some embodiments of Formula (I), $G_2$ is a bond. In some embodiments, $G_2$ is —CR$^6$R$^7$—. In some embodiments, one of $R^6$ and $R^7$ is H, $C_1$-$C_6$ alkyl, halo, or hydroxyl and the other is $C_1$-$C_6$ alkyl, halo, or hydroxyl. In some embodiments, one of $R^6$ and $R^7$ is H, and the other is $C_1$-$C_6$ alkyl, halo, or hydroxyl. In some embodiments, both $R^6$ and $R^7$ are H, such that $G_2$ is —CH$_2$—.

In some embodiments of Formula (I), $G_3$ is —CR$^8$—, wherein $R^8$ is $C_1$-$C_6$ alkyl, halo, or hydroxyl. In some embodiments, $R^8$ is H, such that $G_3$ is —CH—. In some embodiments, $G_3$ is —N—.

In some embodiments of Formula (I), $G_1$ is —CR$^4$R$^5$— and $G_2$ is a bond. In certain embodiments, $G_1$ is —CH$_2$— and $G_2$ is a bond. In some embodiments, $G_1$ is —CR$^4$R$^5$— and $G_2$ is —CR$^6$R$^7$—. In certain embodiments, $G_1$ and $G_2$ are each —CH$_2$—. In some embodiments, $G_1$ is —O— and $G_2$ is a bond. In some embodiments, $G_1$ is —O— and $G_2$ is —CR$^6$R$^7$—. In some embodiments, $G_1$ is —O— and $G_2$ is —CH$_2$—. In some embodiments, $G_1$ is —CR$^4$R$^5$—, $G_2$ is a bond, and $G_3$ is —CR$^8$—. In certain embodiments, $G_1$ is —CH$_2$—, $G_2$ is a bond, and $G_3$ is —CH—. In some embodiments, $G_1$ is —CR$^4$R$^5$—, $G_2$ is —CR$^6$R$^7$—, and $G_3$ is —CR$^8$—. In certain embodiments, $G_1$ and $G_2$ are each —CH$_2$— and $G_3$ is —CH—. In some embodiments, $G_1$ is —O—, $G_2$ is a bond, and $G_3$ is —CR$^8$—. In certain embodiments, $G_1$ is —O—, $G_2$ is a bond, and $G_3$ is —CH—. In some embodiments, $G_1$ is —O—, $G_2$ is —CR$^6$R$^7$—, and $G_3$ is —CR$^8$—. In certain embodiments, $G_1$ is —O—, $G_2$ is —CH$_2$—, and $G_3$ is —CH—. In some embodiments, $G_1$ is —CR$^4$R$^5$—, $G_2$ is a bond, and $G_3$ is —N—. In certain embodiments, $G_1$ is —CH$_2$—, $G_2$ is a bond, and $G_3$ is —N—. In some embodiments, $G_1$ is —CR$^4$R$^5$—, $G_2$ is —CR$^6$R$^7$—, and $G_3$ is —N—. In certain embodiments, $G_1$ and $G_2$ are each —CH$_2$— and $G_3$ is —N—. In some embodiments, $G_1$ is —O—, $G_2$ is a bond, and $G_3$ is —N—. In some embodiments, $G_1$ is —O—, $G_2$ is —CR$^6$R$^7$—, and $G_3$ is —N—. In certain embodiments, $G_1$ is —O—, $G_2$ is —CH$_2$—, and $G_3$ is —N—.

In some embodiments of Formula (I), $R^1$ and $R^3$ are each independently H, $C_1$-$C_6$ alkyl, halo, or hydroxyl, and $R^2$ is H. In some embodiments, one of $R^1$ and $R^3$ is H and the other is $C_1$-$C_6$ alkyl, halo, or hydroxyl, and $R^2$ is H, $C_2$-$C_6$ alkyl, halo, or hydroxyl. In some embodiments, $R^1$ and $R^3$ are each H, and $R^2$ is $C_2$-$C_6$ alkyl, halo, or hydroxyl. In some embodiments, at least one of $R^1$, $R^2$, and $R^3$ is H. In some embodiments, at least one of $R^1$, $R^2$, and $R^3$ is not H. In some embodiments, $R^1$, $R^2$, and $R^3$ are each H.

In some embodiments, when any particular group is substituted, the indicated group is substituted by one or more substituents selected from the group consisting of oxo, $C_1$-$C_6$ alkyl, $C_2$-$C_6$ alkenyl, $C_2$-$C_6$ alkynyl, halogen, —CN, —OR$^{41}$, —SR$^{41}$, —NR$^{42}$R$^{43}$, —NO$_2$, —C=NH(OR$^{41}$), —C(O)R$^{41}$, —OC(O)R$^{41}$, —C(O)OR$^{41}$, —C(O)NR$^{42}$R$^{43}$, —OC(O)NR$^{42}$R$^{43}$, —NR$^{41}$C(O)R$^{42}$, —NR$^{41}$C(O)OR$^{42}$, —NR$^{41}$C(O)NR$^{42}$R$^{43}$, —S(O)R$^{41}$, —S(O)$_2$R$^{41}$, —NR$^{41}$S(O)R$^{42}$, —C(O)NR$^{41}$S(O)R$^{42}$, —NR$^{41}$S(O)$_2$R$^{42}$, —C(O)NR$^{41}$S(O)$_2$R$^{42}$, —S(O)NR$^{42}$R$^{43}$, —S(O)$_2$NR$^{42}$R$^{43}$, —P(O)(OR$^{42}$)(OR$^{43}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^{41}$, —($C_1$-$C_3$ alkylene)SR$^{41}$, —($C_1$-$C_3$ alkylene)NR$^{42}$R$^{43}$, —($C_1$-$C_3$ alkylene)CF$_3$, —($C_1$-$C_3$ alkylene)NO$_2$, —C=NH(OR$^{41}$), —($C_1$-$C_3$ alkylene)C(O)R$^{41}$, —($C_1$-$C_3$ alkylene)OC(O)R$^{41}$, —($C_1$-$C_3$ alkylene)C(O)OR$^{41}$, —($C_1$-$C_3$ alkylene)C(O)NR$^{42}$R$^{43}$, —($C_1$-$C_3$ alkylene)OC(O)NR$^{42}$R$^{43}$, —($C_1$-$C_3$ alkylene)NR$^{41}$C(O)R$^{42}$, —($C_1$-$C_3$ alkylene)NR$^{41}$C(O)OR$^{42}$, —($C_1$-$C_3$ alkylene)NR$^{41}$C(O)NR$^{42}$R$^{43}$, —($C_1$-$C_3$ alkylene)S(O)R$^{41}$, —($C_1$-$C_3$ alkylene)S(O)$_2$R$^{41}$, —($C_1$-$C_3$ alkylene)NR$^{41}$S(O)R$^{42}$, —C(O)($C_1$-$C_3$ alkylene)NR$^{41}$S(O)R$^{42}$, —($C_1$-$C_3$ alkylene)NR$^{41}$S(O)$_2$R$^{42}$, —($C_1$-$C_3$ alkylene)C(O)NR$^{41}$S(O)$_2$R$^{42}$, —($C_1$-$C_3$ alkylene)S(O)NR$^{42}$R$^{43}$, —($C_1$-$C_3$ alkylene)S(O)$_2$NR$^{42}$R$^{43}$, —($C_1$-$C_3$ alkylene)P(O)(OR$^{42}$)(OR$^{43}$), ($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) and —($C_1$-$C_3$ alkylene)($C_6$-$C_{14}$ aryl), wherein the one or more substituents are each independently unsubstituted or substituted with one or more further substituents selected from the group consisting of halogen, oxo, —OR$^{44}$, —NR$^{44}$R$^{45}$, —C(O)R$^{44}$, —CN, —S(O)R$^{44}$, —S(O)$_2$R$^{44}$, —P(O)(OR$^{44}$)(OR$^{45}$), —($C_1$-$C_3$ alkylene)OR$^{44}$, —($C_1$-$C_3$ alkylene)NR$^{44}$R$^{45}$, —($C_1$-$C_3$ alkylene)C(O)R$^{44}$, —($C_1$-$C_3$ alkylene)S(O)R$^{44}$, —($C_1$-$C_3$ alkylene)S(O)$_2$R$^{44}$, —($C_1$-$C_3$ alkylene)P(O)(OR$^{44}$)(OR$^{45}$), $C_3$-$C_8$ cycloalkyl, $C_1$-$C_6$ alkyl, and $C_1$-$C_6$ alkyl substituted by oxo, —OH or halogen; wherein each R$^{41}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl are independently unsubstituted or substituted by halogen, oxo, —CN, —OR$^{46}$, —NR$^{46}$R$^{47}$, —P(O)(OR$^{46}$)(OR$^{46}$), phenyl, phenyl substituted by halogen, $C_1$-$C_6$ alkyl, or $C_1$-$C_6$ alkyl substituted by halogen, —OH or oxo; R$^{42}$ and R$^{43}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl are each independently unsubstituted or substituted by halogen, oxo, —CN, —OR$^{46}$, —NR$^{46}$R$^{47}$, $C_1$-$C_6$ alkyl, or $C_1$-$C_6$ alkyl substituted by halogen, —OH or oxo; and R$^{44}$, R$^{45}$, R$^{46}$ and R$^{47}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In another aspect, the compound of Formula (I) is a compound of Formula (Ia):

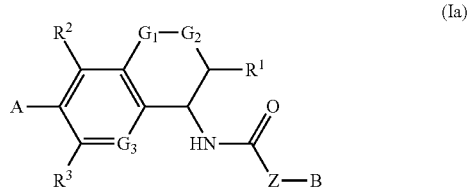

(Ia)

or a salt thereof, wherein A, B, $G_1$, $G_3$, and Z are as defined for Formula (I) or any variation or embodiment thereof.

In some embodiments of Formula (Ia), R$^1$, R$^2$, R$^3$, R$^4$, R$^5$, and R$^8$ are each independently H. In some embodiments of Formula (Ia), at least one of R$^1$, R$^2$, R$^3$, R$^4$, R$^5$, and R$^8$ is not H.

In some variations of Formula (Ia) described herein, $G_1$ is —CR$^4$R$^5$—. In some embodiments, one of R$^4$ and R$^5$ is H, $C_1$-$C_6$ alkyl, halo, or hydroxyl and the other is $C_1$-$C_6$ alkyl, halo, or hydroxyl. In some embodiments, one of R$^4$ and R$^5$ is H, and the other is $C_1$-$C_6$ alkyl, halo, or hydroxyl. In some embodiments, both R$^4$ and R$^5$ are H, such that $G_1$ is —CH$_2$—. In some embodiments of Formula (Ia) described herein, $G_1$ is —O—.

In some embodiments of Formula (Ia), $G_3$ is —CR$^8$—, wherein R$^8$ is $C_1$-$C_6$ alkyl, halo, or hydroxyl. In some embodiments, R$^8$ is H, such that $G_3$ is —CH—. In some embodiments, $G_3$ is —N—.

In some embodiments of Formula (I) or (Ia), $G_1$ is —CR$^4$R$^5$— and $G_3$ is —CR$^8$—. In certain embodiments, $G_1$ is —CH$_2$— and $G_3$ is —CH—. In some embodiments, $G_1$ is —CR$^4$R$^5$— and $G_3$ is —N—. In some embodiments, $G_1$ is —O— and $G_3$ is —CR$^8$—. In certain embodiments, $G_1$ is —O— and $G_3$ is —CH—. In some embodiments, $G_1$ is —O— and $G_3$ is —N—.

In some embodiments of Formula (Ia), R$^1$ and R$^3$ are each independently H, $C_1$-$C_6$ alkyl, halo, or hydroxyl, and R$^2$ is H. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, at least one of R$^1$, R$^2$, and R$^3$ is H. In some embodiments, at least one of R$^1$, R$^2$, and R$^3$ is not H. In some embodiments, R$^1$, R$^2$, and R$^3$ are each H.

In another aspect, the compound of Formula (I) is a compound of Formula (Ib):

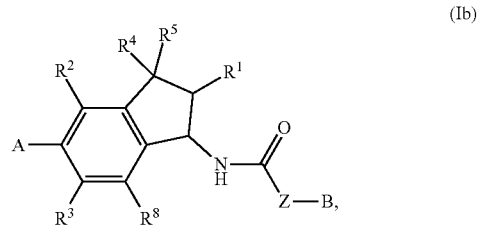

(Ib)

or a salt thereof, wherein A, Z, B, R$^1$, R$^2$, R$^3$, R$^4$, R$^5$, and R$^8$ are as defined for Formula (I) or any variation or embodiment thereof.

In some embodiments of Formula (Ib), R$^1$, R$^2$, R$^3$, R$^4$, R$^5$, and R$^8$ are each independently H. In some embodiments of Formula (Ib), at least one of R$^1$, R$^2$, R$^3$, R$^4$, R$^5$, and R$^8$ is not H. In some embodiments, one of R$^4$ and R$^5$ is H, $C_1$-$C_6$ alkyl, halo, or hydroxyl and the other is $C_1$-$C_6$ alkyl, halo, or hydroxyl. In some embodiments, one of R$^4$ and R$^5$ is H, and the other is $C_1$-$C_6$ alkyl, halo, or hydroxyl. In some embodiments, both R$^4$ and R$^5$ are H, such that $G_1$ is —CH$_2$—. In some embodiments, R$^8$ is $C_1$-$C_6$ alkyl, halo, or hydroxyl. In some embodiments, R$^8$ is H.

In some embodiments of Formula (Ib), R$^1$ and R$^3$ are each independently H, $C_1$-$C_6$ alkyl, halo, or hydroxyl, and R$^2$ is H. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, at least one of R$^1$, R$^2$, and R$^3$ is H. In some embodiments, at least one of R$^1$, R$^2$, and R$^3$ is not H. In some embodiments, R$^1$, R$^2$, and R$^3$ are each H.

In another aspect, the compound of Formula (I) is a compound of Formula (Ic):

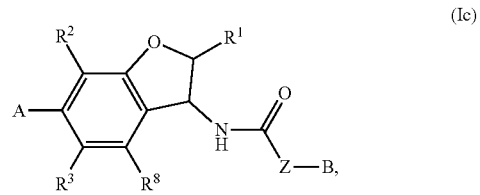

(Ic)

or a salt thereof, wherein A, Z, B, R$^1$, R$^2$, R$^3$, and R$^8$ are as defined for Formula (I) or any variation or embodiment thereof.

In some embodiments of Formula (Ic), R$^1$, R$^2$, R$^3$, and R$^8$ are each independently H. In some embodiments of Formula (Ic), at least one of R$^1$, R$^2$, R$^3$, and R$^8$ is not H. In some embodiments of Formula (Ic), R$^1$ and R$^3$ are each independently H, $C_1$-$C_6$ alkyl, halo, or hydroxyl, and R$^2$ is H. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, one of R$^1$ and R$^3$ is H and the other is $C_1$-$C_6$ alkyl, halo, or hydroxyl, and R$^2$ is H, $C_2$-$C_6$ alkyl, halo, or hydroxyl. In some embodiments, at least one of R$^1$, R$^2$, and R$^3$ is H. In some embodiments, at least one of R$^1$, R$^2$, and R$^3$ is not H. In some embodiments, R$^1$, R$^2$, and R$^3$ are each H. In some embodiments, R$^8$ is $C_1$-$C_6$ alkyl, halo, or hydroxyl. In some embodiments, R$^8$ is H.

In another aspect, the compound of Formula (I) is a compound of Formula (Id):

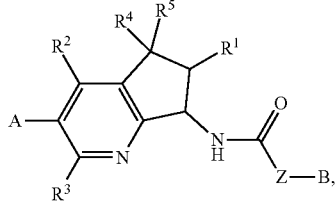

(Id)

or a salt thereof, wherein A, Z, B, $R^1$, $R^2$, $R^3$, $R^4$, and $R^5$ are as defined for Formula (I) or any variation or embodiment thereof.

In some embodiments of Formula (Id), $R^1$, $R^2$, $R^3$, $R^4$, and $R^5$ are each independently H. In some embodiments of Formula (Id), at least one of $R^1$, $R^2$, $R^3$, $R^4$, and $R^5$ is not H.

In some embodiments of Formula (Id), one of $R^4$ and $R^5$ is H, $C_1$-$C_6$ alkyl, halo, or hydroxyl and the other is $C_1$-$C_6$ alkyl, halo, or hydroxyl. In some embodiments, one of $R^4$ and $R^5$ is H, and the other is $C_1$-$C_6$ alkyl, halo, or hydroxyl. In some embodiments, both $R^4$ and $R^5$ are H.

In some embodiments of Formula (Id), $R^1$ and $R^3$ are each independently H, $C_1$-$C_6$ alkyl, halo, or hydroxyl, and $R^2$ is H. In some embodiments, one of $R^1$ and $R^3$ is H and the other is $C_1$-$C_6$ alkyl, halo, or hydroxyl, and $R^2$ is H, $C_2$-$C_6$ alkyl, halo, or hydroxyl. In some embodiments, one of $R^1$ and $R^3$ is H and the other is $C_1$-$C_6$ alkyl, halo, or hydroxyl, and $R^2$ is H, $C_2$-$C_6$ alkyl, halo, or hydroxyl. In some embodiments, at least one of $R^1$, $R^2$, and $R^3$ is H. In some embodiments, at least one of $R^1$, $R^2$, and $R^3$ is not H. In some embodiments, $R^1$, $R^2$, and $R^3$ are each H.

In another aspect, the compound of Formula (I) is a compound of Formula (Ie):

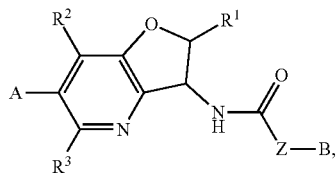

(Ie)

or a salt thereof, wherein A, Z, B, $R^1$, $R^2$, and $R^3$ are as defined for Formula (I) or any variation or embodiment thereof.

In some embodiments of Formula (Ie), $R^1$, $R^2$, and $R^3$ are each H. In some embodiments, $R^1$ and $R^3$ are each independently H, $C_1$-$C_6$ alkyl, halo, or hydroxyl, and $R^2$ is H. In some embodiments, one of $R^1$ and $R^3$ is H and the other is $C_1$-$C_6$ alkyl, halo, or hydroxyl, and $R^2$ is H, $C_2$-$C_6$ alkyl, halo, or hydroxyl. In some embodiments, one of $R^1$ and $R^3$ is H and the other is $C_1$-$C_6$ alkyl, halo, or hydroxyl, and $R^2$ is H, $C_2$-$C_6$ alkyl, halo, or hydroxyl. In some embodiments, at least one of $R^1$, $R^2$, and $R^3$ is H. In some embodiments, at least one of $R^1$, $R^2$, and $R^3$ is not H.

In another aspect, the compound of Formula (I) is a compound of Formula (If) or (Ig):

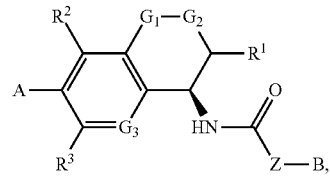

(If)

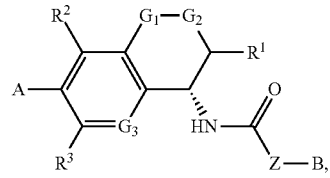

(Ig)

or a salt thereof, wherein A, Z, B, $R^1$, $R^2$, $R^3$ $G_1$, $G_2$, and $G_3$ are as defined for Formula (I) or any variation or embodiment thereof.

In another aspect, the compound of Formula (I) is a compound of Formula (Ih), (Ii), (Ij), or (Ik):

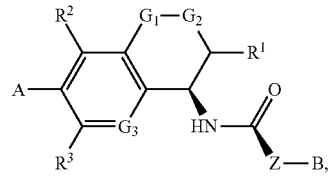

(Ih)

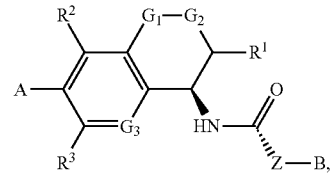

(Ii)

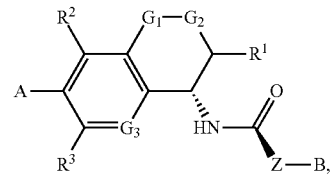

(Ij)

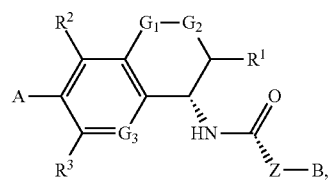

(Ik)

or a salt thereof, wherein A, Z, B, $R^1$, $R^2$, $R^3$ $G_1$, $G_2$, and $G_3$ are as defined for Formula (I) or any variation or embodiment thereof.

In some embodiments of Formula (I), (Ia), (Ib), (Ic), (Id), (Ie), (If), (Ig), (Ih), (Ii), (Ij), or (Ik), Z is a bond. In some embodiments, Z is $C_1$-$C_6$ alkyl. In some embodiments, Z is methylene. In some embodiments, Z is ethylene or propylene. In some embodiments, Z is —O—. In some of these embodiments, Z is —N($R^9$)—, wherein $R^9$ is H, $C_1$-$C_6$ alkyl, or cycloalkyl. In some of these embodiments, Z is —N($R^9$)—, wherein $R^9$ is H, $C_1$-$C_6$ alkyl, or $C_3$-$C_8$ cycloalkyl. In some embodiments, Z is —NH—. In some embodiments, Z is —N(CH$_3$)—. In some embodiments, Z is —R$^x$O—, —OR$^y$—, or —R$^z$S—, wherein R$^x$, R$^y$, and R$^z$ are each C$_1$-C$_6$ alkyl. In some embodiments, Z is —CH$_2$O—. In some embodiments, Z is —OCH$_2$—. In some embodiments, Z is —CH$_2$CH$_2$O—, —CH$_2$CH$_2$CH$_2$O—, —OCH$_2$CH$_2$—, or —OCH$_2$CH$_2$CH$_2$—. In some embodiments, Z is —CH$_2$S—, —CH$_2$CH$_2$S—, —CH$_2$CH$_2$CH$_2$S—, —SCH$_2$—, —SCH$_2$CH$_2$—, or SCH$_2$CH$_2$CH$_2$—.

In some embodiments of Formula (I), (Ia), (Ib), (Ic), (Id), (Ie), (If), (Ig), (Ih), (Ii), (Ij), or (Ik), A is selected from the group consisting of substituted C$_2$ alkynyl, unsubstituted C$_2$ alkynyl, substituted phenyl, unsubstituted phenyl, and 5- or 6-membered heteroaryl comprising at least one annular N atom, wherein the 5- or 6-membered heteroaryl is unsubstituted or substituted with one or more R$^{10}$ substituents; wherein each R$^{10}$ is independently selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_3$-C$_8$ cycloalkyl, substituted or unsubstituted 3- to 12-membered heterocycloalkyl, and —C(O)OR$^a$. In some embodiments, each R$^{10}$ is independently selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_3$-C$_8$ cycloalkyl, substituted or unsubstituted 5- to 6-membered heterocycloalkyl, and —C(O)OR$^a$. In some embodiments, each R$^{10}$ is independently selected from the group consisting of unsubstituted C$_1$-C$_6$ alkyl, C$_1$-C$_6$ alkyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkenyl, C$_2$-C$_6$ alkenyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkynyl, C$_2$-C$_6$ alkynyl substituted with one or more groups selected from D, halo, —C(O)OH, —C(O)OC$_1$-C$_6$ alkyl, —OH, —OC$_1$-C$_6$ alkyl, and C$_3$-C$_8$cycloalkyl, unsubstituted C$_3$-C$_8$ cycloalkyl, C$_3$-C$_8$ cycloalkyl substituted with one or more C$_1$-C$_6$ alkyl groups, unsubstituted 5- to 6-membered heterocycloalkyl, 5- to 6-membered heterocycloalkyl substituted with one or more C$_1$-C$_6$ alkyl groups, and —C(O)OR$^a$, wherein R$^a$ is H or C$_1$-C$_6$ alkyl.

In some embodiments of Formula (I), (Ia), (Ib), (Ic), (Id), (Ie), (If), (Ig), (Ih), (Ii), (Ij), or (Ik), A is unsubstituted C$_2$ alkynyl or substituted C$_2$ alkynyl. In some embodiments, A is unsubstituted C$_2$ alkynyl, such that A is acetylene. In other embodiments, A is C$_2$ alkynyl substituted with C$_1$-C$_6$ alkyl or C$_3$-C$_8$ cycloalkyl.

In some embodiments of Formula (I), (Ia), (Ib), (Ic), (Id), (Ie), (If), (Ig), (Ih), (Ii), (Ij), or (Ik), A is selected from the group consisting of substituted phenyl, unsubstituted phenyl, and 5- or 6-membered heteroaryl comprising at least one annular N atom, wherein the 5- or 6-membered heteroaryl is unsubstituted or substituted with one or more R$^{10}$ substituents In some embodiments of Formula (I), (Ia), (Ib), (Ic), (Id), (Ie), (If), (Ig), (Ih), (Ii), (Ij), or (Ik), A is phenyl, which is unsubstituted or substituted with one or more substituents selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, and —C(O)OR$^a$, wherein R$^a$ is H or C$_1$-C$_6$alkyl. In some embodiments, A is unsubstituted phenyl. In some embodiments, A is unsubstituted phenyl and Z is a bond, C$_1$-C$_6$ alkyl, —N(R$^9$)—, —R$^x$O—, —OR$^y$—, and —R$^z$S—, wherein R$^x$, R$^y$, and R$^z$ are each C$_1$-C$_6$ alkyl. In some embodiments, A is phenyl, wherein the phenyl is substituted with one or more substituents selected from the group consisting of unsubstituted C$_1$-C$_6$alkyl, C$_1$-C$_6$ alkyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkenyl, C$_2$-C$_6$ alkenyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkynyl, C$_2$-C$_6$ alkynyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_3$-C$_8$ cycloalkyl, C$_3$-C$_8$ cycloalkyl substituted with one or more C$_1$-C$_6$ alkyl groups, unsubstituted 5- to 6-membered heterocycloalkyl, 5- to 6-membered heterocycloalkyl substituted with one or more C$_1$-C$_6$ alkyl groups, and —C(O)OR$^a$, wherein R$^a$ is H or C$_1$-C$_6$ alkyl. In some embodiments, A is phenyl, substituted with one or more substituted or unsubstituted C$_1$-C$_6$ alkyl. In some embodiments, A is phenyl, substituted with C$_1$-C$_6$ alkyl, which is not further substituted. In some embodiments, A is phenyl, substituted with C$_1$-C$_6$ alkyl, which is further substituted. In some embodiments, A is phenyl, substituted with C$_1$-C$_6$ alkyl, wherein the C$_1$-C$_6$ alkyl is not further substituted by halo. In some embodiments, A is phenyl, substituted with methyl.

In some embodiments of Formula (I), (Ia), (Ib), (Ic), (Id), (Ie), (If), (Ig), (Ih), (Ii), (Ij), or (Ik), A is a 5- or 6-membered heteroaryl comprising at least one annular N atom. In some embodiments, the 5- or 6-membered heteroaryl is unsubstituted or substituted with one or more substituents selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, and —C(O)OR$^a$, wherein R$^a$ is H or C$_1$-C$_6$ alkyl. In some embodiments, the C$_1$-C$_6$ alkyl, C$_2$-C$_6$ alkenyl, C$_2$-C$_6$ alkynyl, cycloalkyl, or heterocycloalkyl are substituted with one or more groups selected from halo, —OR$^a$, —OC(O)R$^a$, cycloalkyl, heterocycloalkyl, wherein R$^a$ is H or C$_1$-C$_6$ alkyl. In some embodiments, A is 5- or 6-membered heteroaryl, wherein the 5- or 6-membered heteroaryl is substituted with one or more substituents selected from the group consisting of unsubstituted C$_1$-C$_6$alkyl, C$_1$-C$_6$ alkyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkenyl, C$_2$-C$_6$ alkenyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_2$-C$_6$ alkynyl, C$_2$-C$_6$ alkynyl substituted with one or more groups selected from D, halo, —C(O)OH, —C(O)OC$_1$-C$_6$ alkyl, —OH, —OC$_1$-C$_6$ alkyl, and C$_3$-C$_8$ cycloalkyl, unsubstituted C$_3$-C$_8$ cycloalkyl, C$_3$-C$_8$ cycloalkyl substituted with one or more C$_1$-C$_6$ alkyl groups, unsubstituted 5- to 6-membered heterocycloalkyl, 5- to 6-membered heterocycloalkyl substituted with one or more C$_1$-C$_6$ alkyl groups, and —C(O)OR$^a$, wherein R$^a$ is H or C$_1$-C$_6$ alkyl.

In some embodiments of Formula (I), (Ia), (Ib), (Ic), (Id), (Ie), (If), (Ig), (Ih), (Ii), (Ij), or (Ik), A is selected from the group consisting of phenyl, pyrazolyl, oxazolyl, oxadiazolyl, isoxazolyl, tetrazolyl, triazolyl, thiazolyl, pyrimidinyl, pyridinyl, pyrazinyl, and pyridazinyl, each of which is unsubstituted or substituted with one or more R$^{10}$ substituents, wherein each R$^{10}$ is independently selected from the group consisting of substituted or unsubstituted C$_1$-C$_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocycloalkyl, and —C(O)OR$^a$, wherein R$^a$ is H or $C_1$-$C_6$ alkyl. In some embodiments, the $C_1$-$C_6$ alkyl, $C_2$-$C_6$ alkenyl, $C_2$-$C_6$ alkynyl, cycloalkyl, or heterocycloalkyl are substituted with one or more groups selected from halo, —OR$^a$, —OC(O)R$^a$, cycloalkyl, heterocycloalkyl, wherein R$^a$ is H or $C_1$-$C_6$ alkyl. In some embodiments of Formula (I), (Ia), (Ib), (Ic), (Id), (Ie), (If), (Ig), (Ih), (Ii), (Ij), or (Ik), A is oxadiazolyl or isoxazolyl, each of which is unsubstituted or substituted with one or more R$^{10}$ substituents. In some embodiments, A is phenyl, pyrazolyl, oxazolyl, oxadiazolyl, isoxazolyl, tetrazolyl, triazolyl, thiazolyl, pyrimidinyl, pyridinyl, pyrazinyl, and pyridazinyl, each substituted with one or more substituents selected from the group consisting of unsubstituted $C_1$-$C_6$ alkyl, $C_1$-$C_6$ alkyl substituted with one or more groups selected from D, halo, —C(O)OH, —C(O)OC$_1$-C$_6$ alkyl, —OH, —OC$_1$-C$_6$ alkyl, and $C_3$-$C_8$ cycloalkyl, unsubstituted $C_2$-$C_6$ alkenyl, $C_2$-$C_6$ alkenyl substituted with one or more groups selected from D, halo, —C(O)OH, —C(O)OC$_1$-C$_6$ alkyl, —OH, —OC$_1$-C$_6$ alkyl, and $C_3$-$C_8$ cycloalkyl, unsubstituted $C_2$-$C_6$ alkynyl, $C_2$-$C_6$ alkynyl substituted with one or more groups selected from D, halo, —C(O)OH, —C(O)OC$_1$-C$_6$ alkyl, —OH, —OC$_1$-C$_6$ alkyl, and $C_3$-$C_8$ cycloalkyl, unsubstituted $C_3$-$C_8$ cycloalkyl, $C_3$-$C_8$ cycloalkyl substituted with one or more $C_1$-$C_6$ alkyl groups, unsubstituted 5- to 6-membered heterocycloalkyl, 5- to 6-membered heterocycloalkyl substituted with one or more $C_1$-$C_6$ alkyl groups, and —C(O)OR$^a$, wherein R$^a$ is H or $C_1$-$C_6$ alkyl.

In some embodiments of Formula (I), (Ia), (Ib), (Ic), (Id), (Ie), (If), (Ig), (Ih), (Ii), (Ij), or (Ik), A is selected from the group consisting of:

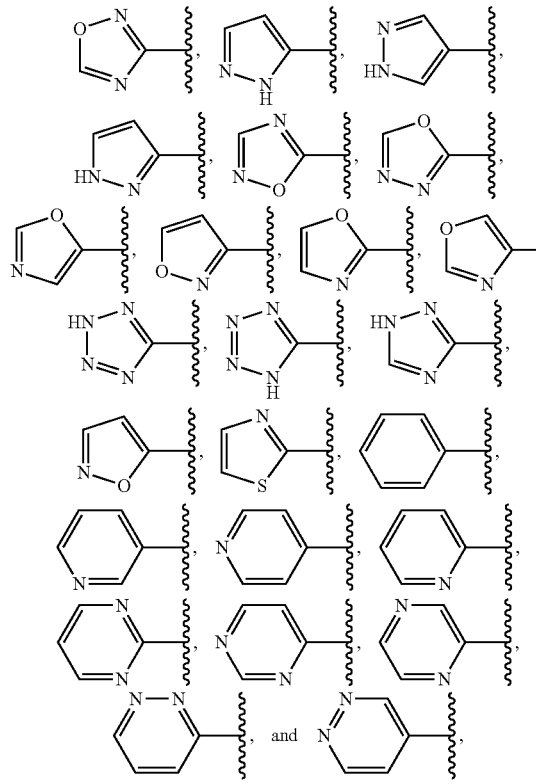

each of which is unsubstituted or substituted with one or more R$^{10}$ substituents. In some embodiments, each $C_1$-$C_6$ alkyl of R$^{10}$ is independently unsubstituted or substituted with one more substituents independently selected from the group consisting of —OR$^k$ and —OC(O)R$^m$, wherein R$^k$ and R$^m$ are each independently H or $C_1$-$C_6$ alkyl. In some embodiments, each R$^{10}$ is independently selected from the group consisting of —C(O)OCH$_3$, methyl, ethyl, isopropyl, difluoromethyl, cyclopropyl, cyclobutyl, and oxetanyl, wherein each methyl, ethyl and isopropyl of R$^{10}$ is independently unsubstituted or substituted with one more substituents independently selected from the group consisting of —OCH$_3$, —OH, and —OC(O)CH$_3$. In some embodiments, R$^{10}$ is methyl or —CD$_3$.

In some embodiments of Formula (I), (Ia), (Ib), (Ic), (Id), (Ie), (If), (Ig), (Ih), (Ii), (Ij), or (Ik), A is oxadiazolyl, which is unsubstituted or substituted with one substituent selected from the group consisting of methyl, methyl substituted with —OCH$_3$, —OH, or —OC(O)CH$_3$, ethyl, ethyl substituted with —OCH$_3$, —OH, —C(O)OCH$_3$, or —OC(O)CH$_3$, ethenyl, isopropyl, isopropyl substituted with —OCH$_3$, —OH, or —OC(O)CH$_3$, difluoromethyl, cyclopropyl, cyclobutyl, oxetanyl, acetyl, and —C(O)OCH$_3$. In some embodiments, A is isoxazolyl, which is unsubstituted or substituted with one or more substituents selected from the group consisting of methyl, ethyl, and difluoromethyl. In some embodiments, A is isoxazolyl, which is unsubstituted or substituted with one substituent selected from the group consisting of methyl, ethyl, and difluoromethyl.

In some embodiments of Formula (I), (Ia), (Ib), (Ic), (Id), (Ie), (If), (Ig), (Ih), (Ii), (Ij), or (Ik), A is selected from the group consisting of:

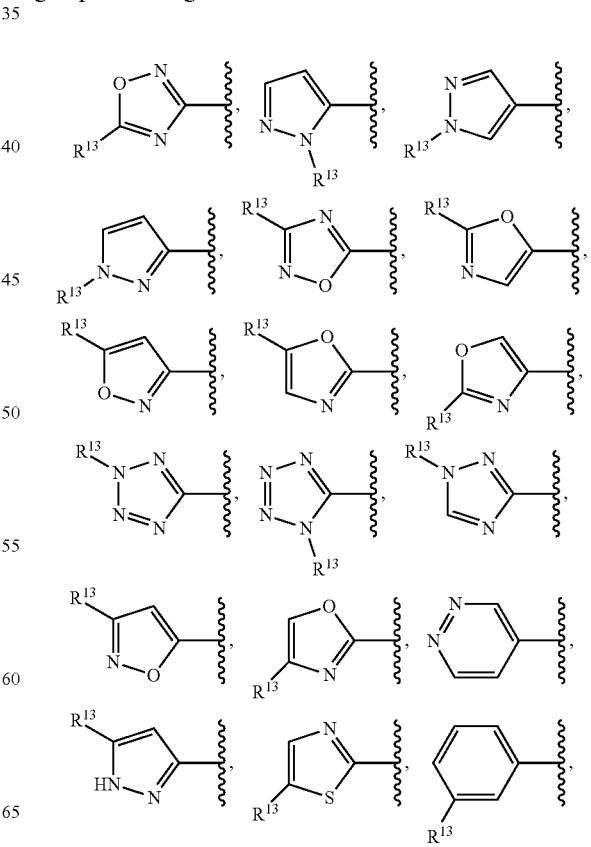

-continued

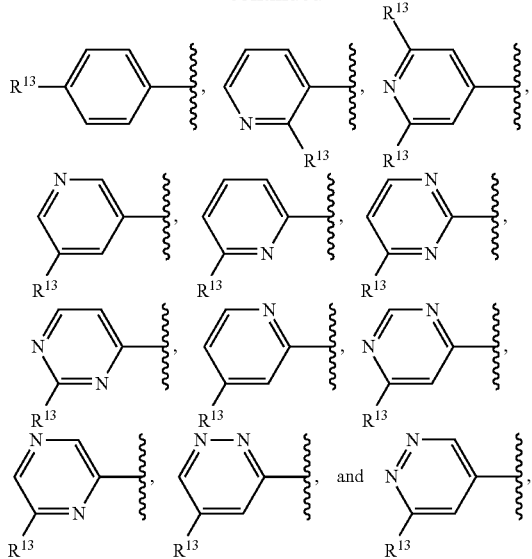

wherein each R¹³ is independently selected from the group consisting of H, substituted or unsubstituted C₁-C₆ alkyl, substituted or unsubstituted cycloalkyl, substituted or unsubstituted heterocycloalkyl, and —C(O)OR$^a$; and R$^a$ is H or C₁-C₆ alkyl. In some embodiments, the C₁-C₆ alkyl, C₂-C₆ alkenyl, C₂-C₆ alkynyl, cycloalkyl, or heterocycloalkyl are substituted with one or more groups selected from halo, —OR$^a$, —OC(O)R$^a$, —C(O)OR$^a$, —C(O)R$^a$, cycloalkyl, heterocycloalkyl, wherein R$^a$ is H or C₁-C₆ alkyl. In some embodiments, each R¹³ is independently selected from the group consisting of H, —C(O)OCH₃, methyl, ethyl, isopropyl, difluoromethyl, cyclopropyl, cyclobutyl, and oxetanyl, wherein each methyl, ethyl and isopropyl of R¹³ is independently unsubstituted or substituted with one more substituents independently selected from the group consisting of —OCH₃, —OH, and —OC(O)CH₃. In some embodiments, R¹³ is methyl or —CD₃.

In some embodiments of Formula (I), (Ia), (Ib), (Ic), (Id), (Ie), (If), (Ig), (Ih), (Ii), (Ij), or (Ik), A is phenyl, unsubstituted or substituted with methyl. In some embodiments, A is pyridine, unsubstituted or substituted with one or two methyl. In some embodiments, A is pyrazine, unsubstituted or substituted with methyl. In some embodiments, A is pyrimidine, unsubstituted or substituted with methyl. In some embodiments, A is pyridazine, unsubstituted or substituted with methyl. In some embodiments, A is pyrazole, unsubstituted or substituted with methyl. In some embodiments, A is thiazole, unsubstituted or substituted with methyl. In some embodiments, A is oxazole, unsubstituted or substituted with methyl. In some embodiments, A is tetrazole, unsubstituted or substituted with methyl. In some embodiments, A is triazole, unsubstituted or substituted with methyl. In some embodiments, A is isoxazole, substituted with methyl, ethyl, or CF₂. In some embodiments, A is oxadiazole, substituted with methyl, ethyl, CF₂, CD₃, cyclopropyl, isopropyl, cyclobutyl, oxetane, or C(O)OCH₃, each of which is optionally further substituted. In some embodiments, A is oxadiazole substituted with methyl, wherein the methyl is optionally further substituted with methoxy, OH, or —OC(O)CH₃. In some embodiments, A is oxadiazole substituted with ethyl, wherein the ethyl is optionally further substituted with methoxy, OH or —OC(O)CH₃. In some embodiments, A is oxadiazole substituted with isopropyl, wherein the isopropyl is optionally further substituted with OH or —OC(O)CH₃. In some embodiments, A is oxadiazole, substituted with methyl, ethyl, CD₃, CF₂, or cyclopropyl. In some embodiments, A is oxadiazole, substituted with ethyl or CF₂.

In some embodiments of Formula (I), (Ia), (Ib), (Ic), (Id), (Ie), (If), (Ig), (Ih), (Ii), (Ij), or (Ik), B is selected from the group consisting of H, C₁-C₆ alkyl, cycloalkyl, aryl, heterocycloalkyl, and heteroaryl, wherein the C₁-C₆ alkyl, cycloalkyl, aryl, heterocycloalkyl, or heteroaryl of B is unsubstituted or substituted with one or more R¹¹ substituents; each R¹¹ is independently selected from the group consisting of heterocycloalkyl, heteroaryl, cycloalkyl, aryl, C₁-C₆ alkyl, C₁-C₆ alkyl-OH, halo, fluoroalkyl, —OR$^b$, —C(O)R$^c$, —C(O)OR$^d$, oxo, and —NR$^e$R$^f$, wherein each heterocycloalkyl and heteroaryl of R¹¹ is unsubstituted or substituted with one or more substituents selected from the group consisting of C₁-C₆ alkyl, C₁-C₆ alkyl-OH, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or C₁-C₆ alkyl.

In some embodiments of Formula (I), (Ia), (Ib), (Ic), (Id), (Ie), (If), (Ig), (Ih), (Ii), (Ij), or (Ik), B is selected from the group consisting of H, C₁-C₆ alkyl, C₃-C₈ cycloalkyl, C₆-C₁₂ aryl, 3- to 12-membered heterocycloalkyl, and 5- to 10-membered heteroaryl, wherein the C₁-C₆ alkyl, C₃-C₈ cycloalkyl, C₆-C₁₂ aryl, 3- to 12-membered heterocycloalkyl, and 5- to 10-membered heteroaryl of B are each unsubstituted or substituted with one or more R¹¹ substituents. In some embodiments, B is unsubstituted or substituted with one or more R¹¹ substituents; wherein each R¹¹ is independently selected from the group consisting of substituted or unsubstituted 3- to 12-membered heterocycloalkyl, substituted or unsubstituted 5- to 10-membered heteroaryl, substituted or unsubstituted C₃-C₈ cycloalkyl, substituted or unsubstituted C₆-C₁₂ aryl, unsubstituted C₁-C₆ alkyl, C₁-C₆ alkyl substituted with one or more R¹² substituents, substituted or unsubstituted C₂-C₆ alkenyl, substituted or unsubstituted C₂-C₆ alkynyl, halo, —OR$^b$, —C(O)R$^c$, —C(O)OR$^d$, oxo, and —NR$^e$R$^f$. In some embodiments, B is unsubstituted or substituted with one or more R¹¹ substituents; wherein each R¹¹ is independently selected from the group consisting of 3- to 12-membered heterocycloalkyl, 5- to 10-membered heteroaryl, C₃-C₈ cycloalkyl, C₆-C₁₂ aryl, C₁-C₆ alkyl, halo, fluoroalkyl, —OR$^b$, —C(O)R$^c$, —C(O)OR$^d$, oxo, and —NR$^e$R$^f$, wherein each heterocycloalkyl and heteroaryl of R¹¹ is unsubstituted or substituted with one or more substituents selected from the group consisting of C₁-C₆ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or C₁-C₆ alkyl. In some embodiments, each heterocycloalkyl or heteroaryl of R¹¹ comprises 1, 2, 3, 4, or 5 heteroatoms selected from the group consisting of N, O, and S. In some embodiments of Formula (I) or any variation thereof, B is a phenyl, unsubstituted or substituted with one or more R¹¹ substituents. In some embodiments, B is a 5- to 6-membered heterocycloalkyl, unsubstituted or substituted with one or more R¹¹ substituents. In other embodiments, B is a 5- to 6-membered heteroaryl, unsubstituted or substituted with one or more R¹¹ substituents.

In some embodiments of Formula (I), (Ia), (Ib), (Ic), (Id), (Ie), (If), (Ig), (Ih), (Ii), (Ij), or (Ik), B is selected from the group consisting of cycloalkyl, aryl, heterocycloalkyl, and heteroaryl, each of which is substituted or unsubstituted. In some embodiments, the cycloalkyl, aryl, heterocycloalkyl, or heteroaryl is unsubstituted or substituted with one or more R¹¹ substituents; each R¹¹ is independently selected from the group consisting of heterocycloalkyl, heteroaryl, cycloalkyl, aryl, $C_1$-$C_6$ alkyl, $C_1$-$C_6$ alkyl-OH, halo, fluoroalkyl, —OR$^b$, —C(O)R$^c$, —C(O)OR$^d$, oxo, and —NR$^e$R$^f$, wherein each heterocycloalkyl and heteroaryl of R$^{11}$ is unsubstituted or substituted with one or more substituents selected from the group consisting of $C_1$-$C_6$ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or $C_1$-$C_6$ alkyl.

In some embodiments of Formula (I), (Ia), (Ib), (Ic), (Id), (Ie), (If), (Ig), (Ih), (Ii), (Ij), or (Ik), B is selected from the group consisting of $C_1$-$C_4$ alkyl, $C_3$-$C_5$ cycloalkyl, 6- to 10-membered aryl (e.g., 6- to 9-membered aryl), 4- to 6-membered heterocycloalkyl comprising at least one annular N or O atom, 5- or 6-membered monocyclic heteroaryl comprising at least one annular N atom, and 8- or 9-membered bicyclic heteroaryl comprising at least one annular N atom, each of which is substituted or unsubstituted. In some embodiments, the $C_1$-$C_4$ alkyl, $C_3$-$C_5$ cycloalkyl, 6- to 10-membered aryl (e.g., 6- to 9-membered aryl), 4- to 6-membered heterocycloalkyl, 5- or 6-membered monocyclic heteroaryl, or 8- or 9-membered bicyclic heteroaryl is unsubstituted or substituted with one or more R$^{11}$ substituents; each R$^{11}$ is independently selected from the group consisting of heterocycloalkyl, heteroaryl, cycloalkyl, aryl, $C_1$-$C_6$ alkyl, $C_1$-$C_6$ alkyl-OH, halo, fluoroalkyl, —OR$^b$, —C(O)R$^c$, —C(O)OR$^d$, oxo, and —NR$^e$R$^f$, wherein each heterocycloalkyl and heteroaryl of R$^{11}$ is unsubstituted or substituted with one or more substituents selected from the group consisting of $C_1$-$C_6$ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or $C_1$-$C_6$ alkyl.

In some embodiments of Formula (I), (Ia), (Ib), (Ic), (Id), (Ie), (If), (Ig), (Ih), (Ii), (Ij), or (Ik), B is selected from the group consisting of methyl, ethyl, isopropyl, isobutyl, tert-butyl, cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl and benzoimidazolyl, each of which is unsubstituted or substituted with one or more R$^{11}$ substituents; each R$^{11}$ is independently selected from the group consisting of heterocycloalkyl, heteroaryl, cycloalkyl, aryl, $C_1$-$C_6$ alkyl, $C_1$-$C_6$ alkyl-OH, halo, fluoroalkyl, —OR$^b$, —C(O)R$^c$, —C(O)OR$^d$, oxo, and —NR$^e$R$^f$, wherein each heterocycloalkyl and heteroaryl of R$^{11}$ is unsubstituted or substituted with one or more substituents selected from the group consisting of $C_1$-$C_6$ alkyl, —C(O)R$^n$, —C(O)OR$^p$, and —C(O)NR$^q$R$^r$; and each R$^b$, R$^c$, R$^d$, R$^e$, R$^f$, R$^n$, R$^p$, R$^q$, and R$^r$ is independently H or $C_1$-$C_6$ alkyl. In some embodiments, each R$^{11}$ is independently selected from the group consisting of methyl, ethyl, isopropyl, cyclopropyl, difluoromethyl, trifluoromethyl, oxo, —C(O)CH$_3$, —C(O)OtBu, —OCH$_3$, —OH, —NH$_2$, —Cl, oxetanyl, oxadiazolyl, and azetidinyl, wherein each oxadiazolyl and azetidinyl of R$^{11}$ is unsubstituted or substituted with one or more substituents selected from the group consisting of ethyl, —C(O)CH$_3$, —C(O)OtBu, —C(O)OCH$_3$, —C(O)NHCH$_3$, —C(O)NH$_2$, and —OCH$_3$.

In some embodiments of Formula (I), (Ia), (Ib), (Ic), (Id), (Ie), (If), (Ig), (Ih), (Ii), (Ij), or (Ik), B is $C_1$-$C_6$ alkyl substituted with —OR$^b$, wherein R$^b$ is H or $C_1$-$C_6$ alkyl. In some embodiments, B is $C_1$-$C_6$ alkyl optionally substituted with —OR$^b$, and Z is —O— or —N(R$^9$)—. In some embodiments, B is $C_1$-$C_6$ alkyl substituted with —OH. In some embodiments, B is $C_1$-$C_6$ alkyl substituted with —OH, and Z is —O—. In some embodiments, B is $C_1$-$C_6$ alkyl substituted with —OH, and Z is —N(R$^9$)—. In some embodiments, B is methyl, ethyl, n-propyl, isopropyl, n-butyl, isobutyl, secbutyl, tert-butyl, each optionally substituted with —OH.

In some embodiments of Formula (I), (Ia), (Ib), (Ic), (Id), (Ie), (If), (Ig), (Ih), (Ii), (Ij), or (Ik), B is methyl, pyrazolyl, oxazolyl, tetrazolyl, isoxazolyl, thiazolyl, imidazolyl, or pyridinyl, each of which is unsubstituted or substituted with one or more R$^{11}$ substituents; each R$^{11}$ is independently selected from the group consisting of heterocycloalkyl, heteroaryl, halo, alkyl, alkyl-OH, cycloalkyl, fluoroalkyl, —OR$^b$, —C(O)R$^c$, —C(O)OR$^d$, oxo, and —NR$^e$R$^f$; and each R$^b$, R$^c$, R$^d$, R$^e$, and R$^f$ is independently H or $C_1$-$C_6$ alkyl.

In some embodiments of Formula (I), (Ia), (Ib), (Ic), (Id), (Ie), (If), (Ig), (Ih), (Ii), (Ij), or (Ik), B is pyrazolyl, oxazolyl, tetrazolyl, isoxazolyl, or pyridinyl, each of which is unsubstituted or substituted with one or more $C_1$-$C_6$ alkyl substituents.

In some embodiments of Formula (I), (Ia), (Ib), (Ic), (Id), (Ie), (If), (Ig), (Ih), (Ii), (Ij), or (Ik), B is selected from the group consisting of:

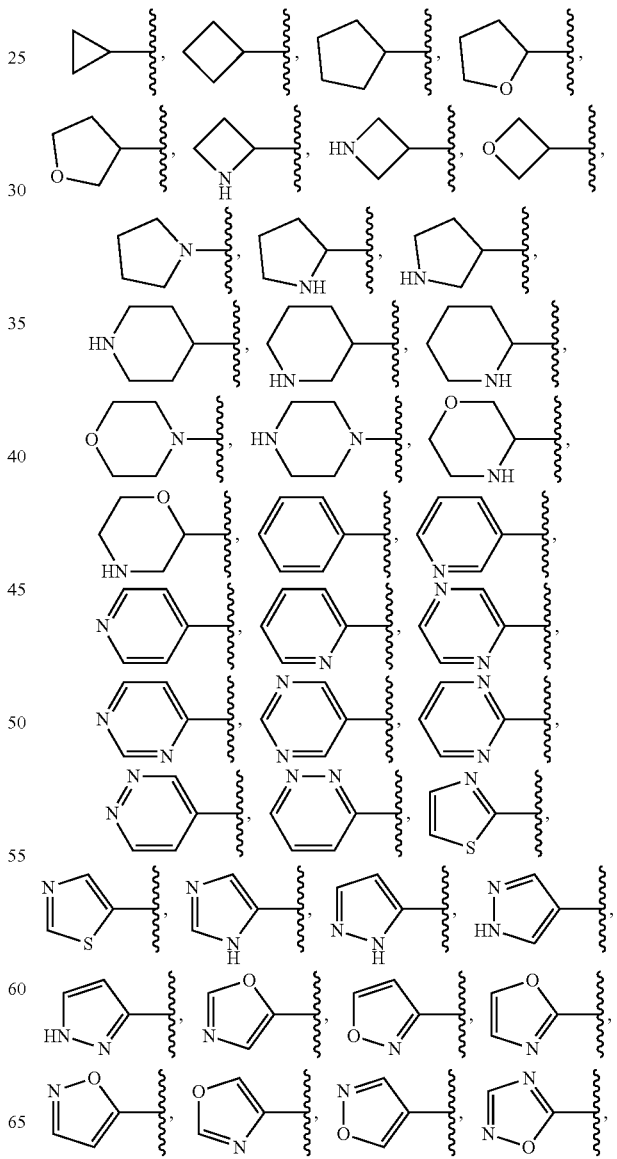

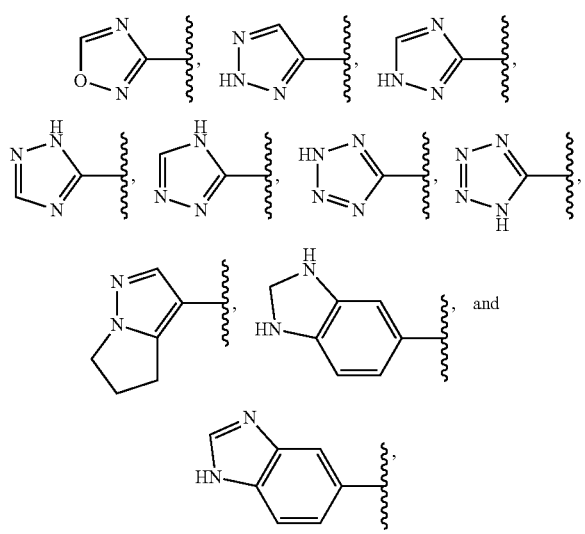

each of which is unsubstituted or substituted with one or more R[11] substituents; each R[11] is independently selected from the group consisting of heterocycloalkyl, heteroaryl, halo, alkyl, alkyl substituted with —OH, cycloalkyl, fluoroalkyl, —OR[b], —C(O)R[c], —C(O)OR[d], oxo, and —NR[e]R[f]; and each R[b], R[c], R[d], R[e], and R[f] is independently H or $C_1$-$C_6$ alkyl. In some embodiments, B is substituted with one or more R[11] substituents, wherein each R[11] is independently selected from the group consisting of heterocycloalkyl; heteroaryl; halo; unsubstituted $C_1$-$C_6$ alkyl; unsubstituted $C_2$-$C_6$ alkenyl; $C_1$-$C_6$ alkyl substituted with halo, —OH, —O$C_1$-$C_6$ alkyl, —C(O)OH, or —C(O)O$C_1$-$C_6$ alkyl; $C_3$-$C_8$cycloalkyl; —OR[b]; —C(O)R[c]; —C(O)OR[d]; oxo; and —NR[e]R[f], wherein each R[b], R[c], R[d], R[e], and R[f] is independently H or $C_1$-$C_6$ alkyl.

In some embodiments of Formula (I), (Ia), (Ib), (Ic), (Id), (Ie), (If), (Ig), (Ih), (Ii), (Ij), or (Ik), B is selected from the group consisting of:

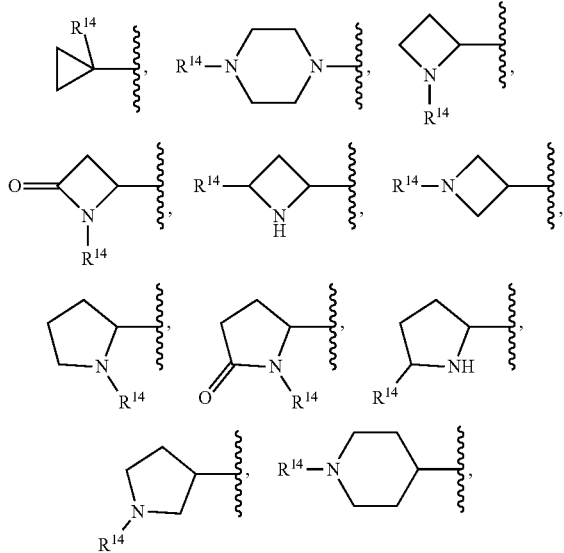

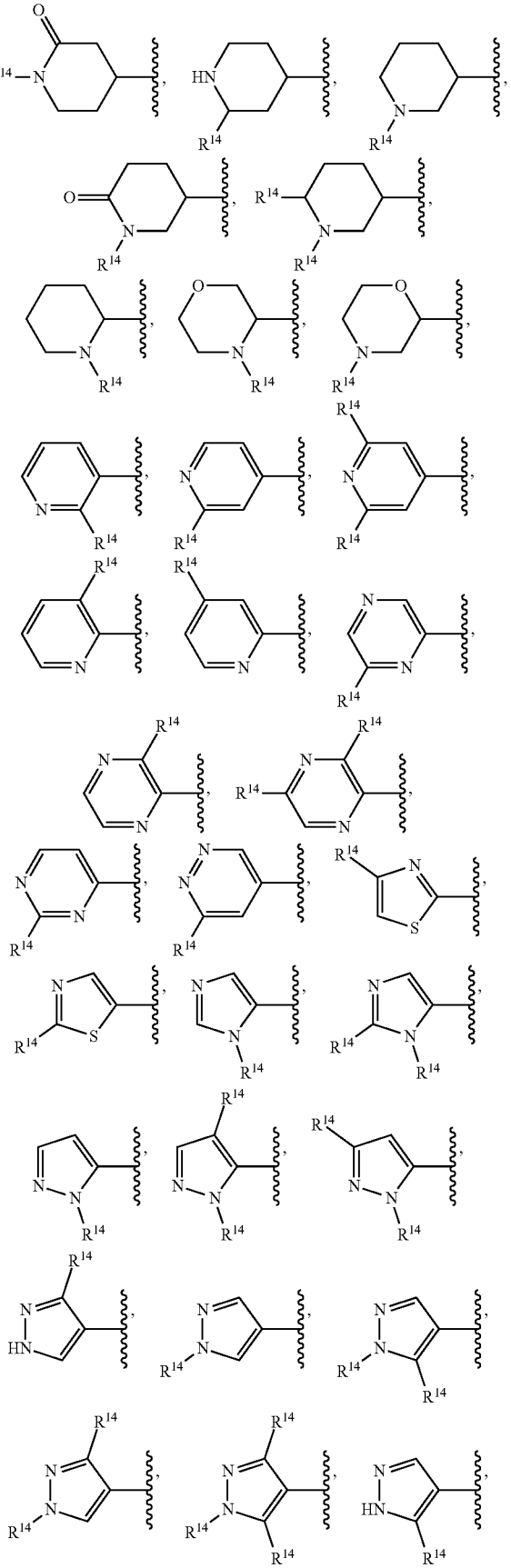

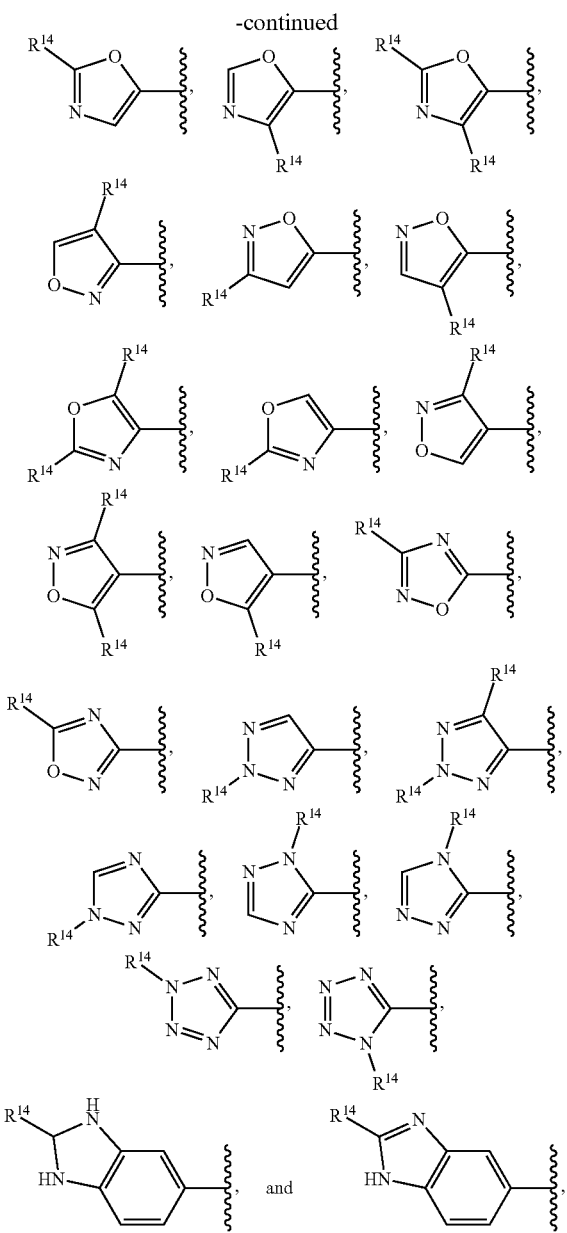

wherein each R[14] is independently selected from the group consisting of hydrogen, heterocycloalkyl, heteroaryl, cycloalkyl, aryl, $C_1$-$C_6$ alkyl, $C_1$-$C_6$ alkyl substituted with —OH, halo, fluoroalkyl, —OR[b], —C(O)R[c], —C(O)OR[d], oxo, and —NR[e]R[f], wherein each heterocycloalkyl and heteroaryl is unsubstituted or substituted with one or more substituents selected from the group consisting of $C_1$-$C_6$ alkyl, —C(O)R[n], —C(O)OR[p], and —C(O)NR[q]R[r]; and each R[b], R[c], R[d], R[e], R[f], R[n], R[p], R[q], and R[r] is independently H or $C_1$-$C_6$ alkyl.

In some embodiments of Formula (I), (Ia), (Ib), (Ic), (Id), (Ie), (If), (Ig), (Ih), (Ii), (Ij), or (Ik), B is H. In some embodiments, B is methyl. In some embodiments, B is $CD_3$. In some embodiments, B is $CF_2$. In some embodiments, B is phenyl. In some embodiments, B is azetidine, unsubstituted or optionally substituted with methyl, —C(O)CH$_3$, —C(O)OCH$_3$, —C(O)OC(CH$_3$)$_3$, —C(O)NH$_2$, —C(O)NHCH$_3$, or oxo. In some embodiments, B is benzoimidazole substituted with oxo. In some embodiments, B is cyclobutyl. In some embodiments, B is cyclopentyl. In some embodiments, B is cyclopropyl. In some embodiments, B is ethyl, unsubstituted or optionally substituted with methoxy. In some embodiments, B is imidazole, substituted with two methyl. In some embodiments, B is indane, substituted with oxadiazole, further substituted with ethyl. In some embodiments, B is isobutyl, unsubstituted or optionally substituted with methoxy. In some embodiments, B is isopropyl, unsubstituted or optionally substituted with OH. In some embodiments, B is isoxazole, substituted with one or two methyl, or isopropyl. In some embodiments, B is isoxazole, substituted with methyl. In some embodiments, B is methyl, unsubstituted or optionally substituted with $CF_2$, cyclopropyl, methoxy, oxetane, or azetidine, wherein the azetidine is further substituted with —C(O)CH$_3$, —C(O)OC(CH$_3$)$_3$, —C(O)NH$_2$, —C(O)NHCH$_3$, or —C(O)OCH$_3$. In some embodiments, B is methyl substituted with cyclopropyl, or cyclopropyl substituted with methyl. In some embodiments, B is morpholine, unsubstituted or optionally substituted with —C(O)CH$_3$ or —C(O)OC(CH$_3$)$_3$. In some embodiments, B is oxadiazole, substituted with methyl. In some embodiments, B is oxazole, substituted with one or two methyl, or cyclopropyl. In some embodiments, B is oxetane. In some embodiments, B is piperazine, substituted with methyl. In some embodiments, B is piperidine, unsubstituted or optionally substituted with one or more groups selected from methyl, oxo, —C(O)CH$_3$, and —C(O)OC(CH$_3$)$_3$. In some embodiments, B is pyrazine, unsubstituted or optionally substituted with one or two methyl. In some embodiments, B is pyrazole, unsubstituted or optionally substituted with one or more groups selected from methyl, ethyl, and $CF_3$. In some embodiments, B is pyrazole, substituted with one or two methyl. In some embodiments, B is pyridazine, unsubstituted or optionally substituted with methyl. In some embodiments, B is pyridine, unsubstituted or optionally substituted with amino, hydroxyl, —NH$_2$, —OH, or one or more methyl. In some embodiments, B is pyridine substituted with methyl. In some embodiments, B is pyrimidine, unsubstituted or optionally substituted with methyl. In some embodiments, B is pyrrolidine, unsubstituted or optionally substituted with methyl, oxo, —C(O)CH$_3$ or —C(O)OC(CH$_3$)$_3$. In some embodiments, B is pyrrolo pyrazole. In some embodiments, B is tert-butyl. In some embodiments, B is tetrahydrofuran. In some embodiments, B is tetrazole, substituted with methyl. In some embodiments, B is thiazole, unsubstituted or optionally substituted with chloro or methyl. In some embodiments, B is triazole, substituted with one or more groups selected from methyl and ethyl.

In some embodiments of any of Formula (I), (Ia), (Ib), (Ic), (Id), (Ie), (If), (Ig), (Ih), (Ii), (Ij), or (Ik), A is a 5-membered heteroaryl comprising at least one annular N atom, wherein the 5-membered heteroaryl is unsubstituted or substituted with one or more R[10] substituents as defined herein, and B is selected from the group consisting of H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more R[11] substituents as defined herein. In some embodiments, A is unsubstituted or substituted pyrazole, thiazole, oxazole, tetrazole, triazole, isoxazole, or oxadiazole; Z is a bond, —NR[9]—, —O—, —R[x]O—, or —OR[y]—, wherein R[9] is H, $C_1$-$C_6$ alkyl, or cycloalkyl, and R[x] and R[y] are each independently $C_1$-$C_6$ alkyl; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more R[11] substituents as defined herein. In some embodiments, A is unsubstituted or substituted pyrazole, thiazole, oxazole, tetrazole, triazole, isoxazole, or oxadiazole, Z is a bond, —NR$^9$—, or —O—, —R$^x$O—, or —OR$^y$—, wherein R$^9$ is H, C$_1$-C$_6$ alkyl, or cycloalkyl, and R$^x$ and R$^y$ are each independently C$_1$-C$_6$ alkyl; and B is unsubstituted or substituted methyl, ethyl, isopropyl, isobutyl, tert-butyl, cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl and benzoimidazolyl.

In some embodiments of any of Formula (I), (Ia), (Ib), (Ic), (Id), (Ie), (If), (Ig), (Ih), (Ii), (Ij), or (Ik), A is selected from pyrazole, thiazole, oxazole, tetrazole, triazole, isoxazole, and oxadiazole, each unsubstituted or substituted with one or more substituents selected from the group consisting of substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, and —C(O)OR$^a$, wherein R$^a$ is H or C$_1$-C$_6$ alkyl; Z is a bond, —NH—, —NCH$_3$—, or —O—, —CH$_3$O—, or —OCH$_3$—; and B is selected from methyl, ethyl, isopropyl, isobutyl, tert-butyl, cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl and benzoimidazolyl, each unsubstituted or substituted with one or more groups selected from heterocycloalkyl, heteroaryl, cycloalkyl, aryl, C$_1$-C$_6$ alkyl, halo, fluoroalkyl, —OR$^b$, —C(O)R$^c$, —C(O)OR$^d$, oxo, and —NR$^e$R$^f$, wherein each R$^b$, R$^c$, R$^d$, R$^e$, and R$^f$ is independently H or C$_1$-C$_6$ alkyl. In some of these embodiments, the C$_1$-C$_6$ alkyl, C$_2$-C$_6$ alkenyl, C$_2$-C$_6$ alkynyl, cycloalkyl, or heterocycloalkyl of A are substituted with one or more groups selected from halo, —OR$^a$, —OC(O)R$^a$, cycloalkyl, heterocycloalkyl, wherein R$^a$ is H or C$_1$-C$_6$ alkyl.

In some embodiments of any of Formula (I), (Ia), (Ib), (Ic), (Id), (Ie), (If), (Ig), (Ih), (Ii), (Ij), or (Ik), A is oxadiazole, optionally substituted with substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, or —C(O)OR$^a$, wherein R$^a$ is H or C$_1$-C$_6$ alkyl; Z is a bond, —NR$^9$—, —O—, —R$^x$O—, or —OR$^y$—, wherein R$^9$ is H, C$_1$-C$_6$ alkyl, or cycloalkyl, and R$^x$ and R$^y$ are each independently C$_1$-C$_6$ alkyl; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments of any of Formula (I), (Ia), (Ib), (Ic), (Id), (Ie), (If), (Ig), (Ih), (Ii), (Ij), or (Ik), A is oxadiazole substituted with C$_1$-C$_6$ alkyl, which is optionally further substituted with halo, —OR$^a$ or —C(O)OR$^a$, wherein R$^a$ is H or C$_1$-C$_6$ alkyl; Z is a bond, —NR$^9$—, or —O—, wherein R$^9$ is H, C$_1$-C$_6$ alkyl, or cycloalkyl; and B is cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl or benzoimidazolyl, each unsubstituted or substituted with one or more R$^{11}$ substituents as defined herein. In some embodiments, A is oxadiazole substituted with C$_1$-C$_6$ alkyl which is optionally further substituted with halo, —OR$^a$ or —C(O)OR$^a$, wherein R$^a$ is H or C$_1$-C$_6$ alkyl; Z is a bond, —NH—, —O—, —OCH$_2$—, or —CH$_2$O—, wherein R$^9$ is H, C$_1$-C$_6$ alkyl, or cycloalkyl; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments, A is oxadiazole substituted with methyl, —CD$_3$, —CF$_2$, ethyl, isopropyl, cyclopropyl, or cyclobutyl; Z is a bond, —NR$^9$—, —O—, —OCH$_2$—, or —CH$_2$O—, wherein R$^9$ is H, C$_1$-C$_6$ alkyl, or cycloalkyl; and B is aryl or heteroaryl optionally substituted with one or more groups selected from C$_1$-C$_6$ alkyl, cycloalkyl, OR$^b$ and —NR$^e$R$^f$, wherein R$^b$, R$^e$, and R$^f$ are each independently H or C$_1$-C$_6$ alkyl. In some embodiments, A is oxadiazole substituted with methyl, —CD$_3$, —CF$_2$, ethyl, isopropyl, cyclopropyl, or cyclobutyl; Z is a bond, —NH—, —N(CH$_3$)—, —O—, —OCH$_2$—, or —CH$_2$O—; and B is C$_1$-C$_6$ alkyl or cycloalkyl, each unsubstituted or substituted with halo. In some embodiments, A is oxadiazole substituted with methyl, —CD$_3$, —CF$_2$, ethyl, —CH$_2$OCH$_3$, isopropyl, cyclopropyl, or cyclobutyl; Z is —O—, —OCH$_2$—, or —CH$_2$O—; and B is C$_1$-C$_6$ alkyl, cycloalkyl, or heterocycloalkyl, wherein the C$_1$-C$_6$ alkyl is unsubstituted or substituted with halo. In some embodiments, A is oxadiazole substituted with methyl, —CD$_3$, —CF$_2$, ethyl, isopropyl, cyclopropyl, or cyclobutyl; Z is a bond, —NH—, —N(CH$_3$)—, —O—, —OCH$_2$—, or —CH$_2$O—; and B is aryl or heteroaryl optionally substituted with one or more groups selected from C$_1$-C$_6$ alkyl, cycloalkyl, OR$^b$ and —NR$^e$R$^f$, wherein R$^b$, R$^e$, and R$^f$ are each independently H or C$_1$-C$_6$ alkyl. In some embodiments, A is oxadiazole substituted with methyl, —CD$_3$, —CF$_2$, ethyl, isopropyl, cyclopropyl, or cyclobutyl; Z is a bond, —NH—, —N(CH$_3$)—, —O—, —OCH$_2$—, or —CH$_2$O—; and B is aryl or heteroaryl optionally substituted with one or more groups selected from C$_1$-C$_6$ alkyl, C$_1$-C$_6$ cycloalkyl, OH and —NH$_2$. In some embodiments, A is oxadiazole substituted with methyl, —CD$_3$, —CF$_2$, ethyl, isopropyl, cyclopropyl, or cyclobutyl; Z is a bond, —NH—, —N(CH$_3$)—, —O—, —OCH$_2$—, or —CH$_2$O—; and B is aryl or heteroaryl optionally substituted with one or more groups selected from C$_1$-C$_6$ alkyl, cycloalkyl, OR$^b$ and —NR$^e$R$^f$, wherein R$^b$, R$^e$, and R$^f$ are each independently H or C$_1$-C$_6$ alkyl. In some embodiments, A is oxadiazole substituted with methyl, —CD$_3$, —CF$_2$, ethyl, isopropyl, cyclopropyl, or cyclobutyl; Z is a bond, —NH—, —N(CH$_3$)—, —O—, —OCH$_2$—, or —CH$_2$O—; and B is methyl; CD$_3$; CF$_2$; phenyl; azetidine, unsubstituted or optionally substituted with methyl, —C(O)CH$_3$, —C(O)OCH$_3$, —C(O)OC(CH$_3$)$_3$, —C(O)NH$_2$, —C(O)NHCH$_3$, or oxo; benzoimidazole substituted with oxo; cyclobutyl; cyclopentyl; cyclopropyl; ethyl, unsubstituted or optionally substituted with methoxy; imidazole, substituted with two methyl; indane, substituted with oxadiazole, further substituted with ethyl; isobutyl, unsubstituted or optionally substituted with methoxy; isopropyl, unsubstituted or optionally substituted with OH; isoxazole, substituted with one or two methyl, or isopropyl; isoxazole, substituted with methyl; methyl, unsubstituted or optionally substituted with CF$_2$, cyclopropyl, methoxy, oxetane, or azetidine, wherein the azetidine is further substituted with —C(O)CH$_3$, —C(O)OC(CH$_3$)$_3$, —C(O)NH$_2$, —C(O)NHCH$_3$, or —C(O)OCH$_3$; methyl substituted with cyclopropyl, or cyclopropyl substituted with methyl; morpholine, unsubstituted or optionally substituted with —C(O)CH$_3$ or —C(O)OC(CH$_3$)$_3$; oxadiazole, substituted with methyl; oxazole, substituted with one or two methyl, or cyclopropyl;

oxetane; piperazine, substituted with methyl; piperidine, unsubstituted or optionally substituted with one or more groups selected from methyl, oxo, —C(O)CH$_3$, and —C(O)OC(CH$_3$)$_3$; pyrazine, unsubstituted or optionally substituted with one or two methyl; pyrazole, unsubstituted or optionally substituted with one or more groups selected from methyl, ethyl, and CF$_3$; pyrazole, substituted with one or two methyl; pyridazine, unsubstituted or optionally substituted with methyl; pyridine, unsubstituted or optionally substituted with amino, hydroxyl, —NH$_2$, —OH, or one or more methyl; pyridine substituted with methyl; pyrimidine, unsubstituted or optionally substituted with methyl; pyrrolidine, unsubstituted or optionally substituted with methyl, oxo, —C(O)CH$_3$ or —C(O)OC(CH$_3$)$_3$; pyrrolo pyrazole; tert-butyl; tetrahydrofuran; tetrazole, substituted with methyl; thiazole, unsubstituted or optionally substituted with chloro or methyl; or triazole, substituted with one or more groups selected from methyl and ethyl.

In some embodiments A is oxadiazole substituted with methyl, wherein the methyl is optionally further substituted with methoxy, OH, or —OC(O)CH$_3$; Z is a bond, —NR$^9$—, or —O—, wherein R$^9$ is H, C$_1$-C$_6$ alkyl, or cycloalkyl; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments A is oxadiazole substituted with methyl; Z is a bond, —NH—, or —O—; and B is C$_1$-C$_6$ alkyl, cycloalkyl, aryl, and heteroaryl, wherein the C$_1$-C$_6$ alkyl, cycloalkyl, aryl, heterocycloalkyl, each unsubstituted or substituted with one or more groups selected from as defined herein. In some embodiments A is oxadiazole substituted with ethyl, wherein the ethyl is optionally further substituted with methoxy, OH or —OC(O)CH$_3$; Z is a bond, —NH—, or —O—, and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments A is oxadiazole substituted with ethyl; Z is a bond, and B is an unsubstituted 5- to 6-membered heteroaryl or 5- to 6-membered heteroaryl substituted with one or more R$^{11}$ substituents as defined herein. In some embodiments A is oxadiazole substituted with —CF$_2$, Z is a bond, —NH—, or —O—, and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments A is oxadiazole substituted with —CF$_2$, Z is a bond, and B is an unsubstituted 5- to 6-membered heteroaryl or 5- to 6-membered heteroaryl substituted with one or more R$^{11}$ substituents as defined herein. In some embodiments A is oxadiazole substituted with isopropyl, Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments A is oxadiazole substituted with isopropyl, Z is a bond, and B is an unsubstituted 5- to 6-membered heteroaryl or 5- to 6-membered heteroaryl substituted with one or more R$^{11}$ substituents as defined herein. In some embodiments, A is oxadiazole substituted with cyclopropyl, Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments, A is oxadiazole substituted with —C(O)OR$^a$, wherein R$^a$ is H or C$_1$-C$_6$ alkyl; Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments, A is oxadiazole substituted with oxetanyl; Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments, A is oxadiazole substituted with cyclobutyl; Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments A is 5-ethyl-1,2,4-oxadiazol-3-yl, 5-(difluoromethyl)-1,2,4-oxadiazol-3-yl, or 5-isopropyl-1,2,4-oxadiazol-3-yl; Z is a bond, and B is an 5- to 6-membered heteroaryl substituted with one or more C$_1$-C$_6$ alkyl.

In some embodiments of any of Formula (I), (Ia), (Ib), (Ic), (Id), (Ie), (If), (Ig), (Ih), (Ii), (Ij), or (Ik), A is oxazole optionally substituted with substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, or —C(O)OR$^a$, wherein R$^a$ is H or C$_1$-C$_6$ alkyl; Z is a bond, —NR$^9$—, —O—, —R$^x$O—, or —OR$^y$—, wherein R$^9$ is H, C$_1$-C$_6$ alkyl, or cycloalkyl, and R$^x$ and R$^y$ are each independently C$_1$-C$_6$ alkyl; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments of any of Formula (I), (Ia), (Ib), (Ic), (Id), (Ie), (If), (Ig), (Ih), (Ii), (Ij), or (Ik), A is oxazole optionally substituted with substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, or —C(O)OR$^a$, wherein R$^a$ is H or C$_1$-C$_6$ alkyl; Z is a bond, —O—, or —NH—; and B is cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl or benzoimidazolyl, each unsubstituted or substituted with one or more R$^{11}$ substituents as defined herein. In some embodiments, A is oxazole substituted with methyl, ethyl, CF$_2$, or isopropyl; Z is a bond, —NH—, or —O—; and B is H, C$_1$-C$_6$ alkyl, cycloalkyl, aryl, heterocycloalkyl, and heteroaryl, wherein the C$_1$-C$_6$ alkyl, cycloalkyl, aryl, heterocycloalkyl, or heteroaryl of B is unsubstituted or substituted with one or more R$^{11}$ substituents as defined herein. In some embodiments of any of Formula (I), (Ia), (Ib), (Ic), (Id), (Ie), (If), (Ig), (Ih), (Ii), (Ij), or (Ik), A is isoxazole optionally substituted with substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted cycloalkyl, substituted or unsubstituted heterocycloalkyl, or —C(O)OR$^a$, wherein R$^a$ is H or C$_1$-C$_6$ alkyl; Z is a bond, —NR$^9$—, —O—, wherein R$^9$ is H, C$_1$-C$_6$ alkyl, or cycloalkyl; and B is H, C$_1$-C$_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments of any of Formula (I), (Ia), (Ib), (Ic), (Id), (Ie), (If), (Ig), (Ih), (Ii), (Ij), or (Ik), A is isoxazole optionally substituted with substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocycloalkyl, or —C(O)OR$^a$, wherein R$^a$ is H or $C_1$-$C_6$ alkyl; Z is a bond, —O—, or —NH—; and B is cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl or benzoimidazolyl, each unsubstituted or substituted with one or more $C_1$-$C_6$ alkyl. In some embodiments, A is isoxazole substituted with methyl, ethyl, $CF_2$, or isopropyl; Z is a bond, —NH—, —N(CH$_3$)—, —O—, —OCH$_2$—, or —CH$_2$O—; and B is H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is tetrazole substituted with methyl; Z is a bond, —NH—, —N(CH$_3$)—, —O—, —OCH$_2$—, or —CH$_2$O—; and B is H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments of any of Formula (I), (Ia), (Ib), (Ic), (Id), (Ie), (If), (Ig), (Ih), (Ii), (Ij), or (Ik), A is tetrazole substituted with methyl; Z is a bond, —NH—, —N(CH$_3$)—, —O—, —OCH$_2$—, or —CH$_2$O—; and B is cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl or benzoimidazolyl, each unsubstituted or substituted with one or more $C_1$-$C_6$ alkyl.

In some embodiments of any of Formula (I), (Ia), (Ib), (Ic), (Id), (Ie), (If), (Ig), (Ih), (Ii), (Ij), or (Ik), A is a 6-membered heteroaryl comprising at least one annular N atom, wherein the 6-membered heteroaryl is unsubstituted or substituted with one or more $R^{10}$ substituents as defined herein, and B is selected from the group consisting of H, $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is unsubstituted or substituted pyridine, pyrazine, pyrimidine, or pyridazine; Z is a bond, —NR$^9$—, —O—, —R$^x$O—, or —OR$^y$—, wherein R$^9$ is H, $C_1$-$C_6$ alkyl, or cycloalkyl, and R$^x$ and R$^y$ are each independently $C_1$-$C_6$ alkyl; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is unsubstituted or substituted pyridine, pyrazine, pyrimidine, or pyridazine; Z is a bond, —NH—, —N(CH$_3$)—, —O—, —OCH$_2$—, or —CH$_2$O—; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted methyl, ethyl, isopropyl, isobutyl, tert-butyl, cyclopropyl, cyclobutyl, cyclopentyl, phenyl, indanyl, azetidinyl, oxetanyl, pyrrolidinyl, tetrahydrofuranyl, piperidinyl, piperazinyl, morpholinyl, thiazolyl, triazolyl, imidazolyl, pyrazolyl, tetrazolyl, oxazolyl, isoxazolyl, oxadiazolyl, pyrazinyl, pyridazinyl, pyrimidinyl, pyridinyl, indanyl, pyrrolopyrazolyl and benzoimidazolyl. In some embodiments, A is unsubstituted or substituted pyridine, pyrazine, pyrimidine, or pyridazine; Z is a bond, —NH—, —N(CH$_3$)—, —O—, —OCH$_2$—, or —CH$_2$O—; and B is methyl; CD$_3$; CF$_2$; phenyl; azetidine, unsubstituted or optionally substituted with methyl, —C(O)CH$_3$, —C(O)OCH$_3$, —C(O)OC(CH$_3$)$_3$, —C(O)NH$_2$, —C(O)NHCH$_3$, or oxo; benzoimidazole substituted with oxo; cyclobutyl; cyclopentyl; cyclopropyl; ethyl, unsubstituted or optionally substituted with methoxy; imidazole, substituted with two methyl; indane, substituted with oxadiazole, further substituted with ethyl; isobutyl, unsubstituted or optionally substituted with methoxy; isopropyl, unsubstituted or optionally substituted with OH; isoxazole, substituted with one or two methyl, or isopropyl; isoxazole, substituted with methyl; methyl, unsubstituted or optionally substituted with CF$_2$, cyclopropyl, methoxy, oxetane, or azetidine, wherein the azetidine is further substituted with —C(O)CH$_3$, —C(O)OC(CH$_3$)$_3$, —C(O)NH$_2$, —C(O)NHCH$_3$, or —C(O)OCH$_3$; methyl substituted with cyclopropyl, or cyclopropyl substituted with methyl; morpholine, unsubstituted or optionally substituted with —C(O)CH$_3$ or —C(O)OC(CH$_3$)$_3$; oxadiazole, substituted with methyl; oxazole, substituted with one or two methyl, or cyclopropyl; oxetane; piperazine, substituted with methyl; piperidine, unsubstituted or optionally substituted with one or more groups selected from methyl, oxo, —C(O)CH$_3$, and —C(O)OC(CH$_3$)$_3$; pyrazine, unsubstituted or optionally substituted with one or two methyl; pyrazole, unsubstituted or optionally substituted with one or more groups selected from methyl, ethyl, and CF$_3$; pyrazole, substituted with one or two methyl; pyridazine, unsubstituted or optionally substituted with methyl; pyridine, unsubstituted or optionally substituted with amino, hydroxyl, —NH$_2$, —OH, or one or more methyl; pyridine substituted with methyl; pyrimidine, unsubstituted or optionally substituted with methyl; pyrrolidine, unsubstituted or optionally substituted with methyl, oxo, —C(O)CH$_3$ or —C(O)OC(CH$_3$)$_3$; pyrrolo pyrazole; tert-butyl; tetrahydrofuran; tetrazole, substituted with methyl; thiazole, unsubstituted or optionally substituted with chloro or methyl; or triazole, substituted with one or more groups selected from methyl and ethyl.

In some embodiments, A is phenyl, optionally substituted with methyl; Z is a bond, —NH—, —N(CH$_3$)—, —O—, —OCH$_2$—, or —CH$_2$O—; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is pyridinyl, optionally substituted with one or two methyl; Z is a bond, —NH—, —N(CH$_3$)—, —O—, —OCH$_2$—, or —CH$_2$O—; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is pyrimidinyl, optionally substituted with methyl; Z is a bond, —NH—, —N(CH$_3$)—, —O—, —OCH$_2$—, or —CH$_2$O—; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more $R^{11}$ substituents as defined herein. In some embodiments, A is pyrimidinyl, optionally substituted with methyl; Z is a bond, —NH—, —N(CH₃)—, —O—, —OCH₂—, or —CH₂O—; and B is aryl or heteroaryl, optionally substituted with one or more R¹¹ substituents as defined herein. In some embodiments, A is pyrimidinyl, optionally substituted with methyl; Z is a bond, —NH—, —N(CH₃)—, —O—, —OCH₂—, or —CH₂O; and B is aryl or heteroaryl, optionally substituted with one or more substituents selected from the group consisting of $C_1$-$C_6$ alkyl, halo, —OR$^b$, —C(O)R$^c$, —C(O)OR$^d$, oxo, and —NR$^e$R$^f$, wherein R$^b$, R$^c$, R$^d$, R$^e$, and R$^f$ is independently H or $C_1$-$C_6$ alkyl. In some embodiments, A is pyrimidinyl, unsubstituted or substituted with methyl; Z is a bond, —NH—, —N(CH₃)—, —O—, —OCH₂—, or —CH₂O; and B is pyrazolyl substituted with methyl. In some embodiments, A is pyrazinyl, optionally substituted with methyl; Z is a bond, —NH—, —N(CH₃)—, —O—, —OCH₂—, or —CH₂O; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more R¹¹ substituents as defined herein. In some embodiments, A is pyridazinyl, optionally substituted with methyl; Z is a bond, —NH—, —N(CH₃)—, —O—, —OCH₂—, or —CH₂O; and B is $C_1$-$C_6$ alkyl, cycloalkyl, aryl, heterocycloalkyl, and heteroaryl, wherein the $C_1$-$C_6$ alkyl, cycloalkyl, aryl, heterocycloalkyl, or heteroaryl of B is unsubstituted or substituted with one or more R¹¹ substituents as defined herein.

In some embodiments of Formula (I), (Ia), (Ib), (Ic), (Id), (Ie), (If), (Ig), (Ih), (Ii), (Ij), or (Ik), A is phenyl, unsubstituted or substituted with methyl; pyridine, unsubstituted or substituted with one or two methyl; pyrazine, unsubstituted or substituted with methyl; pyrimidine, unsubstituted or substituted with methyl; pyridazine, unsubstituted or substituted with methyl; pyrazole, unsubstituted or substituted with methyl; thiazole, unsubstituted or substituted with methyl; oxazole, unsubstituted or substituted with methyl; tetrazole, unsubstituted or substituted with methyl; triazole, unsubstituted or substituted with methyl; isoxazole, substituted with methyl, ethyl, or CF₂; oxadiazole, substituted with methyl, ethyl, CF₂, CD₃, cyclopropyl, isopropyl, cyclobutyl, oxetane, or C(O)OCH₃, each of which is optionally further substituted; oxadiazole substituted with methyl, wherein the methyl is optionally further substituted with methoxy, OH, or —OC(O)CH₃; oxadiazole substituted with ethyl, wherein the ethyl is optionally further substituted with methoxy, OH or —OC(O)CH₃; oxadiazole substituted with isopropyl, wherein the isopropyl is optionally further substituted with OH or —OC(O)CH₃; oxadiazole, substituted with methyl, ethyl, CD₃, CF₂, or cyclopropyl; or oxadiazole, substituted with ethyl or CF₂, Z is a bond, —NH—, —N(CH₃)—, —O—, —OCH₂—, or —CH₂O—, and B is H; methyl; CD₃; CF₂; phenyl; azetidine, unsubstituted or optionally substituted with methyl, —C(O)CH₃, —C(O)OCH₃, —C(O)OC(CH₃)₃, —C(O)NH₂, —C(O)NHCH₃, or oxo; benzoimidazole substituted with oxo; cyclobutyl; cyclopentyl; cyclopropyl; ethyl, unsubstituted or optionally substituted with methoxy; imidazole, substituted with two methyl; indane, substituted with oxadiazole, further substituted with ethyl; isobutyl, unsubstituted or optionally substituted with methoxy; isopropyl, unsubstituted or optionally substituted with OH; isoxazole, substituted with one or two methyl, or isopropyl; isoxazole, substituted with methyl; methyl, unsubstituted or optionally substituted with CF₂, cyclopropyl, methoxy, oxetane, or azetidine, wherein the azetidine is further substituted with —C(O)CH₃, —C(O)OC(CH₃)₃, —C(O)NH₂, —C(O)NHCH₃, or —C(O)OCH₃; methyl substituted with cyclopropyl, or cyclopropyl substituted with methyl; morpholine, unsubstituted or optionally substituted with —C(O)CH₃ or —C(O)OC(CH₃)₃; oxadiazole, substituted with methyl; oxazole, substituted with one or two methyl, or cyclopropyl; oxetane; piperazine, substituted with methyl; piperidine, unsubstituted or optionally substituted with one or more groups selected from methyl, oxo, —C(O)CH₃, and —C(O)OC(CH₃)₃; pyrazine, unsubstituted or optionally substituted with one or two methyl; pyrazole, unsubstituted or optionally substituted with one or more groups selected from methyl, ethyl, and CF₃; pyrazole, substituted with one or two methyl; pyridazine, unsubstituted or optionally substituted with methyl; pyridine, unsubstituted or optionally substituted with amino, hydroxyl, —NH₂, —OH, or one or more methyl; pyridine substituted with methyl; pyrimidine, unsubstituted or optionally substituted with methyl; pyrrolidine, unsubstituted or optionally substituted with methyl, oxo, —C(O)CH₃ or —C(O)OC(CH₃)₃; pyrrolo pyrazole; tert-butyl; tetrahydrofuran; tetrazole, substituted with methyl; thiazole, unsubstituted or optionally substituted with chloro or methyl; or triazole, substituted with one or more groups selected from methyl and ethyl.

In some embodiments, provided herein are compounds and salts thereof described in Table 1.

TABLE 1

| Cmpd No. | Structure | Name |
|---|---|---|
| 1 | 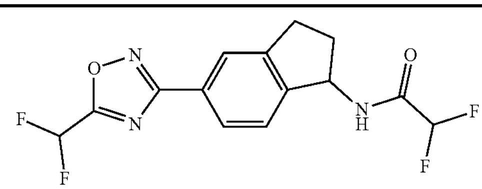 | N-(5-(5-(difluoromethyl)-1,2,4-oxadiazol-3-yl)-2,3-dihydro-1H-inden-1-yl)-2,2-difluoroacetamide |
| 2 | 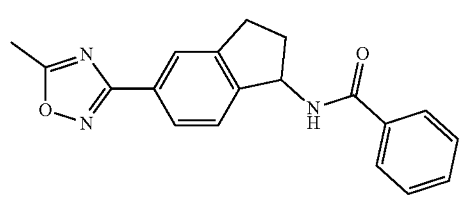 [SMILES: Cc1nc(-c2ccc3c(c2)CCC3NC(=O)c2ccccc2)no1] | N-(5-(5-methyl-1,2,4-oxadiazol-3-yl)-2,3-dihydro-1H-inden-1-yl)benzamide |

TABLE 1-continued

| Cmpd No. | Structure | Name |
|---|---|---|
| 3 | 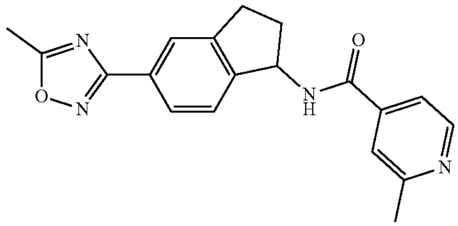 [SMILES: Cc1cc(C(=O)NC2CCc3cc(-c4noc(C)n4)ccc32)ccn1] | 2-methyl-N-(5-(5-methyl-1,2,4-oxadiazol-3-yl)-2,3-dihydro-1H-inden-1-yl)isonicotinamide |
| 4 | 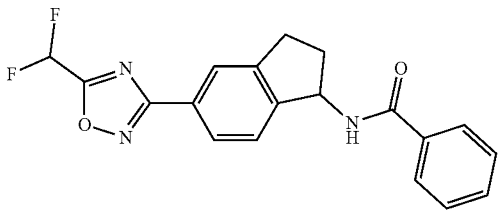 [SMILES: O=C(NC1CCc2cc(-c3noc(C(F)F)n3)ccc21)c1ccccc1] | N-(5-(5-(difluoromethyl)-1,2,4-oxadiazol-3-yl)-2,3-dihydro-1H-inden-1-yl)benzamide |
| 5 | 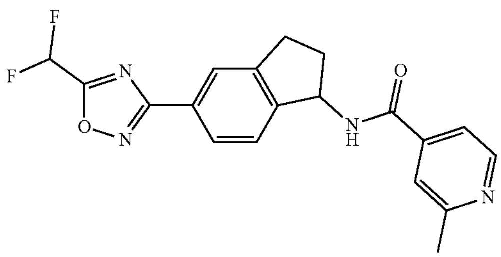 [SMILES: Cc1cc(C(=O)NC2CCc3cc(-c4noc(C(F)F)n4)ccc32)ccn1] | N-(5-(5-(difluoromethyl)-1,2,4-oxadiazol-3-yl)-2,3-dihydro-1H-inden-1-yl)-2-methylisonicotinamide |
| 6 | 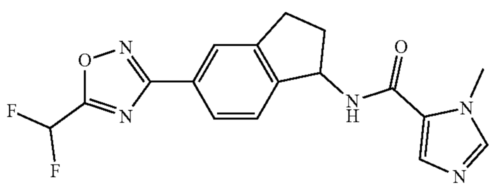 [SMILES: Cn1cncc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-1-methyl-1H-imidazole-5-carboxamide |
| 7 | 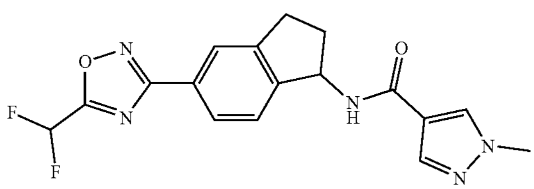 [SMILES: Cn1cc(C(=O)NC2CCc3cc(-c4noc(C(F)F)n4)ccc32)cn1] | N-(5-(5-(difluoromethyl)-1,2,4-oxadiazol-3-yl)-2,3-dihydro-1H-inden-1-yl)-1-methyl-1H-pyrazole-4-carboxamide |
| 8 | 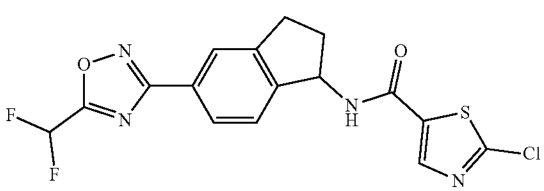 [SMILES: O=C(NC1CCc2cc(-c3noc(C(F)F)n3)ccc21)c1cnc(Cl)s1] | 2-chloro-N-(5-(5-(difluoromethyl)-1,2,4-oxadiazol-3-yl)-2,3-dihydro-1H-inden-1-yl)thiazole-5-carboxamide |
| 9 | 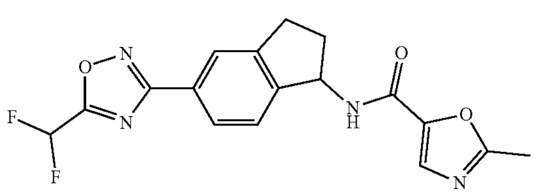 [SMILES: Cc1ncc(C(=O)NC2CCc3cc(-c4noc(C(F)F)n4)ccc32)o1] | N-(5-(5-(difluoromethyl)-1,2,4-oxadiazol-3-yl)-2,3-dihydro-1H-inden-1-yl)-2-methyloxazole-5-carboxamide |

TABLE 1-continued

| Cmpd No. | Structure | Name |
|---|---|---|
| 10 | 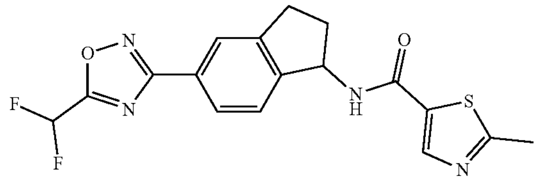 [SMILES: Cc1ncc(C(=O)NC2CCc3cc(-c4noc(C(F)F)n4)ccc32)s1] | N-(5-(5-(difluoromethyl)-1,2,4-oxadiazol-3-yl)-2,3-dihydro-1H-inden-1-yl)-2-methylthiazole-5-carboxamide |
| 11 | 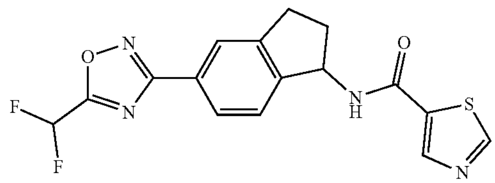 [SMILES: O=C(NC1CCc2cc(-c3noc(C(F)F)n3)ccc21)c1cncs1] | N-(5-(5-(difluoromethyl)-1,2,4-oxadiazol-3-yl)-2,3-dihydro-1H-inden-1-yl)thiazole-5-carboxamide |
| 12 | 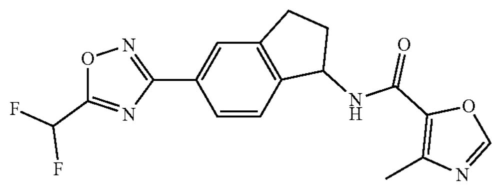 [SMILES: Cc1ncoc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-4-methyloxazole-5-carboxamide |
| 13 | 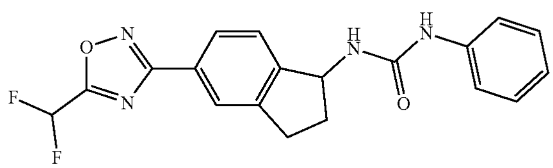 [SMILES: O=C(Nc1ccccc1)NC1CCc2cc(-c3noc(C(F)F)n3)ccc21] | 1-(5-(5-(difluoromethyl)-1,2,4-oxadiazol-3-yl)-2,3-dihydro-1H-inden-1-yl)-3-phenylurea |
| 14 | 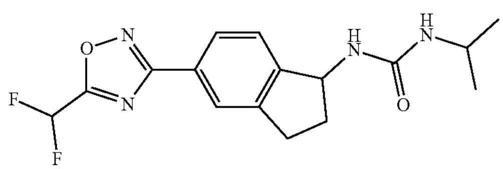 [SMILES: CC(C)NC(=O)NC1CCc2cc(-c3noc(C(F)F)n3)ccc21] | 1-(5-(5-(difluoromethyl)-1,2,4-oxadiazol-3-yl)-2,3-dihydro-1H-inden-1-yl)-3-isopropylurea |
| 15 | 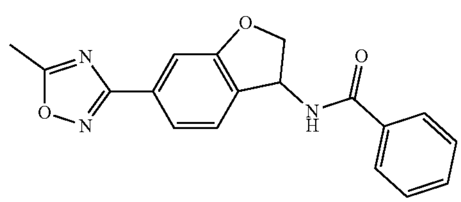 [SMILES: Cc1nc(-c2ccc3c(c2)OCC3NC(=O)c2ccccc2)no1] | N-(6-(5-methyl-1,2,4-oxadiazol-3-yl)-2,3-dihydrobenzofuran-3-yl)benzamide |
| 16 | 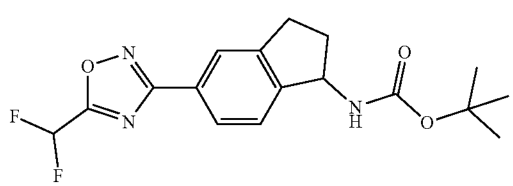 [SMILES: CC(C)(C)OC(=O)NC1CCc2cc(-c3noc(C(F)F)n3)ccc21] | tert-butyl (5-(5-(difluoromethyl)-1,2,4-oxadiazol-3-yl)-2,3-dihydro-1H-inden-1-yl)carbamate |
| 17 | 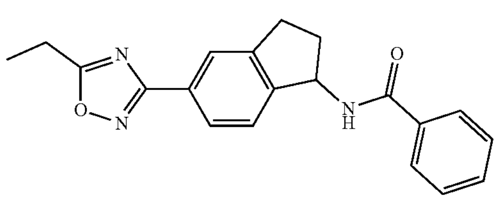 [SMILES: CCc1nc(-c2ccc3c(c2)CCC3NC(=O)c2ccccc2)no1] | N-(3-(5-ethyl-1,2,4-oxadiazol-3-yl)-6,7-dihydro-5H-cyclopenta[b]pyridin-7-yl)benzamide |

TABLE 1-continued

| Cmpd No. | Structure | Name |
| --- | --- | --- |
| 18 | 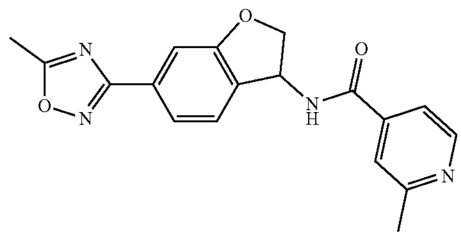 [SMILES: Cc1cc(C(=O)NC2COc3cc(-c4noc(C)n4)ccc32)ccn1] | 2-methyl-N-(6-(5-methyl-1,2,4-oxadiazol-3-yl)-2,3-dihydrobenzofuran-3-yl)isonicotinamide |
| 19 | 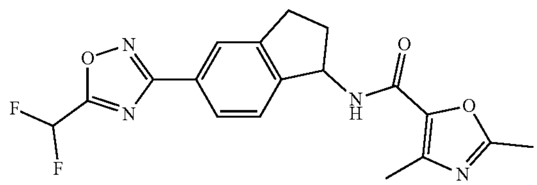 [SMILES: Cc1nc(C)c(C(=O)NC2CCc3cc(-c4noc(C(F)F)n4)ccc32)o1] | N-(5-(5-(difluoromethyl)-1,2,4-oxadiazol-3-yl)-2,3-dihydro-1H-inden-1-yl)-2,4-dimethyloxazole-5-carboxamide |
| 20 | 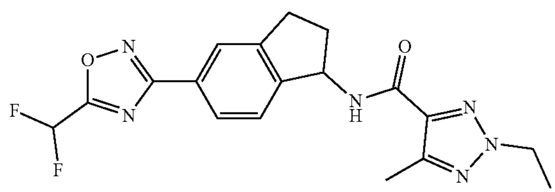 [SMILES: CCn1nc(C)c(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-2-ethyl-5-methyl-2H-1,2,3-triazole-4-carboxamide |
| 21 | 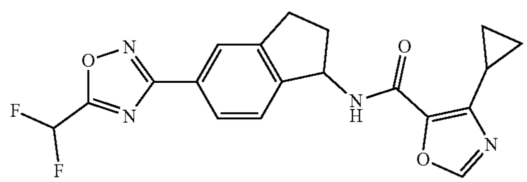 [SMILES: O=C(NC1CCc2cc(-c3noc(C(F)F)n3)ccc21)c1ocnc1C1CC1] | 4-cyclopropyl-N-(5-(5-(difluoromethyl)-1,2,4-oxadiazol-3-yl)-2,3-dihydro-1H-inden-1-yl)oxazole-5-carboxamide |
| 22 | 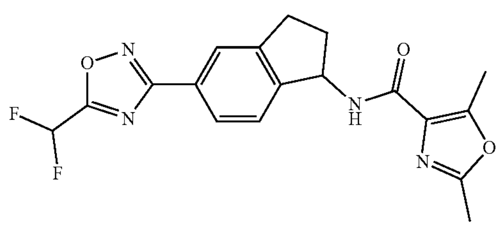 [SMILES: Cc1nc(C(=O)NC2CCc3cc(-c4noc(C(F)F)n4)ccc32)c(C)o1] | N-(5-(5-(difluoromethyl)-1,2,4-oxadiazol-3-yl)-2,3-dihydro-1H-inden-1-yl)-2,5-dimethyloxazole-4-carboxamide |
| 23 | 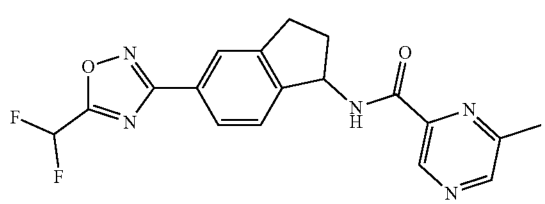 [SMILES: Cc1cncc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-6-methylpyrazine-2-carboxamide |
| 24 | 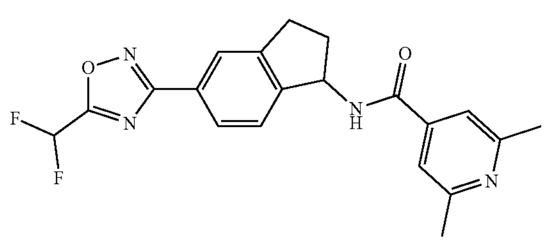 [SMILES: Cc1cc(C(=O)NC2CCc3cc(-c4noc(C(F)F)n4)ccc32)cc(C)n1] | N-(5-(5-(difluoromethyl)-1,2,4-oxadiazol-3-yl)-2,3-dihydro-1H-inden-1-yl)-2,6-dimethylisonicotinamide |

TABLE 1-continued

| Cmpd No. | Structure | Name |
|---|---|---|
| 25 | 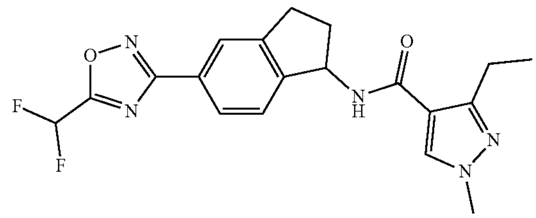 [SMILES: CCc1nn(C)cc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-3-ethyl-1-methyl-1H-pyrazole-4-carboxamide |
| 26 | 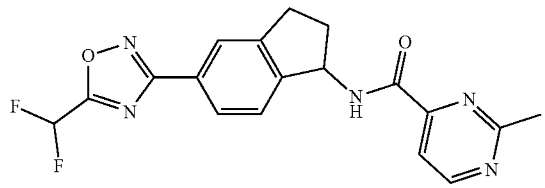 [SMILES: Cc1nccc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-2-methylpyrimidine-4-carboxamide |
| 27 | 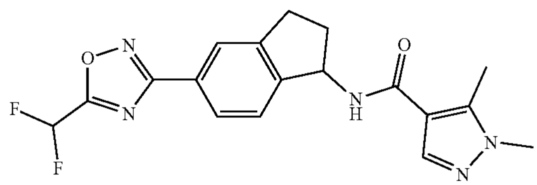 [SMILES: Cc1c(C(=O)NC2CCc3cc(-c4noc(C(F)F)n4)ccc32)cnn1C] | N-(5-(5-(difluoromethyl)-1,2,4-oxadiazol-3-yl)-2,3-dihydro-1H-inden-1-yl)-1,5-dimethyl-1H-pyrazole-4-carboxamide |
| 28 | 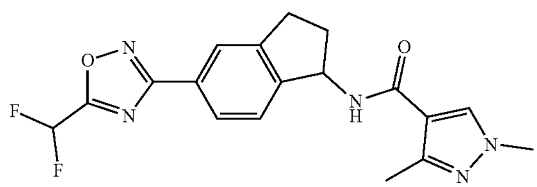 [SMILES: Cc1nn(C)cc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-1,3-dimethyl-1H-pyrazole-4-carboxamide |
| 29 | 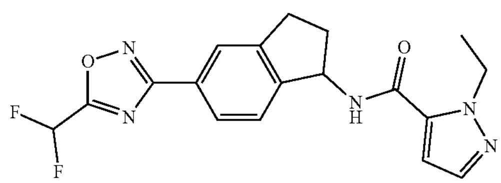 [SMILES: CCn1nccc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-1-ethyl-1H-pyrazole-5-carboxamide |
| 30 | 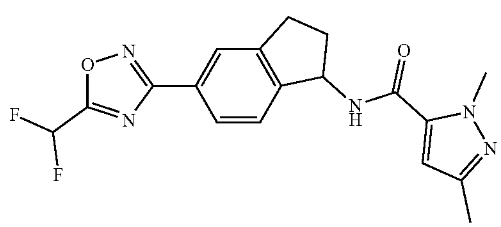 [SMILES: Cc1cc(C(=O)NC2CCc3cc(-c4noc(C(F)F)n4)ccc32)n(C)n1] | N-(5-(5-(difluoromethyl)-1,2,4-oxadiazol-3-yl)-2,3-dihydro-1H-inden-1-yl)-1,3-dimethyl-1H-pyrazole-5-carboxamide |
| 31 | 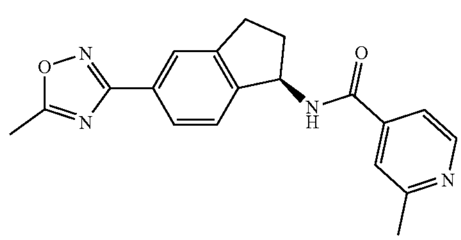 [SMILES: Cc1cc(C(=O)N[C@@H]2CCc3cc(-c4noc(C)n4)ccc32)ccn1] | (R)-2-methyl-N-(5-(5-methyl-1,2,4-oxadiazol-3-yl)-2,3-dihydro-1H-inden-1-yl)isonicotinamide |

TABLE 1-continued

| Cmpd No. | Structure | Name |
|---|---|---|
| 32 | 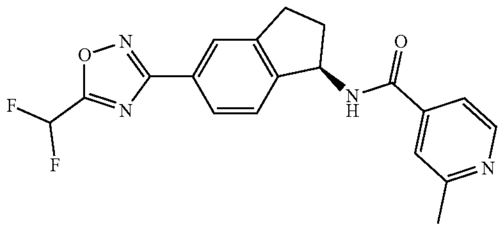 [SMILES: Cc1cc(C(=O)N[C@@H]2CCc3cc(-c4noc(C(F)F)n4)ccc32)ccn1] | (R)-N-(5-(5-(difluoromethyl)-1,2,4-oxadiazol-3-yl)-2,3-dihydro-1H-inden-1-yl)-2-methylisonicotinamide |
| 33 | 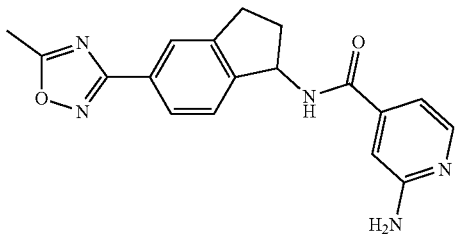 [SMILES: Cc1nc(-c2ccc3c(c2)CCC3NC(=O)c2ccnc(N)c2)no1] | 2-amino-N-(5-(5-methyl-1,2,4-oxadiazol-3-yl)-2,3-dihydro-1H-inden-1-yl)isonicotinamide |
| 34 | 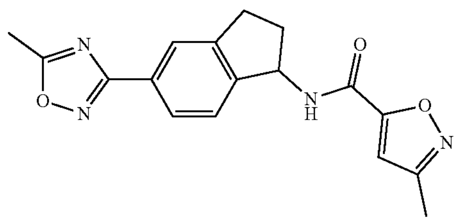 [SMILES: Cc1cc(C(=O)NC2CCc3cc(-c4noc(C)n4)ccc32)on1] | 3-methyl-N-(5-(5-methyl-1,2,4-oxadiazol-3-yl)-2,3-dihydro-1H-inden-1-yl)isoxazole-5-carboxamide |
| 35 | 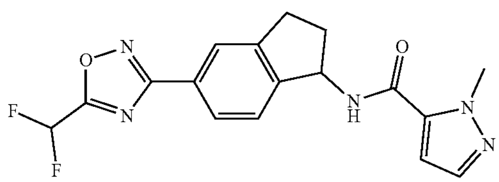 [SMILES: Cn1nccc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-1-methyl-1H-pyrazole-5-carboxamide |
| 36 | 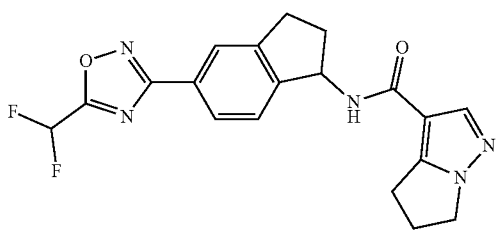 [SMILES: O=C(NC1CCc2cc(-c3noc(C(F)F)n3)ccc21)c1cnn2c1CCC2] | N-(5-(5-(difluoromethyl)-1,2,4-oxadiazol-3-yl)-2,3-dihydro-1H-inden-1-yl)-5,6-dihydro-4H-pyrrolo[1,2-b]pyrazole-3-carboxamide |
| 37 | 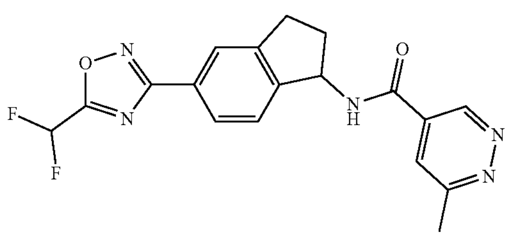 [SMILES: Cc1cc(C(=O)NC2CCc3cc(-c4noc(C(F)F)n4)ccc32)cnn1] | N-(5-(5-(difluoromethyl)-1,2,4-oxadiazol-3-yl)-2,3-dihydro-1H-inden-1-yl)-6-methylpyridazine-4-carboxamide |
| 38 | 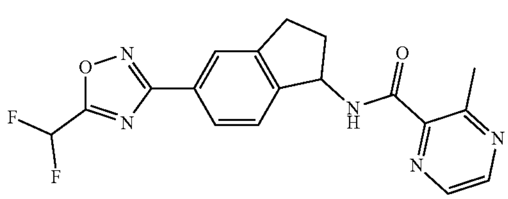 [SMILES: Cc1nccnc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-3-methylpyrazine-2-carboxamide |

TABLE 1-continued

| Cmpd No. | Structure | Name |
|---|---|---|
| 39 | 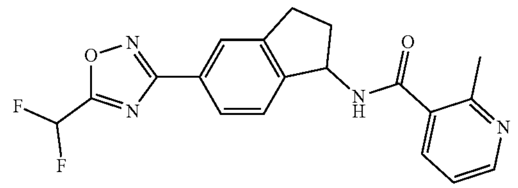 [SMILES: Cc1ncccc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-2-methylnicotinamide |
| 40 | 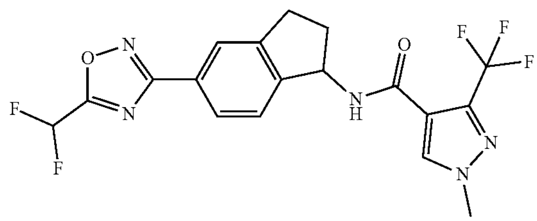 [SMILES: Cn1cc(C(=O)NC2CCc3cc(-c4noc(C(F)F)n4)ccc32)c(C(F)(F)F)n1] | N-(5-(5-(difluoromethyl)-1,2,4-oxadiazol-3-yl)-2,3-dihydro-1H-inden-1-yl)-1-methyl-3-(trifluoromethyl)-1H-pyrazole-4-carboxamide |
| 41 | 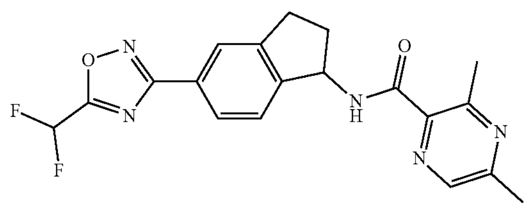 [SMILES: Cc1cnc(C(=O)NC2CCc3cc(-c4noc(C(F)F)n4)ccc32)c(C)n1] | N-(5-(5-(difluoromethyl)-1,2,4-oxadiazol-3-yl)-2,3-dihydro-1H-inden-1-yl)-3,5-dimethylpyrazine-2-carboxamide |
| 42 | 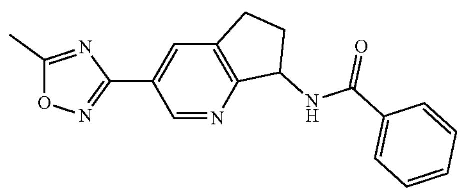 [SMILES: Cc1nc(-c2cnc3c(c2)CCC3NC(=O)c2ccccc2)no1] | N-(3-(5-methyl-1,2,4-oxadiazol-3-yl)-6,7-dihydro-5H-cyclopenta[b]pyridin-7-yl)benzamide |
| 43 | 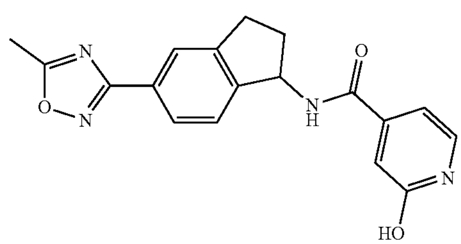 [SMILES: Cc1nc(-c2ccc3c(c2)CCC3NC(=O)c2ccnc(O)c2)no1] | 2-hydroxy-N-(5-(5-methyl-1,2,4-oxadiazol-3-yl)-2,3-dihydro-1H-inden-1-yl)isonicotinamide |
| 44 | 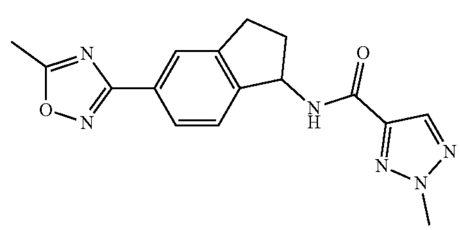 [SMILES: Cc1nc(-c2ccc3c(c2)CCC3NC(=O)c2cnn(C)n2)no1] | 2-methyl-N-(5-(5-methyl-1,2,4-oxadiazol-3-yl)-2,3-dihydro-1H-inden-1-yl)-2H-1,2,3-triazole-4-carboxamide |
| 45 | 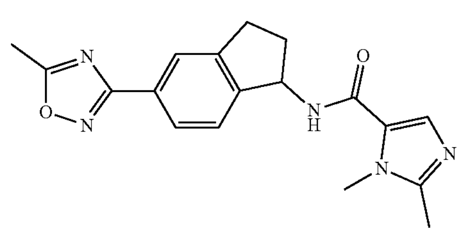 [SMILES: Cc1nc(-c2ccc3c(c2)CCC3NC(=O)c2cnc(C)n2C)no1] | 1,2-dimethyl-N-(5-(5-methyl-1,2,4-oxadiazol-3-yl)-2,3-dihydro-1H-inden-1-yl)-1H-imidazole-5-carboxamide |

TABLE 1-continued

| Cmpd No. | Structure | Name |
|---|---|---|
| 46 | 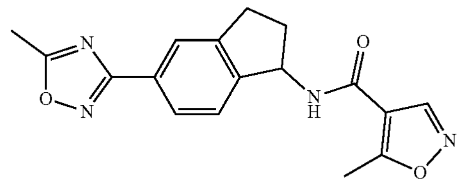 [SMILES: Cc1nc(-c2ccc3c(c2)CCC3NC(=O)c2cnoc2C)no1] | 5-methyl-N-(5-(5-methyl-1,2,4-oxadiazol-3-yl)-2,3-dihydro-1H-inden-1-yl)isoxazole-4-carboxamide |
| 47 | 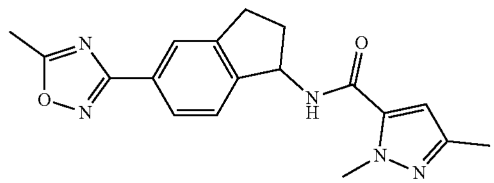 | 1,3-dimethyl-N-(5-(5-methyl-1,2,4-oxadiazol-3-yl)-2,3-dihydro-1H-inden-1-yl)-1H-pyrazole-5-carboxamide |
| 48 | 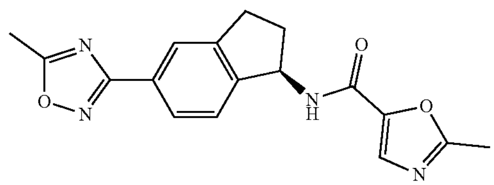 | (R)-2-methyl-N-(5-(5-methyl-1,2,4-oxadiazol-3-yl)-2,3-dihydro-1H-inden-1-yl)oxazole-5-carboxamide |
| 49 | 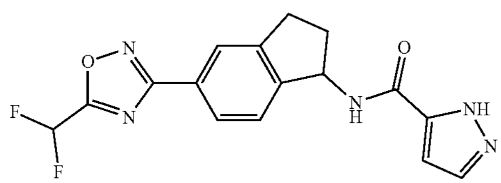 [SMILES: O=C(NC1CCc2cc(-c3noc(C(F)F)n3)ccc21)c1ccn[nH]1] | N-(5-(5-(difluoromethyl)-1,2,4-oxadiazol-3-yl)-2,3-dihydro-1H-inden-1-yl)-1H-pyrazole-5-carboxamide |
| 50 | 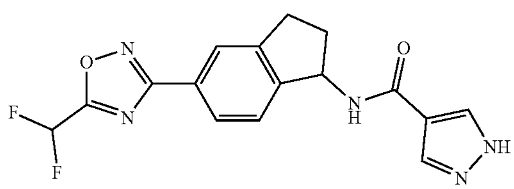 [SMILES: O=C(NC1CCc2cc(-c3noc(C(F)F)n3)ccc21)c1cn[nH]c1] | N-(5-(5-(difluoromethyl)-1,2,4-oxadiazol-3-yl)-2,3-dihydro-1H-inden-1-yl)-1H-pyrazole-4-carboxamide |
| 51 | 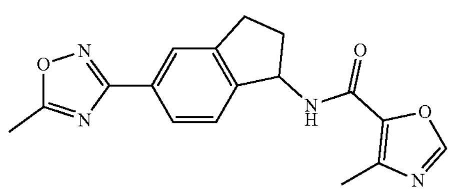 [SMILES: Cc1nc(-c2ccc3c(c2)CCC3NC(=O)c2ocnc2C)no1] | 4-methyl-N-(5-(5-methyl-1,2,4-oxadiazol-3-yl)-2,3-dihydro-1H-inden-1-yl)oxazole-5-carboxamide |
| 52 | 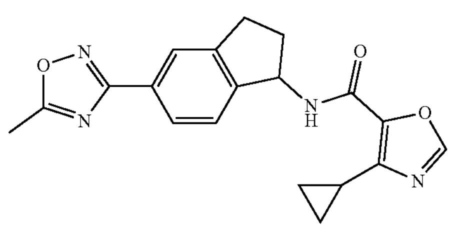 [SMILES: Cc1nc(-c2ccc3c(c2)CCC3NC(=O)c2ocnc2C2CC2)no1] | 4-cyclopropyl-N-(5-(5-methyl-1,2,4-oxadiazol-3-yl)-2,3-dihydro-1H-inden-1-yl)oxazole-5-carboxamide |
| 53 | 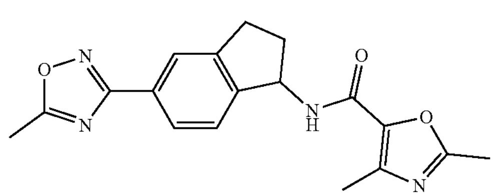 | 2,4-dimethyl-N-(5-(5-methyl-1,2,4-oxadiazol-3-yl)-2,3-dihydro-1H-inden-1-yl)oxazole-5-carboxamide |

TABLE 1-continued

| Cmpd No. | Structure | Name |
|---|---|---|
| 54 | 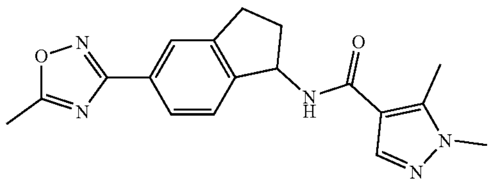 | 1,5-dimethyl-N-(5-(5-methyl-1,2,4-oxadiazol-3-yl)-2,3-dihydro-1H-inden-1-yl)-1H-pyrazole-4-carboxamide |
| 55 | 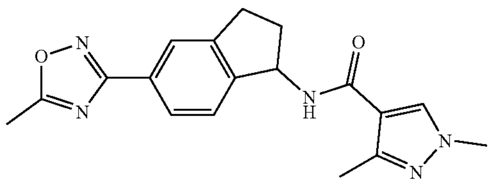 | 1,3-dimethyl-N-(5-(5-methyl-1,2,4-oxadiazol-3-yl)-2,3-dihydro-1H-inden-1-yl)-1H-pyrazole-4-carboxamide |
| 56 | 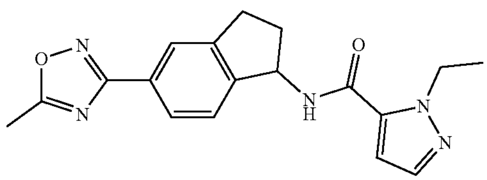 [SMILES: CCn1nccc1C(=O)NC1CCc2cc(-c3noc(C)n3)ccc21] | 1-ethyl-N-(5-(5-methyl-1,2,4-oxadiazol-3-yl)-2,3-dihydro-1H-inden-1-yl)-1H-pyrazole-5-carboxamide |
| 57 | 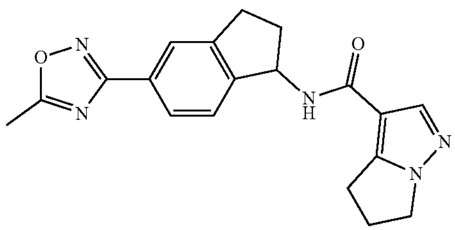 [SMILES: Cc1nc(-c2ccc3c(c2)CCC3NC(=O)c2cnn3c2CCC3)no1] | N-(5-(5-methyl-1,2,4-oxadiazol-3-yl)-2,3-dihydro-1H-inden-1-yl)-5,6-dihydro-4H-pyrrolo[1,2-b]pyrazole-3-carboxamide |
| 58 | 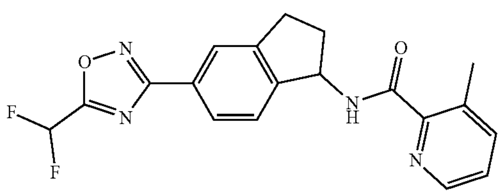 [SMILES: Cc1cccnc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-3-methylpicolinamide |
| 59 | 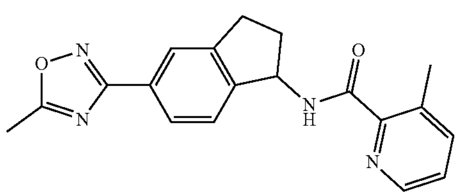 [SMILES: Cc1nc(-c2ccc3c(c2)CCC3NC(=O)c2ncccc2C)no1] | 3-methyl-N-(5-(5-methyl-1,2,4-oxadiazol-3-yl)-2,3-dihydro-1H-inden-1-yl)picolinamide |
| 60 | 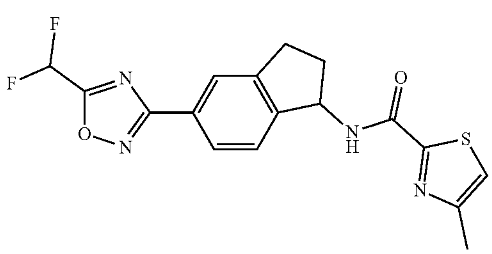 [SMILES: Cc1csc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-4-methylthiazole-2-carboxamide |

TABLE 1-continued

| Cmpd No. | Structure | Name |
|---|---|---|
| 61 | 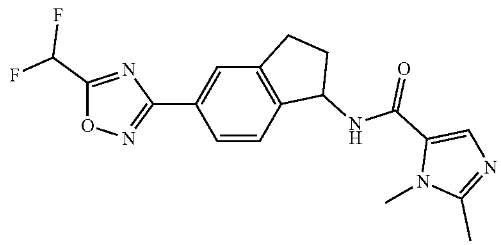 [SMILES: Cc1ncc(C(=O)NC2CCc3cc(-c4noc(C(F)F)n4)ccc32)n1C] | N-(5-(5-(difluoromethyl)-1,2,4-oxadiazol-3-yl)-2,3-dihydro-1H-inden-1-yl)-1,2-dimethyl-1H-imidazole-5-carboxamide |
| 62 | 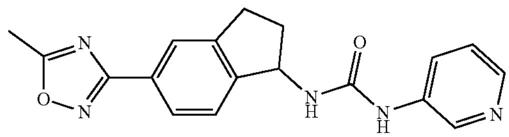 [SMILES: Cc1nc(-c2ccc3c(c2)CCC3NC(=O)Nc2cccnc2)no1] | 1-(5-(5-methyl-1,2,4-oxadiazol-3-yl)-2,3-dihydro-1H-inden-1-yl)-3-(pyridin-3-yl)urea |
| 63 | 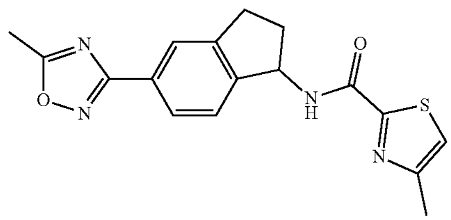 [SMILES: Cc1csc(C(=O)NC2CCc3cc(-c4noc(C)n4)ccc32)n1] | 4-methyl-N-(5-(5-methyl-1,2,4-oxadiazol-3-yl)-2,3-dihydro-1H-inden-1-yl)thiazole-2-carboxamide |
| 64 | 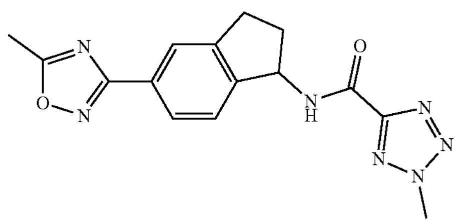 [SMILES: Cc1nc(-c2ccc3c(c2)CCC3NC(=O)c2nnn(C)n2)no1] | 2-methyl-N-(5-(5-methyl-1,2,4-oxadiazol-3-yl)-2,3-dihydro-1H-inden-1-yl)-2H-tetrazole-5-carboxamide |
| 65 | 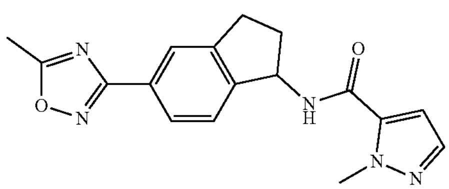 [SMILES: Cc1nc(-c2ccc3c(c2)CCC3NC(=O)c2ccnn2C)no1] | 1-methyl-N-(5-(5-methyl-1,2,4-oxadiazol-3-yl)-2,3-dihydro-1H-inden-1-yl)-1H-pyrazole-5-carboxamide |
| 66 | 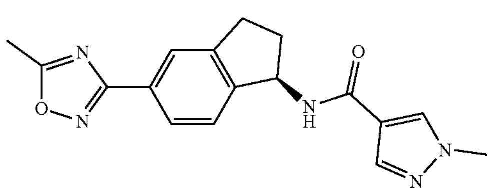 | (R)-1-methyl-N-(5-(5-methyl-1,2,4-oxadiazol-3-yl)-2,3-dihydro-1H-inden-1-yl)-1H-pyrazole-4-carboxamide |
| 67 | 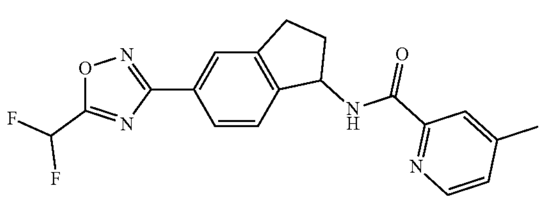 [SMILES: Cc1ccnc(C(=O)NC2CCc3cc(-c4noc(C(F)F)n4)ccc32)c1] | N-(5-(5-(difluoromethyl)-1,2,4-oxadiazol-3-yl)-2,3-dihydro-1H-inden-1-yl)-4-methylpicolinamide |

TABLE 1-continued

| Cmpd No. | Name |
|---|---|
| 68 | 4-methyl-N-(5-(5-methyl-1,2,4-oxadiazol-3-yl)-2,3-dihydro-1H-inden-1-yl)picolinamide |
| 69 | N-(5-(5-(difluoromethyl)-1,2,4-oxadiazol-3-yl)-2,3-dihydro-1H-inden-1-yl)-3-methyl-1H-pyrazole-4-carboxamide |
| 70 | 3-methyl-N-(5-(5-methyl-1,2,4-oxadiazol-3-yl)-2,3-dihydro-1H-inden-1-yl)-1H-pyrazole-4-carboxamide |
| 71 | (R)-N-(5-(5-(difluoromethyl)-1,2,4-oxadiazol-3-yl)-2,3-dihydro-1H-inden-1-yl)-3-methyl-1H-pyrazole-4-carboxamide |
| 72 | (R)-N-(5-(5-(difluoromethyl)-1,2,4-oxadiazol-3-yl)-2,3-dihydro-1H-inden-1-yl)-5-methylisoxazole-4-carboxamide |
| 73 | N-(5-(5-cyclopropyl-1,2,4-oxadiazol-3-yl)-2,3-dihydro-1H-inden-1-yl)-1,3-dimethyl-1H-pyrazole-4-carboxamide |
| 74 | (3-(1-(1,3-dimethyl-1H-pyrazole-4-carboxamido)-2,3-dihydro-1H-inden-5-yl)-1,2,4-oxadiazol-5-yl)methyl acetate |

TABLE 1-continued

| Cmpd No. | Structure | Name |
|---|---|---|
| 75 | 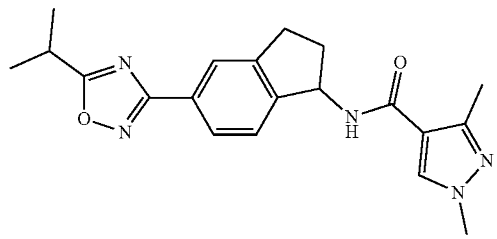 [SMILES: Cc1nn(C)cc1C(=O)NC1CCc2cc(-c3noc(C(C)C)n3)ccc21] | N-(5-(5-isopropyl-1,2,4-oxadiazol-3-yl)-2,3-dihydro-1H-inden-1-yl)-1,3-dimethyl-1H-pyrazole-4-carboxamide |
| 76 | 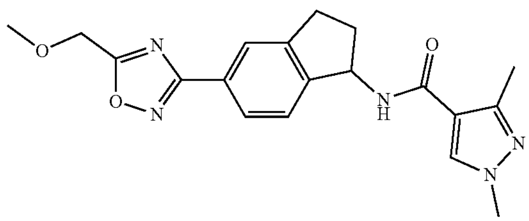 [SMILES: COCc1nc(-c2ccc3c(c2)CCC3NC(=O)c2cn(C)nc2C)no1] | N-(5-(5-(methoxymethyl)-1,2,4-oxadiazol-3-yl)-2,3-dihydro-1H-inden-1-yl)-1,3-dimethyl-1H-pyrazole-4-carboxamide |
| 77 | 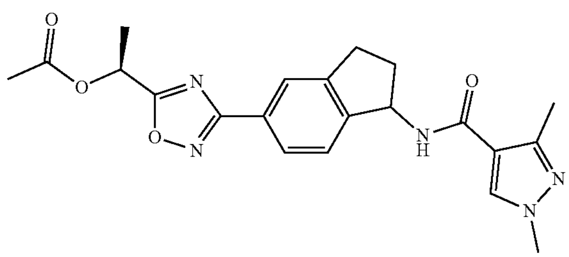 [SMILES: CC(=O)O[C@@H](C)c1nc(-c2ccc3c(c2)CCC3NC(=O)c2cn(C)nc2C)no1] | (1S)-1-(3-(1-(1,3-dimethyl-1H-pyrazole-4-carboxamido)-2,3-dihydro-1H-inden-5-yl)-1,2,4-oxadiazol-5-yl)ethyl acetate |
| 78 | 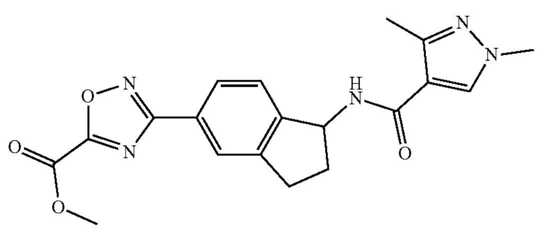 [SMILES: COC(=O)c1nc(-c2ccc3c(c2)CCC3NC(=O)c2cn(C)nc2C)no1] | methyl 3-(1-(1,3-dimethyl-1H-pyrazole-4-carboxamido)-2,3-dihydro-1H-inden-5-yl)-1,2,4-oxadiazole-5-carboxylate |
| 79 | 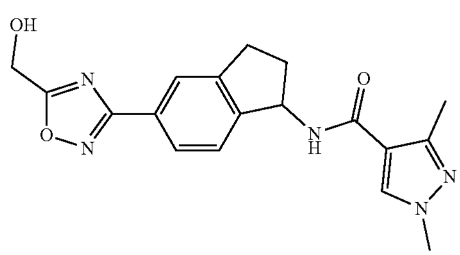 [SMILES: Cc1nn(C)cc1C(=O)NC1CCc2cc(-c3noc(CO)n3)ccc21] | N-(5-(5-(hydroxymethyl)-1,2,4-oxadiazol-3-yl)-2,3-dihydro-1H-inden-1-yl)-1,3-dimethyl-1H-pyrazole-4-carboxamide |
| 80 | 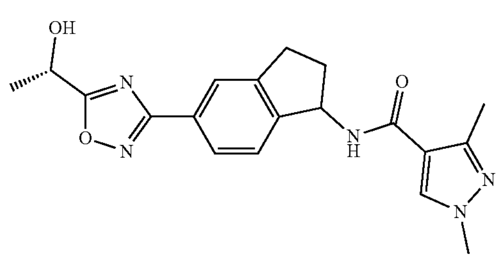 [SMILES: Cc1nn(C)cc1C(=O)NC1CCc2cc(-c3noc([C@H](C)O)n3)ccc21] | N-(5-(5-((S)-1-hydroxyethyl)-1,2,4-oxadiazol-3-yl)-2,3-dihydro-1H-inden-1-yl)-1,3-dimethyl-1H-pyrazole-4-carboxamide |

TABLE 1-continued

| Cmpd No. | Structure | Name |
|---|---|---|
| 81 | 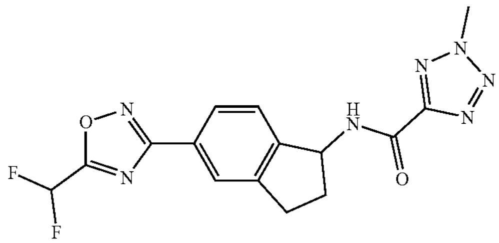 | N-(5-(5-(difluoromethyl)-1,2,4-oxadiazol-3-yl)-2,3-dihydro-1H-inden-1-yl)-2-methyl-2H-tetrazole-5-carboxamide |
| 82 | 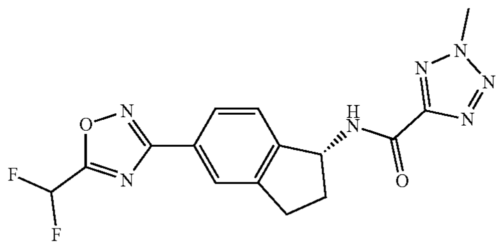 [SMILES: Cn1nnc(C(=O)N[C@@H]2CCc3cc(-c4noc(C(F)F)n4)ccc32)n1] | (R)-N-(5-(5-(difluoromethyl)-1,2,4-oxadiazol-3-yl)-2,3-dihydro-1H-inden-1-yl)-2-methyl-2H-tetrazole-5-carboxamide |
| 83 | 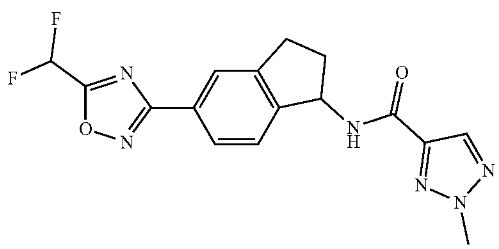 [SMILES: Cn1ncc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-2-methyl-2H-1,2,3-triazole-4-carboxamide |
| 84 | 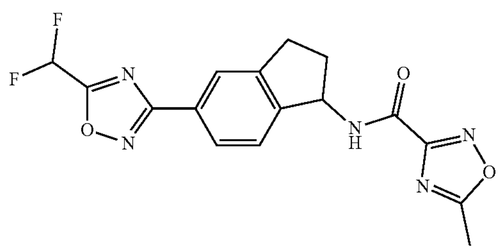 [SMILES: Cc1nc(C(=O)NC2CCc3cc(-c4noc(C(F)F)n4)ccc32)no1] | N-(5-(5-(difluoromethyl)-1,2,4-oxadiazol-3-yl)-2,3-dihydro-1H-inden-1-yl)-5-methyl-1,2,4-oxadiazole-3-carboxamide |
| 85 | 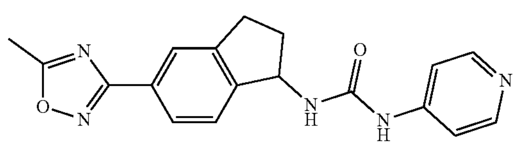 [SMILES: Cc1nc(-c2ccc3c(c2)CCC3NC(=O)Nc2ccncc2)no1] | 1-(5-(5-methyl-1,2,4-oxadiazol-3-yl)-2,3-dihydro-1H-inden-1-yl)-3-(pyridin-4-yl)urea |
| 86 | 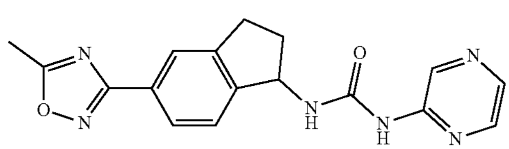 [SMILES: Cc1nc(-c2ccc3c(c2)CCC3NC(=O)Nc2cnccn2)no1] | 1-(5-(5-methyl-1,2,4-oxadiazol-3-yl)-2,3-dihydro-1H-inden-1-yl)-3-(pyrazin-2-yl)urea |
| 87 | 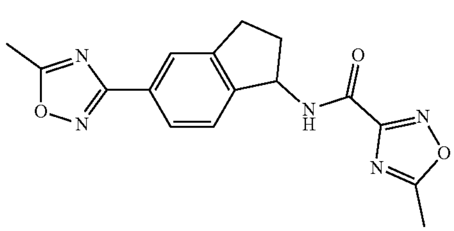 [SMILES: Cc1nc(C(=O)NC2CCc3cc(-c4noc(C)n4)ccc32)no1] | 5-methyl-N-(5-(5-methyl-1,2,4-oxadiazol-3-yl)-2,3-dihydro-1H-inden-1-yl)-1,2,4-oxadiazole-3-carboxamide |

TABLE 1-continued

| Cmpd No. | Structure | Name |
|---|---|---|
| 88 | 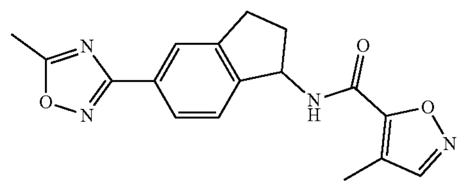 [SMILES: Cc1nc(-c2ccc3c(c2)CCC3NC(=O)c2oncc2C)no1] | 4-methyl-N-(5-(5-methyl-1,2,4-oxadiazol-3-yl)-2,3-dihydro-1H-inden-1-yl)isoxazole-5-carboxamide |
| 89 | 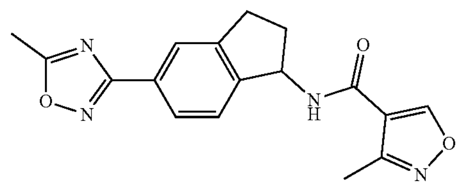 [SMILES: Cc1nc(-c2ccc3c(c2)CCC3NC(=O)c2conc2C)no1] | 3-methyl-N-(5-(5-methyl-1,2,4-oxadiazol-3-yl)-2,3-dihydro-1H-inden-1-yl)isoxazole-4-carboxamide |
| 90 | 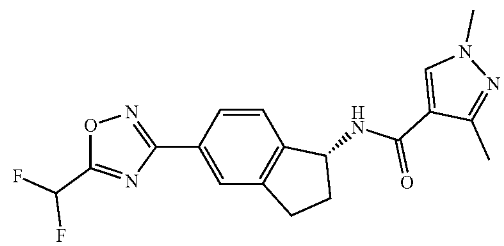 [SMILES: Cc1nn(C)cc1C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-1,3-dimethyl-1H-pyrazole-4-carboxamide |
| 91 | 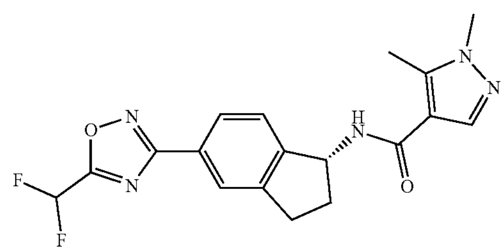 [SMILES: Cc1c(C(=O)N[C@@H]2CCc3cc(-c4noc(C(F)F)n4)ccc32)cnn1C] | (R)-N-(5-(5-(difluoromethyl)-1,2,4-oxadiazol-3-yl)-2,3-dihydro-1H-inden-1-yl)-1,5-dimethyl-1H-pyrazole-4-carboxamide |
| 92 | 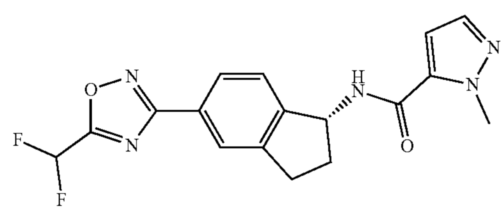 [SMILES: Cn1nccc1C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-1-methyl-1H-pyrazole-5-carboxamide |
| 93 | 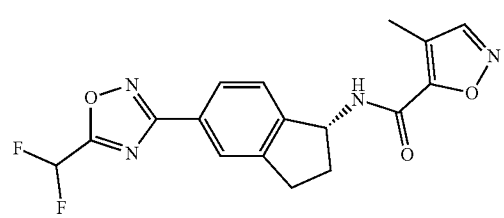 [SMILES: Cc1cnoc1C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-4-methylisoxazole-5-carboxamide |
| 94 | 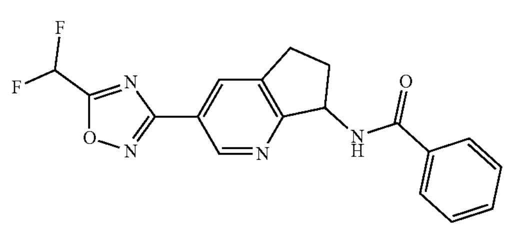 [SMILES: O=C(NC1CCc2cc(-c3noc(C(F)F)n3)cnc21)c1ccccc1] | N-(3-(5-(difluoromethyl)-1,2,4-oxadiazol-3-yl)-6,7-dihydro-5H-cyclopenta[b]pyridin-7-yl)benzamide |

TABLE 1-continued

| Cmpd No. | Structure | Name |
|---|---|---|
| 95 | 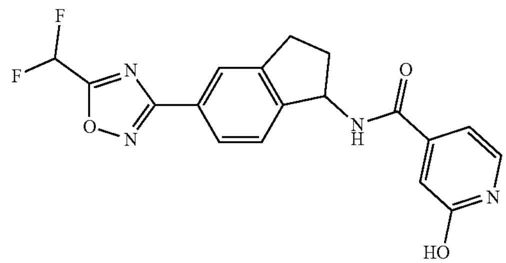 [SMILES: O=C(NC1CCc2cc(-c3noc(C(F)F)n3)ccc21)c1ccnc(O)c1] | N-(5-(5-(difluoromethyl)-1,2,4-oxadiazol-3-yl)-2,3-dihydro-1H-inden-1-yl)-2-hydroxyisonicotinamide |
| 96 | 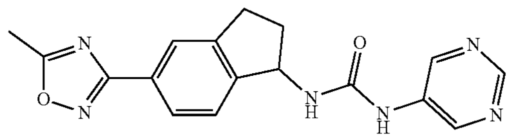 [SMILES: Cc1nc(-c2ccc3c(c2)CCC3NC(=O)Nc2cncnc2)no1] | 1-(5-(5-methyl-1,2,4-oxadiazol-3-yl)-2,3-dihydro-1H-inden-1-yl)-3-(pyrimidin-5-yl)urea |
| 97 | 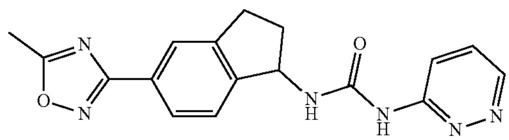 [SMILES: Cc1nc(-c2ccc3c(c2)CCC3NC(=O)Nc2cccnn2)no1] | 1-(5-(5-methyl-1,2,4-oxadiazol-3-yl)-2,3-dihydro-1H-inden-1-yl)-3-(pyridazin-3-yl)urea |
| 98 | 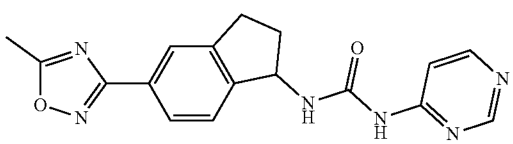 [SMILES: Cc1nc(-c2ccc3c(c2)CCC3NC(=O)Nc2ccncn2)no1] | 1-(5-(5-methyl-1,2,4-oxadiazol-3-yl)-2,3-dihydro-1H-inden-1-yl)-3-(pyrimidin-4-yl)urea |
| 99 | 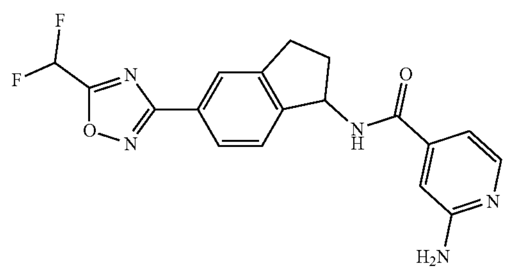 [SMILES: Nc1cc(C(=O)NC2CCc3cc(-c4noc(C(F)F)n4)ccc32)ccn1] | 2-amino-N-(5-(5-(difluoromethyl)-1,2,4-oxadiazol-3-yl)-2,3-dihydro-1H-inden-1-yl)isonicotinamide |
| 100 | 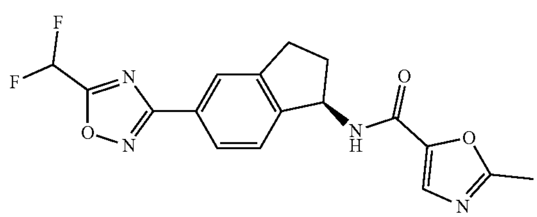 [SMILES: Cc1ncc(C(=O)N[C@@H]2CCc3cc(-c4noc(C(F)F)n4)ccc32)o1] | (R)-N-(5-(5-(difluoromethyl)-1,2,4-oxadiazol-3-yl)-2,3-dihydro-1H-inden-1-yl)-2-methyloxazole-5-carboxamide |
| 101 | 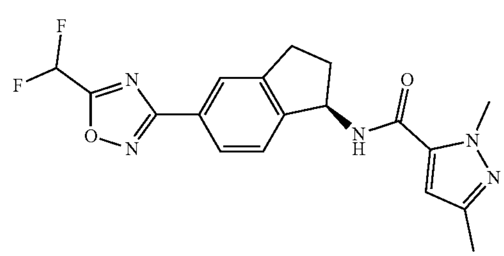 [SMILES: Cc1cc(C(=O)N[C@@H]2CCc3cc(-c4noc(C(F)F)n4)ccc32)n(C)n1] | (R)-N-(5-(5-(difluoromethyl)-1,2,4-oxadiazol-3-yl)-2,3-dihydro-1H-inden-1-yl)-1,3-dimethyl-1H-pyrazole-5-carboxamide |

TABLE 1-continued

| Cmpd No. | Structure | Name |
|---|---|---|
| 102 | 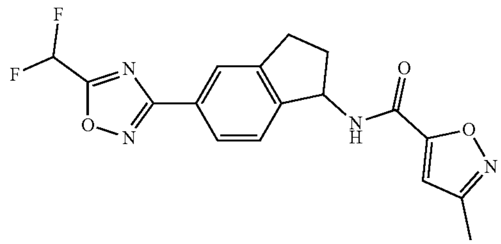 [SMILES: Cc1cc(C(=O)NC2CCc3cc(-c4noc(C(F)F)n4)ccc32)on1] | N-(5-(5-(difluoromethyl)-1,2,4-oxadiazol-3-yl)-2,3-dihydro-1H-inden-1-yl)-3-methylisoxazole-5-carboxamide |
| 103 | 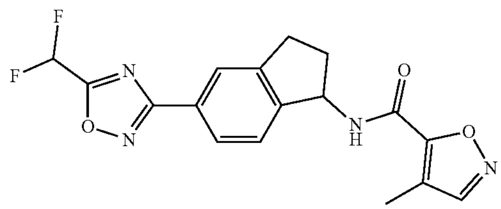 [SMILES: Cc1cnoc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-4-methylisoxazole-5-carboxamide |
| 104 | 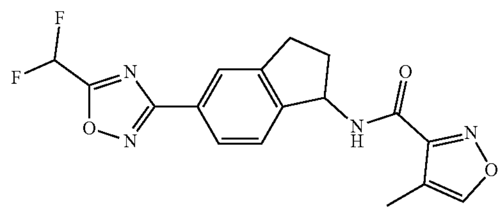 [SMILES: Cc1conc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-4-methylisoxazole-3-carboxamide |
| 105 | 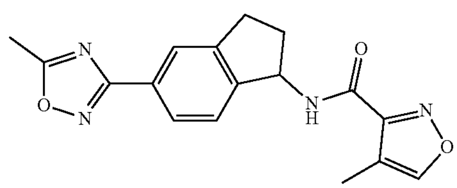 [SMILES: Cc1nc(-c2ccc3c(c2)CCC3NC(=O)c2nocc2C)no1] | 4-methyl-N-(5-(5-methyl-1,2,4-oxadiazol-3-yl)-2,3-dihydro-1H-inden-1-yl)isoxazole-3-carboxamide |
| 106 | 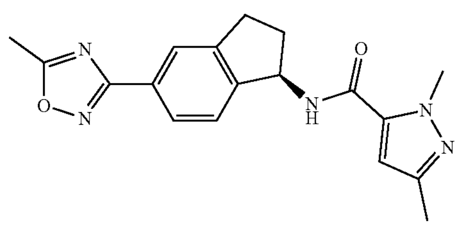 [SMILES: Cc1cc(C(=O)N[C@@H]2CCc3cc(-c4noc(C)n4)ccc32)n(C)n1] | (R)-1,3-dimethyl-N-(5-(5-methyl-1,2,4-oxadiazol-3-yl)-2,3-dihydro-1H-inden-1-yl)-1H-pyrazole-5-carboxamide |
| 107 | 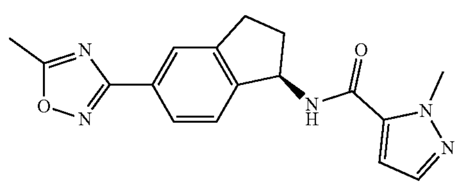 [SMILES: Cc1nc(-c2ccc3c(c2)CC[C@H]3NC(=O)c2ccnn2C)no1] | (R)-1-methyl-N-(5-(5-methyl-1,2,4-oxadiazol-3-yl)-2,3-dihydro-1H-inden-1-yl)-1H-pyrazole-5-carboxamide |
| 108 | 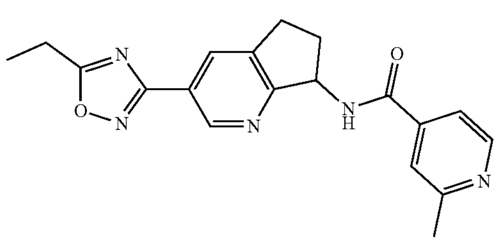 [SMILES: CCc1nc(-c2cnc3c(c2)CCC3NC(=O)c2ccnc(C)c2)no1] | N-(3-(5-ethyl-1,2,4-oxadiazol-3-yl)-6,7-dihydro-5H-cyclopenta[b]pyridin-7-yl)-2-methylisonicotinamide |

TABLE 1-continued

| Cmpd No. | Name |
|---|---|
| 109 | 1-(5-(5-methyl-1,2,4-oxadiazol-3-yl)-2,3-dihydro-1H-inden-1-yl)-3-(pyridin-2-yl)urea |
| 110 | 1-(5-(5-methyl-1,2,4-oxadiazol-3-yl)-2,3-dihydro-1H-inden-1-yl)-3-(pyrimidin-2-yl)urea |
| 111 | (R)-1,3-dimethyl-N-(5-(5-methyl-1,2,4-oxadiazol-3-yl)-2,3-dihydro-1H-inden-1-yl)-1H-pyrazole-4-carboxamide |
| 112 | (R)-2,4-dimethyl-N-(5-(5-methyl-1,2,4-oxadiazol-3-yl)-2,3-dihydro-1H-inden-1-yl)oxazole-5-carboxamide |
| 113 | (R)-4-methyl-N-(5-(5-methyl-1,2,4-oxadiazol-3-yl)-2,3-dihydro-1H-inden-1-yl)isoxazole-5-carboxamide |
| 114 | (R)-N-(5-(5-(methoxymethyl)-1,2,4-oxadiazol-3-yl)-2,3-dihydro-1H-inden-1-yl)-4-methylisoxazole-5-carboxamide |
| 115 | (R)-N-(5-(5-cyclopropyl-1,2,4-oxadiazol-3-yl)-2,3-dihydro-1H-inden-1-yl)-4-methylisoxazole-5-carboxamide |
| 116 | (R)-N-(5-(5-isopropyl-1,2,4-oxadiazol-3-yl)-2,3-dihydro-1H-inden-1-yl)-4-methylisoxazole-5-carboxamide |

TABLE 1-continued

| Cmpd No. | Structure | Name |
|---|---|---|
| 117 | 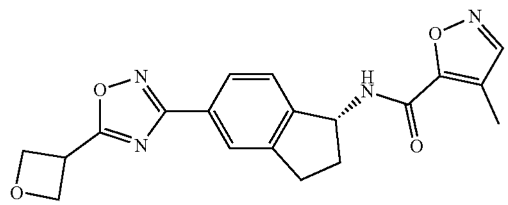 [SMILES: Cc1cnoc1C(=O)N[C@@H]1CCc2cc(-c3noc(C4COC4)n3)ccc21] | (R)-4-methyl-N-(5-(5-(oxetan-3-yl)-1,2,4-oxadiazol-3-yl)-2,3-dihydro-1H-inden-1-yl)isoxazole-5-carboxamide |
| 118 | 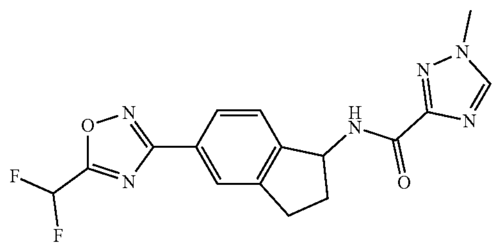 [SMILES: Cn1cnc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-1-methyl-1H-1,2,4-triazole-3-carboxamide |
| 119 | 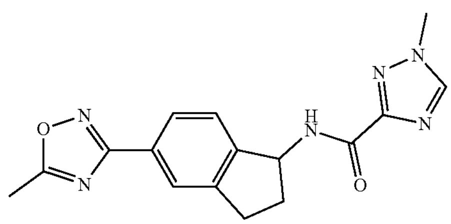 [SMILES: Cc1nc(-c2ccc3c(c2)CCC3NC(=O)c2ncn(C)n2)no1] | 1-methyl-N-(5-(5-methyl-1,2,4-oxadiazol-3-yl)-2,3-dihydro-1H-inden-1-yl)-1H-1,2,4-triazole-3-carboxamide |
| 120 | 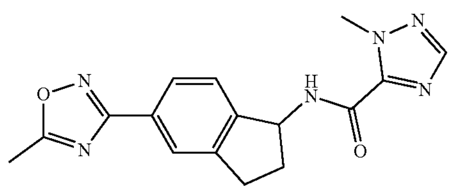 [SMILES: Cc1nc(-c2ccc3c(c2)CCC3NC(=O)c2ncnn2C)no1] | 1-methyl-N-(5-(5-methyl-1,2,4-oxadiazol-3-yl)-2,3-dihydro-1H-inden-1-yl)-1H-1,2,4-triazole-5-carboxamide |
| 121 | 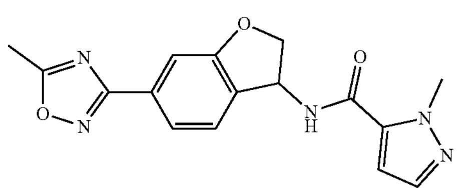 [SMILES: Cc1nc(-c2ccc3c(c2)OCC3NC(=O)c2ccnn2C)no1] | 1-methyl-N-(6-(5-methyl-1,2,4-oxadiazol-3-yl)-2,3-dihydrobenzofuran-3-yl)-1H-pyrazole-5-carboxamide |
| 122 | 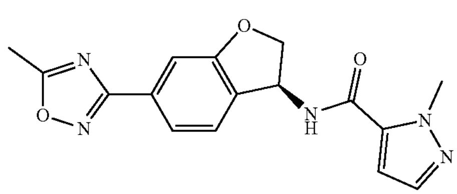 [SMILES: Cc1nc(-c2ccc3c(c2)OC[C@H]3NC(=O)c2ccnn2C)no1] | (S)-1-methyl-N-(6-(5-methyl-1,2,4-oxadiazol-3-yl)-2,3-dihydrobenzofuran-3-yl)-1H-pyrazole-5-carboxamide |
| 123 | 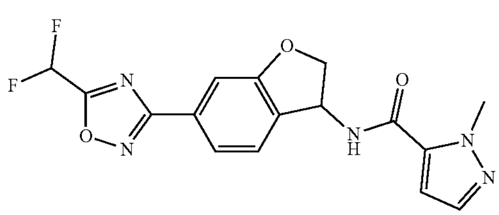 [SMILES: Cn1nccc1C(=O)NC1COc2cc(-c3noc(C(F)F)n3)ccc21] | N-(6-(5-(difluoromethyl)-1,2,4-oxadiazol-3-yl)-2,3-dihydrobenzofuran-3-yl)-1-methyl-1H-pyrazole-5-carboxamide |

| Cmpd No. | Structure | Name |
|---|---|---|
| 124 | 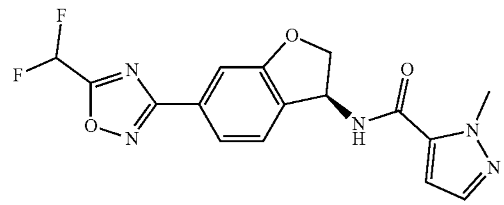 [SMILES: Cn1nccc1C(=O)N[C@@H]1COc2cc(-c3noc(C(F)F)n3)ccc21] | (S)-N-(6-(5-(difluoromethyl)-1,2,4-oxadiazol-3-yl)-2,3-dihydrobenzofuran-3-yl)-1-methyl-1H-pyrazole-5-carboxamide |
| 125 | 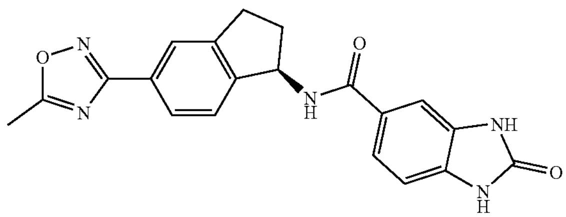 [SMILES: Cc1nc(-c2ccc3c(c2)CC[C@H]3NC(=O)c2ccc3[nH]c(=O)[nH]c3c2)no1] | (R)-N-(5-(5-methyl-1,2,4-oxadiazol-3-yl)-2,3-dihydro-1H-inden-1-yl)-2-oxo-2,3-dihydro-1H-benzo[d]imidazole-5-carboxamide |
| 126 | 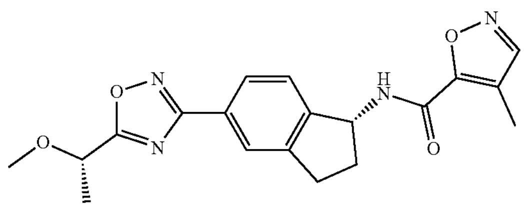 [SMILES: CO[C@@H](C)c1nc(-c2ccc3c(c2)CC[C@H]3NC(=O)c2oncc2C)no1] | N-((R)-5-(5-((S)-1-methoxyethyl)-1,2,4-oxadiazol-3-yl)-2,3-dihydro-1H-inden-1-yl)-4-methylisoxazole-5-carboxamide |
| 127 | 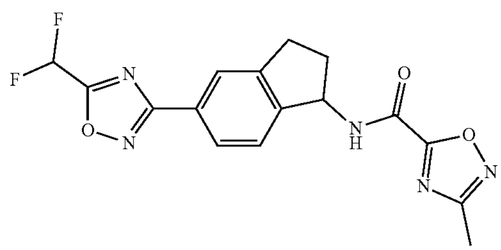 [SMILES: Cc1noc(C(=O)NC2CCc3cc(-c4noc(C(F)F)n4)ccc32)n1] | N-(5-(5-(difluoromethyl)-1,2,4-oxadiazol-3-yl)-2,3-dihydro-1H-inden-1-yl)-3-methyl-1,2,4-oxadiazole-5-carboxamide |
| 128 | 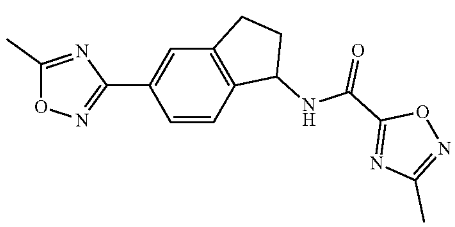 [SMILES: Cc1noc(C(=O)NC2CCc3cc(-c4noc(C)n4)ccc32)n1] | 3-methyl-N-(5-(5-methyl-1,2,4-oxadiazol-3-yl)-2,3-dihydro-1H-inden-1-yl)-1,2,4-oxadiazole-5-carboxamide |
| 129 | 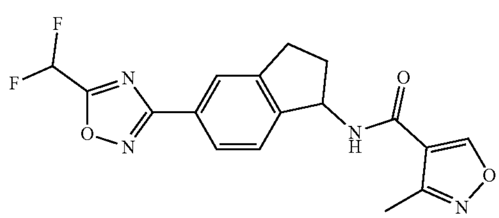 [SMILES: Cc1nocc1C(=O)NC1CCc2cc(-c3noc(C(F)F)n3)ccc21] | N-(5-(5-(difluoromethyl)-1,2,4-oxadiazol-3-yl)-2,3-dihydro-1H-inden-1-yl)-3-methylisoxazole-4-carboxamide |
| 130 | 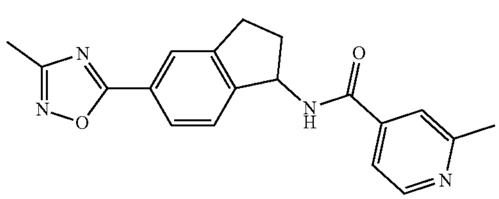 | 2-methyl-N-(5-(3-methyl-1,2,4-oxadiazol-5-yl)-2,3-dihydro-1H-inden-1-yl)isonicotinamide |

TABLE 1-continued

| Cmpd No. | Structure | Name |
|---|---|---|
| 131 | 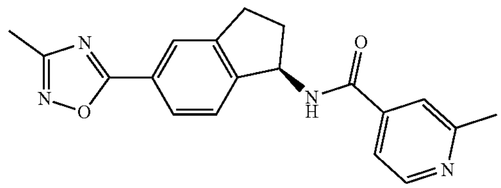 | (R)-2-methyl-N-(5-(3-methyl-1,2,4-oxadiazol-5-yl)-2,3-dihydro-1H-inden-1-yl)isonicotinamide |
| 132 | 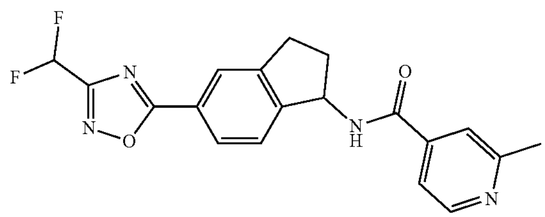 [SMILES: Cc1cc(C(=O)NC2CCc3cc(-c4nc(C(F)F)no4)ccc32)ccn1] | N-(5-(3-(difluoromethyl)-1,2,4-oxadiazol-5-yl)-2,3-dihydro-1H-inden-1-yl)-2-methylisonicotinamide |
| 133 | 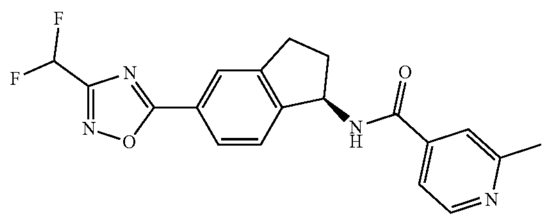 | (R)-N-(5-(3-(difluoromethyl)-1,2,4-oxadiazol-5-yl)-2,3-dihydro-1H-inden-1-yl)-2-methylisonicotinamide |
| 134 | 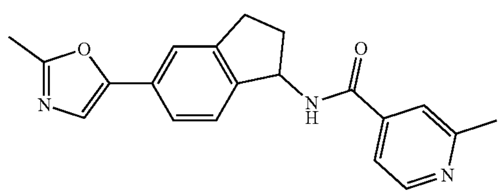 | 2-methyl-N-(5-(2-methyloxazol-5-yl)-2,3-dihydro-1H-inden-1-yl)isonicotinamide |
| 135 | 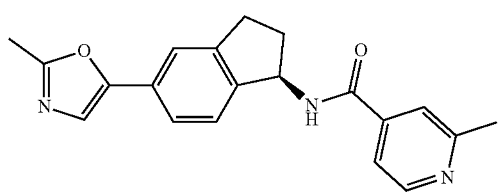 | (R)-2-methyl-N-(5-(2-methyloxazol-5-yl)-2,3-dihydro-1H-inden-1-yl)isonicotinamide |
| 136 | 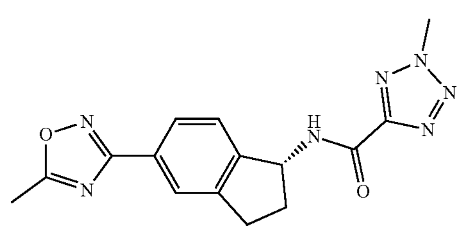 [SMILES: Cc1nc(-c2ccc3c(c2)CC[C@H]3NC(=O)c2nnn(C)n2)no1] | (R)-2-methyl-N-(5-(5-methyl-1,2,4-oxadiazol-3-yl)-2,3-dihydro-1H-inden-1-yl)-2H-tetrazole-5-carboxamide |
| 137 | 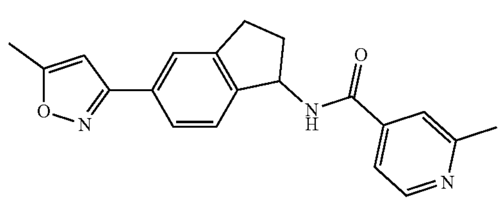 | 2-methyl-N-(5-(5-methylisoxazol-3-yl)-2,3-dihydro-1H-inden-1-yl)isonicotinamide |

TABLE 1-continued

| Cmpd No. | Structure | Name |
|---|---|---|
| 138 | 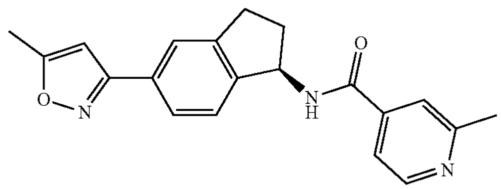 | (R)-2-methyl-N-(5-(5-methylisoxazol-3-yl)-2,3-dihydro-1H-inden-1-yl)isonicotinamide |
| 139 | 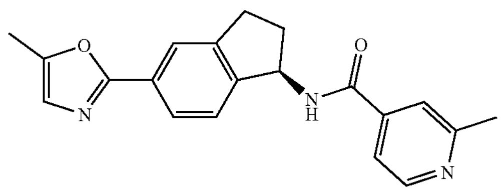 | (R)-2-methyl-N-(5-(5-methyloxazol-2-yl)-2,3-dihydro-1H-inden-1-yl)isonicotinamide |
| 140 | 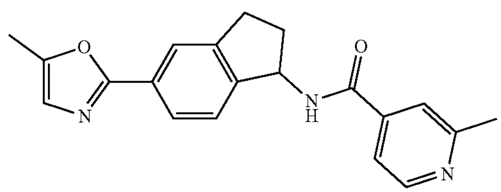 | 2-methyl-N-(5-(5-methyloxazol-2-yl)-2,3-dihydro-1H-inden-1-yl)isonicotinamide |
| 141 | 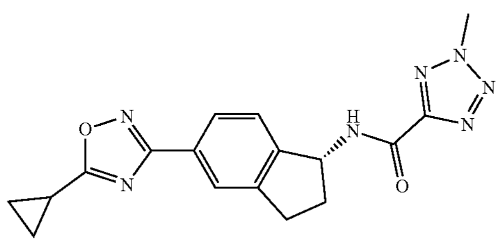 [SMILES: Cn1nnc(C(=O)N[C@@H]2CCc3cc(-c4noc(C5CC5)n4)ccc32)n1] | (R)-N-(5-(5-cyclopropyl-1,2,4-oxadiazol-3-yl)-2,3-dihydro-1H-inden-1-yl)-2-methyl-2H-tetrazole-5-carboxamide |
| 142 | 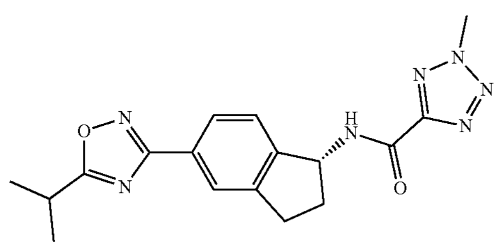 [SMILES: CC(C)c1nc(-c2ccc3c(c2)CC[C@H]3NC(=O)c2nnn(C)n2)no1] | (R)-N-(5-(5-isopropyl-1,2,4-oxadiazol-3-yl)-2,3-dihydro-1H-inden-1-yl)-2-methyl-2H-tetrazole-5-carboxamide |
| 143 | 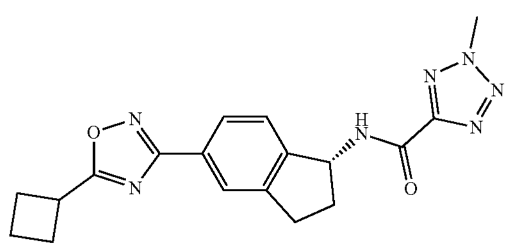 [SMILES: Cn1nnc(C(=O)N[C@@H]2CCc3cc(-c4noc(C5CCC5)n4)ccc32)n1] | (R)-N-(5-(5-cyclobutyl-1,2,4-oxadiazol-3-yl)-2,3-dihydro-1H-inden-1-yl)-2-methyl-2H-tetrazole-5-carboxamide |
| 144 | 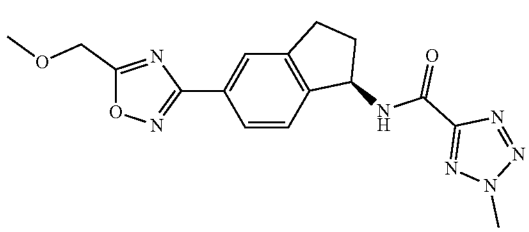 [SMILES: COCc1nc(-c2ccc3c(c2)CC[C@H]3NC(=O)c2nnn(C)n2)no1] | (R)-N-(5-(5-(methoxymethyl)-1,2,4-oxadiazol-3-yl)-2,3-dihydro-1H-inden-1-yl)-2-methyl-2H-tetrazole-5-carboxamide |

TABLE 1-continued

| Cmpd No. | Structure | Name |
|---|---|---|
| 145 | 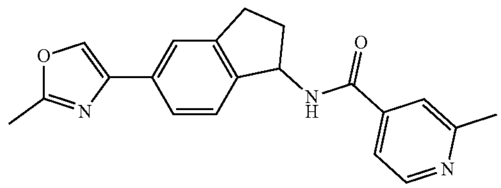 | 2-methyl-N-(5-(2-methyloxazol-4-yl)-2,3-dihydro-1H-inden-1-yl)isonicotinamide |
| 146 | 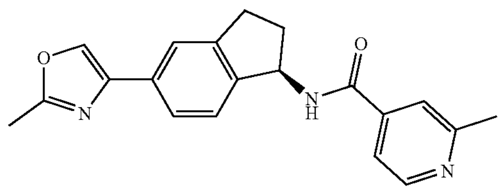 | (R)-2-methyl-N-(5-(2-methyloxazol-4-yl)-2,3-dihydro-1H-inden-1-yl)isonicotinamide |
| 147 | 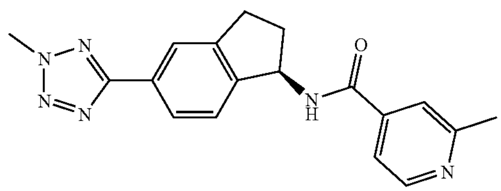 | (R)-2-methyl-N-(5-(2-methyl-2H-tetrazol-5-yl)-2,3-dihydro-1H-inden-1-yl)isonicotinamide |
| 148 | 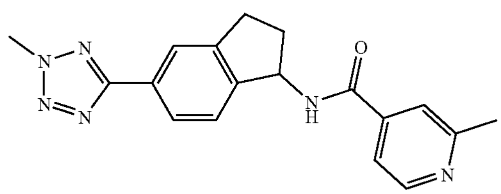 | 2-methyl-N-(5-(2-methyl-2H-tetrazol-5-yl)-2,3-dihydro-1H-inden-1-yl)isonicotinamide |
| 149 | 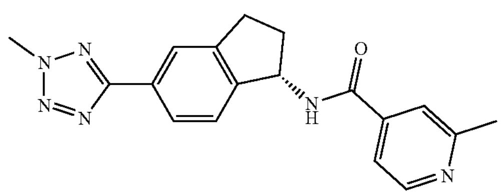 | (S)-2-methyl-N-(5-(2-methyl-2H-tetrazol-5-yl)-2,3-dihydro-1H-inden-1-yl)isonicotinamide |
| 150 | 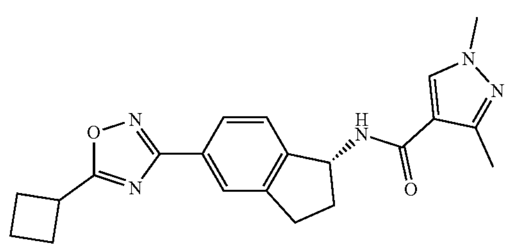 [SMILES: Cc1nn(C)cc1C(=O)N[C@@H]1CCc2cc(-c3noc(C4CCC4)n3)ccc21] | (R)-N-(5-(5-cyclobutyl-1,2,4-oxadiazol-3-yl)-2,3-dihydro-1H-inden-1-yl)-1,3-dimethyl-1H-pyrazole-4-carboxamide |
| 151 | 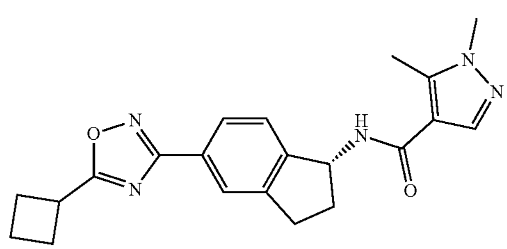 [SMILES: Cc1c(C(=O)N[C@@H]2CCc3cc(-c4noc(C5CCC5)n4)ccc32)cnn1C] | (R)-N-(5-(5-cyclobutyl-1,2,4-oxadiazol-3-yl)-2,3-dihydro-1H-inden-1-yl)-1,5-dimethyl-1H-pyrazole-4-carboxamide |

TABLE 1-continued

| Cmpd No. | Structure | Name |
|---|---|---|
| 152 | 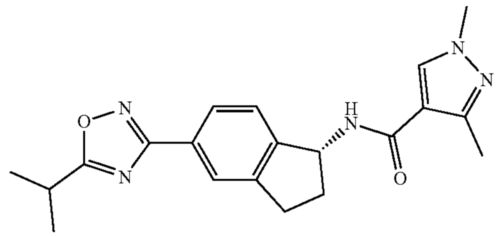 [SMILES: Cc1nn(C)cc1C(=O)N[C@@H]1CCc2cc(-c3noc(C(C)C)n3)ccc21] | (R)-N-(5-(5-isopropyl-1,2,4-oxadiazol-3-yl)-2,3-dihydro-1H-inden-1-yl)-1,3-dimethyl-1H-pyrazole-4-carboxamide |
| 153 | 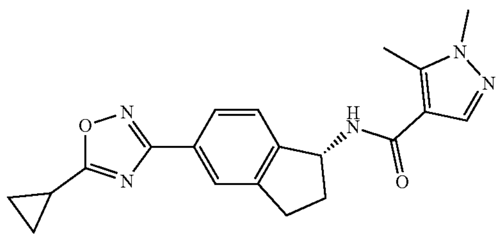 [SMILES: Cc1c(C(=O)N[C@@H]2CCc3cc(-c4noc(C5CC5)n4)ccc32)cnn1C] | (R)-N-(5-(5-cyclopropyl-1,2,4-oxadiazol-3-yl)-2,3-dihydro-1H-inden-1-yl)-1,5-dimethyl-1H-pyrazole-4-carboxamide |
| 154 | 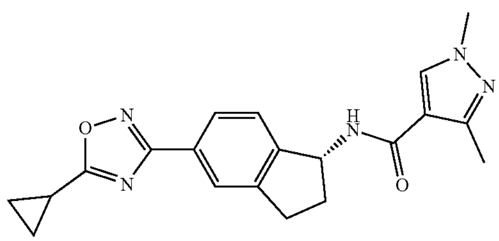 [SMILES: Cc1nn(C)cc1C(=O)N[C@@H]1CCc2cc(-c3noc(C4CC4)n3)ccc21] | (R)-N-(5-(5-cyclopropyl-1,2,4-oxadiazol-3-yl)-2,3-dihydro-1H-inden-1-yl)-1,3-dimethyl-1H-pyrazole-4-carboxamide |
| 155 | 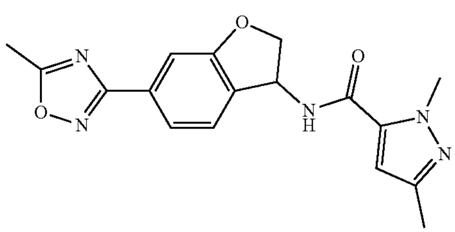 [SMILES: Cc1cc(C(=O)NC2COc3cc(-c4noc(C)n4)ccc32)n(C)n1] | 1,3-dimethyl-N-(6-(5-methyl-1,2,4-oxadiazol-3-yl)-2,3-dihydrobenzofuran-3-yl)-1H-pyrazole-5-carboxamide |
| 156 | 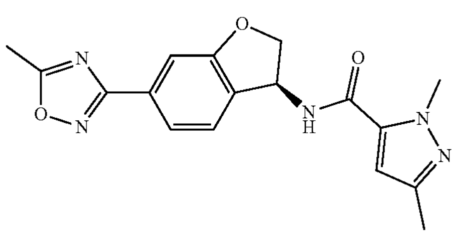 [SMILES: Cc1cc(C(=O)N[C@@H]2COc3cc(-c4noc(C)n4)ccc32)n(C)n1] | (S)-1,3-dimethyl-N-(6-(5-methyl-1,2,4-oxadiazol-3-yl)-2,3-dihydrobenzofuran-3-yl)-1H-pyrazole-5-carboxamide |
| 157 | 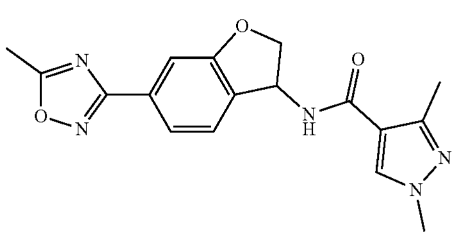 [SMILES: Cc1nc(-c2ccc3c(c2)OCC3NC(=O)c2cn(C)nc2C)no1] | 1,3-dimethyl-N-(6-(5-methyl-1,2,4-oxadiazol-3-yl)-2,3-dihydrobenzofuran-3-yl)-1H-pyrazole-4-carboxamide |

TABLE 1-continued

| Cmpd No. | Name |
|---|---|
| 158 | (S)-1,3-dimethyl-N-(6-(5-methyl-1,2,4-oxadiazol-3-yl)-2,3-dihydrobenzofuran-3-yl)-1H-pyrazole-4-carboxamide |
| 159 | 2,4-dimethyl-N-(6-(5-methyl-1,2,4-oxadiazol-3-yl)-2,3-dihydrobenzofuran-3-yl)oxazole-5-carboxamide |
| 160 | (R)-2,4-dimethyl-N-(6-(5-methyl-1,2,4-oxadiazol-3-yl)-2,3-dihydrobenzofuran-3-yl)oxazole-5-carboxamide |
| 161 | (S)-2,4-dimethyl-N-(6-(5-methyl-1,2,4-oxadiazol-3-yl)-2,3-dihydrobenzofuran-3-yl)oxazole-5-carboxamide |
| 162 | 1,5-dimethyl-N-(6-(5-methyl-1,2,4-oxadiazol-3-yl)-2,3-dihydrobenzofuran-3-yl)-1H-pyrazole-4-carboxamide |
| 163 | (S)-1,5-dimethyl-N-(6-(5-methyl-1,2,4-oxadiazol-3-yl)-2,3-dihydrobenzofuran-3-yl)-1H-pyrazole-4-carboxamide |
| 164 | (R)-4-methyl-N-(5-(5-methyl-1,2,4-oxadiazol-3-yl)-2,3-dihydro-1H-inden-1-yl)-4H-1,2,4-triazole-3-carboxamide |

TABLE 1-continued

| Cmpd No. | Structure | Name |
|---|---|---|
| 165 | 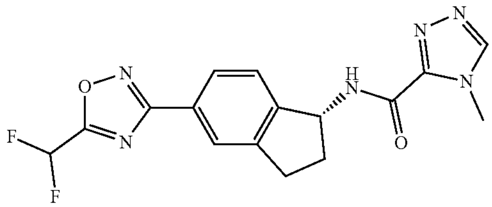 [SMILES: Cn1cnnc1C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-4-methyl-4H-1,2,4-triazole-3-carboxamide |
| 166 | 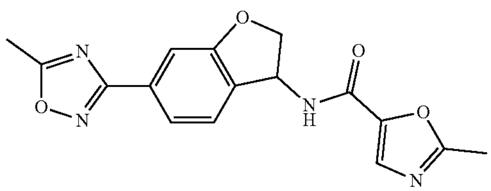 | 2-methyl-N-(6-(5-methyl-1,2,4-oxadiazol-3-yl)-2,3-dihydrobenzofuran-3-yl)oxazole-5-carboxamide |
| 167 | 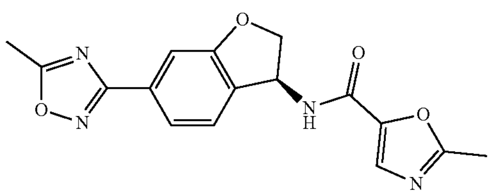 | (S)-2-methyl-N-(6-(5-methyl-1,2,4-oxadiazol-3-yl)-2,3-dihydrobenzofuran-3-yl)oxazole-5-carboxamide |
| 168 | 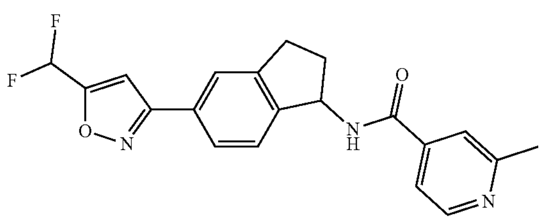 [SMILES: Cc1cc(C(=O)NC2CCc3cc(-c4cc(C(F)F)on4)ccc32)ccn1] | N-(5-(5-(difluoromethyl)isoxazol-3-yl)-2,3-dihydro-1H-inden-1-yl)-2-methylisonicotinamide |
| 169 | 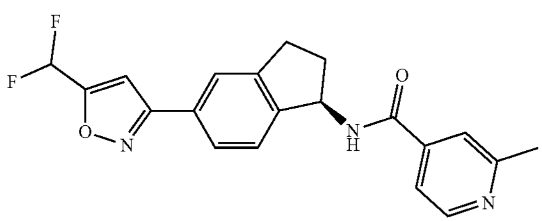 [SMILES: Cc1cc(C(=O)N[C@@H]2CCc3cc(-c4cc(C(F)F)on4)ccc32)ccn1] | (R)-N-(5-(5-(difluoromethyl)isoxazol-3-yl)-2,3-dihydro-1H-inden-1-yl)-2-methylisonicotinamide |
| 170 | 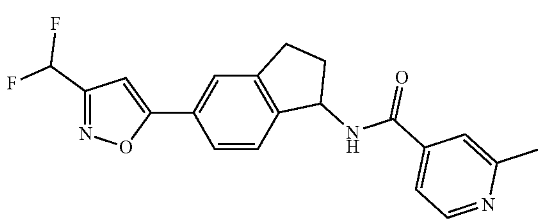 [SMILES: Cc1cc(C(=O)NC2CCc3cc(-c4cc(C(F)F)no4)ccc32)ccn1] | N-(5-(3-(difluoromethyl)isoxazol-5-yl)-2,3-dihydro-1H-inden-1-yl)-2-methylisonicotinamide |
| 171 | 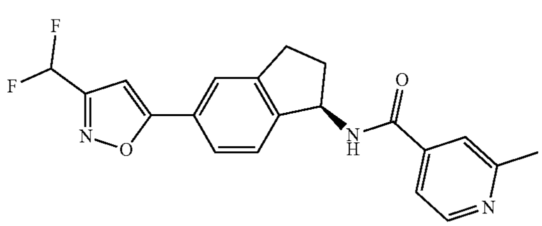 [SMILES: Cc1cc(C(=O)N[C@@H]2CCc3cc(-c4cc(C(F)F)no4)ccc32)ccn1] | (R)-N-(5-(3-(difluoromethyl)isoxazol-5-yl)-2,3-dihydro-1H-inden-1-yl)-2-methylisonicotinamide |

TABLE 1-continued

| Cmpd No. | Structure | Name |
|---|---|---|
| 172 | 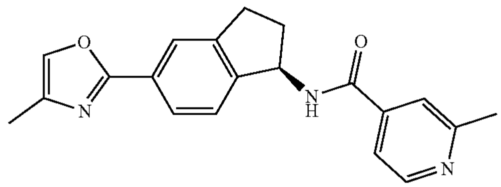 | (R)-2-methyl-N-(5-(4-methyloxazol-2-yl)-2,3-dihydro-1H-inden-1-yl)isonicotinamide |
| 173 | 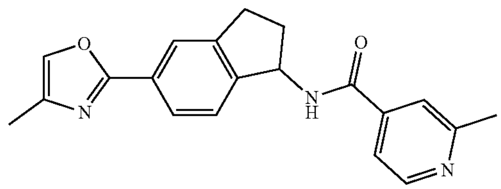 | 2-methyl-N-(5-(4-methyloxazol-2-yl)-2,3-dihydro-1H-inden-1-yl)isonicotinamide |
| 174 | 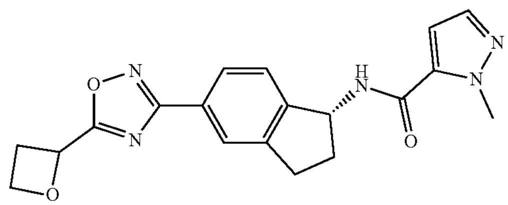 [SMILES: Cn1nccc1C(=O)N[C@@H]1CCc2cc(-c3noc(C4CCO4)n3)ccc21] | 1-methyl-N-((1R)-5-(5-(oxetan-2-yl)-1,2,4-oxadiazol-3-yl)-2,3-dihydro-1H-inden-1-yl)-1H-pyrazole-5-carboxamide |
| 175 | 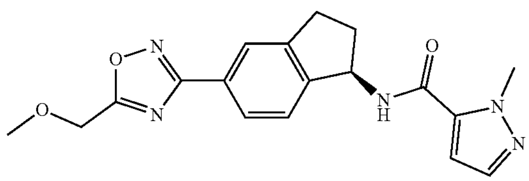 [SMILES: COCc1nc(-c2ccc3c(c2)CC[C@H]3NC(=O)c2ccnn2C)no1] | (R)-N-(5-(5-(methoxymethyl)-1,2,4-oxadiazol-3-yl)-2,3-dihydro-1H-inden-1-yl)-1-methyl-1H-pyrazole-5-carboxamide |
| 176 | 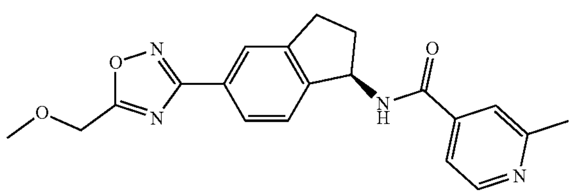 | (R)-N-(5-(5-(methoxymethyl)-1,2,4-oxadiazol-3-yl)-2,3-dihydro-1H-inden-1-yl)-2-methylisonicotinamide |
| 177 | 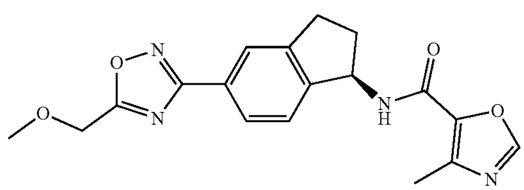 [SMILES: COCc1nc(-c2ccc3c(c2)CC[C@H]3NC(=O)c2ocnc2C)no1] | (R)-N-(5-(5-(methoxymethyl)-1,2,4-oxadiazol-3-yl)-2,3-dihydro-1H-inden-1-yl)-4-methyloxazole-5-carboxamide |
| 178 | 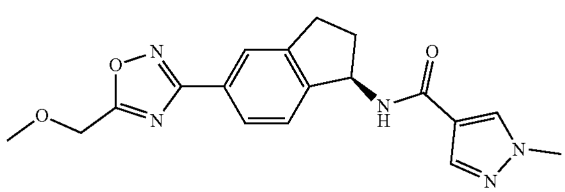 | (R)-N-(5-(5-(methoxymethyl)-1,2,4-oxadiazol-3-yl)-2,3-dihydro-1H-inden-1-yl)-1-methyl-1H-pyrazole-4-carboxamide |
| 179 | 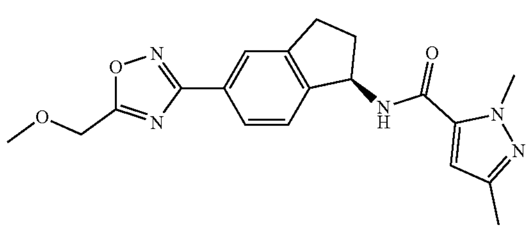 [SMILES: COCc1nc(-c2ccc3c(c2)CC[C@H]3NC(=O)c2cc(C)nn2C)no1] | (R)-N-(5-(5-(methoxymethyl)-1,2,4-oxadiazol-3-yl)-2,3-dihydro-1H-inden-1-yl)-1,3-dimethyl-1H-pyrazole-5-carboxamide |

TABLE 1-continued

| Cmpd No. | Structure | Name |
|---|---|---|
| 180 | 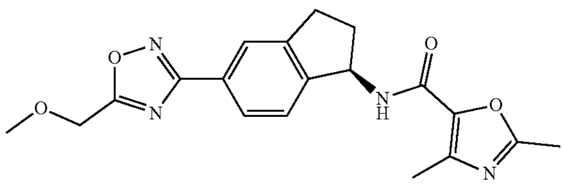 | (R)-N-(5-(5-(methoxymethyl)-1,2,4-oxadiazol-3-yl)-2,3-dihydro-1H-inden-1-yl)-2,4-dimethyloxazole-5-carboxamide |
| 181 | 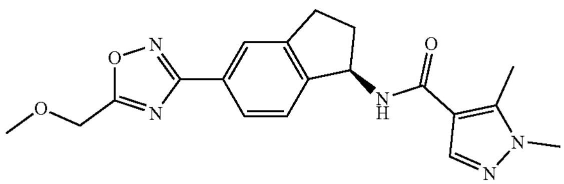 | (R)-N-(5-(5-(methoxymethyl)-1,2,4-oxadiazol-3-yl)-2,3-dihydro-1H-inden-1-yl)-1,5-dimethyl-1H-pyrazole-4-carboxamide |
| 182 | 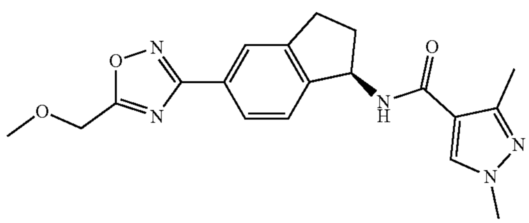 [SMILES: COCc1nc(-c2ccc3c(c2)CC[C@H]3NC(=O)c2cn(C)nc2C)no1] | (R)-N-(5-(5-(methoxymethyl)-1,2,4-oxadiazol-3-yl)-2,3-dihydro-1H-inden-1-yl)-1,3-dimethyl-1H-pyrazole-4-carboxamide |
| 183 | 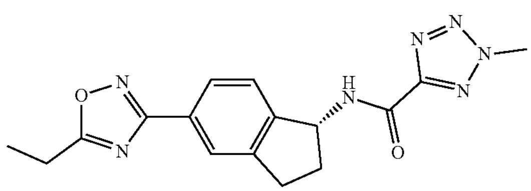 [SMILES: CCc1nc(-c2ccc3c(c2)CC[C@H]3NC(=O)c2nnn(C)n2)no1] | (R)-N-(5-(5-ethyl-1,2,4-oxadiazol-3-yl)-2,3-dihydro-1H-inden-1-yl)-2-methyl-2H-tetrazole-5-carboxamide |
| 184 | 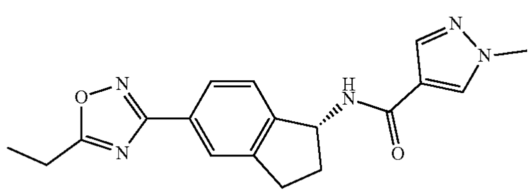 [SMILES: CCc1nc(-c2ccc3c(c2)CC[C@H]3NC(=O)c2cnn(C)c2)no1] | (R)-N-(5-(5-ethyl-1,2,4-oxadiazol-3-yl)-2,3-dihydro-1H-inden-1-yl)-1-methyl-1H-pyrazole-4-carboxamide |
| 185 | 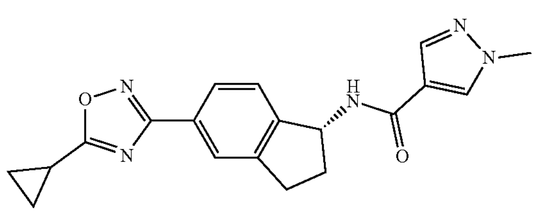 [SMILES: Cn1cc(C(=O)N[C@@H]2CCc3cc(-c4noc(C5CC5)n4)ccc32)cn1] | (R)-N-(5-(5-cyclopropyl-1,2,4-oxadiazol-3-yl)-2,3-dihydro-1H-inden-1-yl)-1-methyl-1H-pyrazole-4-carboxamide |
| 186 | 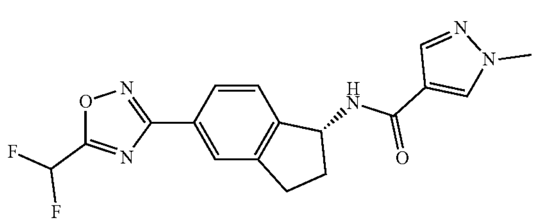 [SMILES: Cn1cc(C(=O)N[C@@H]2CCc3cc(-c4noc(C(F)F)n4)ccc32)cn1] | (R)-N-(5-(5-(difluoromethyl)-1,2,4-oxadiazol-3-yl)-2,3-dihydro-1H-inden-1-yl)-1-methyl-1H-pyrazole-4-carboxamide |

TABLE 1-continued

| Cmpd No. | Structure | Name |
|---|---|---|
| 187 | 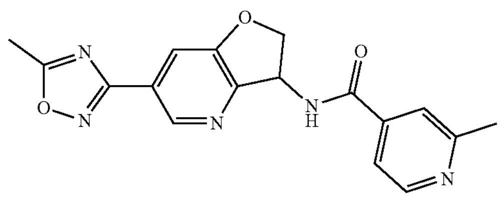 | 2-methyl-N-(6-(5-methyl-1,2,4-oxadiazol-3-yl)-2,3-dihydrofuro[3,2-b]pyridin-3-yl)isonicotinamide |
| 188 | 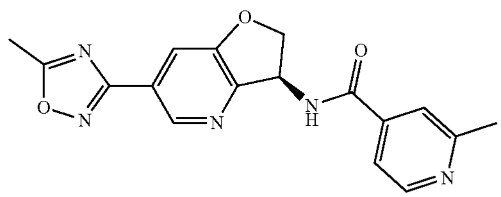 | (S)-2-methyl-N-(6-(5-methyl-1,2,4-oxadiazol-3-yl)-2,3-dihydrofuro[3,2-b]pyridin-3-yl)isonicotinamide |
| 189 | 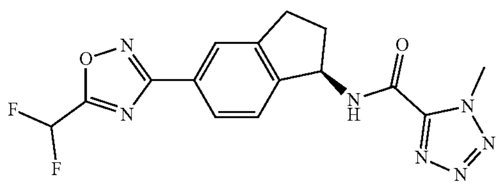 [SMILES: Cn1nnnc1C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-1-methyl-1H-tetrazole-5-carboxamide |
| 190 | 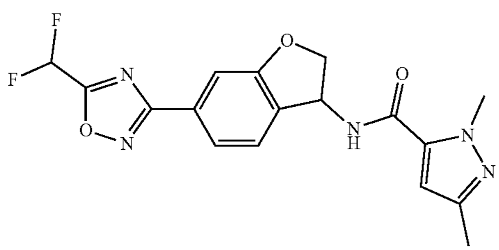 [SMILES: Cc1cc(C(=O)NC2COc3cc(-c4noc(C(F)F)n4)ccc32)n(C)n1] | N-(6-(5-(difluoromethyl)-1,2,4-oxadiazol-3-yl)-2,3-dihydrobenzofuran-3-yl)-1,3-dimethyl-1H-pyrazole-5-carboxamide |
| 191 | 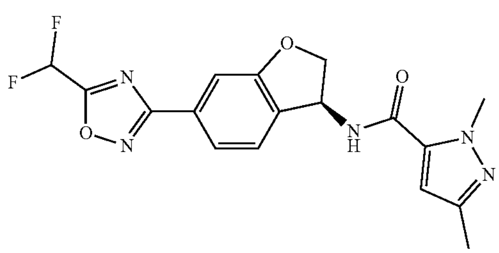 | (S)-N-(6-(5-(difluoromethyl)-1,2,4-oxadiazol-3-yl)-2,3-dihydrobenzofuran-3-yl)-1,3-dimethyl-1H-pyrazole-5-carboxamide |
| 192 | 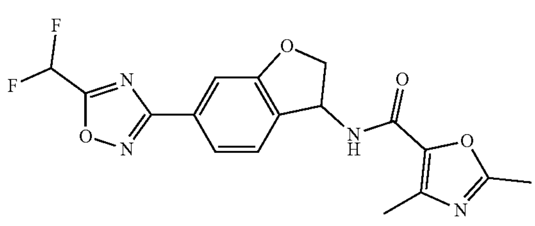 [SMILES: Cc1nc(C)c(C(=O)NC2COc3cc(-c4noc(C(F)F)n4)ccc32)o1] | N-(6-(5-(difluoromethyl)-1,2,4-oxadiazol-3-yl)-2,3-dihydrobenzofuran-3-yl)-2,4-dimethyloxazole-5-carboxamide |
| 193 | 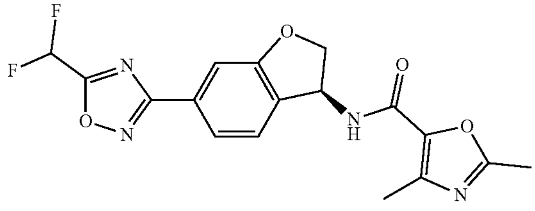 [SMILES: Cc1nc(C)c(C(=O)N[C@@H]2COc3cc(-c4noc(C(F)F)n4)ccc32)o1] | (S)-N-(6-(5-(difluoromethyl)-1,2,4-oxadiazol-3-yl)-2,3-dihydrobenzofuran-3-yl)-2,4-dimethyloxazole-5-carboxamide |

TABLE 1-continued

| Cmpd No. | Structure | Name |
|---|---|---|
| 194 | 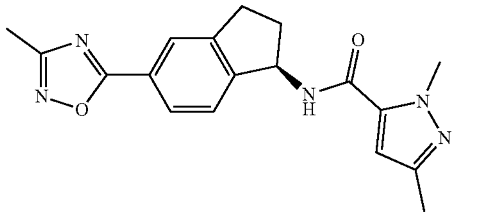 [SMILES: Cc1cc(C(=O)N[C@@H]2CCc3cc(-c4nc(C)no4)ccc32)n(C)n1] | (R)-1,3-dimethyl-N-(5-(3-methyl-1,2,4-oxadiazol-5-yl)-2,3-dihydro-1H-inden-1-yl)-1H-pyrazole-5-carboxamide |
| 195 | 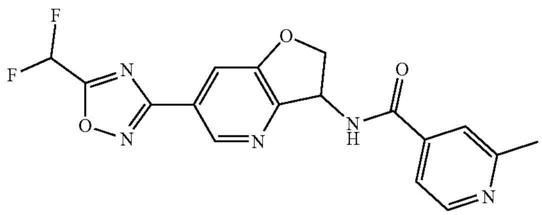 [SMILES: Cc1cc(C(=O)NC2COc3cc(-c4noc(C(F)F)n4)cnc32)ccn1] | N-(6-(5-(difluoromethyl)-1,2,4-oxadiazol-3-yl)-2,3-dihydrofuro[3,2-b]pyridin-3-yl)-2-methylisonicotinamide |
| 196 | 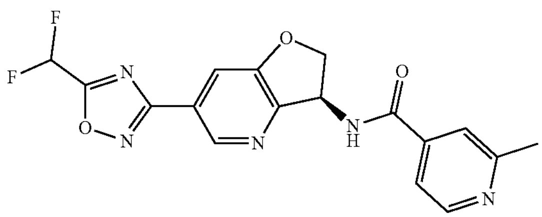 | (S)-N-(6-(5-(difluoromethyl)-1,2,4-oxadiazol-3-yl)-2,3-dihydrofuro[3,2-b]pyridin-3-yl)-2-methylisonicotinamide |
| 197 | 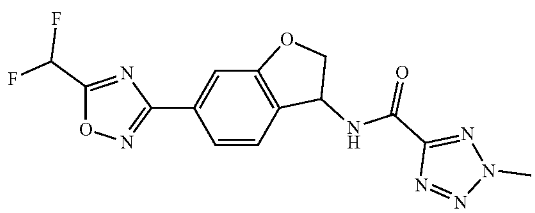 [SMILES: Cn1nnc(C(=O)NC2COc3cc(-c4noc(C(F)F)n4)ccc32)n1] | N-(6-(5-(difluoromethyl)-1,2,4-oxadiazol-3-yl)-2,3-dihydrobenzofuran-3-yl)-2-methyl-2H-tetrazole-5-carboxamide |
| 198 | 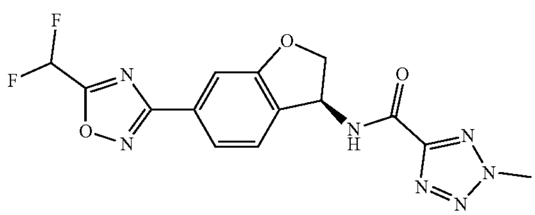 | (S)-N-(6-(5-(difluoromethyl)-1,2,4-oxadiazol-3-yl)-2,3-dihydrobenzofuran-3-yl)-2-methyl-2H-tetrazole-5-carboxamide |
| 199 | 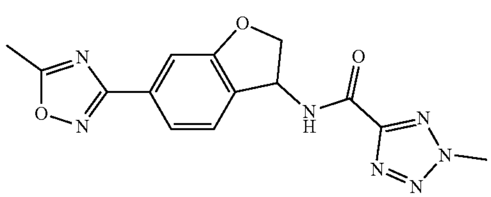 | 2-methyl-N-(6-(5-methyl-1,2,4-oxadiazol-3-yl)-2,3-dihydrobenzofuran-3-yl)-2H-tetrazole-5-carboxamide |
| 200 | 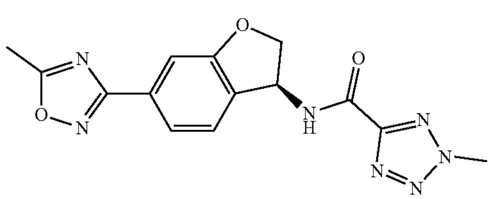 | (S)-2-methyl-N-(6-(5-methyl-1,2,4-oxadiazol-3-yl)-2,3-dihydrobenzofuran-3-yl)-2H-tetrazole-5-carboxamide |

TABLE 1-continued

| Cmpd No. | Structure | Name |
| --- | --- | --- |
| 201 | 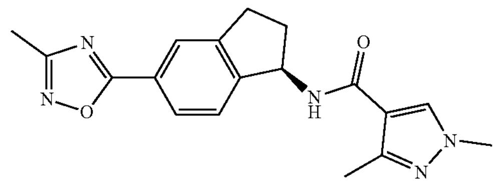 | (R)-1,3-dimethyl-N-(5-(3-methyl-1,2,4-oxadiazol-5-yl)-2,3-dihydro-1H-inden-1-yl)-1H-pyrazole-4-carboxamide |
| 202 | 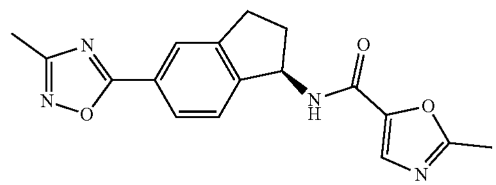 | (R)-2-methyl-N-(5-(3-methyl-1,2,4-oxadiazol-5-yl)-2,3-dihydro-1H-inden-1-yl)oxazole-5-carboxamide |
| 203 | 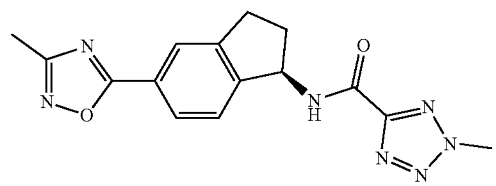 | (R)-2-methyl-N-(5-(3-methyl-1,2,4-oxadiazol-5-yl)-2,3-dihydro-1H-inden-1-yl)-2H-tetrazole-5-carboxamide |
| 204 | 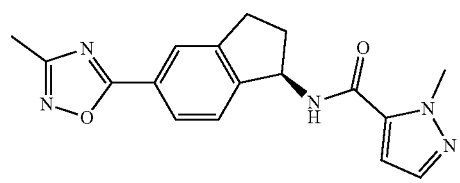 [SMILES: Cc1noc(-c2ccc3c(c2)CC[C@H]3NC(=O)c2ccnn2C)n1] | (R)-1-methyl-N-(5-(3-methyl-1,2,4-oxadiazol-5-yl)-2,3-dihydro-1H-inden-1-yl)-1H-pyrazole-5-carboxamide |
| 205 | 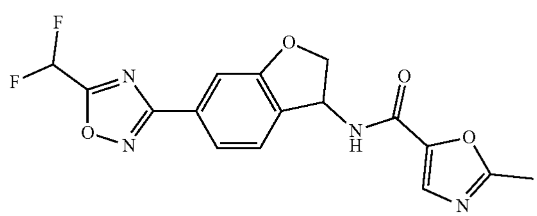 [SMILES: Cc1ncc(C(=O)NC2COc3cc(-c4noc(C(F)F)n4)ccc32)o1] | N-(6-(5-(difluoromethyl)-1,2,4-oxadiazol-3-yl)-2,3-dihydrobenzofuran-3-yl)-2-methyloxazole-5-carboxamide |
| 206 | 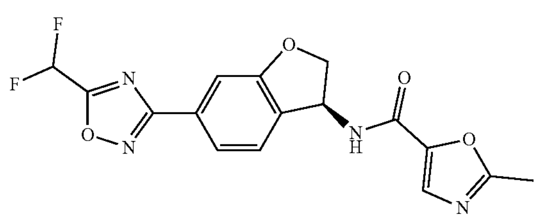 [SMILES: Cc1ncc(C(=O)N[C@@H]2COc3cc(-c4noc(C(F)F)n4)ccc32)o1] | (S)-N-(6-(5-(difluoromethyl)-1,2,4-oxadiazol-3-yl)-2,3-dihydrobenzofuran-3-yl)-2-methyloxazole-5-carboxamide |
| 207 | 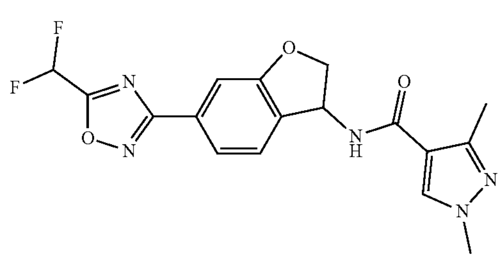 [SMILES: Cc1nn(C)cc1C(=O)NC1COc2cc(-c3noc(C(F)F)n3)ccc21] | N-(6-(5-(difluoromethyl)-1,2,4-oxadiazol-3-yl)-2,3-dihydrobenzofuran-3-yl)-1,3-dimethyl-1H-pyrazole-4-carboxamide |

| Cmpd No. | Structure | Name |
|---|---|---|
| 208 | 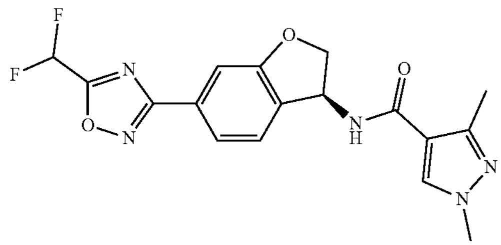 [SMILES: Cc1nn(C)cc1C(=O)N[C@@H]1COc2cc(-c3noc(C(F)F)n3)ccc21] | (S)-N-(6-(5-(difluoromethyl)-1,2,4-oxadiazol-3-yl)-2,3-dihydrobenzofuran-3-yl)-1,3-dimethyl-1H-pyrazole-4-carboxamide |
| 209 | 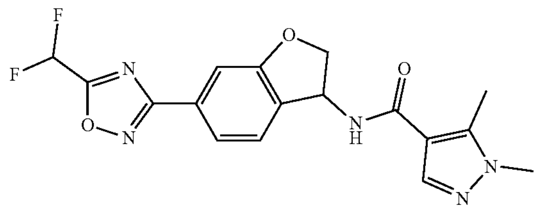 | N-(6-(5-(difluoromethyl)-1,2,4-oxadiazol-3-yl)-2,3-dihydrobenzofuran-3-yl)-1,5-dimethyl-1H-pyrazole-4-carboxamide |
| 210 | 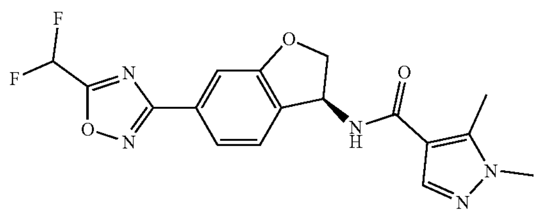 [SMILES: Cc1c(C(=O)N[C@@H]2COc3cc(-c4noc(C(F)F)n4)ccc32)cnn1C] | (S)-N-(6-(5-(difluoromethyl)-1,2,4-oxadiazol-3-yl)-2,3-dihydrobenzofuran-3-yl)-1,5-dimethyl-1H-pyrazole-4-carboxamide |
| 211 | 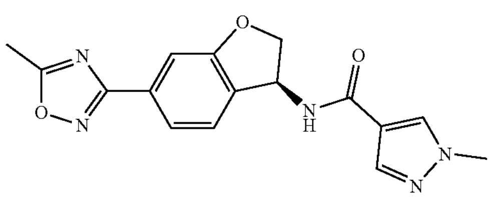 | (S)-1-methyl-N-(6-(5-methyl-1,2,4-oxadiazol-3-yl)-2,3-dihydrobenzofuran-3-yl)-1H-pyrazole-4-carboxamide |
| 212 | 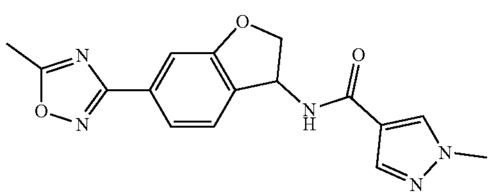 | 1-methyl-N-(6-(5-methyl-1,2,4-oxadiazol-3-yl)-2,3-dihydrobenzofuran-3-yl)-1H-pyrazole-4-carboxamide |
| 213 | 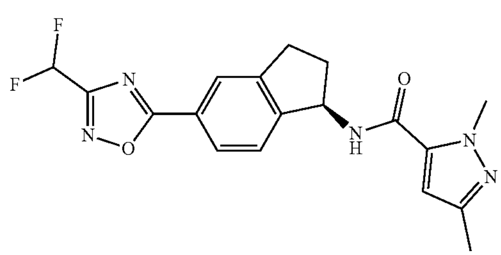 [SMILES: Cc1cc(C(=O)N[C@@H]2CCc3cc(-c4nc(C(F)F)no4)ccc32)n(C)n1] | (R)-N-(5-(3-(difluoromethyl)-1,2,4-oxadiazol-5-yl)-2,3-dihydro-1H-inden-1-yl)-1,3-dimethyl-1H-pyrazole-5-carboxamide |
| 214 | 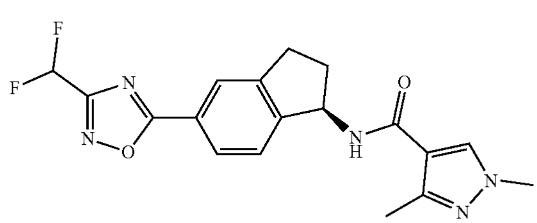 [SMILES: Cc1nn(C)cc1C(=O)N[C@@H]1CCc2cc(-c3nc(C(F)F)no3)ccc21] | (R)-N-(5-(3-(difluoromethyl)-1,2,4-oxadiazol-5-yl)-2,3-dihydro-1H-inden-1-yl)-1,3-dimethyl-1H-pyrazole-4-carboxamide |

TABLE 1-continued

| Cmpd No. | Structure | Name |
|---|---|---|
| 215 | 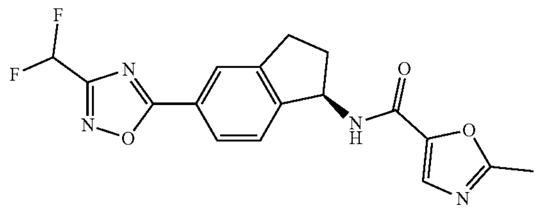 [SMILES: Cc1ncc(C(=O)N[C@@H]2CCc3cc(-c4nc(C(F)F)no4)ccc32)o1] | (R)-N-(5-(3-(difluoromethyl)-1,2,4-oxadiazol-5-yl)-2,3-dihydro-1H-inden-1-yl)-2-methyloxazole-5-carboxamide |
| 216 | 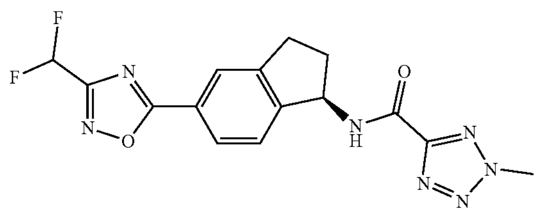 [SMILES: Cn1nnc(C(=O)N[C@@H]2CCc3cc(-c4nc(C(F)F)no4)ccc32)n1] | (R)-N-(5-(3-(difluoromethyl)-1,2,4-oxadiazol-5-yl)-2,3-dihydro-1H-inden-1-yl)-2-methyl-2H-tetrazole-5-carboxamide |
| 217 | 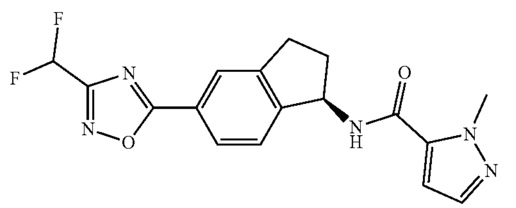 [SMILES: Cn1nccc1C(=O)N[C@@H]1CCc2cc(-c3nc(C(F)F)no3)ccc21] | (R)-N-(5-(3-(difluoromethyl)-1,2,4-oxadiazol-5-yl)-2,3-dihydro-1H-inden-1-yl)-1-methyl-1H-pyrazole-5-carboxamide |
| 218 | 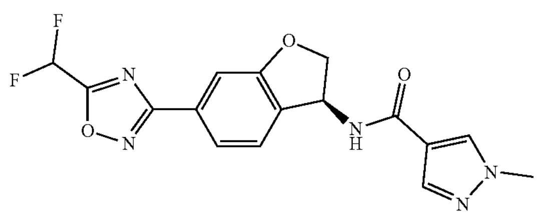 [SMILES: Cn1cc(C(=O)N[C@@H]2COc3cc(-c4noc(C(F)F)n4)ccc32)cn1] | (S)-N-(6-(5-(difluoromethyl)-1,2,4-oxadiazol-3-yl)-2,3-dihydrobenzofuran-3-yl)-1-methyl-1H-pyrazole-4-carboxamide |
| 219 | 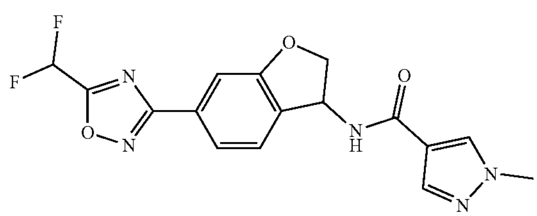 [SMILES: Cn1cc(C(=O)NC2COc3cc(-c4noc(C(F)F)n4)ccc32)cn1] | N-(6-(5-(difluoromethyl)-1,2,4-oxadiazol-3-yl)-2,3-dihydrobenzofuran-3-yl)-1-methyl-1H-pyrazole-4-carboxamide |
| 220 | 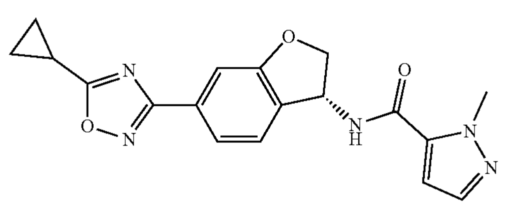 [SMILES: Cn1nccc1C(=O)N[C@H]1COc2cc(-c3noc(C4CC4)n3)ccc21] | (R)-N-(6-(5-cyclopropyl-1,2,4-oxadiazol-3-yl)-2,3-dihydrobenzofuran-3-yl)-1-methyl-1H-pyrazole-5-carboxamide |
| 221 | 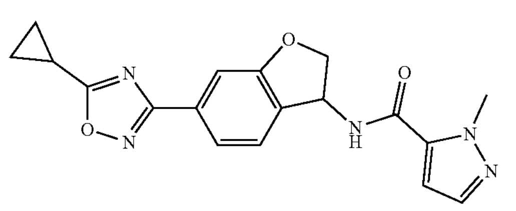 [SMILES: Cn1nccc1C(=O)NC1COc2cc(-c3noc(C4CC4)n3)ccc21] | N-(6-(5-cyclopropyl-1,2,4-oxadiazol-3-yl)-2,3-dihydrobenzofuran-3-yl)-1-methyl-1H-pyrazole-5-carboxamide |

TABLE 1-continued

| Cmpd No. | Structure | Name |
|---|---|---|
| 222 | 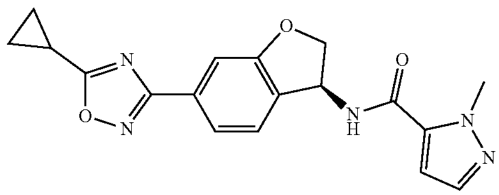 [SMILES: Cn1nccc1C(=O)N[C@@H]1COc2cc(-c3noc(C4CC4)n3)ccc21] | (S)-N-(6-(5-cyclopropyl-1,2,4-oxadiazol-3-yl)-2,3-dihydrobenzofuran-3-yl)-1-methyl-1H-pyrazole-5-carboxamide |
| 223 | 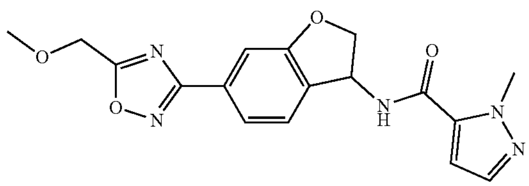 [SMILES: COCc1nc(-c2ccc3c(c2)OCC3NC(=O)c2ccnn2C)no1] | N-(6-(5-(methoxymethyl)-1,2,4-oxadiazol-3-yl)-2,3-dihydrobenzofuran-3-yl)-1-methyl-1H-pyrazole-5-carboxamide |
| 224 | 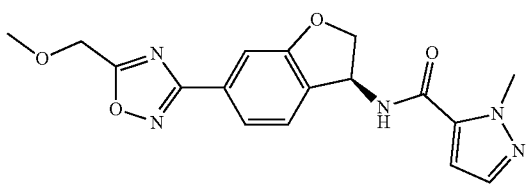 [SMILES: COCc1nc(-c2ccc3c(c2)OC[C@H]3NC(=O)c2ccnn2C)no1] | (S)-N-(6-(5-(methoxymethyl)-1,2,4-oxadiazol-3-yl)-2,3-dihydrobenzofuran-3-yl)-1-methyl-1H-pyrazole-5-carboxamide |
| 225 | 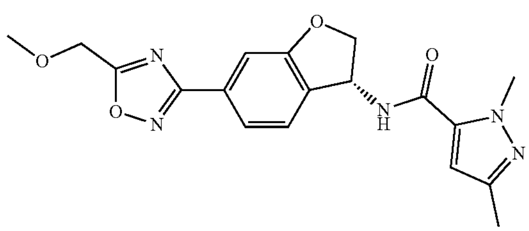 [SMILES: COCc1nc(-c2ccc3c(c2)OC[C@@H]3NC(=O)c2cc(C)nn2C)no1] | (R)-N-(6-(5-(methoxymethyl)-1,2,4-oxadiazol-3-yl)-2,3-dihydrobenzofuran-3-yl)-1,3-dimethyl-1H-pyrazole-5-carboxamide |
| 226 | 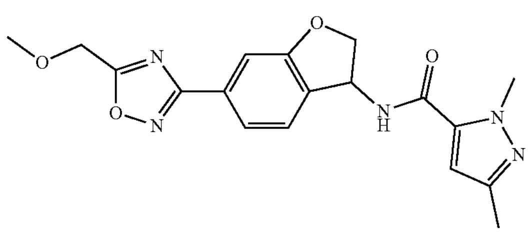 [SMILES: COCc1nc(-c2ccc3c(c2)OCC3NC(=O)c2cc(C)nn2C)no1] | N-(6-(5-(methoxymethyl)-1,2,4-oxadiazol-3-yl)-2,3-dihydrobenzofuran-3-yl)-1,3-dimethyl-1H-pyrazole-5-carboxamide |
| 227 | 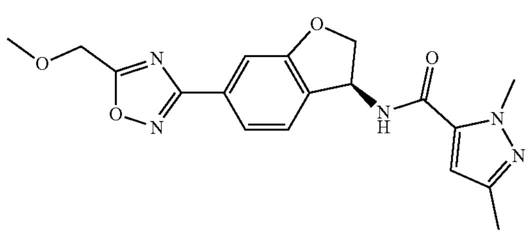 [SMILES: COCc1nc(-c2ccc3c(c2)OC[C@H]3NC(=O)c2cc(C)nn2C)no1] | (S)-N-(6-(5-(methoxymethyl)-1,2,4-oxadiazol-3-yl)-2,3-dihydrobenzofuran-3-yl)-1,3-dimethyl-1H-pyrazole-5-carboxamide |
| 228 | 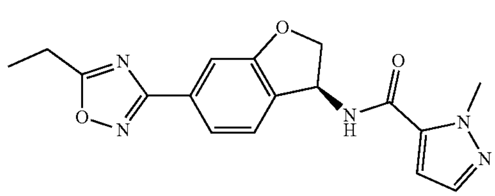 [SMILES: CCc1nc(-c2ccc3c(c2)OC[C@H]3NC(=O)c2ccnn2C)no1] | (S)-N-(6-(5-ethyl-1,2,4-oxadiazol-3-yl)-2,3-dihydrobenzofuran-3-yl)-1-methyl-1H-pyrazole-5-carboxamide |

TABLE 1-continued

| Cmpd No. | Structure | Name |
|---|---|---|
| 229 | 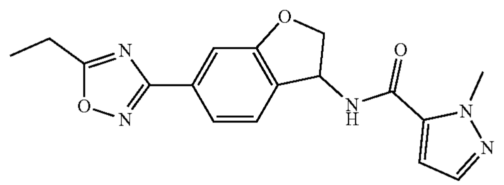 [SMILES: CCc1nc(-c2ccc3c(c2)OCC3NC(=O)c2ccnn2C)no1] | N-(6-(5-ethyl-1,2,4-oxadiazol-3-yl)-2,3-dihydrobenzofuran-3-yl)-1-methyl-1H-pyrazole-5-carboxamide |
| 230 | 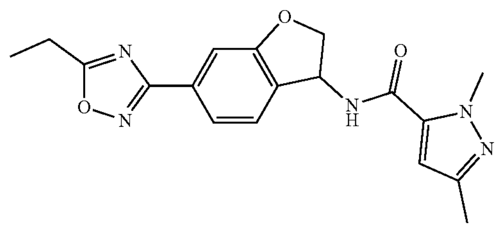 [SMILES: CCc1nc(-c2ccc3c(c2)OCC3NC(=O)c2cc(C)nn2C)no1] | N-(6-(5-ethyl-1,2,4-oxadiazol-3-yl)-2,3-dihydrobenzofuran-3-yl)-1,3-dimethyl-1H-pyrazole-5-carboxamide |
| 231 | 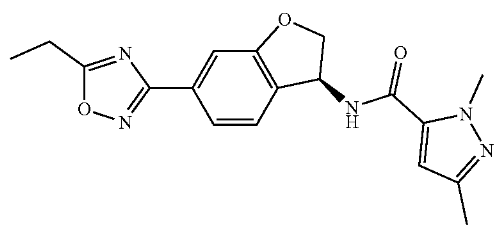 [SMILES: CCc1nc(-c2ccc3c(c2)OC[C@H]3NC(=O)c2cc(C)nn2C)no1] | (S)-N-(6-(5-ethyl-1,2,4-oxadiazol-3-yl)-2,3-dihydrobenzofuran-3-yl)-1,3-dimethyl-1H-pyrazole-5-carboxamide |
| 232 | 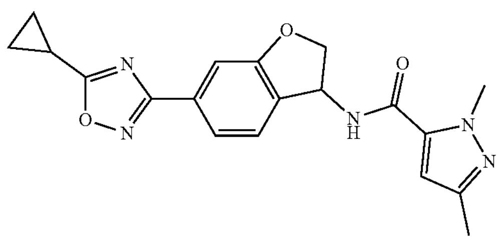 [SMILES: Cc1cc(C(=O)NC2COc3cc(-c4noc(C5CC5)n4)ccc32)n(C)n1] | N-(6-(5-cyclopropyl-1,2,4-oxadiazol-3-yl)-2,3-dihydrobenzofuran-3-yl)-1,3-dimethyl-1H-pyrazole-5-carboxamide |
| 233 | 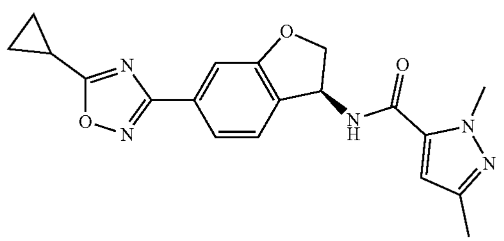 [SMILES: Cc1cc(C(=O)N[C@@H]2COc3cc(-c4noc(C5CC5)n4)ccc32)n(C)n1] | (S)-N-(6-(5-cyclopropyl-1,2,4-oxadiazol-3-yl)-2,3-dihydrobenzofuran-3-yl)-1,3-dimethyl-1H-pyrazole-5-carboxamide |
| 234 | 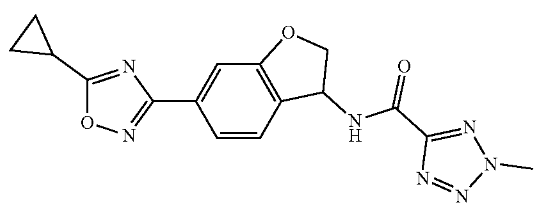 [SMILES: Cn1nnc(C(=O)NC2COc3cc(-c4noc(C5CC5)n4)ccc32)n1] | N-(6-(5-cyclopropyl-1,2,4-oxadiazol-3-yl)-2,3-dihydrobenzofuran-3-yl)-2-methyl-2H-tetrazole-5-carboxamide |
| 235 | 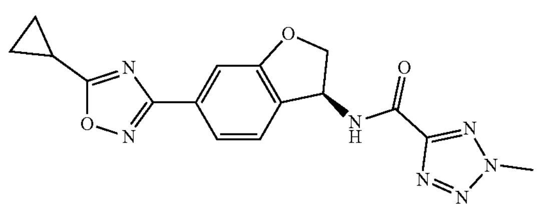 [SMILES: Cn1nnc(C(=O)N[C@@H]2COc3cc(-c4noc(C5CC5)n4)ccc32)n1] | (S)-N-(6-(5-cyclopropyl-1,2,4-oxadiazol-3-yl)-2,3-dihydrobenzofuran-3-yl)-2-methyl-2H-tetrazole-5-carboxamide |

TABLE 1-continued

| Cmpd No. | Structure | Name |
|---|---|---|
| 236 | 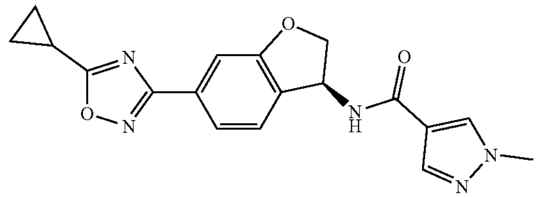 [SMILES: Cn1cc(C(=O)N[C@@H]2COc3cc(-c4noc(C5CC5)n4)ccc32)cn1] | (S)-N-(6-(5-cyclopropyl-1,2,4-oxadiazol-3-yl)-2,3-dihydrobenzofuran-3-yl)-1-methyl-1H-pyrazole-4-carboxamide |
| 237 | 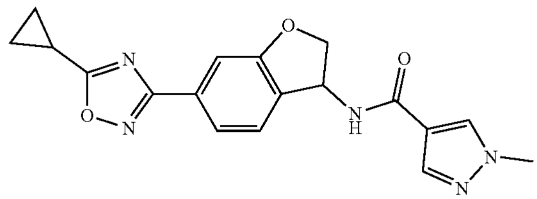 [SMILES: Cn1cc(C(=O)NC2COc3cc(-c4noc(C5CC5)n4)ccc32)cn1] | N-(6-(5-cyclopropyl-1,2,4-oxadiazol-3-yl)-2,3-dihydrobenzofuran-3-yl)-1-methyl-1H-pyrazole-4-carboxamide |
| 238 | 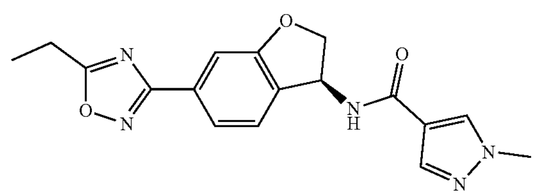 [SMILES: CCc1nc(-c2ccc3c(c2)OC[C@H]3NC(=O)c2cnn(C)c2)no1] | (S)-N-(6-(5-ethyl-1,2,4-oxadiazol-3-yl)-2,3-dihydrobenzofuran-3-yl)-1-methyl-1H-pyrazole-4-carboxamide |
| 239 | 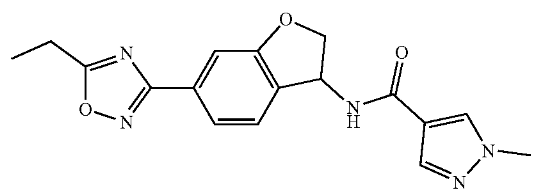 [SMILES: CCc1nc(-c2ccc3c(c2)OCC3NC(=O)c2cnn(C)c2)no1] | N-(6-(5-ethyl-1,2,4-oxadiazol-3-yl)-2,3-dihydrobenzofuran-3-yl)-1-methyl-1H-pyrazole-4-carboxamide |
| 240 | 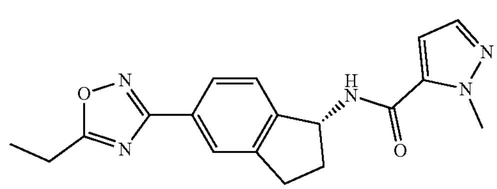 [SMILES: CCc1nc(-c2ccc3c(c2)CC[C@H]3NC(=O)c2ccnn2C)no1] | (R)-N-(5-(5-ethyl-1,2,4-oxadiazol-3-yl)-2,3-dihydro-1H-inden-1-yl)-1-methyl-1H-pyrazole-5-carboxamide |
| 241 | 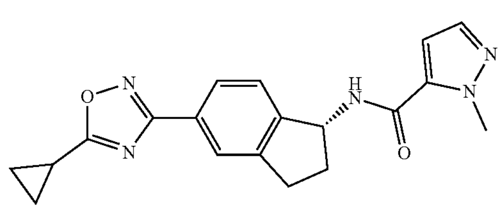 [SMILES: Cn1nccc1C(=O)N[C@@H]1CCc2cc(-c3noc(C4CC4)n3)ccc21] | (R)-N-(5-(5-cyclopropyl-1,2,4-oxadiazol-3-yl)-2,3-dihydro-1H-inden-1-yl)-1-methyl-1H-pyrazole-5-carboxamide |
| 242 | 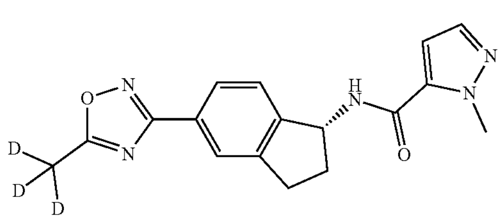 | (R)-1-methyl-N-(5-(5-(methyl-d3)-1,2,4-oxadiazol-3-yl)-2,3-dihydro-1H-inden-1-yl)-1H-pyrazole-5-carboxamide |

TABLE 1-continued

| Cmpd No. | Structure | Name |
|---|---|---|
| 243 | 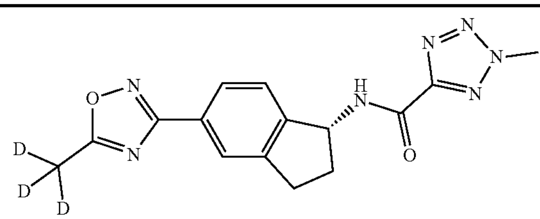 | (R)-2-methyl-N-(5-(5-(methyl-d3)-1,2,4-oxadiazol-3-yl)-2,3-dihydro-1H-inden-1-yl)-2H-tetrazole-5-carboxamide |
| 244 | 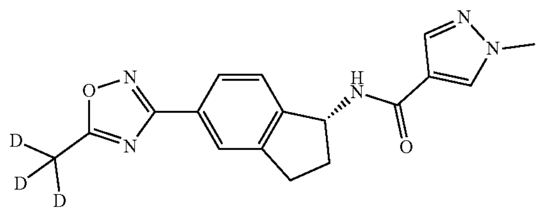 [SMILES: [2H]C([2H])([2H])c1nc(-c2ccc3c(c2)CC[C@H]3NC(=O)c2cnn(C)c2)no1] | (R)-1-methyl-N-(5-(5-(methyl-d3)-1,2,4-oxadiazol-3-yl)-2,3-dihydro-1H-inden-1-yl)-1H-pyrazole-4-carboxamide |
| 245 | 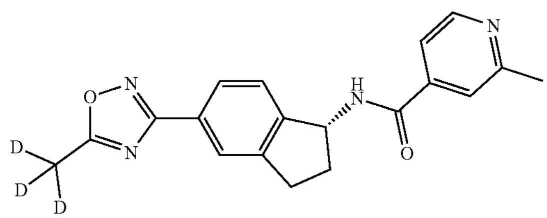 [SMILES: [2H]C([2H])([2H])c1nc(-c2ccc3c(c2)CC[C@H]3NC(=O)c2ccnc(C)c2)no1] | (R)-2-methyl-N-(5-(5-(methyl-d3)-1,2,4-oxadiazol-3-yl)-2,3-dihydro-1H-inden-1-yl)isonicotinamide |
| 246 | 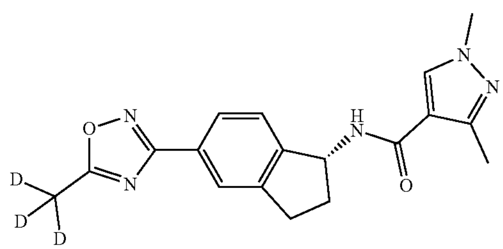 [SMILES: [2H]C([2H])([2H])c1nc(-c2ccc3c(c2)CC[C@H]3NC(=O)c2cn(C)nc2C)no1] | (R)-1,3-dimethyl-N-(5-(5-(methyl-d3)-1,2,4-oxadiazol-3-yl)-2,3-dihydro-1H-inden-1-yl)-1H-pyrazole-4-carboxamide |
| 247 | 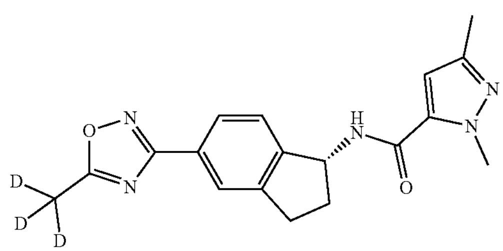 [SMILES: [2H]C([2H])([2H])c1nc(-c2ccc3c(c2)CC[C@H]3NC(=O)c2cc(C)nn2C)no1] | (R)-1,3-dimethyl-N-(5-(5-(methyl-d3)-1,2,4-oxadiazol-3-yl)-2,3-dihydro-1H-inden-1-yl)-1H-pyrazole-5-carboxamide |
| 248 | 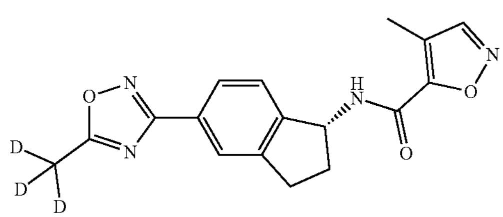 [SMILES: [2H]C([2H])([2H])c1nc(-c2ccc3c(c2)CC[C@H]3NC(=O)c2oncc2C)no1] | (R)-4-methyl-N-(5-(5-(methyl-d3)-1,2,4-oxadiazol-3-yl)-2,3-dihydro-1H-inden-1-yl)isoxazole-5-carboxamide |
| 249 | 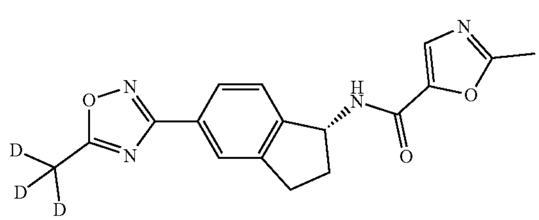 [SMILES: [2H]C([2H])([2H])c1nc(-c2ccc3c(c2)CC[C@H]3NC(=O)c2cnc(C)o2)no1] | (R)-2-methyl-N-(5-(5-(methyl-d3)-1,2,4-oxadiazol-3-yl)-2,3-dihydro-1H-inden-1-yl)oxazole-5-carboxamide |

TABLE 1-continued

| Cmpd No. | Structure | Name |
|---|---|---|
| 250 | 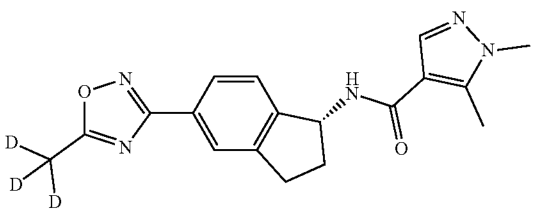 [SMILES: [2H]C([2H])([2H])c1nc(-c2ccc3c(c2)CC[C@H]3NC(=O)c2cnn(C)c2C)no1] | (R)-1,5-dimethyl-N-(5-(5-(methyl-d3)-1,2,4-oxadiazol-3-yl)-2,3-dihydro-1H-inden-1-yl)-1H-pyrazole-4-carboxamide |
| 251 | 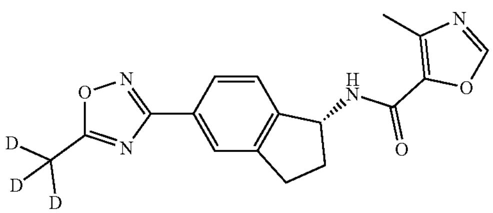 [SMILES: [2H]C([2H])([2H])c1nc(-c2ccc3c(c2)CC[C@H]3NC(=O)c2ocnc2C)no1] | (R)-4-methyl-N-(5-(5-(methyl-d3)-1,2,4-oxadiazol-3-yl)-2,3-dihydro-1H-inden-1-yl)oxazole-5-carboxamide |
| 252 | 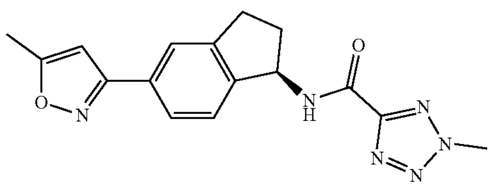 | (R)-2-methyl-N-(5-(5-methylisoxazol-3-yl)-2,3-dihydro-1H-inden-1-yl)-2H-tetrazole-5-carboxamide |
| 253 | 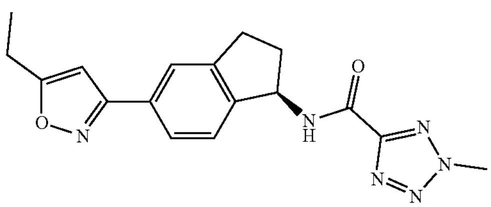 [SMILES: CCc1cc(-c2ccc3c(c2)CC[C@H]3NC(=O)c2nnn(C)n2)no1] | (R)-N-(5-(5-ethylisoxazol-3-yl)-2,3-dihydro-1H-inden-1-yl)-2-methyl-2H-tetrazole-5-carboxamide |
| 254 | 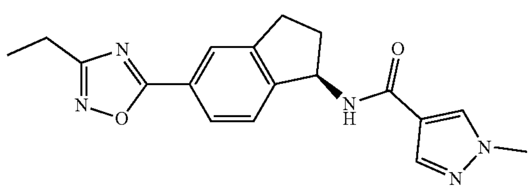 [SMILES: CCc1noc(-c2ccc3c(c2)CC[C@H]3NC(=O)c2cnn(C)c2)n1] | (R)-N-(5-(3-ethyl-1,2,4-oxadiazol-5-yl)-2,3-dihydro-1H-inden-1-yl)-1-methyl-1H-pyrazole-4-carboxamide |
| 255 | 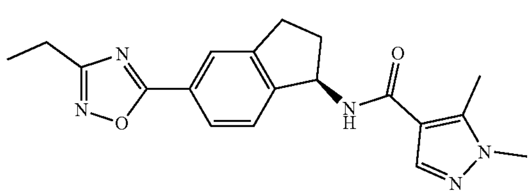 [SMILES: CCc1noc(-c2ccc3c(c2)CC[C@H]3NC(=O)c2cnn(C)c2C)n1] | (R)-N-(5-(3-ethyl-1,2,4-oxadiazol-5-yl)-2,3-dihydro-1H-inden-1-yl)-1,5-dimethyl-1H-pyrazole-4-carboxamide |
| 256 | 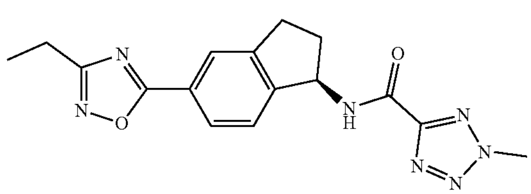 [SMILES: CCc1noc(-c2ccc3c(c2)CC[C@H]3NC(=O)c2nnn(C)n2)n1] | (R)-N-(5-(3-ethyl-1,2,4-oxadiazol-5-yl)-2,3-dihydro-1H-inden-1-yl)-2-methyl-2H-tetrazole-5-carboxamide |

TABLE 1-continued

| Cmpd No. | Structure | Name |
|---|---|---|
| 257 | 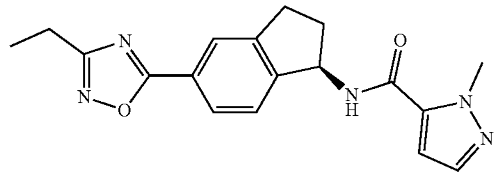 [SMILES: CCc1noc(-c2ccc3c(c2)CC[C@H]3NC(=O)c2ccnn2C)n1] | (R)-N-(5-(3-ethyl-1,2,4-oxadiazol-5-yl)-2,3-dihydro-1H-inden-1-yl)-1-methyl-1H-pyrazole-5-carboxamide |
| 258 | 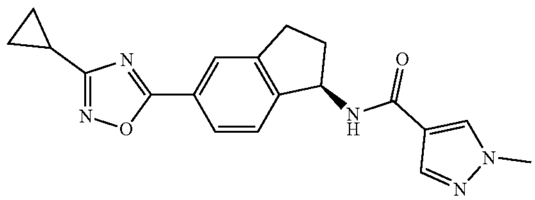 [SMILES: Cn1cc(C(=O)N[C@@H]2CCc3cc(-c4nc(C5CC5)no4)ccc32)cn1] | (R)-N-(5-(3-cyclopropyl-1,2,4-oxadiazol-5-yl)-2,3-dihydro-1H-inden-1-yl)-1-methyl-1H-pyrazole-4-carboxamide |
| 259 | 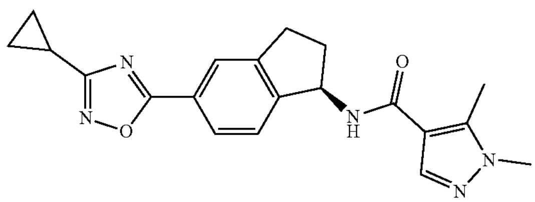 [SMILES: Cc1c(C(=O)N[C@@H]2CCc3cc(-c4nc(C5CC5)no4)ccc32)cnn1C] | (R)-N-(5-(3-cyclopropyl-1,2,4-oxadiazol-5-yl)-2,3-dihydro-1H-inden-1-yl)-1,5-dimethyl-1H-pyrazole-4-carboxamide |
| 260 | 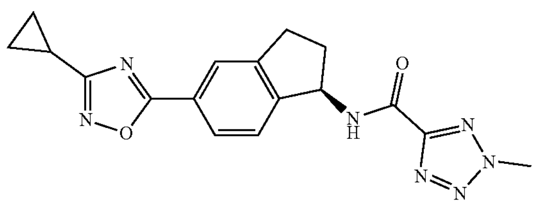 | (R)-N-(5-(3-cyclopropyl-1,2,4-oxadiazol-5-yl)-2,3-dihydro-1H-inden-1-yl)-2-methyl-2H-tetrazole-5-carboxamide |
| 261 | 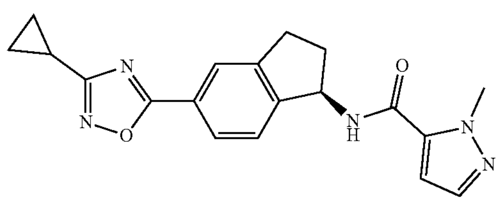 [SMILES: Cn1nccc1C(=O)N[C@@H]1CCc2cc(-c3nc(C4CC4)no3)ccc21] | (R)-N-(5-(3-cyclopropyl-1,2,4-oxadiazol-5-yl)-2,3-dihydro-1H-inden-1-yl)-1-methyl-1H-pyrazole-5-carboxamide |
| 262 | 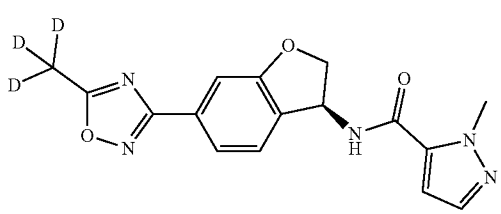 [SMILES: [2H]C([2H])([2H])c1nc(-c2ccc3c(c2)OC[C@H]3NC(=O)c2ccnn2C)no1] | (S)-1-methyl-N-(6-(5-(methyl-d3)-1,2,4-oxadiazol-3-yl)-2,3-dihydrobenzofuran-3-yl)-1H-pyrazole-5-carboxamide |
| 263 | 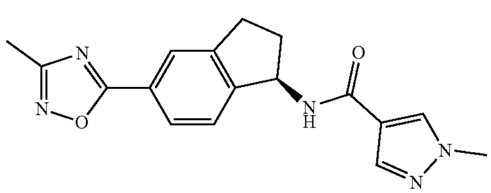 | (R)-1-methyl-N-(5-(3-methyl-1,2,4-oxadiazol-5-yl)-2,3-dihydro-1H-inden-1-yl)-1H-pyrazole-4-carboxamide |

TABLE 1-continued

| Cmpd No. | Structure | Name |
|---|---|---|
| 264 | 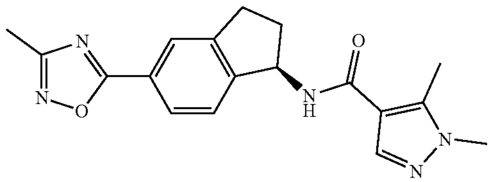 | (R)-1,5-dimethyl-N-(5-(3-methyl-1,2,4-oxadiazol-5-yl)-2,3-dihydro-1H-inden-1-yl)-1H-pyrazole-4-carboxamide |
| 265 | 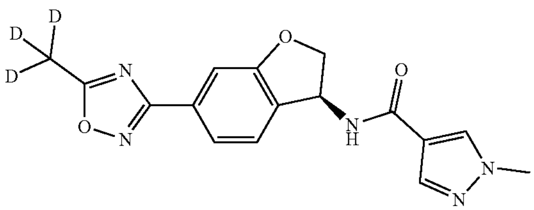 [SMILES: [2H]C([2H])([2H])c1nc(-c2ccc3c(c2)OC[C@H]3NC(=O)c2cnn(C)c2)no1] | (S)-1-methyl-N-(6-(5-(methyl-d3)-1,2,4-oxadiazol-3-yl)-2,3-dihydrobenzofuran-3-yl)-1H-pyrazole-4-carboxamide |
| 266 | 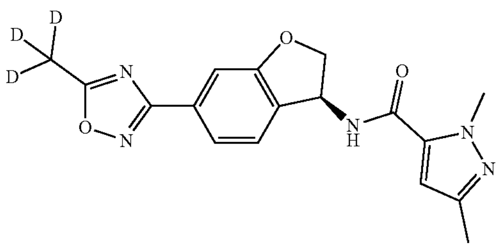 [SMILES: [2H]C([2H])([2H])c1nc(-c2ccc3c(c2)OC[C@H]3NC(=O)c2cc(C)nn2C)no1] | (S)-1,3-dimethyl-N-(6-(5-(methyl-d3)-1,2,4-oxadiazol-3-yl)-2,3-dihydrobenzofuran-3-yl)-1H-pyrazole-5-carboxamide |
| 267 | 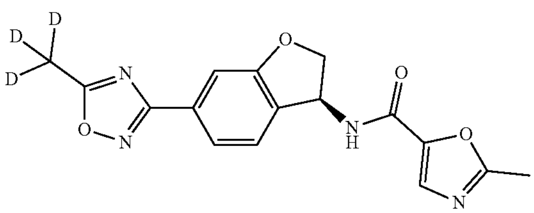 | (S)-2-methyl-N-(6-(5-(methyl-d3)-1,2,4-oxadiazol-3-yl)-2,3-dihydrobenzofuran-3-yl)oxazole-5-carboxamide |
| 268 | 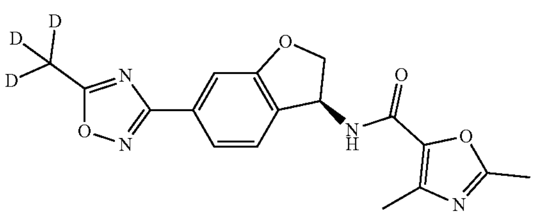 [SMILES: [2H]C([2H])([2H])c1nc(-c2ccc3c(c2)OC[C@H]3NC(=O)c2oc(C)nc2C)no1] | (S)-2,4-dimethyl-N-(6-(5-(methyl-d3)-1,2,4-oxadiazol-3-yl)-2,3-dihydrobenzofuran-3-yl)oxazole-5-carboxamide |
| 269 | 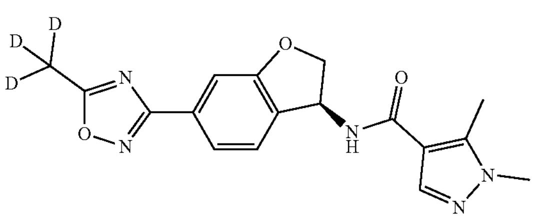 [SMILES: [2H]C([2H])([2H])c1nc(-c2ccc3c(c2)OC[C@H]3NC(=O)c2cnn(C)c2C)no1] | (S)-1,5-dimethyl-N-(6-(5-(methyl-d3)-1,2,4-oxadiazol-3-yl)-2,3-dihydrobenzofuran-3-yl)-1H-pyrazole-4-carboxamide |
| 270 | 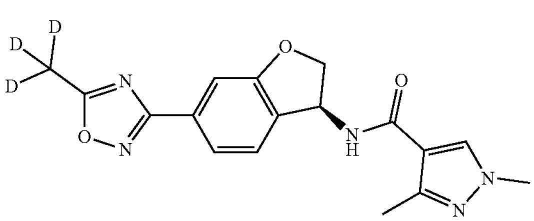 [SMILES: [2H]C([2H])([2H])c1nc(-c2ccc3c(c2)OC[C@H]3NC(=O)c2cn(C)nc2C)no1] | (S)-1,3-dimethyl-N-(6-(5-(methyl-d3)-1,2,4-oxadiazol-3-yl)-2,3-dihydrobenzofuran-3-yl)-1H-pyrazole-4-carboxamide |

TABLE 1-continued

| Cmpd No. | Structure | Name |
| --- | --- | --- |
| 271 | 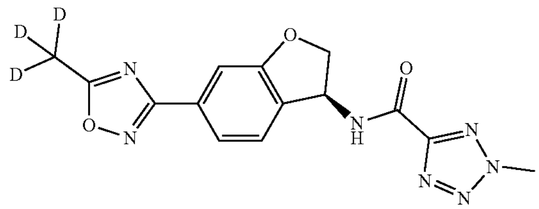 [SMILES: [2H]C([2H])([2H])c1nc(-c2ccc3c(c2)OC[C@H]3NC(=O)c2nnn(C)n2)no1] | (S)-2-methyl-N-(6-(5-(methyl-d3)-1,2,4-oxadiazol-3-yl)-2,3-dihydrobenzofuran-3-yl)-2H-tetrazole-5-carboxamide |
| 272 | 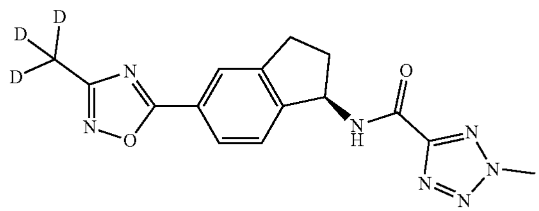 [SMILES: [2H]C([2H])([2H])c1noc(-c2ccc3c(c2)CC[C@H]3NC(=O)c2nnn(C)n2)n1] | (R)-2-methyl-N-(5-(3-(methyl-d3)-1,2,4-oxadiazol-5-yl)-2,3-dihydro-1H-inden-1-yl)-2H-tetrazole-5-carboxamide |
| 273 | 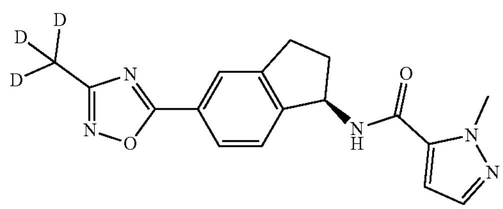 | (R)-1-methyl-N-(5-(3-(methyl-d3)-1,2,4-oxadiazol-5-yl)-2,3-dihydro-1H-inden-1-yl)-1H-pyrazole-5-carboxamide |
| 274 | 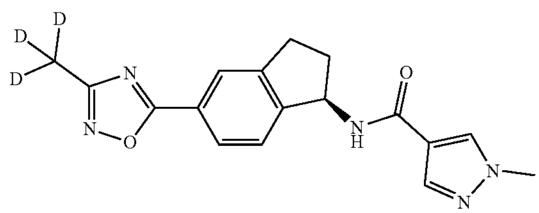 | (R)-1-methyl-N-(5-(3-(methyl-d3)-1,2,4-oxadiazol-5-yl)-2,3-dihydro-1H-inden-1-yl)-1H-pyrazole-4-carboxamide |
| 275 | 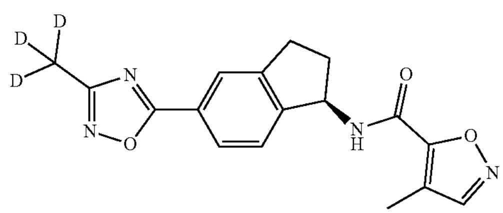 [SMILES: [2H]C([2H])([2H])c1noc(-c2ccc3c(c2)CC[C@H]3NC(=O)c2oncc2C)n1] | (R)-4-methyl-N-(5-(3-(methyl-d3)-1,2,4-oxadiazol-5-yl)-2,3-dihydro-1H-inden-1-yl)isoxazole-5-carboxamide |
| 276 | 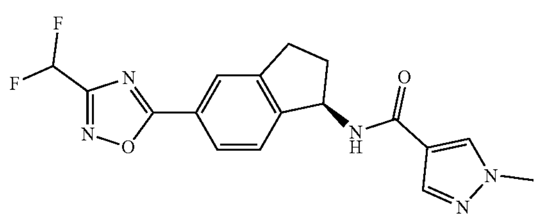 [SMILES: Cn1cc(C(=O)N[C@@H]2CCc3cc(-c4nc(C(F)F)no4)ccc32)cn1] | (R)-N-(5-(3-(difluoromethyl)-1,2,4-oxadiazol-5-yl)-2,3-dihydro-1H-inden-1-yl)-1-methyl-1H-pyrazole-4-carboxamide |
| 277 | 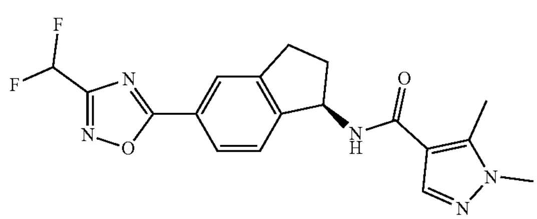 [SMILES: Cc1c(C(=O)N[C@@H]2CCc3cc(-c4nc(C(F)F)no4)ccc32)cnn1C] | (R)-N-(5-(3-(difluoromethyl)-1,2,4-oxadiazol-5-yl)-2,3-dihydro-1H-inden-1-yl)-1,5-dimethyl-1H-pyrazole-4-carboxamide |

TABLE 1-continued

| Cmpd No. | Structure | Name |
|---|---|---|
| 278 | 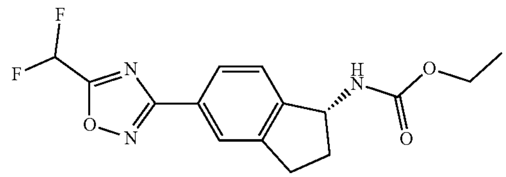 [SMILES: CCOC(=O)N[C@@H]1CCc2cc(-c3noc(C(F)F)n3)ccc21] | ethyl (R)-(5-(5-(difluoromethyl)-1,2,4-oxadiazol-3-yl)-2,3-dihydro-1H-inden-1-yl)carbamate |
| 279 | 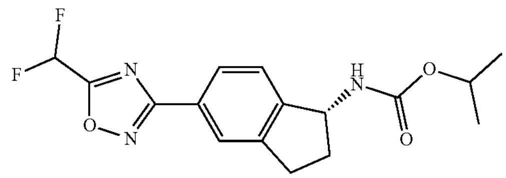 [SMILES: CC(C)OC(=O)N[C@@H]1CCc2cc(-c3noc(C(F)F)n3)ccc21] | isopropyl (R)-(5-(5-(difluoromethyl)-1,2,4-oxadiazol-3-yl)-2,3-dihydro-1H-inden-1-yl)carbamate |
| 280 | 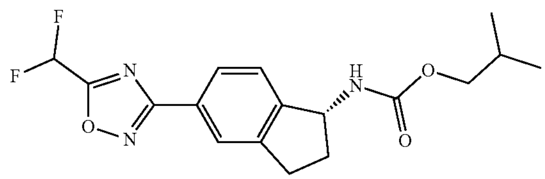 [SMILES: CC(C)COC(=O)N[C@@H]1CCc2cc(-c3noc(C(F)F)n3)ccc21] | isobutyl (R)-(5-(5-(difluoromethyl)-1,2,4-oxadiazol-3-yl)-2,3-dihydro-1H-inden-1-yl)carbamate |
| 281 | 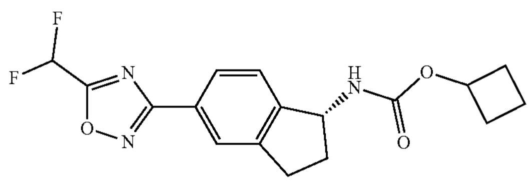 [SMILES: O=C(N[C@@H]1CCc2cc(-c3noc(C(F)F)n3)ccc21)OC1CCC1] | cyclobutyl (R)-(5-(5-(difluoromethyl)-1,2,4-oxadiazol-3-yl)-2,3-dihydro-1H-inden-1-yl)carbamate |
| 282 | 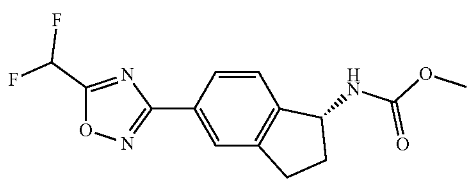 [SMILES: COC(=O)N[C@@H]1CCc2cc(-c3noc(C(F)F)n3)ccc21] | methyl (R)-(5-(5-(difluoromethyl)-1,2,4-oxadiazol-3-yl)-2,3-dihydro-1H-inden-1-yl)carbamate |
| 283 | 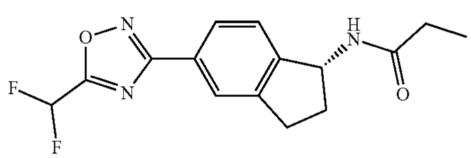 [SMILES: CCC(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)propionamide |
| 284 | 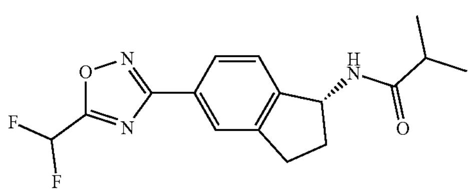 [SMILES: CC(C)C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)isobutyramide |
| 285 | 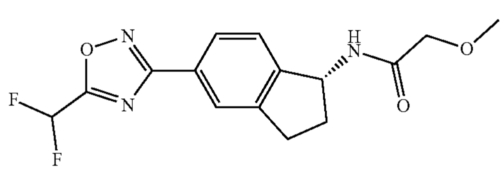 [SMILES: COCC(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-2-methoxyacetamide |

TABLE 1-continued

| Cmpd No. | Structure | Name |
|---|---|---|
| 286 | 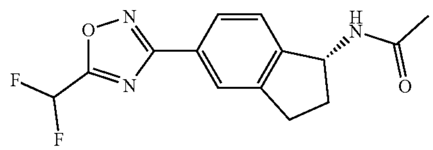 [SMILES: CC(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)acetamide |
| 287 | 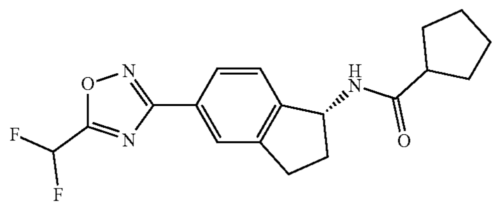 [SMILES: O=C(N[C@@H]1CCc2cc(-c3noc(C(F)F)n3)ccc21)C1CCCC1] | (R)-N-(5-(5-(difluoromethyl)-1,2,4-oxadiazol-3-yl)-2,3-dihydro-1H-inden-1-yl)cyclopentanecarboxamide |
| 288 | 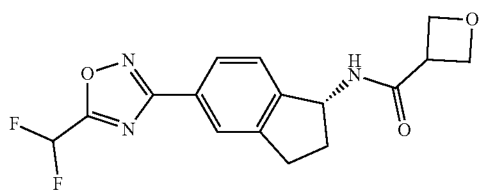 [SMILES: O=C(N[C@@H]1CCc2cc(-c3noc(C(F)F)n3)ccc21)C1COC1] | (R)-N-(5-(5-(difluoromethyl)-1,2,4-oxadiazol-3-yl)-2,3-dihydro-1H-inden-1-yl)oxetane-3-carboxamide |
| 289 | 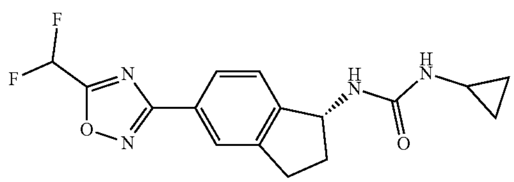 [SMILES: O=C(NC1CC1)N[C@@H]1CCc2cc(-c3noc(C(F)F)n3)ccc21] | (R)-1-cyclopropyl-3-(5-(5-(difluoromethyl)-1,2,4-oxadiazol-3-yl)-2,3-dihydro-1H-inden-1-yl)urea |
| 290 | 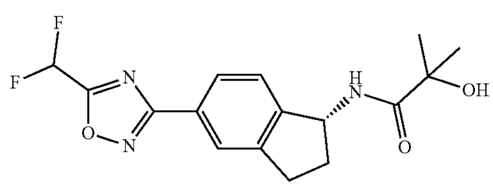 [SMILES: CC(C)(O)C(=O)N[C@@H]1CCc2cc(-c3noc(C(F)F)n3)ccc21] | (R)-N-(5-(5-(difluoromethyl)-1,2,4-oxadiazol-3-yl)-2,3-dihydro-1H-inden-1-yl)-2-hydroxy-2-methylpropanamide |
| 291 | 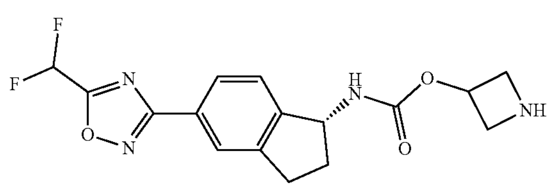 [SMILES: O=C(N[C@@H]1CCc2cc(-c3noc(C(F)F)n3)ccc21)OC1CNC1] | azetidin-3-yl (R)-(5-(5-(difluoromethyl)-1,2,4-oxadiazol-3-yl)-2,3-dihydro-1H-inden-1-yl)carbamate |
| 292 | 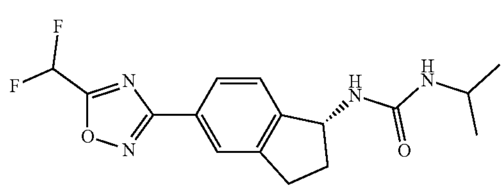 | (R)-1-(5-(5-(difluoromethyl)-1,2,4-oxadiazol-3-yl)-2,3-dihydro-1H-inden-1-yl)-3-isopropylurea |
| 293 | 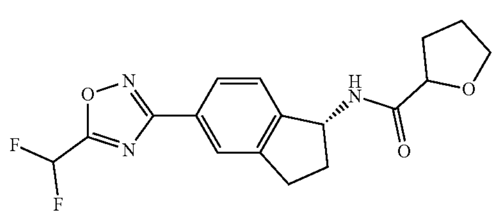 | N-((R)-5-(5-(difluoromethyl)-1,2,4-oxadiazol-3-yl)-2,3-dihydro-1H-inden-1-yl)tetrahydrofuran-2-carboxamide |

TABLE 1-continued

| Cmpd No. | Structure | Name |
|---|---|---|
| 294 | 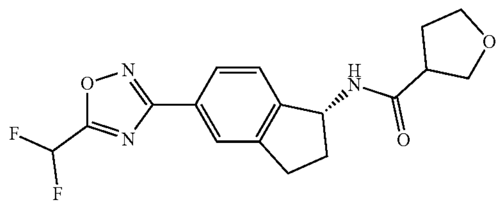 [SMILES: O=C(N[C@@H]1CCc2cc(-c3noc(C(F)F)n3)ccc21)C1CCOC1] | N-((R)-5-(5-(difluoromethyl)-1,2,4-oxadiazol-3-yl)-2,3-dihydro-1H-inden-1-yl)tetrahydrofuran-3-carboxamide |
| 295 | 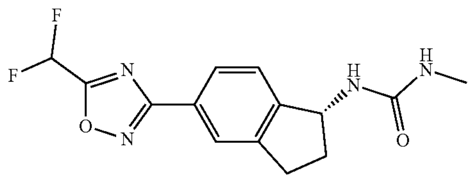 [SMILES: CNC(=O)N[C@@H]1CCc2cc(-c3noc(C(F)F)n3)ccc21] | (R)-1-(5-(5-(difluoromethyl)-1,2,4-oxadiazol-3-yl)-2,3-dihydro-1H-inden-1-yl)-3-methylurea |
| 296 | 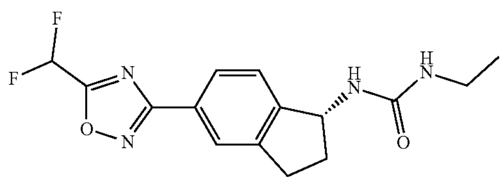 [SMILES: CCNC(=O)N[C@@H]1CCc2cc(-c3noc(C(F)F)n3)ccc21] | (R)-1-(5-(5-(difluoromethyl)-1,2,4-oxadiazol-3-yl)-2,3-dihydro-1H-inden-1-yl)-3-ethylurea |
| 297 | 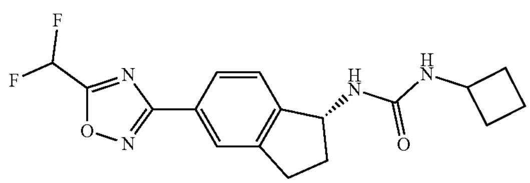 [SMILES: O=C(NC1CCC1)N[C@@H]1CCc2cc(-c3noc(C(F)F)n3)ccc21] | (R)-1-cyclobutyl-3-(5-(5-(difluoromethyl)-1,2,4-oxadiazol-3-yl)-2,3-dihydro-1H-inden-1-yl)urea |
| 298 | 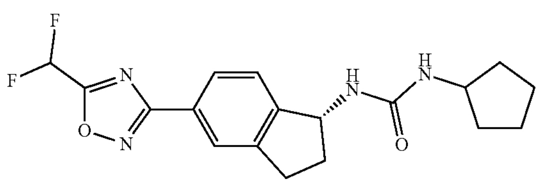 [SMILES: O=C(NC1CCCC1)N[C@@H]1CCc2cc(-c3noc(C(F)F)n3)ccc21] | (R)-1-cyclopentyl-3-(5-(5-(difluoromethyl)-1,2,4-oxadiazol-3-yl)-2,3-dihydro-1H-inden-1-yl)urea |
| 299 | 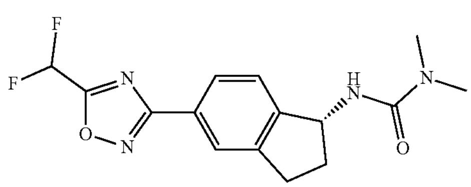 [SMILES: CN(C)C(=O)N[C@@H]1CCc2cc(-c3noc(C(F)F)n3)ccc21] | (R)-3-(5-(5-(difluoromethyl)-1,2,4-oxadiazol-3-yl)-2,3-dihydro-1H-inden-1-yl)-1,1-dimethylurea |
| 300 | 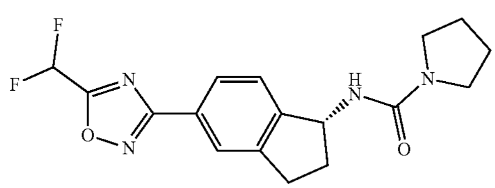 [SMILES: O=C(N[C@@H]1CCc2cc(-c3noc(C(F)F)n3)ccc21)N1CCCC1] | (R)-N-(5-(5-(difluoromethyl)-1,2,4-oxadiazol-3-yl)-2,3-dihydro-1H-inden-1-yl)pyrrolidine-1-carboxamide |
| 301 | 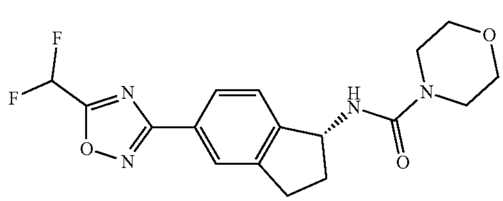 [SMILES: O=C(N[C@@H]1CCc2cc(-c3noc(C(F)F)n3)ccc21)N1CCOCC1] | (R)-N-(5-(5-(difluoromethyl)-1,2,4-oxadiazol-3-yl)-2,3-dihydro-1H-inden-1-yl)morpholine-4-carboxamide |

TABLE 1-continued

| Cmpd No. | Structure | Name |
|---|---|---|
| 302 | 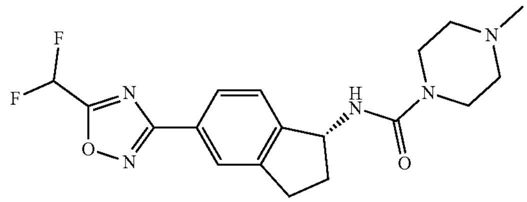 [SMILES: CN1CCN(C(=O)N[C@@H]2CCc3cc(-c4noc(C(F)F)n4)ccc32)CC1] | (R)-N-(5-(5-(difluoromethyl)-1,2,4-oxadiazol-3-yl)-2,3-dihydro-1H-inden-1-yl)-4-methylpiperazine-1-carboxamide |
| 303 | 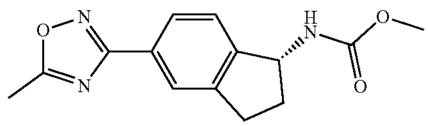 | methyl (R)-(5-(5-methyl-1,2,4-oxadiazol-3-yl)-2,3-dihydro-1H-inden-1-yl)carbamate |
| 304 | 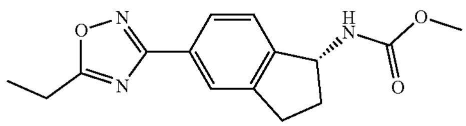 [SMILES: CCc1nc(-c2ccc3c(c2)CC[C@H]3NC(=O)OC)no1] | methyl (R)-(5-(5-ethyl-1,2,4-oxadiazol-3-yl)-2,3-dihydro-1H-inden-1-yl)carbamate |
| 305 | 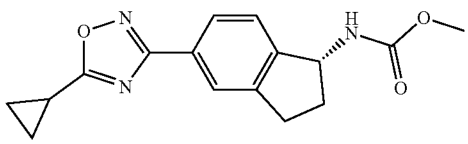 [SMILES: COC(=O)N[C@@H]1CCc2cc(-c3noc(C4CC4)n3)ccc21] | methyl (R)-(5-(5-cyclopropyl-1,2,4-oxadiazol-3-yl)-2,3-dihydro-1H-inden-1-yl)carbamate |
| 306 | 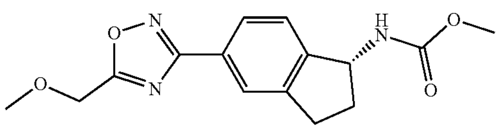 | methyl (R)-(5-(5-(methoxymethyl)-1,2,4-oxadiazol-3-yl)-2,3-dihydro-1H-inden-1-yl)carbamate |
| 307 | 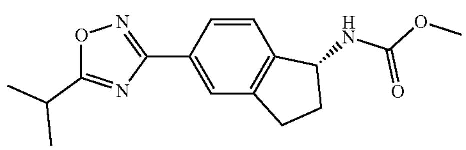 [SMILES: COC(=O)N[C@@H]1CCc2cc(-c3noc(C(C)C)n3)ccc21] | methyl (R)-(5-(5-isopropyl-1,2,4-oxadiazol-3-yl)-2,3-dihydro-1H-inden-1-yl)carbamate |
| 308 | 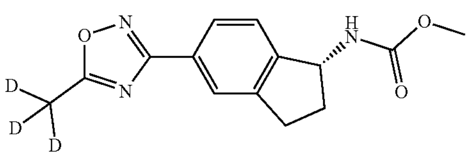 [SMILES: [2H]C([2H])([2H])c1nc(-c2ccc3c(c2)CC[C@H]3NC(=O)OC)no1] | methyl (R)-(5-(5-(methyl-d3)-1,2,4-oxadiazol-3-yl)-2,3-dihydro-1H-inden-1-yl)carbamate |
| 309 | 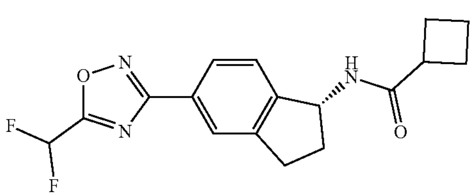 [SMILES: O=C(N[C@@H]1CCc2cc(-c3noc(C(F)F)n3)ccc21)C1CCC1] | (R)-N-(5-(5-(difluoromethyl)-1,2,4-oxadiazol-3-yl)-2,3-dihydro-1H-inden-1-yl)cyclobutanecarboxamide |
| 310 | 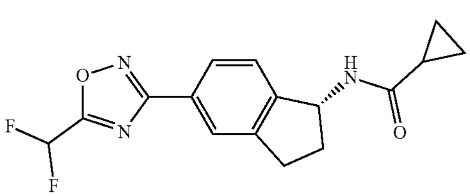 [SMILES: O=C(N[C@@H]1CCc2cc(-c3noc(C(F)F)n3)ccc21)C1CC1] | (R)-N-(5-(5-(difluoromethyl)-1,2,4-oxadiazol-3-yl)-2,3-dihydro-1H-inden-1-yl)cyclopropanecarboxamide |

US 12,065,436 B2

TABLE 1-continued

| Cmpd No. | Structure | Name |
|---|---|---|
| 311 | 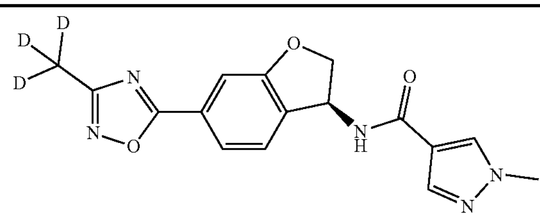 | (S)-1-methyl-N-(6-(3-(methyl-d3)-1,2,4-oxadiazol-5-yl)-2,3-dihydrobenzofuran-3-yl)-1H-pyrazole-4-carboxamide |
| 312 | 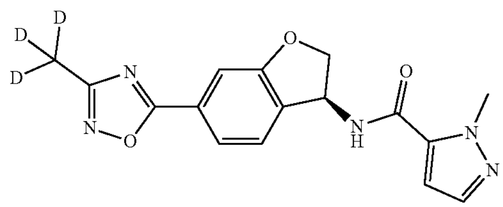 [SMILES: [2H]C([2H])([2H])c1noc(-c2ccc3c(c2)OC[C@H]3NC(=O)c2ccnn2C)n1] | (S)-1-methyl-N-(6-(3-(methyl-d3)-1,2,4-oxadiazol-5-yl)-2,3-dihydrobenzofuran-3-yl)-1H-pyrazole-5-carboxamide |
| 313 | 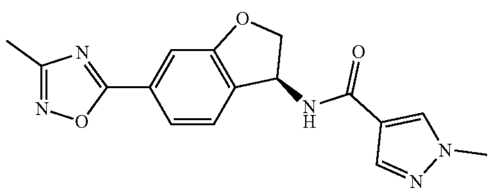 | (S)-1-methyl-N-(6-(3-methyl-1,2,4-oxadiazol-5-yl)-2,3-dihydrobenzofuran-3-yl)-1H-pyrazole-4-carboxamide |
| 314 | 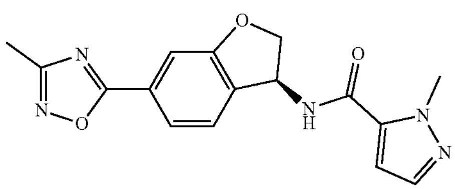 [SMILES: Cc1noc(-c2ccc3c(c2)OC[C@H]3NC(=O)c2ccnn2C)n1] | (S)-1-methyl-N-(6-(3-methyl-1,2,4-oxadiazol-5-yl)-2,3-dihydrobenzofuran-3-yl)-1H-pyrazole-5-carboxamide |
| 315 | 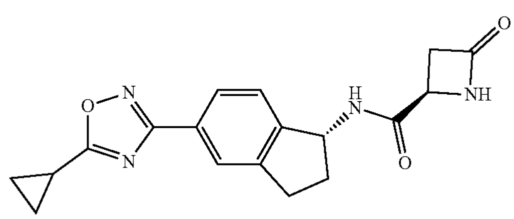 [SMILES: O=C1C[C@H](C(=O)N[C@@H]2CCc3cc(-c4noc(C5CC5)n4)ccc32)N1] | (R)-N-((R)-5-(5-cyclopropyl-1,2,4-oxadiazol-3-yl)-2,3-dihydro-1H-inden-1-yl)-4-oxoazetidine-2-carboxamide |
| 316 | 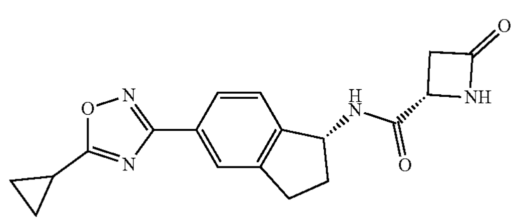 [SMILES: O=C1C[C@@H](C(=O)N[C@@H]2CCc3cc(-c4noc(C5CC5)n4)ccc32)N1] | (S)-N-((R)-5-(5-cyclopropyl-1,2,4-oxadiazol-3-yl)-2,3-dihydro-1H-inden-1-yl)-4-oxoazetidine-2-carboxamide |
| 317 | 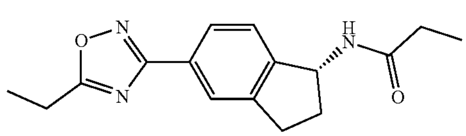 [SMILES: CCC(=O)N[C@@H]1CCc2cc(-c3noc(CC)n3)ccc21] | (R)-N-(5-(5-ethyl-1,2,4-oxadiazol-3-yl)-2,3-dihydro-1H-inden-1-yl)propionamide |
| 318 | 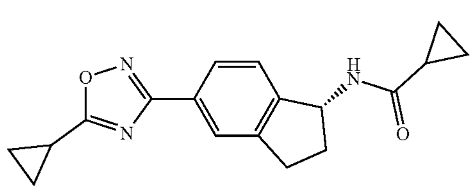 [SMILES: O=C(N[C@@H]1CCc2cc(-c3noc(C4CC4)n3)ccc21)C1CC1] | (R)-N-(5-(5-cyclopropyl-1,2,4-oxadiazol-3-yl)-2,3-dihydro-1H-inden-1-yl)cyclopropanecarboxamide |

| Cmpd No. | Structure | Name |
|---|---|---|
| 319 | 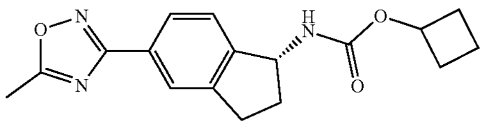 [SMILES: Cc1nc(-c2ccc3c(c2)CC[C@H]3NC(=O)OC2CCC2)no1] | cyclobutyl (R)-(5-(5-methyl-1,2,4-oxadiazol-3-yl)-2,3-dihydro-1H-inden-1-yl)carbamate |
| 320 | 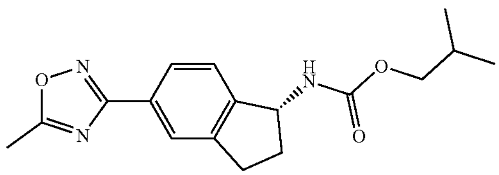 [SMILES: Cc1nc(-c2ccc3c(c2)CC[C@H]3NC(=O)OCC(C)C)no1] | isobutyl (R)-(5-(5-methyl-1,2,4-oxadiazol-3-yl)-2,3-dihydro-1H-inden-1-yl)carbamate |
| 321 | 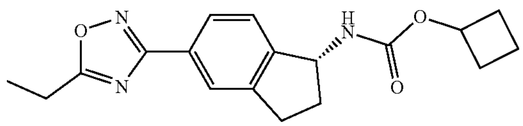 [SMILES: CCc1nc(-c2ccc3c(c2)CC[C@H]3NC(=O)OC2CCC2)no1] | cyclobutyl (R)-(5-(5-ethyl-1,2,4-oxadiazol-3-yl)-2,3-dihydro-1H-inden-1-yl)carbamate |
| 322 | 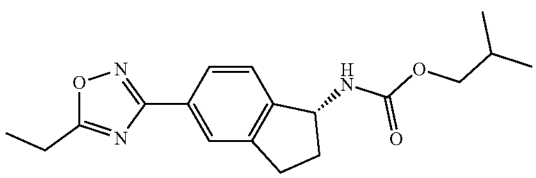 [SMILES: CCc1nc(-c2ccc3c(c2)CC[C@H]3NC(=O)OCC(C)C)no1] | isobutyl (R)-(5-(5-ethyl-1,2,4-oxadiazol-3-yl)-2,3-dihydro-1H-inden-1-yl)carbamate |
| 323 | 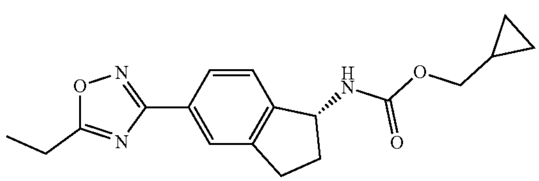 [SMILES: CCc1nc(-c2ccc3c(c2)CC[C@H]3NC(=O)OCC2CC2)no1] | cyclopropylmethyl (R)-(5-(5-ethyl-1,2,4-oxadiazol-3-yl)-2,3-dihydro-1H-inden-1-yl)carbamate |
| 324 | 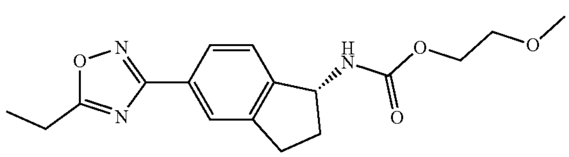 [SMILES: CCc1nc(-c2ccc3c(c2)CC[C@H]3NC(=O)OCCOC)no1] | 2-methoxyethyl (R)-(5-(5-ethyl-1,2,4-oxadiazol-3-yl)-2,3-dihydro-1H-inden-1-yl)carbamate |
| 325 | 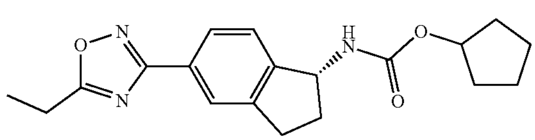 [SMILES: CCc1nc(-c2ccc3c(c2)CC[C@H]3NC(=O)OC2CCCC2)no1] | cyclopentyl (R)-(5-(5-ethyl-1,2,4-oxadiazol-3-yl)-2,3-dihydro-1H-inden-1-yl)carbamate |
| 326 | 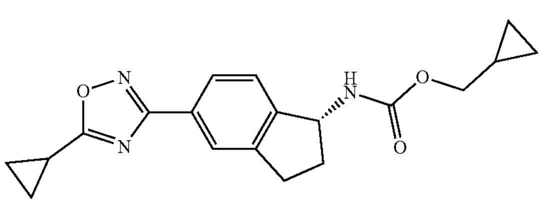 [SMILES: O=C(N[C@@H]1CCc2cc(-c3noc(C4CC4)n3)ccc21)OCC1CC1] | cyclopropylmethyl (R)-(5-(5-cyclopropyl-1,2,4-oxadiazol-3-yl)-2,3-dihydro-1H-inden-1-yl)carbamate |
| 327 | 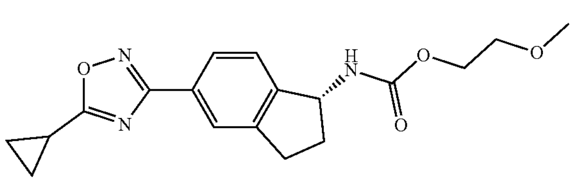 [SMILES: COCCOC(=O)N[C@@H]1CCc2cc(-c3noc(C4CC4)n3)ccc21] | 2-methoxyethyl (R)-(5-(5-cyclopropyl-1,2,4-oxadiazol-3-yl)-2,3-dihydro-1H-inden-1-yl)carbamate |

TABLE 1-continued

| Cmpd No. | Name |
|---|---|
| 328 | cyclopentyl (R)-(5-(5-cyclopropyl-1,2,4-oxadiazol-3-yl)-2,3-dihydro-1H-inden-1-yl)carbamate |
| 329 | (R)-N-(5-(5-ethyl-1,2,4-oxadiazol-3-yl)-2,3-dihydro-1H-inden-1-yl)-1-methylcyclopropane-1-carboxamide |
| 330 | (R)-N-(5-(5-cyclopropyl-1,2,4-oxadiazol-3-yl)-2,3-dihydro-1H-inden-1-yl)-1-methylcyclopropane-1-carboxamide |
| 331 | (R)-1-acetyl-N-((R)-5-(5-cyclopropyl-1,2,4-oxadiazol-3-yl)-2,3-dihydro-1H-inden-1-yl)azetidine-2-carboxamide |
| 332 | (S)-1-acetyl-N-((R)-5-(5-cyclopropyl-1,2,4-oxadiazol-3-yl)-2,3-dihydro-1H-inden-1-yl)azetidine-2-carboxamide |
| 333 | 2,2-difluoroethyl (R)-(5-(5-ethyl-1,2,4-oxadiazol-3-yl)-2,3-dihydro-1H-inden-1-yl)carbamate |
| 334 | 2,2-difluoroethyl (R)-(5-(5-cyclopropyl-1,2,4-oxadiazol-3-yl)-2,3-dihydro-1H-inden-1-yl)carbamate |
| 335 | (R)-N-((R)-5-(5-ethyl-1,2,4-oxadiazol-3-yl)-2,3-dihydro-1H-inden-1-yl)-5-oxopyrrolidine-2-carboxamide |

TABLE 1-continued

| Cmpd No. | Structure | Name |
| --- | --- | --- |
| 336 | 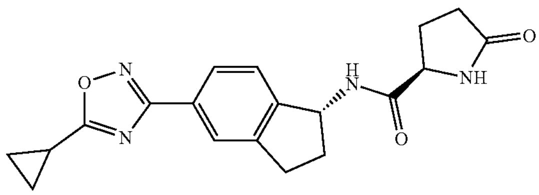 [SMILES: O=C1CC[C@H](C(=O)N[C@@H]2CCc3cc(-c4noc(C5CC5)n4)ccc32)N1] | (R)-N-((R)-5-(5-cyclopropyl-1,2,4-oxadiazol-3-yl)-2,3-dihydro-1H-inden-1-yl)-5-oxopyrrolidine-2-carboxamide |
| 337 | 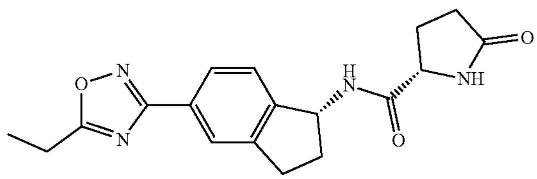 [SMILES: CCc1nc(-c2ccc3c(c2)CC[C@H]3NC(=O)[C@@H]2CCC(=O)N2)no1] | (S)-N-((R)-5-(5-ethyl-1,2,4-oxadiazol-3-yl)-2,3-dihydro-1H-inden-1-yl)-5-oxopyrrolidine-2-carboxamide |
| 338 | 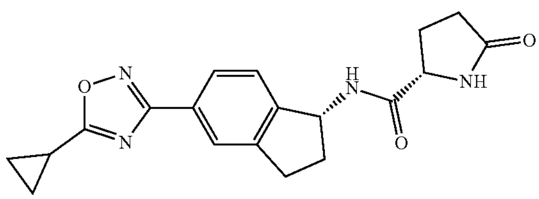 [SMILES: O=C1CC[C@@H](C(=O)N[C@@H]2CCc3cc(-c4noc(C5CC5)n4)ccc32)N1] | (S)-N-((R)-5-(5-cyclopropyl-1,2,4-oxadiazol-3-yl)-2,3-dihydro-1H-inden-1-yl)-5-oxopyrrolidine-2-carboxamide |
| 339 | 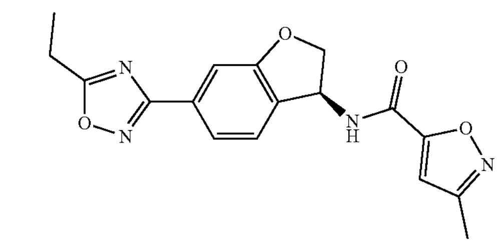 [SMILES: CCc1nc(-c2ccc3c(c2)OC[C@H]3NC(=O)c2cc(C)no2)no1] | (S)-N-(6-(5-ethyl-1,2,4-oxadiazol-3-yl)-2,3-dihydrobenzofuran-3-yl)-3-methylisoxazole-5-carboxamide |
| 340 | 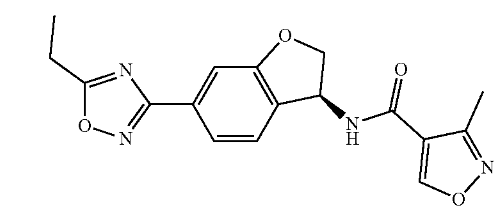 [SMILES: CCc1nc(-c2ccc3c(c2)OC[C@H]3NC(=O)c2conc2C)no1] | (S)-N-(6-(5-ethyl-1,2,4-oxadiazol-3-yl)-2,3-dihydrobenzofuran-3-yl)-3-methylisoxazole-4-carboxamide |
| 341 | 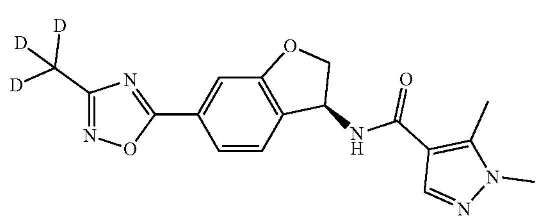 [SMILES: [2H]C([2H])([2H])c1noc(-c2ccc3c(c2)OC[C@H]3NC(=O)c2cnn(C)c2C)n1] | (S)-1,5-dimethyl-N-(6-(3-(methyl-d3)-1,2,4-oxadiazol-5-yl)-2,3-dihydrobenzofuran-3-yl)-1H-pyrazole-4-carboxamide |
| 342 | 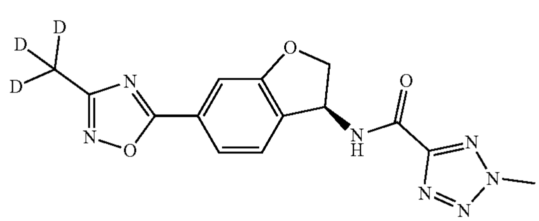 [SMILES: [2H]C([2H])([2H])c1noc(-c2ccc3c(c2)OC[C@H]3NC(=O)c2nnn(C)n2)n1] | (S)-2-methyl-N-(6-(3-(methyl-d3)-1,2,4-oxadiazol-5-yl)-2,3-dihydrobenzofuran-3-yl)-2H-tetrazole-5-carboxamide |

TABLE 1-continued

| Cmpd No. | Structure | Name |
|---|---|---|
| 343 | 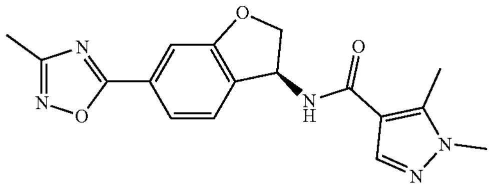 | (S)-1,5-dimethyl-N-(6-(3-methyl-1,2,4-oxadiazol-5-yl)-2,3-dihydrobenzofuran-3-yl)-1H-pyrazole-4-carboxamide |
| 344 | 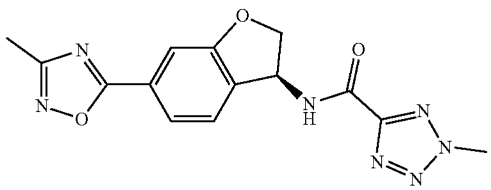 | (S)-2-methyl-N-(6-(3-methyl-1,2,4-oxadiazol-5-yl)-2,3-dihydrobenzofuran-3-yl)-2H-tetrazole-5-carboxamide |
| 345 | 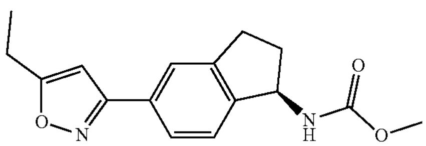 [SMILES: CCc1cc(-c2ccc3c(c2)CC[C@H]3NC(=O)OC)no1] | methyl (R)-(5-(5-ethylisoxazol-3-yl)-2,3-dihydro-1H-inden-1-yl)carbamate |
| 346 | 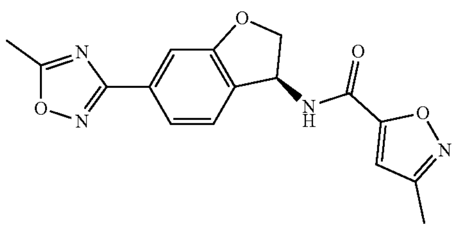 [SMILES: Cc1cc(C(=O)N[C@@H]2COc3cc(-c4noc(C)n4)ccc32)on1] | (S)-3-methyl-N-(6-(5-methyl-1,2,4-oxadiazol-3-yl)-2,3-dihydrobenzofuran-3-yl)isoxazole-5-carboxamide |
| 347 | 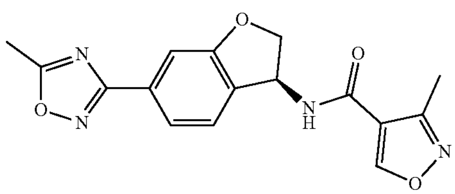 [SMILES: Cc1nc(-c2ccc3c(c2)OC[C@H]3NC(=O)c2conc2C)no1] | (S)-3-methyl-N-(6-(5-methyl-1,2,4-oxadiazol-3-yl)-2,3-dihydrobenzofuran-3-yl)isoxazole-4-carboxamide |
| 348 | 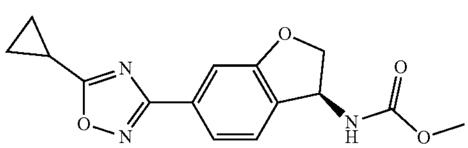 [SMILES: COC(=O)N[C@@H]1COc2cc(-c3noc(C4CC4)n3)ccc21] | methyl (S)-(6-(5-cyclopropyl-1,2,4-oxadiazol-3-yl)-2,3-dihydrobenzofuran-3-yl)carbamate |
| 349 | 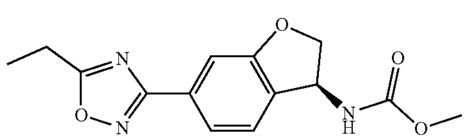 [SMILES: CCc1nc(-c2ccc3c(c2)OC[C@H]3NC(=O)OC)no1] | methyl (S)-(6-(5-ethyl-1,2,4-oxadiazol-3-yl)-2,3-dihydrobenzofuran-3-yl)carbamate |
| 350 | 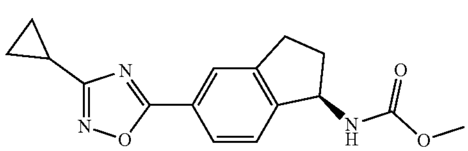 [SMILES: COC(=O)N[C@@H]1CCc2cc(-c3nc(C4CC4)no3)ccc21] | methyl (R)-(5-(3-cyclopropyl-1,2,4-oxadiazol-5-yl)-2,3-dihydro-1H-inden-1-yl)carbamate |

TABLE 1-continued

| Cmpd No. | Structure | Name |
|---|---|---|
| 351 | 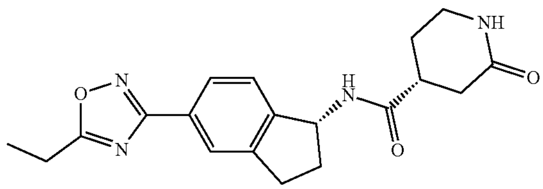 [SMILES: CCc1nc(-c2ccc3c(c2)CC[C@H]3NC(=O)[C@@H]2CCNC(=O)C2)no1] | (R)-N-((R)-5-(5-ethyl-1,2,4-oxadiazol-3-yl)-2,3-dihydro-1H-inden-1-yl)-2-oxopiperidine-4-carboxamide |
| 352 | 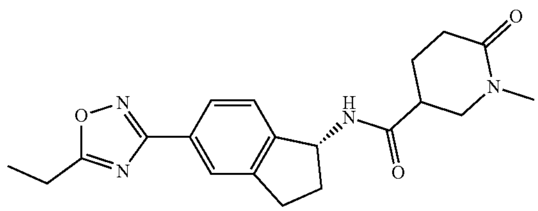 [SMILES: CCc1nc(-c2ccc3c(c2)CC[C@H]3NC(=O)C2CCC(=O)N(C)C2)no1] | N-((R)-5-(5-ethyl-1,2,4-oxadiazol-3-yl)-2,3-dihydro-1H-inden-1-yl)-1-methyl-6-oxopiperidine-3-carboxamide |
| 353 | 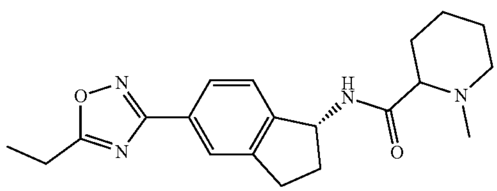 [SMILES: CCc1nc(-c2ccc3c(c2)CC[C@H]3NC(=O)C2CCCCN2C)no1] | N-((R)-5-(5-ethyl-1,2,4-oxadiazol-3-yl)-2,3-dihydro-1H-inden-1-yl)-1-methylpiperidine-2-carboxamide |
| 354 | 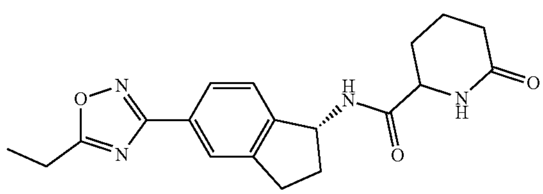 [SMILES: CCc1nc(-c2ccc3c(c2)CC[C@H]3NC(=O)C2CCCC(=O)N2)no1] | N-((R)-5-(5-ethyl-1,2,4-oxadiazol-3-yl)-2,3-dihydro-1H-inden-1-yl)-6-oxopiperidine-2-carboxamide |
| 355 | 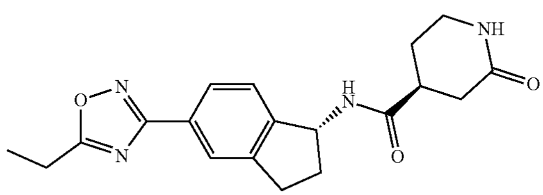 [SMILES: CCc1nc(-c2ccc3c(c2)CC[C@H]3NC(=O)[C@H]2CCNC(=O)C2)no1] | (S)-N-((R)-5-(5-ethyl-1,2,4-oxadiazol-3-yl)-2,3-dihydro-1H-inden-1-yl)-2-oxopiperidine-4-carboxamide |
| 356 | 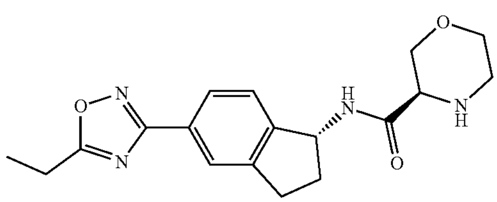 [SMILES: CCc1nc(-c2ccc3c(c2)CC[C@H]3NC(=O)[C@H]2COCCN2)no1] | (R)-N-((R)-5-(5-ethyl-1,2,4-oxadiazol-3-yl)-2,3-dihydro-1H-inden-1-yl)morpholine-3-carboxamide |
| 357 | 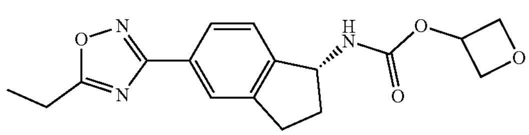 [SMILES: CCc1nc(-c2ccc3c(c2)CC[C@H]3NC(=O)OC2COC2)no1] | oxetan-3-yl (R)-(5-(5-ethyl-1,2,4-oxadiazol-3-yl)-2,3-dihydro-1H-inden-1-yl)carbamate |
| 358 | 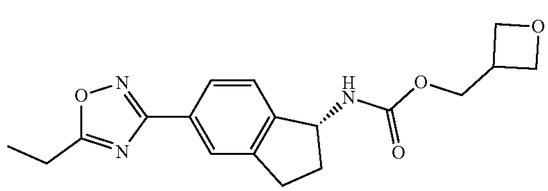 [SMILES: CCc1nc(-c2ccc3c(c2)CC[C@H]3NC(=O)OCC2COC2)no1] | oxetan-3-ylmethyl (R)-(5-(5-ethyl-1,2,4-oxadiazol-3-yl)-2,3-dihydro-1H-inden-1-yl)carbamate |

TABLE 1-continued

| Cmpd No. | Structure | Name |
|---|---|---|
| 359 | 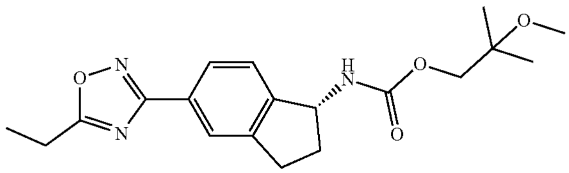 [SMILES: CCc1nc(-c2ccc3c(c2)CC[C@H]3NC(=O)OCC(C)(C)OC)no1] | 2-methoxy-2-methylpropyl (R)-(5-(5-ethyl-1,2,4-oxadiazol-3-yl)-2,3-dihydro-1H-inden-1-yl)carbamate |
| 360 | 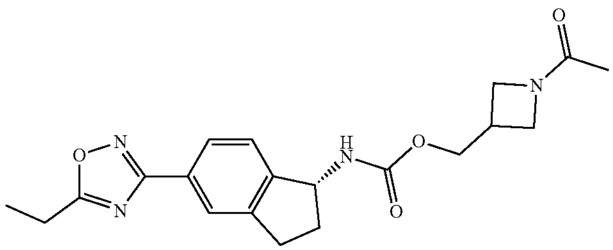 [SMILES: CCc1nc(-c2ccc3c(c2)CC[C@H]3NC(=O)OCC2CN(C(C)=O)C2)no1] | (1-acetylazetidin-3-yl)methyl (R)-(5-(5-ethyl-1,2,4-oxadiazol-3-yl)-2,3-dihydro-1H-inden-1-yl)carbamate |
| 361 | 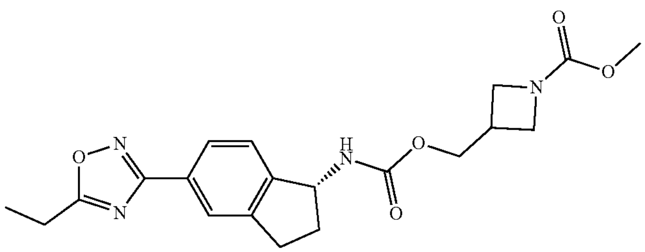 [SMILES: CCc1nc(-c2ccc3c(c2)CC[C@H]3NC(=O)OCC2CN(C(=O)OC)C2)no1] | methyl (R)-3-((((5-(5-ethyl-1,2,4-oxadiazol-3-yl)-2,3-dihydro-1H-inden-1-yl)carbamoyl)oxy)methyl)azetidine-1-carboxylate |
| 362 | 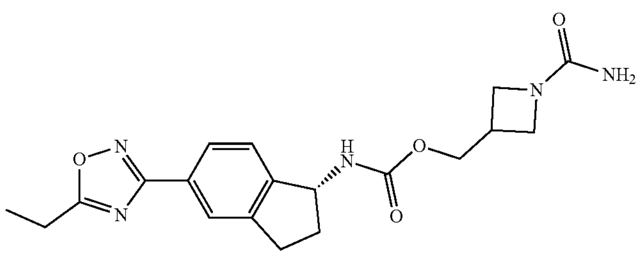 [SMILES: CCc1nc(-c2ccc3c(c2)CC[C@H]3NC(=O)OCC2CN(C(N)=O)C2)no1] | (1-carbamoylazetidin-3-yl)methyl (R)-(5-(5-ethyl-1,2,4-oxadiazol-3-yl)-2,3-dihydro-1H-inden-1-yl)carbamate |
| 363 | 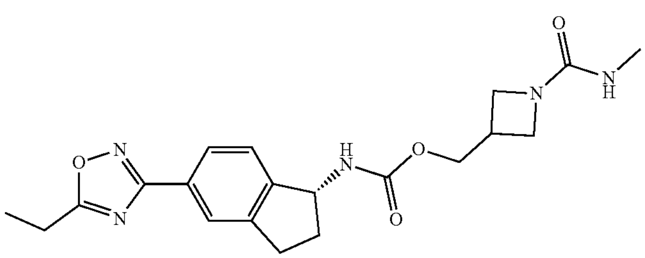 [SMILES: CCc1nc(-c2ccc3c(c2)CC[C@H]3NC(=O)OCC2CN(C(=O)NC)C2)no1] | (1-(methylcarbamoyl)azetidin-3-yl)methyl (R)-(5-(5-ethyl-1,2,4-oxadiazol-3-yl)-2,3-dihydro-1H-inden-1-yl)carbamate |
| 364 | 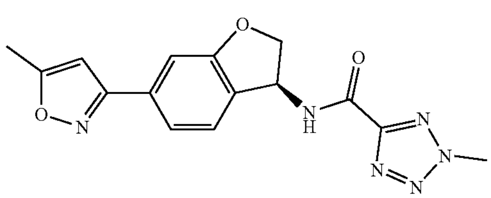 | (S)-2-methyl-N-(6-(5-methylisoxazol-3-yl)-2,3-dihydrobenzofuran-3-yl)-2H-tetrazole-5-carboxamide |
| 365 | 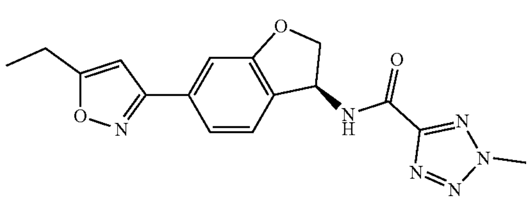 [SMILES: CCc1cc(-c2ccc3c(c2)OC[C@H]3NC(=O)c2nnn(C)n2)no1] | (S)-N-(6-(5-ethylisoxazol-3-yl)-2,3-dihydrobenzofuran-3-yl)-2-methyl-2H-tetrazole-5-carboxamide |

TABLE 1-continued

| Cmpd No. | Name |
|---|---|
| 366 | (R)-1-methyl-N-(5-(pyrimidin-2-yl)-2,3-dihydro-1H-inden-1-yl)-1H-pyrazole-5-carboxamide |
| 367 | (R)-1-methyl-N-(5-(pyridin-2-yl)-2,3-dihydro-1H-inden-1-yl)-1H-pyrazole-5-carboxamide |
| 368 | (R)-1-methyl-N-(5-(pyrazin-2-yl)-2,3-dihydro-1H-inden-1-yl)-1H-pyrazole-5-carboxamide |
| 369 | (R)-1-methyl-N-(5-(pyridazin-4-yl)-2,3-dihydro-1H-inden-1-yl)-1H-pyrazole-5-carboxamide |
| 370 | (R)-1-methyl-N-(5-(thiazol-2-yl)-2,3-dihydro-1H-inden-1-yl)-1H-pyrazole-5-carboxamide |
| 371 | (R)-1-methyl-N-(5-(5-methylthiazol-2-yl)-2,3-dihydro-1H-inden-1-yl)-1H-pyrazole-5-carboxamide |
| 372 | (R)-1-methyl-N-(5-phenyl-2,3-dihydro-1H-inden-1-yl)-1H-pyrazole-5-carboxamide |
| 373 | (R)-1-methyl-N-(5-(m-tolyl)-2,3-dihydro-1H-inden-1-yl)-1H-pyrazole-5-carboxamide |

TABLE 1-continued

| Cmpd No. | Structure | Name |
|---|---|---|
| 374 | 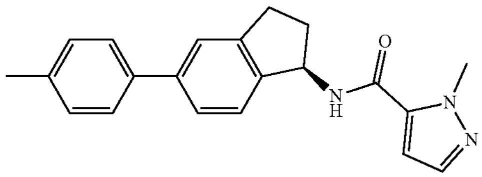 [SMILES: Cc1ccc(-c2ccc3c(c2)CC[C@H]3NC(=O)c2ccnn2C)cc1] | (R)-1-methyl-N-(5-(p-tolyl)-2,3-dihydro-1H-inden-1-yl)-1H-pyrazole-5-carboxamide |
| 375 | 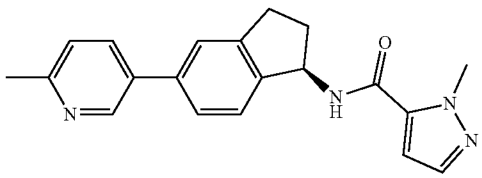 [SMILES: Cc1ccc(-c2ccc3c(c2)CC[C@H]3NC(=O)c2ccnn2C)cn1] | (R)-1-methyl-N-(5-(6-methylpyridin-3-yl)-2,3-dihydro-1H-inden-1-yl)-1H-pyrazole-5-carboxamide |
| 376 | 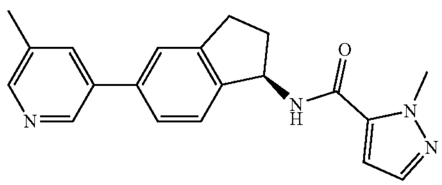 [SMILES: Cc1cncc(-c2ccc3c(c2)CC[C@H]3NC(=O)c2ccnn2C)c1] | (R)-1-methyl-N-(5-(5-methylpyridin-3-yl)-2,3-dihydro-1H-inden-1-yl)-1H-pyrazole-5-carboxamide |
| 377 | 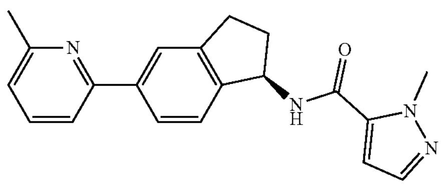 [SMILES: Cc1cccc(-c2ccc3c(c2)CC[C@H]3NC(=O)c2ccnn2C)n1] | (R)-1-methyl-N-(5-(6-methylpyridin-2-yl)-2,3-dihydro-1H-inden-1-yl)-1H-pyrazole-5-carboxamide |
| 378 | 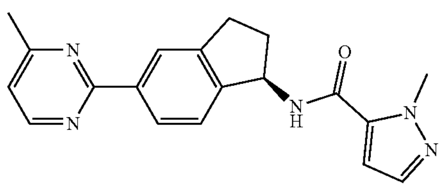 [SMILES: Cc1ccnc(-c2ccc3c(c2)CC[C@H]3NC(=O)c2ccnn2C)n1] | (R)-1-methyl-N-(5-(4-methylpyrimidin-2-yl)-2,3-dihydro-1H-inden-1-yl)-1H-pyrazole-5-carboxamide |
| 379 | 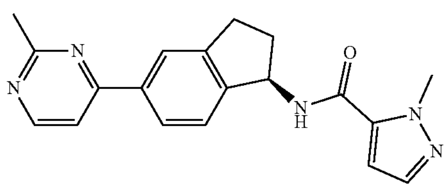 [SMILES: Cc1nccc(-c2ccc3c(c2)CC[C@H]3NC(=O)c2ccnn2C)n1] | (R)-1-methyl-N-(5-(2-methylpyrimidin-4-yl)-2,3-dihydro-1H-inden-1-yl)-1H-pyrazole-5-carboxamide |
| 380 | 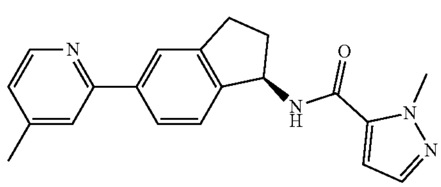 [SMILES: Cc1ccnc(-c2ccc3c(c2)CC[C@H]3NC(=O)c2ccnn2C)c1] | (R)-1-methyl-N-(5-(4-methylpyridin-2-yl)-2,3-dihydro-1H-inden-1-yl)-1H-pyrazole-5-carboxamide |
| 381 | 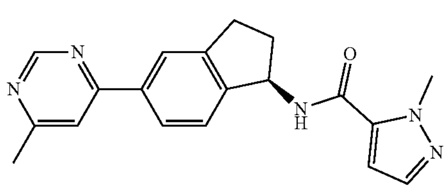 [SMILES: Cc1cc(-c2ccc3c(c2)CC[C@H]3NC(=O)c2ccnn2C)ncn1] | (R)-1-methyl-N-(5-(6-methylpyrimidin-4-yl)-2,3-dihydro-1H-inden-1-yl)-1H-pyrazole-5-carboxamide |

TABLE 1-continued

| Cmpd No. | Structure | Name |
|---|---|---|
| 382 | 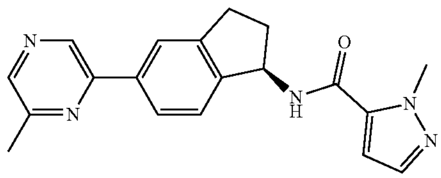 [SMILES: Cc1cncc(-c2ccc3c(c2)CC[C@H]3NC(=O)c2ccnn2C)n1] | (R)-1-methyl-N-(5-(6-methylpyrazin-2-yl)-2,3-dihydro-1H-inden-1-yl)-1H-pyrazole-5-carboxamide |
| 383 | 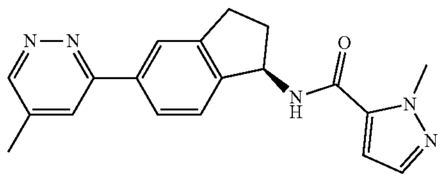 [SMILES: Cc1cnnc(-c2ccc3c(c2)CC[C@H]3NC(=O)c2ccnn2C)c1] | (R)-1-methyl-N-(5-(5-methylpyridazin-3-yl)-2,3-dihydro-1H-inden-1-yl)-1H-pyrazole-5-carboxamide |
| 384 | 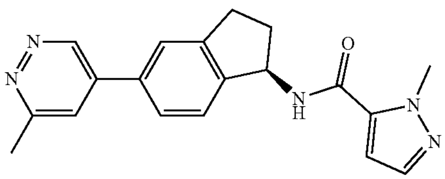 [SMILES: Cc1cc(-c2ccc3c(c2)CC[C@H]3NC(=O)c2ccnn2C)cnn1] | (R)-1-methyl-N-(5-(6-methylpyridazin-4-yl)-2,3-dihydro-1H-inden-1-yl)-1H-pyrazole-5-carboxamide |
| 385 | 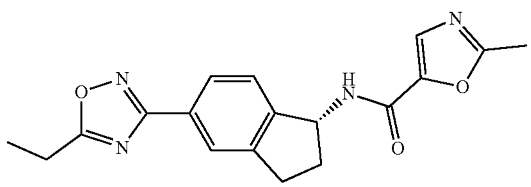 [SMILES: CCc1nc(-c2ccc3c(c2)CC[C@H]3NC(=O)c2cnc(C)o2)no1] | (R)-N-(5-(5-ethyl-1,2,4-oxadiazol-3-yl)-2,3-dihydro-1H-inden-1-yl)-2-methyloxazole-5-carboxamide |
| 386 | 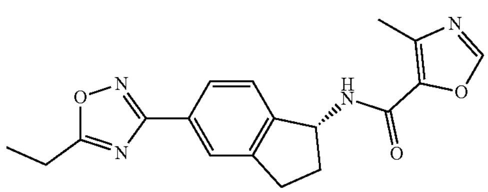 [SMILES: CCc1nc(-c2ccc3c(c2)CC[C@H]3NC(=O)c2ocnc2C)no1] | (R)-N-(5-(5-ethyl-1,2,4-oxadiazol-3-yl)-2,3-dihydro-1H-inden-1-yl)-4-methyloxazole-5-carboxamide |
| 387 | 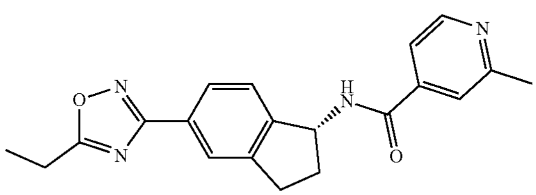 [SMILES: CCc1nc(-c2ccc3c(c2)CC[C@H]3NC(=O)c2ccnc(C)c2)no1] | (R)-N-(5-(5-ethyl-1,2,4-oxadiazol-3-yl)-2,3-dihydro-1H-inden-1-yl)-2-methylisonicotinamide |
| 388 | 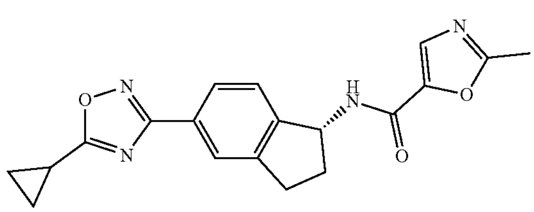 [SMILES: Cc1ncc(C(=O)N[C@@H]2CCc3cc(-c4noc(C5CC5)n4)ccc32)o1] | (R)-N-(5-(5-cyclopropyl-1,2,4-oxadiazol-3-yl)-2,3-dihydro-1H-inden-1-yl)-2-methyloxazole-5-carboxamide |
| 389 | 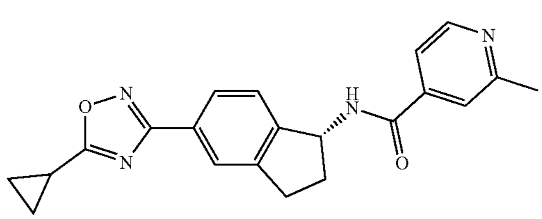 [SMILES: Cc1cc(C(=O)N[C@@H]2CCc3cc(-c4noc(C5CC5)n4)ccc32)ccn1] | (R)-N-(5-(5-cyclopropyl-1,2,4-oxadiazol-3-yl)-2,3-dihydro-1H-inden-1-yl)-2-methylisonicotinamide |

TABLE 1-continued

| Cmpd No. | Structure | Name |
|---|---|---|
| 390 | 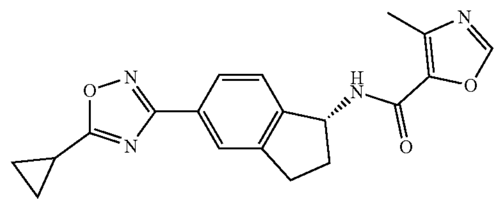 [SMILES: Cc1ncoc1C(=O)N[C@@H]1CCc2cc(-c3noc(C4CC4)n3)ccc21] | (R)-N-(5-(5-cyclopropyl-1,2,4-oxadiazol-3-yl)-2,3-dihydro-1H-inden-1-yl)-4-methyloxazole-5-carboxamide |
| 391 | 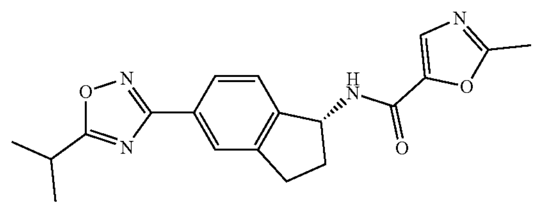 [SMILES: Cc1ncc(C(=O)N[C@@H]2CCc3cc(-c4noc(C(C)C)n4)ccc32)o1] | (R)-N-(5-(5-isopropyl-1,2,4-oxadiazol-3-yl)-2,3-dihydro-1H-inden-1-yl)-2-methyloxazole-5-carboxamide |
| 392 | 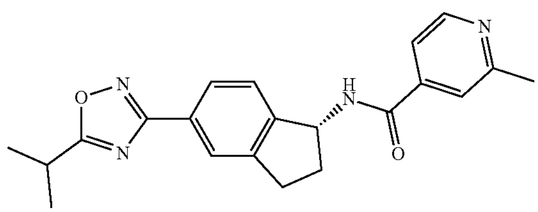 [SMILES: Cc1cc(C(=O)N[C@@H]2CCc3cc(-c4noc(C(C)C)n4)ccc32)ccn1] | (R)-N-(5-(5-isopropyl-1,2,4-oxadiazol-3-yl)-2,3-dihydro-1H-inden-1-yl)-2-methylisonicotinamide |
| 393 | 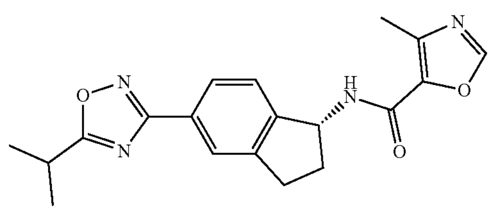 [SMILES: Cc1ncoc1C(=O)N[C@@H]1CCc2cc(-c3noc(C(C)C)n3)ccc21] | (R)-N-(5-(5-isopropyl-1,2,4-oxadiazol-3-yl)-2,3-dihydro-1H-inden-1-yl)-4-methyloxazole-5-carboxamide |
| 394 | 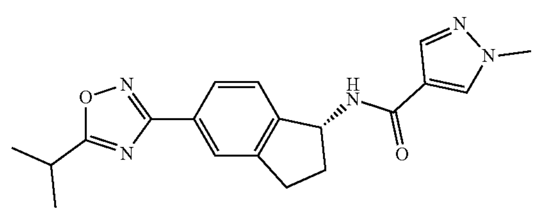 [SMILES: CC(C)c1nc(-c2ccc3c(c2)CC[C@H]3NC(=O)c2cnn(C)c2)no1] | (R)-N-(5-(5-isopropyl-1,2,4-oxadiazol-3-yl)-2,3-dihydro-1H-inden-1-yl)-1-methyl-1H-pyrazole-4-carboxamide |
| 395 | 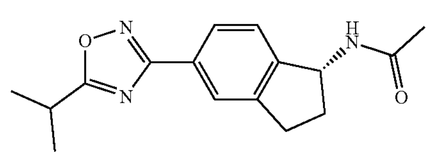 [SMILES: CC(=O)N[C@@H]1CCc2cc(-c3noc(C(C)C)n3)ccc21] | (R)-N-(5-(5-isopropyl-1,2,4-oxadiazol-3-yl)-2,3-dihydro-1H-inden-1-yl)acetamide |
| 396 | 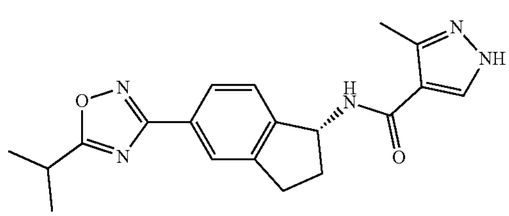 [SMILES: Cc1n[nH]cc1C(=O)N[C@@H]1CCc2cc(-c3noc(C(C)C)n3)ccc21] | (R)-N-(5-(5-isopropyl-1,2,4-oxadiazol-3-yl)-2,3-dihydro-1H-inden-1-yl)-3-methyl-1H-pyrazole-4-carboxamide |

TABLE 1-continued

| Cmpd No. | Structure | Name |
|---|---|---|
| 397 | 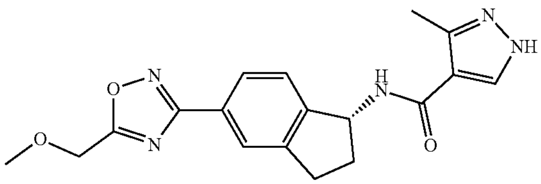 [SMILES: COCc1nc(-c2ccc3c(c2)CC[C@H]3NC(=O)c2c[nH]nc2C)no1] | (R)-N-(5-(5-(methoxymethyl)-1,2,4-oxadiazol-3-yl)-2,3-dihydro-1H-inden-1-yl)-3-methyl-1H-pyrazole-4-carboxamide |
| 398 | 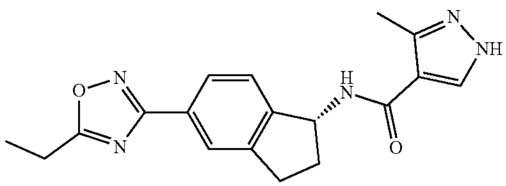 [SMILES: CCc1nc(-c2ccc3c(c2)CC[C@H]3NC(=O)c2c[nH]nc2C)no1] | (R)-N-(5-(5-ethyl-1,2,4-oxadiazol-3-yl)-2,3-dihydro-1H-inden-1-yl)-3-methyl-1H-pyrazole-4-carboxamide |
| 399 | 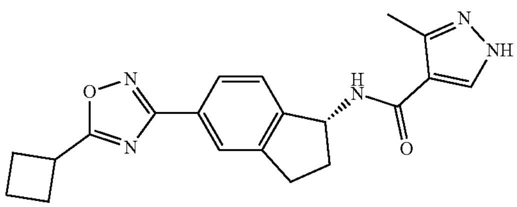 [SMILES: Cc1n[nH]cc1C(=O)N[C@@H]1CCc2cc(-c3noc(C4CCC4)n3)ccc21] | (R)-N-(5-(5-cyclobutyl-1,2,4-oxadiazol-3-yl)-2,3-dihydro-1H-inden-1-yl)-3-methyl-1H-pyrazole-4-carboxamide |
| 400 | 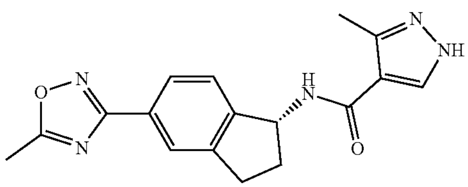 [SMILES: Cc1nc(-c2ccc3c(c2)CC[C@H]3NC(=O)c2c[nH]nc2C)no1] | (R)-3-methyl-N-(5-(5-methyl-1,2,4-oxadiazol-3-yl)-2,3-dihydro-1H-inden-1-yl)-1H-pyrazole-4-carboxamide |
| 401 | 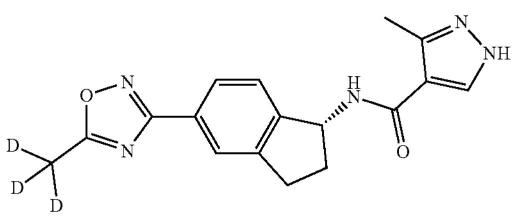 [SMILES: [2H]C([2H])([2H])c1nc(-c2ccc3c(c2)CC[C@H]3NC(=O)c2c[nH]nc2C)no1] | (R)-3-methyl-N-(5-(5-(methyl-d3)-1,2,4-oxadiazol-3-yl)-2,3-dihydro-1H-inden-1-yl)-1H-pyrazole-4-carboxamide |
| 402 | 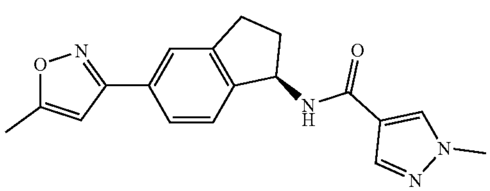 | (R)-1-methyl-N-(5-(5-methylisoxazol-3-yl)-2,3-dihydro-1H-inden-1-yl)-1H-pyrazole-4-carboxamide |
| 403 | 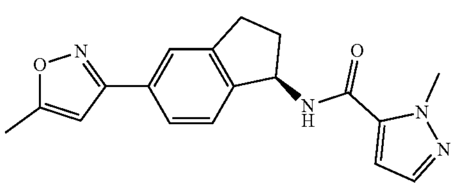 [SMILES: Cc1cc(-c2ccc3c(c2)CC[C@H]3NC(=O)c2ccnn2C)no1] | (R)-1-methyl-N-(5-(5-methylisoxazol-3-yl)-2,3-dihydro-1H-inden-1-yl)-1H-pyrazole-5-carboxamide |
| 404 | 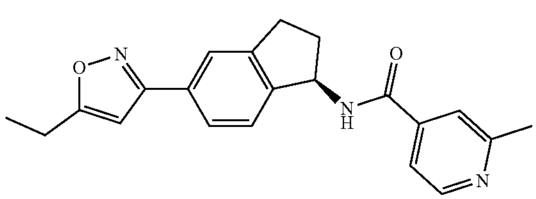 [SMILES: CCc1cc(-c2ccc3c(c2)CC[C@H]3NC(=O)c2ccnc(C)c2)no1] | (R)-N-(5-(5-ethylisoxazol-3-yl)-2,3-dihydro-1H-inden-1-yl)-2-methylisonicotinamide |

TABLE 1-continued

| Cmpd No. | Structure | Name |
|---|---|---|
| 405 | 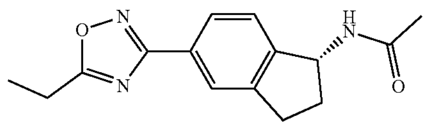 [SMILES: CCc1nc(-c2ccc3c(c2)CC[C@H]3NC(C)=O)no1] | (R)-N-(5-(5-ethyl-1,2,4-oxadiazol-3-yl)-2,3-dihydro-1H-inden-1-yl)acetamide |
| 406 | 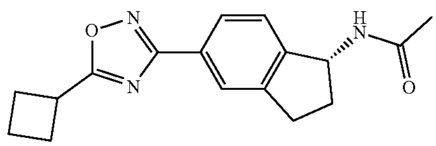 [SMILES: CC(=O)N[C@@H]1CCc2cc(-c3noc(C4CCC4)n3)ccc21] | (R)-N-(5-(5-cyclobutyl-1,2,4-oxadiazol-3-yl)-2,3-dihydro-1H-inden-1-yl)acetamide |
| 407 | 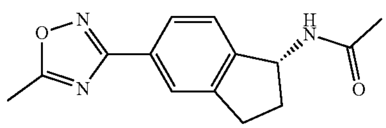 [SMILES: CC(=O)N[C@@H]1CCc2cc(-c3noc(C)n3)ccc21] | (R)-N-(5-(5-methyl-1,2,4-oxadiazol-3-yl)-2,3-dihydro-1H-inden-1-yl)acetamide |
| 408 | 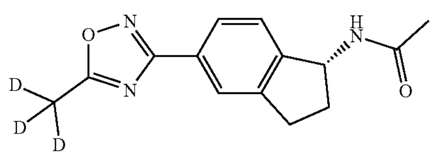 [SMILES: [2H]C([2H])([2H])c1nc(-c2ccc3c(c2)CC[C@H]3NC(C)=O)no1] | (R)-N-(5-(5-(methyl-d3)-1,2,4-oxadiazol-3-yl)-2,3-dihydro-1H-inden-1-yl)acetamide |
| 409 | 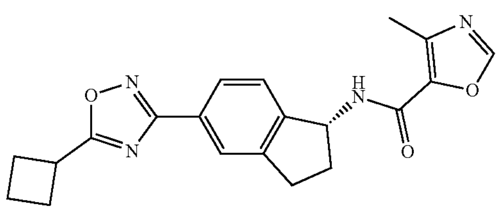 [SMILES: Cc1ncoc1C(=O)N[C@@H]1CCc2cc(-c3noc(C4CCC4)n3)ccc21] | (R)-N-(5-(5-cyclobutyl-1,2,4-oxadiazol-3-yl)-2,3-dihydro-1H-inden-1-yl)-4-methyloxazole-5-carboxamide |
| 410 | 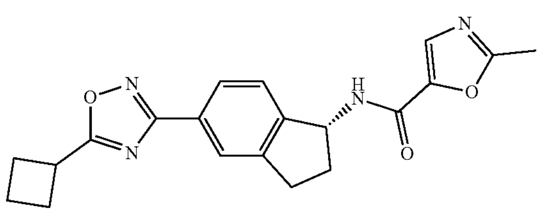 [SMILES: Cc1ncc(C(=O)N[C@@H]2CCc3cc(-c4noc(C5CCC5)n4)ccc32)o1] | (R)-N-(5-(5-cyclobutyl-1,2,4-oxadiazol-3-yl)-2,3-dihydro-1H-inden-1-yl)-2-methyloxazole-5-carboxamide |
| 411 | 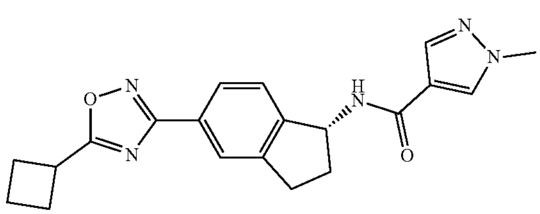 [SMILES: Cn1cc(C(=O)N[C@@H]2CCc3cc(-c4noc(C5CCC5)n4)ccc32)cn1] | (R)-N-(5-(5-cyclobutyl-1,2,4-oxadiazol-3-yl)-2,3-dihydro-1H-inden-1-yl)-1-methyl-1H-pyrazole-4-carboxamide |
| 412 | 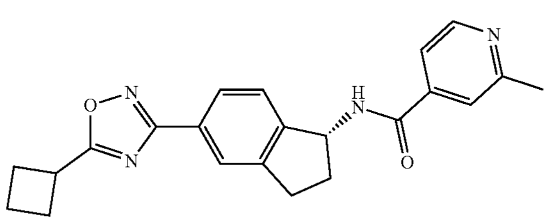 [SMILES: Cc1cc(C(=O)N[C@@H]2CCc3cc(-c4noc(C5CCC5)n4)ccc32)ccn1] | (R)-N-(5-(5-cyclobutyl-1,2,4-oxadiazol-3-yl)-2,3-dihydro-1H-inden-1-yl)-2-methylisonicotinamide |

TABLE 1-continued

| Cmpd No. | Name |
|---|---|
| 413 | (R)-N-(5-(5-ethylisoxazol-3-yl)-2,3-dihydro-1H-inden-1-yl)-1-methyl-1H-pyrazole-4-carboxamide |
| 414 | (R)-N-(5-(5-ethylisoxazol-3-yl)-2,3-dihydro-1H-inden-1-yl)-1-methyl-1H-pyrazole-5-carboxamide |
| 415 | (R)-N-(5-(5-ethylisoxazol-3-yl)-2,3-dihydro-1H-inden-1-yl)-2-methyloxazole-5-carboxamide |
| 416 | (R)-2-methyl-N-(5-(5-methylisoxazol-3-yl)-2,3-dihydro-1H-inden-1-yl)oxazole-5-carboxamide |
| 417 | (R)-N-(5-(5-ethylisoxazol-3-yl)-2,3-dihydro-1H-inden-1-yl)-4-methyloxazole-5-carboxamide |
| 418 | (R)-4-methyl-N-(5-(5-methylisoxazol-3-yl)-2,3-dihydro-1H-inden-1-yl)oxazole-5-carboxamide |
| 419 | (R)-N-(5-(5-cyclopropyl-1,2,4-oxadiazol-3-yl)-2,3-dihydro-1H-inden-1-yl)acetamide |
| 420 | (R)-N-(5-(5-cyclopropyl-1,2,4-oxadiazol-3-yl)-2,3-dihydro-1H-inden-1-yl)-3-methyl-1H-pyrazole-4-carboxamide |

TABLE 1-continued

| Cmpd No. | Structure | Name |
|---|---|---|
| 421 | 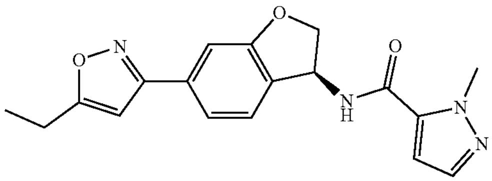 [SMILES: CCc1cc(-c2ccc3c(c2)OC[C@H]3NC(=O)c2ccnn2C)no1] | (S)-N-(6-(5-ethylisoxazol-3-yl)-2,3-dihydrobenzofuran-3-yl)-1-methyl-1H-pyrazole-5-carboxamide |
| 422 | 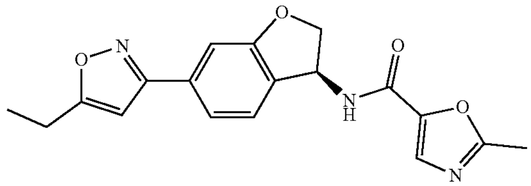 [SMILES: CCc1cc(-c2ccc3c(c2)OC[C@H]3NC(=O)c2cnc(C)o2)no1] | (S)-N-(6-(5-ethylisoxazol-3-yl)-2,3-dihydrobenzofuran-3-yl)-2-methyloxazole-5-carboxamide |
| 423 | 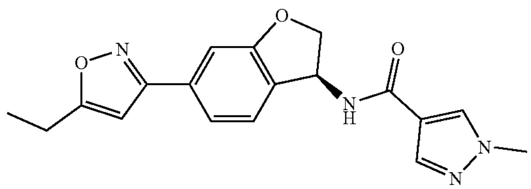 [SMILES: CCc1cc(-c2ccc3c(c2)OC[C@H]3NC(=O)c2cnn(C)c2)no1] | (S)-N-(6-(5-ethylisoxazol-3-yl)-2,3-dihydrobenzofuran-3-yl)-1-methyl-1H-pyrazole-4-carboxamide |
| 424 | 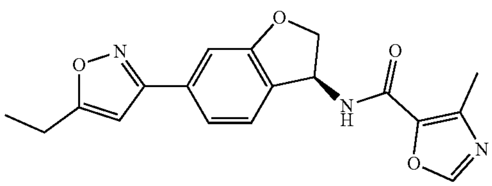 [SMILES: CCc1cc(-c2ccc3c(c2)OC[C@H]3NC(=O)c2ocnc2C)no1] | (S)-N-(6-(5-ethylisoxazol-3-yl)-2,3-dihydrobenzofuran-3-yl)-4-methyloxazole-5-carboxamide |
| 425 | 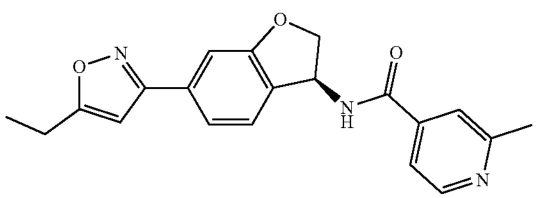 [SMILES: CCc1cc(-c2ccc3c(c2)OC[C@H]3NC(=O)c2ccnc(C)c2)no1] | (S)-N-(6-(5-ethylisoxazol-3-yl)-2,3-dihydrobenzofuran-3-yl)-2-methylisonicotinamide |
| 426 | 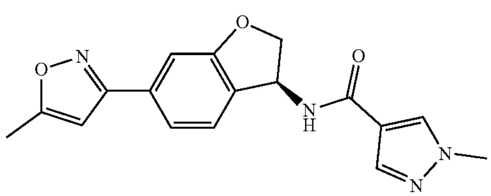 | (S)-1-methyl-N-(6-(5-methylisoxazol-3-yl)-2,3-dihydrobenzofuran-3-yl)-1H-pyrazole-4-carboxamide |
| 427 | 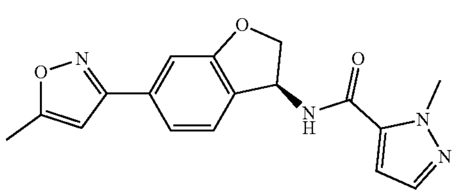 [SMILES: Cc1cc(-c2ccc3c(c2)OC[C@H]3NC(=O)c2ccnn2C)no1] | (S)-1-methyl-N-(6-(5-methylisoxazol-3-yl)-2,3-dihydrobenzofuran-3-yl)-1H-pyrazole-5-carboxamide |
| 428 | 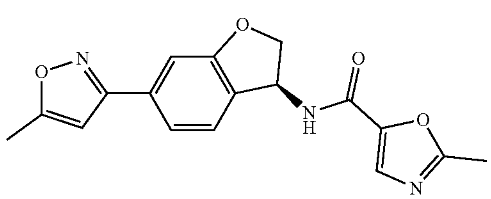 | (S)-2-methyl-N-(6-(5-methylisoxazol-3-yl)-2,3-dihydrobenzofuran-3-yl)oxazole-5-carboxamide |

TABLE 1-continued

| Cmpd No. | Structure | Name |
|---|---|---|
| 429 | 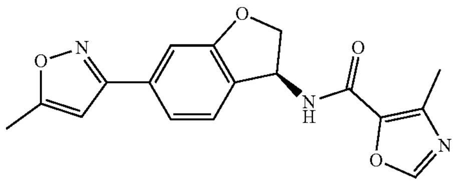 [SMILES: Cc1cc(-c2ccc3c(c2)OC[C@H]3NC(=O)c2ocnc2C)no1] | (S)-4-methyl-N-(6-(5-methylisoxazol-3-yl)-2,3-dihydrobenzofuran-3-yl)oxazole-5-carboxamide |
| 430 | 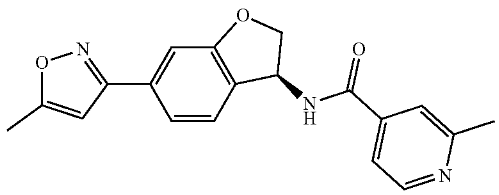 | (S)-2-methyl-N-(6-(5-methylisoxazol-3-yl)-2,3-dihydrobenzofuran-3-yl)isonicotinamide |
| 431 | 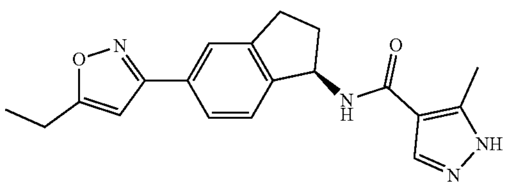 [SMILES: CCc1cc(-c2ccc3c(c2)CC[C@H]3NC(=O)c2cn[nH]c2C)no1] | (R)-N-(5-(5-ethylisoxazol-3-yl)-2,3-dihydro-1H-inden-1-yl)-5-methyl-1H-pyrazole-4-carboxamide |
| 432 | 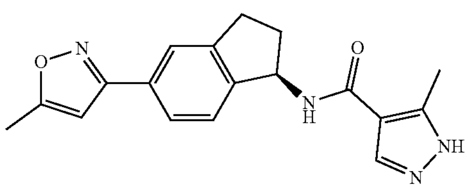 [SMILES: Cc1cc(-c2ccc3c(c2)CC[C@H]3NC(=O)c2cn[nH]c2C)no1] | (R)-5-methyl-N-(5-(5-methylisoxazol-3-yl)-2,3-dihydro-1H-inden-1-yl)-1H-pyrazole-4-carboxamide |
| 433 | 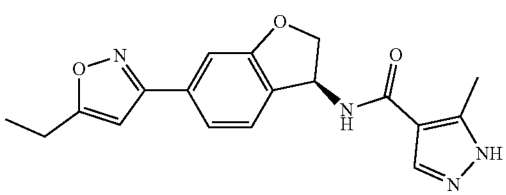 [SMILES: CCc1cc(-c2ccc3c(c2)OC[C@H]3NC(=O)c2cn[nH]c2C)no1] | (S)-N-(6-(5-ethylisoxazol-3-yl)-2,3-dihydrobenzofuran-3-yl)-5-methyl-1H-pyrazole-4-carboxamide |
| 434 | 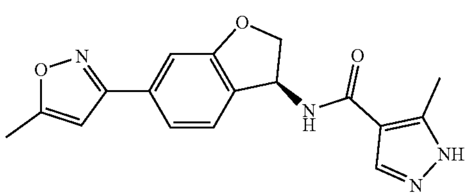 [SMILES: Cc1cc(-c2ccc3c(c2)OC[C@H]3NC(=O)c2cn[nH]c2C)no1] | (S)-5-methyl-N-(6-(5-methylisoxazol-3-yl)-2,3-dihydrobenzofuran-3-yl)-1H-pyrazole-4-carboxamide |
| 435 | 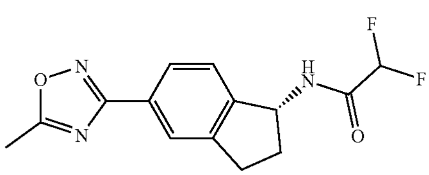 [SMILES: Cc1nc(-c2ccc3c(c2)CC[C@H]3NC(=O)C(F)F)no1] | (R)-2,2-difluoro-N-(5-(5-methyl-1,2,4-oxadiazol-3-yl)-2,3-dihydro-1H-inden-1-yl)acetamide |
| 436 | 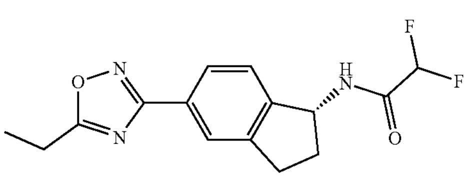 [SMILES: CCc1nc(-c2ccc3c(c2)CC[C@H]3NC(=O)C(F)F)no1] | (R)-N-(5-(5-ethyl-1,2,4-oxadiazol-3-yl)-2,3-dihydro-1H-inden-1-yl)-2,2-difluoroacetamide |

| Cmpd No. | Structure | Name |
|---|---|---|
| 437 | 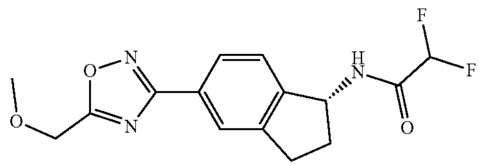 [SMILES: COCc1nc(-c2ccc3c(c2)CC[C@H]3NC(=O)C(F)F)no1] | (R)-2,2-difluoro-N-(5-(5-(methoxymethyl)-1,2,4-oxadiazol-3-yl)-2,3-dihydro-1H-inden-1-yl)acetamide |
| 438 | 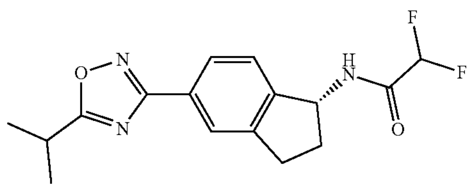 [SMILES: CC(C)c1nc(-c2ccc3c(c2)CC[C@H]3NC(=O)C(F)F)no1] | (R)-2,2-difluoro-N-(5-(5-isopropyl-1,2,4-oxadiazol-3-yl)-2,3-dihydro-1H-inden-1-yl)acetamide |
| 439 | 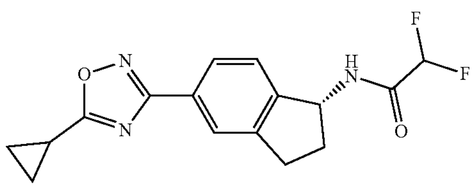 [SMILES: O=C(N[C@@H]1CCc2cc(-c3noc(C4CC4)n3)ccc21)C(F)F] | (R)-N-(5-(5-cyclopropyl-1,2,4-oxadiazol-3-yl)-2,3-dihydro-1H-inden-1-yl)-2,2-difluoroacetamide |
| 440 | 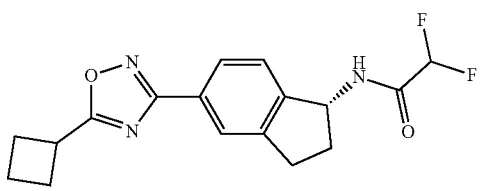 [SMILES: O=C(N[C@@H]1CCc2cc(-c3noc(C4CCC4)n3)ccc21)C(F)F] | (R)-N-(5-(5-cyclobutyl-1,2,4-oxadiazol-3-yl)-2,3-dihydro-1H-inden-1-yl)-2,2-difluoroacetamide |
| 441 | 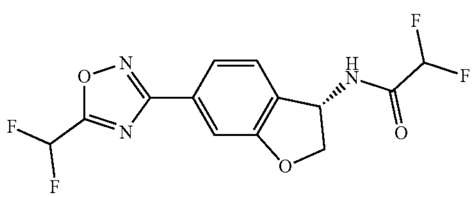 [SMILES: O=C(N[C@@H]1COc2cc(-c3noc(C(F)F)n3)ccc21)C(F)F] | (S)-N-(6-(5-(difluoromethyl)-1,2,4-oxadiazol-3-yl)-2,3-dihydrobenzofuran-3-yl)-2,2-difluoroacetamide |
| 442 | 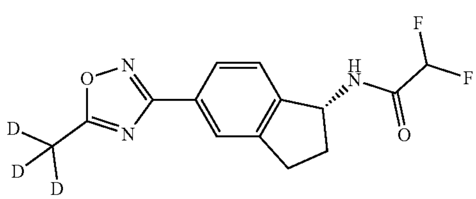 [SMILES: [2H]C([2H])([2H])c1nc(-c2ccc3c(c2)CC[C@H]3NC(=O)C(F)F)no1] | (R)-2,2-difluoro-N-(5-(5-(methyl-d3)-1,2,4-oxadiazol-3-yl)-2,3-dihydro-1H-inden-1-yl)acetamide |
| 443 | 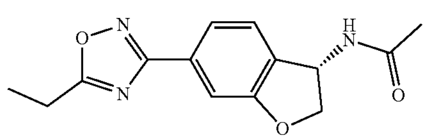 [SMILES: CCc1nc(-c2ccc3c(c2)OC[C@H]3NC(C)=O)no1] | (S)-N-(6-(5-ethyl-1,2,4-oxadiazol-3-yl)-2,3-dihydrobenzofuran-3-yl)acetamide |
| 444 | 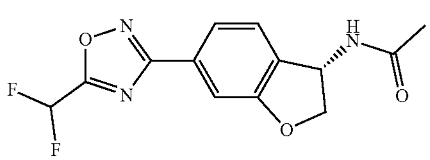 [SMILES: CC(=O)N[C@@H]1COc2cc(-c3noc(C(F)F)n3)ccc21] | (S)-N-(6-(5-(difluoromethyl)-1,2,4-oxadiazol-3-yl)-2,3-dihydrobenzofuran-3-yl)acetamide |

TABLE 1-continued

| Cmpd No. | Structure | Name |
|---|---|---|
| 445 | 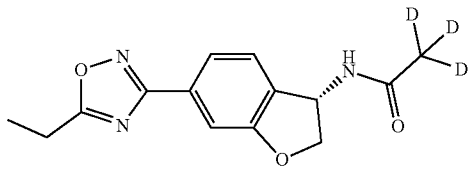 [SMILES: [2H]C([2H])([2H])C(=O)N[C@@H]1COc2cc(-c3noc(CC)n3)ccc21] | (S)-N-(6-(5-ethyl-1,2,4-oxadiazol-3-yl)-2,3-dihydrobenzofuran-3-yl)acetamide-2,2,2-d3 |
| 446 | 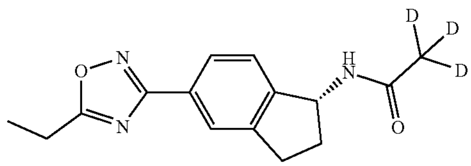 [SMILES: [2H]C([2H])([2H])C(=O)N[C@@H]1CCc2cc(-c3noc(CC)n3)ccc21] | (R)-N-(5-(5-ethyl-1,2,4-oxadiazol-3-yl)-2,3-dihydro-1H-inden-1-yl)acetamide-2,2,2-d3 |
| 447 | 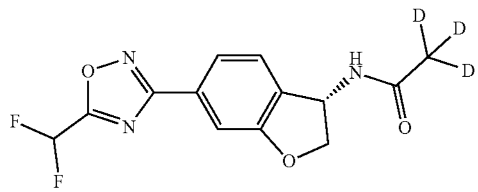 [SMILES: [2H]C([2H])([2H])C(=O)N[C@@H]1COc2cc(-c3noc(C(F)F)n3)ccc21] | (S)-N-(6-(5-(difluoromethyl)-1,2,4-oxadiazol-3-yl)-2,3-dihydrobenzofuran-3-yl)acetamide-2,2,2-d3 |
| 448 | 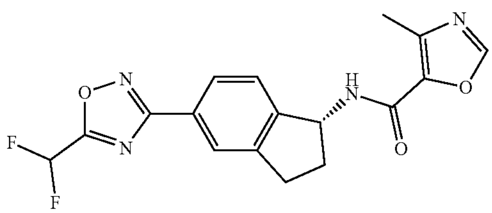 | (R)-N-(5-(5-(difluoromethyl)-1,2,4-oxadiazol-3-yl)-2,3-dihydro-1H-inden-1-yl)-4-methyloxazole-5-carboxamide |
| 449 | 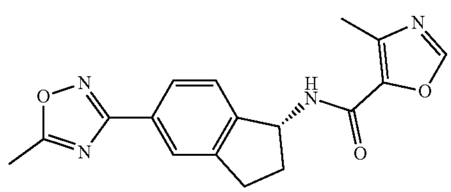 [SMILES: Cc1nc(-c2ccc3c(c2)CC[C@H]3NC(=O)c2ocnc2C)no1] | (R)-4-methyl-N-(5-(5-methyl-1,2,4-oxadiazol-3-yl)-2,3-dihydro-1H-inden-1-yl)oxazole-5-carboxamide |
| 450 | 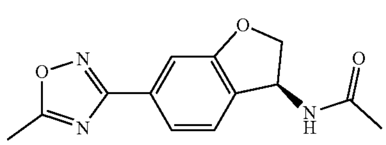 [SMILES: CC(=O)N[C@@H]1COc2cc(-c3noc(C)n3)ccc21] | (S)-N-(6-(5-methyl-1,2,4-oxadiazol-3-yl)-2,3-dihydrobenzofuran-3-yl)acetamide |
| 451 | 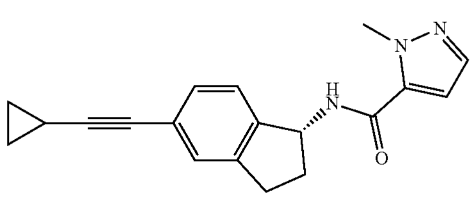 [SMILES: Cn1nccc1C(=O)N[C@@H]1CCc2cc(C#CC3CC3)ccc21] | (R)-N-(5-(cyclopropylethynyl)-2,3-dihydro-1H-inden-1-yl)-1-methyl-1H-pyrazole-5-carboxamide |
| 452 | 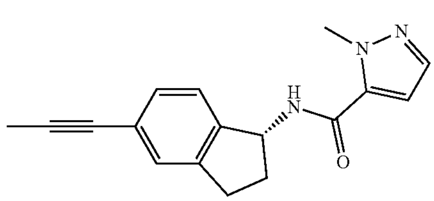 [SMILES: CC#Cc1ccc2c(c1)CC[C@H]2NC(=O)c1ccnn1C] | (R)-1-methyl-N-(5-(prop-1-yn-1-yl)-2,3-dihydro-1H-inden-1-yl)-1H-pyrazole-5-carboxamide |

TABLE 1-continued

| Cmpd No. | Structure | Name |
|---|---|---|
| 453 | 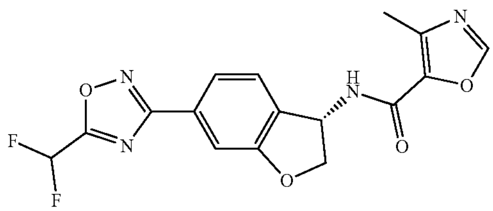 [SMILES: Cc1ncoc1C(=O)N[C@@H]1COc2cc(-c3noc(C(F)F)n3)ccc21] | (S)-N-(6-(5-(difluoromethyl)-1,2,4-oxadiazol-3-yl)-2,3-dihydrobenzofuran-3-yl)-4-methyloxazole-5-carboxamide |
| 454 | 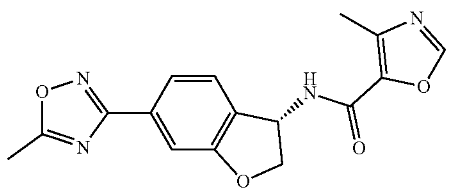 [SMILES: Cc1nc(-c2ccc3c(c2)OC[C@H]3NC(=O)c2ocnc2C)no1] | (S)-4-methyl-N-(6-(5-methyl-1,2,4-oxadiazol-3-yl)-2,3-dihydrobenzofuran-3-yl)oxazole-5-carboxamide |
| 455 | 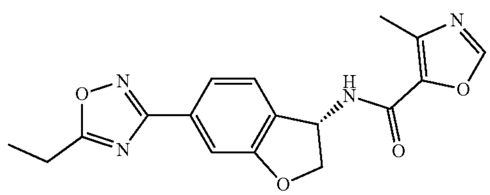 [SMILES: CCc1nc(-c2ccc3c(c2)OC[C@H]3NC(=O)c2ocnc2C)no1] | (S)-N-(6-(5-ethyl-1,2,4-oxadiazol-3-yl)-2,3-dihydrobenzofuran-3-yl)-4-methyloxazole-5-carboxamide |
| 456 | 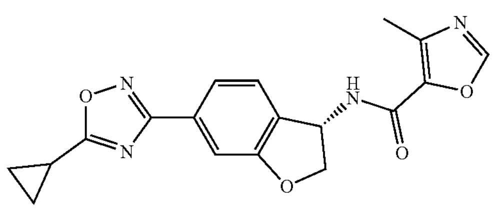 | (S)-N-(6-(5-cyclopropyl-1,2,4-oxadiazol-3-yl)-2,3-dihydrobenzofuran-3-yl)-4-methyloxazole-5-carboxamide |
| 457 | 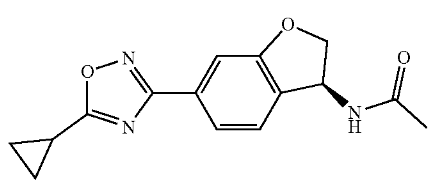 [SMILES: CC(=O)N[C@@H]1COc2cc(-c3noc(C4CC4)n3)ccc21] | (S)-N-(6-(5-cyclopropyl-1,2,4-oxadiazol-3-yl)-2,3-dihydrobenzofuran-3-yl)acetamide |
| 458 | 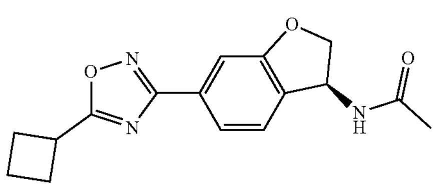 [SMILES: CC(=O)N[C@@H]1COc2cc(-c3noc(C4CCC4)n3)ccc21] | (S)-N-(6-(5-cyclobutyl-1,2,4-oxadiazol-3-yl)-2,3-dihydrobenzofuran-3-yl)acetamide |
| 459 | 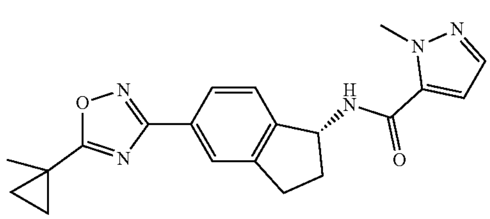 [SMILES: Cn1nccc1C(=O)N[C@@H]1CCc2cc(-c3noc(C4(C)CC4)n3)ccc21] | (R)-1-methyl-N-(5-(5-(1-methylcyclopropyl)-1,2,4-oxadiazol-3-yl)-2,3-dihydro-1H-inden-1-yl)-1H-pyrazole-5-carboxamide |

TABLE 1-continued

| Cmpd No. | Structure | Name |
|---|---|---|
| 460 | 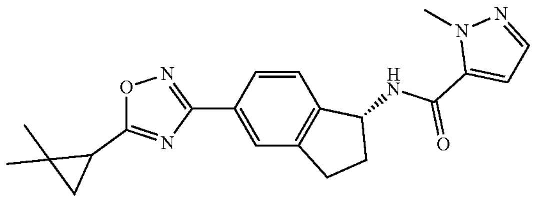 [SMILES: Cn1nccc1C(=O)N[C@@H]1CCc2cc(-c3noc(C4CC4(C)C)n3)ccc21] | N-((1R)-5-(5-(2,2-dimethylcyclopropyl)-1,2,4-oxadiazol-3-yl)-2,3-dihydro-1H-inden-1-yl)-1-methyl-1H-pyrazole-5-carboxamide |
| 461 | 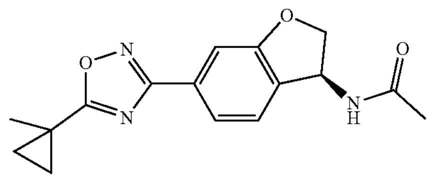 [SMILES: CC(=O)N[C@@H]1COc2cc(-c3noc(C4(C)CC4)n3)ccc21] | (S)-N-(6-(5-(1-methylcyclopropyl)-1,2,4-oxadiazol-3-yl)-2,3-dihydrobenzofuran-3-yl)acetamide |
| 462 | 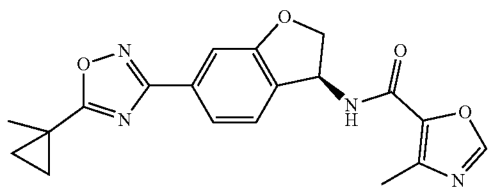 [SMILES: Cc1ncoc1C(=O)N[C@@H]1COc2cc(-c3noc(C4(C)CC4)n3)ccc21] | (S)-4-methyl-N-(6-(5-(1-methylcyclopropyl)-1,2,4-oxadiazol-3-yl)-2,3-dihydrobenzofuran-3-yl)oxazole-5-carboxamide |
| 463 | 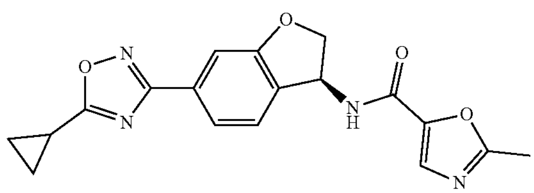 [SMILES: Cc1ncc(C(=O)N[C@@H]2COc3cc(-c4noc(C5CC5)n4)ccc32)o1] | (S)-N-(6-(5-cyclopropyl-1,2,4-oxadiazol-3-yl)-2,3-dihydrobenzofuran-3-yl)-2-methyloxazole-5-carboxamide |
| 464 | 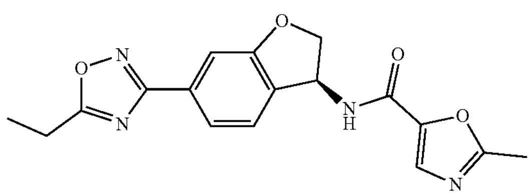 [SMILES: CCc1nc(-c2ccc3c(c2)OC[C@H]3NC(=O)c2cnc(C)o2)no1] | (S)-N-(6-(5-ethyl-1,2,4-oxadiazol-3-yl)-2,3-dihydrobenzofuran-3-yl)-2-methyloxazole-5-carboxamide |
| 465 | 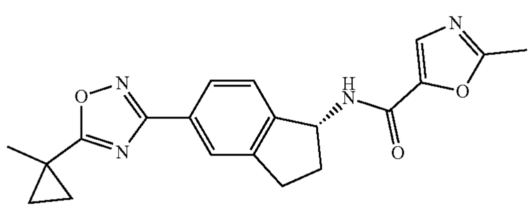 | (R)-2-methyl-N-(5-(5-(1-methylcyclopropyl)-1,2,4-oxadiazol-3-yl)-2,3-dihydro-1H-inden-1-yl)oxazole-5-carboxamide |
| 466 | 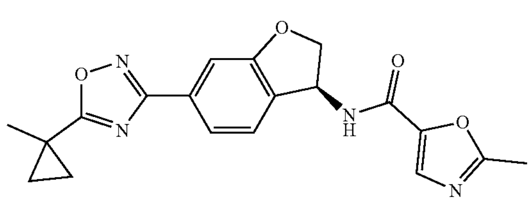 | (S)-2-methyl-N-(6-(5-(1-methylcyclopropyl)-1,2,4-oxadiazol-3-yl)-2,3-dihydrobenzofuran-3-yl)oxazole-5-carboxamide |
| 467 | 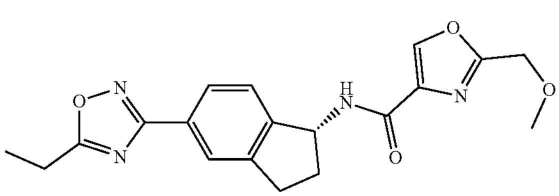 [SMILES: CCc1nc(-c2ccc3c(c2)CC[C@H]3NC(=O)c2coc(COC)n2)no1] | (R)-N-(5-(5-ethyl-1,2,4-oxadiazol-3-yl)-2,3-dihydro-1H-inden-1-yl)-2-(methoxymethyl)oxazole-4-carboxamide |

TABLE 1-continued

| Cmpd No. | Structure | Name |
|---|---|---|
| 468 | 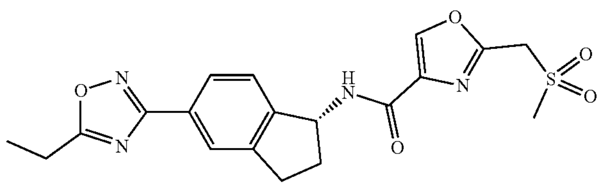 [SMILES: CCc1nc(-c2ccc3c(c2)CC[C@H]3NC(=O)c2coc(CS(C)(=O)=O)n2)no1] | (R)-N-(5-(5-ethyl-1,2,4-oxadiazol-3-yl)-2,3-dihydro-1H-inden-1-yl)-2-((methylsulfonyl)methyl)oxazole-4-carboxamide |
| 469 | 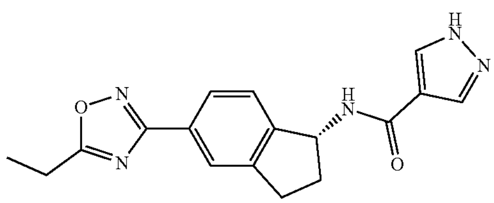 [SMILES: CCc1nc(-c2ccc3c(c2)CC[C@H]3NC(=O)c2cn[nH]c2)no1] | (R)-N-(5-(5-ethyl-1,2,4-oxadiazol-3-yl)-2,3-dihydro-1H-inden-1-yl)-1H-pyrazole-4-carboxamide |
| 470 | 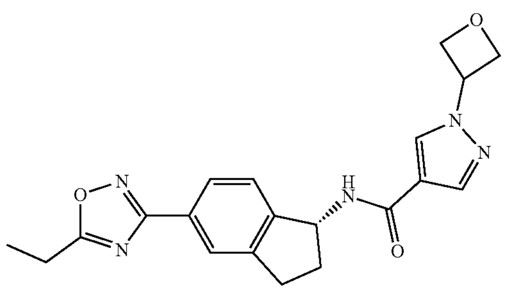 [SMILES: CCc1nc(-c2ccc3c(c2)CC[C@H]3NC(=O)c2cnn(C3COC3)c2)no1] | (R)-N-(5-(5-ethyl-1,2,4-oxadiazol-3-yl)-2,3-dihydro-1H-inden-1-yl)-1-(oxetan-3-yl)-1H-pyrazole-4-carboxamide |
| 471 | 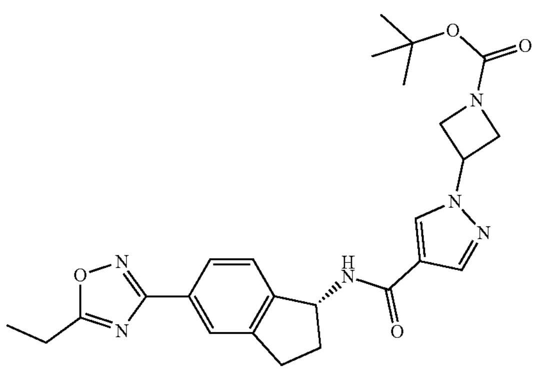 [SMILES: CCc1nc(-c2ccc3c(c2)CC[C@H]3NC(=O)c2cnn(C3CN(C(=O)OC(C)(C)C)C3)c2)no1] | tert-butyl (R)-3-(4-((5-(5-ethyl-1,2,4-oxadiazol-3-yl)-2,3-dihydro-1H-inden-1-yl)carbamoyl)-1H-pyrazol-1-yl)azetidine-1-carboxylate |
| 472 | 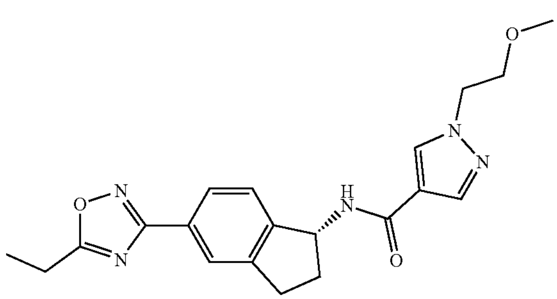 [SMILES: CCc1nc(-c2ccc3c(c2)CC[C@H]3NC(=O)c2cnn(CCOC)c2)no1] | (R)-N-(5-(5-ethyl-1,2,4-oxadiazol-3-yl)-2,3-dihydro-1H-inden-1-yl)-1-(2-methoxyethyl)-1H-pyrazole-4-carboxamide |

TABLE 1-continued

| Cmpd No. | Structure | Name |
|---|---|---|
| 473 | 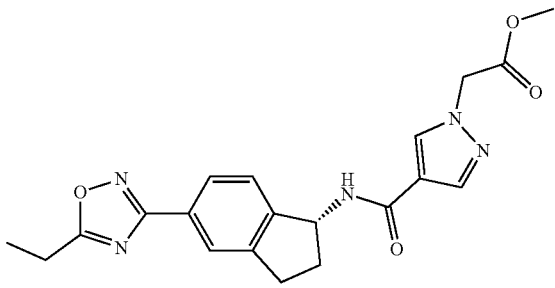 [SMILES: CCc1nc(-c2ccc3c(c2)CC[C@H]3NC(=O)c2cnn(CC(=O)OC)c2)no1] | methyl (R)-2-(4-(((5-(5-ethyl-1,2,4-oxadiazol-3-yl)-2,3-dihydro-1H-inden-1-yl)carbamoyl)-1H-pyrazol-1-yl)acetate |
| 474 | 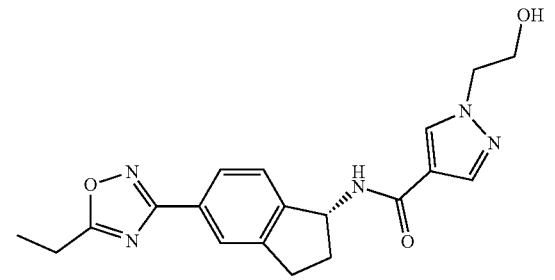 [SMILES: CCc1nc(-c2ccc3c(c2)CC[C@H]3NC(=O)c2cnn(CCO)c2)no1] | (R)-N-(5-(5-ethyl-1,2,4-oxadiazol-3-yl)-2,3-dihydro-1H-inden-1-yl)-1-(2-hydroxyethyl)-1H-pyrazole-4-carboxamide |
| 475 | 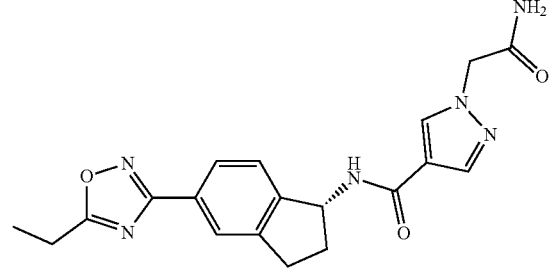 [SMILES: CCc1nc(-c2ccc3c(c2)CC[C@H]3NC(=O)c2cnn(CC(N)=O)c2)no1] | (R)-1-(2-amino-2-oxoethyl)-N-(5-(5-ethyl-1,2,4-oxadiazol-3-yl)-2,3-dihydro-1H-inden-1-yl)-1H-pyrazole-4-carboxamide |
| 476 | 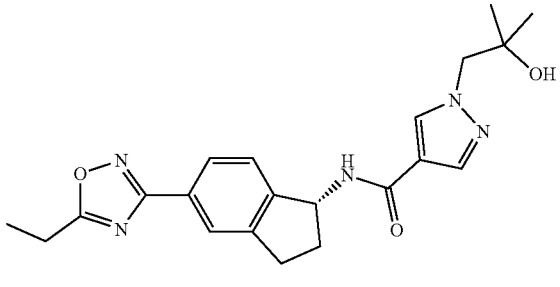 [SMILES: CCc1nc(-c2ccc3c(c2)CC[C@H]3NC(=O)c2cnn(CC(C)(C)O)c2)no1] | (R)-N-(5-(5-ethyl-1,2,4-oxadiazol-3-yl)-2,3-dihydro-1H-inden-1-yl)-1-(2-hydroxy-2-methylpropyl)-1H-pyrazole-4-carboxamide |
| 477 | 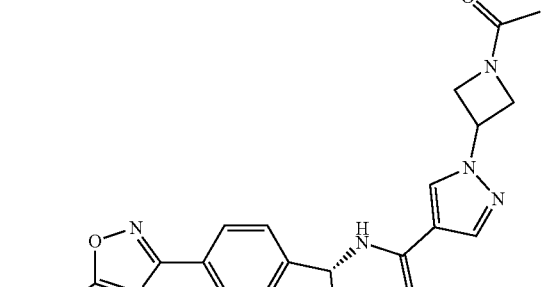 | (R)-1-(1-acetylazetidin-3-yl)-N-(5-(5-ethyl-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 478 | 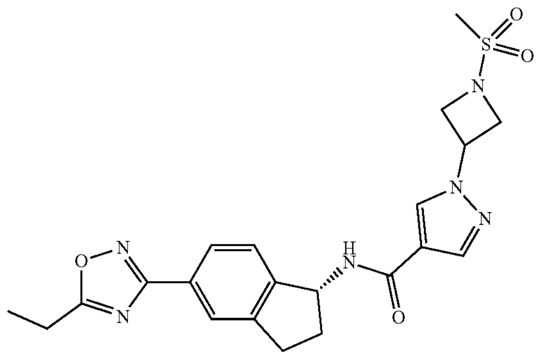 [SMILES: CCc1nc(-c2ccc3c(c2)CC[C@H]3NC(=O)c2cnn(C3CN(S(C)(=O)=O)C3)c2)no1] | (R)-N-(5-(5-ethyl-1,2,4-oxadiazol-3-yl)-2,3-dihydro-1H-inden-1-yl)-1-(1-(methylsulfonyl)azetidin-3-yl)-1H-pyrazole-4-carboxamide |
| 479 | 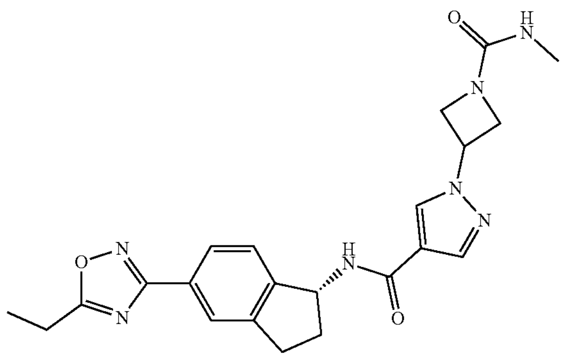 [SMILES: CCc1nc(-c2ccc3c(c2)CC[C@H]3NC(=O)c2cnn(C3CN(C(=O)NC)C3)c2)no1] | (R)-N-(5-(5-ethyl-1,2,4-oxadiazol-3-yl)-2,3-dihydro-1H-inden-1-yl)-1-(1-(methylcarbamoyl)azetidin-3-yl)-1H-pyrazole-4-carboxamide |
| 480 | 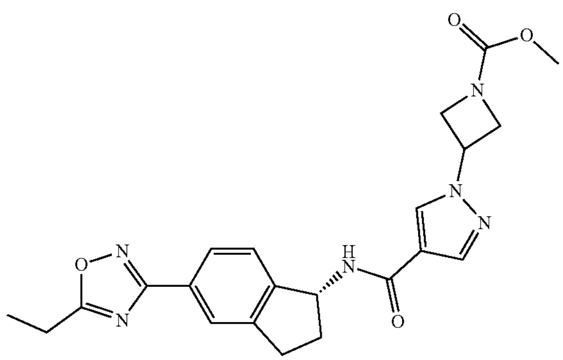 [SMILES: CCc1nc(-c2ccc3c(c2)CC[C@H]3NC(=O)c2cnn(C3CN(C(=O)OC)C3)c2)no1] | methyl (R)-3-(4-((5-(5-ethyl-1,2,4-oxadiazol-3-yl)-2,3-dihydro-1H-inden-1-yl)carbamoyl)-1H-pyrazol-1-yl)azetidine-1-carboxylate |
| 481 | 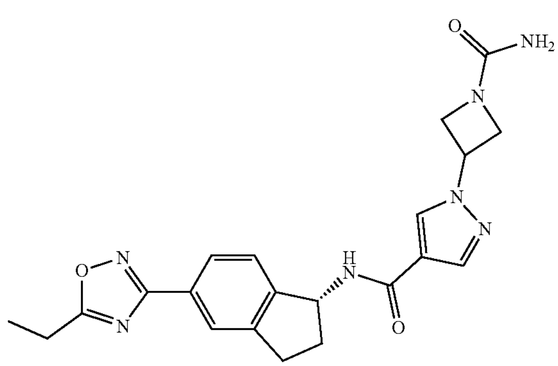 [SMILES: CCc1nc(-c2ccc3c(c2)CC[C@H]3NC(=O)c2cnn(C3CN(C(N)=O)C3)c2)no1] | (R)-1-(1-carbamoylazetidin-3-yl)-N-(5-(5-ethyl-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 482 | 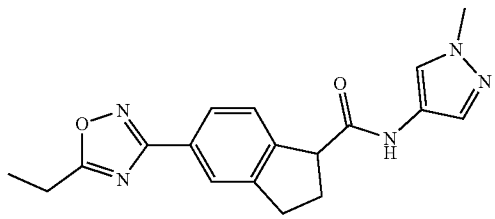 [SMILES: CCc1nc(-c2ccc3c(c2)CCC3C(=O)Nc2cnn(C)c2)no1] | 5-(5-ethyl-1,2,4-oxadiazol-3-yl)-N-(1-methyl-1H-pyrazol-4-yl)-2,3-dihydro-1H-indene-1-carboxamide |
| 483 | 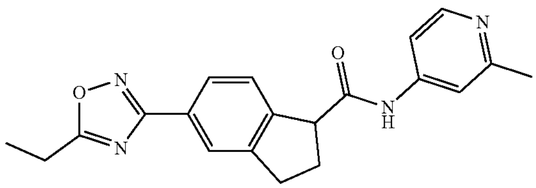 [SMILES: CCc1nc(-c2ccc3c(c2)CCC3C(=O)Nc2ccnc(C)c2)no1] | 5-(5-ethyl-1,2,4-oxadiazol-3-yl)-N-(2-methylpyridin-4-yl)-2,3-dihydro-1H-indene-1-carboxamide |
| 484 | 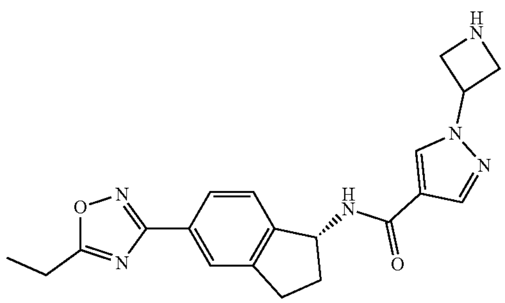 [SMILES: CCc1nc(-c2ccc3c(c2)CC[C@H]3NC(=O)c2cnn(C3CNC3)c2)no1] | (R)-1-(azetidin-3-yl)-N-(5-(5-ethyl-1,2,4-oxadiazol-3-yl)-2,3-dihydro-1H-inden-1-yl)-1H-pyrazole-4-carboxamide |
| 485 | 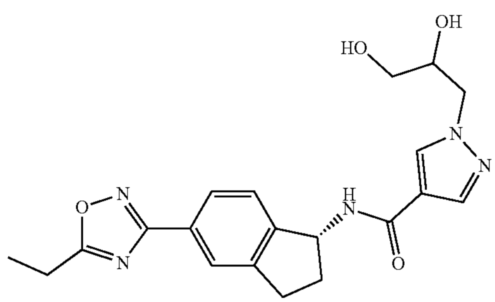 [SMILES: CCc1nc(-c2ccc3c(c2)CC[C@H]3NC(=O)c2cnn(CC(O)CO)c2)no1] | 1-(2,3-dihydroxypropyl)-N-((R)-5-(5-ethyl-1,2,4-oxadiazol-3-yl)-2,3-dihydro-1H-inden-1-yl)-1H-pyrazole-4-carboxamide |
| 486 | 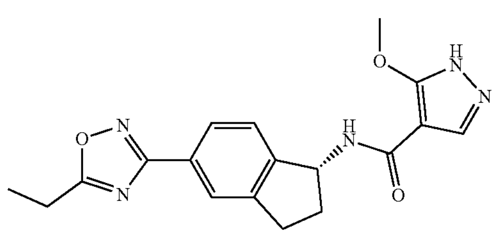 [SMILES: CCc1nc(-c2ccc3c(c2)CC[C@H]3NC(=O)c2cn[nH]c2OC)no1] | (R)-N-(5-(5-ethyl-1,2,4-oxadiazol-3-yl)-2,3-dihydro-1H-inden-1-yl)-5-methoxy-1H-pyrazole-4-carboxamide |
| 487 | 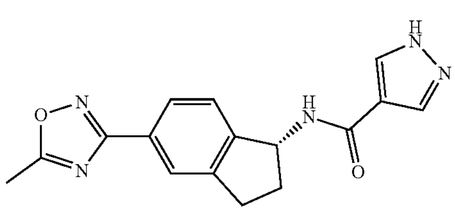 [SMILES: Cc1nc(-c2ccc3c(c2)CC[C@H]3NC(=O)c2cn[nH]c2)no1] | (R)-N-(5-(5-methyl-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 488 | 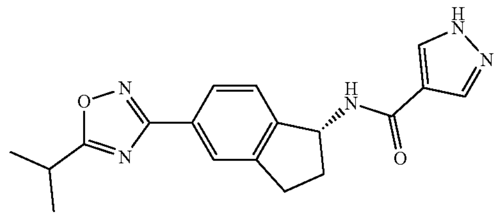 [SMILES: CC(C)c1nc(-c2ccc3c(c2)CC[C@H]3NC(=O)c2cn[nH]c2)no1] | (R)-N-(5-(5-isopropyl-1,2,4-oxadiazol-3-yl)-2,3-dihydro-1H-inden-1-yl)-1H-pyrazole-4-carboxamide |
| 489 | 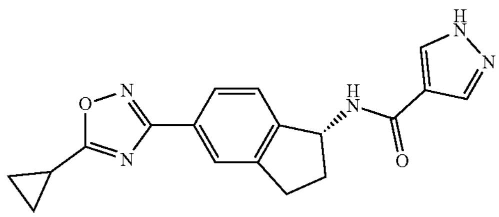 [SMILES: O=C(N[C@@H]1CCc2cc(-c3noc(C4CC4)n3)ccc21)c1cn[nH]c1] | (R)-N-(5-(5-cyclopropyl-1,2,4-oxadiazol-3-yl)-2,3-dihydro-1H-inden-1-yl)-1H-pyrazole-4-carboxamide |
| 490 | 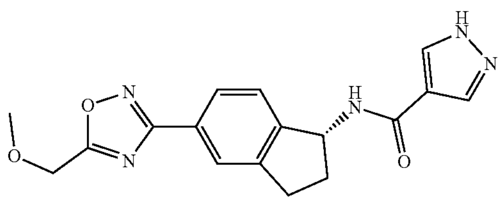 [SMILES: COCc1nc(-c2ccc3c(c2)CC[C@H]3NC(=O)c2cn[nH]c2)no1] | (R)-N-(5-(5-(methoxymethyl)-1,2,4-oxadiazol-3-yl)-2,3-dihydro-1H-inden-1-yl)-1H-pyrazole-4-carboxamide |
| 491 | 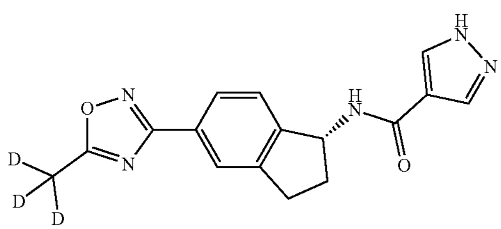 [SMILES: [2H]C([2H])([2H])c1nc(-c2ccc3c(c2)CC[C@H]3NC(=O)c2cn[nH]c2)no1] | (R)-N-(5-(5-(methyl-d3)-1,2,4-oxadiazol-3-yl)-2,3-dihydro-1H-inden-1-yl)-1H-pyrazole-4-carboxamide |
| 492 | 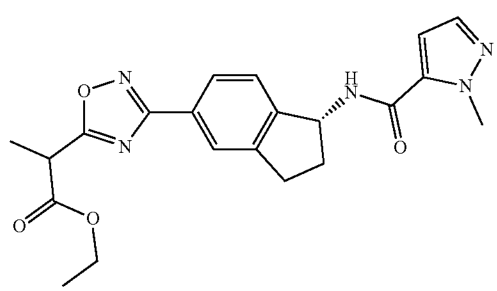 [SMILES: CCOC(=O)C(C)c1nc(-c2ccc3c(c2)CC[C@H]3NC(=O)c2ccnn2C)no1] | ethyl 2-(3-((R)-1-(1-methyl-1H-pyrazole-5-carboxamido)-2,3-dihydro-1H-inden-5-yl)-1,2,4-oxadiazol-5-yl)propanoate |
| 493 | 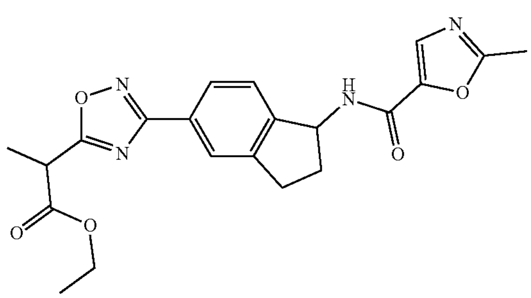 [SMILES: CCOC(=O)C(C)c1nc(-c2ccc3c(c2)CCC3NC(=O)c2cnc(C)o2)no1] | ethyl 2-(3-(1-(2-methyloxazole-5-carboxamido)-2,3-dihydro-1H-inden-5-yl)-1,2,4-oxadiazol-5-yl)propanoate |

| Cmpd No. | Structure | Name |
| --- | --- | --- |
| 494 | 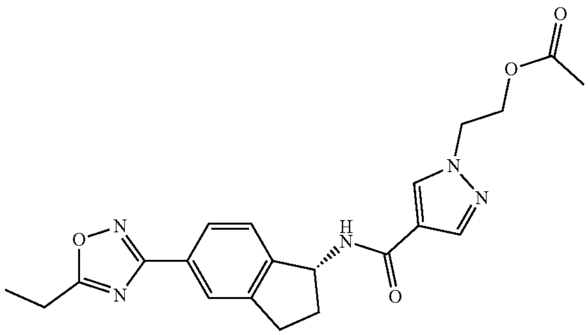 [SMILES: CCc1nc(-c2ccc3c(c2)CC[C@H]3NC(=O)c2cnn(CCOC(C)=O)c2)no1] | (R)-2-(4-((5-(5-ethyl-1,2,4-oxadiazol-3-yl)-2,3-dihydro-1H-inden-1-yl)carbamoyl)-1H-pyrazol-1-yl)ethyl acetate |
| 495 | 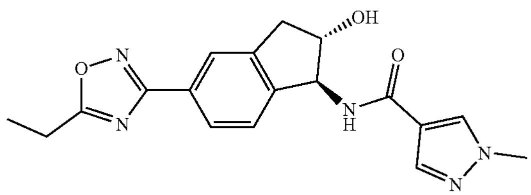 [SMILES: CCc1nc(-c2ccc3c(c2)C[C@H](O)[C@H]3NC(=O)c2cnn(C)c2)no1] | N-((1S,2S)-5-(5-ethyl-1,2,4-oxadiazol-3-yl)-2-hydroxy-2,3-dihydro-1H-inden-1-yl)-1-methyl-1H-pyrazole-4-carboxamide |
| 496 | 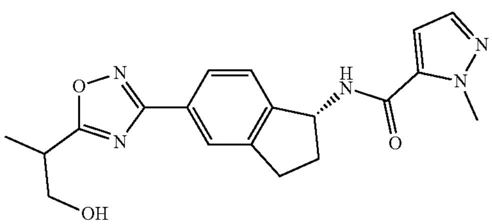 [SMILES: CC(CO)c1nc(-c2ccc3c(c2)CC[C@H]3NC(=O)c2ccnn2C)no1] | N-((1R)-5-(5-(1-hydroxypropan-2-yl)-1,2,4-oxadiazol-3-yl)-2,3-dihydro-1H-inden-1-yl)-1-methyl-1H-pyrazole-5-carboxamide |
| 497 | 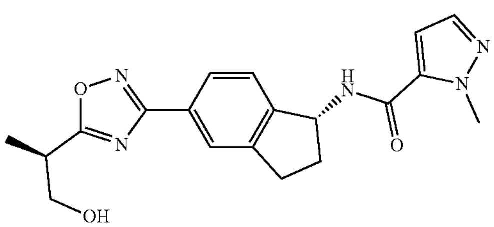 [SMILES: C[C@H](CO)c1nc(-c2ccc3c(c2)CC[C@H]3NC(=O)c2ccnn2C)no1] | N-((R)-5-(5-((R)-1-hydroxypropan-2-yl)-1,2,4-oxadiazol-3-yl)-2,3-dihydro-1H-inden-1-yl)-1-methyl-1H-pyrazole-5-carboxamide |
| 498 | 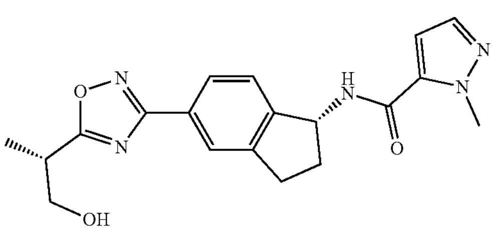 [SMILES: C[C@@H](CO)c1nc(-c2ccc3c(c2)CC[C@H]3NC(=O)c2ccnn2C)no1] | N-((R)-5-(5-((S)-1-hydroxypropan-2-yl)-1,2,4-oxadiazol-3-yl)-2,3-dihydro-1H-inden-1-yl)-1-methyl-1H-pyrazole-5-carboxamide |
| 499 | 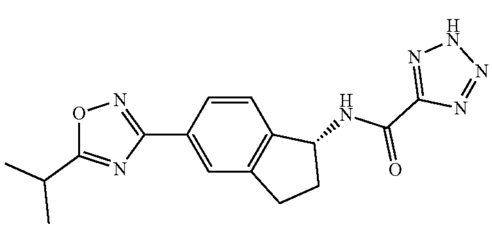 [SMILES: CC(C)c1nc(-c2ccc3c(c2)CC[C@H]3NC(=O)c2nn[nH]n2)no1] | (R)-N-(5-(5-isopropyl-1,2,4-oxadiazol-3-yl)-2,3-dihydro-1H-inden-1-yl)-2H-tetrazole-5-carboxamide |

TABLE 1-continued

| Cmpd No. | Structure | Name |
|---|---|---|
| 500 | 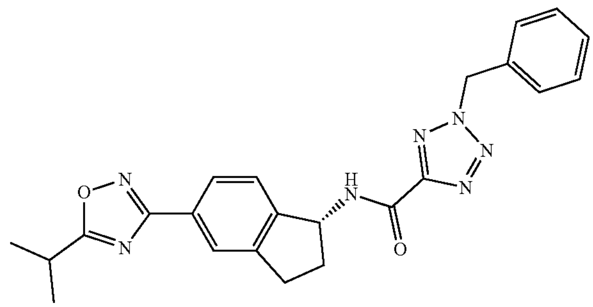 [SMILES: CC(C)c1nc(-c2ccc3c(c2)CC[C@H]3NC(=O)c2nnn(Cc3ccccc3)n2)no1] | (R)-2-benzyl-N-(5-(5-isopropyl-1,2,4-oxadiazol-3-yl)-2,3-dihydro-1H-inden-1-yl)-2H-tetrazole-5-carboxamide |
| 501 | 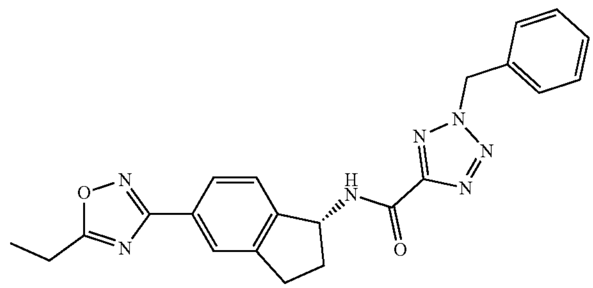 [SMILES: CCc1nc(-c2ccc3c(c2)CC[C@H]3NC(=O)c2nnn(Cc3ccccc3)n2)no1] | (R)-2-benzyl-N-(5-(5-ethyl-1,2,4-oxadiazol-3-yl)-2,3-dihydro-1H-inden-1-yl)-2H-tetrazole-5-carboxamide |
| 502 | 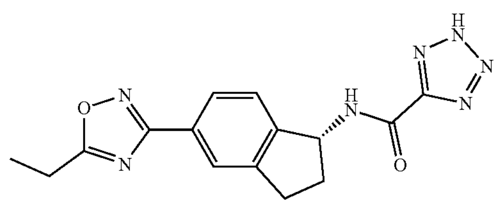 | (R)-N-(5-(5-ethyl-1,2,4-oxadiazol-3-yl)-2,3-dihydro-1H-inden-1-yl)-2H-tetrazole-5-carboxamide |
| 503 | 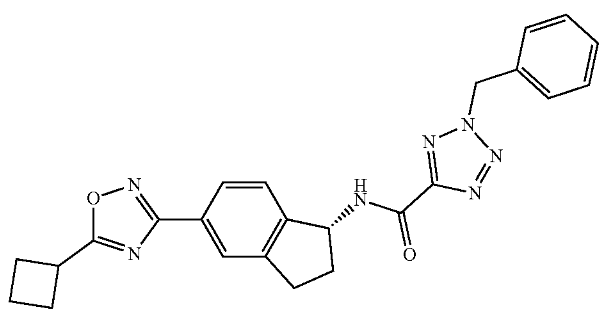 [SMILES: O=C(N[C@@H]1CCc2cc(-c3noc(C4CCC4)n3)ccc21)c1nnn(Cc2ccccc2)n1] | (R)-2-benzyl-N-(5-(5-cyclobutyl-1,2,4-oxadiazol-3-yl)-2,3-dihydro-1H-inden-1-yl)-2H-tetrazole-5-carboxamide |
| 504 | 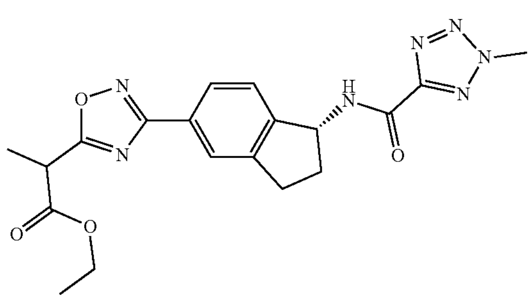 [SMILES: CCOC(=O)C(C)c1nc(-c2ccc3c(c2)CC[C@H]3NC(=O)c2nnn(C)n2)no1] | ethyl 2-(3-((R)-1-(2-methyl-2H-tetrazole-5-carboxamido)-2,3-dihydro-1H-inden-5-yl)-1,2,4-oxadiazol-5-yl)propanoate |

TABLE 1-continued

| Cmpd No. | Structure | Name |
|---|---|---|
| 505 | 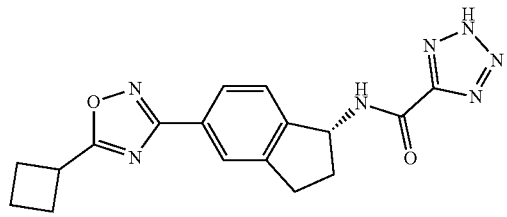 [SMILES: O=C(N[C@@H]1CCc2cc(-c3noc(C4CCC4)n3)ccc21)c1nn[nH]n1] | (R)-N-(5-(5-cyclobutyl-1,2,4-oxadiazol-3-yl)-2,3-dihydro-1H-inden-1-yl)-2H-tetrazole-5-carboxamide |
| 506 | 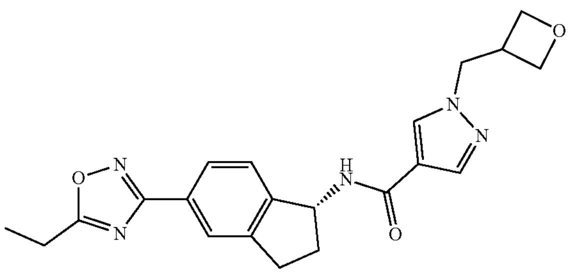 [SMILES: CCc1nc(-c2ccc3c(c2)CC[C@H]3NC(=O)c2cnn(CC3COC3)c2)no1] | (R)-N-(5-(5-ethyl-1,2,4-oxadiazol-3-yl)-2,3-dihydro-1H-inden-1-yl)-1-(oxetan-3-ylmethyl)-1H-pyrazole-4-carboxamide |
| 507 | 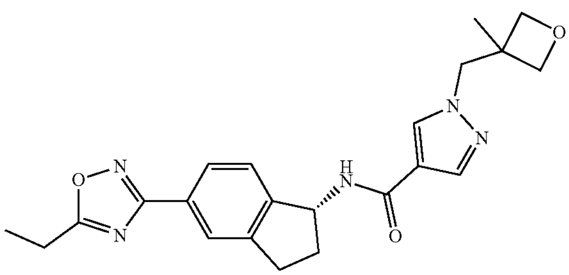 [SMILES: CCc1nc(-c2ccc3c(c2)CC[C@H]3NC(=O)c2cnn(CC3(C)COC3)c2)no1] | (R)-N-(5-(5-ethyl-1,2,4-oxadiazol-3-yl)-2,3-dihydro-1H-inden-1-yl)-1-((3-methyloxetan-3-yl)methyl)-1H-pyrazole-4-carboxamide |
| 508 | 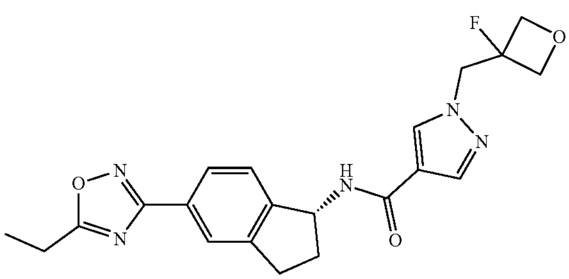 [SMILES: CCc1nc(-c2ccc3c(c2)CC[C@H]3NC(=O)c2cnn(CC3(F)COC3)c2)no1] | (R)-N-(5-(5-ethyl-1,2,4-oxadiazol-3-yl)-2,3-dihydro-1H-inden-1-yl)-1-((3-fluorooxetan-3-yl)methyl)-1H-pyrazole-4-carboxamide |
| 509 | 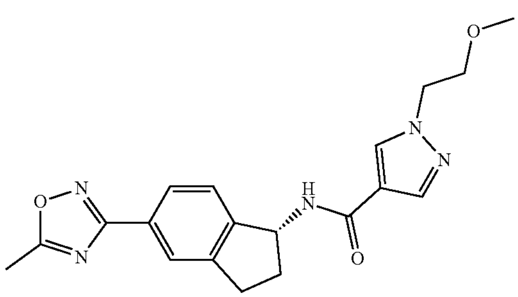 | (R)-1-(2-methoxyethyl)-N-(5-(5-methyl-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 510 | 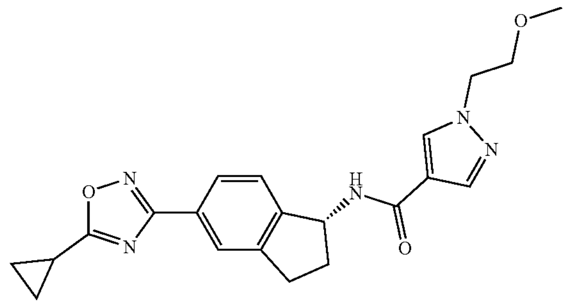 [SMILES: COCCn1cc(C(=O)N[C@@H]2CCc3cc(-c4noc(C5CC5)n4)ccc32)cn1] | (R)-N-(5-(5-cyclopropyl-1,2,4-oxadiazol-3-yl)-2,3-dihydro-1H-inden-1-yl)-1-(2-methoxyethyl)-1H-pyrazole-4-carboxamide |
| 511 | 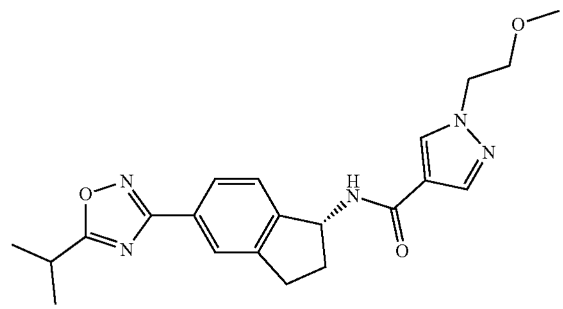 [SMILES: COCCn1cc(C(=O)N[C@@H]2CCc3cc(-c4noc(C(C)C)n4)ccc32)cn1] | (R)-N-(5-(5-isopropyl-1,2,4-oxadiazol-3-yl)-2,3-dihydro-1H-inden-1-yl)-1-(2-methoxyethyl)-1H-pyrazole-4-carboxamide |
| 512 | 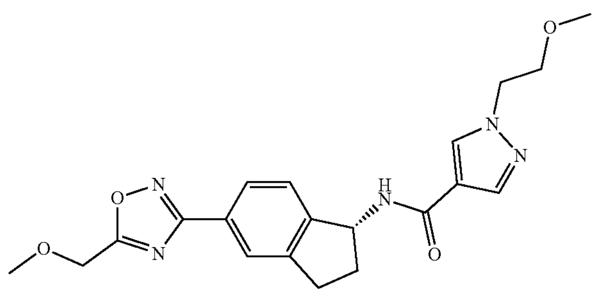 | (R)-1-(2-methoxyethyl)-N-(5-(5-(methoxymethyl)-1,2,4-oxadiazol-3-yl)-2,3-dihydro-1H-inden-1-yl)-1H-pyrazole-4-carboxamide |
| 513 | 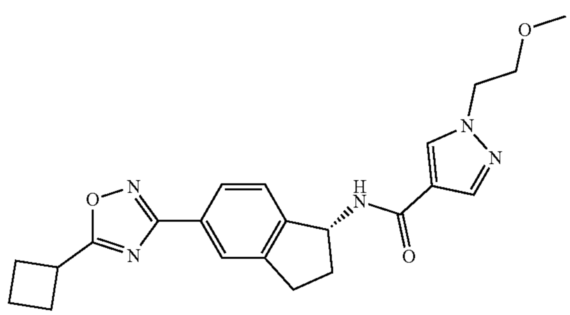 [SMILES: COCCn1cc(C(=O)N[C@@H]2CCc3cc(-c4noc(C5CCC5)n4)ccc32)cn1] | (R)-N-(5-(5-cyclobutyl-1,2,4-oxadiazol-3-yl)-2,3-dihydro-1H-inden-1-yl)-1-(2-methoxyethyl)-1H-pyrazole-4-carboxamide |
| 514 | 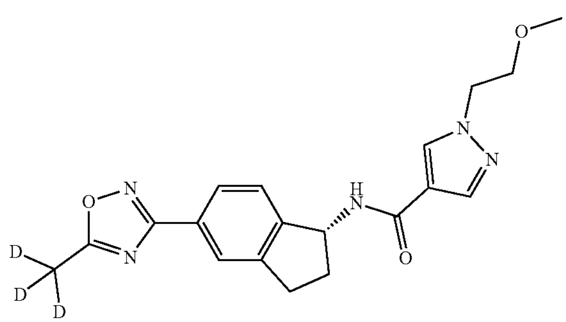 [SMILES: [2H]C([2H])([2H])c1nc(-c2ccc3c(c2)CC[C@H]3NC(=O)c2cnn(CCOC)c2)no1] | (R)-1-(2-methoxyethyl)-N-(5-(5-(methyl-d3)-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 515 | 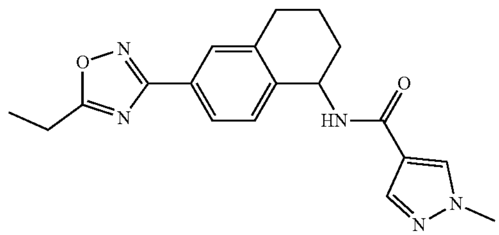 [SMILES: CCc1nc(-c2ccc3c(c2)CCCC3NC(=O)c2cnn(C)c2)no1] | N-(6-(5-ethyl-1,2,4-oxadiazol-3-yl)-1,2,3,4-tetrahydronaphthalen-1-yl)-1-methyl-1H-pyrazole-4-carboxamide |
| 516 | 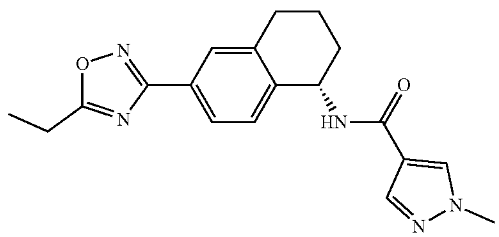 [SMILES: CCc1nc(-c2ccc3c(c2)CCC[C@@H]3NC(=O)c2cnn(C)c2)no1] | (S)-N-(6-(5-ethyl-1,2,4-oxadiazol-3-yl)-1,2,3,4-tetrahydronaphthalen-1-yl)-1-methyl-1H-pyrazole-4-carboxamide |
| 517 | 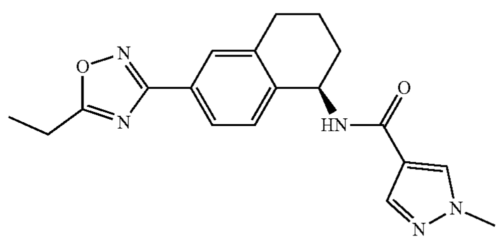 [SMILES: CCc1nc(-c2ccc3c(c2)CCC[C@H]3NC(=O)c2cnn(C)c2)no1] | (R)-N-(6-(5-ethyl-1,2,4-oxadiazol-3-yl)-1,2,3,4-tetrahydronaphthalen-1-yl)-1-methyl-1H-pyrazole-4-carboxamide |
| 518 | 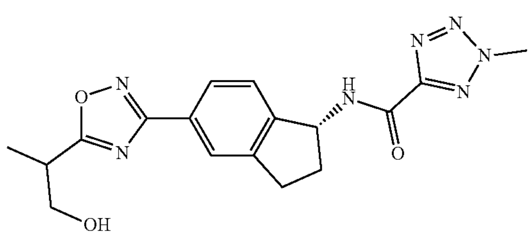 [SMILES: CC(CO)c1nc(-c2ccc3c(c2)CC[C@H]3NC(=O)c2nnn(C)n2)no1] | N-((1R)-5-(5-(1-hydroxypropan-2-yl)-1,2,4-oxadiazol-3-yl)-2,3-dihydro-1H-inden-1-yl)-2-methyl-2H-tetrazole-5-carboxamide |
| 519 | 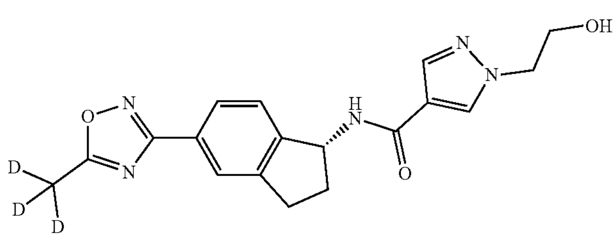 [SMILES: [2H]C([2H])([2H])c1nc(-c2ccc3c(c2)CC[C@H]3NC(=O)c2cnn(CCO)c2)no1] | (R)-1-(2-hydroxyethyl)-N-(5-(5-(methyl-d3)-1,2,4-oxadiazol-3-yl)-2,3-dihydro-1H-inden-1-yl)-1H-pyrazole-4-carboxamide |
| 520 | 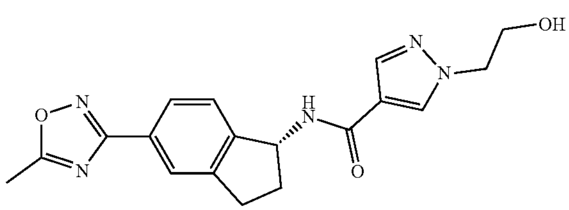 [SMILES: Cc1nc(-c2ccc3c(c2)CC[C@H]3NC(=O)c2cnn(CCO)c2)no1] | (R)-1-(2-hydroxyethyl)-N-(5-(5-methyl-1,2,4-oxadiazol-3-yl)-2,3-dihydro-1H-inden-1-yl)-1H-pyrazole-4-carboxamide |

TABLE 1-continued

| Cmpd No. | Structure | Name |
|---|---|---|
| 521 | 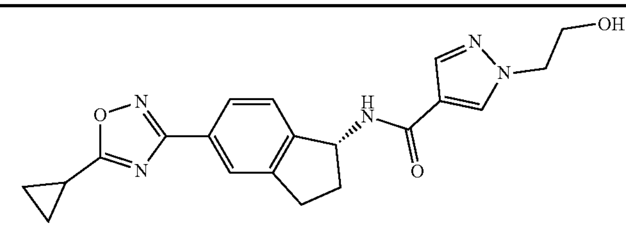 | (R)-N-(5-(5-cyclopropyl-1,2,4-oxadiazol-3-yl)-2,3-dihydro-1H-inden-1-yl)-1-(2-hydroxyethyl)-1H-pyrazole-4-carboxamide |
| 522 | 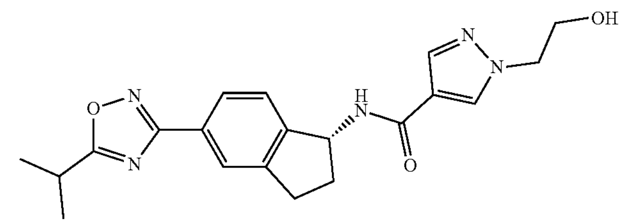 [SMILES: CC(C)c1nc(-c2ccc3c(c2)CC[C@H]3NC(=O)c2cnn(CCO)c2)no1] | (R)-1-(2-hydroxyethyl)-N-(5-(5-isopropyl-1,2,4-oxadiazol-3-yl)-2,3-dihydro-1H-inden-1-yl)-1H-pyrazole-4-carboxamide |
| 523 | 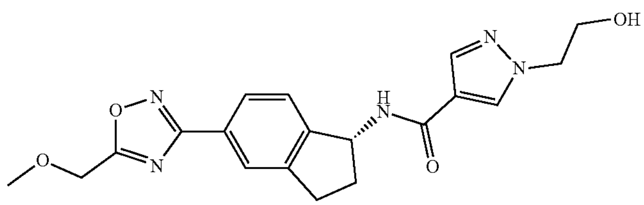 [SMILES: COCc1nc(-c2ccc3c(c2)CC[C@H]3NC(=O)c2cnn(CCO)c2)no1] | (R)-1-(2-hydroxyethyl)-N-(5-(5-(methoxymethyl)-1,2,4-oxadiazol-3-yl)-2,3-dihydro-1H-inden-1-yl)-1H-pyrazole-4-carboxamide |
| 524 | 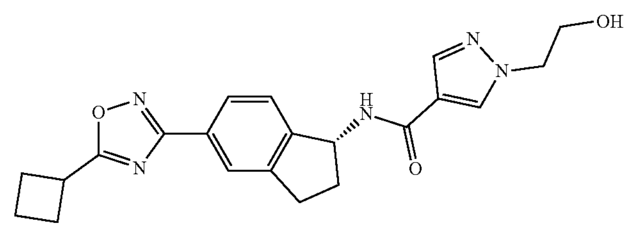 [SMILES: O=C(N[C@@H]1CCc2cc(-c3noc(C4CCC4)n3)ccc21)c1cnn(CCO)c1] | (R)-N-(5-(5-cyclobutyl-1,2,4-oxadiazol-3-yl)-2,3-dihydro-1H-inden-1-yl)-1-(2-hydroxyethyl)-1H-pyrazole-4-carboxamide |
| 525 | 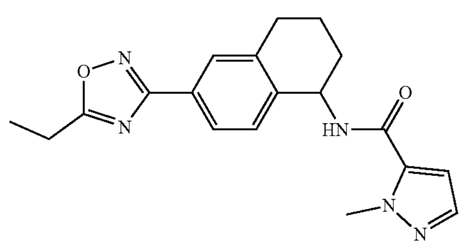 [SMILES: CCc1nc(-c2ccc3c(c2)CCCC3NC(=O)c2ccnn2C)no1] | N-(6-(5-ethyl-1,2,4-oxadiazol-3-yl)-1,2,3,4-tetrahydronaphthalen-1-yl)-1-methyl-1H-pyrazole-5-carboxamide |
| 526 | 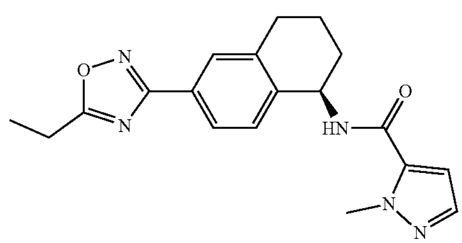 [SMILES: CCc1nc(-c2ccc3c(c2)CCC[C@H]3NC(=O)c2ccnn2C)no1] | (R)-N-(6-(5-ethyl-1,2,4-oxadiazol-3-yl)-1,2,3,4-tetrahydronaphthalen-1-yl)-1-methyl-1H-pyrazole-5-carboxamide |
| 527 | 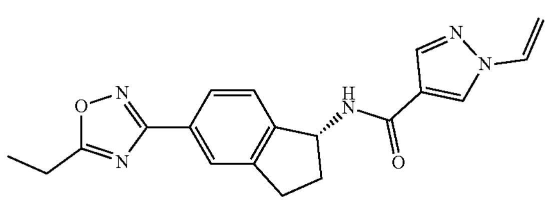 [SMILES: C=Cn1cc(C(=O)N[C@@H]2CCc3cc(-c4noc(CC)n4)ccc32)cn1] | (R)-N-(5-(5-ethyl-1,2,4-oxadiazol-3-yl)-2,3-dihydro-1H-inden-1-yl)-1-vinyl-1H-pyrazole-4-carboxamide |

TABLE 1-continued

| Cmpd No. | Structure | Name |
|---|---|---|
| 528 | 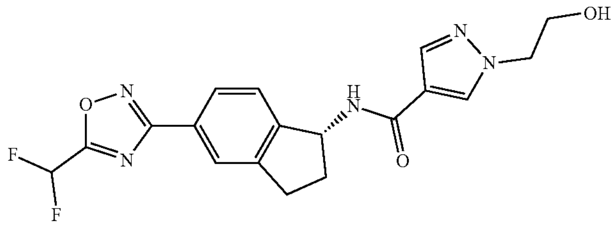 [SMILES: O=C(N[C@@H]1CCc2cc(-c3noc(C(F)F)n3)ccc21)c1cnn(CCO)c1] | (R)-N-(5-(5-(difluoromethyl)-1,2,4-oxadiazol-3-yl)-2,3-dihydro-1H-inden-1-yl)-1-(2-hydroxyethyl)-1H-pyrazole-4-carboxamide |
| 529 | 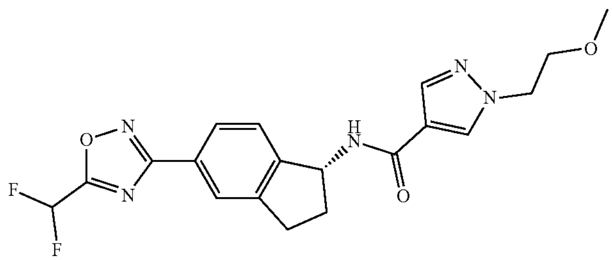 [SMILES: COCCn1cc(C(=O)N[C@@H]2CCc3cc(-c4noc(C(F)F)n4)ccc32)cn1] | (R)-N-(5-(5-(difluoromethyl)-1,2,4-oxadiazol-3-yl)-2,3-dihydro-1H-inden-1-yl)-1-(2-methoxyethyl)-1H-pyrazole-4-carboxamide |
| 530 | 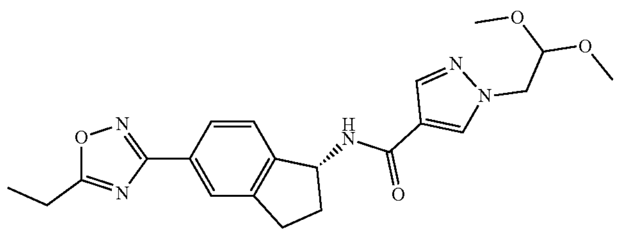 [SMILES: CCc1nc(-c2ccc3c(c2)CC[C@H]3NC(=O)c2cnn(CC(OC)OC)c2)no1] | (R)-1-(2,2-dimethoxyethyl)-N-(5-(5-ethyl-1,2,4-oxadiazol-3-yl)-2,3-dihydro-1H-inden-1-yl)-1H-pyrazole-4-carboxamide |
| 531 | 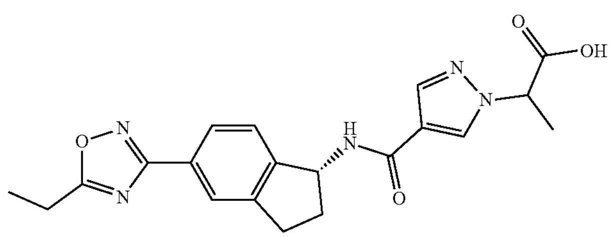 [SMILES: CCc1nc(-c2ccc3c(c2)CC[C@H]3NC(=O)c2cnn(C(C)C(=O)O)c2)no1] | 2-(4-(((R)-5-(5-ethyl-1,2,4-oxadiazol-3-yl)-2,3-dihydro-1H-inden-1-yl)carbamoyl)-1H-pyrazol-1-yl)propanoic acid |
| 532 | 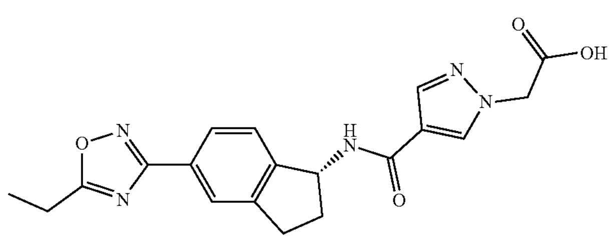 | (R)-2-(4-((5-(5-ethyl-1,2,4-oxadiazol-3-yl)-2,3-dihydro-1H-inden-1-yl)carbamoyl)-1H-pyrazol-1-yl)acetic acid |
| 533 | 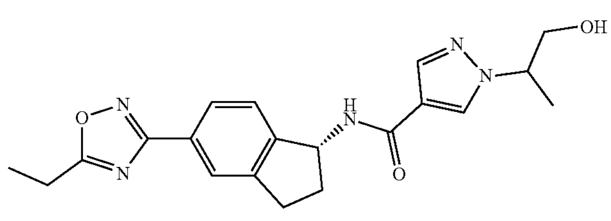 [SMILES: CCc1nc(-c2ccc3c(c2)CC[C@H]3NC(=O)c2cnn(C(C)CO)c2)no1] | N-((R)-5-(5-ethyl-1,2,4-oxadiazol-3-yl)-2,3-dihydro-1H-inden-1-yl)-1-(1-hydroxypropan-2-yl)-1H-pyrazole-4-carboxamide |

TABLE 1-continued

| Cmpd No. | Structure | Name |
|---|---|---|
| 534 | 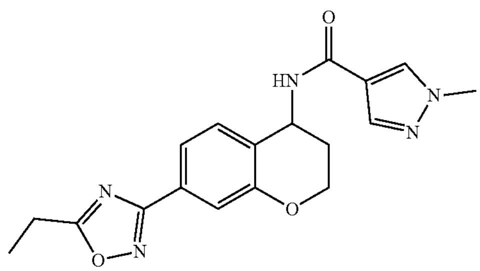 [SMILES: CCc1nc(-c2ccc3c(c2)OCCC3NC(=O)c2cnn(C)c2)no1] | N-(7-(5-ethyl-1,2,4-oxadiazol-3-yl)chroman-4-yl)-1-methyl-1H-pyrazole-4-carboxamide |
| 535 | 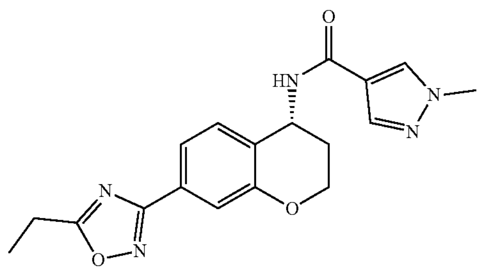 [SMILES: CCc1nc(-c2ccc3c(c2)OCC[C@H]3NC(=O)c2cnn(C)c2)no1] | (R)-N-(7-(5-ethyl-1,2,4-oxadiazol-3-yl)chroman-4-yl)-1-methyl-1H-pyrazole-4-carboxamide |
| 536 | 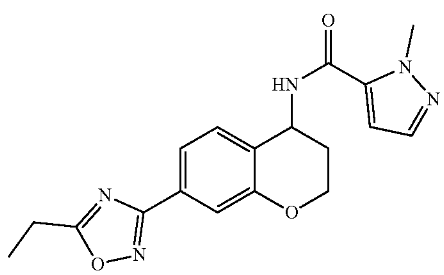 [SMILES: CCc1nc(-c2ccc3c(c2)OCCC3NC(=O)c2ccnn2C)no1] | N-(7-(5-ethyl-1,2,4-oxadiazol-3-yl)chroman-4-yl)-1-methyl-1H-pyrazole-5-carboxamide |
| 537 | 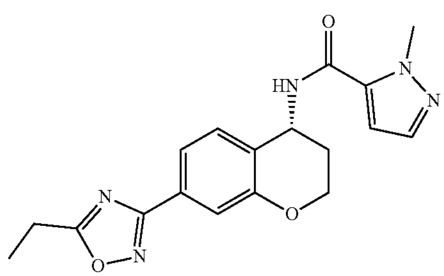 [SMILES: CCc1nc(-c2ccc3c(c2)OCC[C@H]3NC(=O)c2ccnn2C)no1] | (R)-N-(7-(5-ethyl-1,2,4-oxadiazol-3-yl)chroman-4-yl)-1-methyl-1H-pyrazole-5-carboxamide |
| 538 | 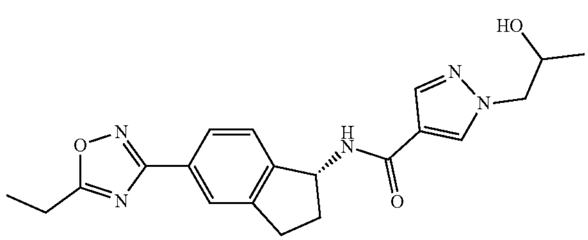 [SMILES: CCc1nc(-c2ccc3c(c2)CC[C@H]3NC(=O)c2cnn(CC(C)O)c2)no1] | N-((R)-5-(5-ethyl-1,2,4-oxadiazol-3-yl)-2,3-dihydro-1H-inden-1-yl)-1-(2-hydroxypropyl)-1H-pyrazole-4-carboxamide |
| 539 | 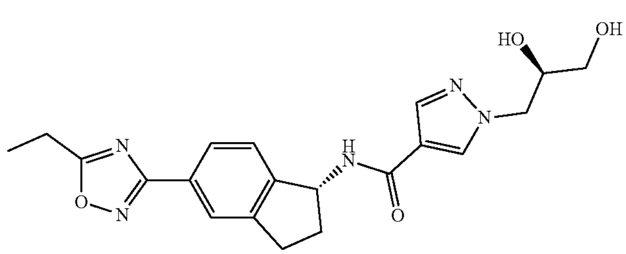 [SMILES: CCc1nc(-c2ccc3c(c2)CC[C@H]3NC(=O)c2cnn(C[C@@H](O)CO)c2)no1] | N-[(1R)-5-(5-ethyl(1,2,4-oxadiazol-3-yl))indanyl][1-((2R)-2,3-dihydroxypropyl)pyrazol-4-yl]carboxamide |

TABLE 1-continued

| Cmpd No. | Structure | Name |
|---|---|---|
| 540 | 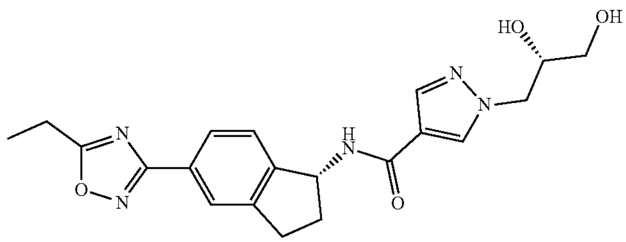 [SMILES: CCc1nc(-c2ccc3c(c2)CC[C@H]3NC(=O)c2cnn(C[C@H](O)CO)c2)no1] | N-[(1R)-5-(5-ethyl(1,2,4-oxadiazol-3-yl))indanyl][1-((2S)-2,3-dihydroxypropyl)pyrazol-4-yl]carboxamide |
| 541 | 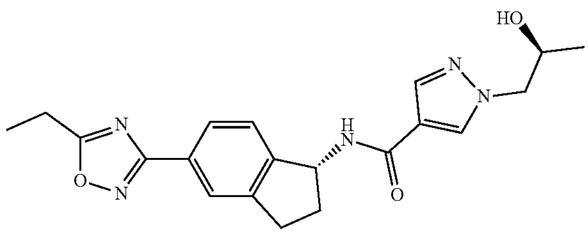 [SMILES: CCc1nc(-c2ccc3c(c2)CC[C@H]3NC(=O)c2cnn(C[C@H](C)O)c2)no1] | N-[(1R)-5-(5-ethyl(1,2,4-oxadiazol-3-yl))indanyl][1-((2S)-2-hydroxypropyl)pyrazol-4-yl]carboxamide |
| 542 | 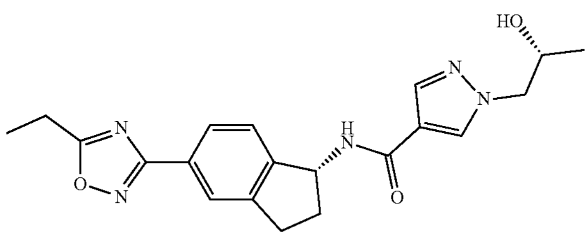 [SMILES: CCc1nc(-c2ccc3c(c2)CC[C@H]3NC(=O)c2cnn(C[C@@H](C)O)c2)no1] | N-[(1R)-5-(5-ethyl(1,2,4-oxadiazol-3-yl))indanyl][1-((2R)-2-hydroxypropyl)pyrazol-4-yl]carboxamide |
| 543 | 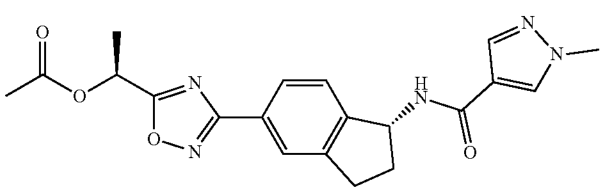 [SMILES: CC(=O)O[C@@H](C)c1nc(-c2ccc3c(c2)CC[C@H]3NC(=O)c2cnn(C)c2)no1] | 1-(3-{(1R)-1-[(1-methylpyrazol-4-yl)carbonylamino]indan-5-yl}(1,2,4-oxadiazol-5-yl))(1S)ethyl acetate |
| 544 | 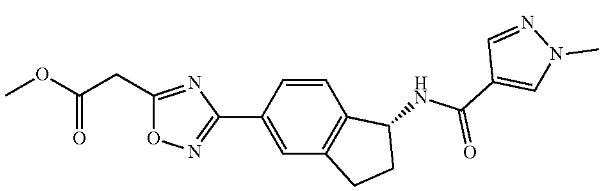 | methyl 2-(3-{(1R)-1-[(1-methylpyrazol-4-yl)carbonylamino]indan-5-yl}-1,2,4-oxadiazol-5-yl)acetate |
| 545 | 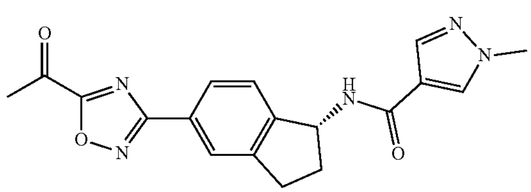 [SMILES: CC(=O)c1nc(-c2ccc3c(c2)CC[C@H]3NC(=O)c2cnn(C)c2)no1] | N-[(1R)-5-(5-acetyl(1,2,4-oxadiazol-3-yl))indanyl](1-methylpyrazol-4-yl)carboxamide |
| 546 | 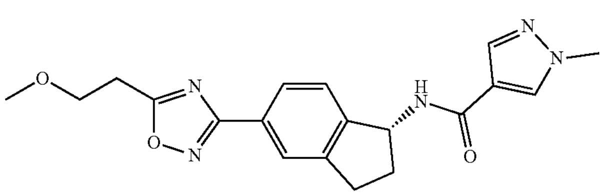 | N-{(1R)-5-[5-(2-methoxyethyl)(1,2,4-oxadiazol-3-yl)]indanyl}(1-methylpyrazol-4-yl)carboxamide |

TABLE 1-continued

| Cmpd No. | Structure | Name |
|---|---|---|
| 547 | 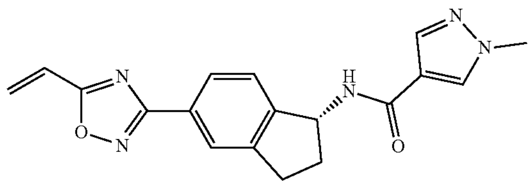 [SMILES: C=Cc1nc(-c2ccc3c(c2)CC[C@H]3NC(=O)c2cnn(C)c2)no1] | N-[(1R)-5-(5-vinyl(1,2,4-oxadiazol-3-yl))indanyl](1-methylpyrazol-4-yl)carboxamide |
| 548 | 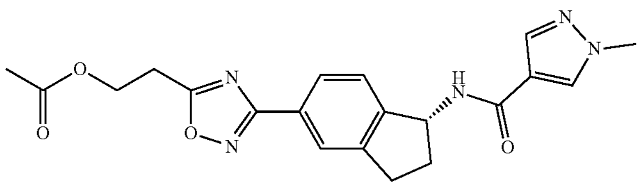 [SMILES: CC(=O)OCCc1nc(-c2ccc3c(c2)CC[C@H]3NC(=O)c2cnn(C)c2)no1] | 2-(3-{(1R)-1-[(1-methylpyrazol-4-yl)carbonylamino]indan-5-yl}-1,2,4-oxadiazol-5-yl)ethyl acetate |
| 549 | 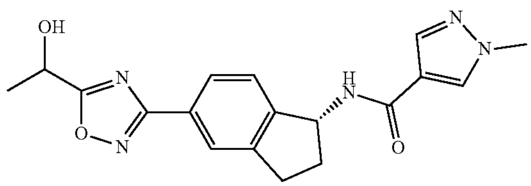 [SMILES: CC(O)c1nc(-c2ccc3c(c2)CC[C@H]3NC(=O)c2cnn(C)c2)no1] | N-{(1R)-5-[5-(hydroxyethyl)(1,2,4-oxadiazol-3-yl)]indanyl}(1-methylpyrazol-4-yl)carboxamide |
| 550 | 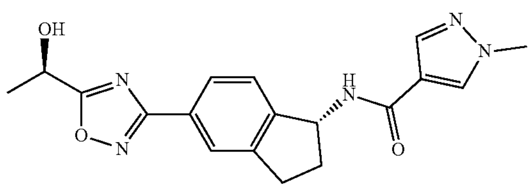 [SMILES: C[C@@H](O)c1nc(-c2ccc3c(c2)CC[C@H]3NC(=O)c2cnn(C)c2)no1] | N-{(1R)-5-[5-((1R)-1-hydroxyethyl)(1,2,4-oxadiazol-3-yl)]indanyl}(1-methylpyrazol-4-yl)carboxamide |
| 551 | 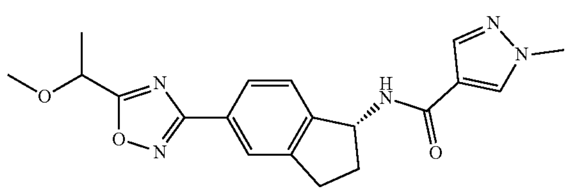 | N-{(1R)-5-[5-(methoxyethyl)(1,2,4-oxadiazol-3-yl)]indanyl}(1-methylpyrazol-4-yl)carboxamide |
| 552 | 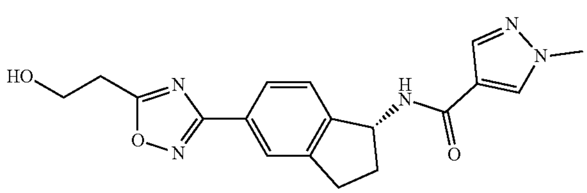 [SMILES: Cn1cc(C(=O)N[C@@H]2CCc3cc(-c4noc(CCO)n4)ccc32)cn1] | N-{(1R)-5-[5-(2-hydroxyethyl)(1,2,4-oxadiazol-3-yl)]indanyl}(1-methylpyrazol-4-yl)carboxamide |
| 553 | 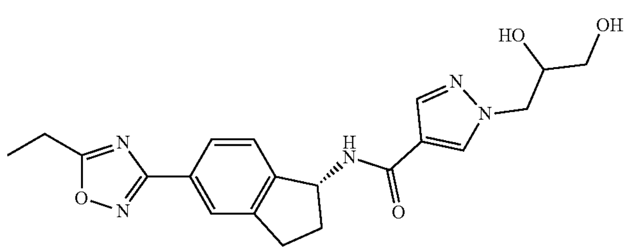 [SMILES: CCc1nc(-c2ccc3c(c2)CC[C@H]3NC(=O)c2cnn(CC(O)CO)c2)no1] | N-{(1R)-5-(5-ethyl(1,2,4-oxadiazol-3-yl))indanyl][1-(2,3-dihydroxypropyl)pyrazol-4-yl]carboxamide |

TABLE 1-continued

| Cmpd No. | Structure | Name |
|---|---|---|
| 554 | 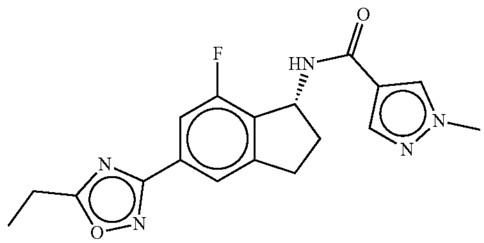 | (R)-N-(5-(5-ethyl-1,2,4-oxadiazol-3-yl)-7-fluoro-2,3-dihydro-1H-inden-1-yl)-1-methyl-1H-pyrazole-4-carboxamide |
| 555 | 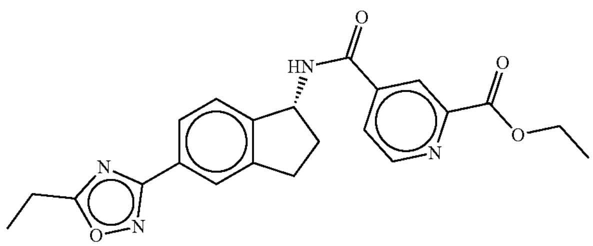 | Ethyl (R)-4-((5-(5-ethyl-1,2,4-oxadiazol-3-yl)-2,3-dihydro-1H-inden-1-yl)carbamoyl)picolinate |
| 556 | 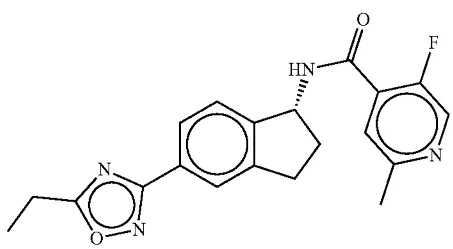 | (R)-N-(5-(5-ethyl-1,2,4-oxadiazol-3-yl)-2,3-dihydro-1H-inden-1-yl)-5-fluoro-2-methylisonicotinamide |
| 557 | 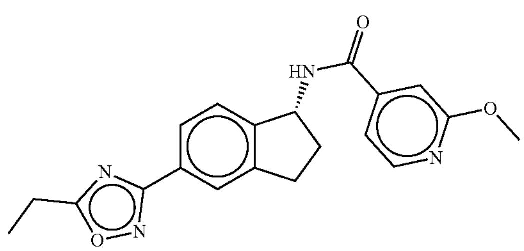 | (R)-N-(5-(5-ethyl-1,2,4-oxadiazol-3-yl)-2,3-dihydro-1H-inden-1-yl)-2-methoxyisonicotinamide |
| 558 | 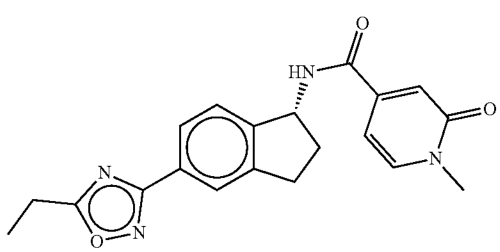 | (R)-N-(5-(5-ethyl-1,2,4-oxadiazol-3-yl)-2,3-dihydro-1H-inden-1-yl)-1-methyl-2-oxo-1,2-dihydropyridine-4-carboxamide |
| 559 | 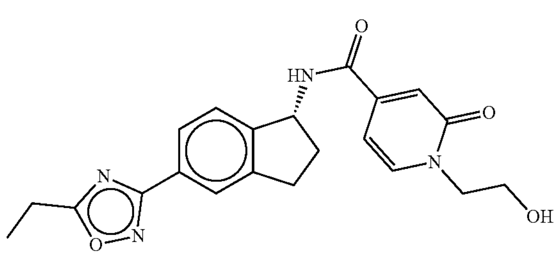 | (R)-N-(5-(5-ethyl-1,2,4-oxadiazol-3-yl)-2,3-dihydro-1H-inden-1-yl)-1-(2-hydroxyethyl)-2-oxo-1,2-dihydropyridine-4-carboxamide |

TABLE 1-continued

| Cmpd No. | Name |
|---|---|
| 560 | N-((R)-5-(5-ethyl-1,2,4-oxadiazol-3-yl)-2,3-dihydro-1H-inden-1-yl)-1-((R)-2-hydroxypropyl)-2-oxo-1,2-dihydropyridine-4-carboxamide |
| 561 | (R)-N-(5-(5-ethyl-1,2,4-oxadiazol-3-yl)-2,3-dihydro-1H-inden-1-yl)-2-methyloxazole-4-carboxamide |
| 562 | (R)-N-(5-(5-ethyl-1,2,4-oxadiazol-3-yl)-4-fluoro-2,3-dihydro-1H-inden-1-yl)-1-methyl-1H-pyrazole-4-carboxamide |
| 563 | (R)-N-(5-(5-ethyl-1,2,4-oxadiazol-3-yl)-2,3-dihydro-1H-inden-1-yl)-1,3-dimethyl-1H-pyrazole-4-carboxamide |
| 564 | (R)-N-(5-(5-ethyl-1,2,4-oxadiazol-3-yl)-2,3-dihydro-1H-inden-1-yl)-5-methylisoxazole-4-carboxamide |
| 565 | (R)-N-(5-(5-ethyl-1,2,4-oxadiazol-3-yl)-2,3-dihydro-1H-inden-1-yl)-3-methylisoxazole-5-carboxamide |

| Cmpd No. | Structure | Name |
|---|---|---|
| 566 | 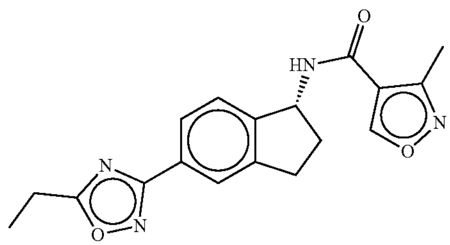 | (R)-N-(5-(5-ethyl-1,2,4-oxadiazol-3-yl)-2,3-dihydro-1H-inden-1-yl)-3-methylisoxazole-4-carboxamide |
| 567 | 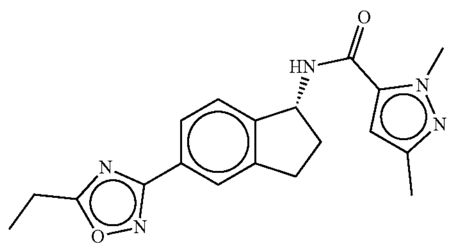 | (R)-N-(5-(5-ethyl-1,2,4-oxadiazol-3-yl)-2,3-dihydro-1H-inden-1-yl)-1,3-dimethyl-1H-pyrazole-5-carboxamide |
| 568 | 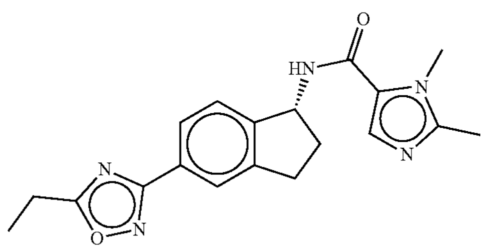 | (R)-N-(5-(5-ethyl-1,2,4-oxadiazol-3-yl)-2,3-dihydro-1H-inden-1-yl)-1,2-dimethyl-1H-imidazole-5-carboxamide |
| 569 | 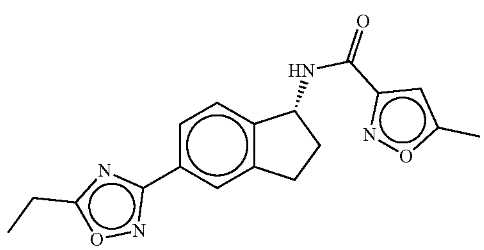 | (R)-N-(5-(5-ethyl-1,2,4-oxadiazol-3-yl)-2,3-dihydro-1H-inden-1-yl)-5-methylisoxazole-3-carboxamide |
| 570 | 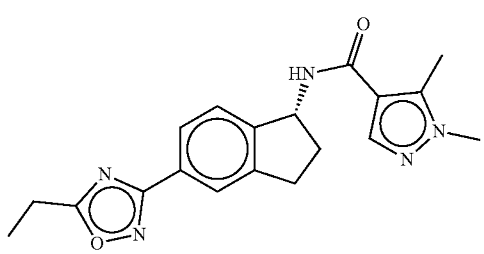 | (R)-N-(5-(5-ethyl-1,2,4-oxadiazol-3-yl)-2,3-dihydro-1H-inden-1-yl)-1,5-dimethyl-1H-pyrazole-4-carboxamide |
| 571 | 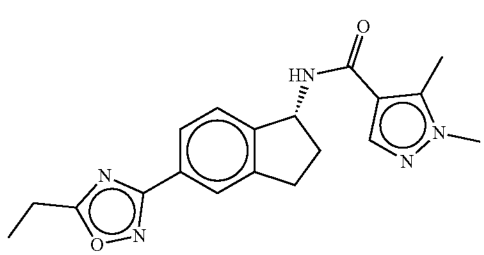 | (R)-N-(5-(5-ethyl-1,2,4-oxadiazol-3-yl)-2,3-dihydro-1H-inden-1-yl)-1,5-dimethyl-1H-pyrazole-4-carboxamide |

TABLE 1-continued

| Cmpd No. | Structure | Name |
|---|---|---|
| 572 | 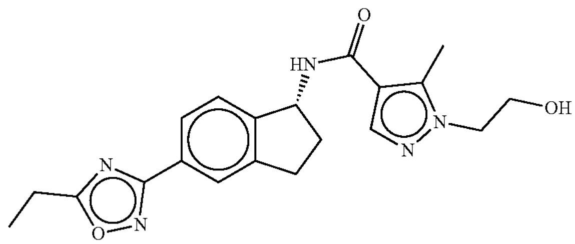 | (R)-N-(5-(5-ethyl-1,2,4-oxadiazol-3-yl)-2,3-dihydro-1H-inden-1-yl)-1-(2-hydroxyethyl)-5-methyl-1H-pyrazole-4-carboxamide |
| 573 | 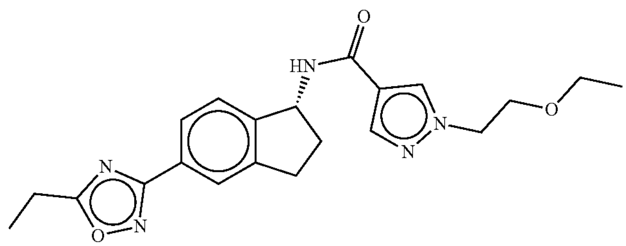 | (R)-1-(2-ethoxyethyl)-N-(5-(5-ethyl-1,2,4-oxadiazol-3-yl)-2,3-dihydro-1H-inden-1-yl)-1H-pyrazole-4-carboxamide |
| 574 | 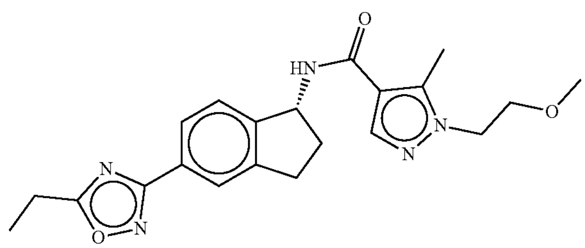 | (R)-N-(5-(5-ethyl-1,2,4-oxadiazol-3-yl)-2,3-dihydro-1H-inden-1-yl)-1-(2-methoxyethyl)-5-methyl-1H-pyrazole-4-carboxamide |
| 575 | 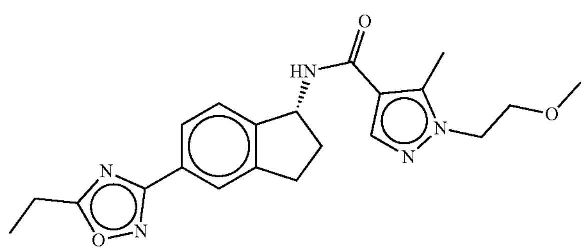 | (R)-N-(5-(5-ethyl-1,2,4-oxadiazol-3-yl)-2,3-dihydro-1H-inden-1-yl)-1-(2-methoxyethyl)-5-methyl-1H-pyrazole-4-carboxamide |
| 576 | 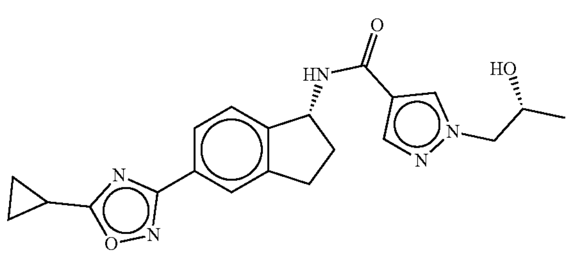 | N-((R)-5-(5-cyclopropyl-1,2,4-oxadiazol-3-yl)-2,3-dihydro-1H-inden-1-yl)-1-((R)-2-hydroxypropyl)-1H-pyrazole-4-carboxamide |
| 577 | 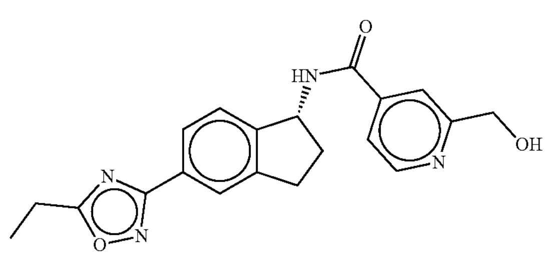 | (R)-N-(5-(5-ethyl-1,2,4-oxadiazol-3-yl)-2,3-dihydro-1H-inden-1-yl)-2-(hydroxymethyl)isonicotinamide |

TABLE 1-continued

| Cmpd No. | Structure | Name |
|---|---|---|
| 578 | 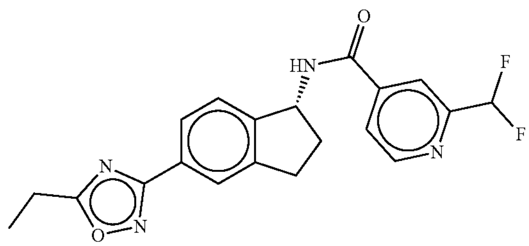 | (R)-2-(difluoromethyl)-N-(5-(5-ethyl-1,2,4-oxadiazol-3-yl)-2,3-dihydro-1H-inden-1-yl)isonicotinamide |
| 579 | 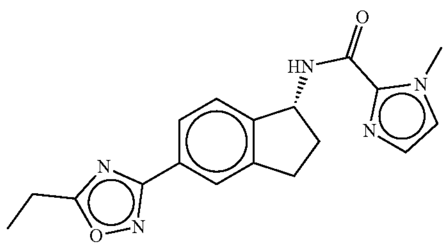 | (R)-N-(5-(5-ethyl-1,2,4-oxadiazol-3-yl)-2,3-dihydro-1H-inden-1-yl)-1-methyl-1H-imidazole-2-carboxamide |
| 580 | 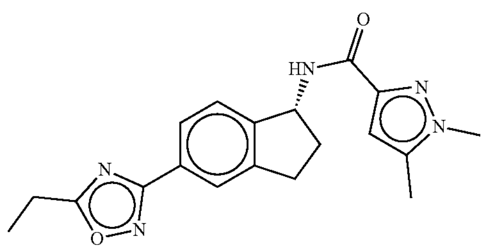 | (R)-N-(5-(5-ethyl-1,2,4-oxadiazol-3-yl)-2,3-dihydro-1H-inden-1-yl)-1,5-dimethyl-1H-pyrazole-3-carboxamide |
| 581 | 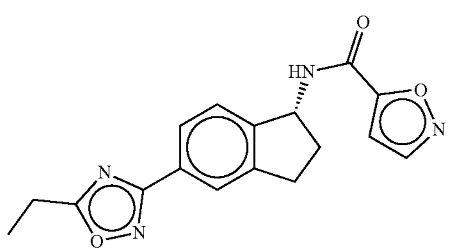 | (R)-N-(5-(5-ethyl-1,2,4-oxadiazol-3-yl)-2,3-dihydro-1H-inden-1-yl)isoxazole-5-carboxamide |
| 582 | 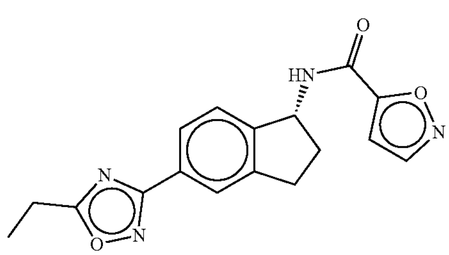 | (R)-N-(5-(5-ethyl-1,2,4-oxadiazol-3-yl)-2,3-dihydro-1H-inden-1-yl)isoxazole-5-carboxamide |
| 583 | 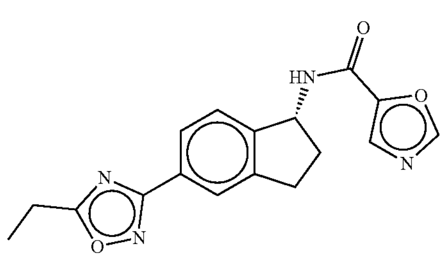 | (R)-N-(5-(5-ethyl-1,2,4-oxadiazol-3-yl)-2,3-dihydro-1H-inden-1-yl)oxazole-5-carboxamide |

TABLE 1-continued

| Cmpd No. | Structure | Name |
|---|---|---|
| 584 | 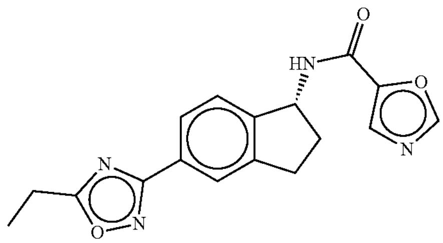 | (R)-N-(5-(5-ethyl-1,2,4-oxadiazol-3-yl)-2,3-dihydro-1H-inden-1-yl)oxazole-5-carboxamide |
| 585 | 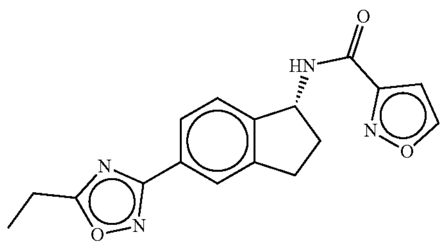 | (R)-N-(5-(5-ethyl-1,2,4-oxadiazol-3-yl)-2,3-dihydro-1H-inden-1-yl)isoxazole-3-carboxamide |
| 586 | 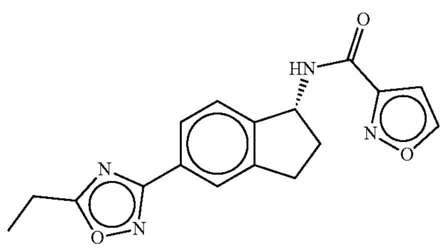 | (R)-N-(5-(5-ethyl-1,2,4-oxadiazol-3-yl)-2,3-dihydro-1H-inden-1-yl)isoxazole-3-carboxamide |
| 587 | 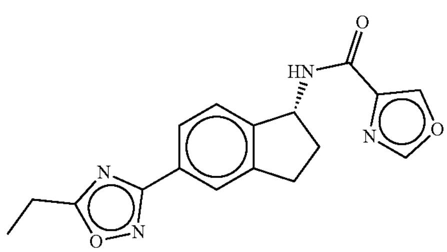 | (R)-N-(5-(5-ethyl-1,2,4-oxadiazol-3-yl)-2,3-dihydro-1H-inden-1-yl)oxazole-4-carboxamide |
| 588 | 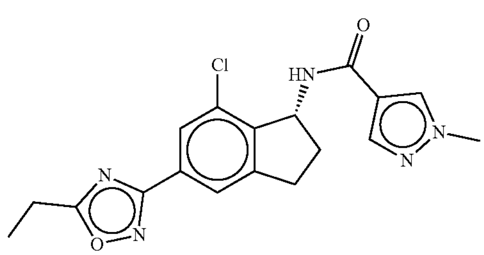 | (R)-N-(7-chloro-5-(5-ethyl-1,2,4-oxadiazol-3-yl)-2,3-dihydro-1H-inden-1-yl)-1-methyl-1H-pyrazole-4-carboxamide |
| 589 | 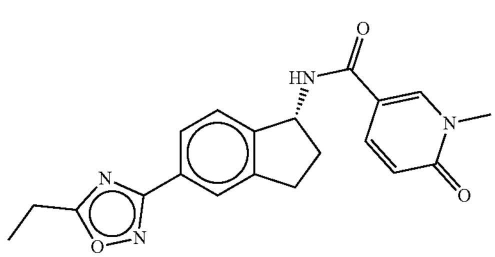 | (R)-N-(5-(5-ethyl-1,2,4-oxadiazol-3-yl)-2,3-dihydro-1H-inden-1-yl)-1-methyl-6-oxo-1,6-dihydropyridine-3-carboxamide |

TABLE 1-continued

| Cmpd No. | Structure | Name |
|---|---|---|
| 590 | 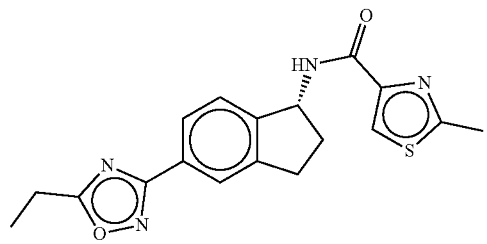 | (R)-N-(5-(5-ethyl-1,2,4-oxadiazol-3-yl)-2,3-dihydro-1H-inden-1-yl)-2-methylthiazole-4-carboxamide |
| 591 | 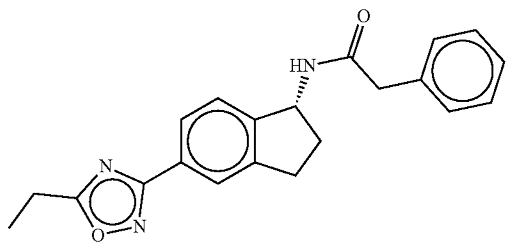 | (R)-N-(5-(5-ethyl-1,2,4-oxadiazol-3-yl)-2,3-dihydro-1H-inden-1-yl)-2-phenylacetamide |
| 592 | 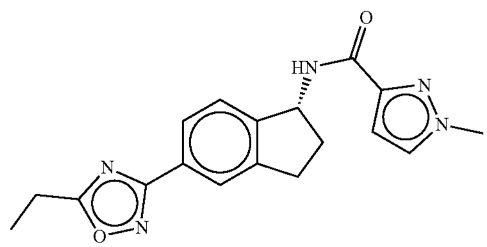 | (R)-N-(5-(5-ethyl-1,2,4-oxadiazol-3-yl)-2,3-dihydro-1H-inden-1-yl)-1-methyl-1H-pyrazole-3-carboxamide |
| 593 | 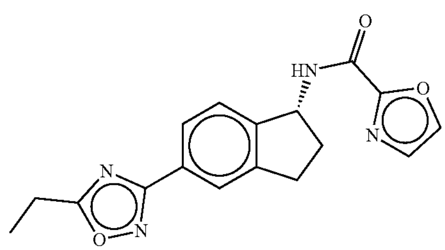 | (R)-N-(5-(5-ethyl-1,2,4-oxadiazol-3-yl)-2,3-dihydro-1H-inden-1-yl)oxazole-2-carboxamide |
| 594 | 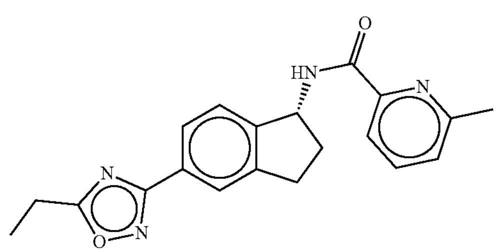 | (R)-N-(5-(5-ethyl-1,2,4-oxadiazol-3-yl)-2,3-dihydro-1H-inden-1-yl)-6-methylpicolinamide |
| 595 | 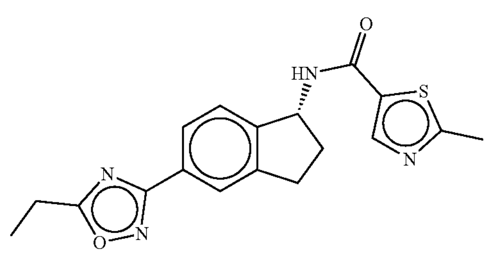 | (R)-N-(5-(5-ethyl-1,2,4-oxadiazol-3-yl)-2,3-dihydro-1H-inden-1-yl)-2-methylthiazole-5-carboxamide |

TABLE 1-continued

| Cmpd No. | Structure | Name |
|---|---|---|
| 596 | 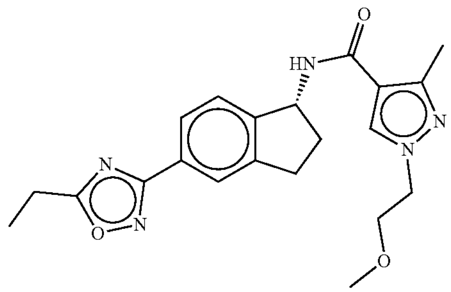 | (R)-N-(5-(5-ethyl-1,2,4-oxadiazol-3-yl)-2,3-dihydro-1H-inden-1-yl)-1-(2-methoxyethyl)-3-methyl-1H-pyrazole-4-carboxamide |
| 597 | 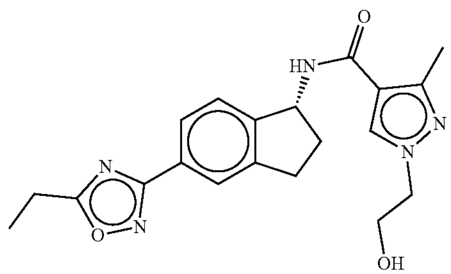 | (R)-N-(5-(5-ethyl-1,2,4-oxadiazol-3-yl)-2,3-dihydro-1H-inden-1-yl)-1-(2-hydroxyethyl)-3-methyl-1H-pyrazole-4-carboxamide |
| 598 | 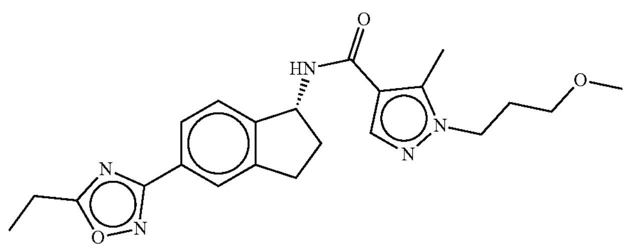 | (R)-N-(5-(5-ethyl-1,2,4-oxadiazol-3-yl)-2,3-dihydro-1H-inden-1-yl)-1-(3-methoxypropyl)-5-methyl-1H-pyrazole-4-carboxamide |
| 599 | 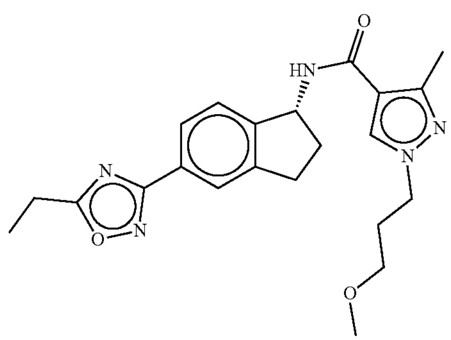 | (R)-N-(5-(5-ethyl-1,2,4-oxadiazol-3-yl)-2,3-dihydro-1H-inden-1-yl)-1-(3-methoxypropyl)-5-methyl-1H-pyrazole-4-carboxamide |
| 600 | 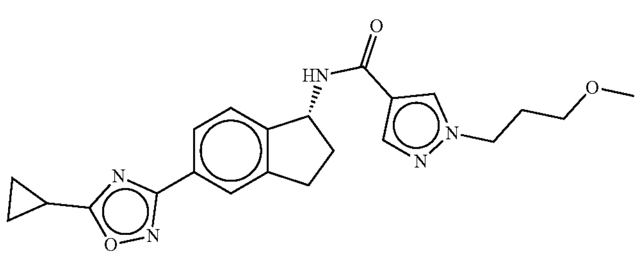 | (R)-N-(5-(5-cyclopropyl-1,2,4-oxadiazol-3-yl)-2,3-dihydro-1H-inden-1-yl)-1-(3-methoxypropyl)-1H-pyrazole-4-carboxamide |

TABLE 1-continued

| Cmpd No. | Structure | Name |
|---|---|---|
| 601 | 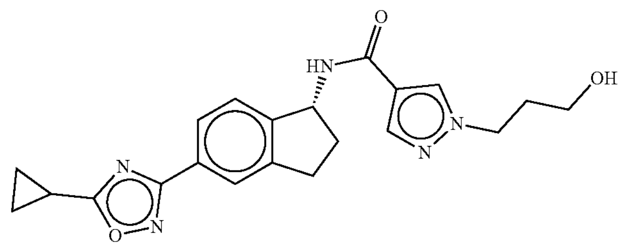 | (R)-N-(5-(5-cyclopropyl-1,2,4-oxadiazol-3-yl)-2,3-dihydro-1H-inden-1-yl)-1-(3-hydroxypropyl)-1H-pyrazole-4-carboxamide |
| 602 | 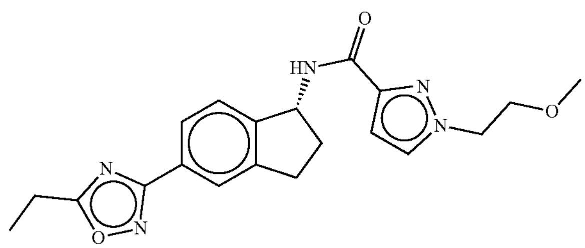 | (R)-N-(5-(5-ethyl-1,2,4-oxadiazol-3-yl)-2,3-dihydro-1H-inden-1-yl)-1-(2-methoxyethyl)-1H-pyrazole-3-carboxamide |
| 603 | 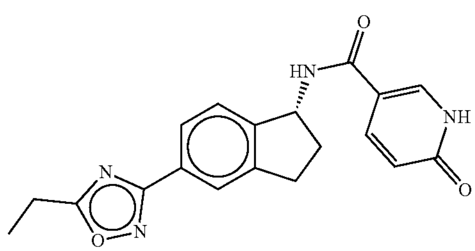 | (R)-N-(5-(5-ethyl-1,2,4-oxadiazol-3-yl)-2,3-dihydro-1H-inden-1-yl)-6-oxo-1,6-dihydropyridine-3-carboxamide |
| 604 | 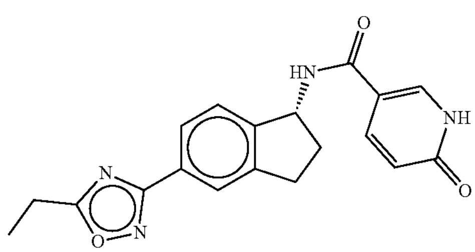 | (R)-N-(5-(5-ethyl-1,2,4-oxadiazol-3-yl)-2,3-dihydro-1H-inden-1-yl)-6-oxo-1,6-dihydropyridine-3-carboxamide |
| 605 | 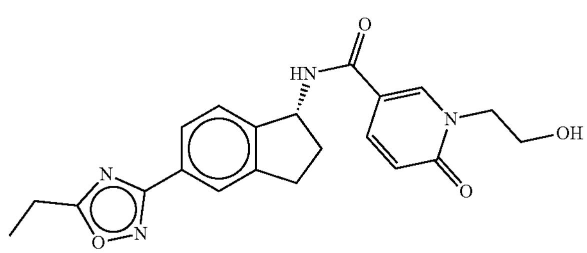 | (R)-N-(5-(5-ethyl-1,2,4-oxadiazol-3-yl)-2,3-dihydro-1H-inden-1-yl)-1-(2-hydroxyethyl)-6-oxo-1,6-dihydropyridine-3-carboxamide |
| 606 | 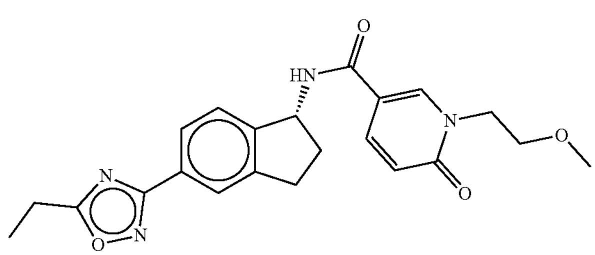 | (R)-N-(5-(5-ethyl-1,2,4-oxadiazol-3-yl)-2,3-dihydro-1H-inden-1-yl)-1-(2-methoxyethyl)-6-oxo-1,6-dihydropyridine-3-carboxamide |

TABLE 1-continued

| Cmpd No. | Structure | Name |
|---|---|---|
| 607 | 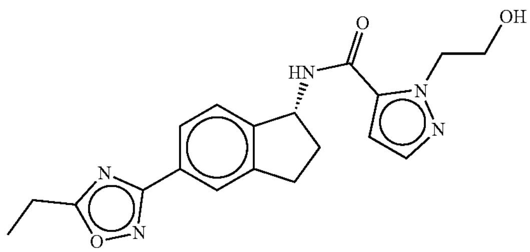 | (R)-N-(5-(5-ethyl-1,2,4-oxadiazol-3-yl)-2,3-dihydro-1H-inden-1-yl)-1-(2-hydroxyethyl)-1H-pyrazole-5-carboxamide |
| 608 | 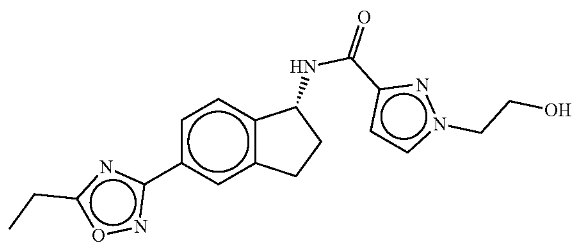 | (R)-N-(5-(5-ethyl-1,2,4-oxadiazol-3-yl)-2,3-dihydro-1H-inden-1-yl)-1-(2-hydroxyethyl)-1H-pyrazole-3-carboxamide |
| 609 | 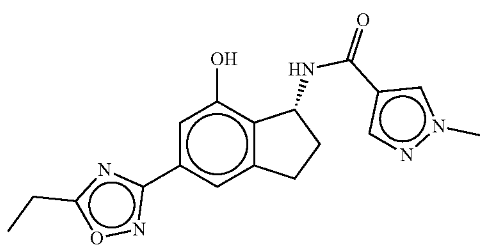 | (R)-N-(5-(5-ethyl-1,2,4-oxadiazol-3-yl)-7-hydroxy-2,3-dihydro-1H-inden-1-yl)-1-methyl-1H-pyrazole-4-carboxamide |
| 610 | 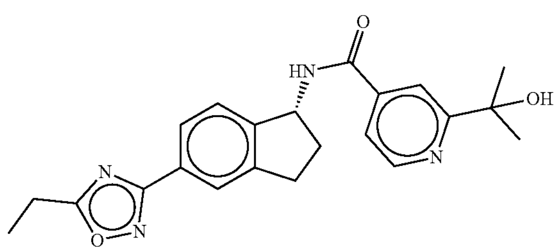 | (R)-N-(5-(5-ethyl-1,2,4-oxadiazol-3-yl)-2,3-dihydro-1H-inden-1-yl)-2-(2-hydroxypropan-2-yl)isonicotinamide |
| 611 | 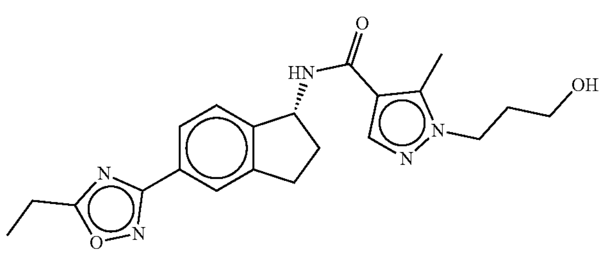 | (R)-N-(5-(5-ethyl-1,2,4-oxadiazol-3-yl)-2,3-dihydro-1H-inden-1-yl)-1-(3-hydroxypropyl)-5-methyl-1H-pyrazole-4-carboxamide |
| 612 | 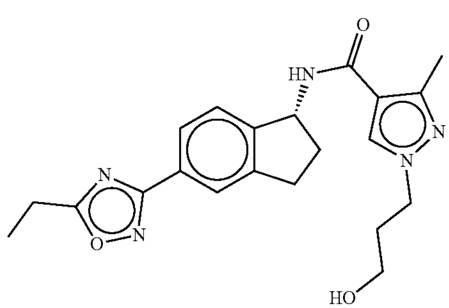 | (R)-N-(5-(5-ethyl-1,2,4-oxadiazol-3-yl)-2,3-dihydro-1H-inden-1-yl)-1-(3-hydroxypropyl)-3-methyl-1H-pyrazole-4-carboxamide |

TABLE 1-continued

| Cmpd No. | Structure | Name |
|---|---|---|
| 613 | 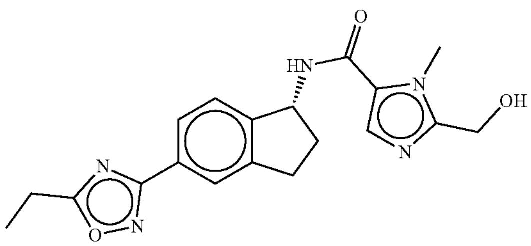 | (R)-N-(5-(5-ethyl-1,2,4-oxadiazol-3-yl)-2,3-dihydro-1H-inden-1-yl)-2-(hydroxymethyl)-1-methyl-1H-imidazole-5-carboxamide |
| 614 | 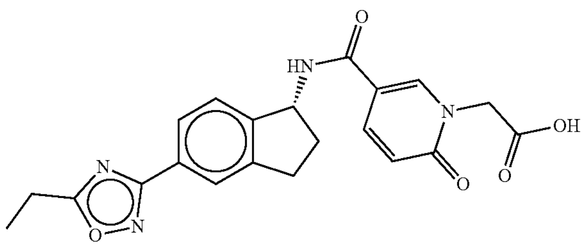 | (R)-2-(5-((5-(5-ethyl-1,2,4-oxadiazol-3-yl)-2,3-dihydro-1H-inden-1-yl)carbamoyl)-2-oxopyridin-1(2H)-yl)acetic acid |
| 615 | 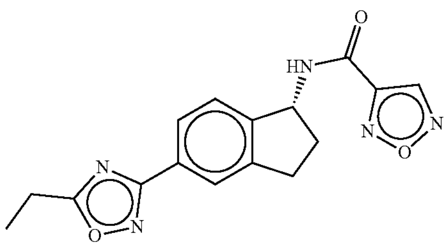 | (R)-N-(5-(5-ethyl-1,2,4-oxadiazol-3-yl)-2,3-dihydro-1H-inden-1-yl)-1,2,5-oxadiazole-3-carboxamide |
| 616 | 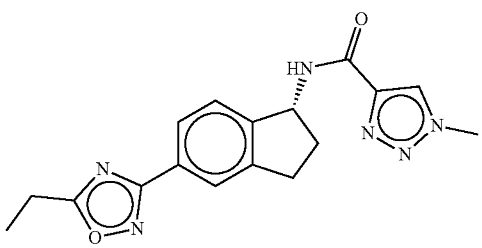 | (R)-N-(5-(5-ethyl-1,2,4-oxadiazol-3-yl)-2,3-dihydro-1H-inden-1-yl)-1-methyl-1H-1,2,3-triazole-4-carboxamide |
| 617 | 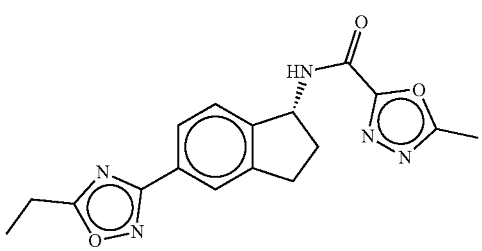 | (R)-N-(5-(5-ethyl-1,2,4-oxadiazol-3-yl)-2,3-dihydro-1H-inden-1-yl)-5-methyl-1,3,4-oxadiazole-2-carboxamide |
| 618 | 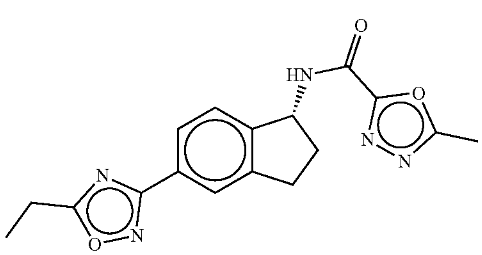 | (R)-N-(5-(5-ethyl-1,2,4-oxadiazol-3-yl)-2,3-dihydro-1H-inden-1-yl)-5-methyl-1,3,4-oxadiazole-2-carboxamide |

| Cmpd No. | Structure | Name |
| --- | --- | --- |
| 619 | 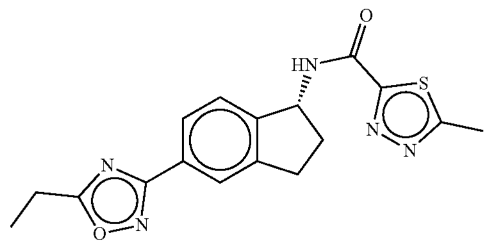 | (R)-N-(5-(5-ethyl-1,2,4-oxadiazol-3-yl)-2,3-dihydro-1H-inden-1-yl)-5-methyl-1,3,4-thiadiazole-2-carboxamide |
| 620 | 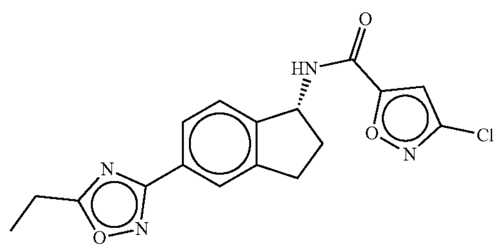 | (R)-3-chloro-N-(5-(5-ethyl-1,2,4-oxadiazol-3-yl)-2,3-dihydro-1H-inden-1-yl)isoxazole-5-carboxamide |
| 621 | 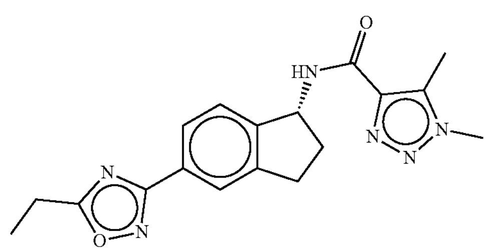 | (R)-N-(5-(5-ethyl-1,2,4-oxadiazol-3-yl)-2,3-dihydro-1H-inden-1-yl)-1,5-dimethyl-1H-1,2,3-triazole-4-carboxamide |
| 622 | 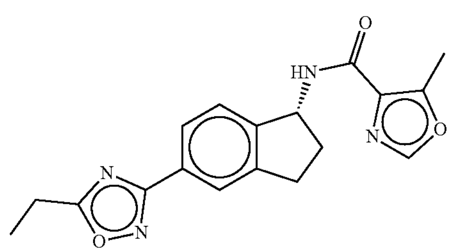 | (R)-N-(5-(5-ethyl-1,2,4-oxadiazol-3-yl)-2,3-dihydro-1H-inden-1-yl)-5-methyloxazole-4-carboxamide |
| 623 | 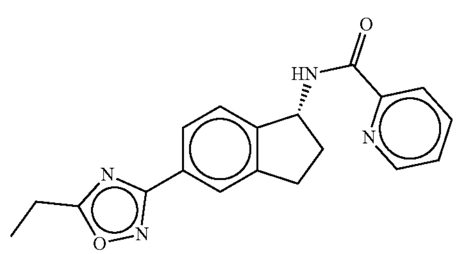 | (R)-N-(5-(5-ethyl-1,2,4-oxadiazol-3-yl)-2,3-dihydro-1H-inden-1-yl)picolinamide |
| 624 | 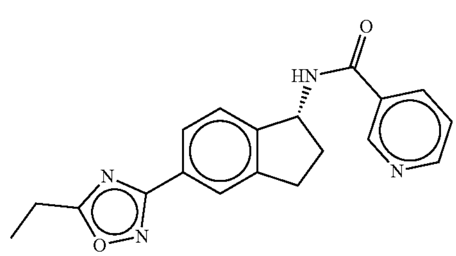 | (R)-N-(5-(5-ethyl-1,2,4-oxadiazol-3-yl)-2,3-dihydro-1H-inden-1-yl)nicotinamide |

TABLE 1-continued

| Cmpd No. | Structure | Name |
|---|---|---|
| 625 | 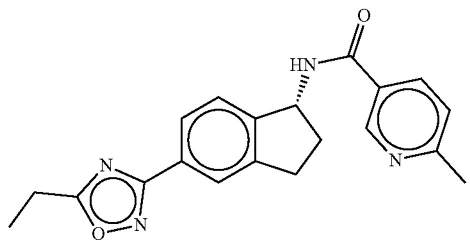 | (R)-N-(5-(5-ethyl-1,2,4-oxadiazol-3-yl)-2,3-dihydro-1H-inden-1-yl)-6-methylnicotinamide |
| 626 | 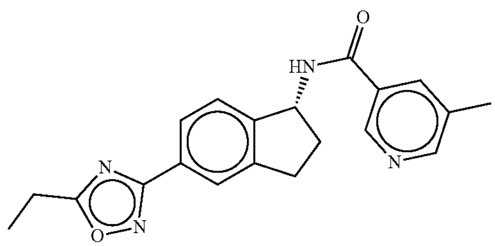 | (R)-N-(5-(5-ethyl-1,2,4-oxadiazol-3-yl)-2,3-dihydro-1H-inden-1-yl)-5-methylnicotinamide |
| 627 | 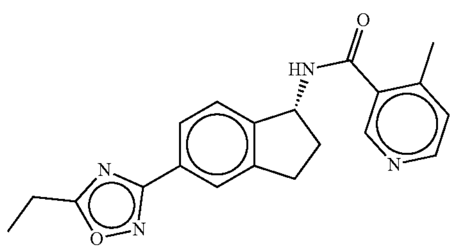 | (R)-N-(5-(5-ethyl-1,2,4-oxadiazol-3-yl)-2,3-dihydro-1H-inden-1-yl)-4-methylnicotinamide |
| 628 | 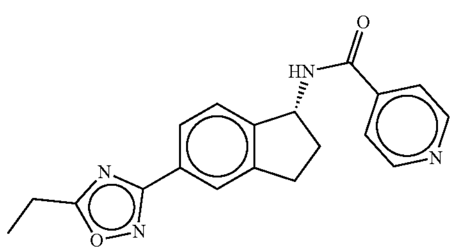 | (R)-N-(5-(5-ethyl-1,2,4-oxadiazol-3-yl)-2,3-dihydro-1H-inden-1-yl)isonicotinamide |
| 629 | 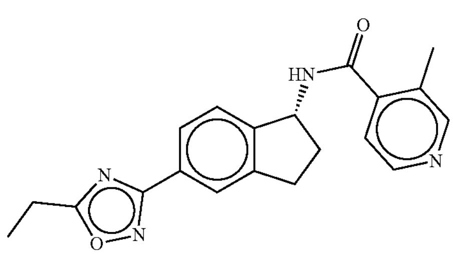 | (R)-N-(5-(5-ethyl-1,2,4-oxadiazol-3-yl)-2,3-dihydro-1H-inden-1-yl)-3-methylisonicotinamide |
| 630 | 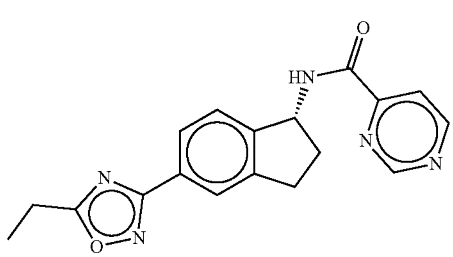 | (R)-N-(5-(5-ethyl-1,2,4-oxadiazol-3-yl)-2,3-dihydro-1H-inden-1-yl)pyrimidine-4-carboxamide |

TABLE 1-continued

| Cmpd No. | Structure | Name |
|---|---|---|
| 631 | 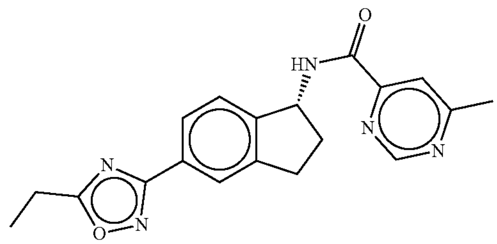 | (R)-N-(5-(5-ethyl-1,2,4-oxadiazol-3-yl)-2,3-dihydro-1H-inden-1-yl)-6-methylpyrimidine-4-carboxamide |
| 632 | 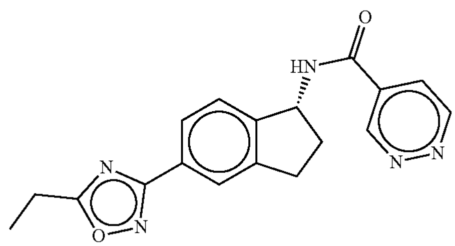 | (R)-N-(5-(5-ethyl-1,2,4-oxadiazol-3-yl)-2,3-dihydro-1H-inden-1-yl)pyridazine-4-carboxamide |
| 633 | 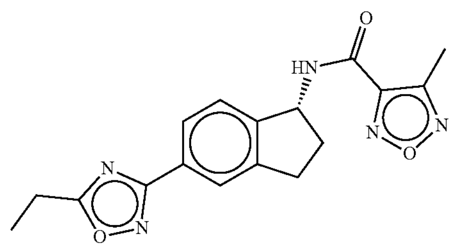 | (R)-N-(5-(5-ethyl-1,2,4-oxadiazol-3-yl)-2,3-dihydro-1H-inden-1-yl)-4-methyl-1,2,5-oxadiazole-3-carboxamide |
| 634 | 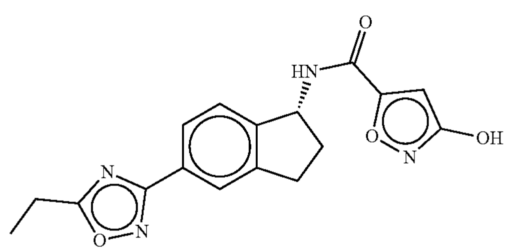 | (R)-N-(5-(5-ethyl-1,2,4-oxadiazol-3-yl)-2,3-dihydro-1H-inden-1-yl)-3-hydroxyisoxazole-5-carboxamide |
| 635 | 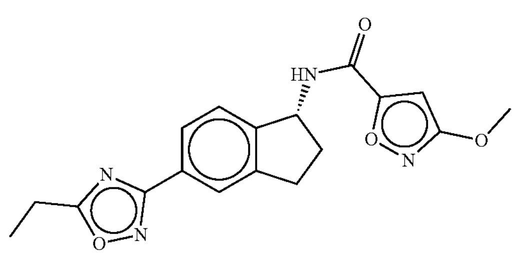 | (R)-N-(5-(5-ethyl-1,2,4-oxadiazol-3-yl)-2,3-dihydro-1H-inden-1-yl)-3-methoxyisoxazole-5-carboxamide |
| 636 | 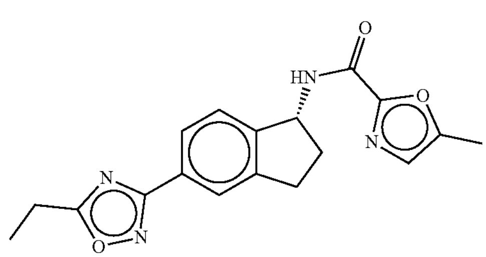 | (R)-N-(5-(5-ethyl-1,2,4-oxadiazol-3-yl)-2,3-dihydro-1H-inden-1-yl)-5-methyloxazole-2-carboxamide |

| Cmpd No. | Structure | Name |
|---|---|---|
| 637 | 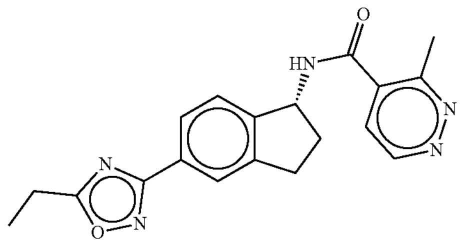 | (R)-N-(5-(5-ethyl-1,2,4-oxadiazol-3-yl)-2,3-dihydro-1H-inden-1-yl)-3-methylpyridazine-4-carboxamide |
| 638 | 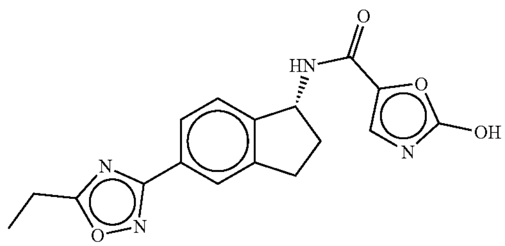 | (R)-N-(5-(5-ethyl-1,2,4-oxadiazol-3-yl)-2,3-dihydro-1H-inden-1-yl)-2-hydroxyoxazole-5-carboxamide |
| 639 | 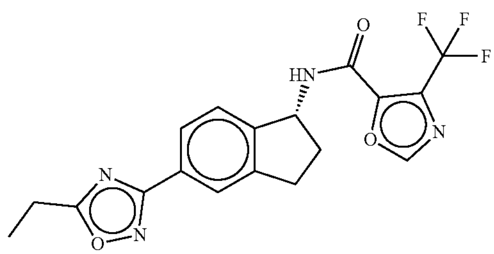 | (R)-N-(5-(5-ethyl-1,2,4-oxadiazol-3-yl)-2,3-dihydro-1H-inden-1-yl)-4-(trifluoromethyl)oxazole-5-carboxamide |
| 640 | 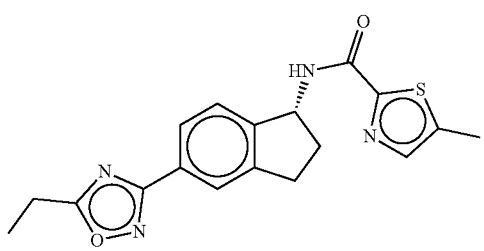 | (R)-N-(5-(5-ethyl-1,2,4-oxadiazol-3-yl)-2,3-dihydro-1H-inden-1-yl)-5-methylthiazole-2-carboxamide |
| 641 | 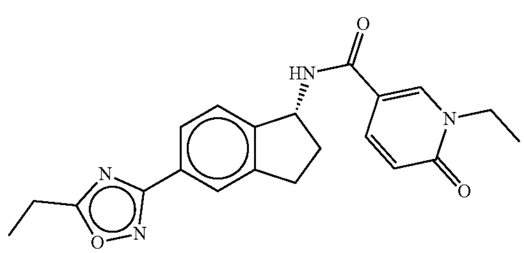 | (R)-1-ethyl-N-(5-(5-ethyl-1,2,4-oxadiazol-3-yl)-2,3-dihydro-1H-inden-1-yl)-6-oxo-1,6-dihydropyridine-3-carboxamide |
| 642 | 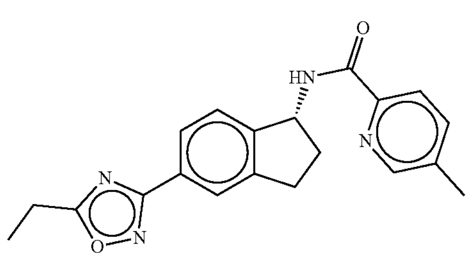 | (R)-N-(5-(5-ethyl-1,2,4-oxadiazol-3-yl)-2,3-dihydro-1H-inden-1-yl)-5-methylpicolinamide |

| Cmpd No. | Structure | Name |
|---|---|---|
| 643 | 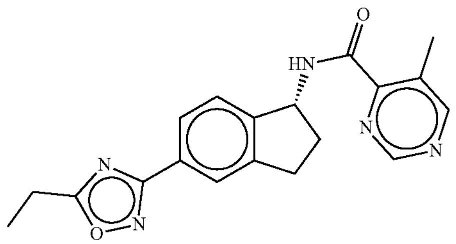 | (R)-N-(5-(5-ethyl-1,2,4-oxadiazol-3-yl)-2,3-dihydro-1H-inden-1-yl)-5-methylpyrimidine-4-carboxamide |
| 644 | 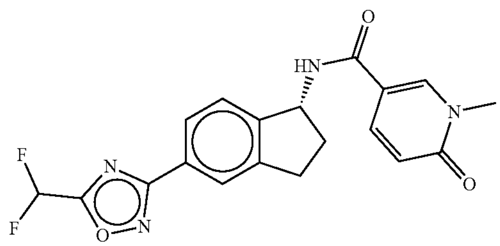 | (R)-N-(5-(5-(difluoromethyl)-1,2,4-oxadiazol-3-yl)-2,3-dihydro-1H-inden-1-yl)-1-methyl-6-oxo-1,6-dihydropyridine-3-carboxamide |
| 645 | 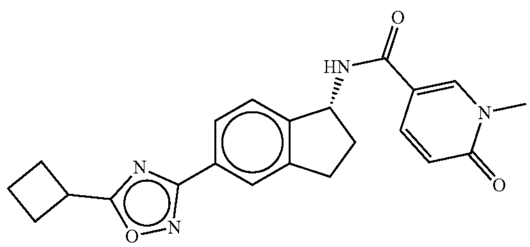 | (R)-N-(5-(5-cyclobutyl-1,2,4-oxadiazol-3-yl)-2,3-dihydro-1H-inden-1-yl)-1-methyl-6-oxo-1,6-dihydropyridine-3-carboxamide |
| 646 | 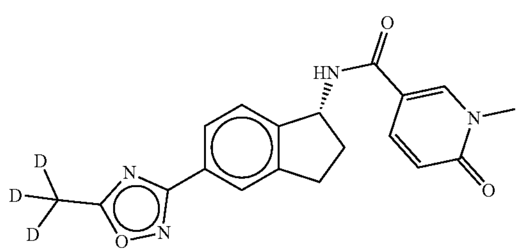 | (R)-1-methyl-N-(5-(5-(methyl-d3)-1,2,4-oxadiazol-3-yl)-2,3-dihydro-1H-inden-1-yl)-6-oxo-1,6-dihydropyridine-3-carboxamide |
| 647 | 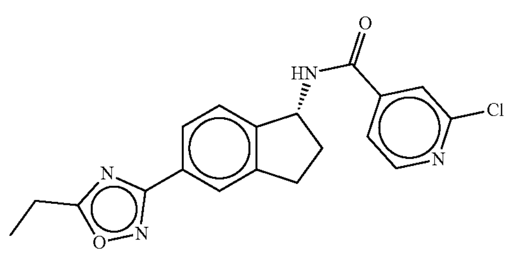 | (R)-2-chloro-N-(5-(5-ethyl-1,2,4-oxadiazol-3-yl)-2,3-dihydro-1H-inden-1-yl)isonicotinamide |
| 648 | 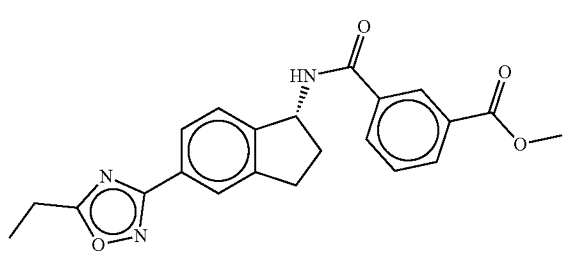 | Methyl (R)-3-((5-(5-ethyl-1,2,4-oxadiazol-3-yl)-2,3-dihydro-1H-inden-1-yl)carbamoyl)benzoate |

TABLE 1-continued

| Cmpd No. | Structure | Name |
|---|---|---|
| 649 | 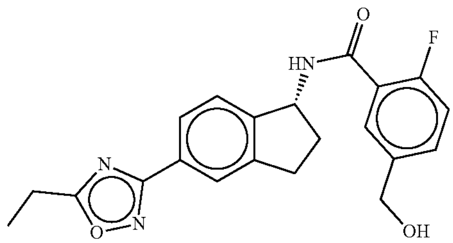 | (R)-N-(5-(5-ethyl-1,2,4-oxadiazol-3-yl)-2,3-dihydro-1H-inden-1-yl)-2-fluoro-5-(hydroxymethyl)benzamide |
| 650 | 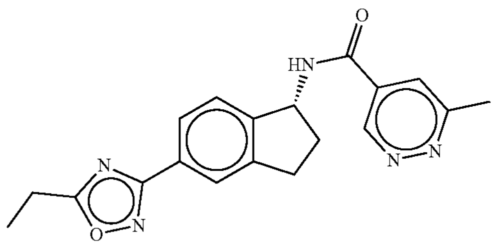 | (R)-N-(5-(5-ethyl-1,2,4-oxadiazol-3-yl)-2,3-dihydro-1H-inden-1-yl)-6-methylpyridazine-4-carboxamide |
| 651 | 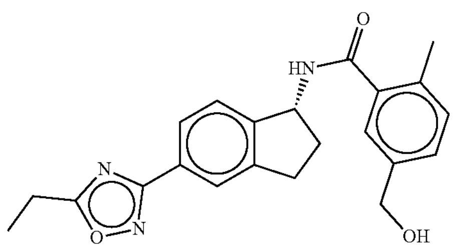 | (R)-N-(5-(5-ethyl-1,2,4-oxadiazol-3-yl)-2,3-dihydro-1H-inden-1-yl)-5-(hydroxymethyl)-2-methylbenzamide |
| 652 | 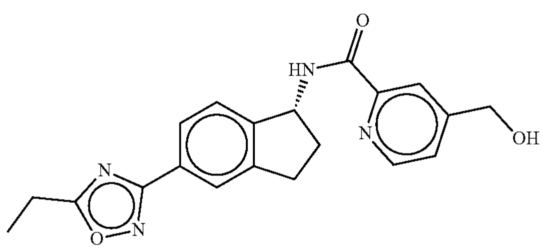 | (R)-N-(5-(5-ethyl-1,2,4-oxadiazol-3-yl)-2,3-dihydro-1H-inden-1-yl)-4-(hydroxymethyl)picolinamide |
| 653 | 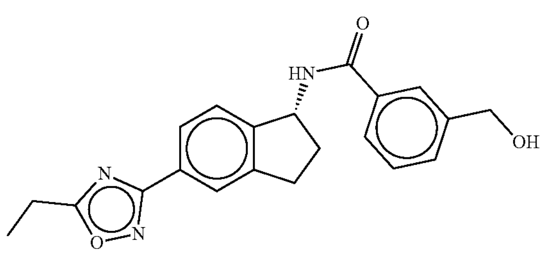 | (R)-N-(5-(5-ethyl-1,2,4-oxadiazol-3-yl)-2,3-dihydro-1H-inden-1-yl)-3-(hydroxymethyl)benzamide |
| 654 | 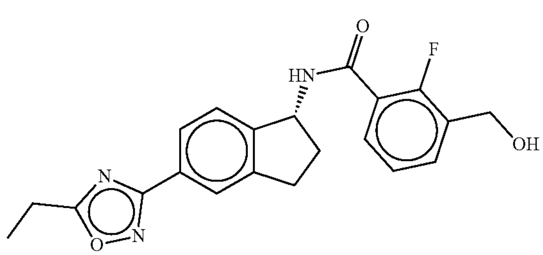 | (R)-N-(5-(5-ethyl-1,2,4-oxadiazol-3-yl)-2,3-dihydro-1H-inden-1-yl)-2-fluoro-3-(hydroxymethyl)benzamide |

TABLE 1-continued

| Cmpd No. | Structure | Name |
|---|---|---|
| 655 | 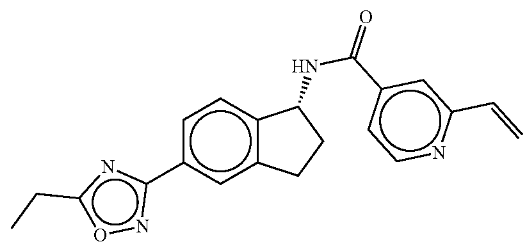 | (R)-N-(5-(5-ethyl-1,2,4-oxadiazol-3-yl)-2,3-dihydro-1H-inden-1-yl)-2-vinylisonicotinamide |
| 656 | 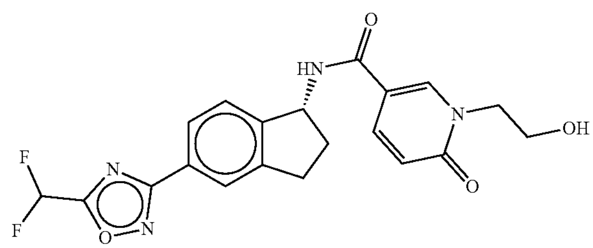 | (R)-N-(5-(5-(difluoromethyl)-1,2,4-oxadiazol-3-yl)-2,3-dihydro-1H-inden-1-yl)-1-(2-hydroxyethyl)-6-oxo-1,6-dihydropyridine-3-carboxamide |
| 657 | 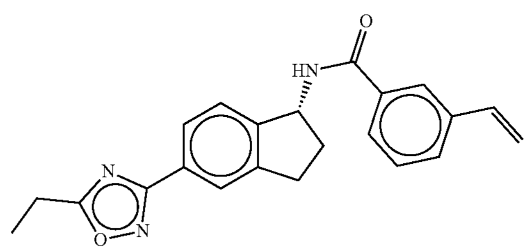 | (R)-N-(5-(5-ethyl-1,2,4-oxadiazol-3-yl)-2,3-dihydro-1H-inden-1-yl)-3-vinylbenzamide |
| 658 | 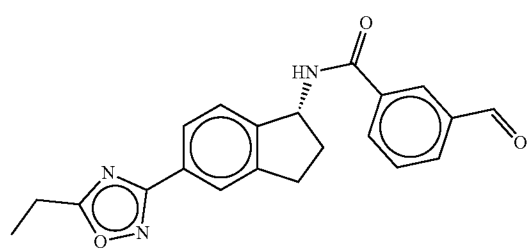 | (R)-N-(5-(5-ethyl-1,2,4-oxadiazol-3-yl)-2,3-dihydro-1H-inden-1-yl)-3-formylbenzamide |
| 659 | 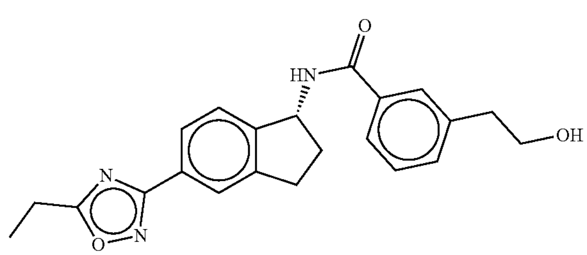 | (R)-N-(5-(5-ethyl-1,2,4-oxadiazol-3-yl)-2,3-dihydro-1H-inden-1-yl)-3-(2-hydroxyethyl)benzamide |
| 660 | 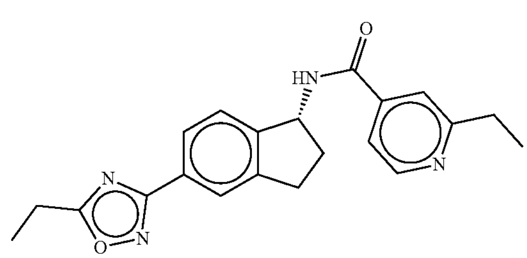 | (R)-2-ethyl-N-(5-(5-ethyl-1,2,4-oxadiazol-3-yl)-2,3-dihydro-1H-inden-1-yl)isonicotinamide |

TABLE 1-continued

| Cmpd No. | Structure | Name |
|---|---|---|
| 661 | 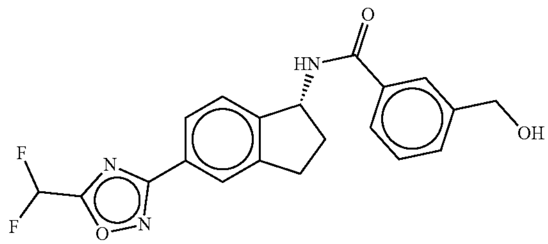 | (R)-N-(5-(5-(difluoromethyl)-1,2,4-oxadiazol-3-yl)-2,3-dihydro-1H-inden-1-yl)-3-(hydroxymethyl)benzamide |
| 662 | 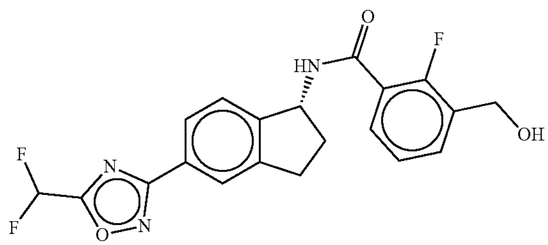 | (R)-N-(5-(5-(difluoromethyl)-1,2,4-oxadiazol-3-yl)-2,3-dihydro-1H-inden-1-yl)-2-fluoro-3-(hydroxymethyl)benzamide |
| 663 | 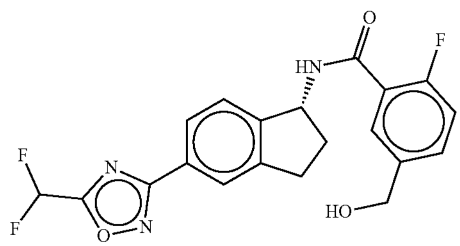 | (R)-N-(5-(5-(difluoromethyl)-1,2,4-oxadiazol-3-yl)-2,3-dihydro-1H-inden-1-yl)-2-fluoro-5-(hydroxymethyl)benzamide |
| 664 | 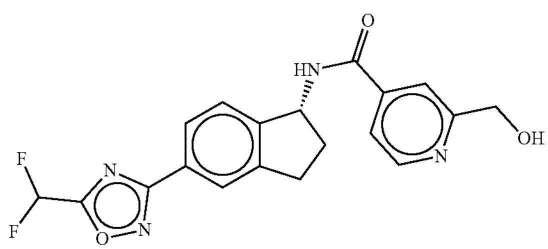 | (R)-N-(5-(5-(difluoromethyl)-1,2,4-oxadiazol-3-yl)-2,3-dihydro-1H-inden-1-yl)-2-(hydroxymethyl)isonicotinamide |
| 665 | 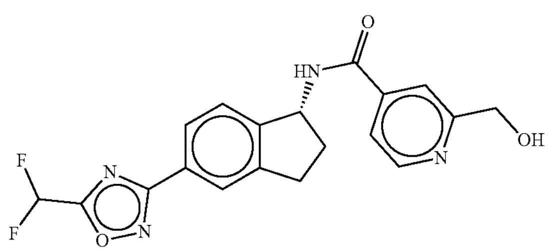 | (R)-N-(5-(5-(difluoromethyl)-1,2,4-oxadiazol-3-yl)-2,3-dihydro-1H-inden-1-yl)-2-(hydroxymethyl)isonicotinamide |
| 666 | 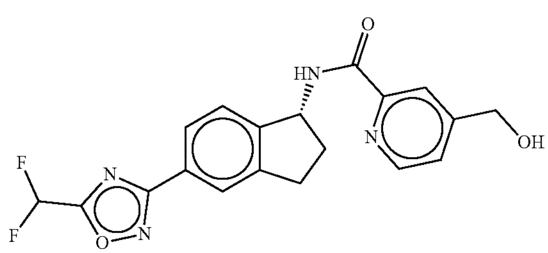 | (R)-N-(5-(5-(difluoromethyl)-1,2,4-oxadiazol-3-yl)-2,3-dihydro-1H-inden-1-yl)-4-(hydroxymethyl)picolinamide |

| Cmpd No. | Structure | Name |
|---|---|---|
| 667 | 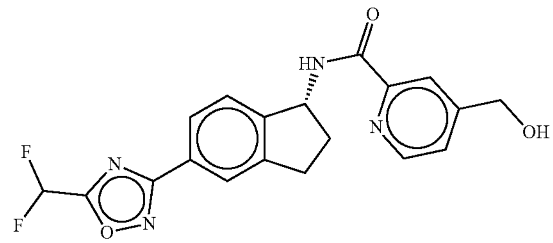 | (R)-N-(5-(5-(difluoromethyl)-1,2,4-oxadiazol-3-yl)-2,3-dihydro-1H-inden-1-yl)-4-(hydroxymethyl)picolinamide |
| 668 | 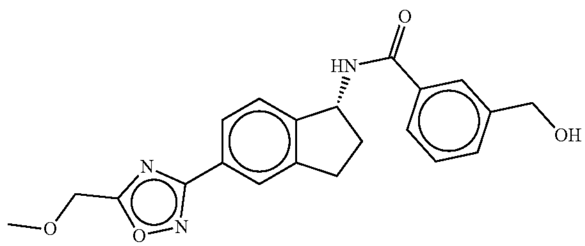 | (R)-3-(hydroxymethyl)-N-(5-(5-(methoxymethyl)-1,2,4-oxadiazol-3-yl)-2,3-dihydro-1H-inden-1-yl)benzamide |
| 669 | 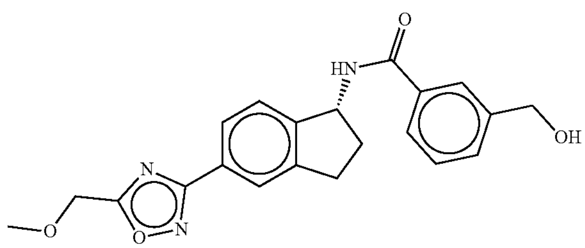 | (R)-3-(hydroxymethyl)-N-(5-(5-(methoxymethyl)-1,2,4-oxadiazol-3-yl)-2,3-dihydro-1H-inden-1-yl)benzamide |
| 670 | 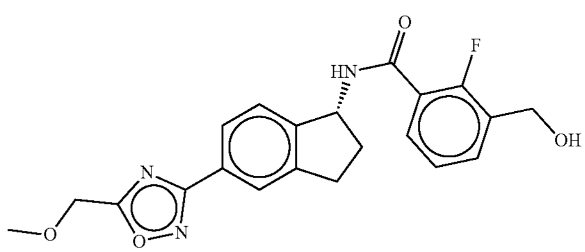 | (R)-2-fluoro-3-(hydroxymethyl)-N-(5-(5-(methoxymethyl)-1,2,4-oxadiazol-3-yl)-2,3-dihydro-1H-inden-1-yl)benzamide |
| 671 | 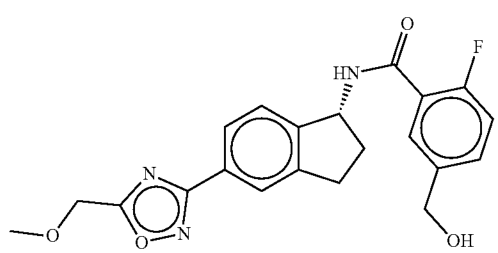 | (R)-2-fluoro-5-(hydroxymethyl)-N-(5-(5-(methoxymethyl)-1,2,4-oxadiazol-3-yl)-2,3-dihydro-1H-inden-1-yl)benzamide |
| 672 | 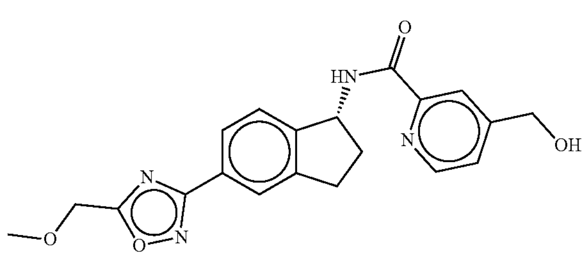 | (R)-4-(hydroxymethyl)-N-(5-(5-(methoxymethyl)-1,2,4-oxadiazol-3-yl)-2,3-dihydro-1H-inden-1-yl)picolinamide |

| Cmpd No. | Structure | Name |
|---|---|---|
| 673 | 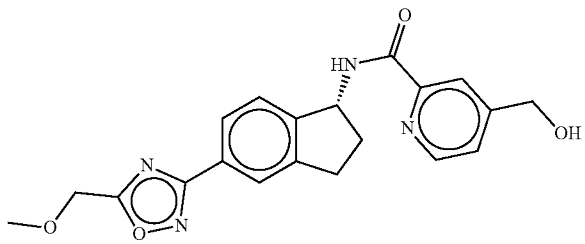 | (R)-4-(hydroxymethyl)-N-(5-(5-(methoxymethyl)-1,2,4-oxadiazol-3-yl)-2,3-dihydro-1H-inden-1-yl)picolinamide |
| 674 | 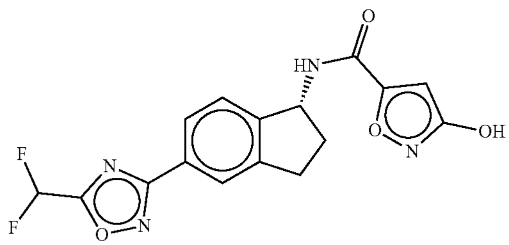 | (R)-N-(5-(5-(difluoromethyl)-1,2,4-oxadiazol-3-yl)-2,3-dihydro-1H-inden-1-yl)-3-hydroxyisoxazole-5-carboxamide |
| 675 | 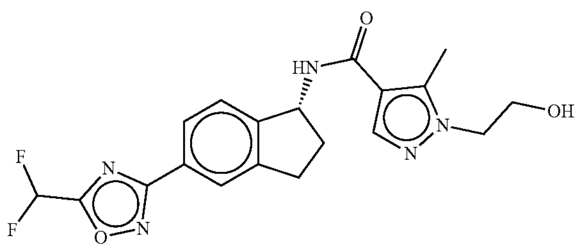 | (R)-N-(5-(5-(difluoromethyl)-1,2,4-oxadiazol-3-yl)-2,3-dihydro-1H-inden-1-yl)-1-(2-hydroxyethyl)-5-methyl-1H-pyrazole-4-carboxamide |
| 676 | 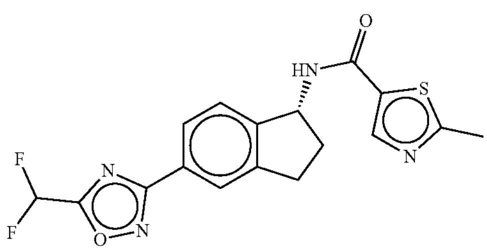 | (R)-N-(5-(5-(difluoromethyl)-1,2,4-oxadiazol-3-yl)-2,3-dihydro-1H-inden-1-yl)-2-methylthiazole-5-carboxamide |
| 677 | 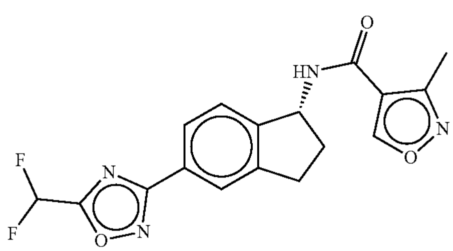 | (R)-N-(5-(5-(difluoromethyl)-1,2,4-oxadiazol-3-yl)-2,3-dihydro-1H-inden-1-yl)-3-methylisoxazole-4-carboxamide |
| 678 | 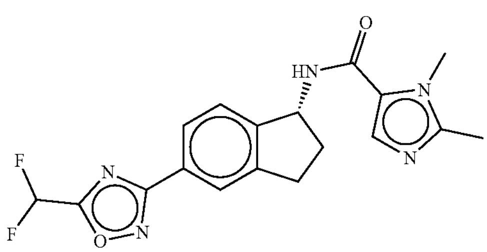 | (R)-N-(5-(5-(difluoromethyl)-1,2,4-oxadiazol-3-yl)-2,3-dihydro-1H-inden-1-yl)-1,2-dimethyl-1H-imidazole-5-carboxamide |

TABLE 1-continued

| Cmpd No. | Structure | Name |
|---|---|---|
| 679 | 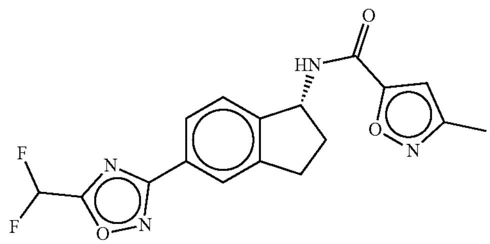 | (R)-N-(5-(5-(difluoromethyl)-1,2,4-oxadiazol-3-yl)-2,3-dihydro-1H-inden-1-yl)-3-methylisoxazole-5-carboxamide |
| 680 | 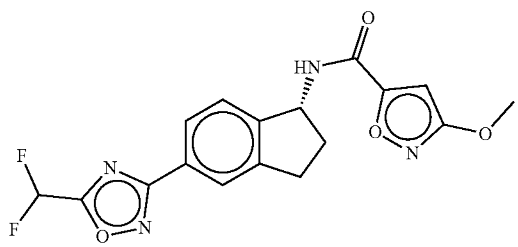 | (R)-N-(5-(5-(difluoromethyl)-1,2,4-oxadiazol-3-yl)-2,3-dihydro-1H-inden-1-yl)-3-methoxyisoxazole-5-carboxamide |
| 681 | 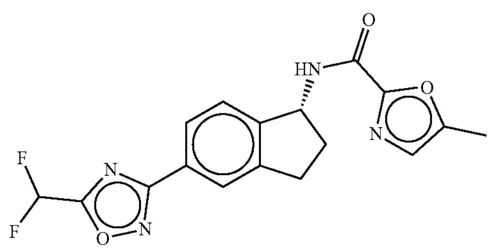 | (R)-N-(5-(5-(difluoromethyl)-1,2,4-oxadiazol-3-yl)-2,3-dihydro-1H-inden-1-yl)-5-methyloxazole-2-carboxamide |
| 682 | 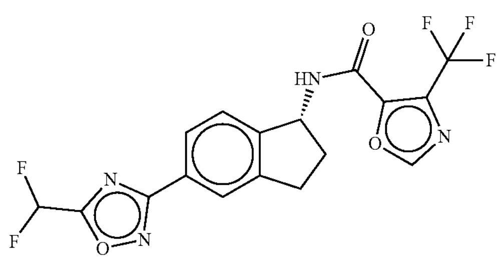 | (R)-N-(5-(5-(difluoromethyl)-1,2,4-oxadiazol-3-yl)-2,3-dihydro-1H-inden-1-yl)-4-(trifluoromethyl)oxazole-5-carboxamide |
| 683 | 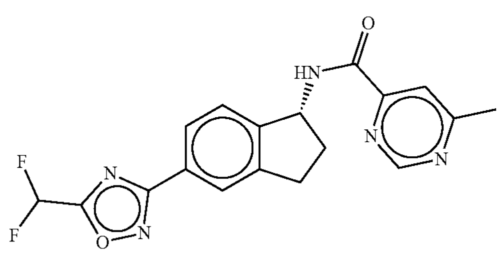 | (R)-N-(5-(5-(difluoromethyl)-1,2,4-oxadiazol-3-yl)-2,3-dihydro-1H-inden-1-yl)-6-methylpyrimidine-4-carboxamide |
| 684 | 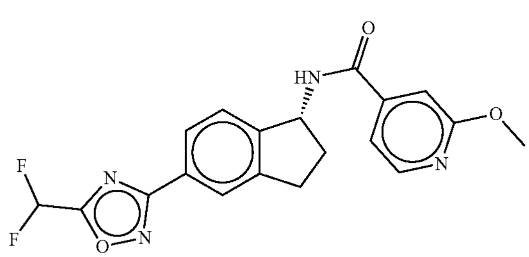 | (R)-N-(5-(5-(difluoromethyl)-1,2,4-oxadiazol-3-yl)-2,3-dihydro-1H-inden-1-yl)-2-methoxyisonicotinamide |

| Cmpd No. | Structure | Name |
|---|---|---|
| 685 | 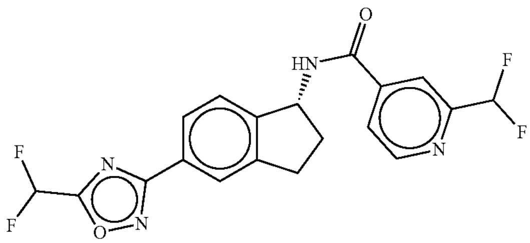 | (R)-2-(difluoromethyl)-N-(5-(5-(difluoromethyl)-1,2,4-oxadiazol-3-yl)-2,3-dihydro-1H-inden-1-yl)isonicotinamide |
| 686 | 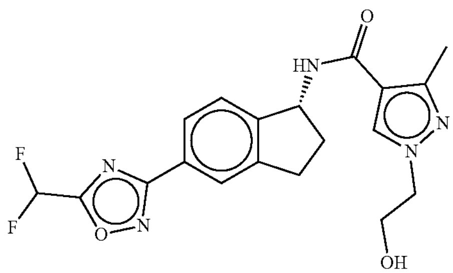 | (R)-N-(5-(5-(difluoromethyl)-1,2,4-oxadiazol-3-yl)-2,3-dihydro-1H-inden-1-yl)-1-(2-hydroxyethyl)-3-methyl-1H-pyrazole-4-carboxamide |
| 687 | 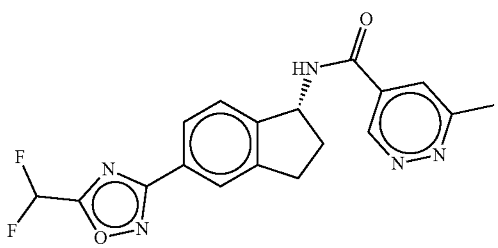 | (R)-N-(5-(5-(difluoromethyl)-1,2,4-oxadiazol-3-yl)-2,3-dihydro-1H-inden-1-yl)-6-methylpyridazine-4-carboxamide |
| 688 | 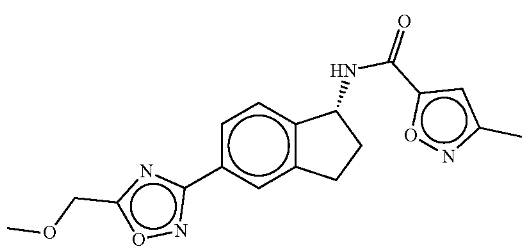 | (R)-N-(5-(5-(methoxymethyl)-1,2,4-oxadiazol-3-yl)-2,3-dihydro-1H-inden-1-yl)-3-methylisoxazole-5-carboxamide |
| 689 | 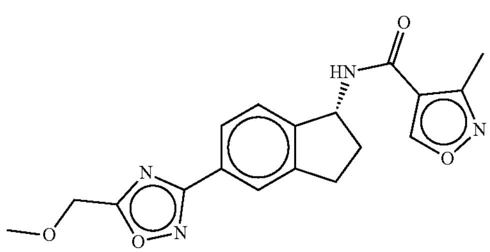 | (R)-N-(5-(5-(methoxymethyl)-1,2,4-oxadiazol-3-yl)-2,3-dihydro-1H-inden-1-yl)-3-methylisoxazole-4-carboxamide |
| 690 | 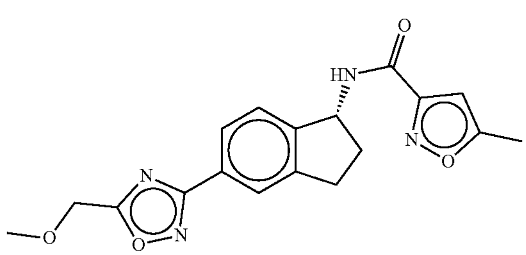 | (R)-N-(5-(5-(methoxymethyl)-1,2,4-oxadiazol-3-yl)-2,3-dihydro-1H-inden-1-yl)-5-methylisoxazole-3-carboxamide |

TABLE 1-continued

| Cmpd No. | Structure | Name |
|---|---|---|
| 691 | 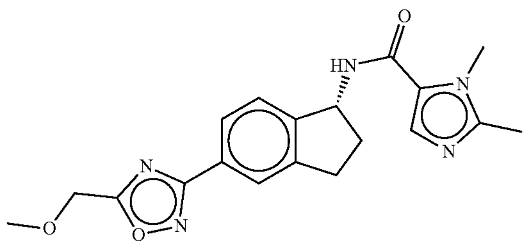 | (R)-N-(5-(5-(methoxymethyl)-1,2,4-oxadiazol-3-yl)-2,3-dihydro-1H-inden-1-yl)-1,2-dimethyl-1H-imidazole-5-carboxamide |
| 692 | 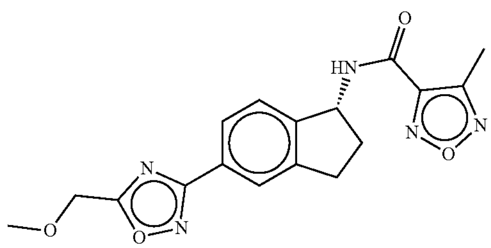 | (R)-N-(5-(5-(methoxymethyl)-1,2,4-oxadiazol-3-yl)-2,3-dihydro-1H-inden-1-yl)-4-methyl-1,2,5-oxadiazole-3-carboxamide |
| 693 | 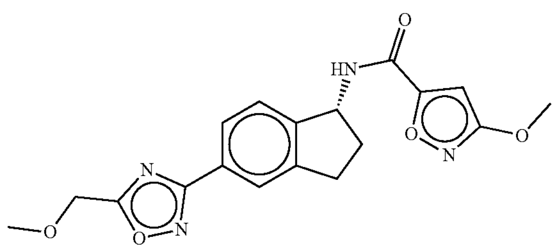 | (R)-3-methoxy-N-(5-(5-(methoxymethyl)-1,2,4-oxadiazol-3-yl)-2,3-dihydro-1H-inden-1-yl)isoxazole-5-carboxamide |
| 694 | 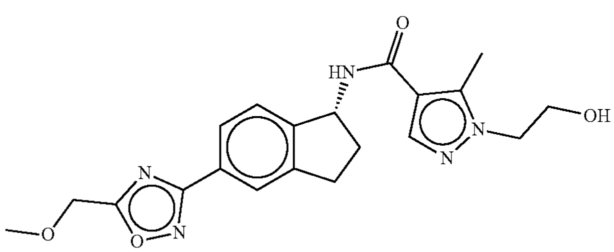 | (R)-1-(2-hydroxyethyl)-N-(5-(5-(methoxymethyl)-1,2,4-oxadiazol-3-yl)-2,3-dihydro-1H-inden-1-yl)-5-methyl-1H-pyrazole-4-carboxamide |
| 695 | 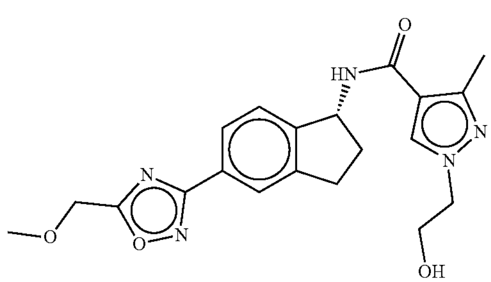 | (R)-1-(2-hydroxyethyl)-N-(5-(5-(methoxymethyl)-1,2,4-oxadiazol-3-yl)-2,3-dihydro-1H-inden-1-yl)-3-methyl-1H-pyrazole-4-carboxamide |
| 696 | 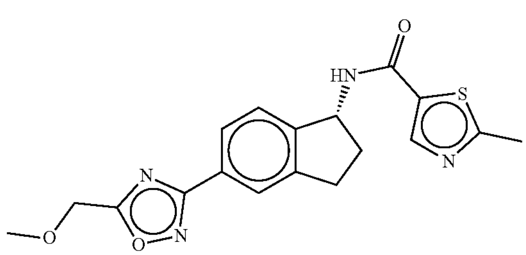 | (R)-N-(5-(5-(methoxymethyl)-1,2,4-oxadiazol-3-yl)-2,3-dihydro-1H-inden-1-yl)-2-methylthiazole-5-carboxamide |

| Cmpd No. | Structure | Name |
|---|---|---|
| 697 | 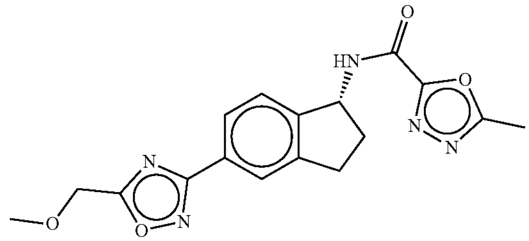 | (R)-N-(5-(5-(methoxymethyl)-1,2,4-oxadiazol-3-yl)-2,3-dihydro-1H-inden-1-yl)-5-methyl-1,3,4-oxadiazole-2-carboxamide |
| 698 | 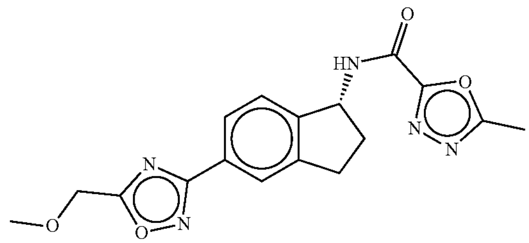 | (R)-N-(5-(5-(methoxymethyl)-1,2,4-oxadiazol-3-yl)-2,3-dihydro-1H-inden-1-yl)-5-methyl-1,3,4-oxadiazole-2-carboxamide |
| 699 | 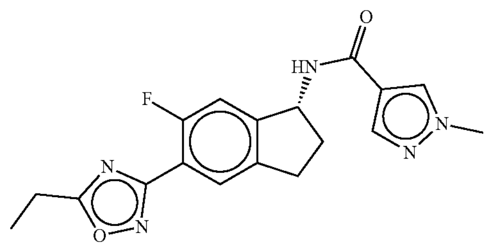 | (R)-N-(5-(5-ethyl-1,2,4-oxadiazol-3-yl)-6-fluoro-2,3-dihydro-1H-inden-1-yl)-1-methyl-1H-pyrazole-4-carboxamide |
| 700 | 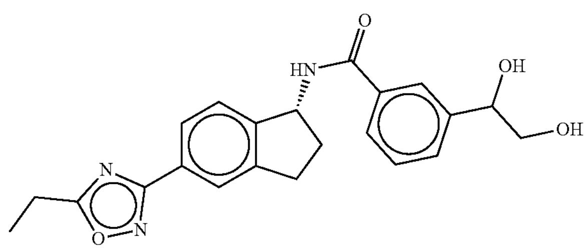 | 3-(1,2-dihydroxyethyl)-N-((R)-5-(5-ethyl-1,2,4-oxadiazol-3-yl)-2,3-dihydro-1H-inden-1-yl)benzamide |
| 701 | 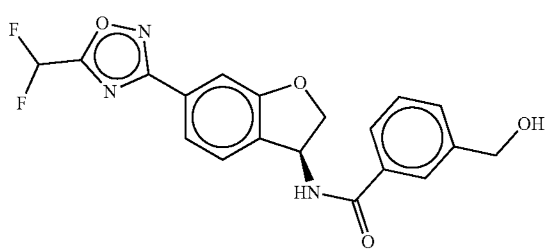 | (S)-N-(6-(5-(difluoromethyl)-1,2,4-oxadiazol-3-yl)-2,3-dihydrobenzofuran-3-yl)-3-(hydroxymethyl)benzamide |
| 702 | 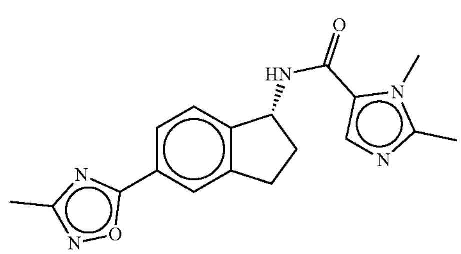 | (R)-1,2-dimethyl-N-(5-(3-methyl-1,2,4-oxadiazol-5-yl)-2,3-dihydro-1H-inden-1-yl)-1H-imidazole-5-carboxamide |

| Cmpd No. | Structure | Name |
|---|---|---|
| 703 | 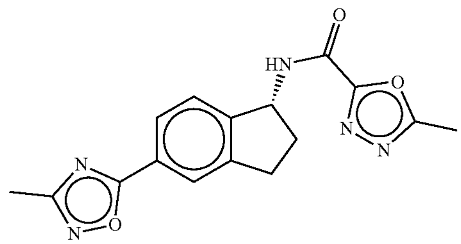 | (R)-5-methyl-N-(5-(3-methyl-1,2,4-oxadiazol-5-yl)-2,3-dihydro-1H-inden-1-yl)-1,3,4-oxadiazole-2-carboxamide |
| 704 | 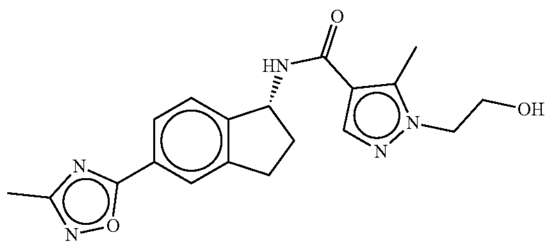 | (R)-1-(2-hydroxyethyl)-5-methyl-N-(5-(3-methyl-1,2,4-oxadiazol-5-yl)-2,3-dihydro-1H-inden-1-yl)-1H-pyrazole-4-carboxamide |
| 705 | 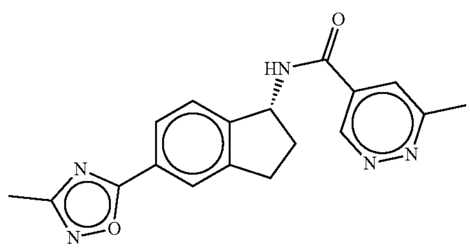 | (R)-6-methyl-N-(5-(3-methyl-1,2,4-oxadiazol-5-yl)-2,3-dihydro-1H-inden-1-yl)pyridazine-4-carboxamide |
| 706 | 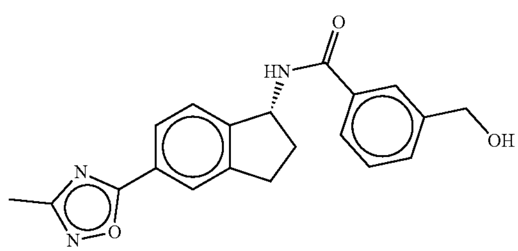 | (R)-3-(hydroxymethyl)-N-(5-(3-methyl-1,2,4-oxadiazol-5-yl)-2,3-dihydro-1H-inden-1-yl)benzamide |
| 707 | 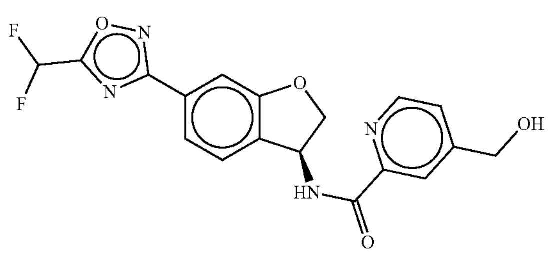 | (S)-N-(6-(5-(difluoromethyl)-1,2,4-oxadiazol-3-yl)-2,3-dihydrobenzofuran-3-yl)-4-(hydroxymethyl)picolinamide |
| 708 | 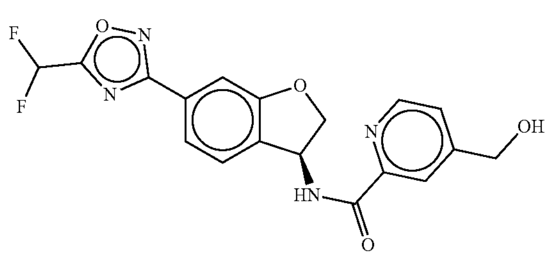 | (S)-N-(6-(5-(difluoromethyl)-1,2,4-oxadiazol-3-yl)-2,3-dihydrobenzofuran-3-yl)-4-(hydroxymethyl)picolinamide |

TABLE 1-continued

| Cmpd No. | Structure | Name |
|---|---|---|
| 709 | 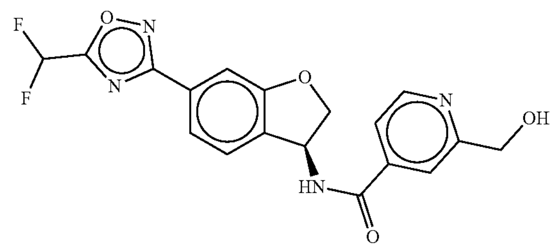 | (S)-N-(6-(5-(difluoromethyl)-1,2,4-oxadiazol-3-yl)-2,3-dihydrobenzofuran-3-yl)-2-(hydroxymethyl)isonicotinamide |
| 710 | 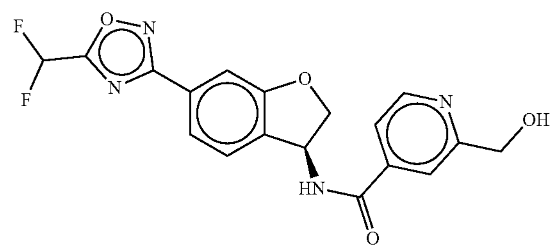 | (S)-N-(6-(5-(difluoromethyl)-1,2,4-oxadiazol-3-yl)-2,3-dihydrobenzofuran-3-yl)-2-(hydroxymethyl)isonicotinamide |
| 711 | 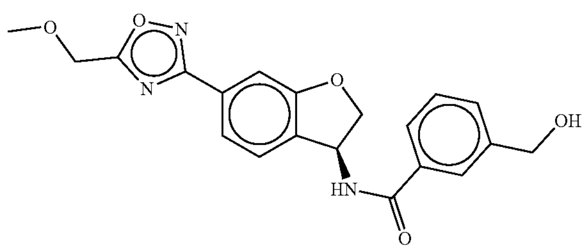 | (S)-3-(hydroxymethyl)-N-(6-(5-(methoxymethyl)-1,2,4-oxadiazol-3-yl)-2,3-dihydrobenzofuran-3-yl)benzamide |
| 712 | 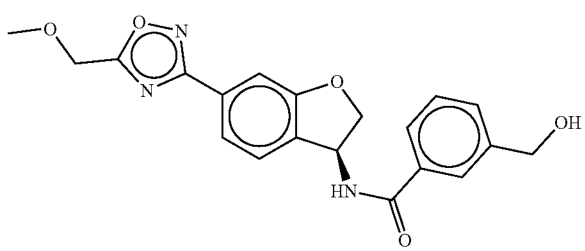 | (S)-3-(hydroxymethyl)-N-(6-(5-(methoxymethyl)-1,2,4-oxadiazol-3-yl)-2,3-dihydrobenzofuran-3-yl)benzamide |
| 713 | 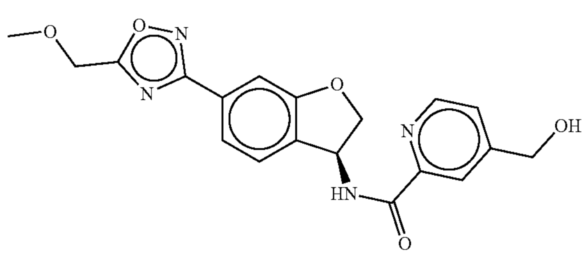 | (S)-4-(hydroxymethyl)-N-(6-(5-(methoxymethyl)-1,2,4-oxadiazol-3-yl)-2,3-dihydrobenzofuran-3-yl)picolinamide |
| 714 | 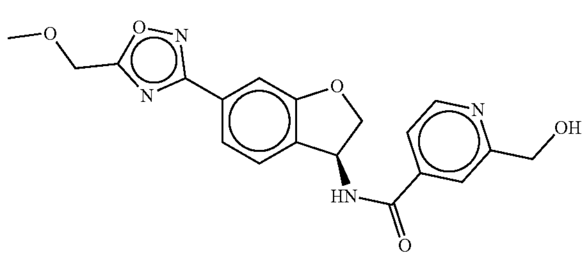 | (S)-2-(hydroxymethyl)-N-(6-(5-(methoxymethyl)-1,2,4-oxadiazol-3-yl)-2,3-dihydrobenzofuran-3-yl)isonicotinamide |

TABLE 1-continued

| Cmpd No. | Structure | Name |
|---|---|---|
| 715 | 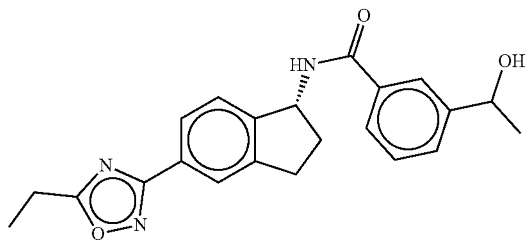 | N-((R)-5-(5-ethyl-1,2,4-oxadiazol-3-yl)-2,3-dihydro-1H-inden-1-yl)-3-(1-hydroxyethyl)benzamide |
| 716 | 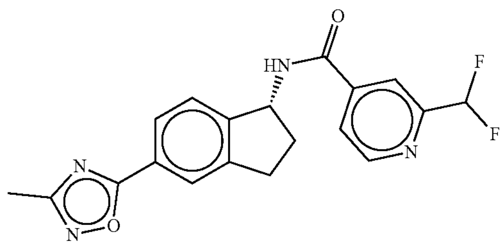 | (R)-2-(difluoromethyl)-N-(5-(3-methyl-1,2,4-oxadiazol-5-yl)-2,3-dihydro-1H-inden-1-yl)isonicotinamide |
| 717 | 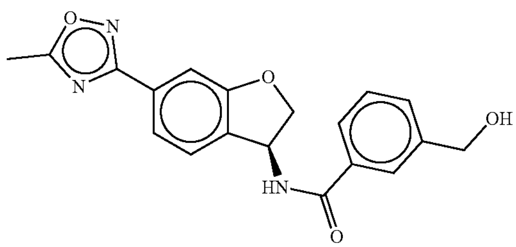 | (S)-3-(hydroxymethyl)-N-(6-(5-methyl-1,2,4-oxadiazol-3-yl)-2,3-dihydrobenzofuran-3-yl)benzamide |
| 718 | 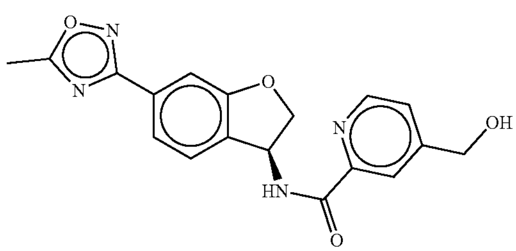 | (S)-4-(hydroxymethyl)-N-(6-(5-methyl-1,2,4-oxadiazol-3-yl)-2,3-dihydrobenzofuran-3-yl)picolinamide |
| 719 | 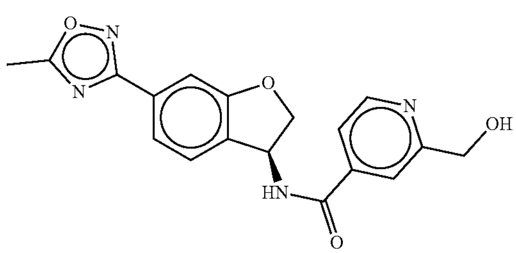 | (S)-2-(hydroxymethyl)-N-(6-(5-methyl-1,2,4-oxadiazol-3-yl)-2,3-dihydrobenzofuran-3-yl)isonicotinamide |
| 720 | 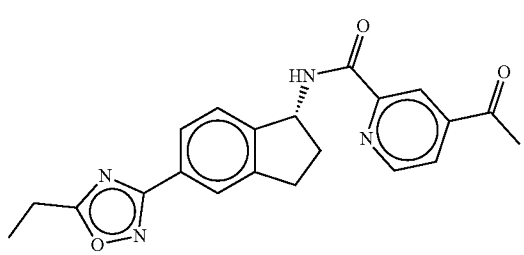 | (R)-4-acetyl-N-(5-(5-ethyl-1,2,4-oxadiazol-3-yl)-2,3-dihydro-1H-inden-1-yl)picolinamide |

TABLE 1-continued

| Cmpd No. | Structure | Name |
|---|---|---|
| 721 | 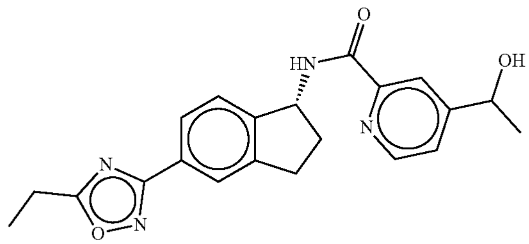 | N-((R)-5-(5-ethyl-1,2,4-oxadiazol-3-yl)-2,3-dihydro-1H-inden-1-yl)-4-(1-hydroxyethyl)picolinamide |
| 722 | 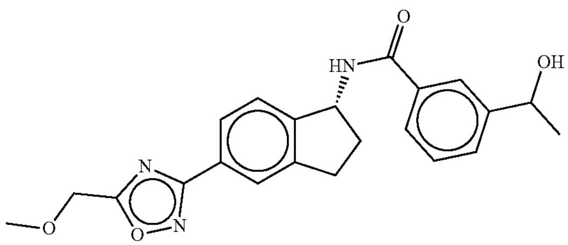 | 3-(1-hydroxyethyl)-N-((R)-5-(5-(methoxymethyl)-1,2,4-oxadiazol-3-yl)-2,3-dihydro-1H-inden-1-yl)benzamide |
| 723 | 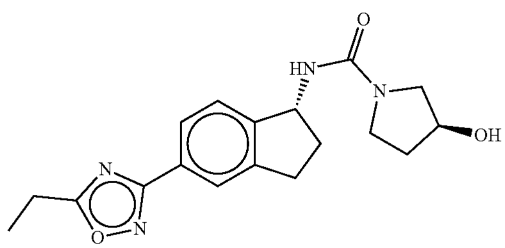 | (S)-N-((R)-5-(5-ethyl-1,2,4-oxadiazol-3-yl)-2,3-dihydro-1H-inden-1-yl)-3-hydroxypyrrolidine-1-carboxamide |
| 724 | 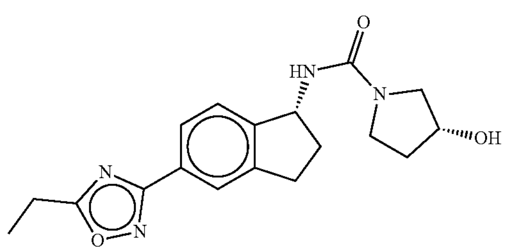 | (R)-N-((R)-5-(5-ethyl-1,2,4-oxadiazol-3-yl)-2,3-dihydro-1H-inden-1-yl)-3-hydroxypyrrolidine-1-carboxamide |
| 725 | 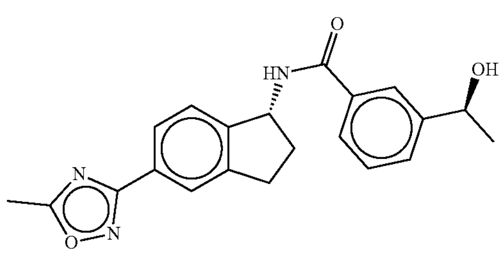 | 3-((S)-1-hydroxyethyl)-N-((R)-5-(5-methyl-1,2,4-oxadiazol-3-yl)-2,3-dihydro-1H-inden-1-yl)benzamide |
| 726 | 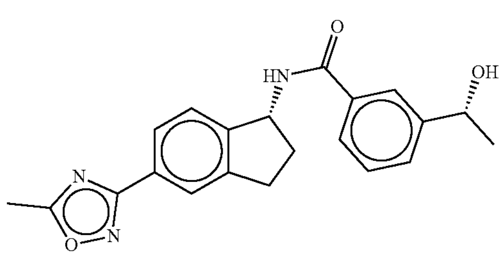 | 3-((R)-1-hydroxyethyl)-N-((R)-5-(5-methyl-1,2,4-oxadiazol-3-yl)-2,3-dihydro-1H-inden-1-yl)benzamide |

TABLE 1-continued

| Cmpd No. | Structure | Name |
|---|---|---|
| 727 | 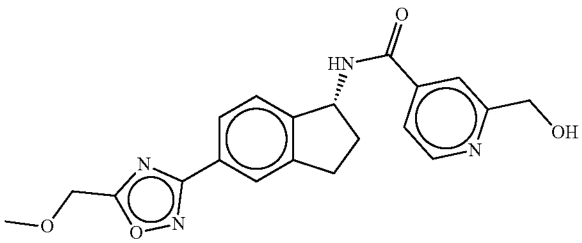 | (R)-2-(hydroxymethyl)-N-(5-(5-(methoxymethyl)-1,2,4-oxadiazol-3-yl)-2,3-dihydro-1H-inden-1-yl)isonicotinamide |
| 728 | 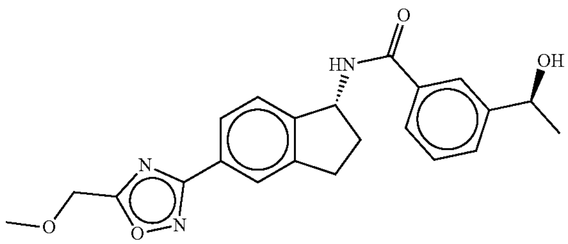 | 3-((S)-1-hydroxyethyl)-N-((R)-5-(5-(methoxymethyl)-1,2,4-oxadiazol-3-yl)-2,3-dihydro-1H-inden-1-yl)benzamide |
| 729 | 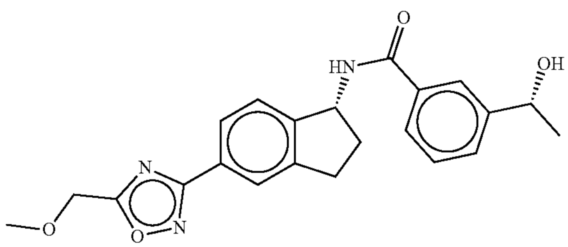 | 3-((R)-1-hydroxyethyl)-N-((R)-5-(5-(methoxymethyl)-1,2,4-oxadiazol-3-yl)-2,3-dihydro-1H-inden-1-yl)benzamide |
| 730 | 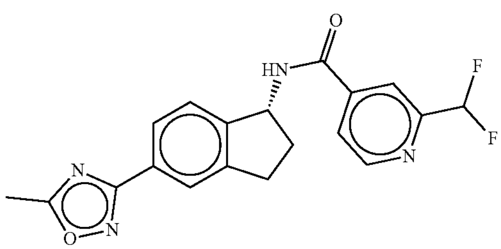 | (R)-2-(difluoromethyl)-N-(5-(5-methyl-1,2,4-oxadiazol-3-yl)-2,3-dihydro-1H-inden-1-yl)isonicotinamide |
| 731 | 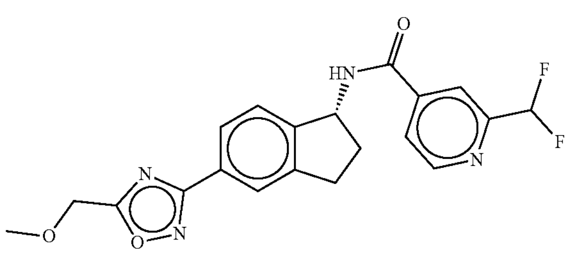 | (R)-2-(difluoromethyl)-N-(5-(5-(methoxymethyl)-1,2,4-oxadiazol-3-yl)-2,3-dihydro-1H-inden-1-yl)isonicotinamide |
| 732 | 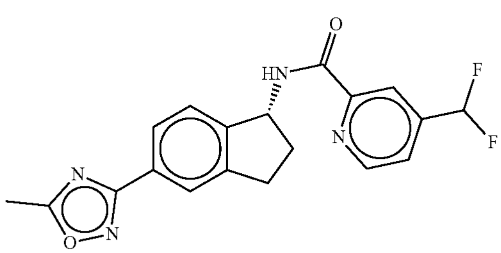 | (R)-4-(difluoromethyl)-N-(5-(5-methyl-1,2,4-oxadiazol-3-yl)-2,3-dihydro-1H-inden-1-yl)picolinamide |

TABLE 1-continued

| Cmpd No. | Structure | Name |
|---|---|---|
| 733 | 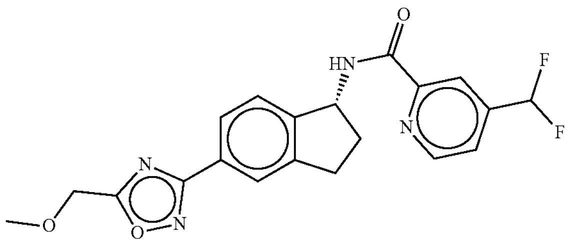 | (R)-4-(difluoromethyl)-N-(5-(5-(methoxymethyl)-1,2,4-oxadiazol-3-yl)-2,3-dihydro-1H-inden-1-yl)picolinamide |
| 734 | 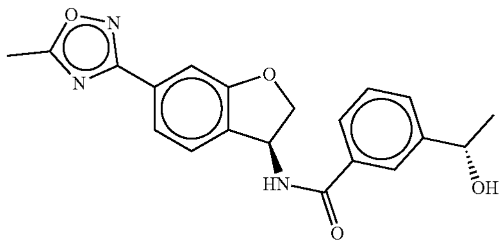 | 3-((S)-1-hydroxyethyl)-N-((S)-6-(5-methyl-1,2,4-oxadiazol-3-yl)-2,3-dihydrobenzofuran-3-yl)benzamide |
| 735 | 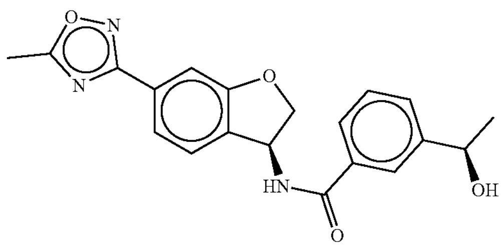 | 3-((R)-1-hydroxyethyl)-N-((S)-6-(5-methyl-1,2,4-oxadiazol-3-yl)-2,3-dihydrobenzofuran-3-yl)benzamide |
| 736 | 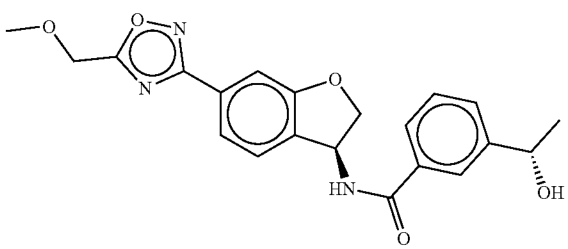 | 3-((S)-1-hydroxyethyl)-N-((S)-6-(5-(methoxymethyl)-1,2,4-oxadiazol-3-yl)-2,3-dihydrobenzofuran-3-yl)benzamide |
| 737 | 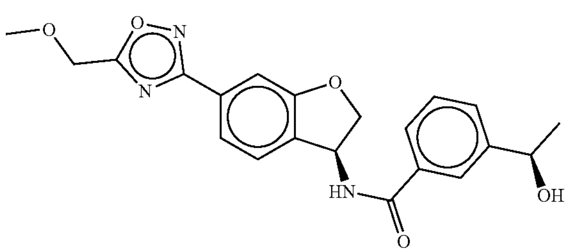 | 3-((R)-1-hydroxyethyl)-N-((S)-6-(5-(methoxymethyl)-1,2,4-oxadiazol-3-yl)-2,3-dihydrobenzofuran-3-yl)benzamide |
| 738 | 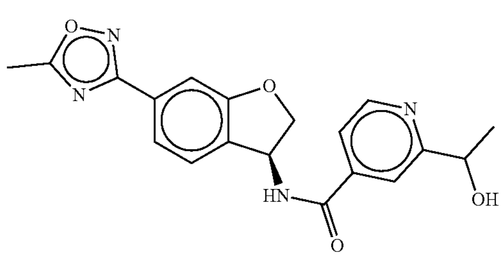 | 2-(1-hydroxyethyl)-N-((S)-6-(5-methyl-1,2,4-oxadiazol-3-yl)-2,3-dihydrobenzofuran-3-yl)isonicotinamide |

TABLE 1-continued

| Cmpd No. | Structure | Name |
|---|---|---|
| 739 | 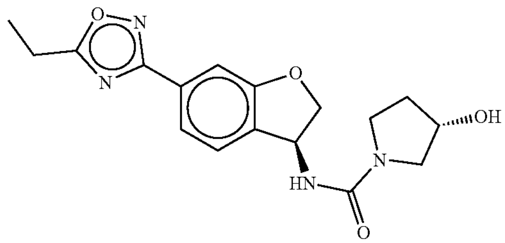 | (S)-N-((S)-6-(5-ethyl-1,2,4-oxadiazol-3-yl)-2,3-dihydrobenzofuran-3-yl)-3-hydroxypyrrolidine-1-carboxamide |
| 740 | 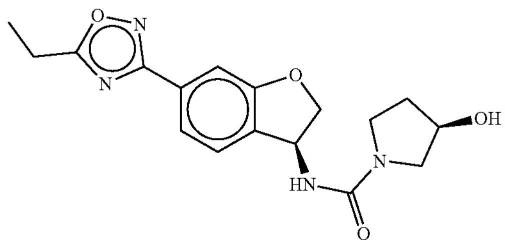 | (R)-N-((S)-6-(5-ethyl-1,2,4-oxadiazol-3-yl)-2,3-dihydrobenzofuran-3-yl)-3-hydroxypyrrolidine-1-carboxamide |
| 741 | 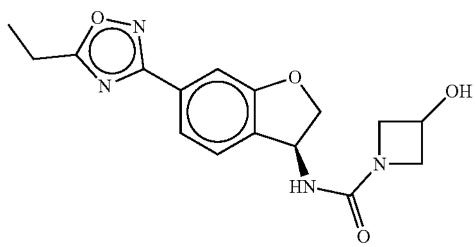 | (S)-N-(6-(5-ethyl-1,2,4-oxadiazol-3-yl)-2,3-dihydrobenzofuran-3-yl)-3-hydroxyazetidine-1-carboxamide |
| 742 | 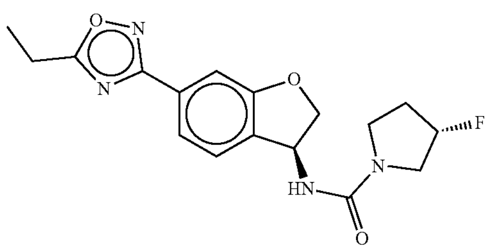 | (S)-N-((S)-6-(5-ethyl-1,2,4-oxadiazol-3-yl)-2,3-dihydrobenzofuran-3-yl)-3-fluoropyrrolidine-1-carboxamide |
| 743 | 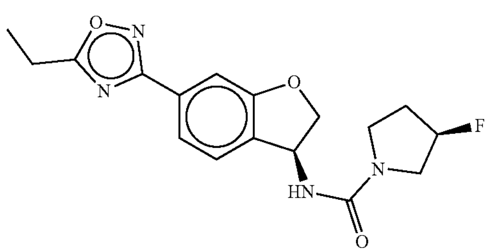 | (R)-N-((S)-6-(5-ethyl-1,2,4-oxadiazol-3-yl)-2,3-dihydrobenzofuran-3-yl)-3-fluoropyrrolidine-1-carboxamide |
| 744 | 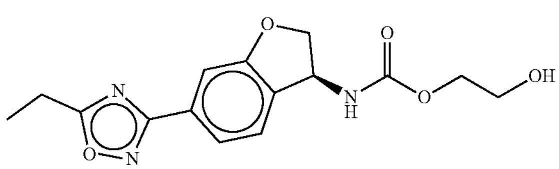 | 2-hydroxyethyl (S)-(6-(5-ethyl-1,2,4-oxadiazol-3-yl)-2,3-dihydrobenzofuran-3-yl)carbamate |
| 745 | 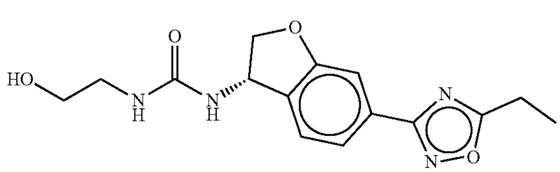 | (S)-1-(6-(5-ethyl-1,2,4-oxadiazol-3-yl)-2,3-dihydrobenzofuran-3-yl)-3-(2-hydroxyethyl)urea |

TABLE 1-continued

| Cmpd No. | Structure | Name |
|---|---|---|
| 746 | 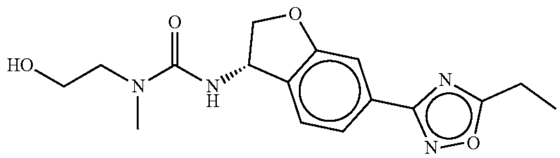 | (S)-3-(6-(5-ethyl-1,2,4-oxadiazol-3-yl)-2,3-dihydrobenzofuran-3-yl)-1-(2-hydroxyethyl)-1-methylurea |

In some variations, any of the compounds described herein, such as a compound of Formula (I), (Ia), (Ib), (Ic), (Id), (Ie), (If), (Ig), (Ih), (Ii), (Ij), or (Ik), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (Ia), (Ib), (Ic), (Id), (Ie), (If), (Ig), (Ih), (Ii), (Ij), or (Ik), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $G_1$, $G_2$, $G_3$, Z, A, B, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^x$, $R^y$, $R^z$, $R^a$, $R^b$, $R^c$, $R^d$, $R^e$, $R^f$, $R^g$, $R^h$, $R^i$, $R^j$, $R^n$, $R^p$, $R^q$, and $R^r$ provided herein can be combined with every other variation or embodiment of $G_1$, $G_2$, $G_3$, Z, A, B, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^x$, $R^y$, $R^z$, $R^a$, $R^b$, $R^c$, $R^d$, $R^e$, $R^f$, $R^g$, $R^h$, $R^i$, $R^j$, $R^n$, $R^p$, $R^q$, and $R^r$, as if each combination had been individually and specifically described.

Other embodiments will be apparent to those skilled in the art from the following detailed description.

As used herein, when any variable occurs more than one time in a chemical formula, its definition on each occurrence is independent of its definition at every other occurrence.

Formula (I) includes all subformulae thereof. For example, Formula (I) includes compounds of Formula (Ia), (Ib), (Ic), (Id), (Ie), (If), (Ig), (Ih), (Ii), (Ij), and (Ik).

The compound names provided herein, including in Table 1, are provided by ChemBioDraw Professional 15.0.0.106. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

The compounds and pharmaceutical compositions herein may be used to treat or prevent a disease or condition in an individual or subject.

Without being bound by theory, the compounds and pharmaceutical compositions disclosed herein are believed to act by inhibiting myosin. This inhibition potentially decreases the number of independent myosin heads interacting with actin filaments reducing the amount of contraction. Reducing contraction of cardiac muscle can be important for the treatment of heart diseases in which over-contraction is an issue. In some embodiments, provided are methods of treating or preventing heart disease in an individual or subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. In some embodiments, provided are methods of treating or preventing heart disease in a subject in need thereof comprising administering to the subject a therapeutically effective amount of at least one chemical entity as described herein. In some embodiments, provided are methods of treating heart disease in a subject in need thereof comprising administering to the subject a therapeutically effective amount of at least one chemical entity as described herein. In some embodiments, provided are methods of treating an established or diagnosed heart disease in a subject in need thereof comprising administering to the subject a therapeutically effective amount of at least one chemical entity as described herein. In some embodiments, provided are methods of preventing heart disease in a subject in need thereof comprising administering to the subject a therapeutically effective amount of at least one chemical entity as described herein.

Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of a heart disease in a subject. In some aspects, provided is a compound or composition as described herein for use in a method of treatment of the human or animal body by therapy. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in a method of treatment of the human or animal body by therapy. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating or preventing heart disease. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating heart disease. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating an established or diagnosed heart disease. In other embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in preventing heart disease. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating a disease or condition associated with HCM. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating a disease or condition associated with secondary left ventricular wall thickening. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in ameliorating a symptom associated with heart disease. In other embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in reducing the risk of a symptom associated with heart disease. In other embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating a disease or condition associated with small left ventricular cavity and cavity obliteration, hyperdynamic left ventricular contraction, myocardial ischemia, or cardiac fibrosis. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating muscular dystrophies. In some embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in treating a glycogen storage disease. In other embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in modulating the cardiac sarcomere, such as inhibiting the cardiac sarcomere. In yet other embodiments, provided herein are compounds of Formula (I), (Ia), (Ib), (Ic), (Id), (Ie), (If), (Ig), (Ih), (Ii), (Ij), or (Ik), or a compound of Table 1, or a pharmaceutically acceptable salt thereof, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated non-catalytic subunit gamma 2 (PRKAG2).

In some embodiments, provided herein are methods of treating a disease or condition associated with HCM, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. In some embodiments, the disease or condition is Fabry's Disease, Danon Disease, mitochondrial cardiomyopathies, or Noonan Syndrome.

Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardio-renal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of reducing the risk of a symptom associated with heart disease in a subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof, wherein the symptom is one or more selected from sudden cardiac death, poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof.

In some embodiments, the provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof.

Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of muscular dystrophies (e.g., Duchenne muscular dystrophy).

In some embodiments, the provided are methods of treating a glycogen storage disease in an individual or subject, comprising administering to the individual or subject in need thereof a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. Also provided herein is the use of a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), (If), (Ig), (Ih), (Ii), (Ij), or (Ik), or a compound of Table 1, or a pharmaceutically acceptable salt thereof in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the compound reduces the contractility of a cardiomyocyte. In some embodiments, the compound reduces the contractility of a cardiomyocyte by greater than 40%, such as greater than 45%, 50%, 60%, 70%, 80%, or 90%. In some embodiments, the compound reduced the contractility of a cardiomyocyte 40%-90%, such as 40%-80%, 40-70%, 50%-90%, 50%-80% or 50%-70%. In some embodiments, the compound does not significantly alter calcium transients in the cardiomyocyte. In some embodiments, the compound decreases the ATPase activity in a cardiomyocyte. Methods of measuring contractility, ATPase activity, and calcium transients are known in the art, for example, by calcium labeling, electrophysiological recordings, and microscopic imaging. In some embodiments, the compound does not significantly inhibit or induce a cytochrome P450 (CYP) protein.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 mL/kg/m$^2$, such as more than 1.2 mL/kg/m$^2$, 1.4 mL/kg/m$^2$, 1.5 mL/kg/m$^2$, 1.7 mL/kg/m$^2$, 2 mL/kg/m$^2$, 2.2 mL/kg/m$^2$, 2.5 mL/kg/m$^2$, 3 mL/kg/m$^2$, 3.2 mL/kg/m$^2$, or 3.5 mL/kg/m$^2$ following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 mL/kg/m$^2$, such as more than 1.2 mL/kg/m$^2$, 1.4 mL/kg/m$^2$, 1.5 mL/kg/m$^2$, 1.7 mL/kg/m$^2$, or 2 mL/kg/m$^2$ and the subject has a reduced NYHA functional class following treatment. In some embodiments, $VO_2$ max is improved by more than 2.5 mL/kg/m$^2$, 3 mL/kg/m$^2$, 3.2 mL/kg/m$^2$, or 3.5 mL/kg/m$^2$ and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

The compounds and compositions described and/or disclosed herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds and compositions described and/or disclosed herein may be combined with one or more other therapies to treat HCM or HFpEF. In some embodiments, the compounds and/compositions may be combined with a β-blocker, verapamil, and/or disopyramide.

General Synthetic Methods

Compounds of Formula (I), (Ia), (Ib), (Ic), (Id), (Ie), (If), (Ig), (Ih), (Ii), (Ij), and (Ik) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (Ia), (Ib), (Ic), (Id), (Ie), (If), (Ig), (Ih), (Ii), (Ij), and (Ik).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (Ia), (Ib), (Ic), (Id), (Ie), (If), (Ig), (Ih), (Ii), (Ij), and (Ik), or any variation thereof. Other compounds described herein may be prepared by similar methods.

In some embodiments, compounds provided herein may be synthesized according to Scheme A.

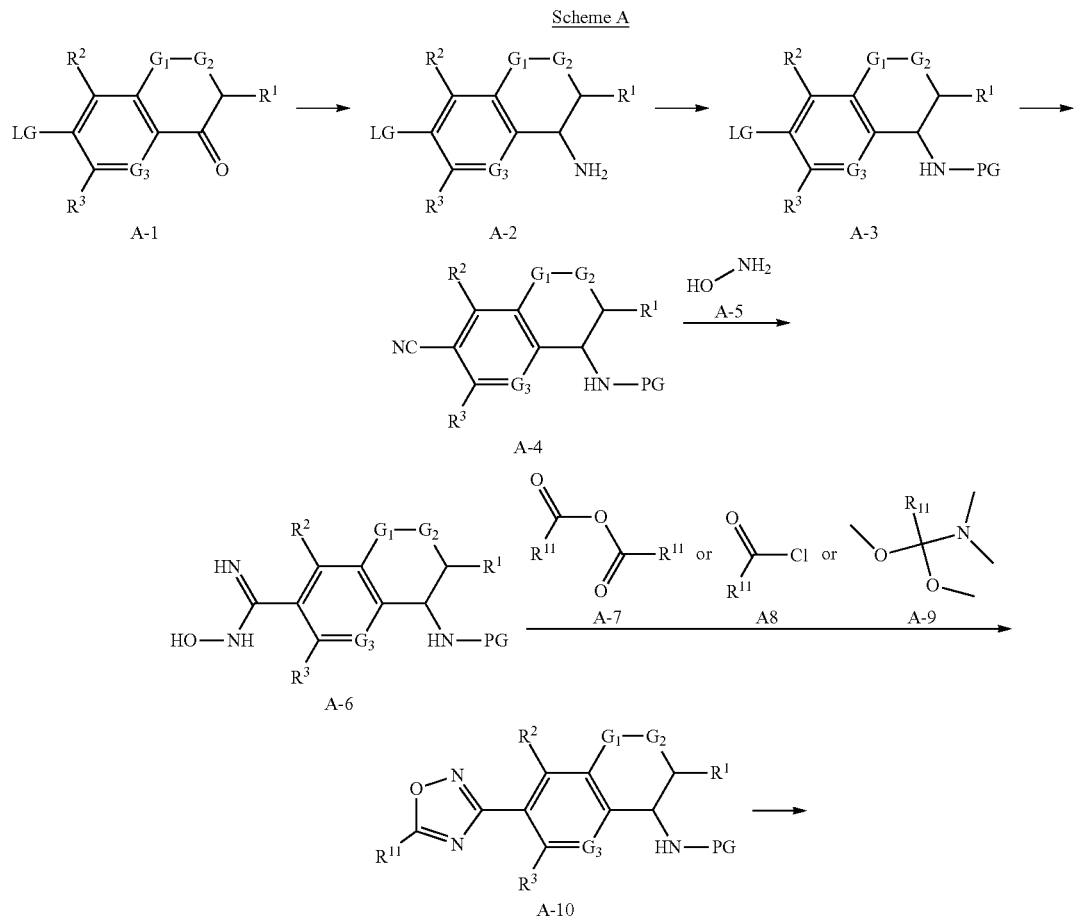

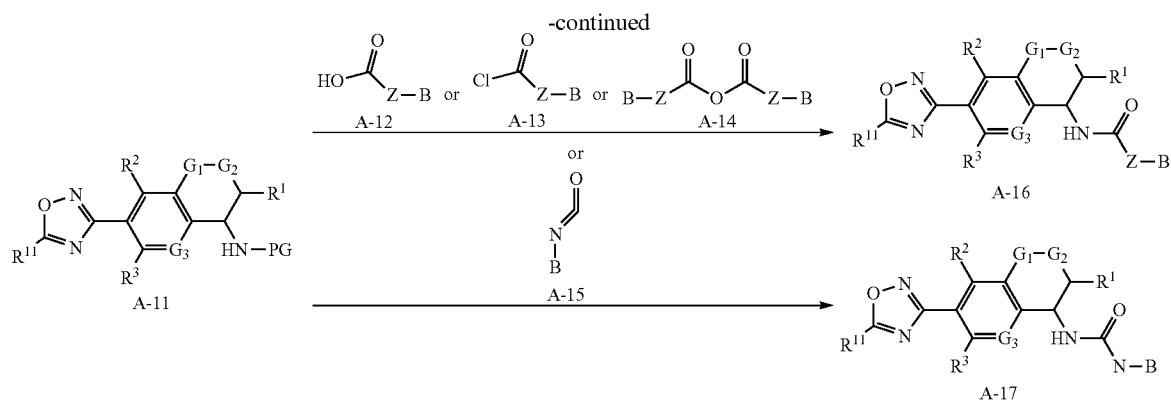

wherein $G_1$, $G_2$, $G_3$, $R^1$, $R^2$, $R^3$, $R^{11}$, Z, and B are as defined for formula (I), or any variation thereof detailed herein, LG is a leaving group, and PG is a protecting group.

In some embodiments, compounds provided herein may be synthesized according to Scheme B.

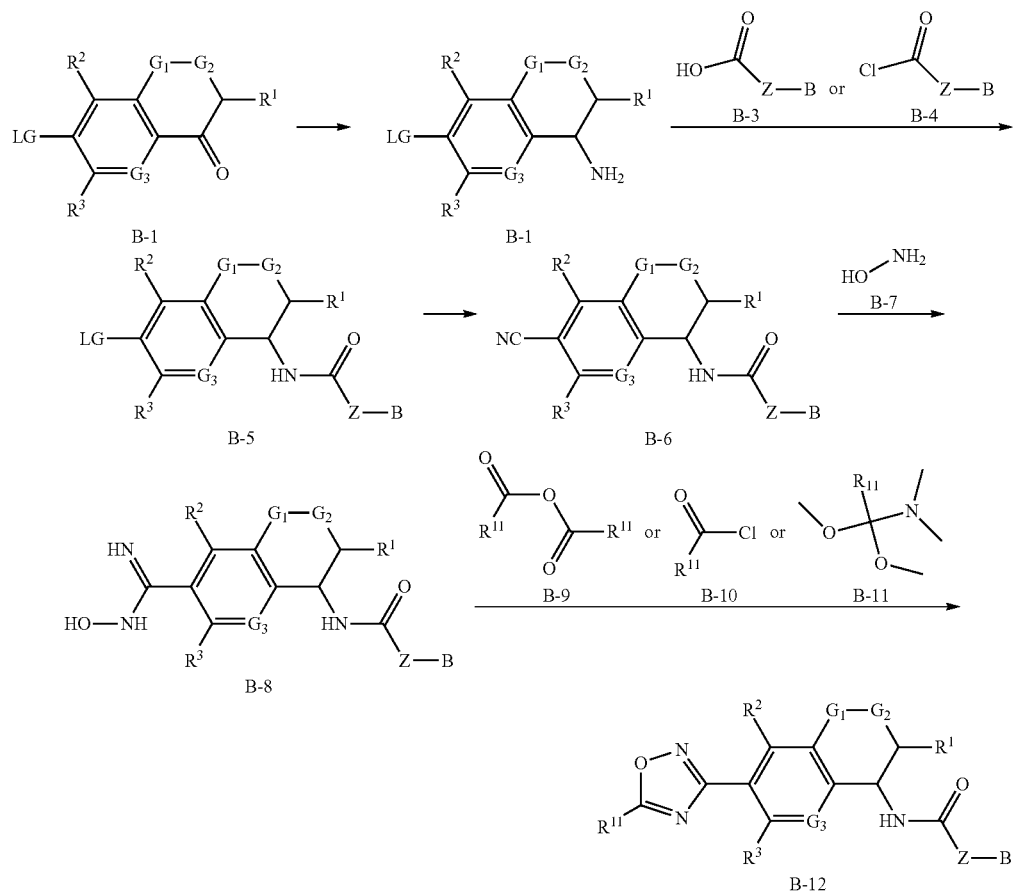

wherein $G_1$, $G_2$, $G_3$, $R^1$, $R^2$, $R^3$, $R^{11}$, Z, and B are as defined for formula (I), or any variation thereof detailed herein, and LG is a leaving group.

In some embodiments, compounds provided herein may be synthesized according to Scheme C.

Scheme C
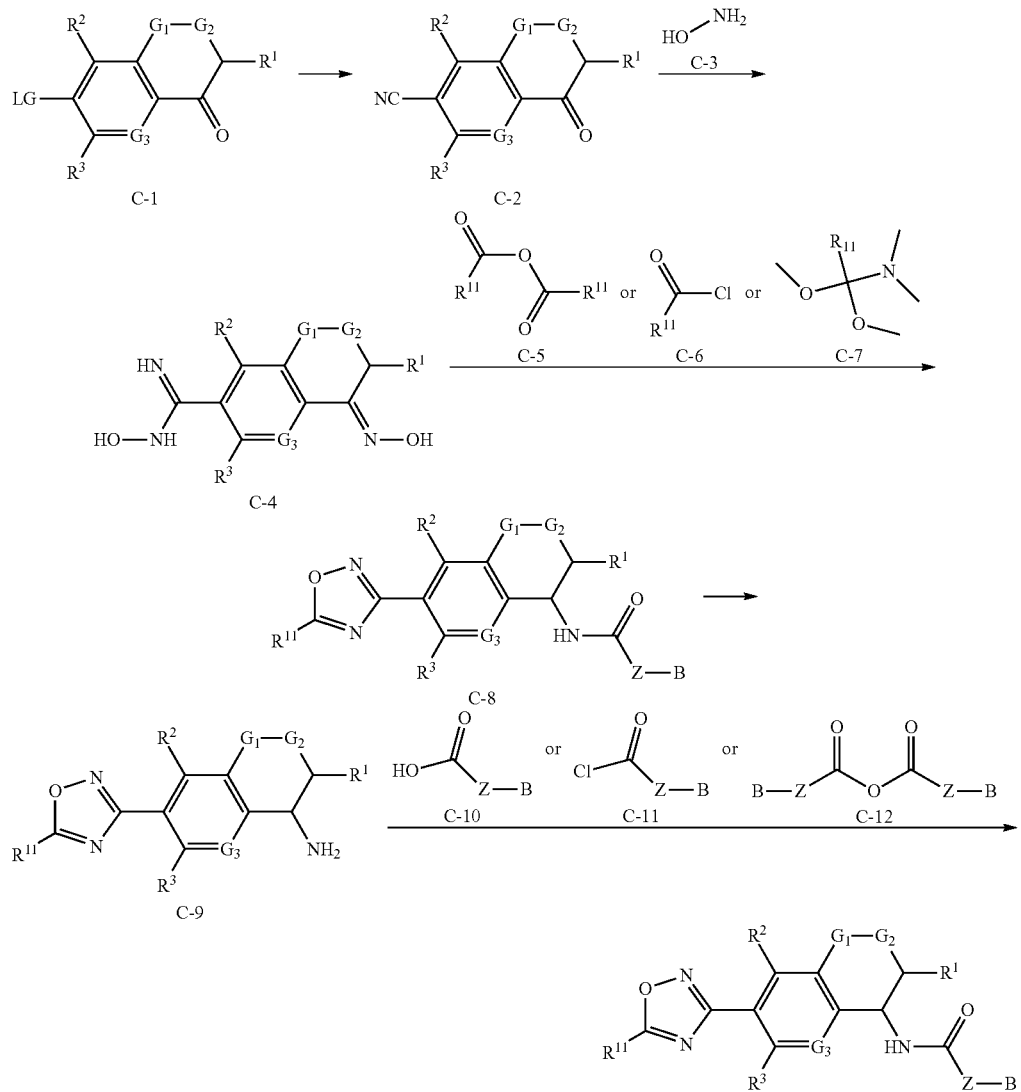
wherein $G_1$, $G_2$, $G_3$, $R^1$, $R^2$, $R^3$, $R^{11}$, Z, and B are as defined for formula (I), or any variation thereof detailed herein, and LG is a leaving group.
In some embodiments, compounds provided herein may be synthesized according to Scheme D.
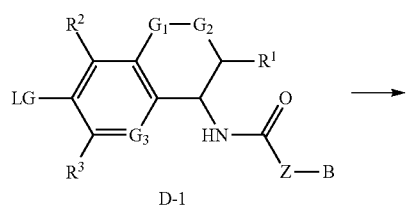
Scheme D
-continued
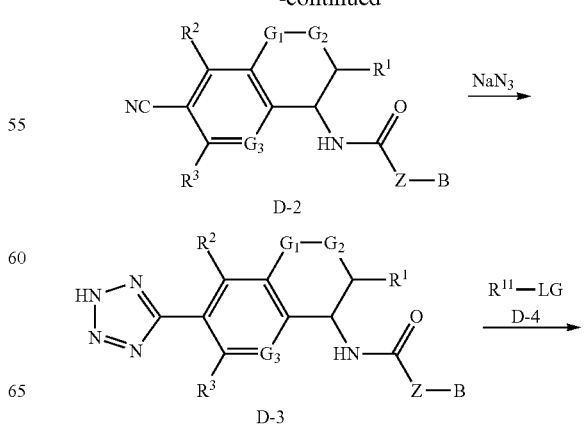

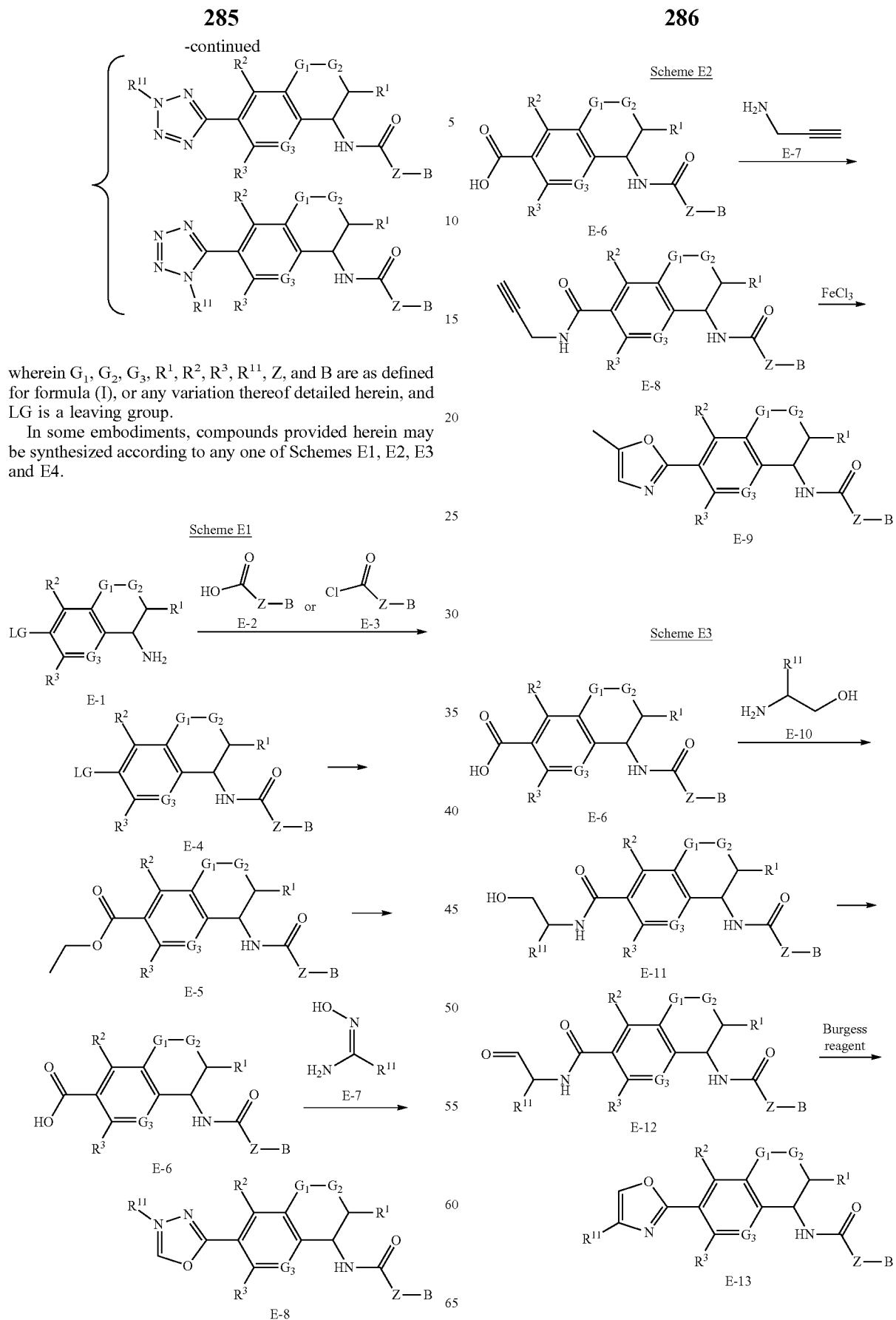
wherein $G_1$, $G_2$, $G_3$, $R^1$, $R^2$, $R^3$, $R^{11}$, Z, and B are as defined for formula (I), or any variation thereof detailed herein, and LG is a leaving group.
In some embodiments, compounds provided herein may be synthesized according to any one of Schemes E1, E2, E3 and E4.

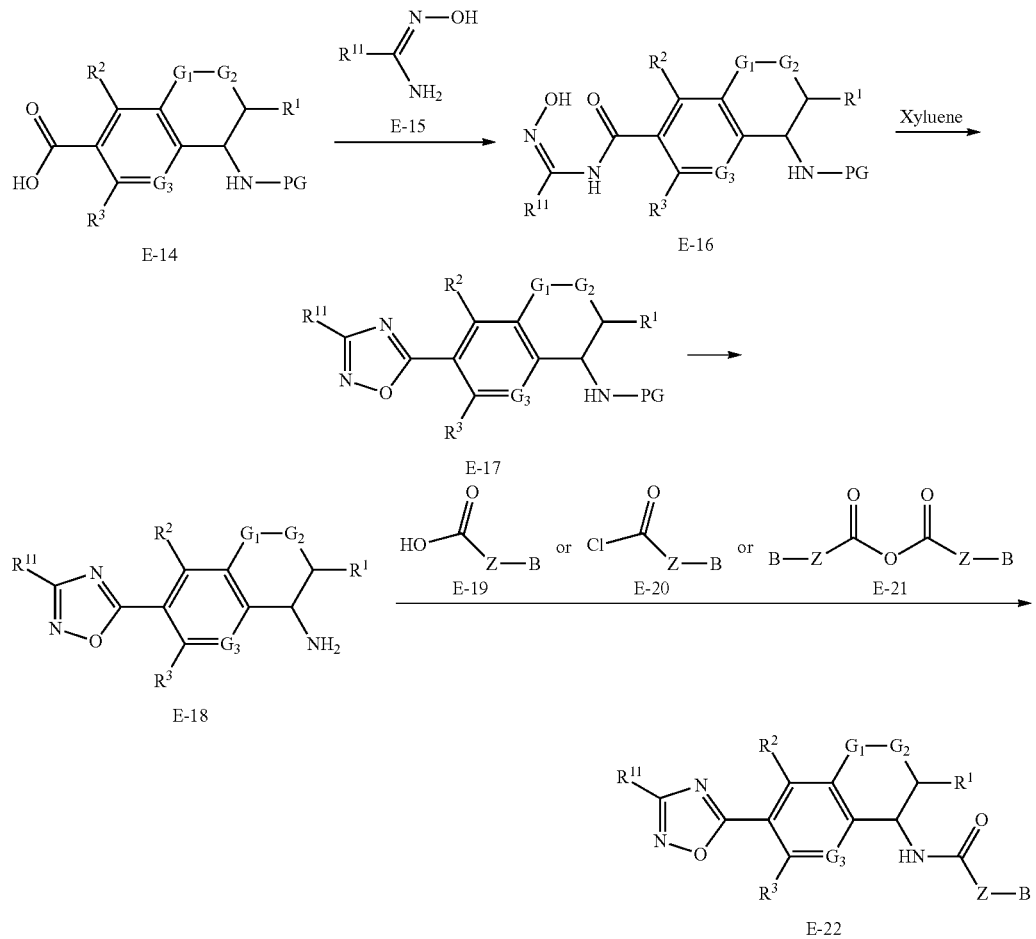
wherein $G_1$, $G_2$, $G_3$, $R^1$, $R^2$, $R^3$, $R^{11}$, Z, and B are as defined for formula (I), or any variation thereof detailed herein, LG is a leaving group, and PG is a protecting group.
In some embodiments, compounds provided herein may be synthesized according to any one of Schemes F1, F2, and F3.
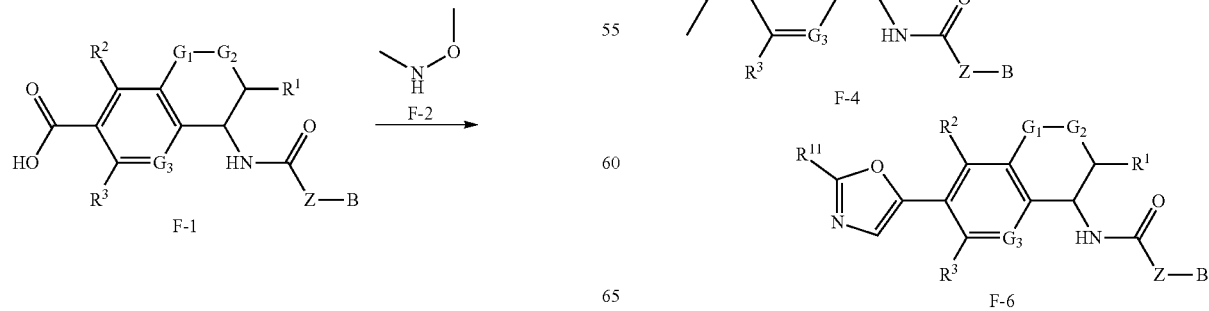

Scheme F2
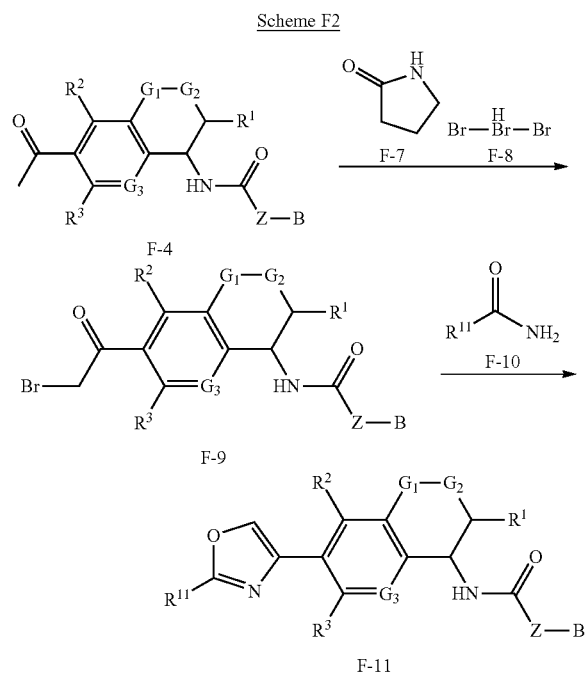
wherein $G_1$, $G_2$, $G_3$, $R^1$, $R^2$, $R^3$, $R^{11}$, Z, and B are as defined for formula (I), or any variation thereof detailed herein, and PG is a protecting group.
In some embodiments, compounds provided herein may be synthesized according to Scheme G.
Scheme G
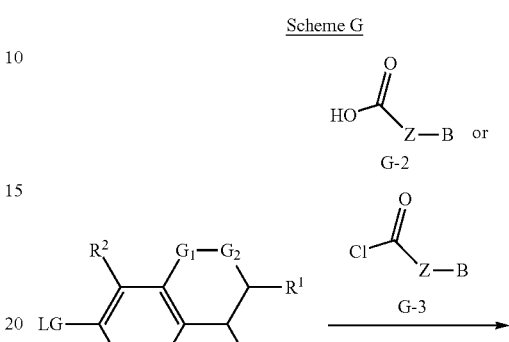
Scheme F3
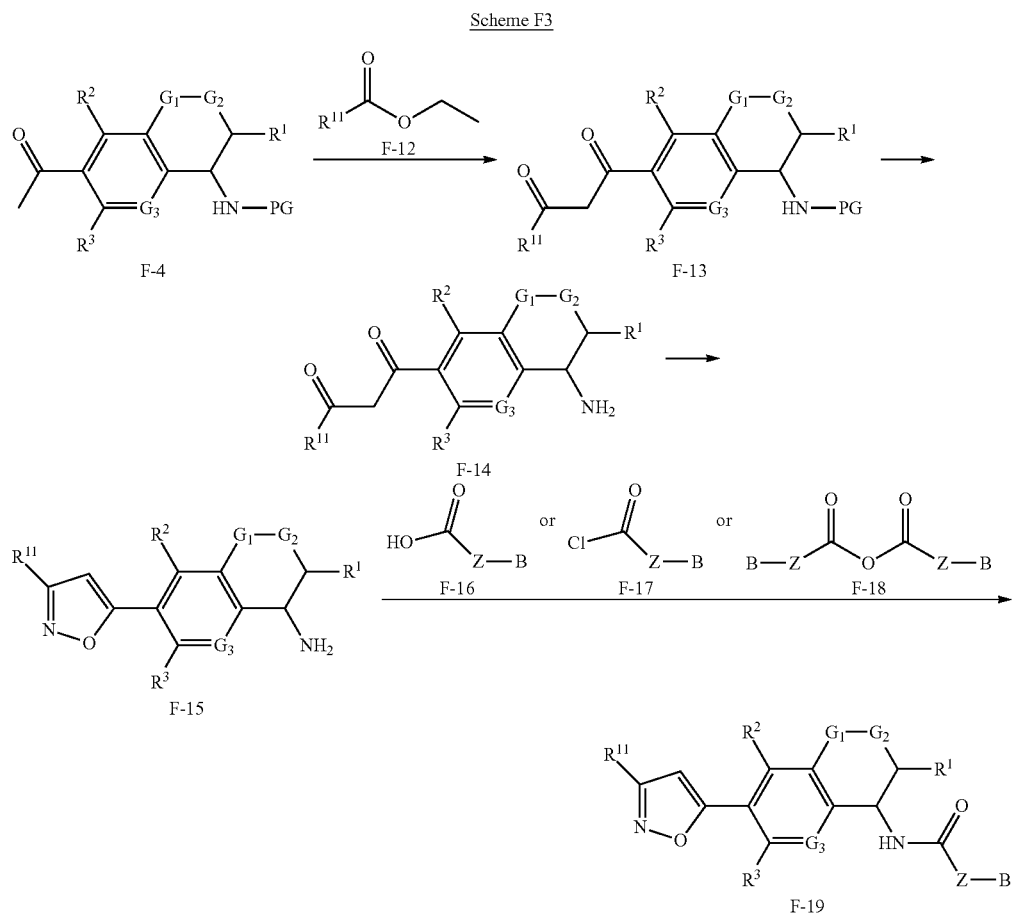

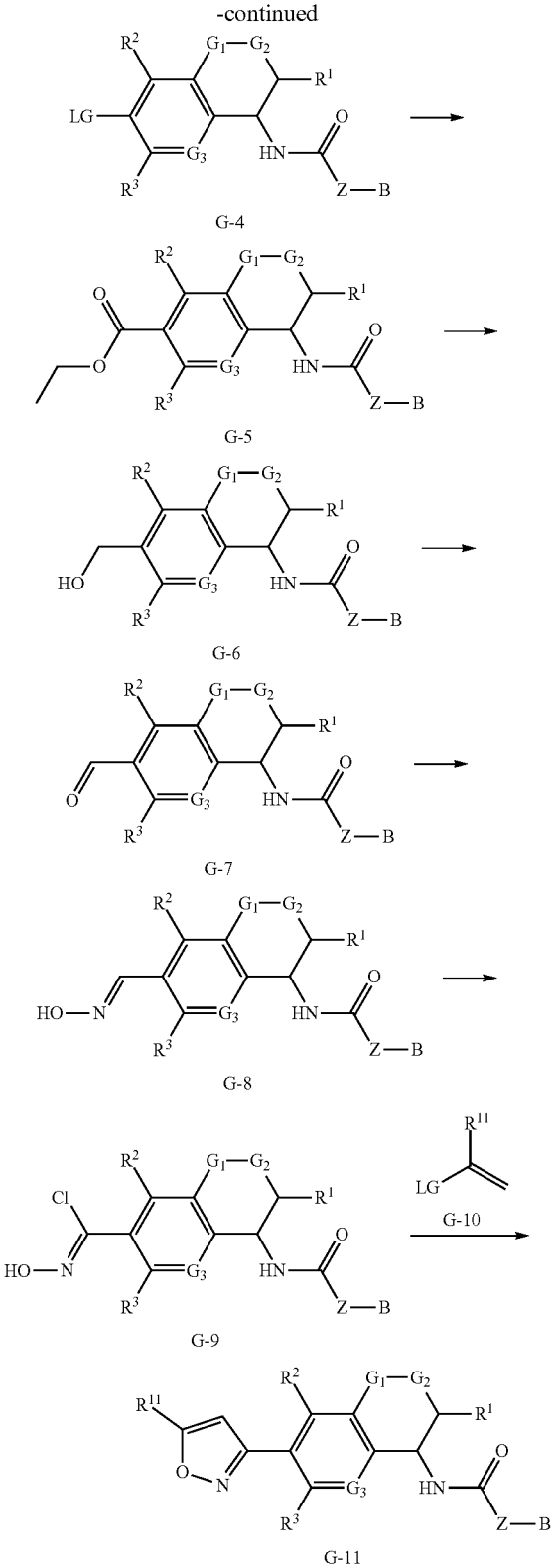

wherein $G_1$, $G_2$, $G_3$, $R^1$, $R^2$, $R^3$, $R^{11}$, Z, and B are as defined for formula (I), or any variation thereof detailed herein, and LG is a leaving group.

In some embodiments, compounds provided herein may be synthesized according to Scheme H.

Scheme H

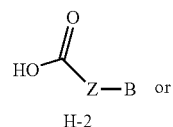

H-2

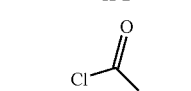

H-3

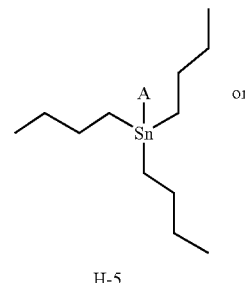

H-1

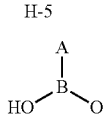

H-5

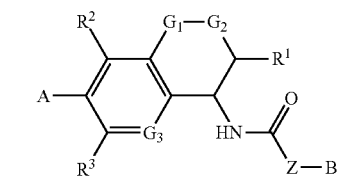

H-4

H-6
Pd complex

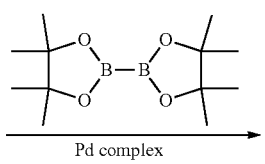

H-7 wherein $G_1$, $G_2$, $G_3$, $R^1$, $R^2$, $R^3$, Z, A, and B are as defined for formula (I), or any variation thereof detailed herein, and LG is a leaving group.

In some embodiments, compounds provided herein may be synthesized according to Scheme I.

Scheme I

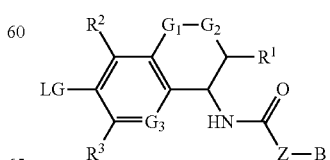

I-1

Pd complex

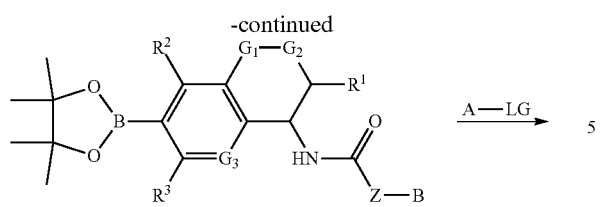
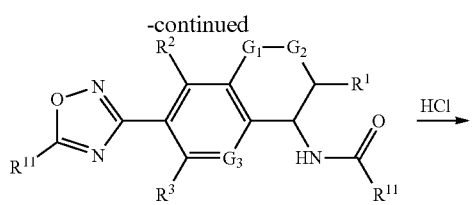
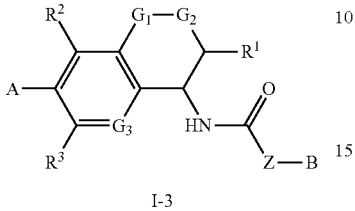
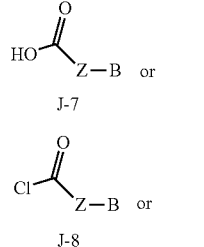

wherein $G_1$, $G_2$, $G_3$, $R^1$, $R^2$, $R^3$, Z, A, and B are as defined for formula (I), or any variation thereof detailed herein, and LG is a leaving group.

In some embodiments, compounds provided herein may be synthesized according to Scheme J.

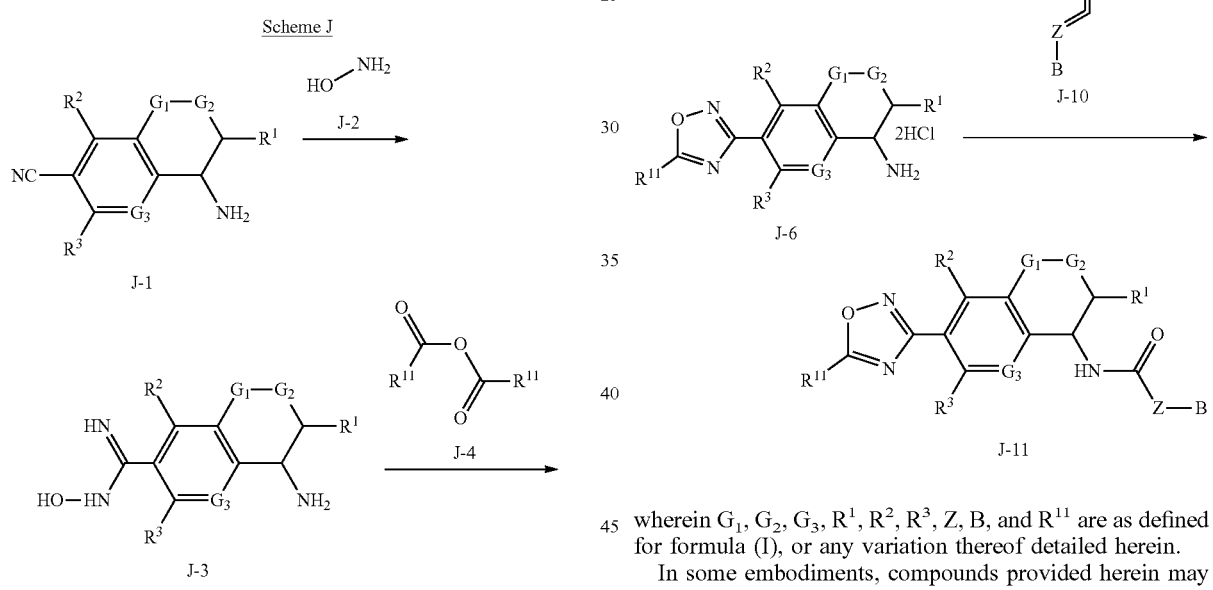

wherein $G_1$, $G_2$, $G_3$, $R^1$, $R^2$, $R^3$, Z, B, and $R^{11}$ are as defined for formula (I), or any variation thereof detailed herein.

In some embodiments, compounds provided herein may be synthesized according to Scheme K.

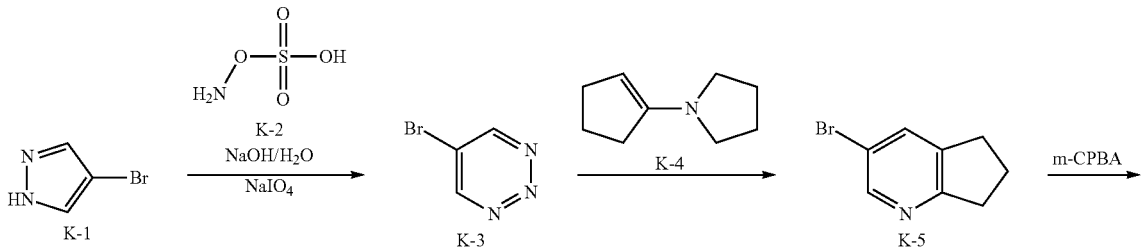

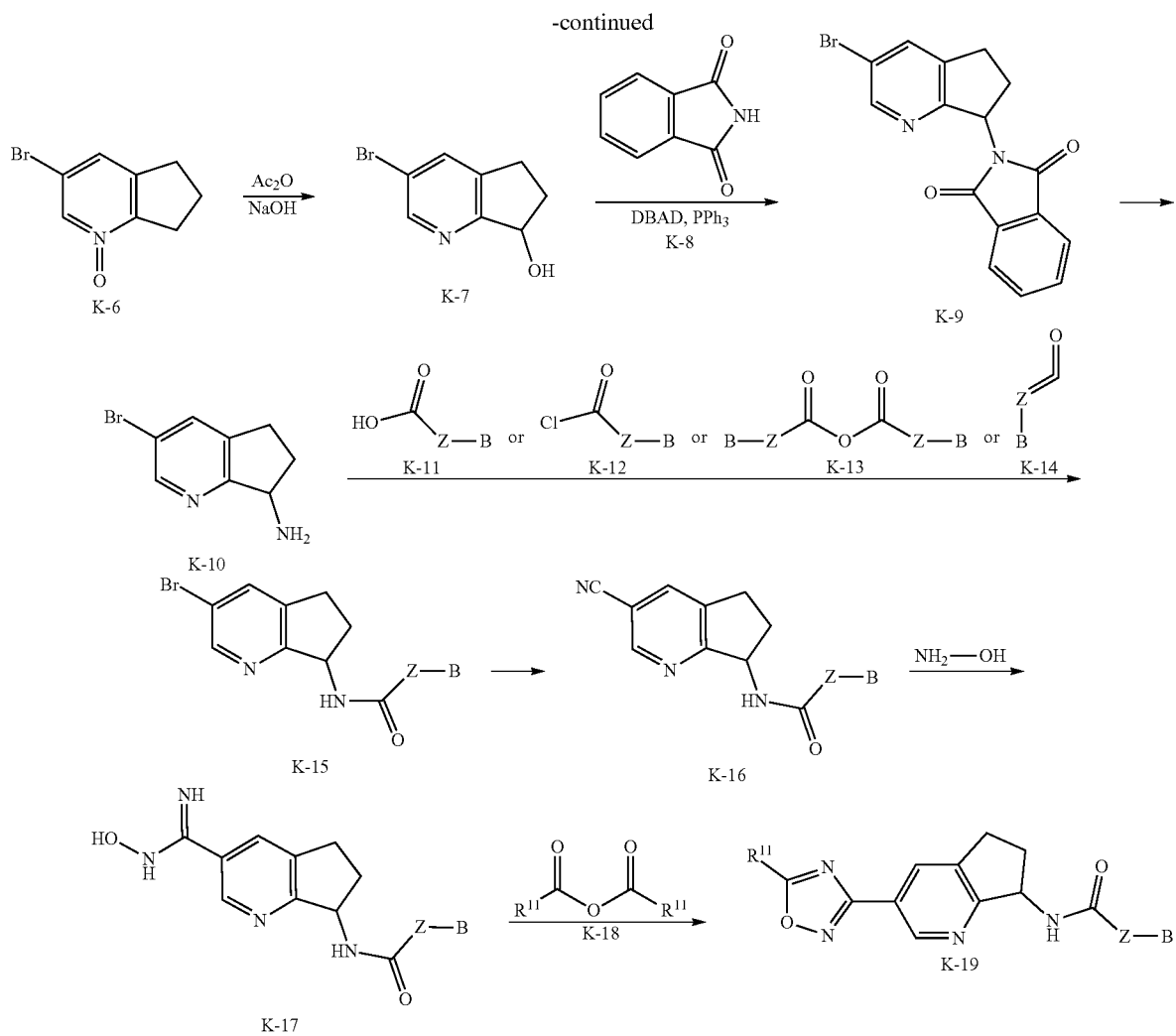
wherein Z, B, and $R^{11}$ are as defined for formula (I), or any variation thereof detailed herein.
In some embodiments, compounds provided herein may be synthesized according to Schemes L1 and L2.
Scheme L1
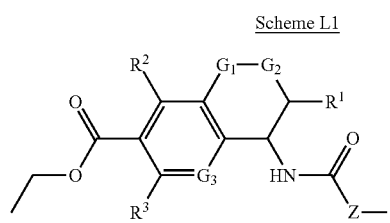
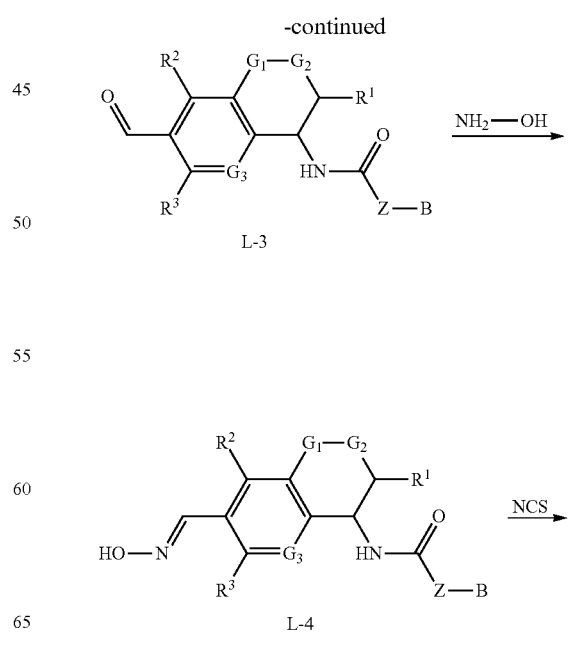

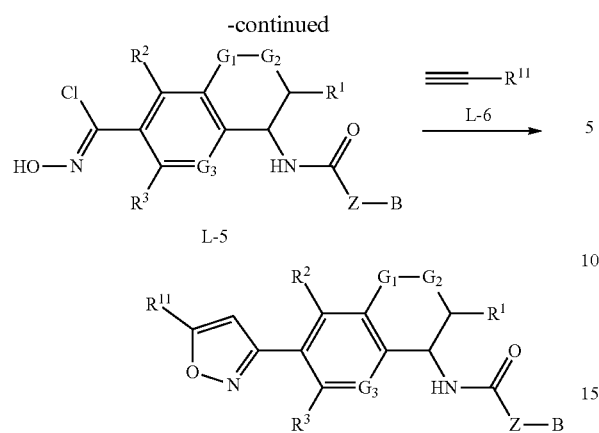
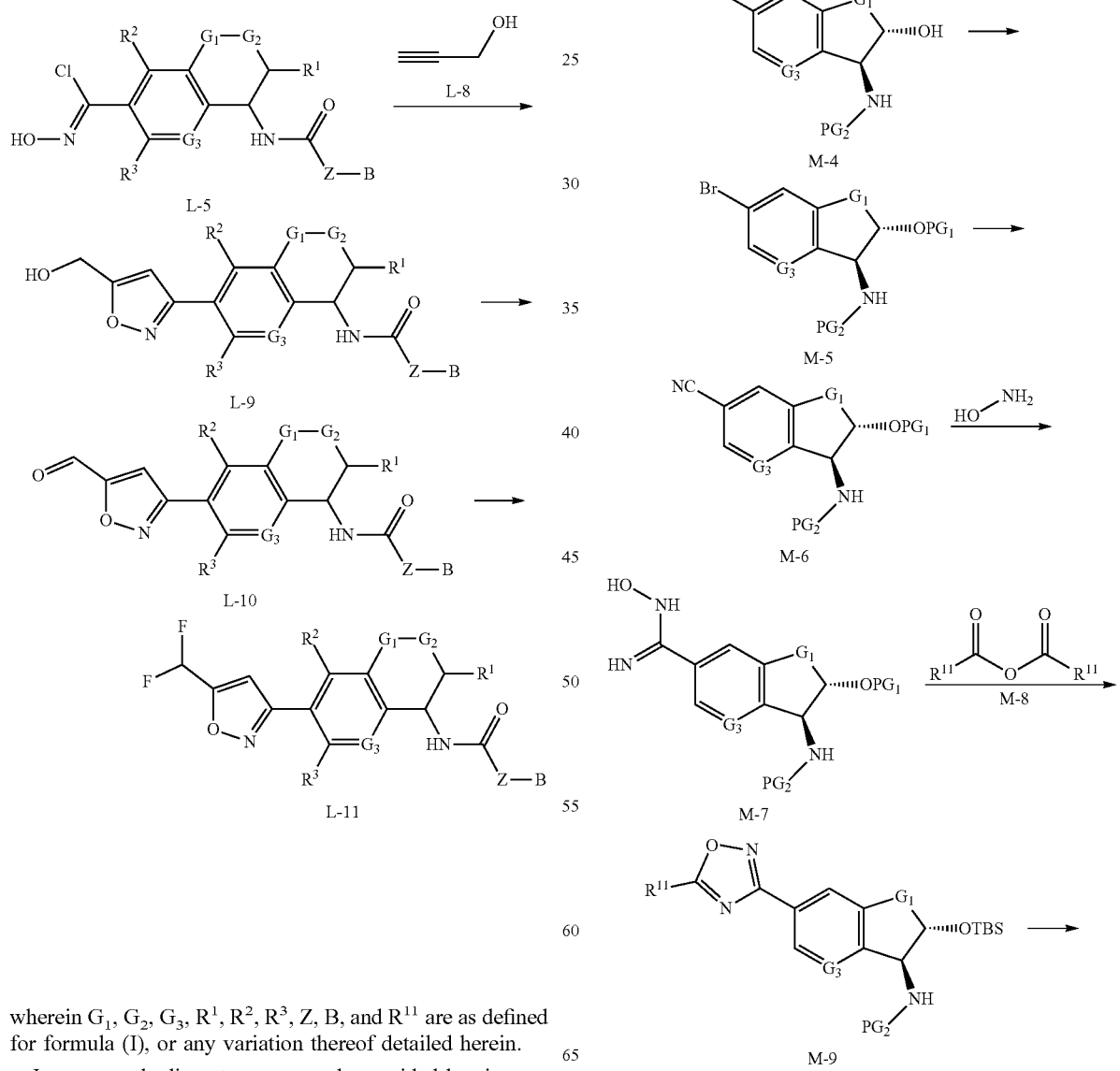
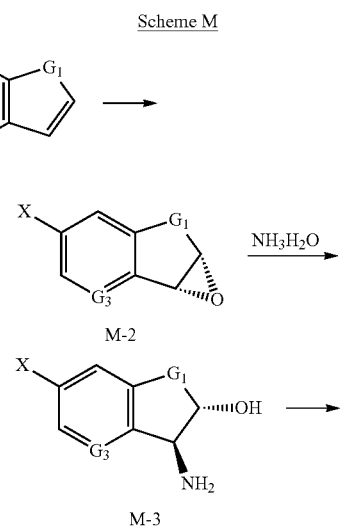
wherein $G_1$, $G_2$, $G_3$, $R^1$, $R^2$, $R^3$, Z, B, and $R^{11}$ are as defined for formula (I), or any variation thereof detailed herein.
In some embodiments, compounds provided herein may be synthesized according to Scheme M.

299
-continued
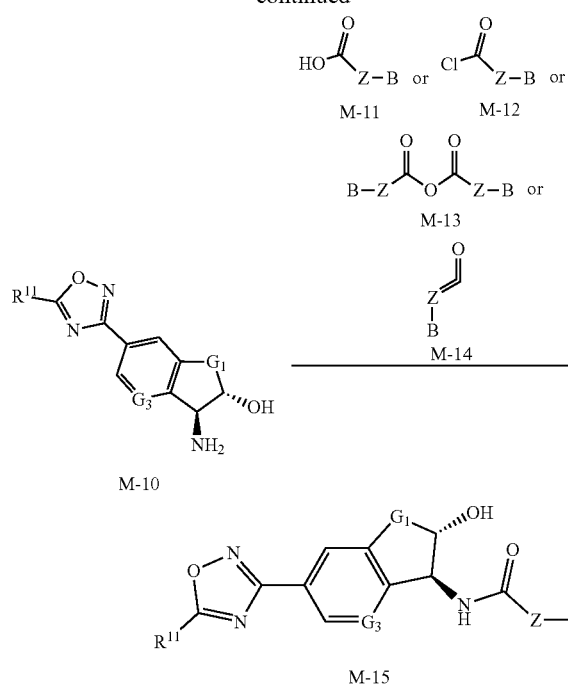
M-10
M-15
wherein $G_1$, $G_3$, $R^1$, $R^2$, $R^3$, Z, B, and $R^{11}$ are as defined for formula (I), or any variation thereof detailed herein.
In some embodiments, compounds provided herein may be synthesized according to Schemes N1 and N2.
Scheme N1
300
-continued
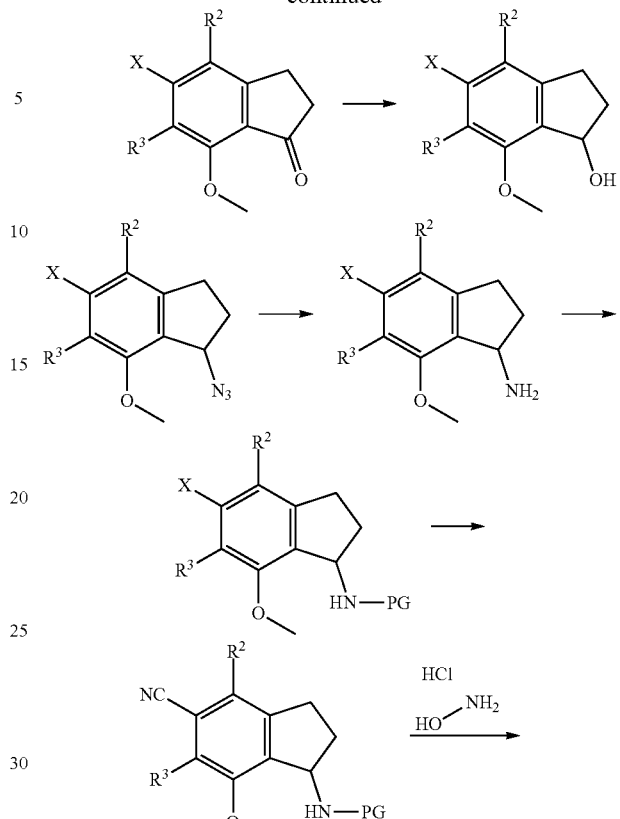
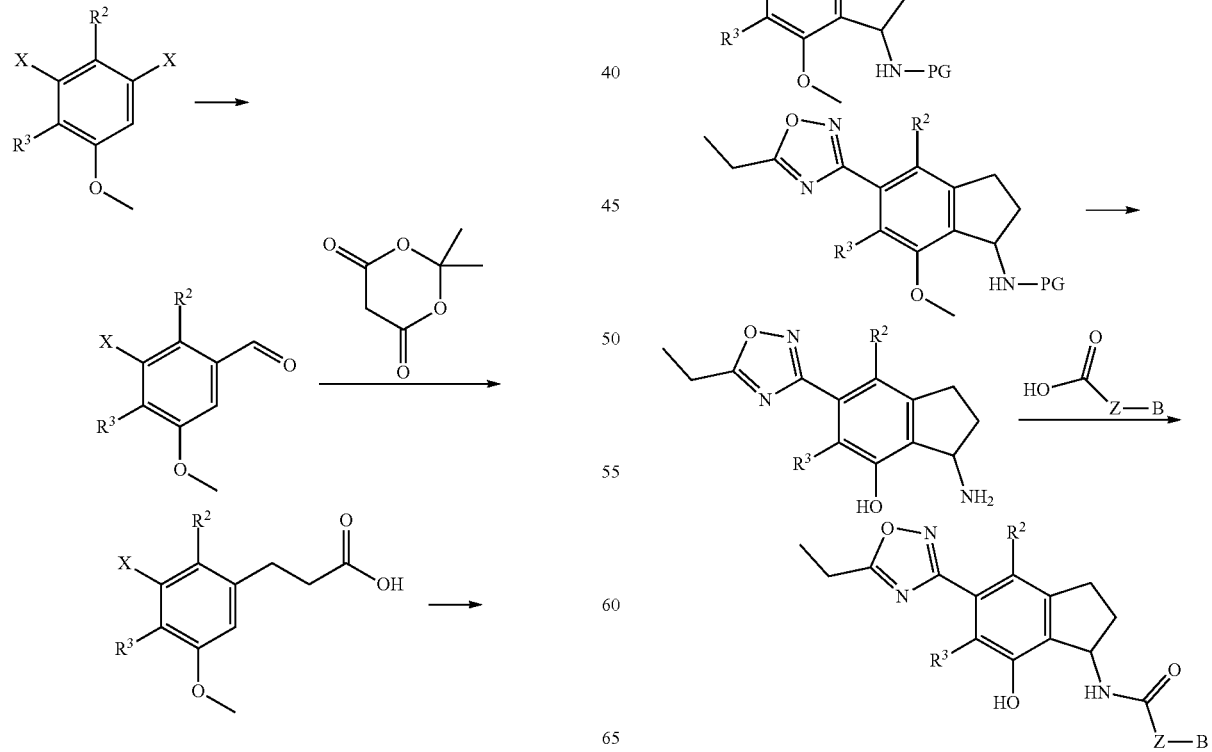

Scheme N2

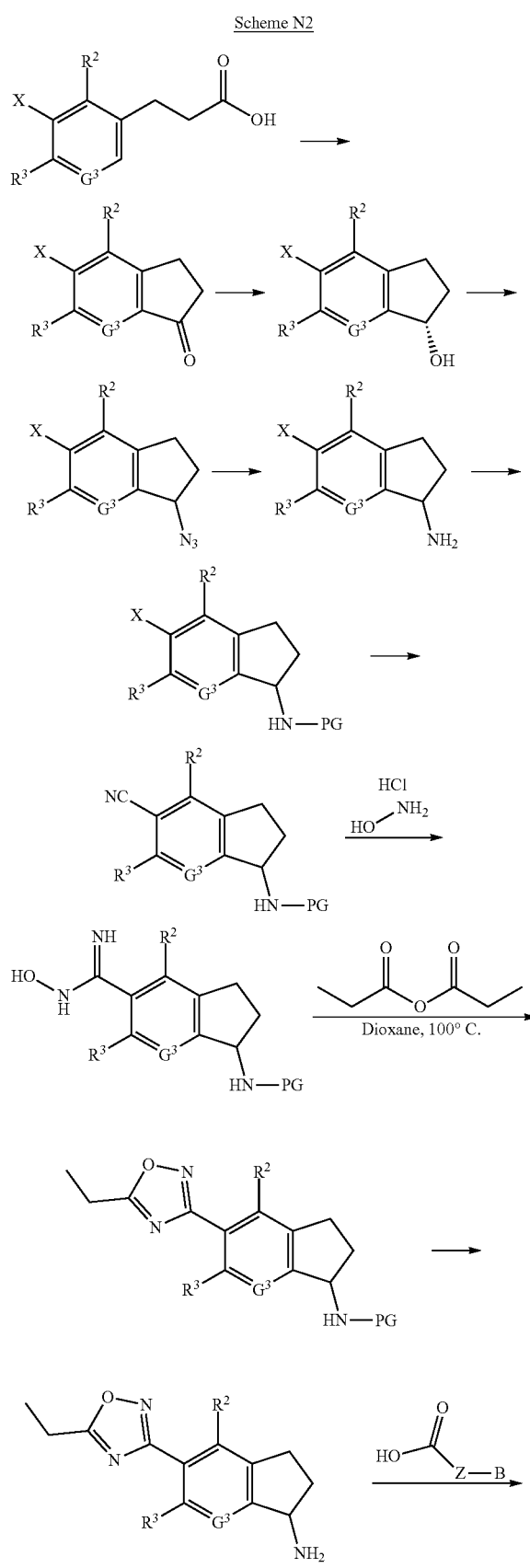

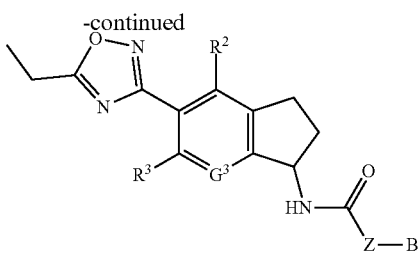

wherein G₃, R², R³, Z, and B are as defined for formula (I), or any variation thereof detailed herein, X is a halogen, and PG is a protecting group.

In some embodiments, compounds provided herein may be synthesized according to Scheme O.

Scheme O

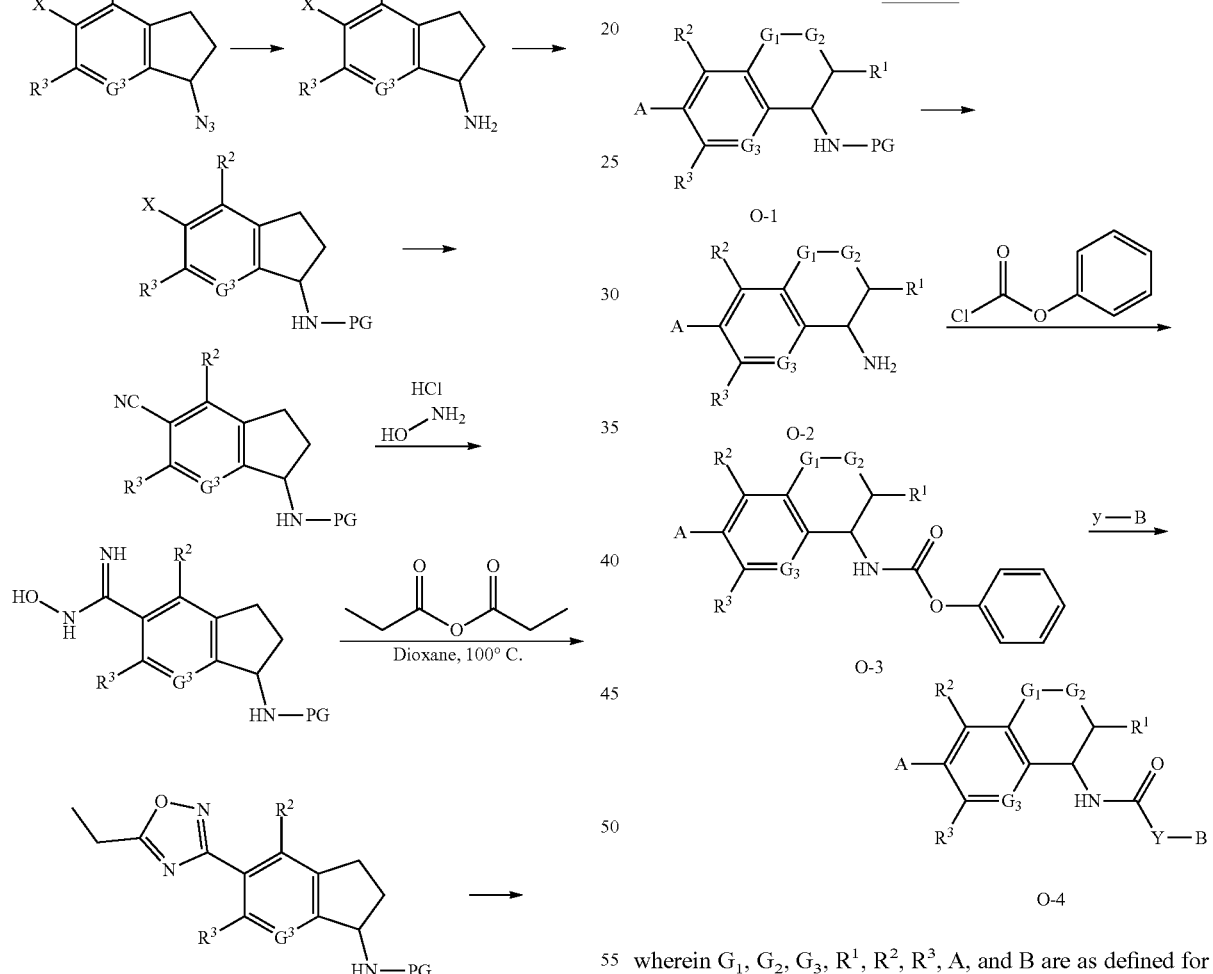

wherein $G_1$, $G_2$, $G_3$, $R^1$, $R^2$, $R^3$, A, and B are as defined for formula (I), or any variation thereof detailed herein, PG is a protecting group, y is HO—, HN(R⁹)—, or HORʸ—, and Y is —O—, —N(R⁹)—, or —ORʸ—.

Particular non-limiting examples are provided in the Example section below.

EXAMPLES

The following examples are offered to illustrate but not to limit the compositions, uses, and methods provided herein. The compounds are prepared using the general methods described above.

The following abbreviations are used throughout the Examples: TEA (trimethylamine), DCM (dichloromethane), (Boc)₂O (di-tert-butyl decarbonate), EA (Ethyl acetate), PE (Petroleum ether, DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), MeOH (methanol), EtOH (ethanol), iPrOH (propan-2-ol), ACN (acetonitrile), TFA (trifluoroacetic acid), DPPA (Diphenylphosphoryl azide), DBU (1,8-Diazabicyclo(5.4.0)undec-7-ene), THF (tetrahydrofuran), PPh₃ (triphenylphosphane), SM (starting material), Hex (hexane), NCS (N-chlorosuccinimide), r.t. (room temperature), DCE (dichloroethane), FA (formic acid), CHCl₃ (Chloroform), BnBr (benzyl bromide), HCl (hydrogen chloride), equiv (equivalent), and DSC (bis(2,5-dioxopyrrolidin-1-yl) carbonate).

Example 1

Synthesis of Compound 17

1. Synthesis of Intermediate 1-2:

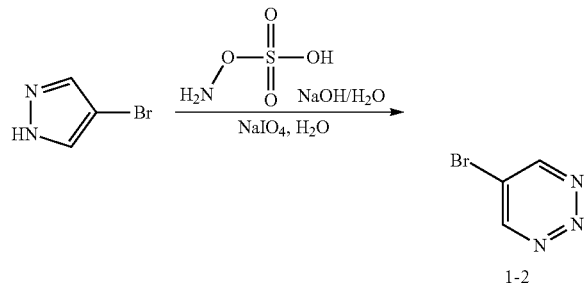

To a solution of 4-bromo-1H-pyrazole (50 g, 340 mmol, 1.0 equiv) in sodium hydroxide (3.7 N, 555 mL) was added (aminooxy)sulfonic acid (116 g, 1.0 mol, 3.0 equiv). The mixture was stirred for 30 min and extracted with DCM (500 mL). The organic layer was washed with brine (200 mL) twice, dried over anhydrous sodium sulfate, concentrated under reduced pressure, and poured into DCM (400 mL) and water (200 mL). To the resulting solution was added NaIO₄ (147 g, 685 mmol, 2.0 equiv) at 0° C. The mixture was stirred overnight, diluted with DCM (500 mL), washed with brine (200 mL) twice, dried over anhydrous sodium sulfate, and concentrated under reduced pressure to afford 25 g of 5-bromo-1,2,3-triazine as brown oil.

2. Synthesis of Intermediate 1-3:

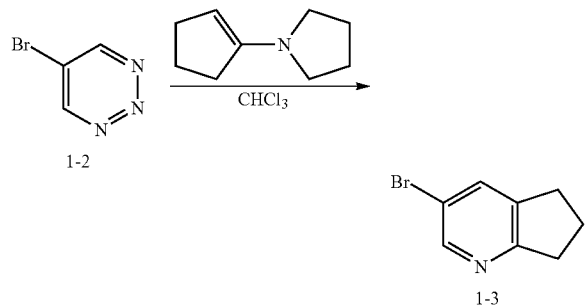

To a solution of 5-bromo-1,2,3-triazine (25 g, 156 mmol, 1.0 equiv) in CHCl₃ (500 mL) was added 1-(cyclopent-1-en-1-yl)pyrrolidine (25.8 g, 188 mmol, 1.1 equiv). The mixture was stirred at 45° C. for 1 h, diluted with DCM (500 mL), washed with brine (300 mL) twice, dried over anhydrous sodium sulfate, concentrated under reduced pressure, and purified by silica gel chromatography (EA/PE, 10/90) to give 11 g (36%) of 3-bromo-5H,6H,7H-cyclopenta[b]pyridine as a brown solid.

3. Synthesis of Intermediate 1-4:

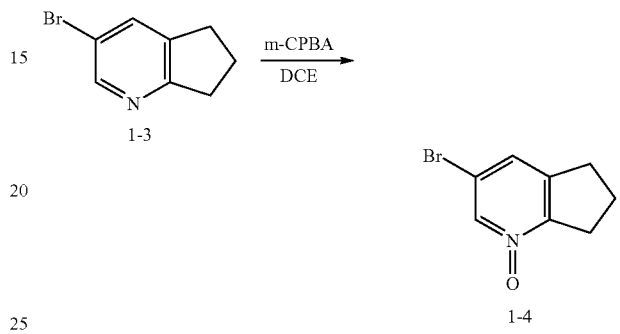

To a solution of 3-bromo-5H,6H,7H-cyclopenta[b]pyridine (11.9 g, 60.0 mmol, 1.0 equiv) in DCE (120 mL) was added m-CPBA (20.7 g, 120 mmol, 2.0 equiv). The mixture was stirred at 70° C. overnight, cooled to r.t., diluted with DCM (200 mL), washed with saturated sodium bicarbonate solution (200 mL) twice, dried over anhydrous sodium sulfate, concentrated under reduced pressure, and purified by silica gel chromatography (MeOH/DCM, 10/90) to afford 12 g (93%) of 3-bromo-5H,6H,7H-cyclopenta[b]pyridin-1-ium-1-olate as an off-white solid.

4. Synthesis of Intermediate 1-5:

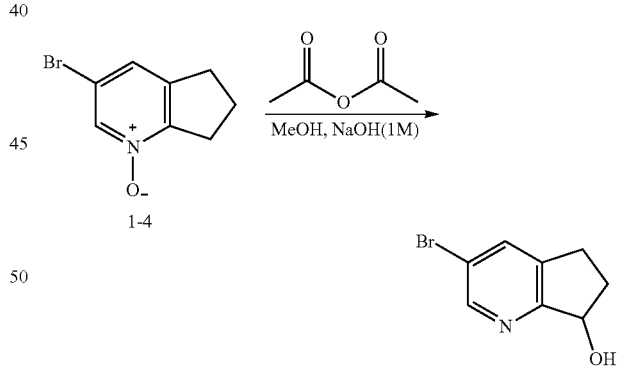

A solution of 3-bromo-5H,6H,7H-cyclopenta[b]pyridin-1-ium-1-olate (12.2 g, 57.0 mmol, 1.0 equiv) in acetic anhydride (30 mL) was stirred at 110° C. for 3 h, cooled to R.T., concentrated under reduced pressure, and poured into a NaOH solution (1 N, 30 mL) and MeOH (30 mL). The mixture was stirred overnight at r.t., diluted with EA (300 mL), washed with brine (100 mL) twice, dried over anhydrous sodium sulfate, concentrated under reduced pressure, and purified by silica gel chromatography (EA/PE, 50/50) to afford 5.7 g (47%) of 3-bromo-5H,6H,7H-cyclopenta[b]pyridin-7-ol as a brown solid.

5. Synthesis of Intermediate 1-6:

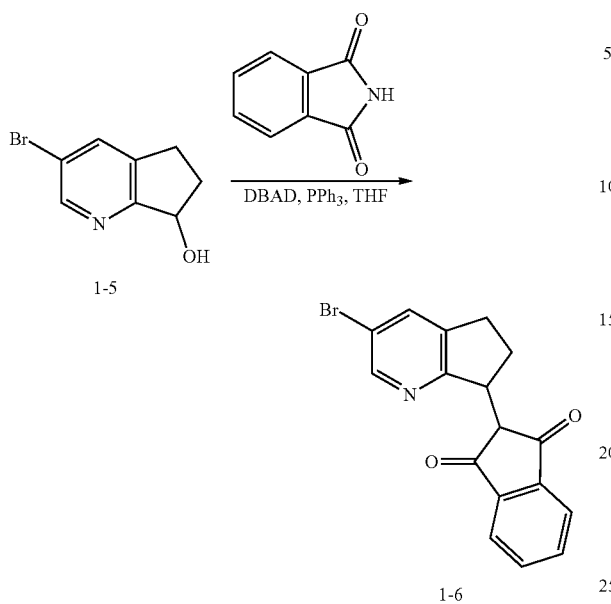

To a solution of 3-bromo-5H,6H,7H-cyclopenta[b]pyridin-7-ol (5.8 g, 27.1 mmol, 1.0 equiv) in THF (100 mL) were added 2,3-dihydro-1H-isoindole-1,3-dione (4.4 g, 29.9 mmol, 1.1 equiv), PPh$_3$ (8.9 g, 34.0 mmol, 1.25 equiv), and DBAD (7.52 g, 32.7 mmol, 1.21 equiv) under nitrogen. The mixture was stirred for 3 h, diluted with EA (300 mL), washed with brine (100 mL) twice, dried over anhydrous sodium sulfate, concentrated under reduced pressure, and purified by silica gel chromatography (EA/PE, 10/90) to afford 7.3 g (79%) of 2-[3-bromo-5H,6H,7H-cyclopenta[b]pyridin-7-yl]-2,3-dihydro-1H-isoindole-1,3-dione as a brown solid.

6. Synthesis of Intermediate 1-7:

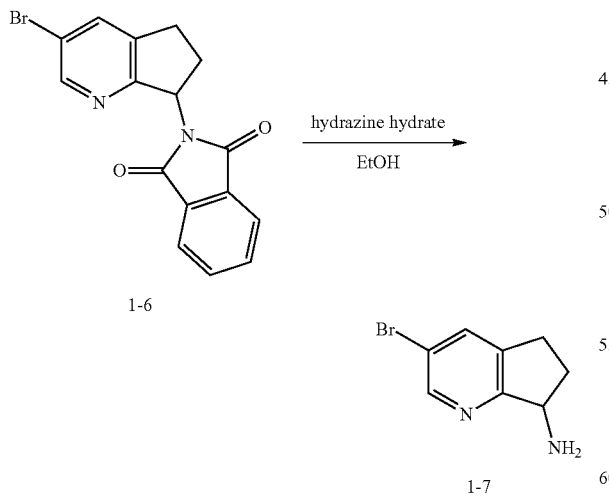

To a solution of 2-[3-bromo-5H,6H,7H-cyclopenta[b]pyridin-7-yl]-2,3-dihydro-1H-isoindole-1,3-dione (7.6 g, 22.2 mmol, 1.0 equiv) in ethanol (80 mL) was added hydrazine hydrate (4.4 g, 88.7 mmol, 4.0 equiv). The mixture was stirred at 80° C. for 2 h, cooled to r.t., concentrated under reduced pressure, and purified by silica gel chromatography (MeOH/DCM, 15/85) to afford 1.5 g (32%) of 3-bromo-5H,6H,7H-cyclopenta[b]pyridin-7-amine as a brown solid.

7. Synthesis of Intermediate 1-8:

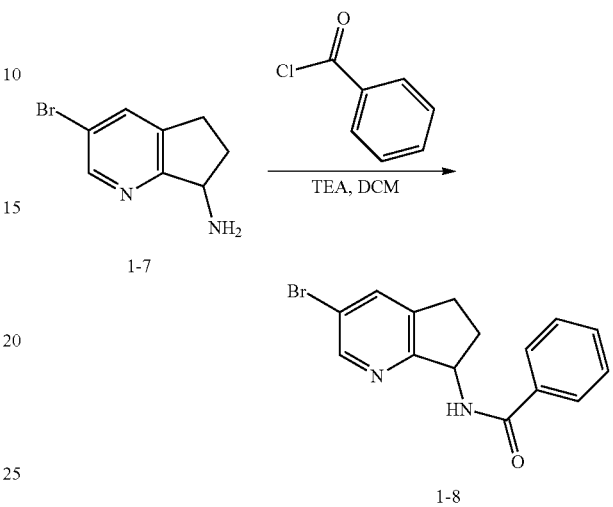

To a solution of 3-bromo-5H,6H,7H-cyclopenta[b]pyridin-7-amine (480 mg, 2.3 mmol, 1.0 equiv) in DCM (10 mL) cooled to 0° C. were added benzoyl chloride (317 mg, 2.3 mmol, 1.0 equiv) and TEA (114 mg, 1.1 mmol, 0.05 equiv). The mixture was stirred for 30 min, diluted with EA (100 mL), washed with brine (30 mL) twice, dried over anhydrous sodium sulfate, concentrated under reduced pressure, and purified by silica gel chromatography (EA/PE, 30/70) to afford 240 mg (34%) of N-[3-bromo-5H,6H,7H-cyclopenta[b]pyridin-7-yl]benzamide as a white solid.

8. Synthesis of Intermediate 1-9:

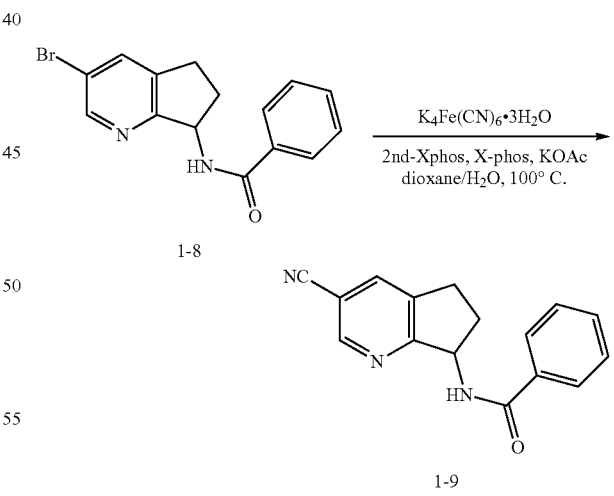

To a solution of N-[3-bromo-5H,6H,7H-cyclopenta[b]pyridin-7-yl]benzamide (230 mg, 0.7 mmol, 1.0 equiv) in a mixture of dioxane (6 mL) and water (6 mL) were added FeK$_4$(CN)$_6$·3H$_2$O (376 mg, 1.2 equiv), 2nd-Xphos (112 mg, 0.2 equiv), X-phos (72 mg, 0.2 equiv), and KOAc (214 mg, 2.2 mmol, 3.0 equiv) under nitrogen. The mixture was stirred at 90° C. overnight, cooled to r.t., diluted with EA (50 mL), washed with brine (20 mL) twice, dried over anhydrous sodium sulfate, concentrated under reduced pressure, and purified by silica gel chromatography (EA/PE, 30/70) to afford 100 mg (52%) of N-[3-cyano-5H,6H,7H-cyclopenta[b]pyridin-7-yl]benzamide as an off-white solid.

9. Synthesis of Intermediate 1-10:

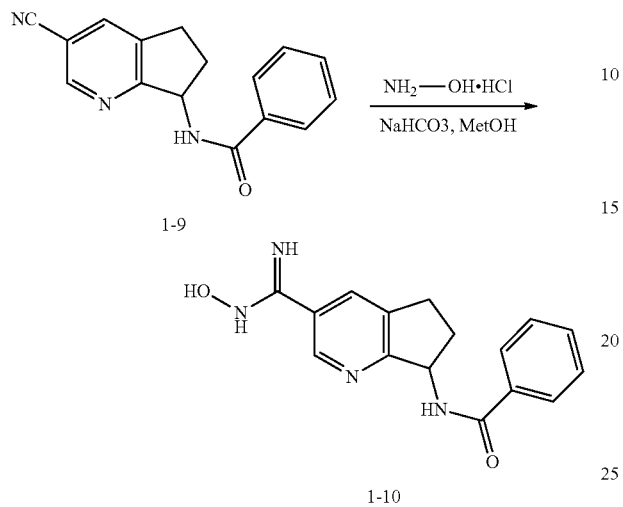

To a solution of N-[3-cyano-5H,6H,7H-cyclopenta[b]pyridin-7-yl]benzamide (100 mg, 0.38 mmol, 1.00 equiv) in MeOH (8 mL) were added hydroxylamine hydrogen chloride (79 mg, 1.15 mmol, 3.0 equiv) and sodium bicarbonate (128 mg, 1.5 mmol, 4.0 equiv). The mixture was stirred at 80° C. for 2 h and concentrated under reduced pressure to afford 110 mg of N-[3-(N-hydroxycarbamimidoyl)-5H,6H,7H-cyclopenta[b]pyridin-7-yl]benzamide as an off-white solid.

10. Synthesis of Compound 17:

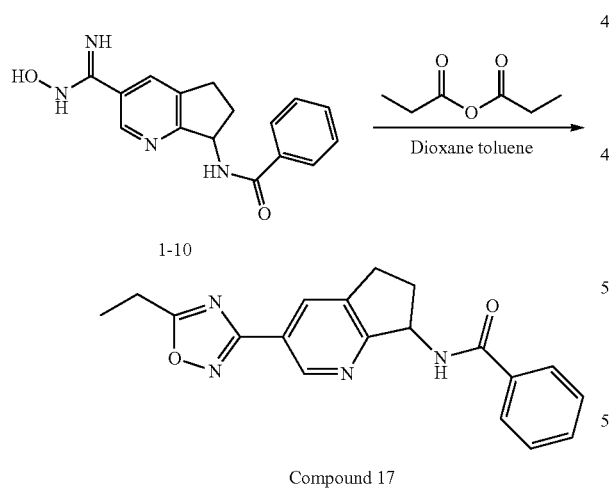

To a solution of N-[3-(N-hydroxycarbamimidoyl)-5H,6H,7H-cyclopenta[b]pyridin-7-yl]benzamide (100 mg, 0.34 mmol, 1.0 equiv) in dioxane (8 mL) was added propanoyl propanoate (0.8 mL). The mixture was stirred at 90° C. for 2 h and concentrated under reduced pressure. The mixture was re-dissolved in toluene (3 mL) and heated at 150° C. for 2 h. The mixture was then cooled to r.t., concentrated under reduced pressure, and purified by Prep-HPLC with the following conditions: (2#-AnalyseHPLC-SHIMADZU (HPLC-10)): Column, XBridge Shield RP18 OBD Column, 5 um, 19*150 mm; mobile phase, water (0.05% NH$_3$H$_2$O) and ACN (24.0% ACN up to 54.0% in 8 min); Detector, UV 220 nm. This resulted in 5.9 mg (5%) of N-(3-(5-ethyl-1,2,4-oxadiazol-3-yl)-6,7-dihydro-5H-cyclopenta[b]pyridin-7-yl)benzamide (Compound 17) as a white solid. LRMS (ES) m/z 335 (M+H). $^1$H-NMR: (CDCl$_3$, ppm): 8.93 (m, 1H), 8.85 (m, 1H), 8.19 (m, 1H), 7.86 (m, 2H), 7.46 (m, 3H), 5.55 (m, 1H), 3.01 (m, 4H), 2.53 (m, 1H), 2.02 (m, 1H), 1.31 (m, 3H).

The following compounds were prepared by methods analogous to the method described for Compound 17:

| Compound No. | LRMS (ES) m/z |
|---|---|
| 108 | M + H = 350 |

Example 2

Synthesis of Compound 42

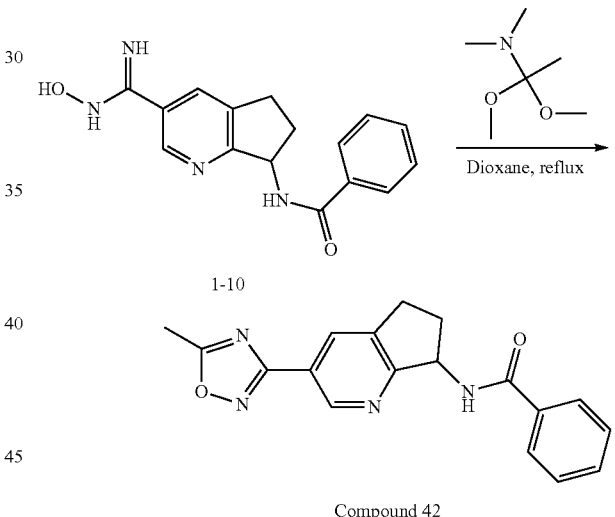

To a solution of N-[3-(N-hydroxycarbamimidoyl)-5H,6H,7H-cyclopenta[b]pyridin-7-yl]benzamide (80 mg, 0.27 mmol, 1.0 equiv) in dioxane (6 mL) was added (1,1-dimethoxyethyl)dimethylamine (144 mg, 1.08 mmol, 4.0 equiv). The mixture was stirred at 90° C. for 2 h, concentrated under reduced pressure, and purified by Prep-HPLC with the following conditions: (Column, X-Bridge, C18, Shield RP, 19*150 mm 5 um; mobile phase, water with 0.05% NH$_3$H$_2$O and ACN (20.0% ACN up to 48.0% in 8 min); Detector, UV 210/254 nm. This purification afforded 7.6 mg (9%) of N-(3-(5-methyl-1,2,4-oxadiazol-3-yl)-6,7-dihydro-5H-cyclopental[b]pyridin-7-yl)benzamide (Compound 42) as a white solid. LRMS (ES) m/z 321 (M+H). $^1$H-NMR: (300 MHz, Methanol-d$_4$, ppm) δ 9.02-8.95 (m, 1H), 8.33-8.26 (m, 1H), 7.92-7.82 (m, 2H), 7.57-7.45 (m, 1H), 7.44 (dd, J=8.3, 6.5 Hz, 2H), 5.62 (t, J=8.5 Hz, 1H), 3.22-2.93 (m, 2H), 2.82-2.64 (m, 1H), 2.65 (s, 3H), 2.11 (dq, J=12.8, 9.0 Hz, 1H).

Example 3

Synthesis of Compound 94

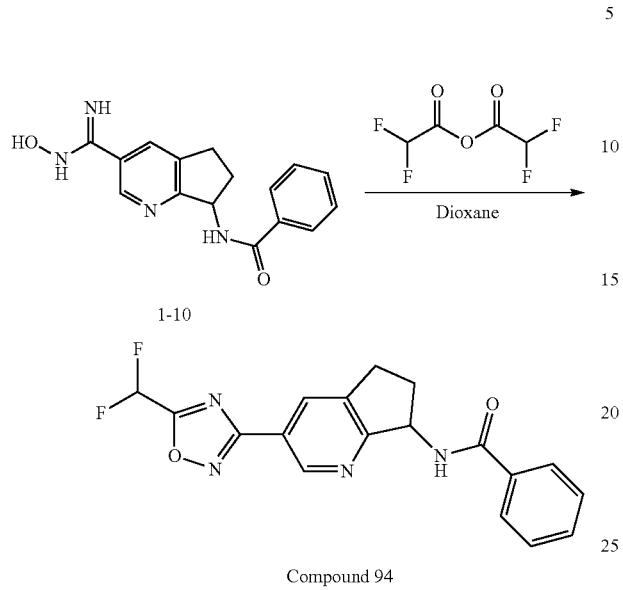

1-10

Compound 94

To a solution of N-[3-(N-hydroxycarbamimidoyl)-5H,6H,7H-cyclopenta[b]pyridin-7-yl]benzamide (60 mg, 0.2 mmol, 1.0 equiv) in dioxane (5 mL) was added 2,2-difluoroacetyl 2,2-difluoroacetate (53 mg, 0.3 mmol, 1.5 equiv). The mixture was stirred at 60° C. for 2 h, concentrated under reduced pressure, and purified by Prep-HPLC with the following conditions: (Column, X-Bridge, C18, Shield RP, 19*150 mm 5 um; mobile phase, water with 0.05% NH₃H₂O and ACN (27.0% ACN up to 57.0% in 8 min); Detector, UV 210/254 nm. This purification afforded 7.5 mg (10%) of N-(3-(5-(difluoromethyl)-1,2,4-oxadiazol-3-yl)-6,7-dihydro-5H-cyclopenta[b]pyridin-7-yl)benzamide (Compound 94) as a white solid. LRMS (ES) mz/357; $^1$H-NMR: (300 MHz, Methanol-$d_4$, ppm) δ 9.09-9.01 (m, 1H), 8.37 (dt, J=2.0, 1.0 Hz, 1H), 7.93-7.82 (m, 2H), 7.58-7.35 (m, 3H), 5.63 (t, J=8.5 Hz, 1H), 3.25-2.95 (m, 3H), 2.74 (dtd, J=12.9, 8.1, 2.9 Hz, 1H), 2.13 (dq, J=12.8, 9.1 Hz, 1H).

Example 4

Synthesis of Compound 62

1. Synthesis of Intermediate 4-2:

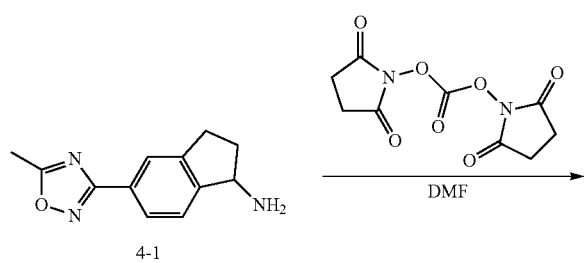

4-1

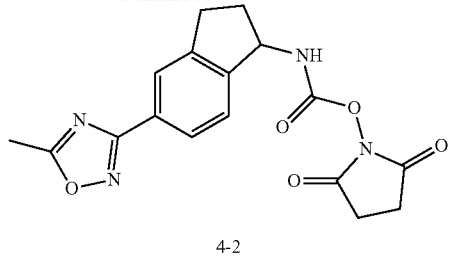

4-2

To a solution of 5-(5-methyl-1,2,4-oxadiazol-3-yl)-2,3-dihydro-1H-inden-1-amine (200 mg, 0.93 mmol, 1.00 equiv) in DMF (10 mL) was added DSC (432 mg, 1.69 mmol, 1.82 equiv). After stirring for 2 h at room temperature and 4 h at 60° C., the resulting solution was diluted with EA (60 mL). The mixture was washed with water (30 mL) twice and brine (30 mL), dried over anhydrous sodium sulfate, and concentrated under reduced pressure to afford 260 mg of 2,5-dioxopyrrolidin-1-yl N-[5-(5-methyl-1,2,4-oxadiazol-3-yl)-2,3-dihydro-1H-inden-1-yl]carbamate as a yellow solid. This yellow solid was used in next step without further purification. LRMS (ES) m/z 357 (M+H).

2. Synthesis of Compound 62:

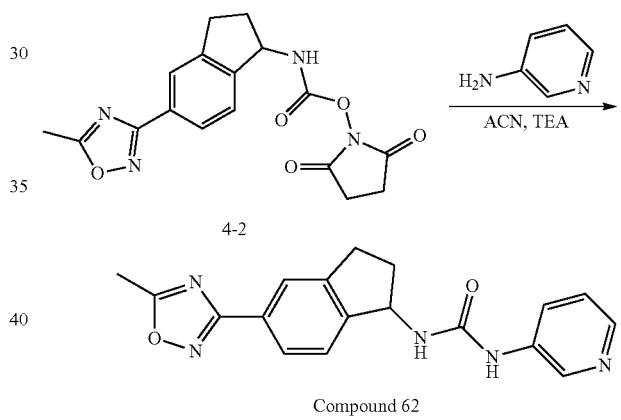

4-2

Compound 62

To a solution of 2,5-dioxopyrrolidin-1-yl N-[5-(5-methyl-1,2,4-oxadiazol-3-yl)-2,3-dihydro-1H-inden-1-yl]carbamate (60 mg, 0.17 mmol, 1.00 equiv) in ACN (5 mL) were added pyridin-3-amine (40 mg, 0.43 mmol, 2.52 equiv) and TEA (100 mg, 0.99 mmol, 5.87 equiv). The mixture was stirred at 80° C. for 4 h, concentrated under vacuum, and purified by Prep-HPLC with the following conditions: (2#-AnalyseHPLC-SHIMADZU(HPLC-10)): Column, XBridge Shield RP18 OBD Column, 5 um, 19*150 mm; mobile phase, water (0.05% NH₃.H₂O) and ACN (20.0% ACN up to 50.0% in 8 min); Detector, UV 254 nm. This resulted in 10 mg (18%) of 1-(5-(5-methyl-1,2,4-oxadiazol-3-yl)-2,3-dihydro-1H-inden-1-yl)-3-(pyridin-3-yl)urea (Compound 62) as a white solid. LRMS (ES) m/z 336 (M+H). $^1$H-NMR: (400 MHz, DMSO-$d_6$, ppm) δ 8.64 (s, 1H), 8.56 (s, 1H), 8.13 (d, J=4.6 Hz, 1H), 7.93 (ddd, J=8.4, 2.7, 1.5 Hz, 1H), 7.89-7.81 (m, 2H), 7.44 (d, J=7.8 Hz, 1H), 7.27 (dd, J=8.4, 4.6 Hz, 1H), 6.78 (d, J=8.1 Hz, 1H), 5.24 (q, J=8.0 Hz, 1H), 2.99 (dd, J=8.1, 5.1 Hz, 1H), 2.88 (q, J=8.0 Hz, 1H), 2.64 (s, 3H), 2.49 (m, 1H), 1.92-1.77 (m, 1H).

The following compounds were prepared by methods analogous to the method described for Compound 62:

| Compound No. | LRMS (ES) m/z |
| --- | --- |
| 31 | M + H = 335.1 |
| 33 | M + H = 336 |
| 34 | M + H = 325 |
| 43 | M + H = 337 |
| 44 | M + H = 325 |
| 45 | M + H = 338 |
| 46 | M + H = 325 |
| 47 | M + H = 338 |
| 48 | M + H = 325 |
| 63 | M + H = 341 |
| 64 | M + H = 326 |
| 65 | M + H = 324 |
| 66 | M + H = 324.1 |
| 85 | M + H = 336 |
| 86 | M + H = 335 |
| 87 | M + H = 326 |
| 88 | M + H = 325 |
| 89 | M + H = 325 |
| 96 | M + H = 337 |
| 97 | M + H = 337 |
| 98 | M + H = 337 |
| 105 | M + H = 325 |
| 106 | M + H = 338 |
| 107 | M + H = 324 |
| 109 | M + H = 336 |
| 110 | M + H = 337 |
| 111 | M + H = 338 |
| 112 | M + H = 339 |

Example 5

Synthesis of Compound 100

1. Synthesis of Intermediate 5-2:

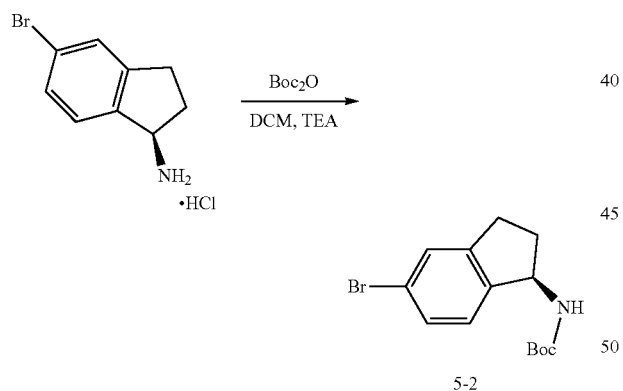

To a solution of (1R)-5-bromo-2,3-dihydro-1H-inden-1-amine hydrochloride (44.4 g, 178.8 mmol, 1 equiv) in DCM (330 mL) at 0° C. was added TEA (39.8 g, 393.3 mmol, 2.2 equiv) and a solution of (Boc)₂O (42.9 g, 196.3 mmol, 1.1 equiv) in DCM (120 mL) dropwise over a period of 1 h. The mixture was stirred at r.t. for 3 h. Water (500 mL) was added and the mixture was extracted with DCM (500 mL) twice. The combined organic layers were washed twice with aqueous NH₄Cl solution (500 mL) and twice with brine (500 mL), dried over anhydrous sodium sulfate, and concentrated under reduced pressure to give 57.4 g (92%) of tert-butyl N-[(1R)-5-bromo-2,3-dihydro-1H-inden-1-yl]carbamate as white solid.

2. Synthesis of Intermediate 5-3:

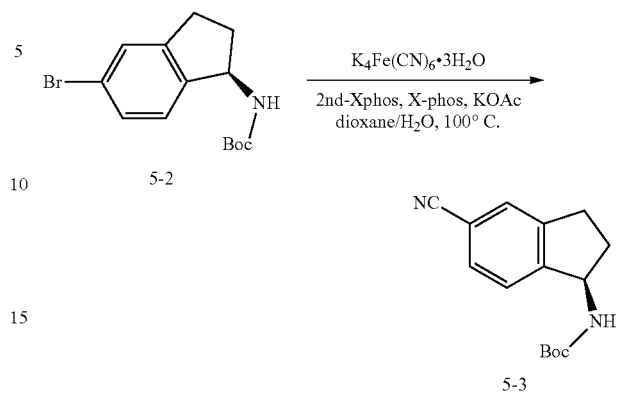

To a solution of tert-butyl N-[(1R)-5-bromo-2,3-dihydro-1H-inden-1-yl] carbamate (57.4 g, 184 mmol, 1.0 equiv) in a mixture of dioxane (285 mL) and water (285 mL) were added potassium acetate (36.0 g, 367 mmol, 2.0 equiv), K₄Fe(CN)₆·3H₂O (31.1 g, 73.5 mmol, 0.4 equiv), XPhos (1.3 g, 2.8 mmol, 0.015 equiv), and 2nd Generation XPhos pre-catalyst (2.2 g, 2.8 mmol, 0.015 equiv) under nitrogen. The mixture was stirred at 100° C. for 2 h, cooled to r.t., and filtered to remove solids. The aqueous layer was extracted with EA (500 ml) twice. The combined organic layers were dried over Na₂SO₄, concentrated under reduced pressure, and triturated with a mixture of ethyl acetate and hexanes (300 mL, 1/10) to give 42 g (88%) of tert-butyl N-[(1R)-5-cyano-2,3-dihydro-1H-inden-1-yl]carbamate as a light yellow solid. LRMS (ES) m/z 203 (M+H-56).

3. Synthesis of Intermediate 5-4:

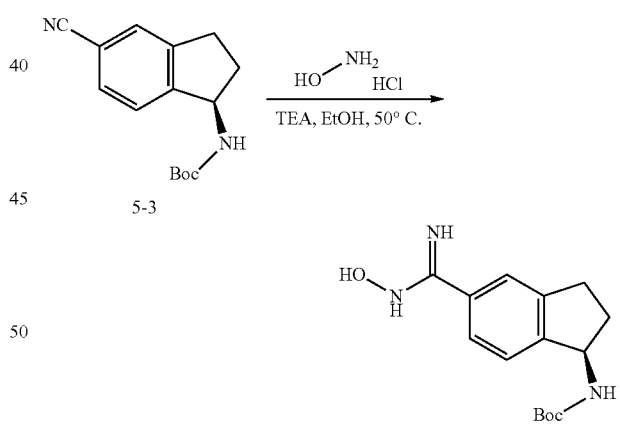

To a solution of tert-butyl N-[(1R)-5-cyano-2,3-dihydro-1H-inden-1-yl]carbamate (42.2 g, 163.4 mmol, 1 equiv) in ethanol (420 mL) were added hydroxylamine hydrochloride (22.7 g, 326.7 mmol, 2.0 equiv) and TEA (33.1 g, 326.7 mmol, 2.0 equiv). The mixture was stirred at 50° C. for 4 h, concentrated under reduced pressure, dissolved in EA (1 L), washed with water, dried over Na₂SO₄, and concentrated under reduced pressure to give 54.6 g (98%) of tert-butyl N-[(1R)-5-(N-hydroxycarbamimidoyl)-2,3-dihydro-1H-inden-1-yl]carbamate as an off-white solid. LRMS (ES) m/z 292 (M+H).

4. Synthesis of Intermediate 5-5:

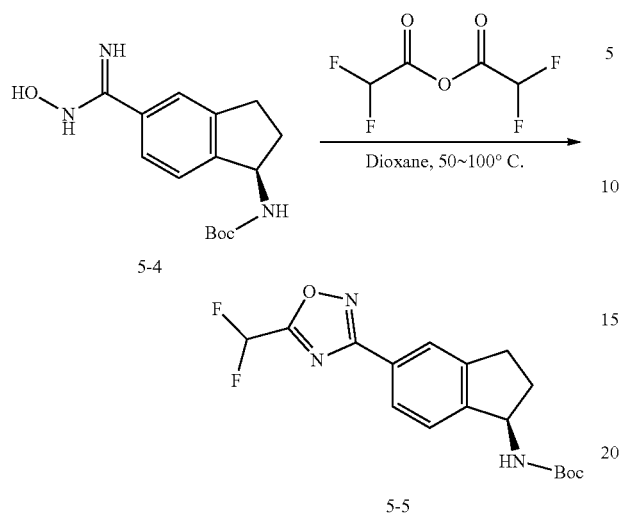

5-4

To a solution tert-butyl N-[(1R)-5-(N-hydroxycarbamimidoyl)-2,3-dihydro-1H-inden-1-yl]carbamate (54.6 g, 187.4 mmol, 1 equiv) in dioxane (500 mL) was added 2,2-difluoroacetyl 2,2-difluoroacetate (34.2 g, 196.8 mmol, 1.05 equiv). The mixture was stirred at 50° C. for 1 h and at 100° C. for 2 h. The solution was then cooled to RT and poured into water (500 mL). The aqueous layer was extracted with EA (500 mL) twice. The combined organic layers were washed with brine (1 L), dried over Na₂SO₄, and concentrated under reduced pressure to give 53.2 g (73%) of tert-butyl N-[(1R)-5-[5-(difluoromethyl)-1,2,4-oxadiazol-3-yl]-2,3-dihydro-1H-inden-1-yl]carbamate as a white solid. LRMS (ES) m/z 295 (M+H-56).

5. Synthesis of Intermediate 5-6:)

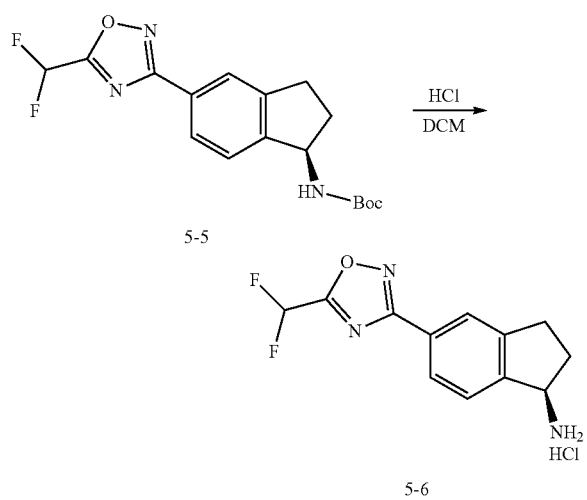

To a solution of tert-butyl N-[(1R)-5-[5-(difluoromethyl)-1,2,4-oxadiazol-3-yl]-2,3-dihydro-1H-inden-1-yl]carbamate (53.2 g, 151.4 mmol, 1 equiv) in DCM (375 mL) was added HCl (4 M in dioxane, 125 mL, 4.1 mol, 27.2 equiv). The mixture was stirred at rt for 3 h and diluted with ethyl acetate (300 mL). The precipitate was collected and dried under high vacuum to give 44 g (94%) of (1R)-5-[5-(difluoromethyl)-1,2,4-oxadiazol-3-yl]-2,3-dihydro-1H-inden-1-amine hydrochloride as an off-white solid. LRMS (ES) m/z 235 (M+H-17).

6. Synthesis of Compound 100:

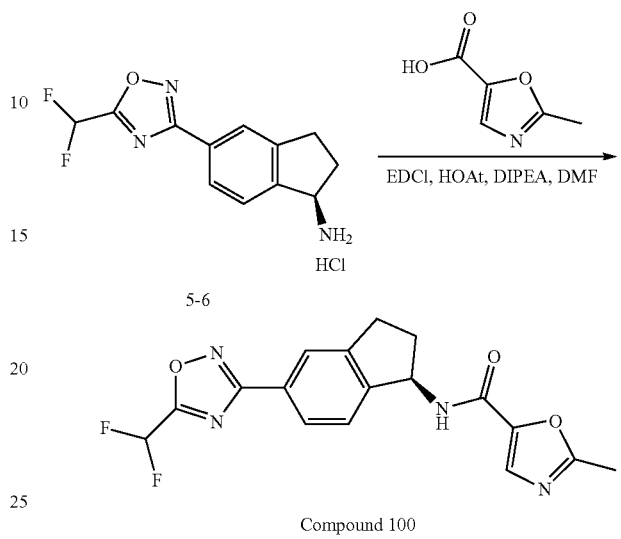

Compound 100

To a solution of 2-methyl-1,3-oxazole-5-carboxylic acid (10.0 g, 78.3 mmol, 1.0 equiv) in DMF (220 mL) were added HOAt (16.0 g, 117.4 mmol, 1.5 equiv), EDCI (22.5 g, 117.4 mmol, 1.5 equiv), and DIEA (40.5 g, 313.1 mmol, 4.0 equiv). The mixture was stirred for 15 min and (1R)-5-[5-(difluoromethyl)-1,2,4-oxadiazol-3-yl]-2,3-dihydro-1H-inden-1-amine hydrochloride (22.6 g, 78.3 mmol, 1.05 equiv) was added. The mixture was allowed to continue stirring overnight. Ice water (700 mL) was added and the mixture was stirred for an additional 1 h. The precipitate was collected, dissolved in EA (500 mL), dried over Na₂SO₄, and concentrated reduced pressure. The residue was triturated with a mixture of EA and PE (700 mL, 1/20) to give 26 g of the light brown solid. This batch was combined with another batch made using the same procedure (obtained 7.5 g from 24.33 mmol of amine). The combined products were dissolved in a mixture of DCM and MeOH (500 mL, 10/1), concentrated to ~100 mL of volume, and diluted with hexane (1 L). The precipitate was collected and dried to give 32.8 g of (R)—N-(5-(5-(difluoromethyl)-1,2,4-oxadiazol-3-yl)-2,3-dihydro-1H-inden-1-yl)-2-methyloxazole-5-carboxamide (Compound 100) as an off-white solid. LRMS (ES) m/z 361 (M+H). $^1$H-NMR: (400 MHz, Chloroform-d, ppm) δ 8.03 (s, 1H), 8.02-7.97 (m, 1H), 7.66 (s, 1H), 7.49 (d, J=7.9 Hz, 1H), 6.88 (t, J=52.2 Hz, 1H), 6.42 (d, J=8.7 Hz, 1H), 5.74 (q, J=8.0 Hz, 1H), 3.14 (ddd, J=16.2, 8.9, 3.6 Hz, 1H), 3.02 (dt, J=16.4, 8.3 Hz, 1H), 2.76 (dtd, J=13.0, 7.9, 3.6 Hz, 1H), 2.53 (s, 3H), 2.01 (dq, J=13.0, 8.5 Hz, 1H).

The following compounds were prepared by methods analogous to the method described for Compound 100:

| Compound No. | LRMS (ES) m/z |
| --- | --- |
| 32 | M + H = 371 |
| 61 | M + H = 374 |
| 83 | M + H = 361 |
| 84 | M + NH4 = 379 |
| 95 | M + H = 373 |
| 99 | M + H = 372 |

| Compound No. | LRMS (ES) m/z |
| --- | --- |
| 101 | M + H = 374 |
| 102 | M + H = 359 |
| 103 | M + H = 359 |
| 104 | M + H = 361 |

Example 6

Synthesis of Compound 107

1. Synthesis of Intermediate 6-2:

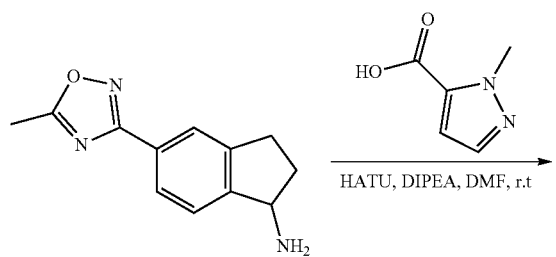

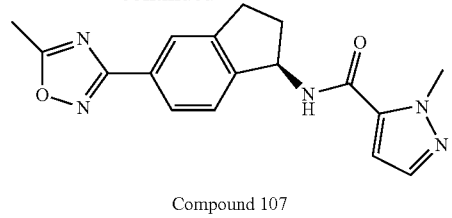

Compound 107

The racemic mixture (390 mg) was purified by Chiral-Prep-HPLC with the following conditions. (Prep-HPLC-009): Column, Chiralpak ID-2, 2*25 cm, 5 um; mobile phase, Hex and ethanol (hold 25.0% ethanol—for 20 min); Detector, UV 220/254 nm. This separation afforded 114.5 mg (29%) of (R)-1-methyl-N-(5-(5-methyl-1,2,4-oxadiazol-3-yl)-2,3-dihydro-1H-inden-1-yl)-1H-pyrazole-5-carboxamide (Compound 107) as a white solid. LRMS (ES) m/z 324 (M+H). ¹H-NMR: (DMSO, 400 MHz, ppm): δ 8.84-8.82 (1H, d, J=8.0), 7.89-7.86 (2H, m), 7.45-7.38 (2H, m), 6.92 (1H, s), 5.60-5.53 (1H, dd, J=8.4, 16.8), 4.11 (3H, s), 3.10-3.04 (1H, m), 2.97-2.89 (1H, m), 2.65 (3H, s), 2.50 (1H, m), 2.07-1.97 (1H, m)

Example 7

Synthesis of Compound 108

1. Synthesis of Intermediate 7-2:

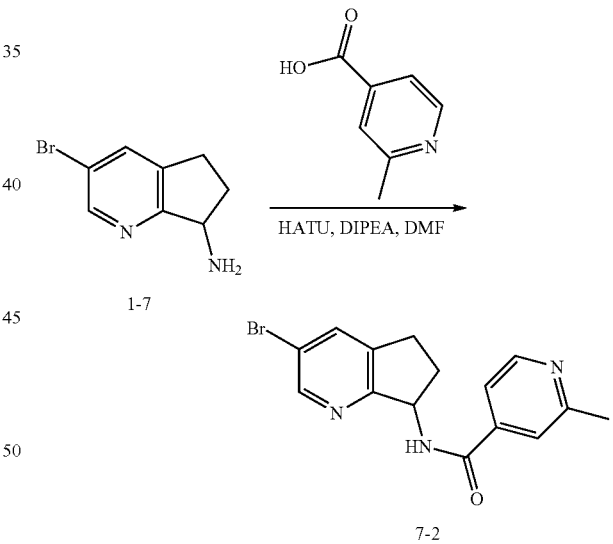

To a solution of 1-methyl-1H-pyrazole-5-carboxylic acid (205 mg, 1.6 mmol, 1.0 equiv) in DMF (6 mL) were added DIEA (630 mg, 3.00 equiv) and HATU (928 mg, 2.44 mmol, 1.50 equiv). The mixture was stirred for 15 min and 5-(5-methyl-1,2,4-oxadiazol-3-yl)-2,3-dihydro-1H-inden-1-amine (350 mg, 1.63 mmol, 1.00 equiv) was added. The mixture was then stirred overnight, diluted with EA (100 mL), washed with brine (100 mL) three times, concentrated under reduced pressure, and purified by silica gel chromatography (EA/PE, 1/3) to give 390 mg (74%) of 1-methyl-N-[5-(5-methyl-1,2,4-oxadiazol-3-yl)-2,3-dihydro-1H-inden-1-yl]-1H-pyrazole-5-carboxamide as a white solid. LRMS (ES) m/z 324 (M+H).

2. Synthesis of Compound 107:

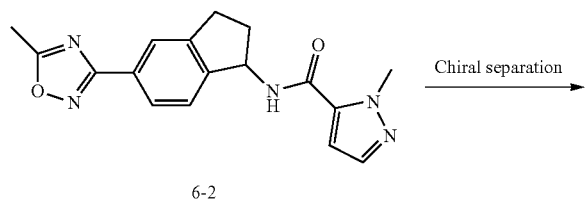

To a solution of 3-bromo-5H,6H,7H-cyclopenta[b]pyridin-7-amine (480 mg, 2.25 mmol, 1.0 equiv) in DMF (10 mL) were added 2-methylpyridine-4-carboxylic acid (620 mg, 4.5 mmol, 2.0 equiv), HATU (1.3 g, 3.4 mmol, 1.5 equiv) and DIEA (876 mg, 6.8 mmol, 3.0 equiv). The mixture was stirred for 2 h, diluted with EA (100 mL), washed with brine (30 mL) twice, dried over anhydrous sodium sulfate, concentrated under reduced pressure, and purified by silica gel chromatography (EA/PE, 70/30) to afford 460 mg (61%) of N-[3-bromo-5H,6H,7H-cyclopenta[b]pyridin-7-yl]-2-methylpyridine-4-carboxamide as a brown solid.

2. Synthesis of Intermediate 7-3:

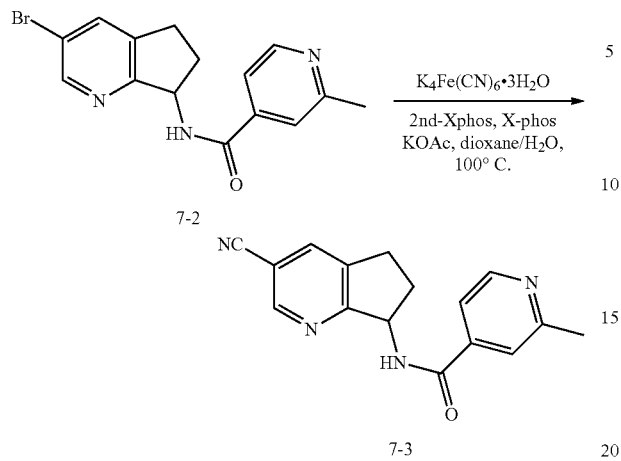

To a solution of N-[3-bromo-5H,6H,7H-cyclopenta[b]pyridin-7-yl]-2-methylpyridine-4-carboxamide (450 mg, 1.4 mmol, 1.0 equiv) in dioxane (5 mL) were added $K_4Fe(CN)_6 \cdot 3H_2O$ (586 mg, 1.4 mmol, 1.0 equiv), X-phos (67 mg, 0.14 mmol, 0.1 equiv), 2nd-Xphos (105 mg, 0.14 mmol, 0.1 equiv), KOAc (266 mg, 2.7 mmol, 2.0 equiv) and water (5 mL) under nitrogen. The mixture was stirred at 80° C. for 6 h, cooled to r.t., diluted with EA (100 mL), washed with brine (30 mL) twice, dried over anhydrous sodium sulfate, concentrated under reduced pressure, and purified by silica gel chromatography (EA/PE, 99/1) to afford 40 mg (11%) of N-[3-cyano-5H,6H,7H-cyclopenta[b]pyridin-7-yl]-2-methylpyridine-4-carboxamide as a brown solid.

3. Synthesis of Intermediate 7-4:

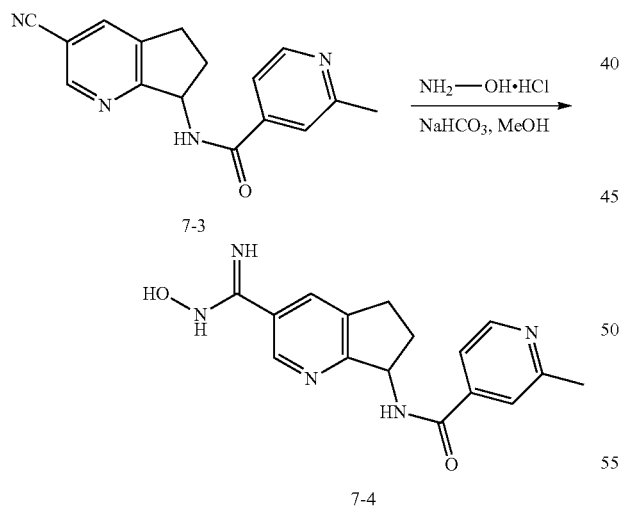

To a solution of N-[3-cyano-5H,6H,7H-cyclopenta[b]pyridin-7-yl]-2-methylpyridine-4-carboxamide (40 mg, 0.14 mmol, 1.0 equiv) in MeOH (6 mL) were added hydroxylamine hydrochloride (20 mg, 0.3 mmol, 2.0 equiv) and sodium bicarbonate (36 mg, 0.4 mmol, 3.0 equiv). The mixture was stirred at 80° C. for 5 h, cooled to r.t., and concentrated under reduced pressure to afford 50 mg of N-[3-(N-hydroxycarbamimidoyl)-5H,6H,7H-cyclopenta[b]pyridin-7-yl]-2-methylpyridine-4-carboxamide as a white solid.

4. Synthesis of Compound 108:

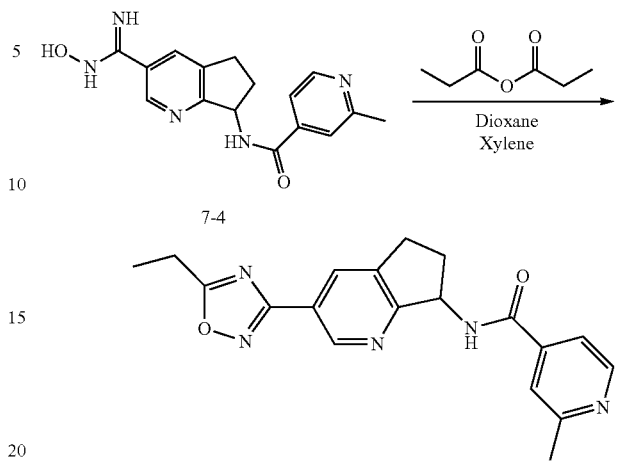

Compound 108

To a solution of N-[3-(N-hydroxycarbamimidoyl)-5H,6H,7H-cyclopenta[b]pyridin-7-yl]-2-methylpyridine-4-carboxamide (45 mg, 0.14 mmol, 1.0 equiv) in dioxane (5 mL) was added propanoyl propanoate (56 mg, 0.4 mmol, 3.0 equiv). The mixture was stirred at 90° C. for 2 h, cooled to r.t., and concentrated under reduced pressure. Xylenes (5 mL) was then added and the mixture was heated to 150° C. for 2 h, cooled to r.t., concentrated under reduced pressure, and purified by Prep-HPLC with the following conditions: (Column, X-Bridge, C18, Shield RP, 19*150 mm 5 um; mobile phase, water with 0.05% $NH_3H_2O$ and ACN (20.0% ACN up to 40.0% in 8 min, up to 100.0% in 5 min, down to 0% in 1 min); Detector, UV 210/254 nm. This purification afforded 12.3 mg (24%) of N-(3-(5-ethyl-1,2,4-oxadiazol-3-yl)-6,7-dihydro-5H-cyclopenta[b]pyridin-7-yl)-2-methylisonicotinamide (Compound 108) as a white solid. LRMS (ES) m/z 350 (M+H). $^1$H-NMR: (300 MHz, DMSO-$d_6$, ppm): δ 9.09 (d, J=8.4 Hz, 1H), 8.94 (d, J=1.9 Hz, 1H), 8.55 (dd, J=5.2, 0.8 Hz, 1H), 8.21 (d, J=1.9 Hz, 1H), 7.68-7.60 (m, 1H), 7.56 (dd, J=5.1, 1.6 Hz, 1H), 5.54 (q, J=8.5 Hz, 1H), 3.14-2.98 (m, 2H), 3.02-2.84 (m, 2H), 2.62-2.48 (m, 1H), 2.49 (s, 3H), 2.01 (dq, J=12.6, 9.0 Hz, 1H), 1.31 (t, J=7.6 Hz, 3H).

Example 8

Synthesis of Compound 122

1. Synthesis of Intermediate 8-2:

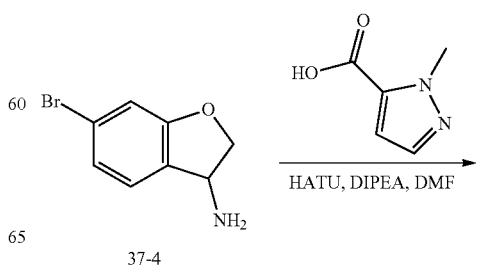

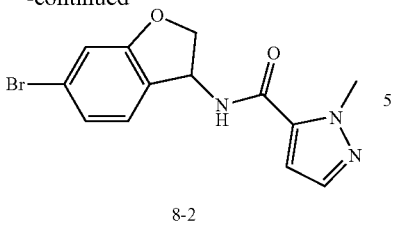

8-2

To a solution of 1-methyl-1H-pyrazole-5-carboxylic acid (592 mg, 479 mmol, 1.0 equiv) in DMF (10 mL) were added DIEA (1.8 g, 13.9 mmol, 3.0 equiv) and HATU (2.7 g, 7.1 mmol, 1.5 equiv). The mixture was stirred for 15 min and 6-bromo-2,3-dihydro-1-benzofuran-3-amine (1 g, 4.7 mmol, 1.0 equiv) was added. The mixture was then stirred overnight, diluted with EA (200 mL), washed with brine (200 mL) three times, concentrated under reduced pressure, and purified by silica gel chromatography (EA/PE, 1/1) to give 1.3 g (86%) of N-(6-bromo-2,3-dihydro-1-benzofuran-3-yl)-1-methyl-1H-pyrazole-5-carboxamide as an off-white solid.

2. Synthesis of Intermediate 8-3:

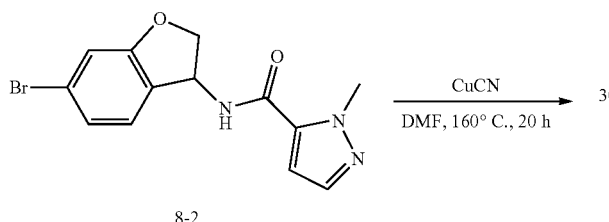

8-2

8-3

To a solution of N-(6-bromo-2,3-dihydro-1-benzofuran-3-yl)-1-methyl-1H-pyrazole-5-carboxamide (1.4 g, 4.4 mmol, 1.0 equiv) in DMF (10 mL) was added CuCN (587 mg, 6.6 mmol, 1.5 equiv). The mixture was stirred at 160° C. for 2 days, diluted with EA (200 mL), washed with brine (200 mL) three times, concentrated under reduced pressure, and purified by silica gel chromatography (EA/PE, 1/2) to give 530 mg (45%) of N-(6-cyano-2,3-dihydro-1-benzofuran-3-yl)-1-methyl-1H-pyrazole-5-carboxamide as an off-white solid.

3. Synthesis of Intermediate 8-4:

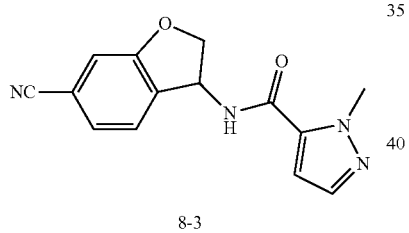

8-3

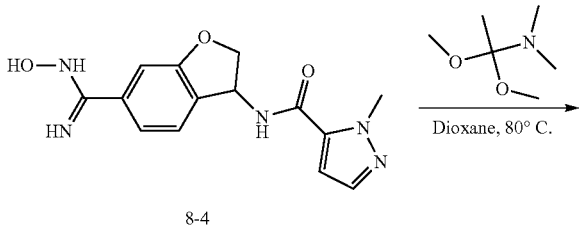

8-4

To a solution of N-(6-cyano-2,3-dihydro-1-benzofuran-3-yl)-1-methyl-1H-pyrazole-5-carboxamide (530 mg, 2.0 mmol, 1.0 equiv) in MeOH (8 mL) were added sodium bicarbonate (250 mg, 1.5 equiv) and hydroxylamine hydrogen chloride (164 mg, 2.4 mmol, 1.2 equiv). The mixture was heated at 60° C. for 2 h and concentrated under reduced pressure to give 580 mg of N-[6-(N-hydroxycarbamimidoyl)-2,3-dihydro-1-benzofuran-3-yl]-1-methyl-1H-pyrazole-5-carboxamide as a light yellow solid. This light yellow solid was used for next step without further purification.

4. Synthesis of Intermediate 8-5:

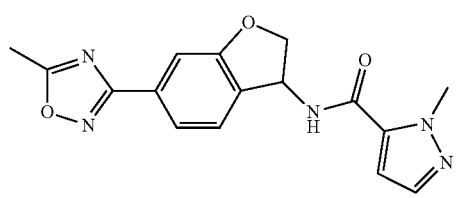

8-4

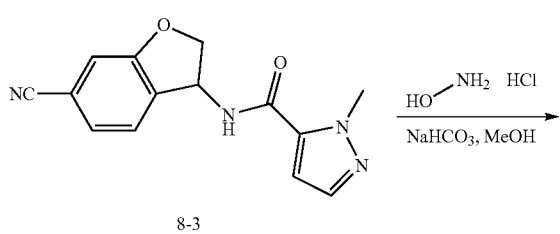

8-5

To a solution of N-[6-(N-hydroxycarbamimidoyl)-2,3-dihydro-1-benzofuran-3-yl]-1-methyl-1H-pyrazole-5-carboxamide (190 mg, 0.6 mmol, 1.0 equiv) in dioxane (5 mL) was added (1,1-dimethoxyethyl)dimethylamine (168 mg, 1.3 mmol, 2.0 equiv). The mixture was stirred at 80° C. for 2 h, concentrated under reduced pressure, and purified by Prep-HPLC using the following conditions: (2#-AnalyseHPLC-SHIMADZU(HPLC-10)): Column, XBridge Shield RP18 OBD Column, 5 um, 19*150 mm; mobile phase, Water (0.05% $NH_3 \cdot H_2O$) and ACN (25.0% ACN up to 45.0% in 8 min); Detector, UV 220 nm. This purification provided 133 mg of 1-methyl-N-[6-(5-methyl-1,2,4-oxadiazol-3-yl)-2,3-dihydro-1-benzofuran-3-yl]-1H-pyrazole-5-carboxamide as a white solid. LRMS (ES) m/z 326 (M+H). $^1$H-NMR: ($CD_3OD$, 400 MHz, ppm): δ 7.67-7.65 (1H, d, J=8.0), 7.54-7.45 (3H, m), 6.82 (1H, m), 5.89-5.85 (1H, m), 4.86-4.84 (1H, m), 4.51-4.48 (1H, dd, J=5.2, 9.6), 4.17 (3H, s), 2.66 (3H, s)

5. Synthesis of Compound 122:

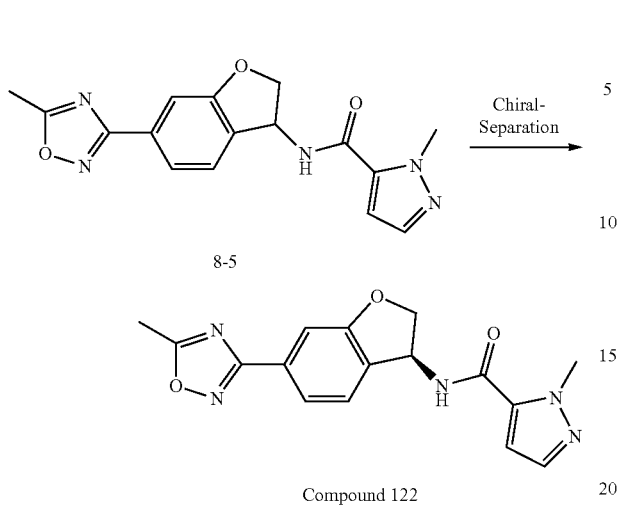

8-5

Compound 122

The racemic mixture (95 mg) was purified by Chiral-Prep-HPLC with the following conditions: (Prep-HPLC-004): Column, CHIRALART Cellulose-SB, 2*25 cm, 5 um; mobile phase, Hex- and ethanol- (hold 50.0% ethanol- in 9 min); Detector, UV 254/220 nm. This purification resulted in 28.3 mg (30%) of (S)-1-methyl-N-(6-(5-methyl-1,2,4-oxadiazol-3-yl)-2,3-dihydrobenzofuran-3-yl)-1H-pyrazole-5-carboxamide (Compound 122) as a white solid. LRMS (ES) m/z 326 (M+H). $^1$H-NMR: (CD$_3$OD, 300 MHz, ppm): 67.62-7.59 (1H, dd, J=1.2, 7.8), 7.49-7.40 (3H, m), 6.77-6.76 (1H, d, J=2.1), 5.84-5.79 (1H, dd, J=4.8, 8.7), 4.80-4.77 (1H, m), 4.47-4.42 (1H, dd, J=4.8, 9.9), 4.11 (3H, s), 2.61 (3H, s)

The following compounds were prepared by methods analogous to the method described for Compound 122:

| Compound No. | LRMS (ES) m/z |
|---|---|
| 15 | M + H = 322 |
| 18 | M + H = 337 |
| 121 | M + H = 326 |
| 123 | M + H = 362 |

Example 9

Synthesis of Compound 124

1. Synthesis of Intermediate 9-2:

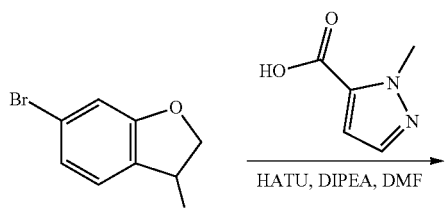

37-4

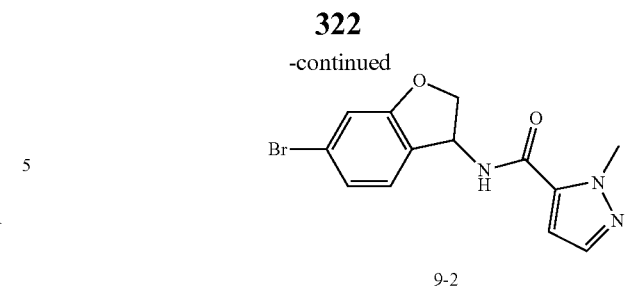

9-2

To a solution of 1-methyl-1H-pyrazole-5-carboxylic acid (592 mg, 4.7 mmol, 1.0 equiv) in DMF (10 mL) were added DIEA (1.8 g, 13.9 mmol, 3.0 equiv) and HATU (2.7 g, 7.1 mmol, 1.5 equiv). The mixture was stirred for 15 min and 6-bromo-2,3-dihydro-1-benzofuran-3-amine (1 g, 4.7 mmol, 1.0 equiv) was then added. The mixture was then stirred overnight, diluted with ethyl acetate (200 mL), washed with brine (200 mL) three times, concentrated under reduced pressure, and purified by silica gel chromatography (EA/PE, 1/1) to give 1.3 g (86%) of N-(6-bromo-2,3-dihydro-1-benzofuran-3-yl)-1-methyl-1H-pyrazole-5-carboxamide as an off-white solid.

2. Synthesis of Intermediate 9-3:

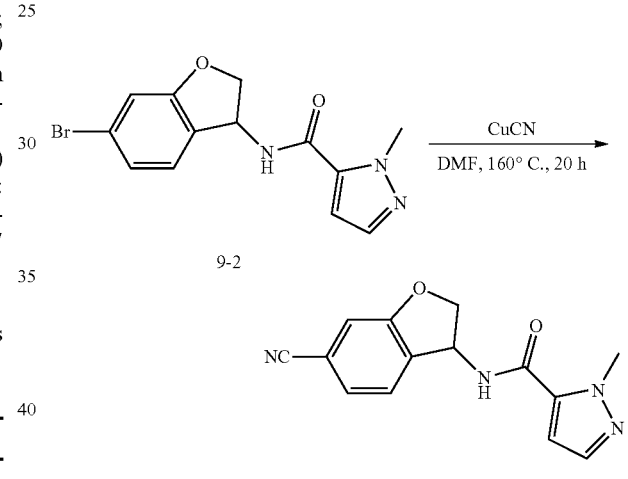

To a solution of N-(6-bromo-2,3-dihydro-1-benzofuran-3-yl)-1-methyl-1H-pyrazole-5-carboxamide (1.4 g, 4.4 mmol, 1.0 equiv) in DMF (10 mL) was added CuCN (587 mg, 6.6 mmol, 1.5 equiv). The mixture was stirred at 160° C. for 2 days, diluted with EA (200 mL), washed with brine (200 mL) three times, concentrated under reduced pressure, and purified by silica gel chromatography (EA/PE, 1/2) to give 530 mg (45%) of N-(6-cyano-2,3-dihydro-1-benzofuran-3-yl)-1-methyl-1H-pyrazole-5-carboxamide as an off-white solid.

3. Synthesis of Intermediate 9-4:

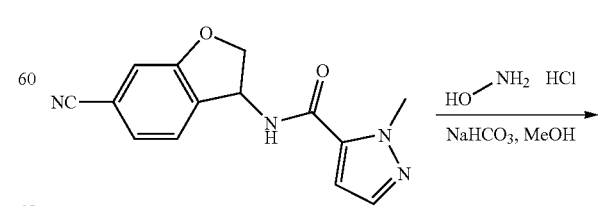

9-3

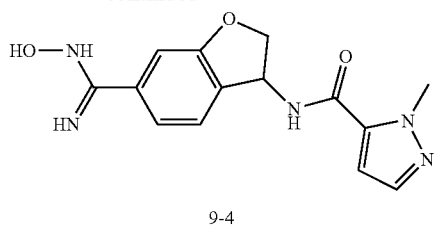

9-4

To a solution of N-(6-cyano-2,3-dihydro-1-benzofuran-3-yl)-1-methyl-1H-pyrazole-5-carboxamide (530 mg, 2.0 mmol, 1.0 equiv) in MeOH (8 mL) were added sodium bicarbonate (250 mg, 1.5 equiv) and hydroxylamine hydrogen chloride (164 mg, 2.4 mmol, 1.2 equiv). The mixture was heated at 60° C. for 2 h and concentrated under reduced pressure to give 580 mg of N-[6-(N-hydroxycarbamimidoyl)-2,3-dihydro-1-benzofuran-3-yl]-1-methyl-1H-pyrazole-5-carboxamide as a light yellow solid. This light yellow solid was used for next step without further purification.

4. Synthesis of Intermediate 9-5:

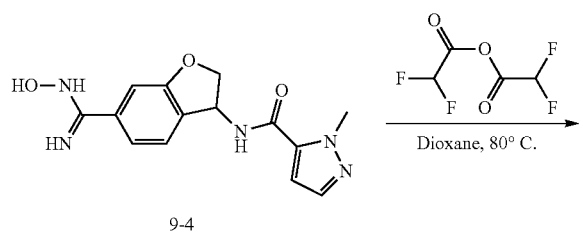

9-4

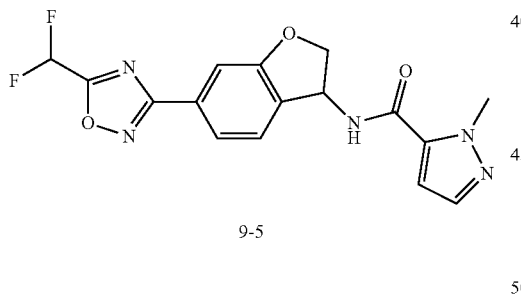

9-5

To a solution of N-[6-(N-hydroxycarbamimidoyl)-2,3-dihydro-1-benzofuran-3-yl]-1-methyl-1H-pyrazole-5-carboxamide (190 mg, 0.6 mmol, 1.0 equiv) in dioxane (5 mL) was added 2,2-difluoroacetyl 2,2-difluoroacetate (220 mg, 1.3 mmol, 2.0 equiv) dropwise. After stirring at 80° C. for 2 h, the resulting mixture was concentrated under reduced pressure and purified by Prep-HPLC with the following conditions: (2#-AnalyseHPLC-SHIMADZU(HPLC-10)): Column, XBridge Shield RP18 OBD Column, 5 um, 19*150 mm; mobile phase, water (0.05% NH₃H₂O) and ACN (33.0% ACN up to 55.0% in 8 min); Detector, UV 220 nm. This purification provided 130 mg of N-[6-[5-(difluoromethyl)-1,2,4-oxadiazol-3-yl]-2,3-dihydro-1-benzofuran-3-yl]-1-methyl-1H-pyrazole-5-carboxamide as a white solid. LRMS (ES) m/z 362 (M+H).

5. Synthesis of Compound 124:

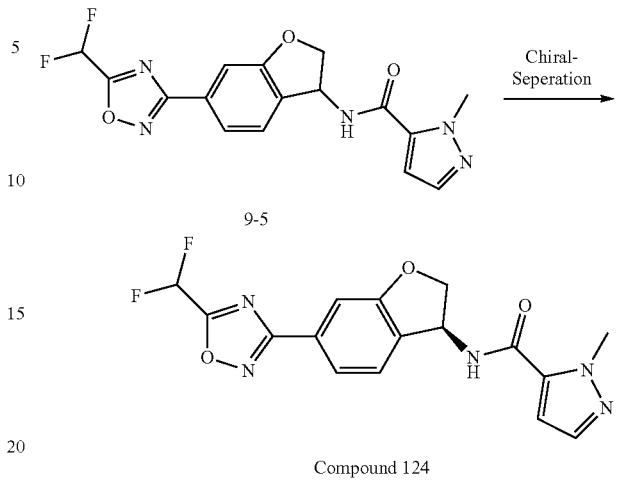

Compound 124

The racemic mixture (85 mg) was purified by Chiral-Prep-HPLC using the following conditions: (Prep-HPLC-004): Column, CHIRAL ART Cellulose-SB, 2*25 cm, 5 um; mobile phase, Hex- and ethanol- (hold 35.0% ethanol- in 8 min); Detector, UV 254/220 nm. This purification provided 26.8 mg (32%) of (S)—N-(6-(5-(difluoromethyl)-1,2,4-oxadiazol-3-yl)-2,3-dihydrobenzofuran-3-yl)-1-methyl-1H-pyrazole-5-carboxamide (Compound 124) as a white solid. LRMS (ES) m/z 362 (M+H). ¹H-NMR: (CD₃OD, 300 MHz, ppm): δ 7.70-7.67 (1H, dd, J=1.5, 7.8), 7.54-7.50 (2H, m), 7.41-7.40 (1H, m), 7.34-7.00 (1H, t, J=51.9), 6.77-6.76 (1H, d, J=2.1), 5.86-5.81 (1H, dd, J=5.1, 9), 4.86-4.79 (1H, m), 4.49-4.44 (1H, dd, J=5.1, 9.9), 4.11 (3H, s).

Example 10

Synthesis of Compound 139

1. Synthesis of Intermediate 10-2:

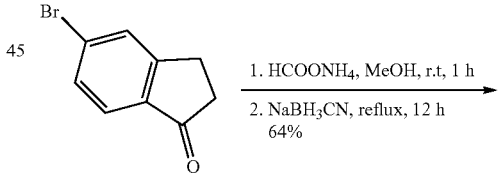

10-2

To a solution of 5-bromo-2,3-dihydro-1H-inden-1-one (100 g, 474 mmol, 1.00 equiv) in methanol (1.5 L) was added ammonium formate (300 g, 4.76 mol, 10.0 equiv). After stirring for 1 h, NaBH₃CN (90 g, 1.43 mol, 3.02 equiv) was added. The mixture was heated at 60° C. for 2 h, concentrated under reduced pressure, and purified by silica gel chromatography (EA/PE, 1/10) to afford 64 g (64%) of 5-bromo-2,3-dihydro-1H-inden-1-amine as a brown solid.

2. Synthesis of Intermediate 10-3:

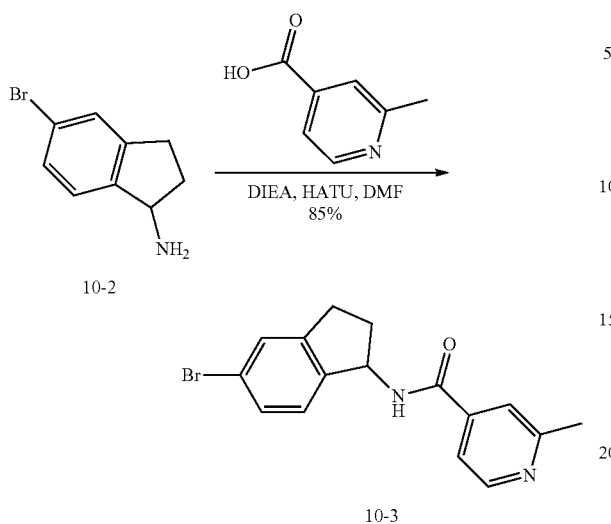

To a solution of 2-methylpyridine-4-carboxylic acid (1.95 g, 14.2 mmol, 1.00 equiv) in DMF (20 mL) were added DIEA (5.5 g, 42.6 mmol, 3.00 equiv) and HATU (8.1 g, 21.3 mmol, 1.50 equiv). After stirring at r.t. for 15 min, 5-bromo-2,3-dihydro-1H-inden-1-amine (3.0 g, 14.2 mmol, 1.00 equiv) was added and the solution was stirred for 3 h. The resulting solution was diluted with aqueous NH₄Cl solution and extracted with EA. The combined organic layers were dried over anhydrous sodium sulfate, concentrated under reduced pressure, and purified by silica gel column (EA/PE=2/1) to afford 4 g (85%) of N-(5-bromo-2,3-dihydro-1H-inden-1-yl)-2-methylpyridine-4-carboxamide as a yellow solid.

3. Synthesis of Intermediate 10-4:

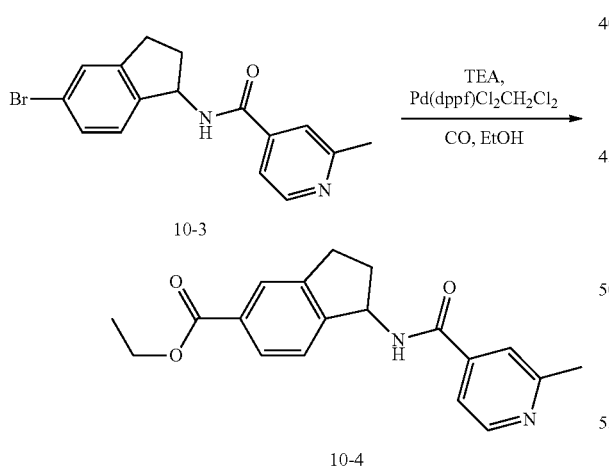

To a solution of N-(5-bromo-2,3-dihydro-1H-inden-1-yl)-2-methylpyridine-4-carboxamide (4.28 g, 13.0 mmol, 1.00 equiv) in a mixture of ethanol (120 mL) and DMSO (12 mL) were added TEA (3.9 g, 38.6 mmol, 3.00 equiv) and Pd(dppf)Cl₂·CH₂Cl₂ (1.06 g, 1.3 mmol, 0.1 equiv). This mixture was then charged with CO (20 atm). The mixture was stirred at 120° C. under CO for 2 days, purged to release CO, poured into water, and extracted with EA three times. The combined organic layers were concentrated under reduced pressure and purified by silica gel chromatography (EA/PE, 3/2) to afford 3.5 g (83%) of ethyl 1-(2-methylpyridine-4-amido)-2,3-dihydro-1H-indene-5-carboxylate as a yellow solid.

4. Synthesis of Intermediate 10-5:

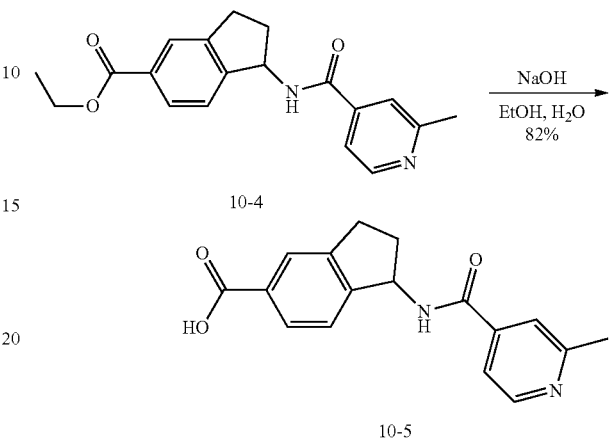

To a solution of ethyl 1-(2-methylpyridine-4-amido)-2,3-dihydro-1H-indene-5-carboxylate (1.2 g, 3.70 mmol, 1.00 equiv) in ethanol (10 mL) was added sodium hydroxide (300 mg, 7.50 mmol, 2.03 equiv) in water (2 mL). After stirring for 12 h at room temperature, the pH of the solution was adjusted to 4-5 with HCl (1 N). The solids were collected by filtration and dried in an oven to afford 0.9 g (82%) of 1-(2-methylpyridine-4-amido)-2,3-dihydro-1H-indene-5-carboxylic acid as a white solid.

5. Synthesis of Intermediate 10-6:

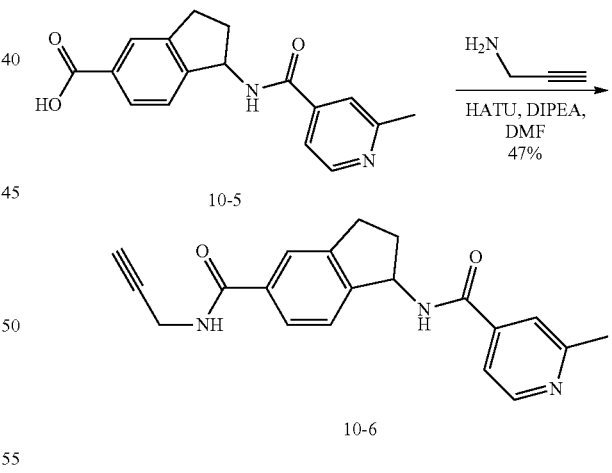

To a solution of 1-(2-methylpyridine-4-amido)-2,3-dihydro-1H-indene-5-carboxylic acid (300 mg, 1.01 mmol, 1.00 equiv) in DMF (5 mL) were added DIEA (523 mg, 4.05 equiv) and HATU (578 mg, 1.52 mmol, 1.50 equiv). After stirring for 15 min at r.t., prop-2-yn-1-amine (167 mg, 3.03 mmol, 3.00 equiv) was added. The mixture was continued to stir for 2 h and purified by Combi-Flash with a C18 column: mobile phase, Mobile Phase A: Water (0.05% NH₄HCO₃ in H₂O), Mobile Phase B: ACN; Flow rate: 50 mL/min; Gradient: 5% B to 70% B in 26 min; Detector, UV 254 nm. This resulted in 160 mg (47%) of 2-methyl-N-[5-[(prop-2- yn-1-yl)carbamoyl]-2,3-dihydro-1H-inden-1-yl]pyridine-4-carboxamide as a white solid.

6. Synthesis of Intermediate 10-7:

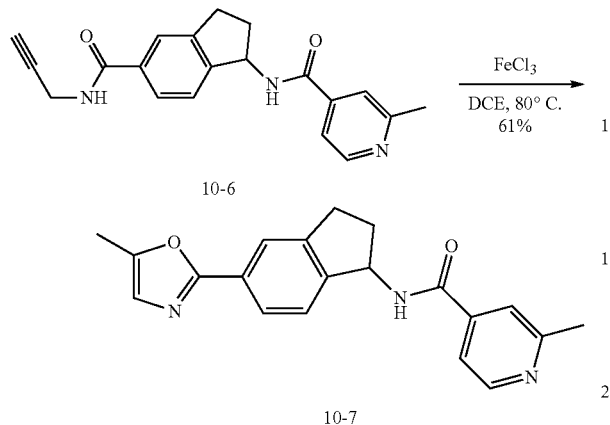

To a solution of 2-methyl-N-[5-[(prop-2-yn-1-yl)carbamoyl]-2,3-dihydro-1H-inden-1-yl]pyridine-4-carboxamide (150 mg, 0.45 mmol, 1.00 equiv) in DCE (5 mL) was added FeCl$_3$ (37 mg, 0.23 mmol, 0.50 equiv). The mixture was stirred at 80° C. for 2 days, concentrated under reduced pressure, and purified by Combi-Flash with C18 column: mobile phase, Mobile Phase A: Water (0.05% NH$_4$HCO$_3$ in H$_2$O), Mobile Phase B: ACN; Flow rate: 50 mL/min; Gradient: 5% B to 70% B in 36 min; Detector, UV 254 nm. This resulted in 91.7 mg (61%) of 2-methyl-N-[5-(5-methyl-1,3-oxazol-2-yl)-2,3-dihydro-1H-inden-1-yl] pyridine-4-carboxamide as a white solid.

7. Synthesis of Compound 139:

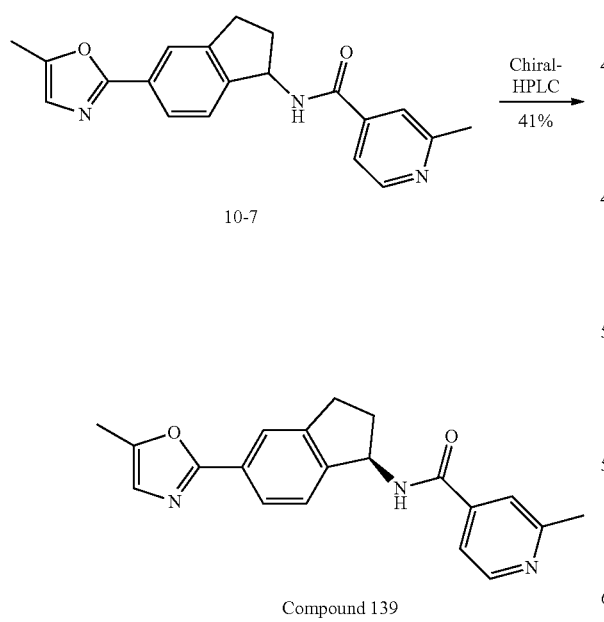

The racemic mixture (80 mg) was purified by Chiral-Prep-HPLC. Column: Chiralpak IB, 2*25 cm, 5 um; Mobile Phase A:Hex—HPLC, Mobile Phase B: EtOH—HPLC; Flow rate: 20 mL/min; Gradient: 30 B to 30 B in 8 min; 220/254 nm; RT1:5.20; RT2:6.55. This resulted in 32.4 mg (41%) of (R)-2-methyl-N-(5-(5-methyloxazol-2-yl)-2,3-dihydro-1H-inden-1-yl)isonicotinamide (Compound 139) as a white solid. LRMS (ES) m/z 334 (M+H). $^1$H-NMR: (CD$_3$OD, 300 MHz, ppm): δ 8.55-8.53 (1H, d, J=5.4), 7.88-7.83 (2H, m), 7.70 (1H, s), 7.63-7.61 (1H, d, J=5.1), 7.43-7.41 (1H, d, J=7.8), 6.90 (1H, s), 5.71-5.65 (1H, t, J=7.8), 3.20-3.10 (1H, m), 3.08-2.94 (1H, m), 2.70-2.60 (4H, m), 2.41 (3H, s), 2.15-2.05 (1H, m).

The following compounds were prepared by methods analogous to the method described for Compound 139:

| Compound No. | LRMS (ES) m/z |
| --- | --- |
| 140 | M + H = 334 |

Example 11

Synthesis of Compound 141

1. Synthesis of Intermediate 11-2:

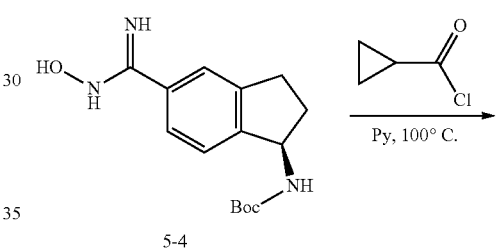

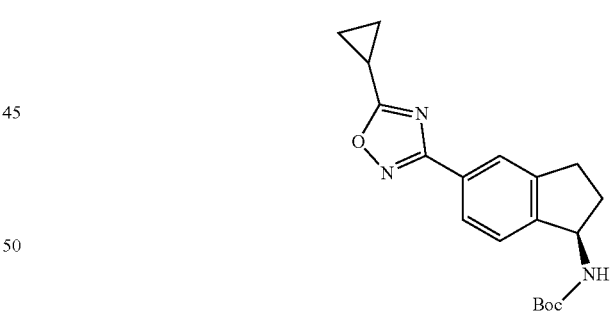

To a solution of tert-butyl N-[(1R)-5-(N-hydroxycarbamimidoyl)-2,3-dihydro-1H-inden-1-yl]carbamate (22 g, 75.5 mmol, 1.0 equiv) in pyridine (350 mL) was added cyclopropanecarbonyl chloride (8.7 g, 82.8 mmol, 1.1 equiv). The mixture was heated to 60° C. for 2 h followed by 100° C. overnight. The mixture was then cooled to r.t., concentrated under reduced pressure, and purified by silica gel chromatography (EA/PE, 15/85) to give 15 g (58%) of tert-butyl N-[(1R)-5-(5-cyclopropyl-1,2,4-oxadiazol-3-yl)-2,3-dihydro-1H-inden-1-yl]carbamate as a white solid. LRMS (ES) m/z 286 (M+H-56).

2. Synthesis of Intermediate 11-3:

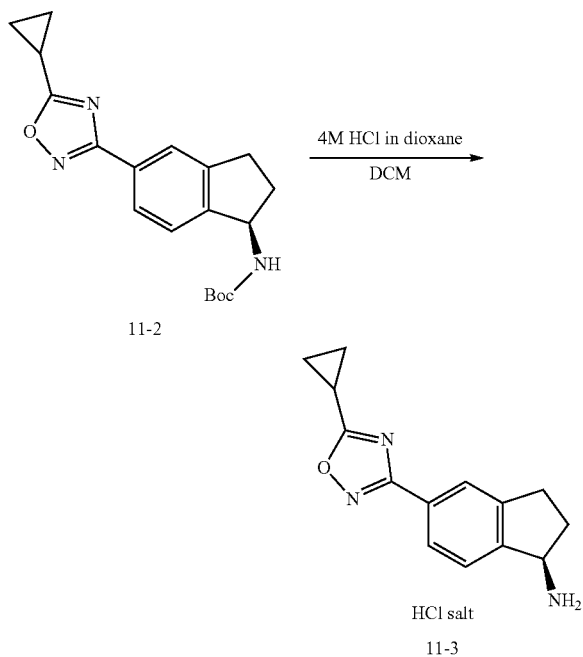

To a solution of tert-butyl N-[(1R)-5-(5-cyclopropyl-1,2,4-oxadiazol-3-yl)-2,3-dihydro-1H-inden-1-yl]carbamate (2.9 g, 8.4 mmol, 1.0 equiv) in DCM (42 mL) was added HCl (4M in dioxane, 21 mL, 10.0 equiv). The mixture was stirred overnight and the precipitate was collected and dried to give 2.9 g of (1R)-5-(5-cyclopropyl-1,2,4-oxadiazol-3-yl)-2,3-dihydro-1H-inden-1-amine dihydrochloride as a white solid. LRMS (ES) m/z 225 (M+H-17).

3. Synthesis of Compound 141:

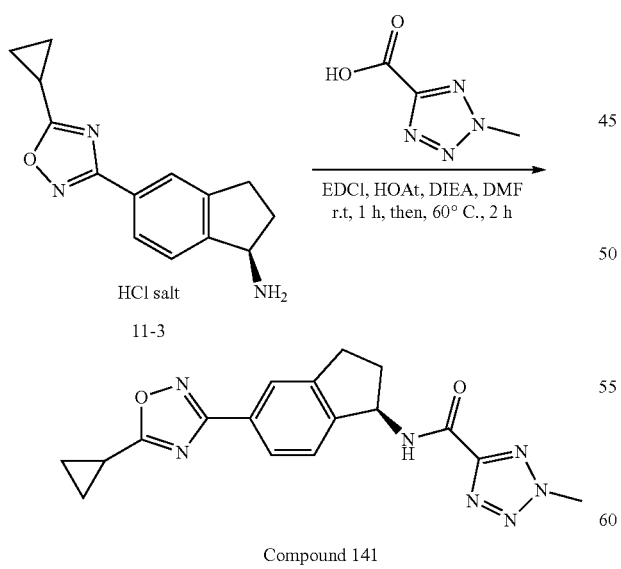

To a solution of 2-methyl-2H-1,2,3,4-tetrazole-5-carboxylic acid (5 g, 39.1 mmol, 2.3 equiv) in DMF (150 mL) were added HOAt (6 g, 44.1 mmol, 2.5 equiv), EDCI (8 g, 41.7 mmol, 2.5 equiv), DIEA (11.3 g, 87.4 mmol, 5.0 equiv), and (1R)-5-(5-cyclopropyl-1,2,4-oxadiazol-3-yl)-2,3-dihydro-1H-inden-1-amine hydrochloride (4.8 g, 17.3 mmol, 1.0 equiv). The mixture was stirred 1 h at room temperature, heated to 60° C. for 4 h, cooled to r.t., diluted with EA (300 mL), washed with water (100 mL) and brine (100 mL) twice, dried over anhydrous sodium sulfate, concentrated under reduced pressure, and purified by silica gel chromatography (DCM/MeOH, 95/5) to give an intermediate product. This intermediate product was then triturated with a mixture of hexane and EA (15/1) to give 4.75 g (88%) of product as a gray solid. This batch was combined with previous batch (obtained 6.5 g from 11.6 g of amine). The mixture was dissolved in DCM (120 mL) and added into n-hexane (1.5 L) dropwise with stirring. The precipitate was collected and dried to afford 10.8 g of (R)—N-(5-(5-cyclopropyl-1,2,4-oxadiazol-3-yl)-2,3-dihydro-1H-inden-1-yl)-2-methyl-2H-tetrazole-5-carboxamide (Compound 141) as an off-white solid. LRMS (ES) m/z 352 (M+H). $^1$H-NMR: (400 MHz, Chloroform-d, ppm) δ 7.95 (s, 1H), 7.91 (d, J=7.9 Hz, 1H), 7.43 (d, J=7.9 Hz, 1H), 7.33 (d, J=8.7 Hz, 1H), 5.78 (q, J=7.9 Hz, 1H), 4.44 (s, 3H), 3.11 (ddd, J=16.2, 8.8, 3.8 Hz, 1H), 2.98 (dt, J=16.2, 8.1 Hz, 1H), 2.75 (dtd, J=12.0, 7.8, 3.9 Hz, 1H), 2.25 (ddd, J=9.6, 7.4, 4.1 Hz, 1H), 2.03 (dq, J=12.9, 8.2 Hz, 1H), 1.45-1.19 (m, 4H).

The following compounds were prepared by methods analogous to the method described for Compound 141:

| Compound No. | LRMS (ES) m/z |
| --- | --- |
| 82 | M + H = 362.1 |
| 90 | M + H = 374.1 |
| 91 | M + H = 374.1 |
| 92 | M + H = 360.1 |
| 93 | M + H = 461.1 |
| 113 | M + H = 325.1 |
| 114 | M + H = 355.1 |
| 115 | M + H = 351.1 |
| 116 | M + H = 353.1 |
| 117 | M + H = 367.1 |
| 125 | M + H = 376.1 |
| 126 | M + H = 369.1 |
| 136 | M + H = 326.1 |
| 144 | M + H = 356.1 |
| 150 | M + H = 378.2 |
| 151 | M + H = 378.2 |
| 152 | M + H = 366.2 |
| 153 | M + H = 364.2 |
| 154 | M + H = 364.2 |
| 164 | M + H = 325.2 |
| 165 | M + H = 361.1 |
| 174 | M + H = 366.2 |
| 175 | M + H = 354.1 |
| 176 | M + H = 365.1 |
| 177 | M + H = 355.1 |
| 178 | M + H = 354.2 |
| 179 | M + H = 368.2 |
| 180 | M + H = 369.1 |
| 181 | M + H = 368.2 |
| 182 | M + H = 368.2 |
| 185 | M + H = 350.1 |
| 186 | M + H = 360.1 |
| 189 | M − H = 360 |
| 194 | M + H = 338 |
| 201 | M + H = 338 |
| 202 | M + H = 325 |
| 203 | M − H = 324 |
| 204 | M + H = 324 |
| 240 | M + H = 338.1 |
| 241 | M + H = 350.1 |
| 242 | M + H = 327.1 |
| 243 | M + H = 329.1 |
| 245 | M + H = 338.1 |
| 246 | M + H = 341.1 |
| 247 | M + H = 341.1 |
| 248 | M + H = 328.1 |
| 249 | M + H = 328.1 |
| 250 | M + H = 341.1 |

-continued

| Compound No. | LRMS (ES) m/z |
|---|---|
| 251 | M + H = 328.1 |
| 281 | M + H = 350.1 |
| 283 | M + H = 308.1 |
| 284 | M + H = 322.1 |
| 285 | M + H = 324.1 |
| 286 | M + H = 294.1 |
| 287 | M + H = 348.1 |
| 288 | M + H = 336.1 |
| 290 | M + H = 338.1 |
| 293 | M + H = 350.1 |
| 294 | M + H = 350.1 |
| 308 | M + H = 277.1 |
| 309 | M + H = 334.1 |
| 310 | M + H = 320.1 |
| 315 | M + H = 339.1 |
| 316 | M + H = 339.1 |
| 317 | M + H = 286.1 |
| 318 | M + H = 286.1 |
| 329 | M + H = 312.2 |
| 330 | M + H = 324.2 |
| 331 | M + H = 367.2 |
| 332 | M + H = 367.2 |
| 336 | M + H = 353.2 |
| 337 | M + H = 341.1 |
| 338 | M + H = 353.2 |
| 351 | M + H = 355.1 |
| 352 | M + H = 369.2 |
| 353 | M + H = 355.1 |
| 354 | M + H = 355.1 |
| 355 | M + H = 355.1 |
| 356 | M + H = 343.2 |
| 357 | M + H = 330.1 |
| 385 | M + H = 339.1 |
| 386 | M + H = 339.1 |
| 387 | M + H = 349.1 |
| 388 | M + H = 351.1 |
| 389 | M + H = 361.1 |
| 390 | M + H = 351.1 |
| 391 | M + H = 353.1 |
| 392 | M + H = 363.1 |
| 393 | M + H = 353.1 |
| 394 | M + H = 352.1 |
| 395 | M + H = 286.1 |
| 396 | M + H = 352.1 |
| 397 | M + H = 354.1 |
| 398 | M + H = 338.1 |
| 399 | M + H = 364.1 |
| 400 | M + H = 324.1 |
| 401 | M + H = 327.1 |
| 405 | M + H = 272.1 |
| 406 | M + H = 298.1 |
| 407 | M + H = 258.1 |
| 408 | M + H = 261.1 |
| 409 | M + H = 365.1 |
| 410 | M + H = 365.1 |
| 411 | M + H = 3641 |
| 412 | M + H = 375.1 |
| 419 | M + H = 284.1 |
| 420 | M + H = 350.1 |
| 435 | M + H = 294.1 |
| 436 | M + H = 308.1 |
| 437 | M + H = 324.1 |
| 438 | M + H = 322.1 |
| 439 | M + H = 320.1 |
| 440 | M + H = 334.1 |
| 442 | M + H = 297.1 |
| 446 | M + H = 275.2 |
| 448 | M + H = 361.1 |
| 449 | M + H = 325.1 |
| 459 | M + H = 364.2 |
| 460 | M + H = 378.2 |
| 465 | M + H = 365.1 |
| 467 | M + H = 369.1 |
| 468 | M + H = 417.1 |
| 469 | M + H = 324.1 |
| 470 | M + H = 380.1 |
| 471 | M + H-tBu = 423.1 |

-continued

| Compound No. | LRMS (ES) m/z |
|---|---|
| 472 | M + H = 382.2 |
| 473 | M + H = 396.1 |
| 475 | M + H = 381.2 |
| 476 | M + H = 396.2 |
| 477 | M + H = 421.1 |
| 478 | M + H = 457.1 |
| 479 | M + H = 436.2 |
| 480 | M + H = 436.2 |
| 481 | M + H = 422.2 |
| 484 | M + H = 379.2 |
| 485 | M + H = 398.2 |
| 486 | M + H = 354.1 |
| 487 | M + H = 310.1 |
| 488 | M + H = 338.1 |
| 489 | M + H = 336.1 |
| 490 | M + H = 340.1 |
| 491 | M + H = 313.1 |
| 492 | M + H = 410.1 |
| 493 | M + H = 411.1 |
| 495 | M + H = 410.1 |
| 496 | M + H = 368.1 |
| 497 | M + H = 368.1 |
| 498 | M + H = 368.1 |
| 499 | M + H = 340.1 |
| 500 | M + H = 430.1 |
| 501 | M + H = 416.1 |
| 502 | M + H = 326.1 |
| 503 | M + H = 442.2 |
| 504 | M + H = 412.2 |
| 505 | M + H = 352.1 |
| 506 | M + H = 394.1 |
| 507 | M + H = 408.2 |
| 508 | M + H = 412.1 |
| 509 | M + H = 368.1 |
| 510 | M + H = 394.2 |
| 511 | M + H = 396.2 |
| 512 | M + H = 398.2 |
| 513 | M + H = 408.2 |
| 514 | M + H = 371.1 |
| 518 | M + H = 370.1 |
| 519 | M + H = 357.1 |
| 520 | M + H = 354.1 |
| 521 | M + H = 380.2 |
| 522 | M + H = 382.1 |
| 523 | M + H = 384.1 |
| 524 | M + H = 394.2 |
| 553 | M + H = 398.2 |
| 555 | M + H = 407.1 |
| 556 | M + H = 367.1 |
| 557 | M + H = 365.1 |
| 558 | M + H = 365.1 |
| 559 | M + H = 395.1 |
| 560 | M + H = 409.1 |
| 561 | M + H = 339.1 |
| 563 | M + H = 352.1 |
| 564 | M + H = 339.1 |
| 565 | M + H = 339.1 |
| 566 | M + H = 339.1 |
| 567 | M + H = 352.2 |
| 568 | M + H = 352.1 |
| 569 | M + H = 339.1 |
| 570 | M + H = 352.3 |
| 571 | M + H = 352 |
| 573 | M + H = 396.2 |
| 574 | M + H = 396.2 |
| 575 | M + H = 396.2 |
| 578 | M + H = 385.2 |
| 579 | M + H = 338 |
| 580 | M + H = 352 |
| 581 | M + H = 325 |
| 582 | M + H = 325 |
| 583 | M + H = 325 |
| 584 | M + H = 325 |
| 585 | M + H = 325 |
| 586 | M + H = 325 |
| 587 | M + H = 325 |
| 589 | M + H = 365.1 |

-continued

| Compound No. | LRMS (ES) m/z |
|---|---|
| 590 | M + H = 355.2 |
| 591 | M + H = 348.2 |
| 592 | M + H = 338 |
| 593 | M + H = 325 |
| 594 | M + H = 349 |
| 595 | M + H = 355 |
| 596 | M + H = 396.2 |
| 597 | M + H = 382.2 |
| 598 | M + H = 410.2 |
| 599 | M + H = 410.2 |
| 600 | M + H = 408.2 |
| 601 | M + H = 394.2 |
| 602 | M + H = 382.2 |
| 603 | M + H = 351.1 |
| 604 | M + H = 351.2 |
| 605 | M + H = 395.2 |
| 606 | M + H = 409.2 |
| 607 | M + H = 368.2 |
| 608 | M + H = 368.2 |
| 609 | M + H = 354 |
| 610 | M + H = 393.2 |
| 611 | M + H = 396.2 |
| 612 | M + H = 396.2 |
| 613 | M + H = 368.1 |
| 614 | M + H = 409.1 |
| 615 | M + H = 326 |
| 616 | M + H = 339 |
| 617 | M + H = 340 |
| 618 | M + H = 340 |
| 619 | M + H = 356 |
| 620 | M + H = 359 |
| 621 | M + H = 353 |
| 622 | M + H = 339 |
| 623 | M + H = 335 |
| 624 | M + H = 335 |
| 625 | M + H = 349 |
| 626 | M + H = 349 |
| 627 | M + H = 349 |
| 628 | M + H = 335 |
| 629 | M + H = 349 |
| 630 | M + H = 336 |
| 631 | M + H = 350 |
| 632 | M + H = 336 |
| 633 | M + H = 340 |
| 634 | M + H = 341 |
| 635 | M + H = 355 |
| 636 | M + H = 339 |
| 637 | M + H = 350 |
| 638 | M + H = 341 |
| 639 | M + H = 393 |
| 640 | M + H = 355 |
| 641 | M + H = 379.2 |
| 642 | M + H = 349 |
| 643 | M + H = 350 |
| 644 | M + H = 387.1 |
| 645 | M + H = 391.2 |
| 646 | M + H = 354.2 |
| 647 | M + H = 369.1 |
| 648 | M + H = 392.1 |
| 650 | M + H = 350 |
| 655 | M + H = 361.2 |
| 656 | M + H = 417.1 |
| 657 | M + H = 360.2 |
| 658 | M + H = 362.1 |
| 660 | M + H = 363.1 |
| 661 | M + H = 386 |
| 662 | M + H = 404 |
| 663 | M + H = 404 |
| 664 | M + H = 387 |
| 665 | M + H = 387 |
| 666 | M + H = 387 |
| 667 | M + H = 387 |
| 668 | M + H = 380 |
| 669 | M + H = 380 |
| 670 | M + H = 398 |
| 671 | M + H = 398 |
| 672 | M + H = 381 |

-continued

| Compound No. | LRMS (ES) m/z |
|---|---|
| 673 | M + H = 381 |
| 674 | M + H = 363 |
| 675 | M + H = 404 |
| 676 | M + H = 377 |
| 677 | M + H = 361 |
| 678 | M + H = 374 |
| 679 | M + H = 361 |
| 680 | M + H = 377 |
| 681 | M + H = 361 |
| 682 | M + H = 415 |
| 683 | M + H = 372 |
| 684 | M + H = 387 |
| 685 | M + H = 407 |
| 686 | M + H = 404 |
| 687 | M + H = 372 |
| 688 | M + H = 355 |
| 689 | M + H = 355 |
| 690 | M + H = 355 |
| 691 | M + H = 356 |
| 692 | M + H = 356 |
| 693 | M + H = 371 |
| 694 | M + H = 398 |
| 695 | M + H = 398 |
| 696 | M + H = 371 |
| 697 | M + H = 356 |
| 698 | M + H = 356 |
| 702 | M + H = 338 |
| 703 | M + H = 326 |
| 704 | M + H = 368 |
| 705 | M + H = 336 |
| 706 | M + H = 350 |
| 715 | M + H = 378.1 |
| 716 | M + H = 371 |
| 720 | M + H = 377 |
| 721 | M + H = 379 |
| 722 | M + H = 394 |
| 725 | M + H = 364 |
| 726 | M + H = 364 |
| 728 | M + H = 394 |
| 729 | M + H = 394 |
| 730 | M + H = 371 |
| 731 | M + H = 401 |
| 732 | M + H = 371 |
| 733 | M + H = 401 |
| 734 | M + H = 366 |
| 735 | M + H = 366 |
| 736 | M − H = 394 |
| 737 | M + H = 396 |
| 738 | M + H = 367 |

Example 12

Synthesis of Compound 142

1. Synthesis of Intermediate 12-2:

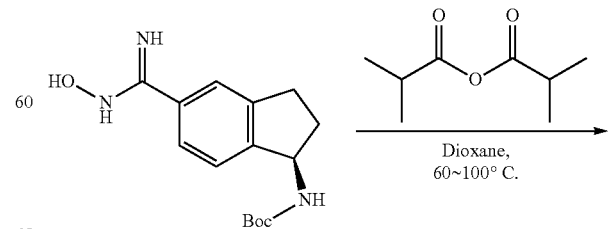

5-4

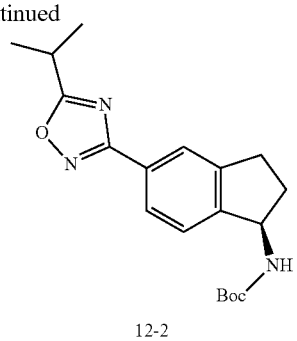

12-2

To a solution of tert-butyl N-[(1R)-5-(N-hydroxycarbamimidoyl)-2,3-dihydro-1H-inden-1-yl]carbamate (50.0 g, 172 mmol, 1.00 equiv) in dioxane (500 mL) was added 2-methylpropanoyl 2-methylpropanoate (28.5 g, 180 mmol, 1.1 equiv). The mixture was stirred at 60° C. for 1 h followed by 100° C. for 6 h, cooled to r.t., diluted with EA (500 mL), washed with water (300 mL) and brine (500 mL), dried over anhydrous sodium sulfate, concentrated under reduced pressure, and purified by silica gel chromatography (EA/PE, 1/9) to give 47 g (79%) of tert-butyl N-[(1R)-5-[5-(propan-2-yl)-1,2,4-oxadiazol-3-yl]-2,3-dihydro-1H-inden-1-yl]carbamate as a white solid.

2. Synthesis of Intermediate 12-3:

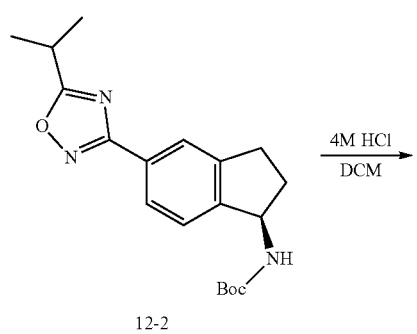

12-2

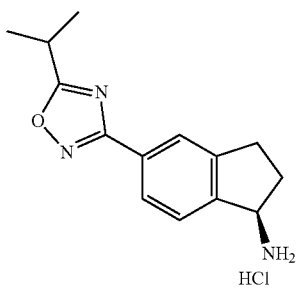

12-3

To a solution of tert-butyl N-[(1R)-5-[5-(propan-2-yl)-1,2,4-oxadiazol-3-yl]-2,3-dihydro-1H-inden-1-yl]carbamate (21.2 g, 61.7 mmol, 1.0 equiv) in DCM (400 mL) was added hydrogen chloride (4 M in dioxane, 155 mL, 10.0 equiv). The mixture was stirred at r.t. overnight and the solid was collected and dried to afford 16.3 g (83%) of (1R)-5-[5-(propan-2-yl)-1,2,4-oxadiazol-3-yl]-2,3-dihydro-1H-inden-1-amine hydrochloride as a white solid.

3. Synthesis of Compound 142:

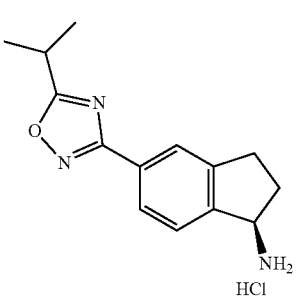 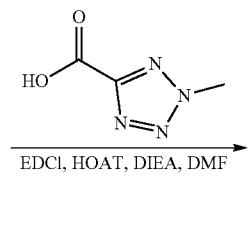

12-3

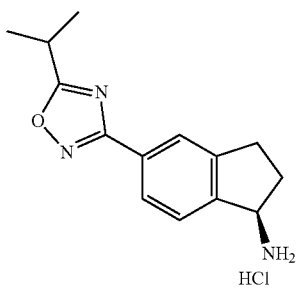

Compound 142

To a solution of 2-methyl-2H-1,2,3,4-tetrazole-5-carboxylic acid (37.8 g, 295 mmol, 1.5 equiv) in DMF (500 mL) were added HOAt (40.1 g, 295 mmol, 1.5 equiv), EDCI (56.7 g, 296 mmol, 1.50 equiv), DIEA (102 g, 785 mmol, 4.0 equiv), and (1R)-5-[5-(propan-2-yl)-1,2,4-oxadiazol-3-yl]-2,3-dihydro-1H-inden-1-amine hydrochloride (55.0 g, 197 mmol, 1.0 equiv). The mixture was stirred at 40° C. for 2 h and combined with 4 other batches made using the same procedure (3.6, 35.7, 197 and 197 mmol scale of SM amine) for further work up. To the combined solutions was added water. The precipitate was collected by filtration, washed with more water, and re-dissolved in DCM. The DCM solution was washed with water and saturated NH₄Cl solution, dried over anhydrous sodium sulfate, and concentrated under reduced pressure to afford 210 g of (R)—N-(5-(5-isopropyl-1,2,4-oxadiazol-3-yl)-2,3-dihydro-1H-inden-1-yl)-2-methyl-2H-tetrazole-5-carboxamide (Compound 142) as an off-white solid. LRMS (ES) m/z 354 (M+H). ¹H-NMR: (300 MHz, Chloroform-d, ppm) δ 7.97 (d, J=1.4 Hz, 1H), 7.93 (dd, J=7.9, 1.1 Hz, 1H), 7.42 (d, J=7.9 Hz, 1H), 7.30 (d, J=8.8 Hz, 1H), 5.77 (q, J=7.9 Hz, 1H), 4.42 (s, 3H), 3.26 (hept, J=7.0 Hz, 1H), 3.10 (ddd, J=16.2, 8.7, 3.9 Hz, 1H), 2.97 (dt, J=16.1, 8.0 Hz, 1H), 2.83-2.65 (m, 1H), 2.02 (dt, J=13.0, 8.1 Hz, 1H), 1.44 (d, J=7.0 Hz, 6H).

Example 13

Synthesis of Compound 143

1. Synthesis of Intermediate 13-2:

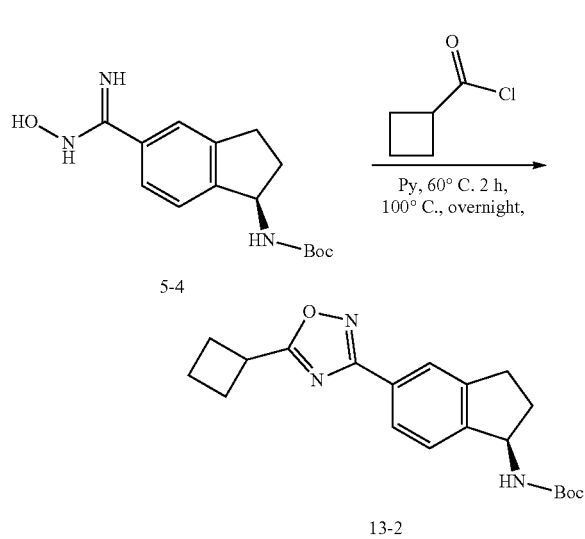

To a solution of tert-butyl N-[(1R)-5-(N-hydroxycarbamimidoyl)-2,3-dihydro-1H-inden-1-yl]carbamate (4 g, 13.7 mmol, 1.0 equiv) in pyridine (80 mL) was added cyclobutanecarbonyl chloride (2 g, 16.9 mmol, 1.2 equiv). The mixture was heated to 60° C. for 3 h and then 100° C. overnight. The reaction was then cooled to r.t., concentrated under reduced pressure, and purified by silica gel chromatography (EA/PE, 5/95) to give 3.3 g (68%) of tert-butyl N-[(1R)-5-(5-cyclobutyl-1,2,4-oxadiazol-3-yl)-2,3-dihydro-1H-inden-1-yl]carbamate as an off-white solid.

2. Synthesis of Intermediate 13-3:

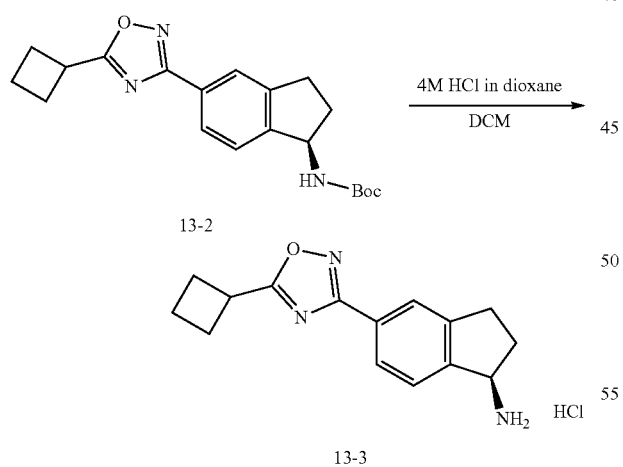

To a solution of tert-butyl N-[(1R)-5-(5-cyclobutyl-1,2,4-oxadiazol-3-yl)-2,3-dihydro-1H-inden-1-yl]carbamate (3 g, 8.4 mmol, 1.0 equiv) in dichloromethane (60 mL) was added hydrogen chloride (4 M in dioxane, 21 mL, 10.0 equiv). The mixture was stirred at r.t. overnight and the precipitate was collected and dried to give 2 g (81%) of (1R)-5-(5-cyclobutyl-1,2,4-oxadiazol-3-yl)-2,3-dihydro-1H-inden-1-amine hydrochloride as a white solid.

3. Synthesis of Compound 143:

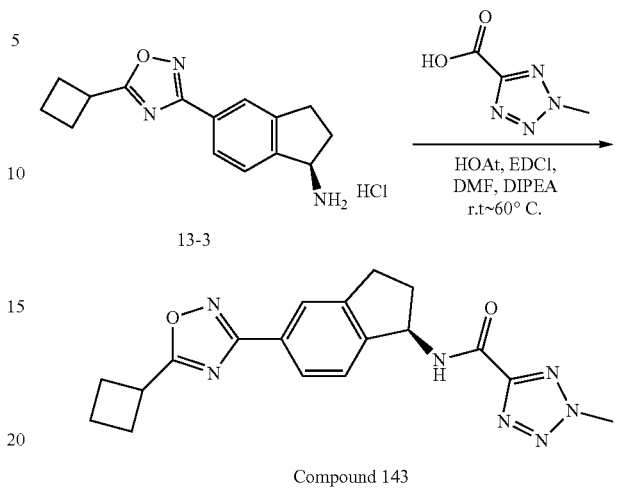

Compound 143

To a solution of 2-methyl-2H-1,2,3,4-tetrazole-5-carboxylic acid (1.0 g, 7.8 mmol, 1.3 equiv) in DMF (100 mL) were added (1R)-5-(5-cyclobutyl-1,2,4-oxadiazol-3-yl)-2,3-dihydro-1H-inden-1-amine hydrochloride (1.8 g, 6.2 mmol, 1.0 equiv), HOAt (1.5 g, 11.0 mmol, 1.8 equiv), EDCI (2.1 g, 11.0 mmol, 1.8 equiv), and DIEA (4.0 g, 31.0 mmol, 5.0 equiv). The mixture was stirred for 30 min and EA (100 mL) and water (100 mL) were added. The aqueous layer was extracted with EA (50 mL) three times. The combined organic layers were dried over anhydrous sodium sulfate, concentrated under reduced pressure, and purified by a C18 column with ACN:H$_2$O (35:65) as eluent to give 946 mg (42%) of (R)—N-(5-(5-cyclobutyl-1,2,4-oxadiazol-3-yl)-2,3-dihydro-1H-inden-1-yl)-2-methyl-2H-tetrazole-5-carboxamide (Compound 143) as a white solid. LRMS (ES) m/z 366.0 (M+H). $^1$H-NMR: (300 MHz, Methanol-d$_4$, ppm): δ 8.01-7.88 (m, 2H), 7.44 (d, J=7.9 Hz, 1H), 5.74 (t, J=8.0 Hz, 1H), 4.45 (s, 3H), 3.97-3.79 (m, 1H), 3.26-3.09 (m, 1H), 3.00 (dd, J=16.1, 8.4 Hz, 1H), 2.75-2.45 (m, 5H), 2.32-2.05 (m, 3H).

Example 14

Synthesis of Compound 183

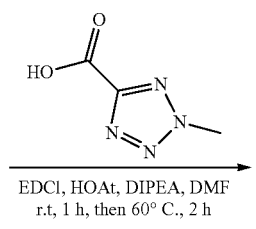

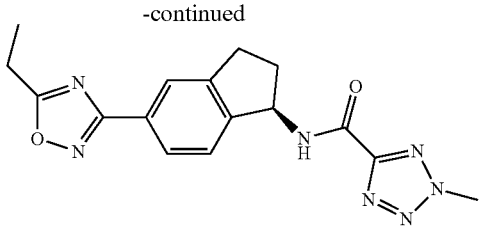

Compound 183

To a solution of 2-methyl-2H-1,2,3,4-tetrazole-5-carboxylic acid (5 g, 39.0 mmol, 1.00 equiv) in DMF (150 mL) were added HOAt (9.6 g, 70.5 mmol, 1.8 equiv), EDCI (13.5 g, 70.4 mmol, 1.0 equiv), DIEA (19.2 g, 148.2 mmol, 3.80 equiv), and a solution of (1R)-5-(5-ethyl-1,2,4-oxadiazol-3-yl)-2,3-dihydro-1H-inden-1-amine (9.0 g, 39.0 mmol, 1.0 equiv) in DMF (50 mL). The mixture was stirred at 60° C. for 3 h, cooled to room temperature, and poured into DCM (1 L) and water (1 L). The aqueous layer was extracted with DCM (500 mL) five times. The combined organic layers were washed with saturated NH$_4$Cl solution (500 mL) five times, dried over anhydrous sodium sulfate, concentrated under reduced pressure, and purified by silica gel chromatography (EA/PE, 2/3) to give 8.7 g (66%) of (R)—N-(5-(5-ethyl-1,2,4-oxadiazol-3-yl)-2,3-dihydro-1H-inden-1-yl)-2-methyl-2H-tetrazole-5-carboxamide (Compound 183) as a white solid. LRMS (ES) m/z 340 (M+H). $^1$H-NMR: 1H NMR (300 MHz, DMSO-d6) δ 9.42 (d, J=8.4 Hz, 1H), 7.89-7.76 (m, 2H), 7.34 (d, J=7.9 Hz, 1H), 5.58 (q, J=8.2 Hz, 1H), 4.41 (s, 3H), 3.14-2.80 (m, 4H), 2.47-2.38 (m, 1H), 2.13 (dq, J=12.5, 8.7 Hz, 1H), 1.31 (t, J=7.5 Hz, 3H).

Example 15

Synthesis of Compound 184

1. Synthesis of Intermediate 15-2:

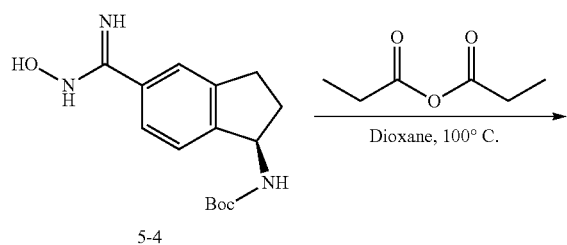

To a solution of tert-butyl N-[(1R)-5-(N-hydroxycarbamimidoyl)-2,3-dihydro-1H-inden-1-yl] carbamate (16 g, 54.9 mmol, 1.0 equiv) in dioxane (300 mL) was added propanoyl propanoate (8.4 g, 64.5 mmol, 1.2 equiv). The mixture was stirred at 105° C. for 8 h, cooled to r.t., concentrated under reduced pressure, and purified by silica gel chromatography (EA/PE, 1/9) to give 17.5 g (97%) of tert-butyl N-[(1R)-5-(5-ethyl-1,2,4-oxadiazol-3-yl)-2,3-dihydro-1H-inden-1-yl] carbamate as a white solid.

2. Synthesis of Intermediate 15-3:

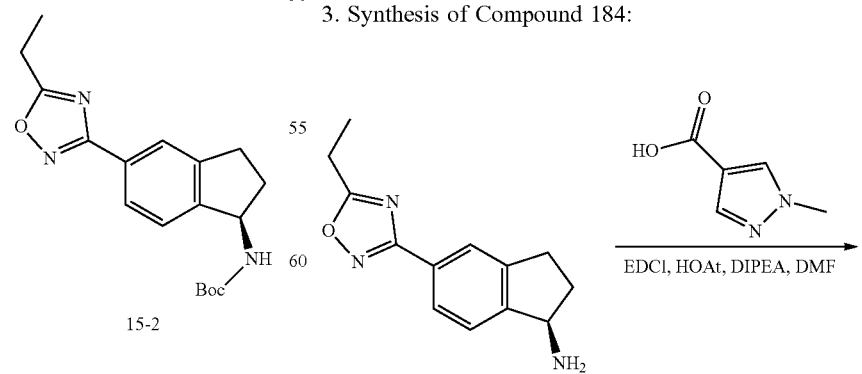

To a solution of tert-butyl N-[(1R)-5-(5-ethyl-1,2,4-oxadiazol-3-yl)-2,3-dihydro-1H-inden-1-yl]carbamate (17.6 g, 53.4 mmol, 1.0 equiv) in DCM (120 mL) was added TFA (24 mL). The mixture was stirred at room temperature overnight and concentrated under reduced pressure. The mixture was then poured into ethanol (50 mL) and water (5 mL) and the pH was adjusted to 12 with sodium hydroxide solution (2 N). The mixture was then extracted with dichloromethane (200 mL) three times. The combined organic layers were dried over anhydrous sodium sulfate and concentrated under reduced pressure to give 11.2 g of (1R)-5-(5-ethyl-1,2,4-oxadiazol-3-yl)-2,3-dihydro-1H-inden-1-amine as a brown oil.

3. Synthesis of Compound 184:

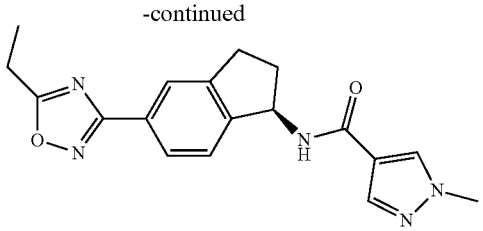

Compound 184

To a solution of 1-methyl-1H-pyrazole-4-carboxylic acid (6.1 g, 48.4 mmol, 1.0 equiv) in DMF (300 mL) were added DIEA (12.6 g, 97.5 mmol, 2.0 equiv), HOAt (19.8 g, 145.8 mmol, 3.0 equiv), and EDCI (28 g, 146.1 mmol, 3.0 equiv). The mixture was stirred for 15 min, and (1R)-5-(5-ethyl-1,2,4-oxadiazol-3-yl)-2,3-dihydro-1H-inden-1-amine (11.2 g, 48.9 mmol, 1.0 equiv) was then added. The mixture was then stirred for 3 h, diluted with DCM, washed with NH$_4$Cl solution three times, dried over sodium sulfate, concentrated under reduced pressure, and purified by silica gel chromatography (EA/PE, 74/26) to give an intermediate product. The intermediate product was triturated with a mixture of EA and PE (1/10) to afford 14.5 g (88%) of (R)—N-(5-(5-ethyl-1,2,4-oxadiazol-3-yl)-2,3-dihydro-1H-inden-1-yl)-1-methyl-1H-pyrazole-4-carboxamide (Compound 184) as a white solid. LRMS (ES) m/z 338 (M+H). $^1$H-NMR: (DMSO, 300 MHz, ppm): δ 8.41 (1H, d, J=8.4 Hz), 8.16 (1H, s), 7.91-7.79 (3H, m), 7.34 (1H, d, J=7.9 Hz), 5.53 (1H, q, J=8.3 Hz), 3.84 (3H, s), 3.13-2.81 (4H, m), 2.44 (1H, dd, J=7.9, 4.7 Hz), 1.95 (1H, m), 1.33 (3H, t, J=7.5 Hz).

Example 16

Synthesis of Compound 196

1. Synthesis of Intermediate 16-2:

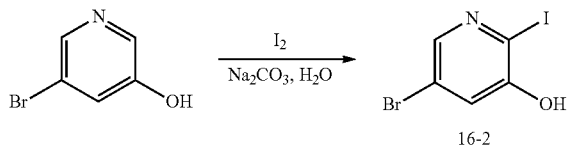

To a solution of 5-bromopyridin-3-ol (25 g, 144 mmol, 1.0 equiv) in water (500 mL) were added sodium carbonate (45.9 g, 434 mmol, 3.0 equiv) and I2 (36.6 g, 144 mmol, 1.00 equiv) in portions for a period of 3 h. The mixture was stirred for 1 h and brought to pH 7 with hydrogen chloride (2 N). The resulting precipitate was collected and dried to afford 39 g (91%) of 5-bromo-2-iodopyridin-3-ol as a white solid.

2. Synthesis of Intermediate 16-3:

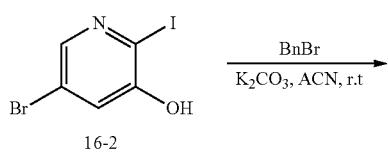

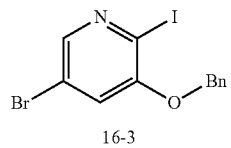

To a solution of 5-bromo-2-iodopyridin-3-ol (39.5 g, 132 mmol, 1.1 equiv) in ACN (600 mL) was added potassium carbonate (54.5 g, 396 mmol, 3.0 equiv) and BnBr (23.6 g, 138 mmol, 1.05 equiv) dropwise with stirring at 0° C. The mixture was stirred at r.t. for 5.5 h, cooled to 0° C., and quenched with the dropwise addition of water at 0° C. The solids were collected by filtration and triturated with 5% EA in PE (100 mL) to afford 44.4 g (86%) of 3-(benzyloxy)-5-bromo-2-iodopyridine as a white solid.

3. Synthesis of Intermediate 16-4:

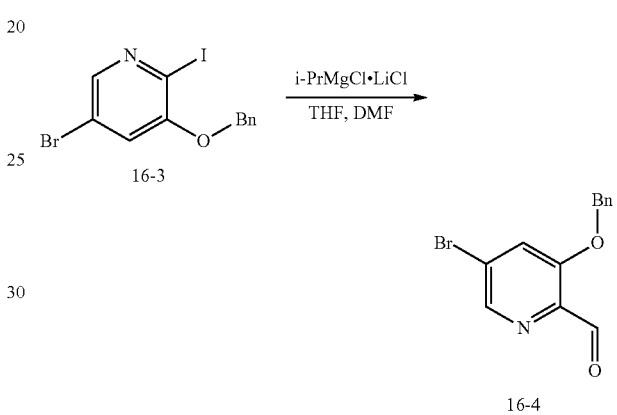

To a solution of 3-(benzyloxy)-5-bromo-2-iodopyridine (40 g, 103 mmol, 1.0 equiv) in THF (1 L) cooled to −20° C. was added i-PrMgCl.LiCl (1.3 M in THF, 87 mL, 103 mmol, 1.1 equiv) dropwise. The mixture was stirred at −20° C. for 2 h and DMF (11.2 g, 154 mmol, 1.5 equiv) was added. The mixture was stirred for 2 h at r.t., cooled back down to −20° C., and quenched with aqueous NH$_4$Cl solution. The resulting solution was extracted with EA (500 mL) twice. The combined organic layers were washed with brine (500 mL) twice, dried over anhydrous sodium sulfate, concentrated under reduced pressure, and purified by silica gel chromatography (EA/PE, 1/10) to give 28 g (93%) of 3-(benzyloxy)-5-bromopyridine-2-carbaldehyde as an off-white solid.

4. Synthesis of Intermediate 16-5:

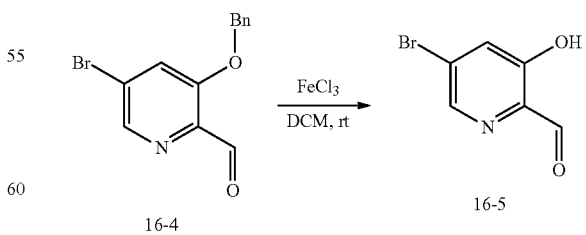

To a solution of 3-(benzyloxy)-5-bromopyridine-2-carbaldehyde (27 g, 92.4 mmol, 1.0 equiv) in DCM (600 mL) cooled to 0° C. was added FeCl$_3$ (30 g, 185 mmol, 2.00 equiv). The mixture was stirred at r.t. for 2 h, poured into water (1 L), and extracted with DCM (500 mL) three times. The combined organic layers were washed with brine (500 mL) three times, dried over anhydrous sodium sulfate, concentrated under reduced pressure, and purified by silica gel chromatography (EA/PE, 1/10) to give 11 g (59%) of 5-bromo-3-hydroxypyridine-2-carbaldehyde as a light yellow solid.

5. Synthesis of Intermediate 16-6:

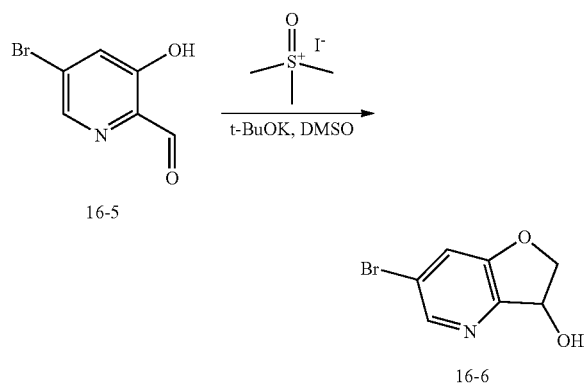

To a solution of 5-bromo-3-hydroxypyridine-2-carbaldehyde (11 g, 54.5 mmol, 1.0 equiv) in DMSO (200 mL) were added trimethyl(oxo)-6-sulfanylium iodide (30 g, 136 mmol, 2.5 equiv) and t-BuOK (15.3 g, 136 mmol, 2.5 equiv) in portions for a period of 20 min. The mixture was stirred at r.t. for 1 h, cooled to 0° C., and quenched with saturated NH₄Cl solution (300 mL) at 0° C. The resulting solution was extracted with EA (100 mL) four times. The combined organic layers were washed with brine, dried over anhydrous sodium sulfate, concentrated under reduced pressure, and purified by silica gel chromatography (EA/PE, 1/3) to give 7.6 g (65%) of 6-bromo-2H,3H-furo[3,2-b]pyridin-3-ol as a yellow solid.

6. Synthesis of Intermediate 16-7:

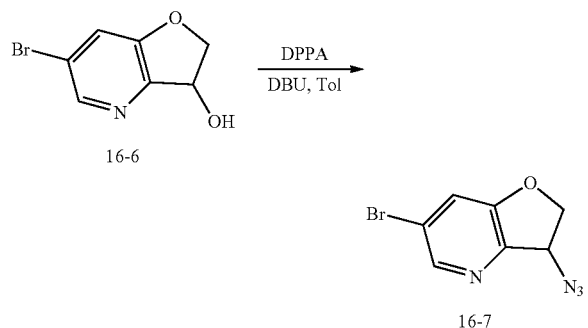

To a solution of 6-bromo-2H,3H-furo[3,2-b]pyridin-3-ol (4.1 g, 18.8 mmol, 1.0 equiv) in toluene (85 mL) cooled to 0° C. were added DPPA (5.7 g, 20.6 mmol, 1.1 equiv) and DBU (3.1 g, 20.6 mmol, 1.1 equiv) dropwise for a period of 20 min. After stirring at r.t. for 1 h, the resulting solution was diluted with EA (150 mL), washed with water (100 mL) twice and brine (100 mL), dried over anhydrous sodium sulfate, concentrated under reduced pressure, and purified by silica gel chromatography (EA/PE, 1/9) to give 1.6 g (35%) of 3-azido-6-bromo-2H,3H-furo[3,2-b]pyridine as colorless oil.

7. Synthesis of Intermediate 16-8:

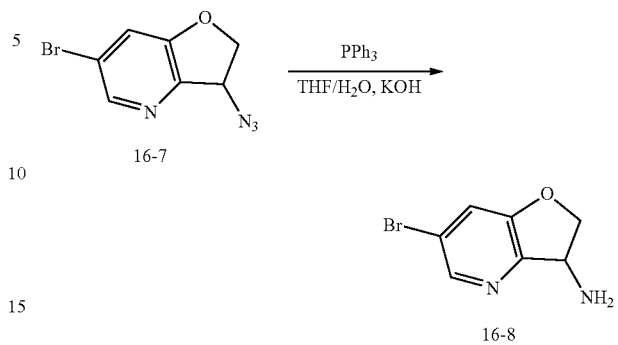

To a solution of 3-azido-6-bromo-2H,3H-furo[3,2-b]pyridine (1.0 g, 4.2 mmol, 1.0 equiv) in THF (22 mL) were added PPh₃ (1.3 g, 5.0 mmol, 1.2 equiv) and a solution of potassium hydroxide (583 mg, 10.4 mmol, 2.5 equiv) in water (5.5 mL). The mixture was stirred at r.t for 1 h followed by 55° C. for 4 h, cooled to r.t., and diluted with sodium hydroxide (2N, 20 mL). The resulting solution was extracted with EA (50 mL) three times. The combined organic layers were dried over anhydrous sodium sulfate, concentrated under reduced pressure, and purified by silica gel chromatography (EA) to give 1.0 g of 6-bromo-2H,3H-furo[3,2-b]pyridin-3-amine as yellow oil.

8. Synthesis of Intermediate 16-9:

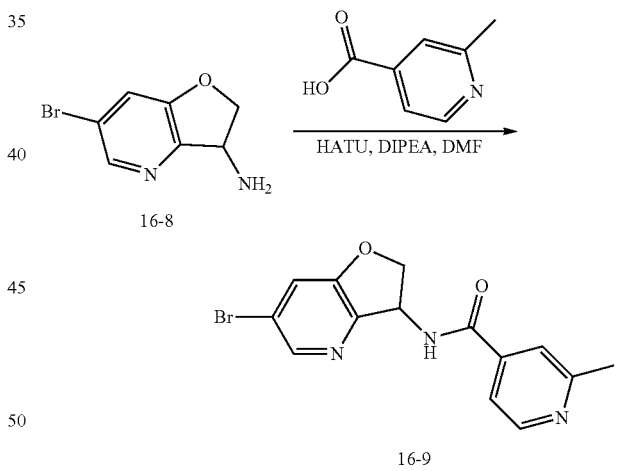

To a solution of 2-methylpyridine-4-carboxylic acid (306 mg, 2.3 mmol, 1.3 equiv) in DMF (5 mL) were added HATU (981 mg, 2.6 mmol, 1.5 equiv) and DIEA (666 mg, 5.2 mmol, 3.0 equiv). The mixture was stirred for 5 min before 6-bromo-2H,3H-furo[3,2-b]pyridin-3-amine (370 mg, 1.7 mmol, 1.0 equiv) was added. The mixture was then stirred for 2 h and poured into EA and water. The aqueous layer was extracted with EA (100 mL) twice. The combined organic layers were washed with brine (100 mL), dried over anhydrous sodium sulfate, concentrated under reduced pressure, and purified by Prep-TLC (MeOH/DCM, 1/10) to give 440 mg (77%) of N-[6-bromo-2H,3H-furo[3,2-b]pyridin-3-yl]-2-methylpyridine-4-carboxamide as a yellow solid.

9. Synthesis of Intermediate 16-10:

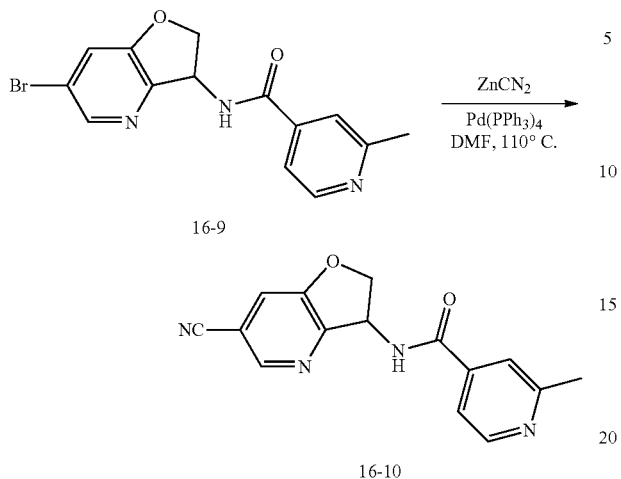

16-9

16-10

To a solution of N-[6-bromo-2H,3H-furo[3,2-b]pyridin-3-yl]-2-methylpyridine-4-carboxamide (700 mg, 2.1 mmol, 1.0 equiv) in DMF (20 mL) were added Zn(CN)$_2$ (243 mg, 2.1 mmol, 1.0 equiv) and Pd(PPh$_3$)$_4$ (242 mg, 0.2 mmol, 0.1 equiv). The mixture was stirred at 110° C. overnight, cooled to r.t., diluted with EA (80 mL), washed with water (40 mL) twice and brine (40 mL), dried over anhydrous sodium sulfate, concentrated under reduced pressure, and purified by silica gel chromatography (MeOH/DCM, 1/15) to give 400 mg (68%) of N-[6-cyano-2H,3H-furo[3,2-b]pyridin-3-yl]-2-methylpyridine-4-carboxamide as a light yellow solid.

10. Synthesis of Intermediate 16-11:

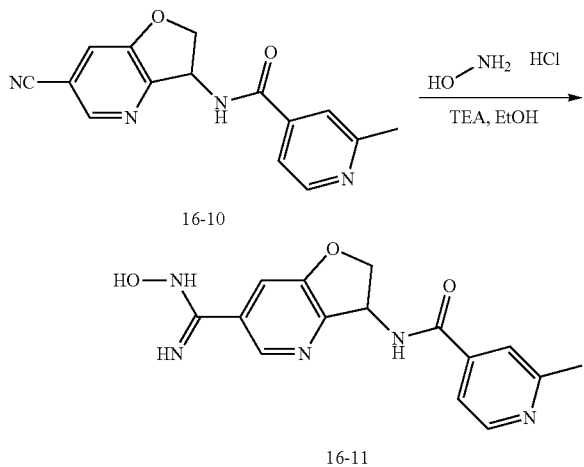

16-10

16-11

To a solution of N-[6-cyano-2H,3H-furo[3,2-b]pyridin-3-yl]-2-methylpyridine-4-carboxamide (50 mg, 0.18 mmol, 1.00 equiv) in ethanol (5 mL) were added NH$_2$OH.HCl (25 mg, 0.36 mmol, 2.3 equiv) and TEA (55 mg, 0.54 mmol, 3.05 equiv). The mixture was stirred 75° C. for 2 h and concentrated under reduced pressure to afford 50 mg of N-[6-(N-hydroxycarbamimidoyl)-2H,3H-furo[3,2-b]pyridin-3-yl]-2-methylpyridine-4-carboxamide as a yellow solid.

11. Synthesis of Intermediate 16-12:

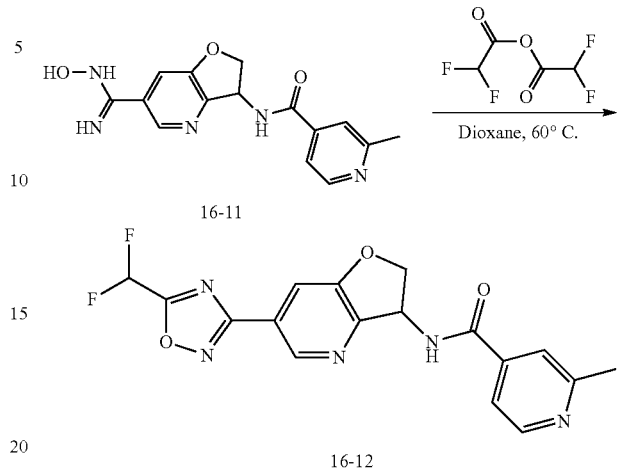

16-11

16-12

To a solution of N-[6-(N-hydroxycarbamimidoyl)-2H,3H-furo[3,2-b]pyridin-3-yl]-2-methylpyridine-4-carboxamide (300 mg, 0.96 mmol, 1.0 equiv) in dioxane (10 mL) was added 2,2-difluoroacetyl 2,2-difluoroacetate (416 mg, 2.39 mmol, 2.5 equiv). The mixture was stirred at 60° C. for 1.5 h, concentrated under reduced pressure, and purified by Flash-Prep-HPLC with the following conditions: (Combi-Flash-1): Column, C18 silica gel; mobile phase, water (0.5% NH$_4$HCO$_3$)/ACN=95/5 increasing to water (0.5% NH$_4$HCO$_3$)/ACN=75/25 within 10 min; Detector, UV 254 nm. This purification afforded 120 mg (30%) of N-[6-[5-(difluoromethyl)-1,2,4-oxadiazol-3-yl]-2H,3H-furo[3,2-b]pyridin-3-yl]-2-methylpyridine-4-carboxamide as a white solid. LRMS (ES) m/z 374 (M+H). $^1$H-NMR: (400 MHz, Methanol-d$_4$, ppm): δ 8.82 (d, J=1.7 Hz, 1H), 8.54 (d, J=5.3 Hz, 1H), 7.87 (d, J=1.7 Hz, 1H), 7.69 (s, 1H), 7.64-7.57 (m, 1H), 7.24 (t, J=51.8 Hz, 1H), 5.86 (dd, J=9.2, 5.7 Hz, 1H), 5.05 (t, J=9.6 Hz, 1H), 4.60 (dd, J=10.1, 5.7 Hz, 1H), 2.59 (s, 3H).

12. Synthesis of Compound 196:

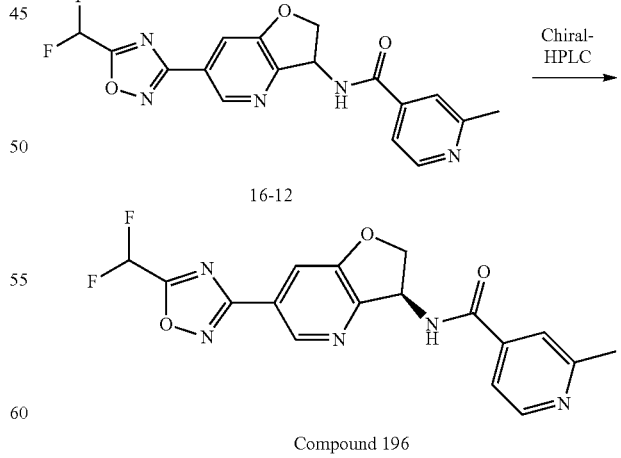

16-12

Compound 196

N-[6-[5-(difluoromethyl)-1,2,4-oxadiazol-3-yl]-2H,3H-furo[3,2-b]pyridin-3-yl]-2-methylpyridine-4-carboxamide (90 mg, 0.24 mmol, 1.00 equiv) was purified by Chiral-Prep-HPLC with the following conditions: (Prep-HPLC-009): Column, CHIRALPAK IA, 2.12*15 cm, 5 μm; mobile phase, Hexane and ethanol (hold 50.0% ethanol in 13 min); Detector, UV 220/254 nm. This purification resulted in 37.4 mg (42%) of (S)—N-(6-(5-(difluoromethyl)-1,2,4-oxadiazol-3-yl)-2,3-dihydrofuro[3,2-b]pyridin-3-yl)-2-methylisonicotinamide (Compound 196) as a white solid. LRMS (ES) m/z 374 (M+H). $^{1}$H-NMR: (400 MHz, Methanol-$d_4$, ppm): δ 8.82 (d, J=1.7 Hz, 1H), 8.54 (d, J=5.3 Hz, 1H), 7.87 (d, J=1.7 Hz, 1H), 7.69 (s, 1H), 7.64-7.57 (m, 1H), 7.24 (t, J=51.8 Hz, 1H), 5.86 (dd, J=9.2, 5.7 Hz, 1H), 5.05 (t, J=9.6 Hz, 1H), 4.60 (dd, J=10.1, 5.7 Hz, 1H), 2.59 (s, 3H).

The following compounds were prepared by methods analogous to the method described for Compound 196:

| Compound No. | LRMS (ES) m/z |
| --- | --- |
| 187 | M + H = 338 |
| 188 | M + H = 338 |
| 196 | M + H = 374 |

Example 17

Synthesis of Compound 217

1. Synthesis of Intermediate 17-2:

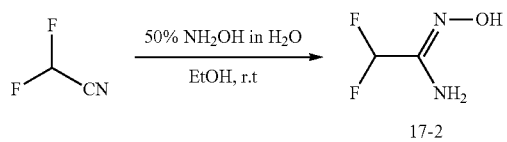 [SMILES: N#CC(F)F ; N/C(=N\O)C(F)F]

To a solution of 2,2-difluoroacetonitrile (25 g, 325 mmol, 1.00 equiv) in ethanol (100 mL) cooled to −10° C. was added NH$_2$OH (23 g, 349 mmol, 1.1 equiv, 50% wt. in water). The mixture was stirred at r.t. overnight, concentrated under reduced pressure, and azeotroped twice with THF to afford 37 g of (Z)-2,2-difluoro-N'-hydroxy acetimidamide as a green liquid.

2. Synthesis of Intermediate 17-3:

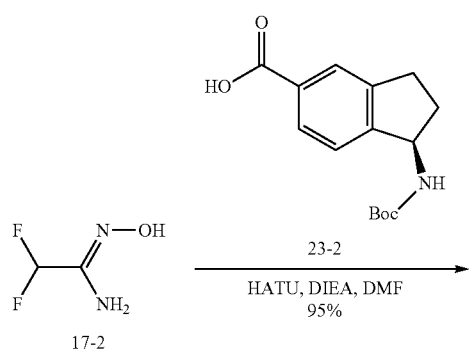

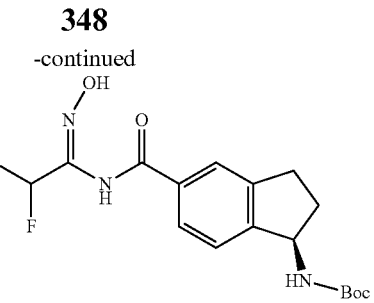

To a solution of (1R)-1-[[(tert-butoxy)carbonyl]amino]-2,3-dihydro-1H-indene-5-carboxylic acid (2.0 g, 7.2 mmol, 1.0 equiv) in DMF (20 mL) were added DIEA (2.8 g, 21.7 mmol, 3.0 equiv), HATU (4.11 g, 10.8 mmol, 1.50 equiv), and (Z)-2,2-difluoro-N'-hydroxyacetimidamide (2.38 g, 21.6 mmol, 3.0 equiv). The mixture was stirred for 2 h and poured into a saturated NH$_4$Cl solution (200 mL). The resulting solution was extracted with DCM (200 mL) twice. The combined organic layers were concentrated under reduced pressure and purified by silica gel chromatography (EA/PE, 3/2) to afford 2.52 g (95%) of tert-butyl N-[(1R)-5-[[(1Z)-2,2-difluoro-1-(hydroxyimino)ethyl]carbamoyl]-2,3-dihydro-1H-inden-1-yl]carbamate as a brown solid.

3. Synthesis of Intermediate 17-4:

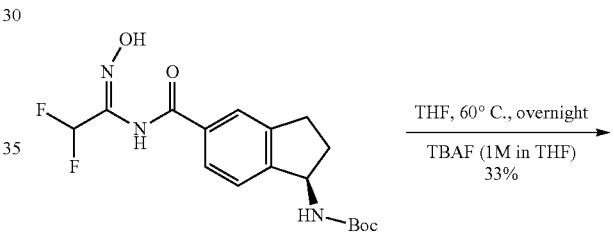

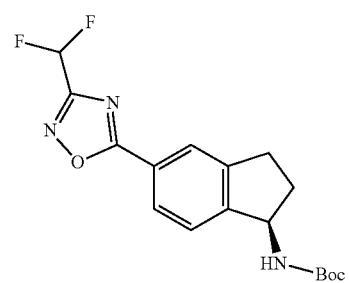

To a solution of tert-butyl N-[(1R)-5-[[(1Z)-2,2-difluoro-1-(hydroxyimino)ethyl]carbamoyl]-2,3-dihydro-1H-inden-1-yl]carbamate (1.53 g, 4.1 mmol, 1.0 equiv) in THF (70 mL) was added TBAF (1 M in THF, 8.3 mL, 2.0 equiv). The mixture was stirred at 60° C. overnight, cooled to r.t., concentrated under reduced pressure, and purified by silica gel chromatography (EA/PE, 1/3) to afford 490 mg (33%) of tert-butyl N-[(1R)-5-[3-(difluoromethyl)-1,2,4-oxadiazol-5-yl]-2,3-dihydro-1H-inden-1-yl]carbamate as a light orange solid.

4. Synthesis of Intermediate 17-5:

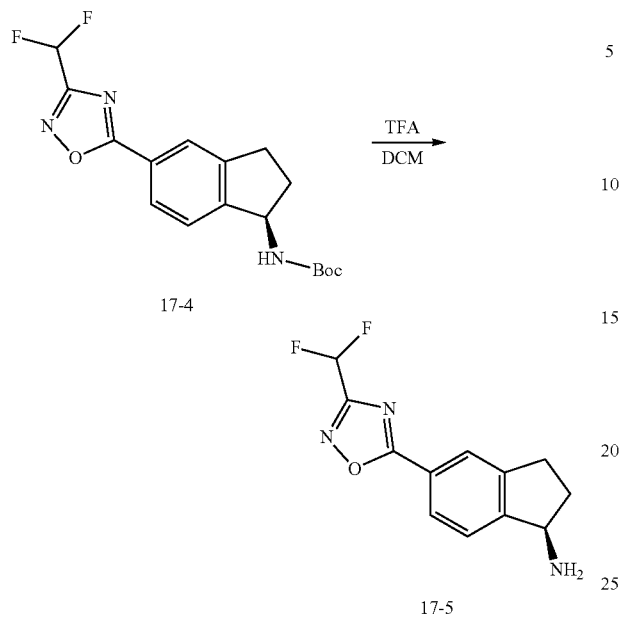

To a solution of tert-butyl N-[(1R)-5-[3-(difluoromethyl)-1,2,4-oxadiazol-5-yl]-2,3-dihydro-1H-inden-1-yl]carbamate (490 mg, 1.4 mmol, 1.0 equiv) in DCM (5 mL) was added TFA (1 mL). The mixture was stirred for 1 h, concentrated under reduced pressure, and redissolved in THF and water. The pH of the solution was adjusted to 12 with NaOH (2 N) and extracted with EA four times. The combined organic layers were dried over anhydrous $Na_2SO_4$ and concentrated under vacuum to afford 500 mg of (1R)-5-[3-(difluoromethyl)-1,2,4-oxadiazol-5-yl]-2,3-dihydro-1H-inden-1-amine as a green oil.

5. Synthesis of Compound 217

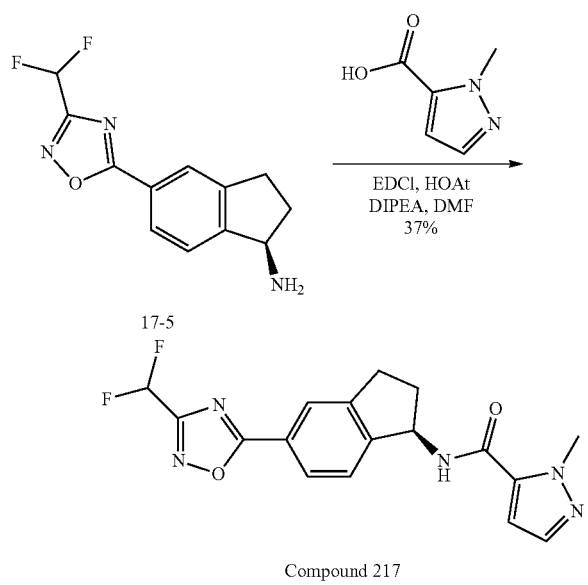

To a solution of 1-methyl-1H-pyrazole-5-carboxylic acid (30 mg, 0.24 mmol, 1.0 equiv) in DMF (4 mL) were added DIEA (62 mg, 0.48 mmol, 2.00 equiv), EDCI (138 mg, 0.72 mmol, 3.00 equiv), and HOAt (98 mg, 0.72 mmol, 3.00 equiv). The mixture was stirred for 5 min and (1R)-5-[3-(difluoromethyl)-1,2,4-oxadiazol-5-yl]-2,3-dihydro-1H-inden-1-amine (60 mg, 0.24 mmol, 1.0 equiv) was added. The mixture was stirred for 1 h, filtered to remove the solid precipitate, and purified by Prep-HPLC with the following conditions: (2#-AnalyseHPLC-SHIMADZU(HPLC-10)): Column, XBridge Shield RP18 OBD Column, 5 μm, 19*150 mm; mobile phase, water (0.05% $NH_3H_2O$) and ACN (35.0% ACN up to 55.0% in 8 min); Detector, UV 220 nm. This purification afforded 31.4 mg (37%) of (R)—N-(5-(3-(difluoromethyl)-1,2,4-oxadiazol-5-yl)-2,3-dihydro-1H-inden-1-yl)-1-methyl-1H-pyrazole-5-carboxamide (Compound 217) as a white solid. LRMS (ES) m/z 360 (M+H). $^1$H-NMR: ($CD_3OD$, 300 MHz, δ ppm): δ 8.10-8.07 (2H, m), 7.56-7.48 (2H, m), 7.25-6.90 (1H, t, J=52.2), 6.84 (1H, s), 5.72-5.67 (1H, t, J=8.1), 4.19 (3H, s), 3.25-3.10 (1H, m), 3.07-2.99 (1H, m), 2.75-2.59 (1H, m), 2.21-2.02 (1H, m).

The following compounds were prepared by methods analogous to the method described for Compound 217:

| Compound No. | LRMS (ES) m/z |
| --- | --- |
| 213 | M + H = 374 |
| 215 | M + H = 361 |
| 216 | M + H = 362 |

Example 18

Synthesis of Compound 222

1. Synthesis of Intermediate 18-2:

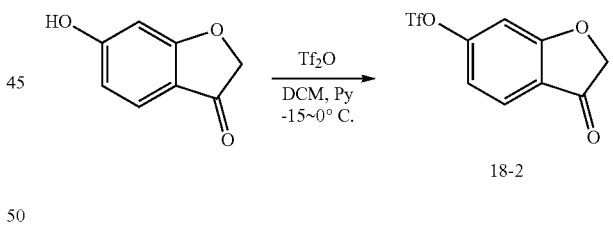

To solution of 6-hydroxy-2,3-dihydro-1-benzofuran-3-one (100 g, 666.7 mmol, 1.0 equiv) in DCM (2.5 L) was added pyridine (158 g, 2.0 mol, 3.0 equiv). The mixture was cooled to −10° C. and a solution of (trifluoromethane)sulfonyl trifluoromethanesulfonate (300 g, 1.1 mol, 1.6 equiv) in DCM (0.5 L) was added dropwise over a period of 2 h. The mixture was then stirred at 0-4° C. for 3 h, quenched with water (1 L), and extracted with dichloromethane (300 mL) three times. The combined organic layers were washed with citric acid (1 N, 500 mL) twice, saturated sodium bicarbonate (500 mL) and brine (500 mL), dried over anhydrous sodium sulfate, and concentrated under reduced pressure to give 194.5 g of 3-oxo-2,3-dihydro-1-benzofuran-6-yl trifluoromethanesulfonate as a black solid. The black solid was used for the next step without further purification. LRMS (ES) m/z 285 (M+H).

2. Synthesis of Intermediate 18-3:

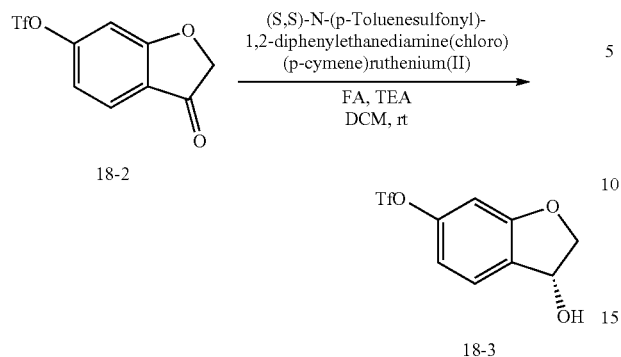

To formic acid (107.3 g, 2.3 mol, 3.5 equiv) in a RB flask cooled to 0° C. was added TEA (76 g, 751.1 mmol, 2.3 equiv) dropwise with stirring for a period of 30 min. To this mixture were added a solution of 3-oxo-2,3-dihydro-1-benzofuran-6-yl trifluoromethanesulfonate (194.5 g, 666.7 mmol, 1.0 equiv) in DCM (4 L) and (S,S)—N-(p-toluenesulfonyl)-1-2-diphenylethanediamine(chloro)(p-cymene)ruthenium(II) (6.45 g, 10.1 mmol, 0.015 equiv). The mixture was stirred overnight and an additional amount of (S,S)—N-(p-toluenesulfonyl)-1-2-diphenylethanediamine(chloro)(p-cymene)ruthenium(II) (2 g, 3.2 mmol, 0.05 equiv) was added. The mixture was stirred for an additional 1 day, poured into water, stirred for 30 min, and filtered to remove the solid byproduct. The aqueous layer was extracted with DCM (1 L) twice. The combined organic layers were washed with brine (1 L), dried over anhydrous sodium sulfate, and concentrated under reduced pressure to give 208 g of (3R)-3-hydroxy-2,3-dihydro-1-benzofuran-6-yl trifluoromethanesulfonate as dark brown oil. The dark brown oil was used in the next step without further purification. LRMS (ES) m/z 267 (M+H).

3. Synthesis of Intermediate 18-4:

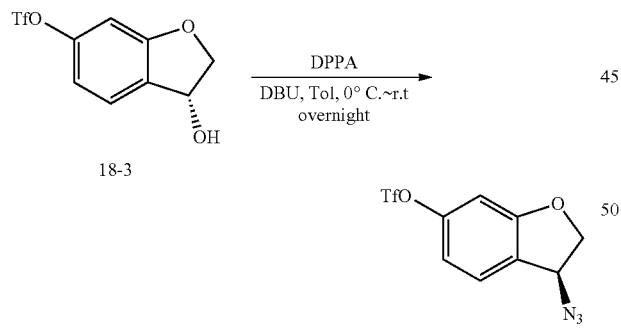

To a solution of (3R)-3-hydroxy-2,3-dihydro-1-benzofuran-6-yl trifluoromethanesulfonate (208 g, 665.5 mmol, 1.0 equiv) in toluene (2.5 L) cooled to 0° C. were added DPPA (228.8 g, 831.9 mmol, 1.25 equiv) and DBU (151.7 g, 998.249 mmol, 1.50 equiv) dropwise over a period of 50 min. The mixture was stirred overnight, poured into EA (2 L) and water (1 L), stirred for 30 min, and extracted with EA (500 mL) three times. The combined organic layers were washed with brine, dried over anhydrous sodium sulfate, concentrated under reduced pressure, and purified by silica gel chromatography (EA/PE, 5/95) to give 162 g of (3S)-3-azido-2,3-dihydro-1-benzofuran-6-yl trifluoromethanesulfonate as a yellow oil.

4. Synthesis of Intermediate 18-5:

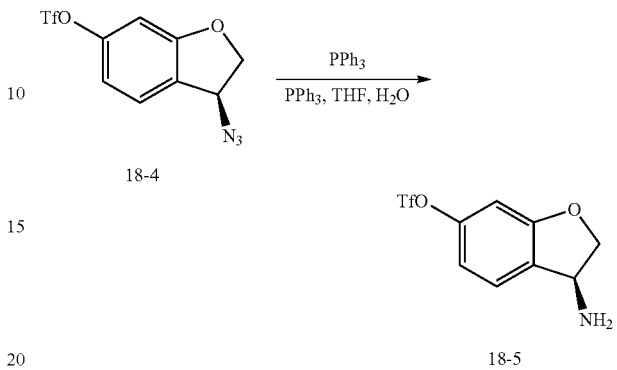

To a solution of (3S)-3-azido-2,3-dihydro-1-benzofuran-6-yl trifluoromethanesulfonate (162.4 g, 525.2 mmol, 1.0 equiv) in THF (1.5 L) was added PPh$_3$ (165.2 g, 629.9 mmol, 1.2 equiv) slowly. The mixture was stirred for 30 min, poured into water (300 mL), heated to 50° C. for 4 h, diluted with EA (800 mL), washed with water (300 mL) three times, dried over anhydrous sodium sulfate, and concentrated under reduced pressure to give 338.5 g of (3S)-3-amino-2,3-dihydro-1-benzofuran-6-yl trifluoromethanesulfonate as a dark red oil, which was used for next step without further purification. LRMS (ES) m/z 267 (M+H-17).

5. Synthesis of Intermediate 18-6:

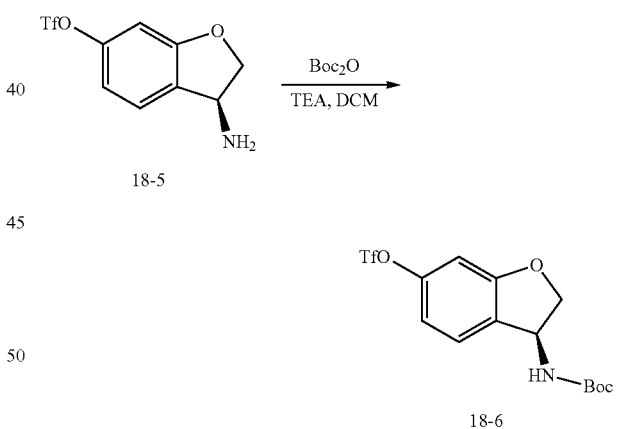

To a solution of (3S)-3-amino-2,3-dihydro-1-benzofuran-6-yl trifluoromethanesulfonate (338 g, dark red oil from previous step, 0.52 mol, 1.0 equiv) in DCM (3 L) cooled to 0° C. were added TEA (158 g, 1.6 mol, 3.0 equiv) and a solution of Boc$_2$O (228 g, 1.0 mol, 2.0 equiv) in DCM (500 mL) dropwise. The mixture was stirred at r.t. overnight, washed with water (2 L) twice, dried over anhydrous sodium sulfate, concentrated under reduced pressure, and purified by silica gel chromatography (DCM/PE, 4/6) to give 101.2 g of tert-butyl N-[(3S)-6-[(trifluoromethane)sulfonyloxy]-2,3-dihydro-1-benzofuran-3-yl]carbamate as a white solid. LRMS (ES) m/z 328 (M+H-56).

6. Synthesis of Intermediate 18-7:

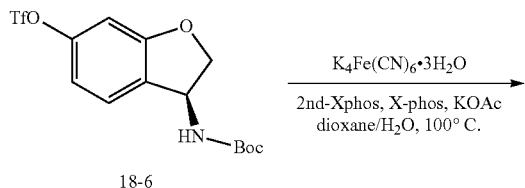

To a solution of tert-butyl N-[(3S)-6-[(trifluoromethane)sulfonyloxy]-2,3-dihydro-1-benzofuran-3-yl]carbamate (62.3 g, 162.5 mmol, 1.0 equiv) in dioxane (620 mL) were added K$_4$Fe(CN)$_6$.3H$_2$O (34.3 g, 81.3 mmol, 0.5 equiv), 2nd Generation XPhos Pre-catalyst (1.9 g, 2.4 mmol, 0.015 equiv), X-Phos (1.2 g, 2.4 mmol, 0.015 equiv), KOAc (31.9 g, 325.0 mmol, 2.0 equiv), and water (620 mL) under nitrogen. The mixture was stirred at 100° C. for 4 h, cooled to r.t., and combined with other batches (100 g of triflate SM in total). The resulting solution was poured into EA (1 L) and brine (500 mL) and the solids were removed by filtration. The aqueous layer was extracted with ethyl acetate (600 mL) three times. The combined organic layers were washed with brine (600 mL), dried over anhydrous sodium sulfate, concentrated under reduced pressure, and purified by silica gel chromatography (EA/PE, 15/85) to give an intermediate product. The intermediate product was purified with a mixture of EtOH and water (3/2) to give 45 g (23% over 6 steps) of tert-butyl N-[(3S)-6-cyano-2,3-dihydro-1-benzofuran-3-yl]carbamate as a white solid after filtration and drying. LRMS (ES) m/z 261 (M+H). Chiral_SFC: 98.6% ee., CHIRALPAK AD-H (4.6*100 mm, 5 um), 7. Synthesis of Intermediate 18-8:

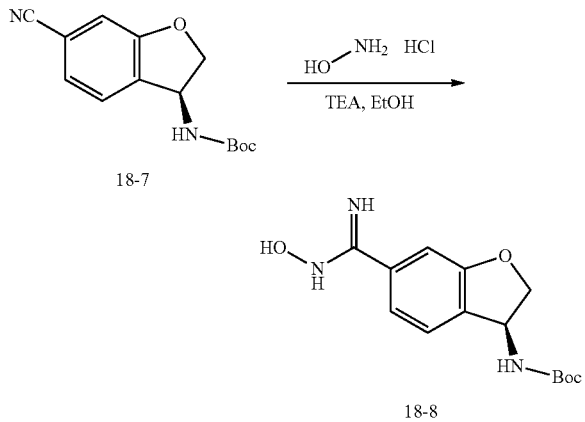

To a solution of tert-butyl N-[(3S)-6-cyano-2,3-dihydro-1-benzofuran-3-yl]carbamate (11 g, 42.3 mmol, 1.0 equiv) in ethanol (240 mL) were added hydroxylamine hydrochloride (5.8 g, 84.0 mmol, 2.0 equiv) and TEA (10.7 g, 105.7 mmol, 2.5 equiv). The mixture was stirred at 55° C. for 4 h, cooled to r.t., combined with the previous batch (300 mg, 1.2 mmol of nitrile SM), and concentrated under reduced pressure. The mixture was dissolved in EA (500 mL), washed twice with water (200 mL) and brine (200 mL), dried over anhydrous sodium sulfate, and concentrated under reduced pressure to give 12.8 g of tert-butyl N-[(3S)-6-(N-hydroxycarbamimidoyl)-2,3-dihydro-1-benzofuran-3-yl]carbamate as a white solid. The white solid product was used directly for next step without further purification. LRMS (ES) m/z 294 (M+H).

8. Synthesis of Intermediate 18-9:

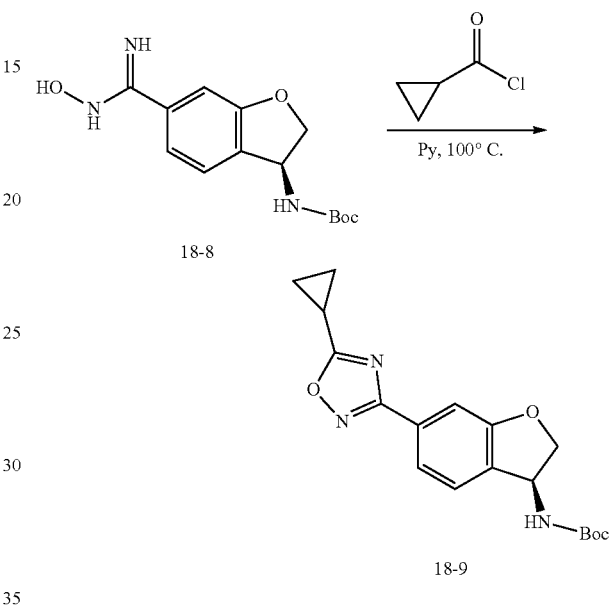

To a solution of tert-butyl N-[(3S)-6-(N-hydroxycarbamimidoyl)-2,3-dihydro-1-benzofuran-3-yl]carbamate (16 g, 54.6 mmol, 1.0 equiv) in pyridine (200 mL) was added cyclopropanecarbonyl chloride (6.3 g, 59.8 mmol, 1.1 equiv). The mixture was stirred at 100° C. for 2 h, cooled to r.t., concentrated under reduced pressure, dissolved in EA (500 mL), and poured into saturated NH$_4$Cl solution (500 mL). The aqueous layer was extracted with EA (500 mL) four times and the combined organic layers were washed with NH$_4$Cl solution (500 mL) four times, dried over anhydrous sodium sulfate, concentrated under reduced pressure, and purified by silica gel chromatography (EA/PE, 1/3) to give 17 g (91%) tert-butyl N-[(3S)-6-(5-cyclopropyl-1,2,4-oxadiazol-3-yl)-2,3-dihydro-1-benzofuran-3-yl]carbamate as a light yellow solid. LRMS (ES) m/z 288 (M+H-56).

9. Synthesis of Intermediate 18-10:

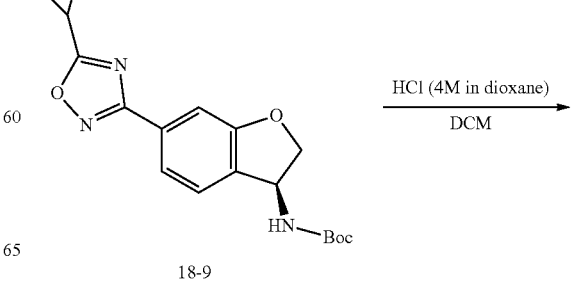

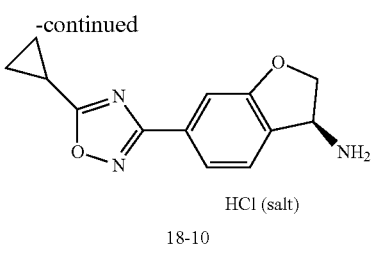

18-10 HCl (salt)

To a solution of tert-butyl N-[(3S)-6-(5-cyclopropyl-1,2,4-oxadiazol-3-yl)-2,3-dihydro-1-benzofuran-3-yl]carbamate (17 g, 49.5 mmol, 1.0 equiv) in DCM (500 mL) was added hydrogen chloride (4M in dioxane, 125 mL, 10.0 equiv). The mixture was stirred at r.t. overnight and diluted with a mixture of EA and PE (1.1 L, 1/10). The solids were collected and dried to give 13.5 g (97%) of (3S)-6-(5-cyclopropyl-1,2,4-oxadiazol-3-yl)-2,3-dihydro-1-benzofuran-3-amine hydrochloride as a white solid. LRMS (ES) m/z 227 (M+H-17).

10. Synthesis of Compound 222:

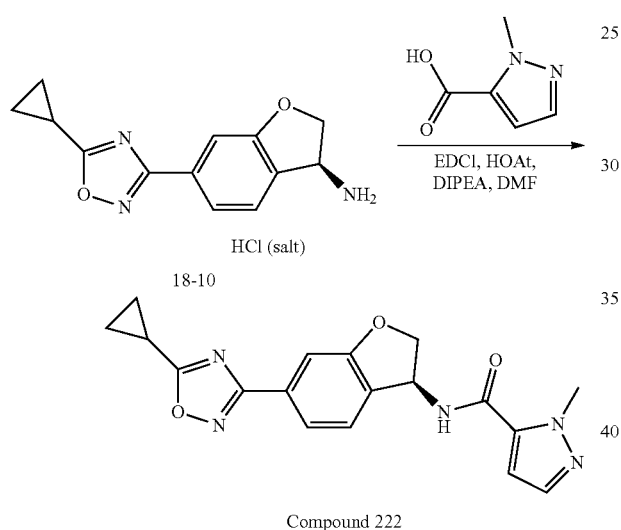

Compound 222

To a solution of 1-methyl-1H-pyrazole-5-carboxylic acid (8.2 g, 64.9 mmol, 1.3 equiv) in DMF (200 mL) were added (3S)-6-(5-cyclopropyl-1,2,4-oxadiazol-3-yl)-2,3-dihydro-1-benzofuran-3-amine hydrochloride (14 g, 50.1 mmol, 1.0 equiv), HOAt (10.9 g, 79.9 mmol, 1.6 equiv), EDCI (15.4 g, 80.1 mmol, 1.6 equiv), and DIEA (32.3 g, 249.5 mmol, 5.0 equiv). The mixture was stirred at r.t. overnight and poured into DCM (200 mL) and water (200 mL). The aqueous layer was extracted with DCM (200 mL) five times. The combined organic layers were washed with saturated NH$_4$Cl solution (200 mL) six times, dried over anhydrous sodium sulfate, concentrated under reduced pressure, and triturated with ACN to give 12.2 g (69%) of (S)—N-(6-(5-cyclopropyl-1,2,4-oxadiazol-3-yl)-2,3-dihydrobenzofuran-3-yl)-1-methyl-1H-pyrazole-5-carboxamide (Compound 222) as a white solid. LRMS (ES) m/z 352 (M+H). $^1$H-NMR: (300 MHz, DMSO-d$_6$, ppm) δ 9.12 (d, J=7.6 Hz, 1H), 7.56 (dd, J=7.8, 1.4 Hz, 1H), 7.51 (d, J=7.8 Hz, 1H), 7.46 (d, J=2.1 Hz, 1H), 7.38 (d, J=1.3 Hz, 1H), 6.92 (d, J=2.1 Hz, 1H), 5.82 (td, J=8.3, 5.1 Hz, 1H), 4.85 (t, J=9.4 Hz, 1H), 4.46 (dd, J=9.7, 5.2 Hz, 1H), 4.10 (s, 3H), 2.41 (tt, J=8.2, 4.8 Hz, 1H), 1.35-1.25 (m, 2H), 1.25-1.15 (m, 2H).

The following compounds were prepared by methods analogous to the method described for Compound 222:

| Compound No. | LRMS (ES) m/z |
| --- | --- |
| 155 | M + H = 340 |
| 156 | M + H = 340 |
| 157 | M + H = 340 |
| 158 | M + H = 340 |
| 159 | M + H = 341 |
| 160 | M + H = 341 |
| 161 | M + H = 341 |
| 162 | M + H = 340 |
| 163 | M + H = 340 |
| 166 | M + H = 327 |
| 167 | M + H = 327 |
| 190 | M + H = 376 |
| 191 | M + H = 376 |
| 192 | M + H = 377 |
| 193 | M + H = 377 |
| 197 | M − H = 362 |
| 198 | M − H = 362 |
| 199 | M − H = 326 |
| 200 | M − H = 326 |
| 205 | M + H = 363 |
| 206 | M + H = 363 |
| 207 | M + H = 376 |
| 208 | M + H = 376 |
| 209 | M + H = 376 |
| 210 | M + H = 376 |
| 211 | M − H = 324 |
| 212 | M − H = 324 |
| 218 | M + H = 362 |
| 219 | M − H = 360 |
| 220 | M + H = 352 |
| 221 | M + H = 352 |
| 223 | M + H = 356 |
| 224 | M + H = 356 |
| 225 | M + H = 370 |
| 226 | M + H = 370 |
| 227 | M + H = 370 |
| 229 | M − H = 338 |
| 230 | M + H = 354 |
| 231 | M + H = 354 |
| 232 | M + H = 366 |
| 233 | M + H = 366 |
| 234 | M − H = 352 |
| 235 | M + H = 354 |
| 236 | M + H = 352 |
| 237 | M + H = 352 |
| 239 | M − H = 338 |
| 262 | M = H = 329 |
| 265 | M + H = 329 |
| 266 | M + H = 343 |
| 267 | M + H = 330 |
| 268 | M + H = 344 |
| 269 | M + H = 343 |
| 270 | M + H = 343 |
| 271 | M + H = 331 |
| 339 | M + H = 341 |
| 340 | M + H = 341 |
| 346 | M + H = 327 |
| 347 | M + H = 327 |
| 402 | M + H = 323 |
| 403 | M + H = 323 |
| 404 | M + H = 348 |
| 441 | M − H-330.1 |
| 443 | M + H = 274.1 |
| 444 | M + H = 296.1 |
| 445 | M + H = 277.1 |
| 447 | M + H = 299.1 |
| 450 | M + Na = 282 |
| 453 | M + H = 363.1 |
| 454 | M + H = 327.1 |
| 455 | M + H = 341 |
| 456 | M + H = 353.1 |
| 457 | M + H = 286 |
| 458 | M + H = 300 |
| 461 | M + H = 300 |
| 462 | M + H = 367 |

357 -continued

| Compound No. | LRMS (ES) m/z |
|---|---|
| 463 | M + H = 353 |
| 464 | M + H = 341 |
| 466 | M + H = 367 |
| 701 | M + H = 388 |
| 707 | M + H = 389 |
| 708 | M + H = 389 |
| 709 | M + H = 389 |
| 710 | M + H = 389 |
| 711 | M + H = 382 |
| 712 | M + H = 382 |
| 713 | M + H = 383 |
| 714 | M + H = 383 |
| 717 | M + H = 352 |
| 718 | M + H = 353 |
| 719 | M + H = 353 |

Example 19

Synthesis of Compound 228

1. Synthesis of Intermediate 19-2:

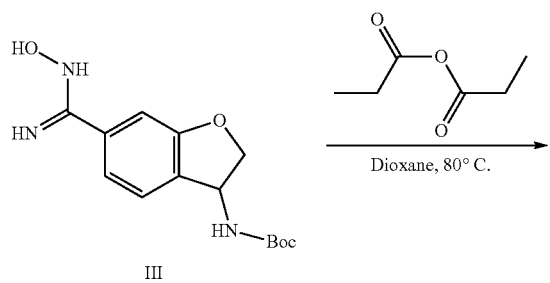

To a solution of tert-butyl N-[6-(N-hydroxycarbamimidoyl)-2,3-dihydro-1-benzofuran-3-yl]carbamate (3 g, 10.2 mmol, 1.0 equiv) in dioxane (30 mL) was added propanoyl propanoate (2.7 g, 20.5 mmol, 2.0 equiv). The mixture was stirred at 80° C. for 7 h, cooled to r.t., and poured into EA (100 mL) and water (100 mL). The aqueous layer was extracted with ethyl acetate (100 mL). The combined organic layers were dried over anhydrous sodium sulfate, concentrated under reduced pressure, and purified by silica gel chromatography (EA/PE, 1/3) to give 1.9 g (56%) of tert-butyl N-[6-(5-ethyl-1,2,4-oxadiazol-3-yl)-2,3-dihydro-1-benzofuran-3-yl]carbamate as an off-white solid.

2. Synthesis of Intermediate 19-3:

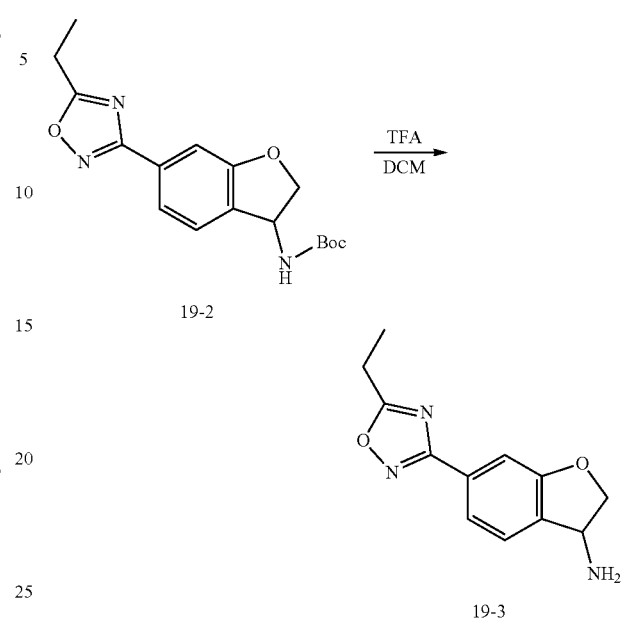

To a solution of tert-butyl N-[6-(5-ethyl-1,2,4-oxadiazol-3-yl)-2,3-dihydro-1-benzofuran-3-yl]carbamate (1.9 g, 5.7 mmol, 1.0 equiv) in DCM (30 mL) was added TFA (5 mL). The mixture was stirred for 1 h, concentrated under reduced pressure, and dissolved in water (100 mL). The pH of the mixture was then adjusted to 7 with a saturated sodium bicarbonate solution and extracted with ethyl acetate (100 mL) twice. The combined organic layers were dried over anhydrous sodium sulfate and concentrated under reduced pressure to give 1.3 g (98%) of 6-(5-ethyl-1,2,4-oxadiazol-3-yl)-2,3-dihydro-1-benzofuran-3-amine as brown oil.

3. Synthesis of Intermediate 19-4:

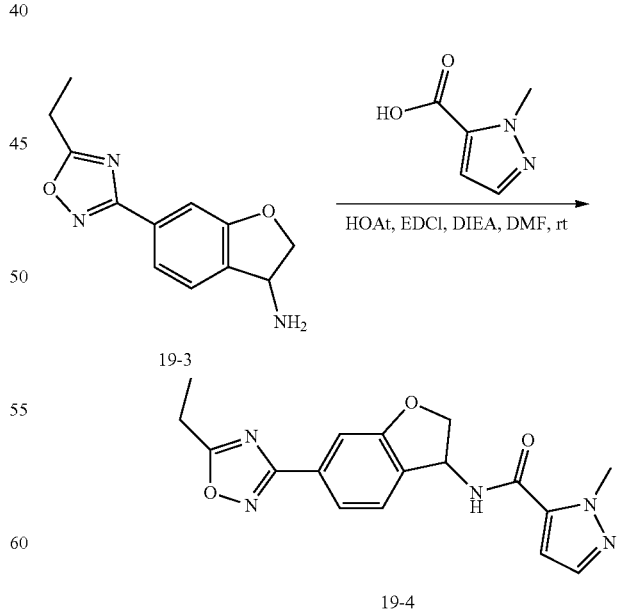

To a solution of 6-(5-ethyl-1,2,4-oxadiazol-3-yl)-2,3-dihydro-1-benzofuran-3-amine (100 mg, 0.4 mmol, 1.0 equiv) in DMF (10 mL) were added 1-methyl-1H-pyrazole-5-carboxylic acid (54.5 mg, 0.4 mmol, 1.0 equiv), HOAt (176.6 mg, 1.0 mmol, 3.0 equiv), EDCI (249 mg, 1.3 mmol, 3.0 equiv), and DIEA (112 mg, 0.9 mmol, 2.0 equiv). The mixture was stirred for 2 h and purified directly by Prep-HPLC with the following conditions: (2#-AnalyseHPLC-SHIMADZU(HPLC-10)): Column, XBridge Shield RP18 OBD Column, 5 um, 19*150 mm; mobile phase, Water (0.05% NH3H2O) and ACN (30.0% ACN up to 50.0% in 8 min); Detector, UV 220 nm. This purification gave 90 mg (61%) of N-[6-(5-ethyl-1,2,4-oxadiazol-3-yl)-2,3-dihydro-1-benzofuran-3-yl]-1-methyl-1H-pyrazole-5-carboxamide as a white solid.

4. Synthesis of Compound 228:

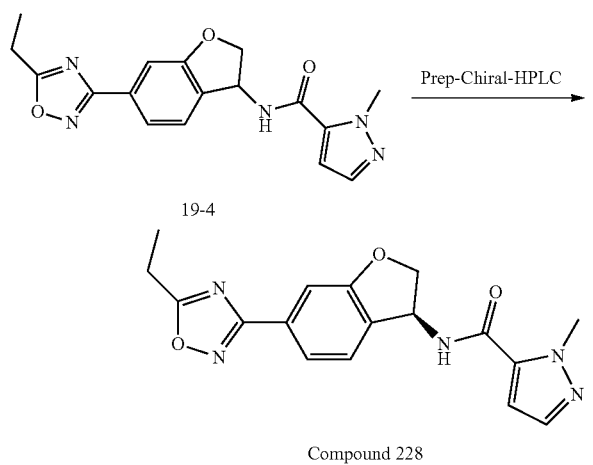

N-[6-(5-ethyl-1,2,4-oxadiazol-3-yl)-2,3-dihydro-1-benzofuran-3-yl]-1-methyl-1H-pyrazole-5-carboxamide (80 mg, 0.2 mmol, 1.0 equiv) was purified by Chiral-Prep-HPLC with the following conditions: (Prep-HPLC-009): Column, CHIRAL ART Cellulose-SB, 250*20 mmI.D.; mobile phase, Hex and ethanol (hold 50.0% ethanol in 9 min); Detector, UV 254/220 nm. This purification afforded 32.7 mg (41%) of (S)—N-(6-(5-ethyl-1,2,4-oxadiazol-3-yl)-2,3-dihydrobenzofuran-3-yl)-1-methyl-1H-pyrazole-5-carboxamide (Compound 228) as a white solid. LRMS (ES) m/z 340 (M+H). $^1$H-NMR: (300 MHz, DMSO-d6, ppm): δ 9.09 (d, J=7.7 Hz, 1H), 7.56 (dd, J=7.7, 1.4 Hz, 1H), 7.48 (d, J=7.8 Hz, 1H), 7.39 (dd, J=13.0, 1.7 Hz, 2H), 6.87 (d, J=2.1 Hz, 1H), 5.78 (td, J=8.2, 5.2 Hz, 1H), 4.80 (t, J=9.3 Hz, 1H), 4.41 (dd, J=9.8, 5.3 Hz, 1H), 4.05 (s, 3H), 2.97 (q, J=7.6 Hz, 2H), 1.30 (t, J=7.6 Hz, 3H).

Example 20

Synthesis of Compound 236

1. Synthesis of Intermediate 20-2:

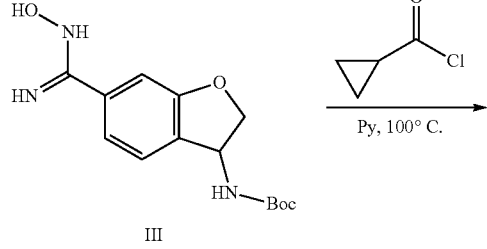

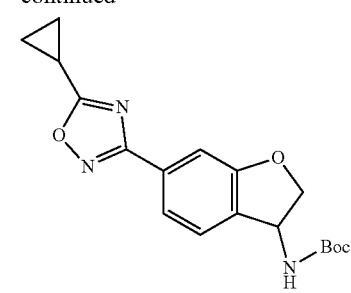

20-2

To a solution of tert-butyl N-[6-(N-hydroxycarbamimidoyl)-2,3-dihydro-1-benzofuran-3-yl]carbamate (3 g, 10.2 mmol, 1.0 equiv) in pyridine (50 mL) was added cyclopropanecarbonyl chloride (1.3 g, 12.4 mmol, 1.2 equiv) under nitrogen. The mixture was stirred at 100° C. for 6 h, cooled to r.t., concentrated under reduced pressure, and purified by silica gel chromatography (EA/PE, 1/9) to give 1.47 g (42%) of tert-butyl N-[6-(5-cyclopropyl-1,2,4-oxadiazol-3-yl)-2,3-dihydro-1-benzofuran-3-yl]carbamate as a white solid.

2. Synthesis of Intermediate 20-3:

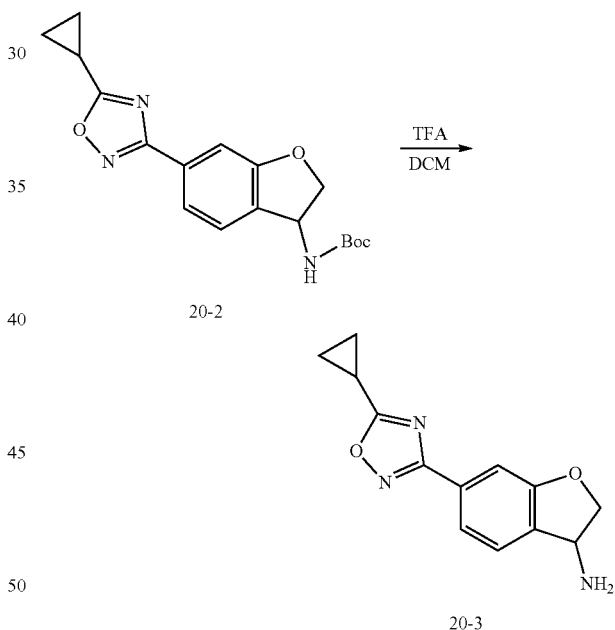

To a solution of tert-butyl N-[6-(5-cyclopropyl-1,2,4-oxadiazol-3-yl)-2,3-dihydro-1-benzofuran-3-yl]carbamate (1.47 g, 4.3 mmol, 1.0 equiv) in DCM (25 mL) was added TFA (5 mL). The mixture was stirred at room temperature for 2 h and then cooled to 0° C. The pH of the mixture was then adjusted to 9 with a saturated NaHCO$_3$ solution and extracted with ethyl acetate (50 mL) five times. The combined organic layers were dried over anhydrous sodium sulfate and concentrated under reduced pressure to give 1 g of 6-(5-cyclopropyl-1,2,4-oxadiazol-3-yl)-2,3-dihydro-1-benzofuran-3-amine as an off-white solid. The off-white solid was used directly in next step without further purification.

3. Synthesis of Intermediate 20-4:

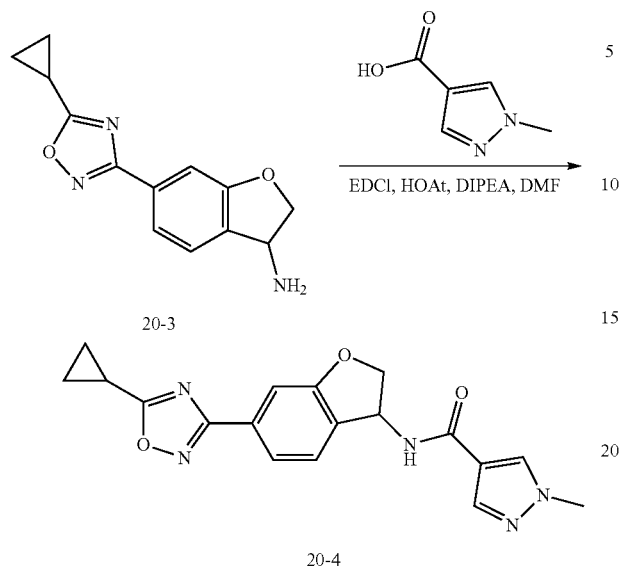

To a solution of 1-methyl-1H-pyrazole-4-carboxylic acid (78 mg, 0.6 mmol, 1.0 equiv) in DMF (4 mL) were added HOAt (101 mg, 0.7 mmol, 1.2 equiv), EDCI (142 mg, 0.7 mmol, 1.2 equiv), DIEA (160 mg, 1.2 mmol, 2.0 equiv), and 6-(5-cyclopropyl-1,2,4-oxadiazol-3-yl)-2,3-dihydro-1-benzofuran-3-amine (150 mg, 0.6 mmol, 1.0 equiv). The mixture was stirred at r.t. overnight and purified by Flash-Prep-HPLC with the following conditions: (CombiFlash-1): Column, C18 silica gel; mobile phase, H₂O (0.5% NH₄HCO₃)/ACN=90/10 increasing to H₂O (0.5% NH₄HCO₃)/ACN=70/30 within 15 min; Detector, UV 254 nm. This purification resulted in 120 mg of N-[6-(5-cyclopropyl-1,2,4-oxadiazol-3-yl)-2,3-dihydro-1-benzofuran-3-yl]-1-methyl-1H-pyrazole-4-carboxamide as a white solid. LRMS (ES) m/z 352 (M+H). ¹H-NMR: (400 MHz, Methanol-d₄, ppm): δ 8.06 (s, 1H), 7.90 (d, J=0.9 Hz, 1H), 7.60 (dd, J=7.8, 1.4 Hz, 1H), 7.48 (d, J=7.8 Hz, 1H), 7.43 (d, J=1.4 Hz, 1H), 5.83 (dd, J=8.6, 4.7 Hz, 1H), 4.82 (dd, J=9.9, 8.6 Hz, 1H), 4.44 (dd, J=9.9, 4.8 Hz, 1H), 3.90 (s, 3H), 2.32 (tt, J=8.2, 5.0 Hz, 1H), 1.29 (dt, J=7.7, 2.6 Hz, 2H), 1.25 (dt, J=5.1, 3.0 Hz, 2H).

4. Synthesis of Compound 236:

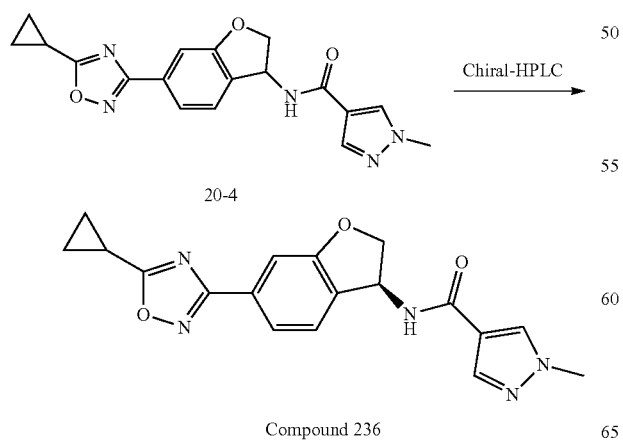

N-[6-(5-cyclopropyl-1,2,4-oxadiazol-3-yl)-2,3-dihydro-1-benzofuran-3-yl]-1-methyl-1H-pyrazole-4-carboxamide (90 mg, 0.3 mmol, 1.0 equiv) was purified by Chiral-Prep-HPLC with the following conditions: (Prep-HPLC-009): Column, Chiralpak IA, 2*25 cm, 5 μm; mobile phase, Hex- and ethanol- (hold 50.0% ethanol- in 15 min); Detector, UV 220/254 nm, Rt=1.569 min. This resulted in 37.8 mg (42%) of (S)—N-(6-(5-cyclopropyl-1,2,4-oxadiazol-3-yl)-2,3-dihydrobenzofuran-3-yl)-1-methyl-1H-pyrazole-4-carboxamide (Compound 236) as a white solid. LRMS (ES) m/z 352 (M+H). ¹H-NMR: (400 MHz, Methanol-d₄, ppm): δ 8.06 (s, 1H), 7.90 (d, J=0.9 Hz, 1H), 7.60 (dd, J=7.8, 1.4 Hz, 1H), 7.48 (d, J=7.8 Hz, 1H), 7.43 (d, J=1.4 Hz, 1H), 5.83 (dd, J=8.6, 4.7 Hz, 1H), 4.82 (dd, J=9.9, 8.6 Hz, 1H), 4.44 (dd, J=9.9, 4.8 Hz, 1H), 3.90 (s, 3H), 2.32 (tt, J=8.2, 5.0 Hz, 1H), 1.29 (dt, J=7.7, 2.6 Hz, 2H), 1.25 (dt, J=5.1, 3.0 Hz, 2H).

Example 21

Synthesis of Compound 238

1. Synthesis of Intermediate 21-2:

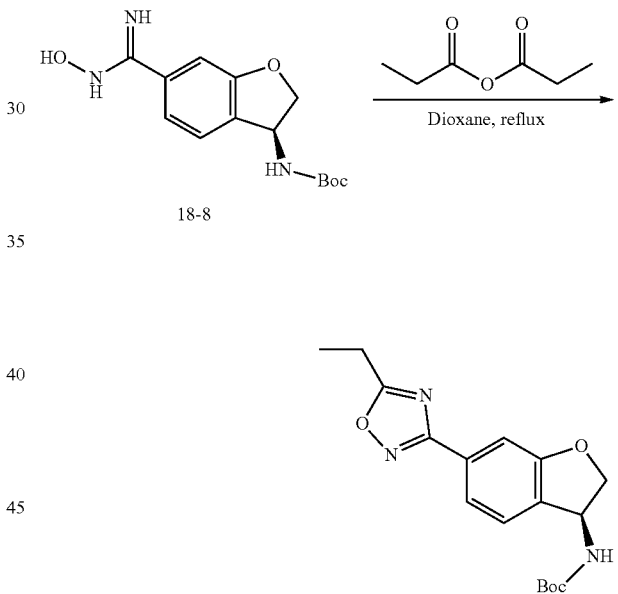

To a solution of tert-butyl N-[(3S)-6-(N-hydroxycarbamimidoyl)-2,3-dihydro-1-benzofuran-3-yl]carbamate (24.7 g, 84.2 mmol, 1.0 equiv) in dioxane (700 mL) was added propanoyl propanoate (16.4 g, 126.0 mmol, 1.5 equiv). The mixture was stirred at 60° C. for 2 h, diluted with EA (500 mL), washed with water (200 mL), dried over anhydrous sodium sulfate, concentrated under reduced pressure, and purified by silica gel chromatography (EA/PE, 7/93) to give 18.4 g (66%) of tert-butyl N-[(3S)-6-(5-ethyl-1,2,4-oxadiazol-3-yl)-2,3-dihydro-1-benzofuran-3-yl]carbamate as a white powder.

2. Synthesis of Intermediate 21-3:

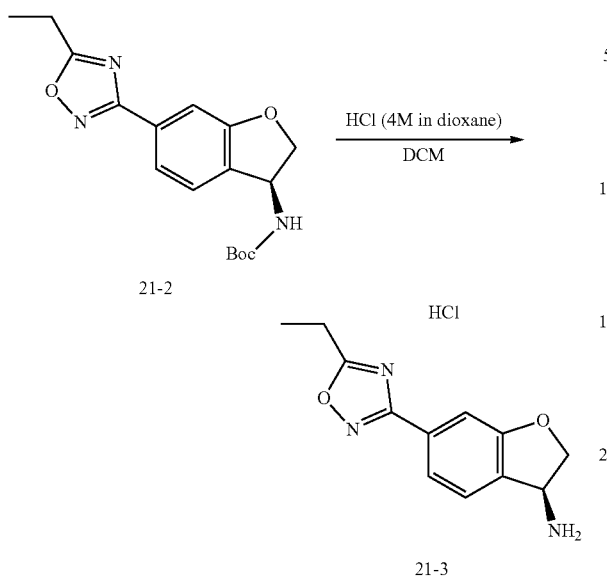

To a solution of tert-butyl N-[(3S)-6-(5-ethyl-1,2,4-oxadiazol-3-yl)-2,3-dihydro-1-benzofuran-3-yl]carbamate (16.3 g, 49.2 mmol, 1.0 equiv) in DCM (350 mL) was added hydrogen chloride (4 M in dioxane, 122 mL). The mixture was stirred at r.t. overnight and diluted with PE (100 mL). The solid was collected and dried to give 13.0 g of (3S)-6-(5-ethyl-1,2,4-oxadiazol-3-yl)-2,3-dihydro-1-benzofuran-3-amine hydrochloride salt as an off-white solid.

3. Synthesis of Compound 238:

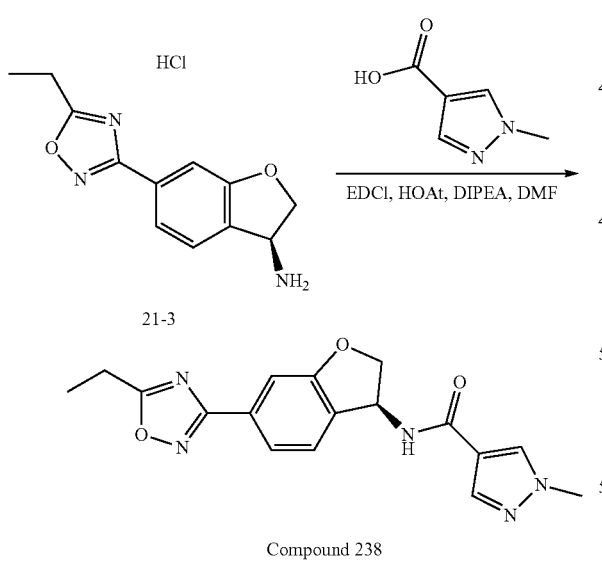

To a solution of (3S)-6-(5-ethyl-1,2,4-oxadiazol-3-yl)-2,3-dihydro-1-benzofuran-3-amine hydrochloride salt (9.0 g, 33.6 mmol, 1.0 equiv) in DMF (200 mL) were added HOAt (5.5 g, 40.4 mmol, 1.2 equiv), DIEA (13.0 g, 100.6 mmol, 3.0 equiv), EDCI (7.7 g, 40.2 mmol, 1.2 equiv), and 1-methyl-1H-pyrazole-4-carboxylic acid (4.4 g, 34.9 mmol, 1.04 equiv). The mixture was stirred at room temperature overnight, diluted with EA (300 mL), washed with water (200 mL) three times, dried over anhydrous sodium sulfate, and concentrated under reduced pressure. The product from the above procedure was combined with previous batch (2.4 g of amine SM) and purified with DCM/PE to give 12.0 g of (S)—N-(6-(5-ethyl-1,2,4-oxadiazol-3-yl)-2,3-dihydrobenzofuran-3-yl)-1-methyl-1H-pyrazole-4-carboxamide (Compound 238) as a white solid after filtration and drying. LRMS (ES) m/z 340 (M+H). $^1$H-NMR: (400 MHz, DMSO-$d_6$, ppm): δ 8.71 (d, J=7.6 Hz, 1H), 8.16 (s, 1H), 7.86 (s, 1H), 7.57 (dd, J=7.7, 1.4 Hz, 1H), 7.47 (d, J=7.7 Hz, 1H), 7.38 (d, J=1.4 Hz, 1H), 5.76 (td, J=8.3, 5.3 Hz, 1H), 4.80 (t, J=9.3 Hz, 1H), 4.39 (dd, J=9.7, 5.2 Hz, 1H), 3.82 (s, 3H), 2.99 (q, J=7.5 Hz, 2H), 1.32 (t, J=7.6 Hz, 3H).

Example 22

Synthesis of Compound 253

1. Synthesis of Intermediate 22-2:

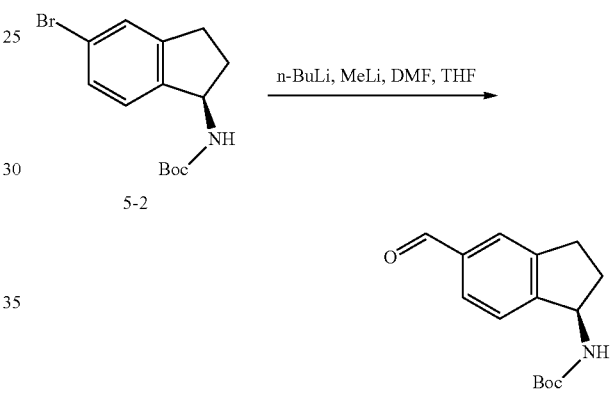

To a solution of tert-butyl N-[(1R)-5-bromo-2,3-dihydro-1H-inden-1-yl]carbamate (2 g, 6.4 mmol, 1.0 equiv) in THF (30 mL) cooled to −78° C. was added MeLi (4.8 mL, 1.6 M) dropwise at −78° C. under argon. The mixture was stirred at −78° C. for 15 min and n-BuLi (5.2 mL, 2.5 M) was added dropwise. The mixture was then stirred for 1 h at −78° C. and DMF (1.43 g, 19.2 mmol, 3.0 equiv) was added dropwise. The solution was stirred for 1 h at −78° C., quenched with a saturated NH$_4$Cl solution (5 mL), and concentrated under vacuum. The residue was purified by silica gel chromatography (EA/PE, 1/10) to give 1.5 g (90%) of tert-butyl N-[(1R)-5-formyl-2,3-dihydro-1H-inden-1-yl]carbamate as a yellow solid.

2. Synthesis of Intermediate 22-3:

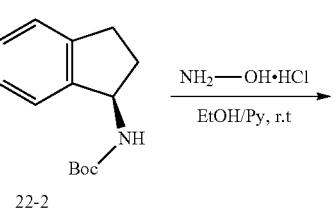

-continued

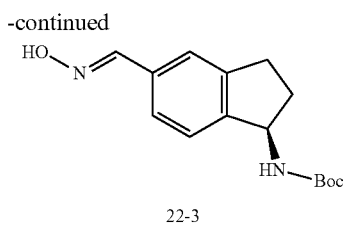

22-3

To a solution of tert-butyl N-[(1R)-5-formyl-2,3-dihydro-1H-inden-1-yl]carbamate (1.6 g, 6.1 mmol, 1.0 equiv) in a mixture of ethanol and pyridine (21 mL, 2/1) was added NH₂OH.HCl (509 mg, 1.2 equiv). The mixture was stirred at room temperature for 2 h and concentrated under reduced pressure to give 1.7 g of tert-butyl N-[(1R)-5-[(1E)-(hydroxyimino)methyl]-2,3-dihydro-1H-inden-1-yl]carbamate as a white solid.

3. Synthesis of Intermediate 22-4:

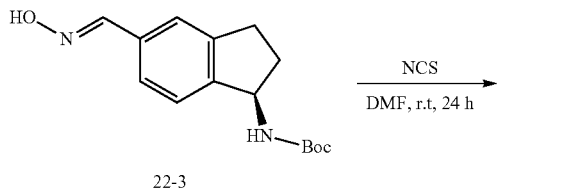

To a solution of tert-butyl N-[(1R)-5-[(1E)-(hydroxyimino)methyl]-2,3-dihydro-1H-inden-1-yl]carbamate (1.7 g, 6.1 mmol, 1.0 equiv) in DMF (15 mL) was added NCS (977 mg, 7.3 mmol, 1.2 equiv). The mixture was stirred at r.t. overnight, diluted with EA (50 mL), washed with saturated NH₄Cl solution (50 mL) twice, dried over anhydrous sodium sulfate, and concentrated under vacuum to give 1.8 g (95%) of tert-butyl N-[(1R)-5-[(1Z)-chloro(hydroxyimino)methyl]-2,3-dihydro-1H-inden-1-yl]carbamate as a brown oil.

4. Synthesis of Intermediate 22-5:

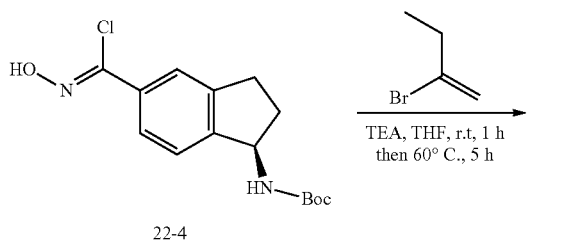

-continued

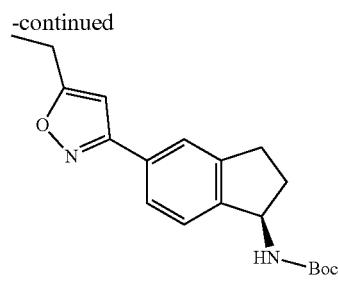

22-5

To a solution of 2-bromobut-1-ene (2 g, 14.8 mmol, 1.0 equiv) in THF (30 mL) were added tert-butyl N-[(1R)-5-[(1Z)-chloro(hydroxyimino)methyl]-2,3-dihydro-1H-inden-1-yl]carbamate (955 mg, 3.1 mmol, 1.1 equiv) and TEA (1.3 g, 12.9 mmol, 2.1 equiv). The mixture was stirred at r.t. for 1 h, heated to 60° C. for 5 h, cooled to r.t., diluted with EA (200 mL), washed with saturated NH₄Cl solution (100 mL) twice, dried over anhydrous sodium sulfate, concentrated under reduced pressure, and purified by silica gel chromatography (EA/PE, 1/10) to give 1.1 g (23%) of tert-butyl N-[(1R)-5-(5-ethyl-1,2-oxazol-3-yl)-2,3-dihydro-1H-inden-1-yl]carbamate as a yellow solid.

5. Synthesis of Intermediate 22-6:

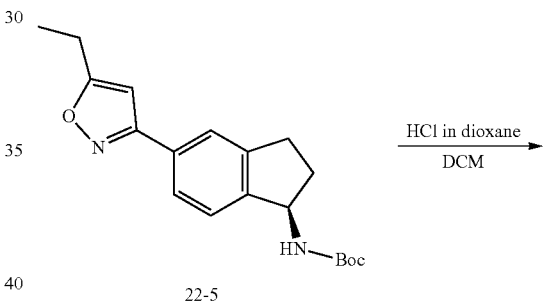

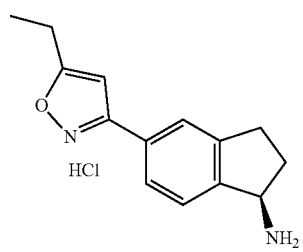

22-6

To a solution of tert-butyl N-[(1R)-5-(5-ethyl-1,2-oxazol-3-yl)-2,3-dihydro-1H-inden-1-yl]carbamate (1.08 g, 3.3 mmol, 1.0 equiv) in DCM (15 ml) was added hydrochloric acid (4 M in dioxane, 15 mL, 18.2 equiv). The mixture was stirred at r.t. for 2 h and concentrated under reduced pressure to give 870 mg of (1R)-5-(5-ethyl-1,2-oxazol-3-yl)-2,3-dihydro-1H-inden-1-amine hydrochloride as an off-white solid.

6. Synthesis of Compound 253:

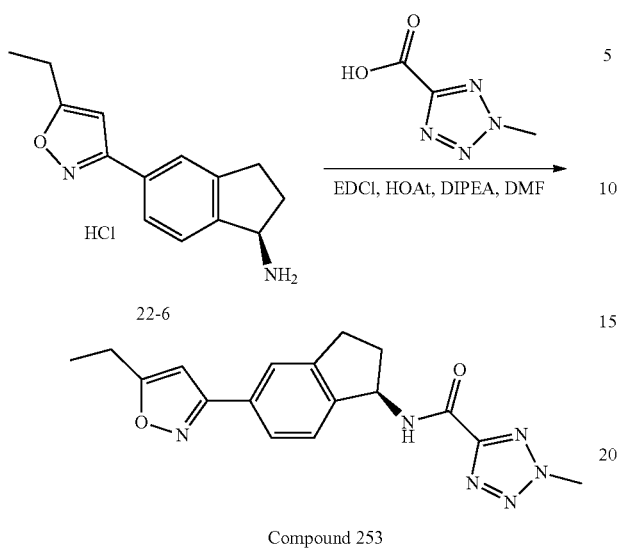

Compound 253

To a solution of (1R)-5-(5-ethyl-1,2-oxazol-3-yl)-2,3-dihydro-1H-inden-1-amine hydrochloride (625 mg, 2.4 mmol, 1.0 equiv) in DMF (20 mL) were added 2-methyl-2H-1,2,3,4-tetrazole-5-carboxylic acid (606 mg, 4.7 mmol, 2.0 equiv), EDCI (909 mg, 4.7 mmol, 2.0 equiv), HOAt (643 mg, 4.7 mmol, 2.0 equiv), and DIEA (1.53 g, 11.9 mmol, 5.0 equiv). The mixture was stirred at r.t. for 2 h, heated to 60° C. for 2 h, cooled to r.t., and poured into EA (100 mL) and water (100 mL). The aqueous layer was extracted with ethyl acetate (100 mL) twice. The combined organic layers were washed with saturated NH$_4$Cl solution (50 mL) twice, dried over anhydrous sodium sulfate, concentrated under reduced pressure, and purified by Flash-Prep-HPLC with the following conditions: (IntelFlash-1): Column, C18 silica gel; mobile phase, ACN/H2O=1:3 increasing to ACN/H$_2$O=1:2 within 10 min; Detector, UV 254 nm. This purification resulted in 758 mg (82%) of (R)—N-(5-(5-ethylisoxazol-3-yl)-2,3-dihydro-1H-inden-1-yl)-2-methyl-2H-tetrazole-5-carboxamide (Compound 253) as an off-white solid. LRMS (ES) m/z 338 (M+H). $^1$H-NMR: (300 MHz, DMSO-d$_6$, ppm) δ 9.38 (d, J=8.4 Hz, 1H), 7.74-7.59 (m, 2H), 7.29 (d, J=7.9 Hz, 1H), 6.79-6.71 (m, 1H), 5.56 (q, J=8.1 Hz, 1H), 4.41 (s, 3H), 3.04 (ddd, J=16.0, 8.9, 3.3 Hz, 1H), 2.96-2.69 (m, 3H), 2.41 (td, J=8.1, 3.6 Hz, 1H), 2.21-2.01 (m, 1H), 1.23 (t, J=7.6 Hz, 3H).

The following compounds were prepared by methods analogous to the method described for Compound 253:

| Compound No. | LRMS (ES) m/z |
|---|---|
| 137 | M + H = 334 |
| 138 | M + H = 334 |
| 252 | M + H = 325 |
| 413 | M + H = 337 |
| 414 | M + H = 337 |
| 415 | M + H = 338 |
| 416 | M + H = 324 |
| 417 | M + H = 338 |
| 418 | M + H = 324 |
| 431 | M + H = 337 |
| 432 | M + H = 323 |

Example 23

Synthesis of Compound 414

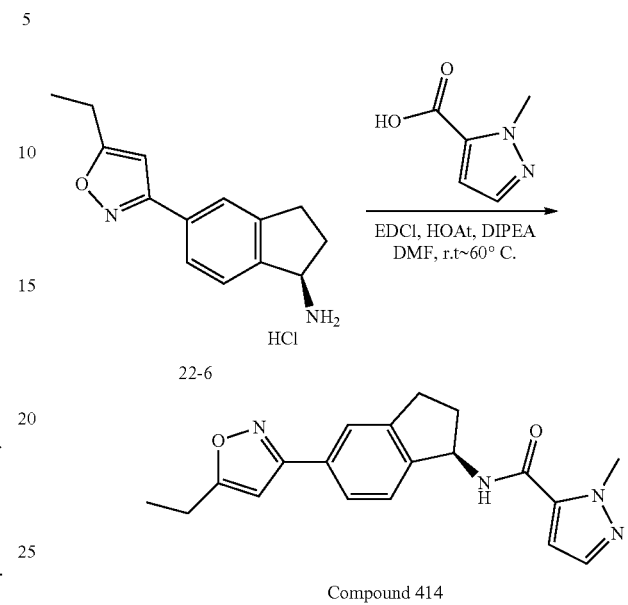

Compound 414

To a solution of 1-methyl-1H-pyrazole-5-carboxylic acid (166 mg, 1.3 mmol, 1.7 equiv) in DMF (4 mL) were added DIEA (566 mg, 4.4 mmol, 5.8 equiv), EDCI (337 mg, 1.7 mmol, 2.3 equiv) and HOAt (238 mg, 1.8 mmol, 2.3 equiv). The mixture was stirred 5 min at room temperature and (1R)-5-(5-ethyl-1,2-oxazol-3-yl)-2,3-dihydro-1H-inden-1-amine hydrogen chloride (200 mg, 0.8 mmol, 1.00 equiv) was added. The mixture was then stirred for 2 h at room temperature and filtered to remove the solids. The filtrate was purified by Prep-HPLC with the following conditions: (2#-AnalyseHPLC-SHIMADZU(HPLC-10)): Column, XBridge Shield RP18 OBD Column, 5 um, 19*150 mm; mobile phase, Water (10 MMOL/L NH$_4$HCO$_3$) and ACN (38.0% ACN up to 52.0% in 8 min); Detector, UV 254 nm. This purification afforded 111.4 mg (38%) of (R)—N-(5-(5-ethylisoxazol-3-yl)-2,3-dihydro-1H-inden-1-yl)-1-methyl-1H-pyrazole-5-carboxamide (Compound 414) as a white solid. LRMS (ES) m/z 337 (M+H).

$^1$H-NMR: (300 MHz, CD$_3$OD, ppm): δ 7.76-7.63 (m, 2H), 7.49-7.34 (m, 2H), 6.81 (d, J=2.1 Hz, 1H), 6.57 (d, J=1.0 Hz, 1H), 5.64 (t, J=8.0 Hz, 1H), 4.17 (d, J=1.1 Hz, 3H), 3.13 (m, 1H), 2.98 (m, 1H), 2.91-2.77 (m, 2H), 2.71-2.54 (m, 1H), 2.06 (m, 1H), 1.35 (t, J=7.6 Hz, 3H).

The following compounds were prepared by methods analogous to the method described for Compound 414:

| Compound No. | LRMS (ES) m/z |
|---|---|
| 137 | M + H = 334 |
| 138 | M + H = 334 |
| 252 | M + H = 335 |
| 253 | M + H = 339 |
| 413 | M + H = 337 |
| 415 | M + H = 338 |
| 416 | M + H = 324 |
| 417 | M + H = 338 |
| 418 | M + H = 324 |
| 432 | M + H = 323 |

Example 24

Synthesis of Compound 261

1. Synthesis of Intermediate 23-2:

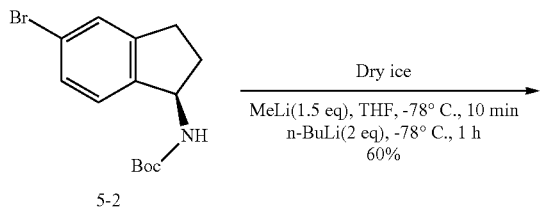

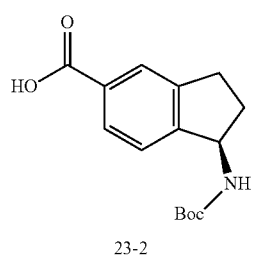

To a solution of tert-butyl N-[(1R)-5-bromo-2,3-dihydro-1H-inden-1-yl]carbamate (10 g, 32.2 mmol, 1.0 equiv) in THF (300 mL) cooled to −78° C. was added MeLi (30.1 mL, 1.6 M, 1.5 equiv) dropwise. The mixture was stirred at −78° C. for 10 min and n-BuLi (25.7 mL, 2.5 M, 2.0 equiv) was added dropwise at −78° C. The mixture was stirred for an additional hour at −78° C. and dry ice (30 g) was added. The mixture was then stirred for 30 min at −78° C. and quenched by adding saturated NH₄Cl solution (30 mL) at −78° C. slowly. The resulting solution was warmed to r.t. and extracted with EA (400 mL) twice. The combined organic layers were concentrated under reduced pressure and triturated with a mixture of EA, PE, and ethyl ether (1/20/10) to afford 6.2 g (70%) of (1R)-1-[[(tert-butoxy)carbonyl]amino]-2,3-dihydro-1H-indene-5-carboxylic acid as a white solid.

2. Synthesis of Intermediate 23-3:

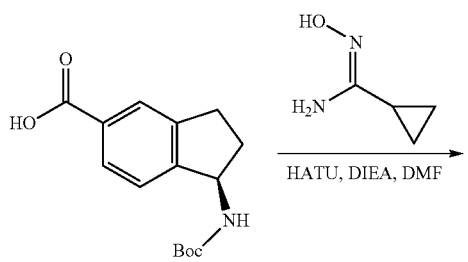

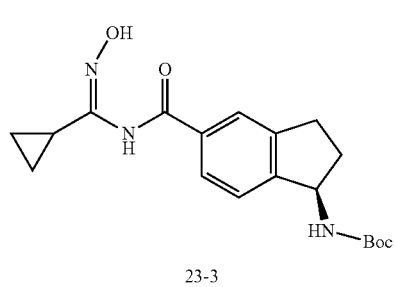

To a solution of (1R)-1-[[(tert-butoxy)carbonyl]amino]-2,3-dihydro-1H-indene-5-carboxylic acid (1.5 g, 5.4 mmol, 1.0 equiv) in DMF (20 mL) were added DIEA (2.1 g, 16.3 mmol, 3.0 equiv) and HATU (3.1 g, 8.2 mmol, 1.5 equiv). The mixture was stirred for 5 min, and (Z)—N-ydroxycycloprop-1-carboximidamide (542 mg, 5.4 mmol, 1.0 equiv) was added. The mixture was then stirred for 2 h, diluted with DCM (200 mL), washed with saturated NH₄Cl solution (200 mL) three times, concentrated under reduced pressure, and purified by silica gel chromatography (EA/PE, 14/86) to give 800 mg (41%) of tert-butyl-N-[(1R)-5-[[(1Z)-cyclopropyl(hydroxyimino)methyl]carbamoyl]-2,3-dihydro-1H-inden-1-yl] carbamate as an off-white solid.

3. Synthesis of Intermediate 23-4:

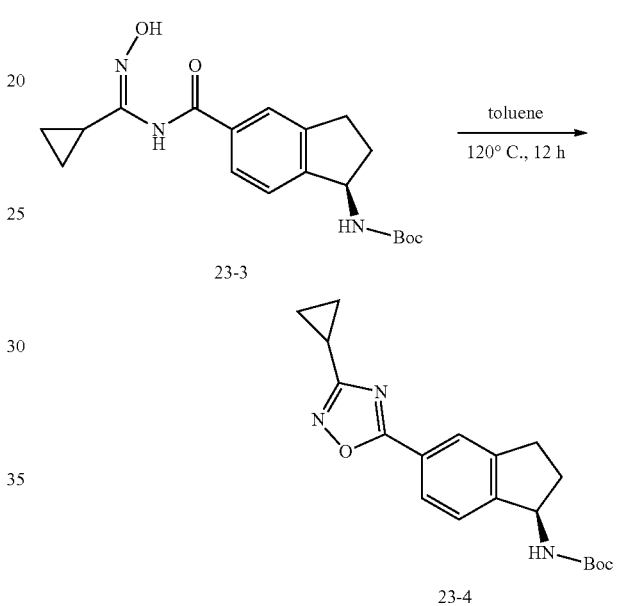

A solution of tert-butyl N-[(1R)-5-[[(1Z)-cyclopropyl(hydroxyimino)methyl]carbamoyl]-2,3-dihydro-1H-inden-1-yl]carbamate (680 mg, 1.9 mmol, 1.0 equiv) in toluene (10 mL) was heated to 100° C. overnight, cooled to r.t., concentrated under reduced pressure, and purified by silica gel chromatography (EA/PE, 1/9) to give 540 mg (84%) of tert-butyl N-[(1R)-5-(3-cyclopropyl-1,2,4-oxadiazol-5-yl)-2,3-dihydro-1H-inden-1-yl]carbamate as a light yellow solid.

4. Synthesis of Intermediate 23-5:

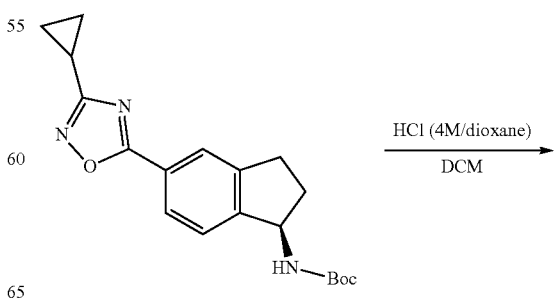

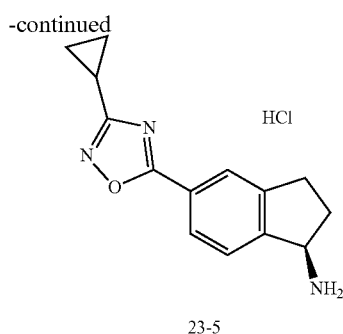

To a solution of tert-butyl N-[(1R)-5-(3-cyclopropyl-1,2,4-oxadiazol-5-yl)-2,3-dihydro-1H-inden-1-yl]carbamate (490 mg, 1.4 mmol, 1.0 equiv) in DCM (5 mL) was added hydrogen chloride (4 M in dioxane, 10 mL). The mixture was stirred overnight and concentrated to afford 660 mg of (1R)-5-(3-cyclopropyl-1,2,4-oxadiazol-5-yl)-2,3-dihydro-1H-inden-1-amine hydrochloride salt as a light yellow solid.

5. Synthesis of Compound 261:

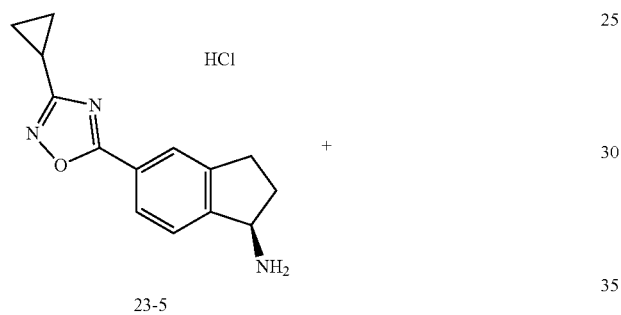

Compond 261

To a solution of 1-methyl-1H-pyrazole-5-carboxylic acid (26 mg, 0.2 mmol, 1.2 equiv) in DMF (4 mL) were added DIEA (80 mg, 0.62 mmol, 3.50 equiv), HOAt (60 mg, 0.4 mmol, 2.3 equiv), and EDCI (84 mg, 0.4 mmol, 2.3 equiv). The mixture was stirred for 5 min and (1R)-5-(3-cyclopropyl-1,2,4-oxadiazol-5-yl)-2,3-dihydro-1H-inden-1-amine hydrochloride salt (50 mg, 0.2 mmol, 1.0 equiv) was added. The mixture was then stirred for 2 h and purified by Flash-Prep-HPLC with the following conditions: (Combi-Flash-1): Column, C18 silica gel; mobile phase, ACN/H₂O (0.05% NH₄HCO₃); Detector, UV 254 nm. This purification afforded 20.8 mg (33%) of (R)—N-(5-(3-cyclopropyl-1,2,4-oxadiazol-5-yl)-2,3-dihydro-1H-inden-1-yl)-1-methyl-1H-pyrazole-5-carboxamide (Compound 261) as a white solid. LRMS (ES) m/z 350 (M+H). ¹H-NMR: (CD₃OD, 300 MHz, ppm): δ 7.99-7.88 (2H, m), 7.49-7.39 (2H, m), 6.79 (1H, d, J=2.2 Hz), 5.63 (1H, t, J=8.1 Hz), 4.14 (3H, s), 3.20-2.88 (2H, m), 2.61 (1H, m), 2.08 (2H, m), 1.07 (4H, m)

The following compounds were prepared by methods analogous to the method described for Compound 261:

| Compound No. | LRMS (ES) m/z |
| --- | --- |
| 254 | M + H = 338 |
| 255 | M + H = 352 |
| 256 | M + H = 340 |
| 257 | M + H = 338 |
| 258 | M + H = 350 |
| 259 | M + H = 364 |
| 260 | M + H = 352 |
| 263 | M + H = 324 |
| 264 | M + H = 338 |
| 272 | M + H = 329 |
| 273 | M + H = 327 |
| 274 | M + H = 327 |
| 275 | M + H = 328 |
| 276 | M + H = 360 |
| 277 | M + H = 374 |
| 311 | M + H = 329 |
| 312 | M + H = 329 |
| 313 | M + H = 326 |
| 314 | M + H = 326 |
| 341 | M + H = 343 |
| 342 | M + H = 331 |
| 343 | M + H = 340 |
| 344 | M + H = 328 |

Example 25

Synthesis of Compound 372

1. Synthesis of Intermediate 24-2:

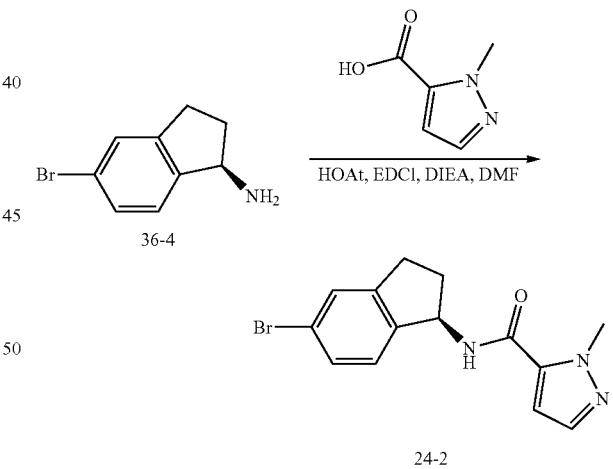

24-2

To a solution (1R)-5-bromo-2,3-dihydro-1H-inden-1-amine hydrochloride (3.0 g, 12.1 mmol, 1.00 equiv) in DMF (60 mL) were added 1-methyl-1H-pyrazole-5-carboxylic acid (1.65 g, 13.1 mmol, 1.08 equiv), HOAt (2.5 g, 18.37 mmol, 1.52 equiv), EDCI (3.5 g, 18.3 mmol, 1.51 equiv), and DIEA (6.3 g, 48.8 mmol, 4.04 equiv). The mixture was stirred at r.t. overnight, diluted with EA (200 mL), washed with water (100 mL) and brine (100 mL), dried over anhydrous sodium sulfate, concentrated under vacuum, and purified by a silica gel chromatography (EA/PE, 19/81) to give a solid, which was triturated with PE to afford 2.67 g (69%) of N-[(1R)-5-bromo-2,3-dihydro-1H-inden-1-yl]-1-methyl-1H-pyrazole-5-carboxamide as an off-white solid. LRMS (ES) m/z 320 (M+H). LC-MS: (ES, m/z): [M+H]+ 320 322

2. Synthesis of Compound 372:

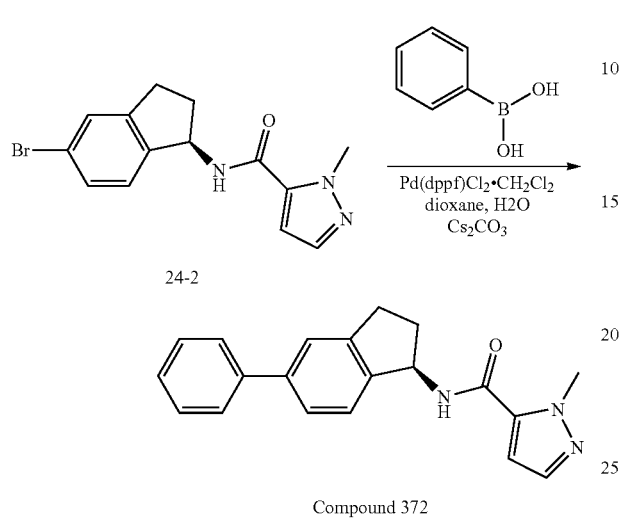

Compound 372

To a solution of N-[(1R)-5-bromo-2,3-dihydro-1H-inden-1-yl]-1-methyl-1H-pyrazole-5-carboxamide (100 mg, 0.31 mmol, 1.00 equiv) in dioxane (5 mL) were added phenylboronic acid (57 mg, 0.47 mmol, 1.50 equiv), Pd(dppf)Cl₂CH₂Cl₂ (26 mg, 0.03 mmol, 0.10 equiv), Cs₂CO₃ (204 mg, 0.63 mmol, 2.00 equiv), and water (0.5 mL). After stirring at 80° C. for 3 h, the resulting solution was diluted with EA (20 mL) and filtered to remove the solid. The organic layer was separated, washed with brine, dried over anhydrous sodium sulfate, concentrated under reduced pressure, and purified by Prep-TLC (PE/EA, 1/1). This product (67 mg) was further purified by Flash-Prep-HPLC with the following conditions: (CombiFlash-1): Column, C18 silica gel; mobile phase, water (0.5% NH₄HCO₃)/ACN=95/5 increasing to water (0.5% NH4HCO3)/ACN=90/10 within 10 min; Detector, UV 254 nm. This resulted in 46.7 mg (47%) of (R)-1-methyl-N-(5-phenyl-2,3-dihydro-1H-inden-1-yl)-1H-pyrazole-5-carboxamide (Compound 372) as a white solid. LRMS (ES) m/z 318 (M+H). ¹H-NMR: (400 MHz, DMSO-d6, ppm): δ 8.76 (d, J=8.4 Hz, 1H), 7.65-7.57 (m, 2H), 7.53 (d, J=1.6 Hz, 1H), 7.50-7.39 (m, 4H), 7.38-7.26 (m, 2H), 6.91 (d, J=2.1 Hz, 1H), 5.54 (q, J=8.1 Hz, 1H), 4.10 (s, 3H), 3.04 (ddd, J=15.9, 8.9, 3.2 Hz, 1H), 2.90 (dt, J=16.1, 8.4 Hz, 1H), 2.48-2.43 (m, 1H), 1.99 (dq, J=12.5, 8.7 Hz, 1H)

The following compounds were prepared by methods analogous to the method described for Compound 372:

| Compound No. | LRMS (ES) m/z |
| --- | --- |
| 373 | M + H = 332 |
| 374 | M + H = 332 |
| 375 | M + H = 333.1 |
| 376 | M + H = 333 |

Example 26

Synthesis of Compound 378

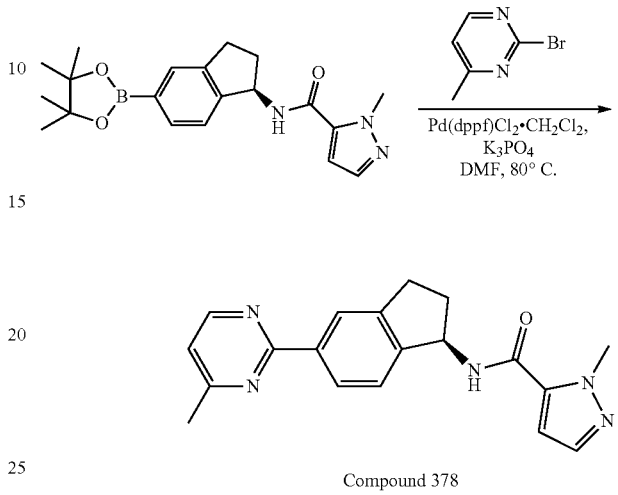

Compound 378

To a solution of 1-methyl-N-[(1R)-5-(tetramethyl-1,3,2-dioxaborolan-2-yl)-2,3-dihydro-1H-inden-1-yl]-1H-pyrazole-5-carboxamide (100 mg, 0.27 mmol, 1.00 equiv) in DMF (4 mL) were added Pd(dppf)Cl₂.CH₂Cl₂ (44 mg, 0.05 mmol, 0.20 equiv), K₃PO₄ (116 mg, 0.55 mmol, 2.00 equiv), and 2-bromo-4-methylpyrimidine (94 mg, 0.54 mmol, 2.00 equiv) under nitrogen. The mixture was stirred at 80° C. for 2 h, cooled to r.t., diluted with EA (10 mL), washed with water (10 mL), dried over anhydrous sodium sulfate, concentrated under reduced pressure, and purified by a silica gel chromatography (EA/PE, 1/1) to give a product, which was further purified by Prep-HPLC with the following conditions: (2#-AnalyseHPLC-SHIMADZU(HPLC-10)): Column, XBridge Shield RP18 OBD Column, 5 um, 19*150 mm; mobile phase, Water (10 MMOL/L NH₄HCO₃+0.1% NH₃.H₂O) and ACN (31.0% ACN up to 44.0% in 8 min); Detector, UV 220 nm. This result in 17.6 mg (19%) of (R)-1-methyl-N-(5-(4-methylpyrimidin-2-yl)-2,3-dihydro-1H-inden-1-yl)-1H-pyrazole-5-carboxamide (Compound 378) as a white solid. LRMS (ES) m/z 334 (M+H). ¹H-NMR: (300 MHz, Methanol-d₄, ppm): δ 8.65 (d, J=5.1 Hz, 3H), 8.28 (s, 4H), 7.50-7.38 (m, 4H), 7.23 (s, 1H), 6.83 (d, J=2.1 Hz, 2H), 5.66 (s, 1H), 4.18 (s, 7H), 2.59 (s, 7H), 0.20 (s, 1H).

The following compounds were prepared by methods analogous to the method described for Compound 378:

| Compound No. | LRMS (ES) m/z |
| --- | --- |
| 377 | M + H = 333 |
| 379 | M + H = 334 |
| 380 | M + H = 333 |
| 381 | M + H = 334 |
| 384 | M + H = 334 |

Example 27

Synthesis of Compound 383

1. Synthesis of Intermediate 26-2:

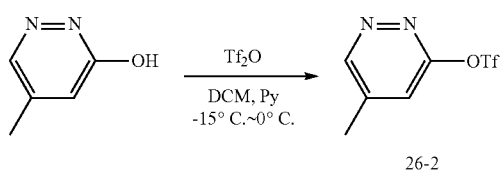

26-2

To a solution of 5-methylpyridazin-3-ol (500 mg, 4.54 mmol, 1.00 equiv) in DCM (10 mL) cooled to −15° C. were added pyridine (1.1 g, 13.9 mmol, 3.06 equiv) and a solution of (trifluoromethane)sulfonyl trifluoromethanesulfonate (2.0 g, 7.09 mmol, 1.56 equiv) in DCM (5 mL) dropwise with stirring at −15° C. After stirring at −15-0° C. for 2 h under nitrogen, the reaction was quenched with water (20 mL). The resulting solution was separated and the aqueous layer was extracted with DCM (20 mL) twice. The combined organic layers were washed with brine (20 mL), dried over anhydrous magnesium sulfate, concentrated under reduced pressure, and purified by silica gel chromatography (EA/PE, 16/84) to afford 400 mg (36%) of 5-methylpyridazin-3-yl trifluoromethanesulfonate as colorless oil.

2. Synthesis of Compound 383:

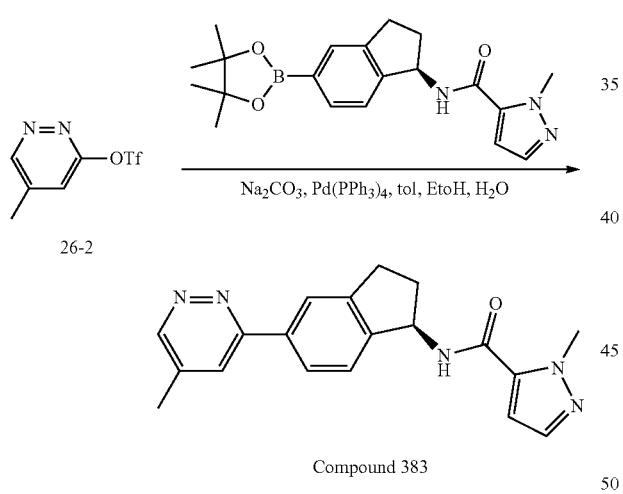

Compound 383

To a solution of 1-methyl-N-[(1R)-5-(tetramethyl-1,3,2-dioxaborolan-2-yl)-2,3-dihydro-1H-inden-1-yl]-1H-pyrazole-5-carboxamide (100 mg, 0.27 mmol, 1.00 equiv) in toluene (9 mL) were added 5-methylpyridazin-3-yl trifluoromethanesulfonate (80 mg, 0.33 mmol, 1.21 equiv), ethanol (3 mL), Pd(PPh$_3$)$_4$ (47 mg, 0.04 mmol, 0.15 equiv), and a solution of sodium carbonate (318 mg, 3.00 mmol, 11.0 equiv) in water (1.5 mL). After stirring for 3 h at 80° C., the resulting solution was diluted with 30 mL of EA. The mixture was washed with water (20 mL) and brine (20 mL), dried over anhydrous sodium sulfate, and concentrated under vacuum. The product was purified by Prep-TLC (EA) followed by Prep-HPLC with the following conditions: (2#-AnalyseHPLC-SHIMADZU(HPLC-10)): Column, XBridge Shield RP18 OBD Column, 5 um, 19*150 mm; mobile phase, water (10 mmol/L NH$_4$HCO$_3$+0.1% NH$_3$.H$_2$O) and ACN (25.0% ACN up to 38.0% in 8 min); Detector, UV 220 nm. This resulted in 7.9 mg (9%) of (R)-1-methyl-N-(5-(5-methylpyridazin-3-yl)-2,3-dihydro-1H-inden-1-yl)-1H-pyrazole-5-carboxamide (Compound 383) as a white solid. LRMS (ES) m/z 334 (M+H). $^1$H-NMR: (300 MHz, Methanol-d$_4$, ppm) δ 9.01 (d, J=1.9 Hz, 1H), 8.04-7.99 (m, 1H), 7.99-7.95 (m, 1H), 7.91 (d, J=7.8 Hz, 1H), 7.51-7.42 (m, 2H), 6.83 (d, J=2.1 Hz, 1H), 5.68 (t, J=7.8 Hz, 1H), 4.18 (s, 3H), 3.18 (ddd, J=15.9, 9.1, 3.5 Hz, 1H), 3.01 (dd, J=16.0, 8.3 Hz, 1H), 2.65 (dtd, J=12.6, 7.9, 3.5 Hz, 1H), 2.48 (s, 3H), 2.09 (dq, J=12.8, 8.6 Hz, 1H).

The following compounds were prepared by methods analogous to the method described for Compound 383:

| Compound No. | LRMS (ES) m/z |
|---|---|
| 382 | M + H = 334 |

Example 28

Synthesis of Compound 423

1. Synthesis of Intermediate 28-2:

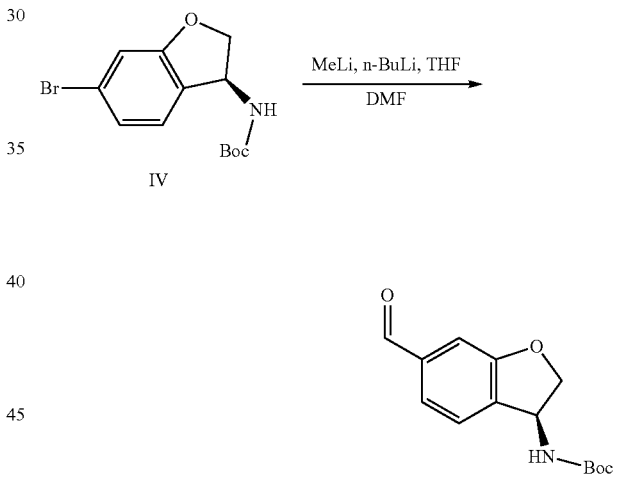

28-2

To a solution of tert-butyl N-[(3S)-6-bromo-2,3-dihydro-1-benzofuran-3-yl]carbamate (1.7 g, 5.4 mmol, 1.0 equiv) in THF (20 mL) cooled to −78° C. was added MeLi (5.07 mL, 1.50 equiv) under nitrogen. The mixture was stirred at −78° C. for 10 min and n-BuLi (2.5 M, 4.32 mL, 2.0 equiv) was added. The mixture was then stirred at −78° C. for 30 min and DMF (1.19 g, 16.3 mmol, 3.0 equiv) was added. The mixture was then stirred for an additional hour at −78° C. and quenched with a saturated NH$_4$Cl solution. The resulting solution was extracted with EA (300 mL) three times. The combined organic layers were washed with saturated NH$_4$Cl solution (200 mL), dried over anhydrous sodium sulfate, concentrated under reduced pressure, and triturated with n-hexane (30 ml) to afford 1.32 g (93%) of tert-butyl N-[(3S)-6-formyl-2,3-dihydro-1-benzofuran-3-yl]carbamate as a light yellow solid.

2. Synthesis of Intermediate 28-3:

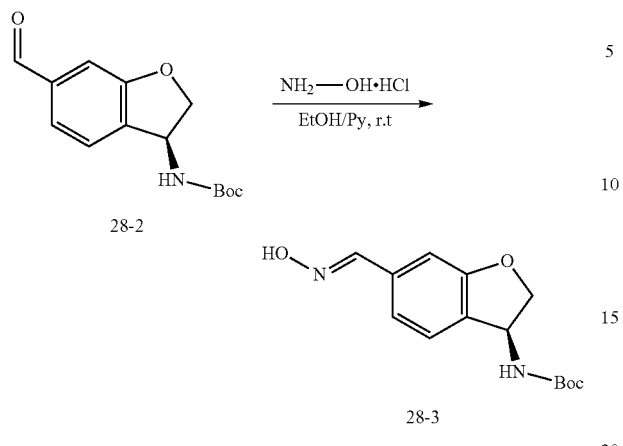

To a solution of tert-butyl N-[(3S)-6-formyl-2,3-dihydro-1-benzofuran-3-yl]carbamate (5.8 g, 22.0 mmol, 1.0 equiv) in a mixture of ethanol (100 mL) and Pyridine (50 mL) was added hydroxylamine hydrochloride (1.83 g, 26.3 mmol, 1.2 equiv). The mixture was stirred for 3 h, concentrated under reduced pressure, and poured into water. The aqueous solution was extracted with EA twice. The combined organic layers were washed with brine, dried over anhydrous sodium sulfate, and concentrated to afford 6.0 g of tert-butyl N-[(3S)-6-[(1E)-(hydroxyimino)methyl]-2,3-dihydro-1-benzofuran-3-yl]carbamate as a white solid.

3. Synthesis of Intermediate 28-4:

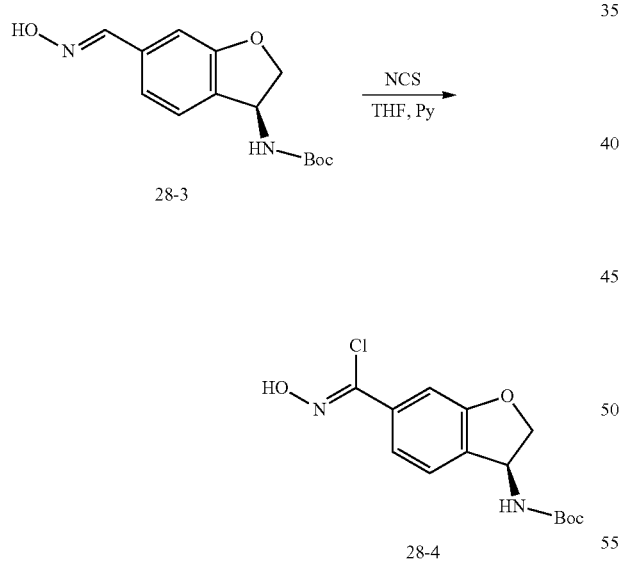

To a solution of tert-butyl N-[(3S)-6-[(1E)-(hydroxyimino)methyl]-2,3-dihydro-1-benzofuran-3-yl]carbamate (6.0 g, 21.5 mmol, 1.0 equiv) in THF (120 mL) were added pyridine (1.36 g, 17.1 mmol, 0.98 equiv) and NCS (5.17 mg, 38.7 mmol, 1.8 equiv). The resulting solution was stirred overnight, diluted with EA, washed with water, dried over anhydrous sodium sulfate, and concentrated under reduced pressure to afford 9.1 g of tert-butyl N-[(3S)-6-[(1Z)-chloro(hydroxyimino)methyl]-2,3-dihydro-1-benzofuran-3-yl]carbamate as a white solid.

4. Synthesis of Intermediate 28-5:

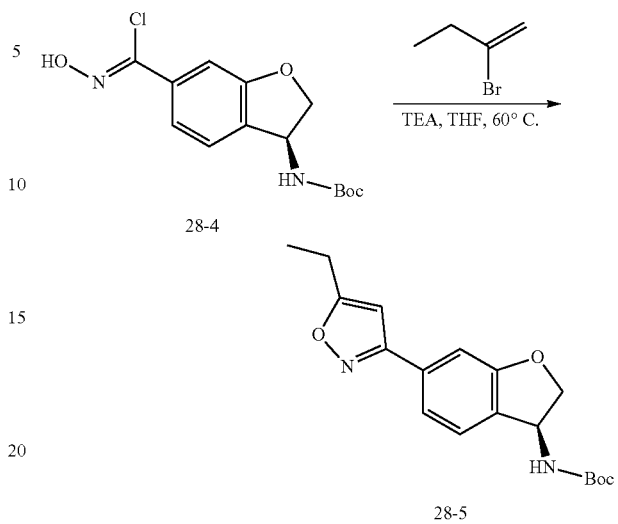

To a solution of tert-butyl N-[(3S)-6-[(1Z)-chloro(hydroxyimino)methyl]-2,3-dihydro-1-benzofuran-3-yl]carbamate (3.6 g, 11.6 mmol, 1.0 equiv) in THF (80 mL) were added TEA (4.3 g, 42.9 mmol, 5.0 equiv) and 2-bromobut-1-ene (1.74 g, 12.9 mmol, 1.5 equiv). The resulting solution was stirred at r.t for 2 h, heated at 60° C. for 2 h, poured into water, and extracted with EA twice. The combined organic layers were washed with aqueous NH$_4$Cl solution, dried over anhydrous sodium sulfate, concentrated under reduced pressure, and purified by silica gel chromatography (EA/PE, 1/9) to afford 424 mg (11%) of tert-butyl N-[(3S)-6-(5-ethyl-1,2-oxazol-3-yl)-2,3-dihydro-1-benzofuran-3-yl]carbamate as a white solid.

5. Synthesis of Intermediate 28-6:

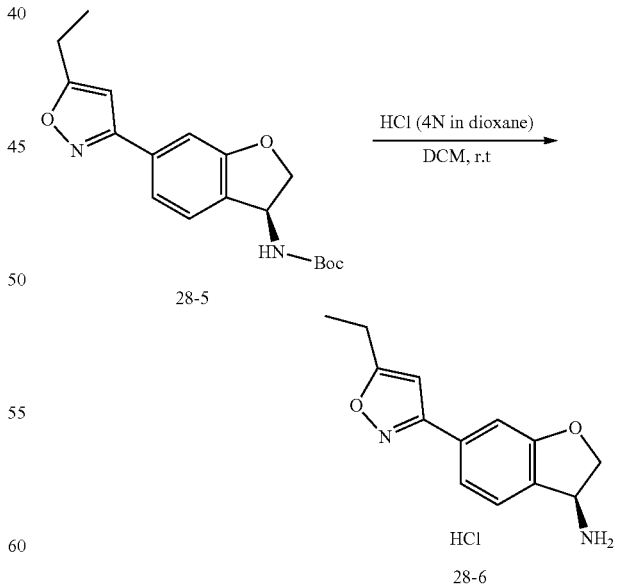

To a solution of tert-butyl N-[(3S)-6-(5-ethyl-1,2-oxazol-3-yl)-2,3-dihydro-1-benzofuran-3-yl]carbamate (420 mg, 1.3 mmol, 1.0 equiv) in DCM (20 mL) was added hydrogen chloride (4M in dioxane, 3.2 mL, 10.0 equiv). The resulting solution was stirred at r.t. overnight. The solids were collected by filtration to afford 275 mg (81%) of (3S)-6-(5-ethyl-1,2-oxazol-3-yl)-2,3-dihydro-1-benzofuran-3-amine hydrochloride as a light yellow solid.

6. Synthesis of Compound 423:

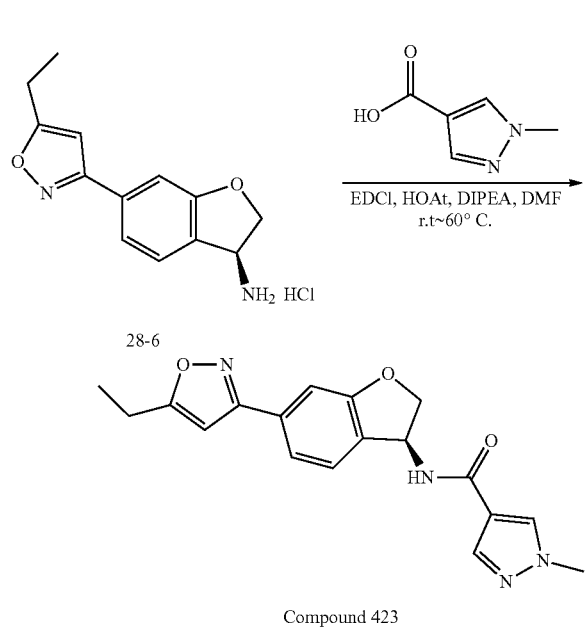

Compound 423

To a solution of (3S)-6-(5-ethyl-1,2-oxazol-3-yl)-2,3-dihydro-1-benzofuran-3-amine hydrochloride (65 mg, 0.24 mmol, 1.0 equiv) in DMF (2 mL) were added 1-methyl-1H-pyrazole-4-carboxylic acid (37 mg, 0.29 mmol, 1.2 equiv), EDCI (56 mg, 0.29 mmol, 1.2 equiv), HOAt (40 mg, 0.29 mmol, 1.20 equiv), and DIEA (94 mg, 0.73 mmol, 3.0 equiv). The mixture was stirred at r.t. overnight and combined with previous batches (0.21 and 1.16 mmol of amine SM). The resulting solution was poured into water (10 mL) and extracted with EA (10 mL) three times. The combined organic layers were dried over anhydrous sodium sulfate, concentrated under reduced pressure, and purified by C-18 column chromatography (H₂O/ACN=45/55) to afford 111 mg of (S)—N-(6-(5-ethylisoxazol-3-yl)-2,3-dihydrobenzofuran-3-yl)-1-methyl-1H-pyrazole-4-carboxamide (Compound 423) as a white solid. LRMS (ES) m/z 339 (M+H). ¹H-NMR: (400 MHz, DMSO-d6, ppm): δ 8.68 (d, J=7.5 Hz, 1H), 8.18 (s, 1H), 7.88 (d, J=0.8 Hz, 1H), 7.43 (d, J=1.6 Hz, 2H), 7.33 (d, J=1.2 Hz, 1H), 6.82 (t, J=0.9 Hz, 1H), 5.81-5.70 (m, 1H), 4.80 (dd, J=9.7, 8.8 Hz, 1H), 4.38 (dd, J=9.7, 5.0 Hz, 1H), 3.85 (s, 3H), 2.81 (qd, J=7.6, 0.9 Hz, 2H), 1.28 (t, J=7.6 Hz, 3H).

The following compounds were prepared by methods analogous to the method described for Compound 423:

| Compound No. | LRMS (ES) m/z |
|---|---|
| 421 | M + H = 339 |
| 422 | M + H = 340 |
| 424 | M + H = 340 |
| 425 | M + H = 350 |
| 426 | M + Na = 347 |
| 427 | M + H = 325 |
| 428 | M + H = 326 |
| 429 | M + H = 326 |
| 430 | M + H = 336 |
| 434 | M + H = 325 |

Example 29

Synthesis of Compound 431

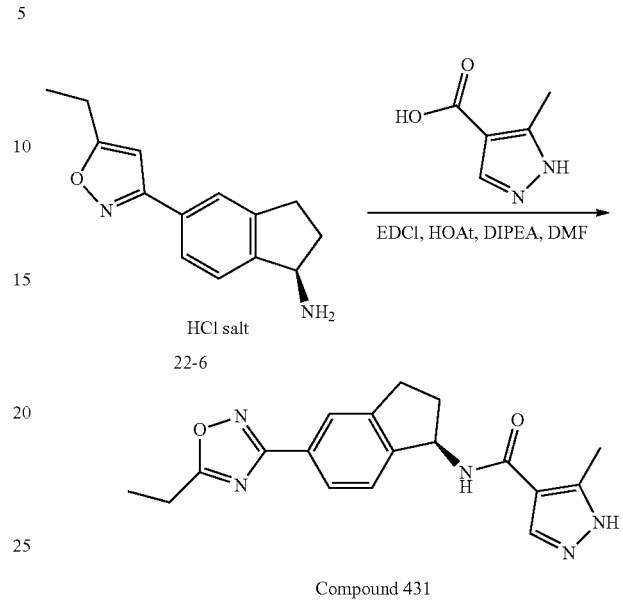

Compound 431

To a solution of 5-methyl-1H-pyrazole-4-carboxylic acid (73 mg, 0.58 mmol, 1.50 equiv) in DMF (2 mL) were added HOAt (105 mg, 0.8 mmol, 2.0 equiv), EDCI (148 mg, 0.8 mmol, 2.00 equiv), DIEA (249 mg, 1.9 mmol, 5.0 equiv), and (R)-5-(5-ethylisoxazol-3-yl)-2,3-dihydro-1H-inden-1-amine hydrochloride (102.5 mg, 0.4 mmol, 1.00 equiv). The mixture was stirred at r.t. overnight and purified by Prep-HPLC with the following conditions: (2#-AnalyseHPLC-SHIMADZU(HPLC-10): Column, X-Bridge Shield RP18 OBD Column, 5 um, 19*150 mm; mobile phase, Water (10 mmol/L NH₄HCO₃) and ACN (30.0% ACN up to 45.0% in 8 min; Detector, UV 254 nm). This purification gave 28.5 mg (22%) of (R)—N-(5-(5-ethylisoxazol-3-yl)-2,3-dihydro-1H-inden-1-yl)-5-methyl-1H-pyrazole-4-carboxamide (Compound 431) as a white solid. LRMS (ES) m/z 337 (M+H). ¹H-NMR: (400 MHz, Methanol-d₄) δ 7.96 (s, 1H), 7.74 (s, 1H), 7.71-7.65 (m, 1H), 7.40 (d, J=7.9 Hz, 1H), 6.58 (t, J=0.9 Hz, 1H), 5.65 (t, J=8.0 Hz, 1H), 3.19-3.07 (m, 1H), 3.05-2.93 (m, 1H), 2.86 (qd, J=7.4, 0.9 Hz, 2H), 2.64 (ddd, J=12.7, 7.9, 3.2 Hz, 1H), 2.56 (s, 3H), 2.05 (dq, J=12.8, 8.7 Hz, 1H), 1.37 (t, J=7.6 Hz, 3H).

Example 30

Synthesis of Compound 433

1. Synthesis of Intermediate 30-2:

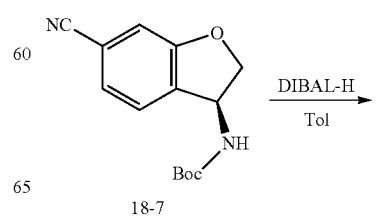

18-7

-continued

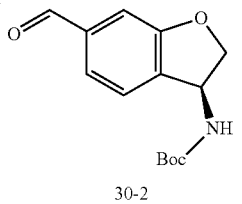

30-2

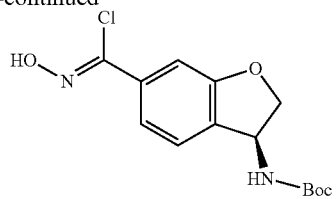

30-4

To a solution of tert-butyl N-[(3S)-6-cyano-2,3-dihydro-1-benzofuran-3-yl]carbamate (6.4 g, 24.6 mmol, 1.0 equiv) in toluene (100 mL) cooled to 0° C. was added DIBAL-H (43.9 mL, 2.20 equiv) dropwise under nitrogen. The mixture was stirred at 0° C. for 2 h, quenched with ice water (10 mL) and NaOH solution (10%, 10 mL), and filtered to remove the solids. The filtrate was dried over anhydrous sodium sulfate and concentrated under reduced pressure to afford 5.8 g of tert-butyl N-[(3S)-6-formyl-2,3-dihydro-1-benzofuran-3-yl]carbamate as a light yellow solid, which was used into the next step without further purification.

2. Synthesis of Intermediate 30-3:

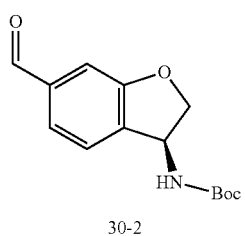

30-2

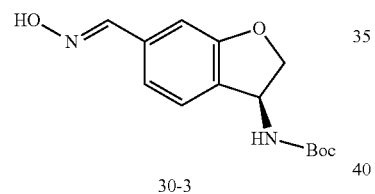

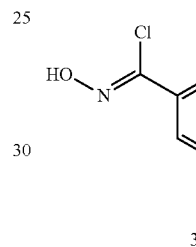

30-3

To a solution of tert-butyl N-[(3S)-6-formyl-2,3-dihydro-1-benzofuran-3-yl]carbamate (5.8 g, 22.0 mmol, 1.0 equiv) in a mixture of ethanol and Py (100/50 mL) was added hydroxylamine hydrochloride (1.83 g, 26.3 mmol, 1.2 equiv). The mixture was stirred at room temperature for 3 h, concentrated under vacuum to ~20 mL in volume, and poured into EA (40 mL) and water (40 mL). The aqueous layer was extracted with ethyl acetate (50 mL) three times. The combined organic layers were washed with brine (100 mL) and concentrated under vacuum to afford 6.0 g of tert-butyl N-[(3S)-6-[(1E)-(hydroxyimino)methyl]-2,3-dihydro-1-benzofuran-3-yl]carbamate as a white solid, which was used into the next step without further purification.

3. Synthesis of Intermediate 30-4:

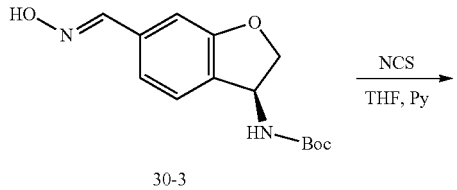

30-3

To a solution of tert-butyl N-[(3S)-6-[(1E)-(hydroxyimino)methyl]-2,3-dihydro-1-benzofuran-3-yl]carbamate (6.0 g, 21.5 mmol, 1.0 equiv) in THF (10 mL) were added pyridine (1.4 g, 17.1 mmol, 0.8 equiv) and NCS (5.2 g, 38.7 mmol, 1.80 equiv). The mixture was stirred at r.t. overnight and concentrated to dryness to give 9.1 g of tert-butyl N-[(3S)-6-[(1Z)-chloro(hydroxyimino)methyl]-2,3-dihydro-1-benzofuran-3-yl]carbamate as a white solid, which was used into the next step without further purification.

4. Synthesis of Intermediate 30-5:

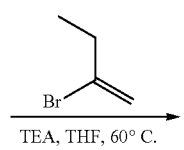

30-4

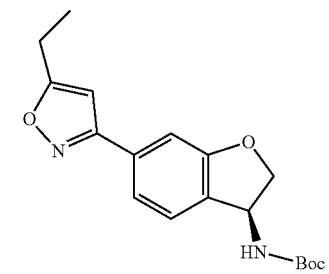

30-5

To a solution of tert-butyl N-[(3S)-6-[(1Z)-chloro(hydroxyimino)methyl]-2,3-dihydro-1-benzofuran-3-yl]carbamate (3.6 g, 11.6 mmol, 1.0 equiv) in THF (80 mL) were added TEA (4.3 g, 42.9 mmol, 5.0 equiv) and 2-bromobut-1-ene (1.7 g, 12.9 mmol, 1.5 equiv). The mixture was stirred at room temperature for 2 h, heated to 60° C. for 2 h, and poured into EA (100 mL) and water (100 mL). The aqueous layer was extracted with ethyl acetate (50 mL) three times. The combined organic layers were dried over anhydrous sodium sulfate, concentrated under reduced pressure, and purified by a C18 column with H$_2$O:ACN (50:50) as eluent to afford 424 mg (11%) of tert-butyl N-[(3S)-6-(5-ethyl-1,2-oxazol-3-yl)-2,3-dihydro-1-benzofuran-3-yl]carbamate as a white solid.

5. Synthesis of Intermediate 30-6:

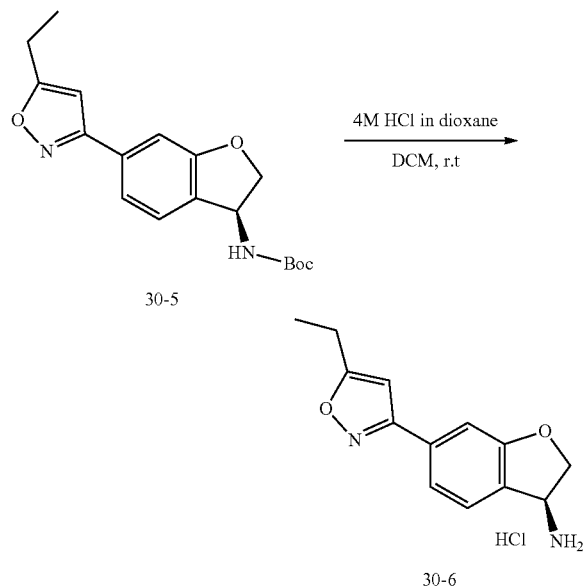

To a solution of tert-butyl N-[(3S)-6-(5-ethyl-1,2-oxazol-3-yl)-2,3-dihydro-1-benzofuran-3-yl]carbamate (420 mg, 1.8 mmol, 1.0 equiv) in DCM (20 mL) was added hydrogen chloride (4 M in dioxane, 3.2 mL, 10.0 equiv). The mixture was stirred overnight at room temperature and the solid was collected by filtration to afford 275 mg of (3S)-6-(5-ethyl-1,2-oxazol-3-yl)-2,3-dihydro-1-benzofuran-3-amine hydrochloride as a light yellow solid, which was used into the next step without further purification.

6. Synthesis of Compound 433:

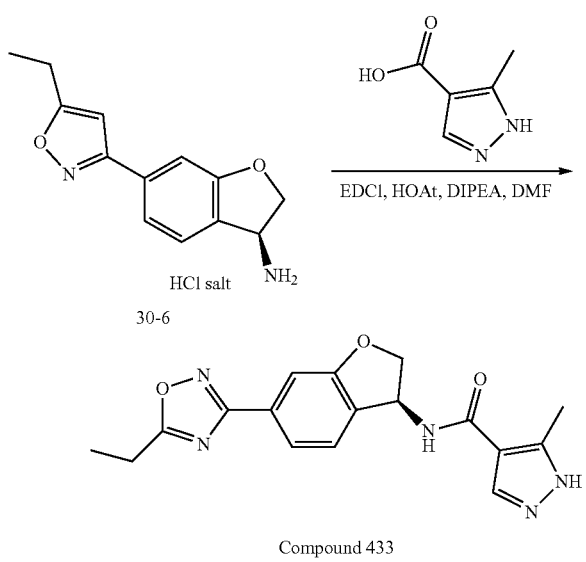

To a solution of (3S)-6-(5-ethyl-1,2-oxazol-3-yl)-2,3-dihydro-1-benzofuran-3-amine hydrochloride (70 mg, 0.3 mmol, 1.0 equiv) in DMF (2 mL) were added 5-methyl-1H-pyrazole-4-carboxylic acid (40 mg, 0.3 mmol, 1.2 equiv), EDCI (60 mg, 0.3 mmol, 1.2 equiv), HOAt (43 mg, 0.3 mmol, 1.2 equiv), and DIEA (101 mg, 3.00 equiv). The mixture was stirred overnight, diluted with water (20 mL), and extracted with EA (20 mL) three times. The combined organic layers were dried over anhydrous sodium sulfate, concentrated under reduced pressure, and purified by Prep-HPLC with the following conditions: (2#-AnalyseHPLC-SHIMADZU(HPLC-10)): Column, XBridge Prep C18 OBD Column, 5 um, 19*150 mm; mobile phase, Water (10 MMOL/L $NH_4HCO_3$) and ACN (29.0% ACN up to 43.0% in 8 min); Detector, UV 254 nm. The purification afforded 60.3 mg (68%) of (S)—N-(6-(5-ethylisoxazol-3-yl)-2,3-dihydrobenzofuran-3-yl)-5-methyl-1H-pyrazole-4-carboxamide (Compound 433) as a white solid. LRMS (ES) m/z 339 (M+H). $^1$H-NMR: (400 MHz, DMSO-d6, ppm): δ 12.87 (s, 1H), 8.52 (d, J=7.5 Hz, 1H), 7.92 (s, 1H), 7.48-7.38 (m, 2H), 7.32 (s, 1H), 6.82 (d, J=1.0 Hz, 1H), 5.77 (d, J=8.1 Hz, 1H), 4.81 (t, J=9.2 Hz, 1H), 4.37 (dd, J=9.6, 5.4 Hz, 1H), 2.86-2.75 (m, 2H), 2.46 (s, 2H), 2.38 (s, 1H), 1.28 (t, J=7.6 Hz, 3H).

Example 31

Synthesis of Compound 474

1. Synthesis of Intermediate 31-2:

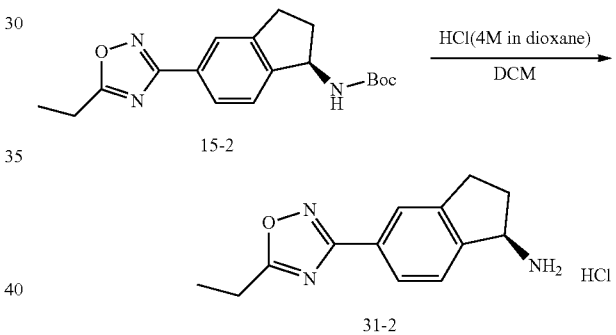

To a solution of tert-butyl N-[(1R)-5-(5-ethyl-1,2,4-oxadiazol-3-yl)-2,3-dihydro-1H-inden-1-yl]carbamate (23 g, 70 mmol, 1 equiv) in DCM was added HCl (4 M in dioxane, 174.8 mL, 698.3 mmol, 10 equiv) at r.t. The mixture was stirred at r.t. overnight and diluted with EA (500 mL). The precipitated solids were collected by filtration, washed with PE (200 mL) twice, and dried under high vacuum to afford (1R)-5-(5-ethyl-1,2,4-oxadiazol-3-yl)-2,3-dihydro-1H-inden-1-amine hydrochloride (16 g, 86%) as a white solid.

2. Synthesis of Intermediate 31-3:

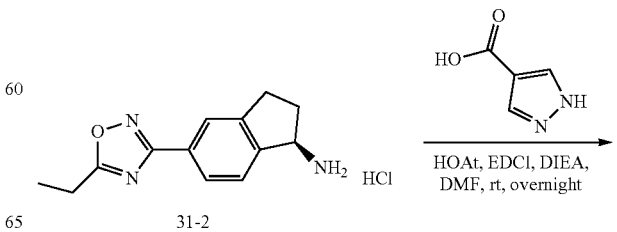

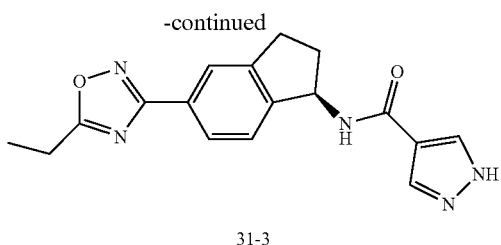

31-3

To a solution of (1R)-5-(5-ethyl-1,2,4-oxadiazol-3-yl)-2,3-dihydro-1H-inden-1-amine hydrochloride (15 g, 56.5 mmol, 1.0 equiv) and 1H-pyrazole-4-carboxylic acid (6.4 g, 57.1 mmol, 1.0 equiv) in DMF (300 mL) were added HOAt (11.5 g, 84.5 mmol, 1.5 equiv), DIEA (29.2 g, 225.9 mmol, 4.0 equiv), and EDCI (16.2 g, 84.5 mmol, 1.5 equiv) in portions at room temperature. After stirring for overnight at r.t, water (450 mL) was added slowly with stirring at 0° C. The precipitated solids were collected by filtration, washed with water (150 mL) twice, and dried under vacuum to afford (R)—N-(5-(5-ethyl-1,2,4-oxadiazol-3-yl)-2,3-dihydro-1H-inden-1-yl)-1H-pyrazole-4-carboxamide (14 g, 76.7%) as an off-white solid.

3. Synthesis of Compound 474:

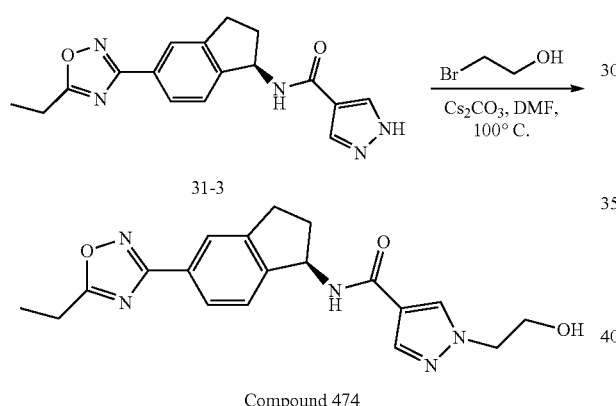

To a mixture of (R)—N-(5-(5-ethyl-1,2,4-oxadiazol-3-yl)-2,3-dihydro-1H-inden-1-yl)-1H-pyrazole-4-carboxamide (11.2 g, 34.67 mmol, 1 equiv) and Cs₂CO₃ (22.8 g, 70.1 mmol, 2.0 equiv) in DMF (200 mL) was added 2-bromoethan-1-ol (5.2 g, 41.3 mmol, 1.2 equiv) dropwise at r.t. under nitrogen atmosphere. After stirring at 100° C. for 1.5 h under nitrogen atmosphere, the resulting mixture was filtered, diluted with water (1 L) and extracted with EA (600 mL) three times. The combined organic layers were washed with brine (600 mL), dried over anhydrous Na₂SO₄, concentrated under reduced pressure, and purified by silica gel column chromatography (PE/EA 10/90) to afford product (8.3 g, 92% purity) as an off-white solid. The off-white solid was combined with a previous batch (Compound 474, 1.8 g, 92% purity) and purified by reverse phase to afford product (8.1 g, 98% purity, 92.4% ee) as a white solid. It was then stirred in a mixture of THF/EA (1/2) and filtered to afford (R)—N-(5-(5-ethyl-1,2,4-oxadiazol-3-yl)-2,3-dihydro-1H-inden-1-yl)-1-(2-hydroxyethyl)-1H-pyrazole-4-carboxamide (Compound 474) (5.36 g, 99.6% ee) as a white solid. LRMS (ES) m/z 368 (M+H). LC-MS: (ES, m/z): [M+H]⁺ 368. ¹H-NMR: (400 MHz, DMSO-d₆, ppm) δ 8.46 (d, J=8.4 Hz, 1H), 8.22 (s, 1H), 7.91 (s, 1H), 7.90 (s, 1H), 7.86 (d, J=7.7 Hz, 1H), 7.36 (d, J=7.9 Hz, 1H), 5.56 (q, J=8.3 Hz, 1H), 4.94 (t, J=5.3 Hz, 1H), 4.15 (t, J=5.4 Hz, 2H), 3.73 (q, J=5.4 Hz, 2H), 3.03 (m, 3H), 2.92 (dt, J=16.4, 8.5 Hz, 1H), 2.57-2.34 (m, 1H), 1.99 (dt, J=12.5, 8.9 Hz, 1H), 1.35 (t, J=7.6 Hz, 3H).

The following compounds were prepared by methods analogous to the method described for Compound 474:

| Compound No. | LRMS (ES) m/z |
|---|---|
| 539 | M + H = 398 |
| 540 | M + H = 398 |

Alternative Synthesis of Compound 474

1. Synthesis of Intermediate 31-2a:

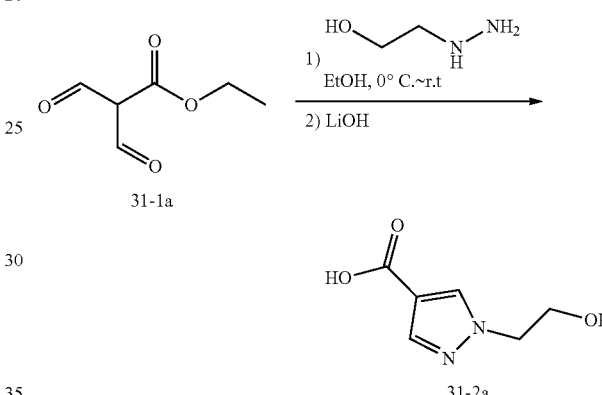

To a solution of ethyl 2-formyl-3-oxopropanoate (25.3 g, 144.1 mmol, 1.09 equiv) in EtOH (100 mL) was added 2-hydrazinylethan-1-ol (96% pure, 12.4 g, 156 mmol, 1.00 equiv) in EtOH (50.0 mL) at 0° C. The mixture was stirred at r.t. overnight, added LiOH (7.5 g, 312.5 mmol), heated to reflux overnight, cooled to r.t. and added MTBE (400 mL). The solid was collected and dried. The solid was then transferred to a 500 mL RB in ice bath. To this mixture was added HCl (6 N) until it reached to pH 1 and continue to stirred at 0° C. for 30 min before filtration. The solid was collected and dried to give (18.8 g, 120.4 mmol, 77.1%) of 1-(2-hydroxyethyl)-1H-pyrazole-4-carboxylic acid as a pale yellow solid. LRMS (ES) m/z 157.1 (M+H). ¹H NMR (400 MHz, DMSO-d₆) δ 12.26 (s, 1H), 8.18 (d, J=0.7 Hz, 1H), 7.79 (d, J=0.7 Hz, 1H), 4.92 (t, J=5.3 Hz, 1H), 4.17 (t, J=5.5 Hz, 2H), 3.77-3.70 (m, 2H).

2. Synthesis of Compound 474:

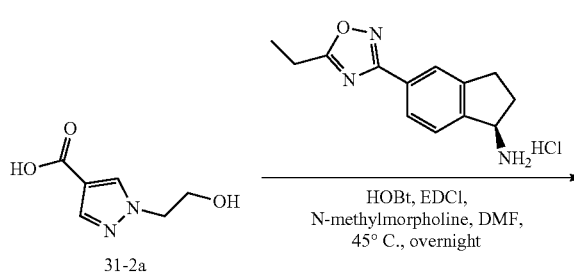

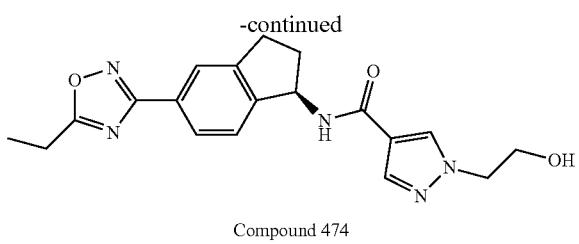

Compound 474

To a solution of 1-(2-hydroxyethyl)-1H-pyrazole-4-carboxylic acid (15.0 g, 96.1 mmol, 1.05 equiv), (R)-5-(5-ethyl-1,2,4-oxadiazol-3-yl)-2,3-dihydro-1H-inden-1-amine hydrochloride (24.3 g, 91.5 mmol, 1.0 equiv), HOBt (0.62 g, 4.6 mmol, 9.05 mmol), N-methylmorpholine (32.4 g, 320.2 mmol, 3.5 equiv.) in EtOH (200 mL) was added EDCI (19.3 g, 100.6 mmol, 1.10 equiv) at r.t. The mixture was then heated to 45° C. overnight, added water (700 mL), stirred for 1 h with heat off, and filtered. The solid was washed with additional water (200 mL) and dried to give (R)—N-(5-(5-ethyl-1,2,4-oxadiazol-3-yl)-2,3-dihydro-1H-inden-1-yl)-1-(2-hydroxyethyl)-1H-pyrazole-4-carboxamide (Compound 474) (32.9 g, 89.5 mmol) as an off-white solid. LRMS (ES) m/z 368.2 (M+H). $^1$H NMR (400 MHz, DMSO-$d_6$) δ 8.45 (d, J=8.4 Hz, 1H), 8.21 (d, J=0.7 Hz, 1H), 7.94-7.88 (m, 2H), 7.85 (dd, J=7.8, 1.5 Hz, 1H), 7.36 (d, J=7.9 Hz, 1H), 5.56 (q, J=8.3 Hz, 1H), 4.94 (t, J=5.3 Hz, 1H), 4.15 (t, J=5.4 Hz, 2H), 3.72 (q, J=5.4 Hz, 2H), 3.11-2.86 (m, 4H), 2.43-2.51 (m, 1H), 1.98 (dq, J=12.5, 9.0 Hz, 1H), 1.35 (t, J=7.6 Hz, 3H).

The following compounds were prepared by methods analogous to the method described for the alternative synthesis of Compound 474:

| Compound No. | LRMS (ES) m/z |
|---|---|
| 572 | M + H = 382.2 |
| 576 | M + H = 394.1 |
| 577 | M + H = 365.1 |
| 649 | M + H = 382.2 |
| 651 | M + H = 378.2 |
| 652 | M + H = 365.2 |
| 653 | M + H = 364.2 |
| 654 | M + H = 382.2 |
| 659 | M + H = 378.2 |
| 700 | M + H = 394.1 |
| 727 | M + H = 381.1 |

Example 32

Synthesis of Compound 495

1. Synthesis of Intermediate 32-2:

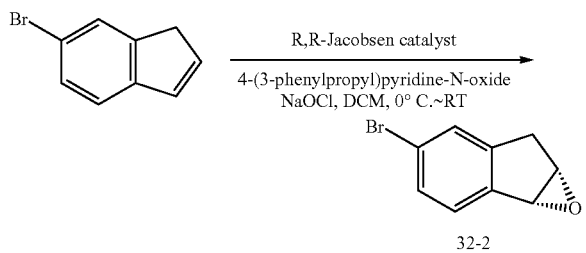

To a solution of 4-(3-phenylpropyl)pyridine-N-oxide (230 mg, 0.02 equiv) in DCM (20 mL) cooled to 0° C. were added R,R-Jacobsen catalyst (200 mg, 0.07 equiv) and sodium hypochlorite (8%-10% aqueous solution, 21.9 g, 1.7 equiv) dropwise under nitrogen. The mixture was stirred at 0° C. for 15 min and a solution of 6-bromo-1H-indene (3.0 g, 15.4 mmol, 1.00 equiv) in DCM (20 mL) was added dropwise at 0° C., followed by sodium hypochlorite (8%-10% aqueous solution, 21.9 g, 1.7 equiv). The mixture was then stirred at 0° C. for 1 h and r.t. for 2.5 h, poured into water (100 mL) and DCM (50 mL), and filtered to remove the solids. The aqueous layer was extracted with DCM (100 mL) twice. The combined organic layers were washed with brine (100 mL), dried over anhydrous sodium sulfate, concentrated under reduced pressure, and purified by silica gel chromatography (EA/PE, 1/3) to afford 700 mg (22%) of a mixture of (1aS,6bR)-4-bromo-1aH,2H,6bH-indeno[1,2-b] oxirene and (1aR,6aS)-4-bromo-1a,6a-dihydro-6H-indeno[1,2-b]oxirene.

2. Synthesis of Intermediate 32-3:

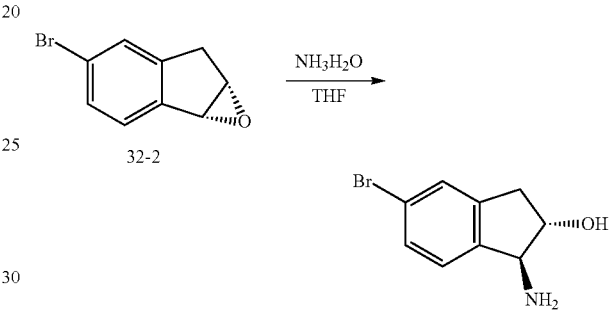

To a solution of (1aR,6aS)-4-bromo-1a,6a-dihydro-6H-indeno[1,2-b]oxirene (700 mg, 3.32 mmol, 1.0 equiv) in THF (7 mL) was added ammonium hydroxide (25%-28%, 7 mL). The mixture was stirred at 80° C. overnight and concentrated under reduced pressure to afford 760 mg of (1S,2S)-1-amino-5-bromo-2,3-dihydro-1H-inden-2-ol as a brown solid.

3. Synthesis of Intermediate 32-4:

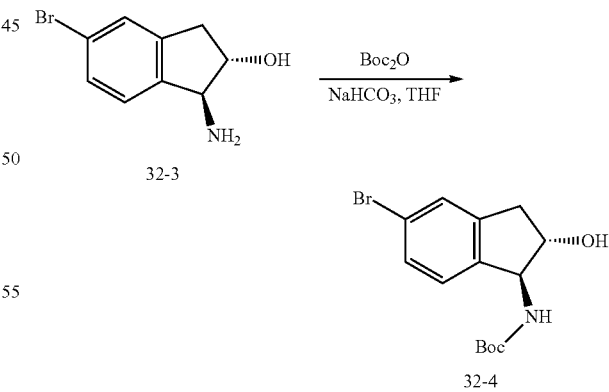

To a solution of (1S,2S)-1-amino-5-bromo-2,3-dihydro-1H-inden-2-ol (760 mg, 3.3 mmol, 1.0 equiv) in THF (6 mL) were added sodium bicarbonate (844 mg, 10.0 mmol, 3.0 equiv) and a solution of (Boc)$_2$O (876 mg, 4.01 mmol, 1.2 equiv) in THF (4 mL) dropwise. The mixture was stirred for 3 h, poured into water (50 mL), and extracted with EA (80 mL) twice. The combined organic layers were washed with brine (80 mL), dried over anhydrous sodium sulfate, and concentrated under reduced pressure to afford 1.1 g of tert-butyl N-[(1S,2S)-5-bromo-2-hydroxy-2,3-dihydro-1H-inden-1-yl]carbamate as a yellow solid.

4. Synthesis of Intermediate 32-5:

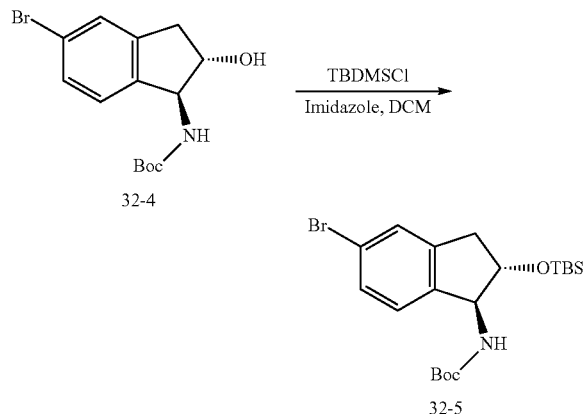

To a solution of tert-butyl N-[(1S,2S)-5-bromo-2-hydroxy-2,3-dihydro-1H-inden-1-yl]carbamate (1.1 g, 3.4 mmol, 1.0 equiv) in DCM (10 mL) were added imidazole (0.46 g, 2.0 equiv) and tert-butyl(chloro)dimethylsilane (530 mg, 3.52 mmol, 1.5 equiv). The mixture was stirred for 3 h, poured into water (80 mL), and extracted with EA (80 mL) twice. The combined organic layers were washed with brine (80 mL), dried over anhydrous sodium sulfate, concentrated under reduced pressure, and purified by silica gel chromatography (EA/PE, 3/97) to afford 0.95 g (64%) of tert-butyl N-[(1S,2S)-5-bromo-2-[(tert-butyldimethylsilyl)oxy]-2,3-dihydro-1H-inden-1-yl]carbamate as a light yellow solid.

5. Synthesis of Intermediate 32-6:

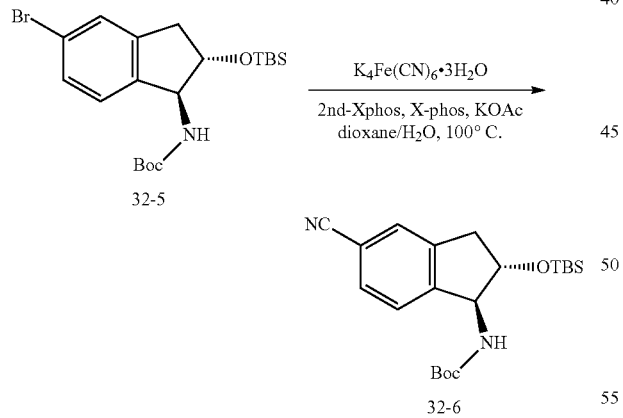

To a solution of tert-butyl N-[(1S,2S)-5-bromo-2-[(tert-butyldimethylsilyl)oxy]-2,3-dihydro-1H-inden-1-yl]carbamate (950 mg, 2.15 mmol, 1.00 equiv) in a mixture of dioxane and water (30 mL, 1/1) were added KOAc (422 mg, 4.3 mmol, 2.0 equiv), X-phos (103 mg, 0.22 mmol, 0.10 equiv), 2nd-Xphos (169 mg, 0.21 mmol, 0.10 equiv) and $K_4Fe(CN)_6 \cdot 3H_2O$ (909 mg, 2.15 mmol, 1.0 equiv) under nitrogen. The mixture was stirred at 90° C. for 3 h, cooled to r.t., poured into water (100 mL), and extracted with EA (100 mL) twice. The combined organic layers were washed with brine (100 mL) twice, dried over anhydrous sodium sulfate, concentrated under reduced pressure, and purified by silica gel chromatography (EA/PE, 8/92) to afford 644 mg (77%) of tert-butyl N-[(1S,2S)-2-[(tert-butyldimethylsilyl)oxy]-5-cyano-2,3-dihydro-1H-inden-1-yl]carbamate as a light yellow foam.

6. Synthesis of Intermediate 32-7:

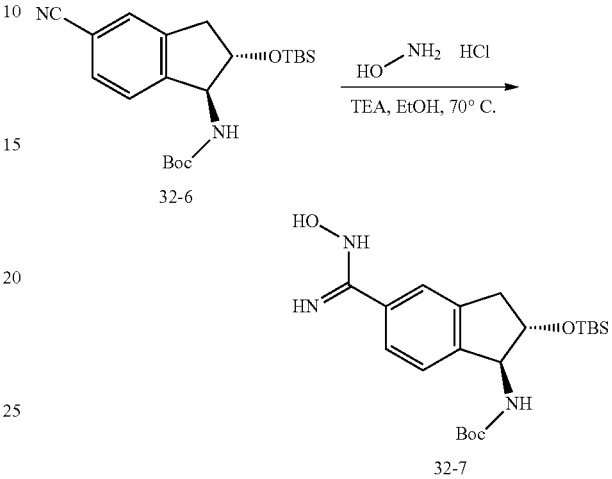

To a solution of tert-butyl N-[(1S,2S)-2-[(tert-butyldimethylsilyl)oxy]-5-cyano-2,3-dihydro-1H-inden-1-yl]carbamate (520 mg, 1.34 mmol, 1.0 equiv) in ethanol (10 mL) were added TEA (271 mg, 2.68 mmol, 2.0 equiv) and hydroxylamine hydrochloride (139 mg, 2.0 mmol, 1.5 equiv). The mixture was stirred at 70° C. for 3 h, cooled to r.t., and concentrated under reduced pressure to afford 560 mg of tert-butyl N-[(1S,2S)-2-[(tert-butyldimethylsilyl)oxy]-5-(N-hydroxycarbamimidoyl)-2,3-dihydro-1H-inden-1-yl]carbamate as a white solid.

7. Synthesis of Intermediate 32-8:

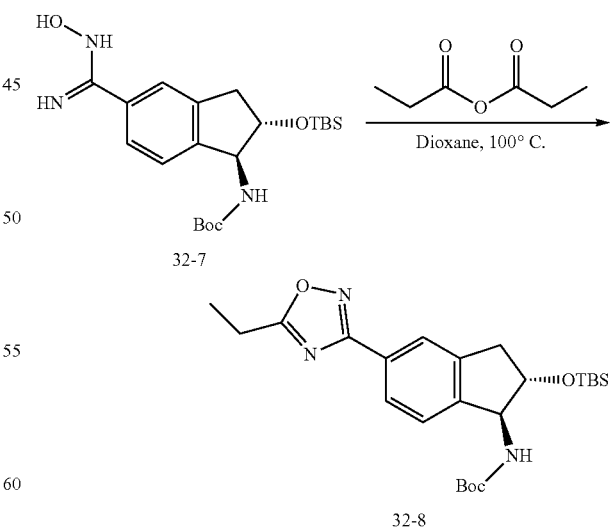

To a solution of tert-butyl N-[(1S,2S)-2-[(tert-butyldimethylsilyl)oxy]-5-(N-hydroxycarbamimidoyl)-2,3-dihydro-1H-inden-1-yl]carbamate (560 mg, 1.33 mmol, 1.0 equiv) in dioxane (11 mL) was added propanoyl propanoate (190 mg, 1.46 mmol, 1.1 equiv). The mixture was stirred at 50° C. for 1 h and at 100° C. overnight, cooled to r.t., concentrated under reduced pressure, and purified by silica gel chromatography (EA/PE, 9/91) to afford 460 mg (75%) of tert-butyl N-[(1S,2S)-2-[(tert-butyldimethylsilyl)oxy]-5-(5-ethyl-1,2,4-oxadiazol-3-yl)-2,3-dihydro-1H-inden-1-yl]carbamate as a white solid.

8. Synthesis of Intermediate 32-9:

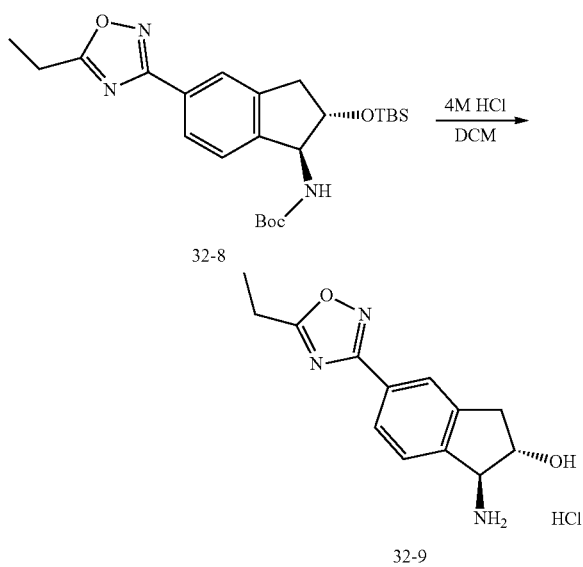

To a solution of tert-butyl N-[(1S,2S)-2-[(tert-butyldimethylsilyl)oxy]-5-(5-ethyl-1,2,4-oxadiazol-3-yl)-2,3-dihydro-1H-inden-1-yl]carbamate (460 mg, 1.0 mmol, 1.0 equiv) in DCM (5 mL) was added hydrogen chloride (4 M in dioxane, 10 mL). The mixture was stirred overnight and concentrated under reduced pressure to afford 280 mg (99%) of (1S,2S)-1-amino-5-(5-ethyl-1,2,4-oxadiazol-3-yl)-2,3-dihydro-1H-inden-2-ol hydrochloride as an off-white solid.

9. Synthesis of Compound 495:

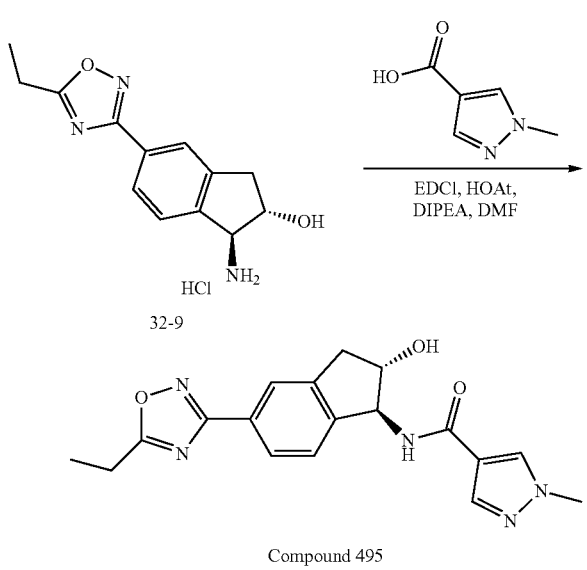

Compound 495

To a solution of 1-methyl-1H-pyrazole-4-carboxylic acid (60 mg, 0.48 mmol, 1.2 equiv) in DMF (2 mL) were added EDCI (38 mg, 0.20 mmol, 2.0 equiv), DIEA (64 mg, 0.50 mmol, 5.0 equiv), HOAt (108 mg, 0.79 mmol, 2.00 equiv), and (1S,2S)-1-amino-5-(5-ethyl-1,2,4-oxadiazol-3-yl)-2,3-dihydro-1H-inden-2-ol hydrochloride (112 mg, 0.4 mmol, 1.0 equiv). The mixture was stirred for 2 h and purified by Prep-HPLC with the following conditions: (2#-Analyse HPLC-SHIMADZU(HPLC-10)): Column, XBridge Prep C18 OBD Column, 5 um, 19*150 mm; mobile phase, Water (10 MMOL/L $NH_4HCO_3$) and ACN (21.0% ACN up to 33.0% in 8 min); Detector, UV 254 nm. This resulted in 48 mg (34%) of N-((1S,2S)-5-(5-ethyl-1,2,4-oxadiazol-3-yl)-2-hydroxy-2,3-dihydro-1H-inden-1-yl)-1-methyl-1H-pyrazole-4-carboxamide (Compound 495) as a white solid. LRMS (ES) m/z 354 (M+H). $^1$H-NMR: 1H NMR (400 MHz, DMSO-d6) δ 8.43 (d, J=8.5 Hz, 1H), 8.20 (s, 1H), 7.92 (s, 1H), 7.86 (d, J=5.5 Hz, 2H), 7.26 (d, J=8.0 Hz, 1H), 5.44 (d, J=5.8 Hz, 1H), 5.28 (t, J=7.9 Hz, 1H), 4.40 (q, J=7.1 Hz, 1H), 3.88 (d, J=1.7 Hz, 3H), 3.27 (dd, J=15.6, 7.3 Hz, 1H), 3.07-2.96 (m, 2H).

Example 33

Synthesis of Compound 517

1. Synthesis of Intermediate 33-2:

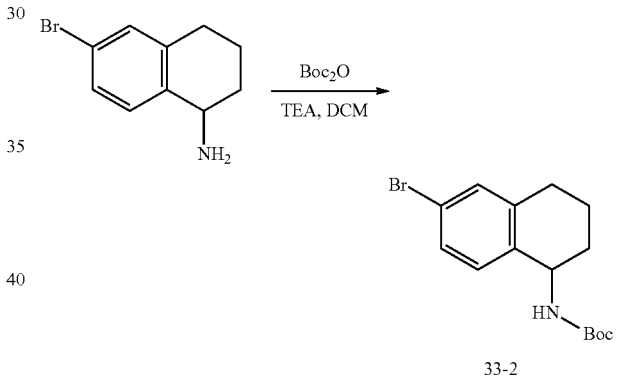

To a stirred mixture of 6-bromo-1,2,3,4-tetrahydronaphthalen-1-amine (1 g, 4.44 mmol, 1.0 equiv) and TEA (0.9 g, 8.9 mmol, 2.0 equiv) in DCM (10 mL) cooled to 0° C. was added (Boc)$_2$O (1.4 g, 6.42 mmol, 1.45 equiv) in portions under argon atmosphere. The mixture was stirred for 1 h, diluted with DCM, washed with brine three times, dried over anhydrous sodium sulfate, and concentrated under reduced pressure to afford 1.5 g of tert-butyl N-(6-bromo-1,2,3,4-tetrahydronaphthalen-1-yl)carbamate as a light yellow solid.

2. Synthesis of Intermediate 33-3:

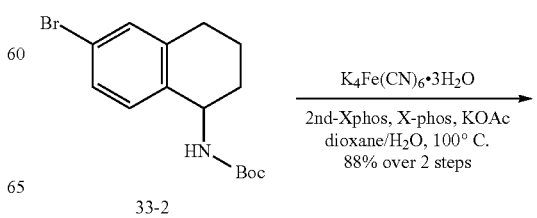

-continued

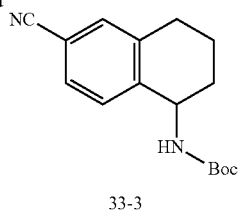

33-3

To a solution of tert-butyl N-(6-bromo-1,2,3,4-tetrahydronaphthalen-1-yl)carbamate (1.6 g, 4.92 mmol, 1.00 equiv) in a mixture of dioxane and water (32 mL, 1/1) were added KOAc (962 mg, 9.82 mmol, 2.0 equiv), X-phos (234 mg, 0.49 mmol, 0.1 equiv), 2nd-Xphos (386 mg, 0.49 mmol, 0.1 equiv), and $K_4Fe(CN)_6 \cdot 3H_2O$ (2.1 g, 4.98 mmol, 1.0 equiv) under nitrogen. The mixture was stirred at 80° C. for 2 h, cooled to r.t., poured into water (100 mL), and extracted with EA (50 mL) twice. The combined organic layers were washed with brine (100 mL) twice, dried over anhydrous sodium sulfate, concentrated under reduced pressure, and purified by silica gel chromatography (EA/PE, 1/10) to afford 1.06 g (79%) of tert-butyl N-(6-cyano-1,2,3,4-tetrahydronaphthalen-1-yl)carbamate as a white solid.

3. Synthesis of Intermediate 33-4:

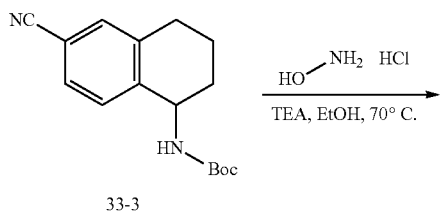

To a solution of tert-butyl N-(6-cyano-1,2,3,4-tetrahydronaphthalen-1-yl)carbamate (1.01 g, 3.71 mmol, 1.00 equiv) in ethanol (10 mL) were added TEA (750 mg, 7.42 mmol, 2.0 equiv) and hydroxylamine hydrochloride (384 mg, 5.57 mmol, 1.5 equiv). The mixture was stirred at 70° C. for 3 h, cooled to r.t., diluted with EA (50 mL), washed with brine (100 mL) twice, dried over anhydrous sodium sulfate, and concentrated under reduced pressure to afford 1.2 g of tert-butyl N-[6-(N-hydroxycarbamimidoyl)-1,2,3,4-tetrahydronaphthalen-1-yl]carbamate as a light yellow solid.

4. Synthesis of Intermediate 33-5:

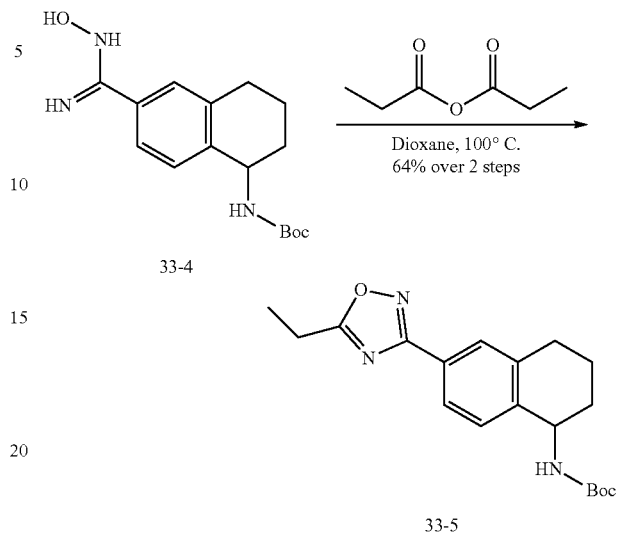

To a solution of tert-butyl N-[6-(N-hydroxycarbamimidoyl)-1,2,3,4-tetrahydronaphthalen-1-yl]carbamate (1.1 g, 3.60 mmol, 1.00 equiv) in dioxane (30 mL) was added propanoyl propanoate (703 mg, 5.40 mmol, 1.5 equiv). The mixture was stirred at 50° C. for 1 h and at 100° C. overnight, cooled to r.t., diluted with EA (50 mL), washed with brine (100 mL) twice, dried over anhydrous sodium sulfate, concentrated under reduced pressure, and purified by silica gel chromatography (EA/PE, 1/8) to afford 860 mg (70%) of tert-butyl N-[6-(5-ethyl-1,2,4-oxadiazol-3-yl)-1,2,3,4-tetrahydronaphthalen-1-yl]carbamate as a white solid.

5. Synthesis of Intermediate 33-6:

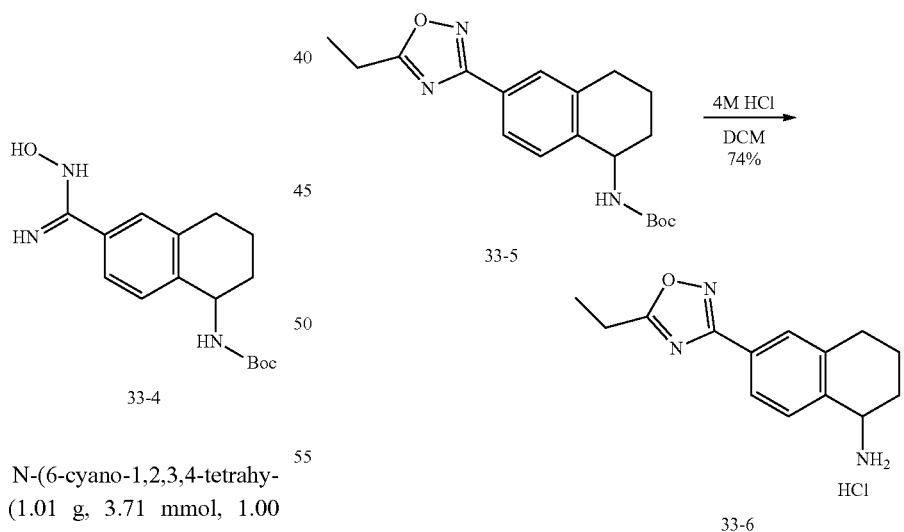

To a solution of tert-butyl N-[6-(5-ethyl-1,2,4-oxadiazol-3-yl)-1,2,3,4-tetrahydronaphthalen-1-yl]carbamate (860 mg, 2.50 mmol, 1.00 equiv) in DCM (5 mL) was added hydrogen chloride (4 M in dioxane, 10 mL). The mixture was stirred overnight and the solids were collected and dried to afford 520 mg (74%) of 6-(5-ethyl-1,2,4-oxadiazol-3-yl)-1,2,3,4-tetrahydronaphthalen-1-amine hydrogen chloride as a white solid.

6. Synthesis of Intermediate 33-7:

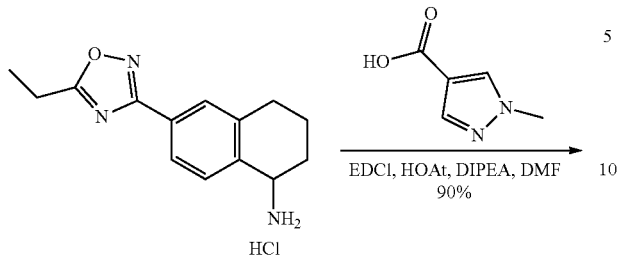

33-6

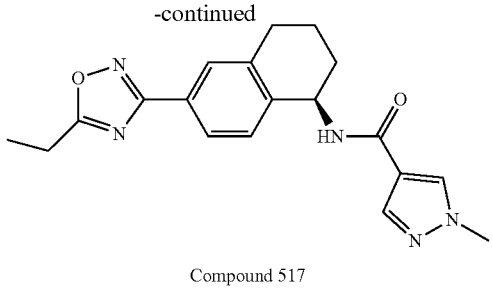

Compound 517

The racemic mixture (90 mg) was purified by Chiral-Prep-HPLC with the following conditions: (Prep-HPLC-009): Column, Chiralpak ID-2, 2*25 cm, 5 um; mobile phase, Hex- and ethanol- (hold 25.0% ethanol- in 20 min); Detector, UV 220/254 nm. This purification afforded 33.3 mg (37%) of (R)—N-(6-(5-ethyl-1,2,4-oxadiazol-3-yl)-1,2,3,4-tetrahydronaphthalen-1-yl)-1-methyl-1H-pyrazole-4-carboxamide (Compound 517) as a white solid. LRMS (ES) m/z 352 (M+H). $^1$H-NMR: (CD$_3$OD, 400 MHz, ppm): δ 8.10 (s, 1H), 7.94 (s, 1H), 7.83 (d, J=7.1 Hz, 2H), 7.39 (d, J=8.3 Hz, 1H), 5.35 (s, 1H), 3.94 (s, 3H), 3.06-2.85 (m, 4H), 2.16 (d, J=14.2 Hz, 1H), 2.06 (s, 1H), 1.93 (q, J=9.1, 8.4 Hz, 2H), 1.44 (t, J=7.6 Hz, 3H).

The following compounds were prepared by methods analogous to the method described for Compound 517:

| Compound No. | LRMS (ES) m/z |
| --- | --- |
| 516 | M + H = 352 |
| 525 | M + H = 352 |
| 526 | M + H = 352 |

33-7

To a solution of 1-methyl-1H-pyrazole-4-carboxylic acid (93 mg, 0.74 mmol, 1.38 equiv) in DMF (3.5 mL) were added DIEA (398 mg, 3.08 mmol, 5.7 equiv), HOAt (168 mg, 1.23 mmol, 2.3 equiv), and EDCI (237 mg, 1.23 mmol, 2.28 equiv). The mixture was stirred for 5 min and 6-(5-ethyl-1,2,4-oxadiazol-3-yl)-1,2,3,4-tetrahydronaphthalen-1-amine hydrogen chloride (150 mg, 0.54 mmol, 1.0 equiv) was added and the mixture was stirred for 1.5 h and subsequently purified by Prep-HPLC with the following conditions: (2#-AnalyseHPLC-SHIMADZU(HPLC-10)): Column, XBridge Prep C18 OBD Column, 5 um, 19*150 mm; mobile phase, Water (10 MMOL/L NH$_4$HCO$_3$) and ACN (25.0% ACN up to 55.0% in 8 min); Detector, UV 220 nm. This purification resulted in 170 mg (90%) of N-[6-(5-ethyl-1,2,4-oxadiazol-3-yl)-1,2,3,4-tetrahydronaphthalen-1-yl]-1-methyl-1H-pyrazole-4-carboxamide as a white solid. LRMS (ES) m/z 352 (M+H). $^1$H-NMR: 1H NMR (300 MHz, DMSO-d6) δ 8.43 (d, J=8.8 Hz, 1H), 8.19 (s, 1H), 7.90 (d, J=0.7 Hz, 1H), 7.78 (m, 2H), 7.34 (dd, J=8.5, 0.9 Hz, 1H), 5.23 (d, J=6.1 Hz, 1H), 3.85 (s, 3H), 3.01 (q, J=7.6 Hz, 2H), 2.87 (s, 2H), 2.03-1.93 (m, 2H), 1.80 (d, J=6.9 Hz, 2H), 1.34 (t, J=7.6 Hz, 3H).

7. Synthesis of Compound 517:

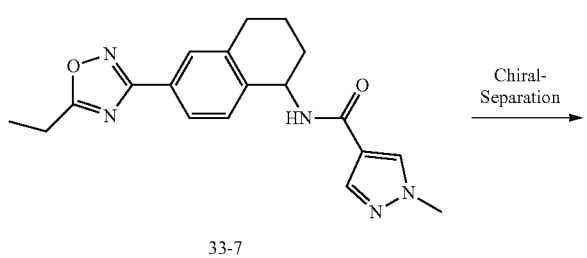

33-7

Chiral-Separation →

Example 34

Compound 538

1. Synthesis of Intermediate 34-2:

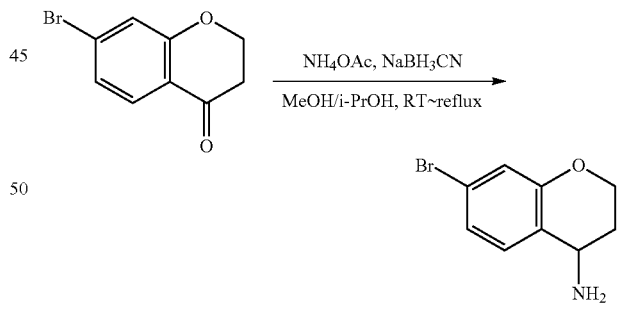

34-2

To a solution of 7-bromo-3,4-dihydro-2H-1-benzopyran-4-one (4.0 g, 17.6 mmol, 1.0 equiv) and NH$_4$OAc (27.2 g, 353 mmol, 20.0 equiv) in a mixture of MeOH (40 mL) and i-PrOH (50 mL) was added NaBH$_3$CN (5.5 g, 87.5 mmol, 5.0 equiv). The mixture was stirred at r.t. for 4 h and at 80° C. for 12 h, and concentrated to ~10 mL. The pH of the mixture was then adjusted to 8-9 with saturated NaHCO$_3$ solution and mixed with EA (100 mL) and water (100 mL). The resulting solution was separated and the aqueous phase was extracted with EA (100 mL) four times. The combined organic layers were washed with brine (100 mL), dried over anhydrous sodium sulfate, and concentrated under reduced pressure to afford 5.2 g of 7-bromo-3,4-dihydro-2H-1-benzopyran-4-amine as light yellow oil.

2. Synthesis of Intermediate 34-3:

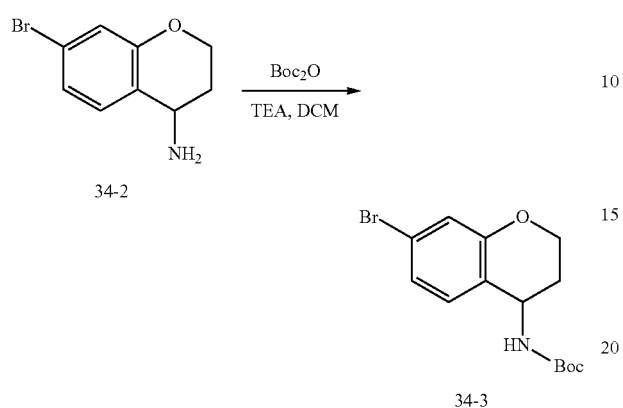

To a solution of 7-bromo-3,4-dihydro-2H-1-benzopyran-4-amine (4.0 g, 17.5 mmol, 1.0 equiv) in DCM (30 mL) cooled to −5° C. were added TEA (3.5 g, 35.1 mmol, 2.0 equiv) and a solution of (Boc)₂O (4.6 g, 21.1 mmol, 1.2 equiv) in DCM (10 mL) dropwise over a period of 45 min. The mixture was stirred at r.t. for 2 h, diluted with DCM (50 mL), washed with water (50 mL) and brine (30 mL) twice, dried over anhydrous sodium sulfate, concentrated under reduced pressure, and triturated with hexane to afford (7.2 g, 99%) of tert-butyl N-(7-bromo-3,4-dihydro-2H-1-benzopyran-4-yl)carbamate as a white solid.

3. Synthesis of Intermediate 34-4:

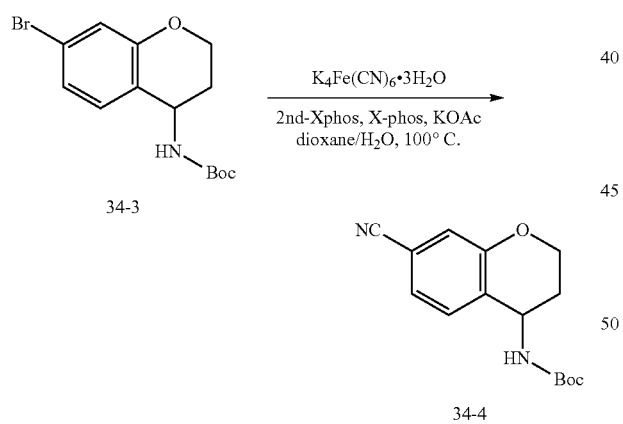

To a solution of tert-butyl N-(7-bromo-3,4-dihydro-2H-1-benzopyran-4-yl)carbamate (7.2 g, 21.9 mol, 1.0 equiv) in a mixture of dioxane and water (20 mL, 1/1) were added K₄Fe(CN)₆·3H₂O (0.7 g, 1.63 mmol, 0.3 equiv), X-phos (0.1 g, 0.11 mmol, 0.02 equiv), 2nd Generation X-Phos precatalyst (0.1 g, 0.11 mmol, 0.02 equiv) and potassium acetate (4.4 g, 44.8 mol, 2.04 equiv) under nitrogen. The mixture was stirred at 100° C. for 2 h, cooled to r.t., filtered to remove solids, poured into water (100 mL), and extracted with EA (50 mL) twice. The combined organic layers were washed with brine (100 mL) twice, dried over anhydrous sodium sulfate, concentrated under reduced pressure, and purified by silica gel chromatography (EA/PE, 1/10) to afford 3.0 g (50%) of tert-butyl N-(7-cyano-3,4-dihydro-2H-1-benzopyran-4-yl)carbamate as a white solid.

4. Synthesis of Intermediate 34-5:

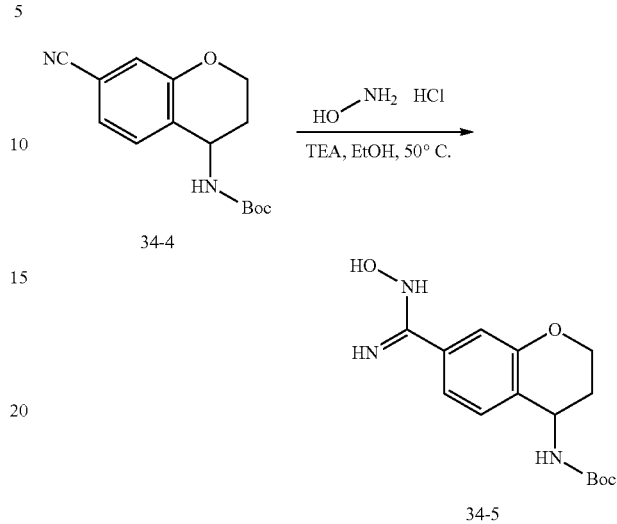

To a solution of tert-butyl N-(7-cyano-3,4-dihydro-2H-1-benzopyran-4-yl)carbamate (2.0 g, 7.29 mmol, 1.0 equiv) in ethanol (20 mL) were added TEA (1.5 g, 14.6 mmol, 2.0 equiv) and hydroxylamine hydrochloride (1.0 g, 14.6 mmol, 2.0 equiv). The mixture was stirred at 50° C. for 4 h, cooled to r.t., diluted with EA (120 mL), washed with brine (10 mL) twice, dried over anhydrous sodium sulfate, and concentrated under reduced pressure to afford 2.15 g of tert-butyl N-[7-(N-hydroxycarbamimidoyl)-3,4-dihydro-2H-1-benzopyran-4-yl]carbamate as light yellow oil.

5. Synthesis of Intermediate 34-6:

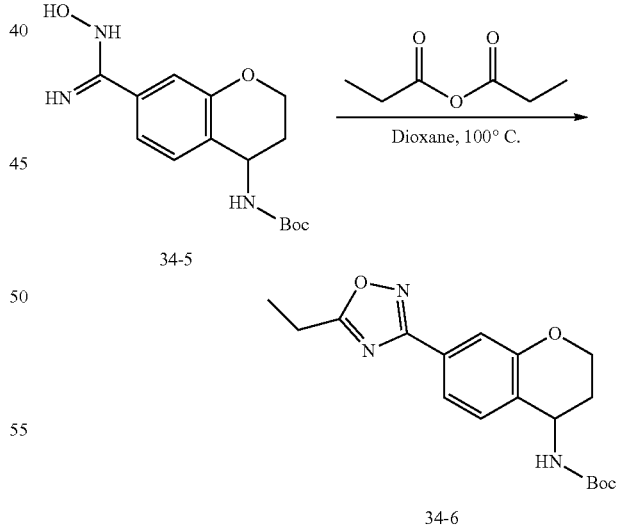

To a solution of tert-butyl N-[7-(N-hydroxycarbamimidoyl)-3,4-dihydro-2H-1-benzopyran-4-yl]carbamate (1.0 g, 3.3 mmol, 1 equiv) in dioxane (10 ml) was added propanoyl propanoate (466 mg, 3.8 mmol, 1.1 equiv). The mixture was stirred at 50° C. for 1 h and at 100° C. for 2 h, cooled to r.t., diluted with EA (100 mL), washed with brine, dried over anhydrous sodium sulfate, concentrated under reduced pressure, and purified by silica gel chromatography (EA/PE, 1/3) to afford 630 mg (56%) of tert-butyl N-[7-(5-ethyl-1,2,4-oxadiazol-3-yl)-3,4-dihydro-2H-1-benzopyran-4-yl]carbamate as a white solid.

6. Synthesis of Intermediate 34-7:

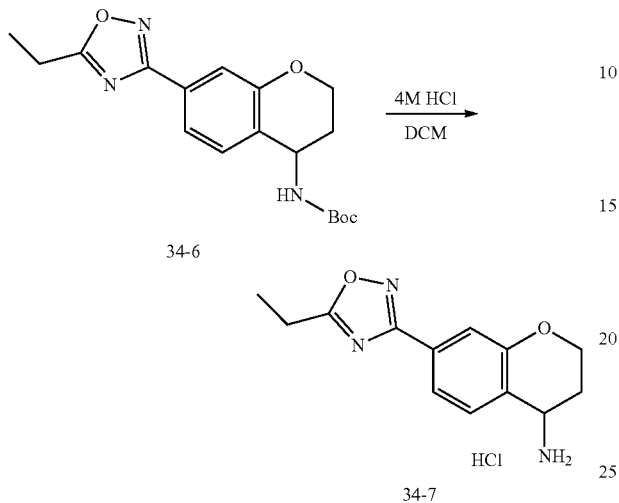

To a solution of tert-butyl N-[7-(N-hydroxycarbamimidoyl)-3,4-dihydro-2H-1-benzopyran-4-yl]carbamate (350 mg, 1.14 mmol, 1.0 equiv) in DCM (3 mL, 47.2 mmol, 41.4 equiv) was added HCl (4 M in dioxane, 1 mL). The mixture was stirred for 5 hours at room temperature, diluted with EA, and stirred for 20 min. The solid product was collected by filtration and dried under high vacuum to afford 400 mg of 7-(5-ethyl-1,2,4-oxadiazol-3-yl)-3,4-dihydro-2H-1-benzopyran-4-amine as a white solid.

7. Synthesis of Intermediate 34-8:

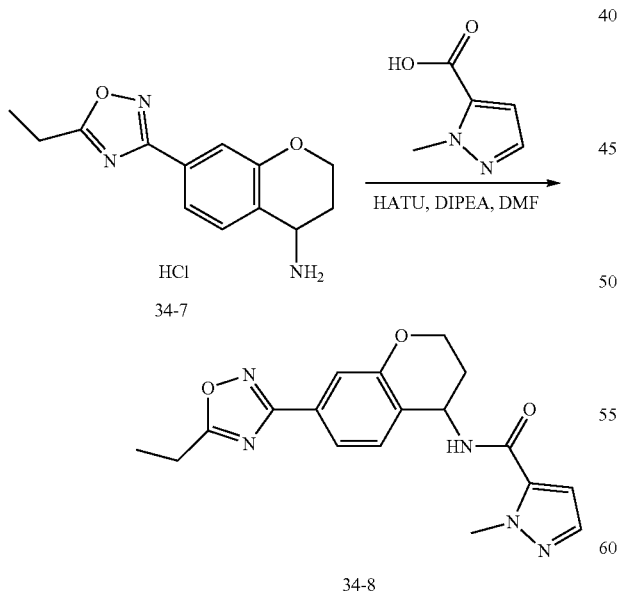

To a solution of 1-methyl-1H-pyrazole-5-carboxylic acid (46.6 mg, 0.37 mmol, 1.3 equiv) in DMF (1 ml) were added HATU (140 mg, 0.37 mmol, 1.3 equiv), DIEA (147 mg, 1.14 mmol, 4.0 equiv), and 7-(5-ethyl-1,2,4-oxadiazol-3-yl)-3,4-dihydro-2H-1-benzopyran-4-amine hydrochloride (80 mg, 0.28 mmol, 1.0 equiv). The mixture was stirred overnight and purified by Prep-HPLC with the following conditions: (2#-AnalyseHPLC-SHIMADZU(HPLC-10)): Column, XBridge Prep C18 OBD Column, 5 µm, 19*150 mm; mobile phase, water (10 MMOL/L NH$_4$HCO$_3$) and ACN (34.0% ACN up to 47.0% in 8 min); Detector, UV 220 nm. This purification resulted in 170 mg (90%) of N-[6-(5-ethyl-1,2,4-oxadiazol-3-yl)-1,2,3,4-tetrahydronaphthalen-1-yl]-1-methyl-1H-pyrazole-4-carboxamide as a white solid. LRMS (ES) m/z 354 (M+H).

8. Synthesis of Compound 538:

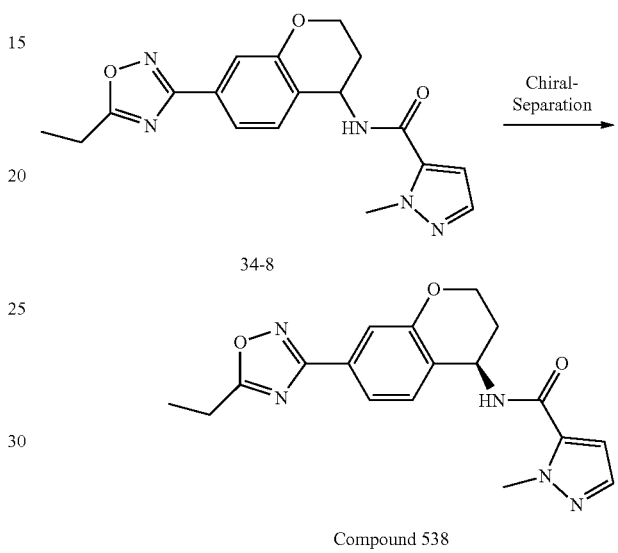

The racemic mixture of N-[7-(5-ethyl-1,2,4-oxadiazol-3-yl)-3,4-dihydro-2H-1-benzopyran-4-yl]-1-methyl-1H-pyrazole-5-carboxamide (40 mg, 0.11 mmol, 1.0 equiv) was purified by chiral-HPLC with the follow conditions: (Column: Repaired Chiral IC; Column size: (R,R) WHELK-014 0.46*10 cm; 3.5 µm; Mobile phase:Hex (0.1% DEA): EtOH=80:20; Instrument: LC-79; Detector: UV-254 nm). This purification provided (R)—N-(7-(5-ethyl-1,2,4-oxadiazol-3-yl)chroman-4-yl)-1-methyl-1H-pyrazole-5-carboxamide (Compound 538) (15.1 mg, 38%) as a white solid. LRMS (ES) m/z 354 (M+H). $^1$H-NMR: (400 MHz, Chloroform-d, ppm) δ 7.68-7.58 (m, 2H), 7.47 (d, J=2.1 Hz, 1H), 7.37 (d, J=8.0 Hz, 1H), 6.51 (d, J=2.1 Hz, 1H), 6.22 (d, J=7.8 Hz, 1H), 5.37 (q, J=6.2 Hz, 1H), 4.37 (ddd, J=10.4, 6.7, 3.2 Hz, 1H), 4.32-4.21 (m, 1H), 4.26 (s, 3H), 2.99 (q, J=7.6 Hz, 2H), 2.43-2.30 (m, 1H), 2.20 (dtd, J=13.9, 6.5, 3.0 Hz, 1H), 1.47 (t, J=7.6 Hz, 3H).

Example 35

Synthesis of Compound 542

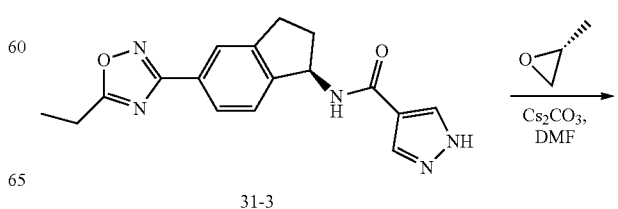

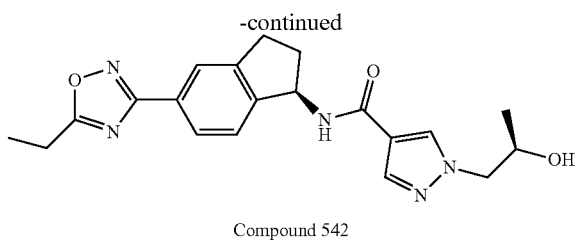

Compound 542

To a stirred solution of N-[(1R)-5-(5-ethyl-1,2,4-oxadiazol-3-yl)-2,3-dihydro-1H-inden-1-yl]-1H-pyrazole-4-carboxamide (1.5 g, 4.6 mmol, 1 equiv) and $Cs_2CO_3$ (3.0 g, 9.2 mmol, 2 eq) in DMF (20 mL) was added (2R)-2-methyloxirane (0.4 g, 6.9 mmol, 1.5 equiv; J&K Scientific, lot #352062) at r.t. under argon atmosphere. The resulting mixture was stirred for 2 h at 80° C. under an argon atmosphere. The resulting mixture was diluted with ethyl acetate (100 mL) and washed with $NH_4Cl$ (sat) (100 mL×3). The organic phase was concentrated under reduced pressure to afford a product (1.48 g, 47.3% ee). This product was combined with a previous batch made using same procedure (680 mg). It was purified by stirring in a mixture of ACN/EtOH (60 mL, 2/1) and filtered to afford N-[(1R)-5-(5-ethyl-1,2,4-oxadiazol-3-yl)-2,3-dihydro-1H-inden-1-yl]-1-[(2R)-2-hydroxypropyl]-1H-pyrazole-4-carboxamide (1.2 g, 97% ee) as an off-white solid. LRMS (ES) m/z 382 (M+H); $^1$H-NMR (300 MHz, DMSO-d6) δ 8.46 (d, J=8.4 Hz, 1H), 8.20 (s, 1H), 7.88 (m, 3H), 7.38 (d, J=7.8 Hz, 1H), 5.57 (dd, J=8.1, 16.2 Hz, 1H), 4.96 (d, J=4.5 Hz, 1H), 4.03 (m, 3H), 3.01 (m, 4H), 2.46 (m, 1H), 2.09-1.89 (m, 1H), 1.36 (t, J=6.0 Hz, 3H), 1.06 (d, J=6.0 Hz, 3H).

Example 36

Synthesis of Compound 541

Compound 541 was prepared by a method analogous to the method described for Compound 541, using (2S)-2-methyloxirane in place of the (2R)-2-methyloxirane. LRMS (ES) m/z 382 (M+H).

Example 37

Intermediate I

1. Synthesis of Intermediate 37-2:

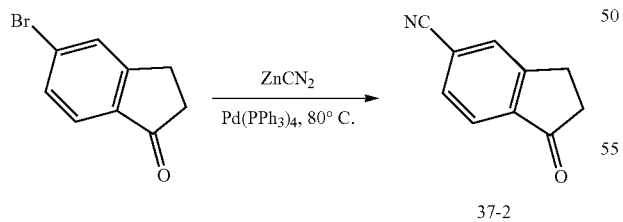

37-2

To a solution of 5-bromo-2,3-dihydro-1H-inden-1-one (80 g, 381 mmol, 1.00 equiv) in DMF (500 mL) were added $Zn(CN)_2$ (27.8 g, 237.61 mmol, 0.63 equiv) and $Pd(PPh_3)_4$ (15.8 g, 13.67 mmol, 0.036 equiv). After stirring overnight at 80° C. in an oil bath, the mixture was cooled and the solids were filtered off. The filtrate was diluted with a mixture of ethyl acetate and water (800 mL, 1/1). The organic layer was separated and the aqueous layer was extracted with ethyl acetate (400 mL) twice. The combined organic layers were dried over anhydrous sodium sulfate and concentrated under reduced pressure. The residue was purified by silica gel chromatography (EA/PE) to give a product. This product was triturated with a mixture of PE/EA (80 mL, 10/1) to afford 48.3 g (81%) of 1-oxo-2,3-dihydro-1H-indene-5-carbonitrile as a yellow solid.

2. Synthesis of Intermediate 37-3:

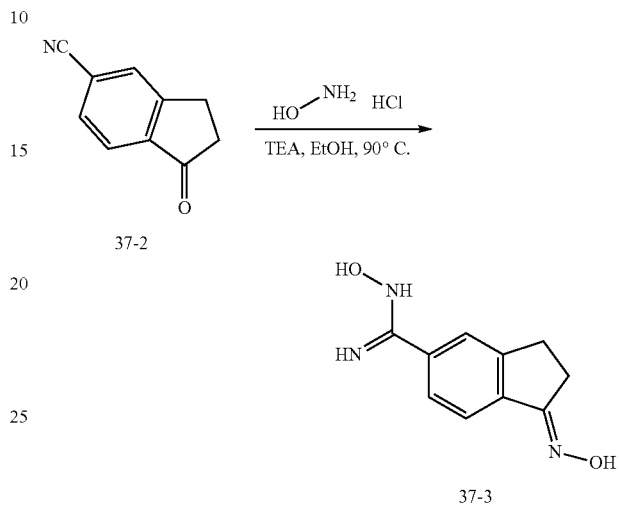

37-3

To a solution of 1-oxo-2,3-dihydro-1H-indene-5-carbonitrile (61.5 g, 392 mmol, 1.00 equiv) in ethanol (1.5 L) were added HO—$NH_2$.HCl (81.1 g, 1.2 mol, 3.00 equiv) and TEA (158.3 g, 1.6 mol, 4.00 equiv). After stirring for 2.5 h at 85° C., the resulting mixture was cooled to RT and concentrated under reduced pressure. The residue was purified by silica gel chromatography (DCM/MeOH) to give 80 g (99%) of (1Z)—N-hydroxy-1-(hydroxyimino)-2,3-dihydro-1H-indene-5-carboximidamide as a yellow solid.

3. Synthesis of Intermediate 37-4:

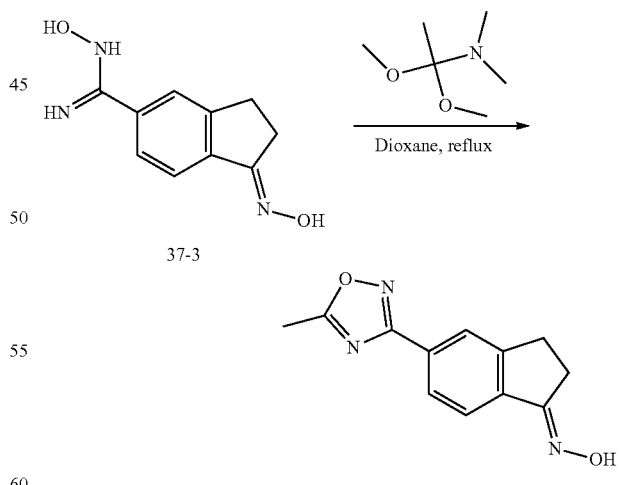

37-4

To a solution of (1Z)—N-hydroxy-1-(hydroxyimino)-2,3-dihydro-1H-indene-5-carboximidamide (30 g, 146 mmol, 1.00 equiv) in dioxane (60 mL) was added (1,1-dimethoxyethyl)dimethylamine (20 g, 150 mmol, 1.00 equiv). After stirring overnight at 90° C., the resulting mixture was concentrated under reduced pressure. The residue was purified by silica gel chromatography (EA/PE) to give 22 g (66%) of N-[(1Z)-5-(5-methyl-1,2,4-oxadiazol-3-yl)-2,3-dihydro-1H-inden-1-ylidene]hydroxylamine as a brown solid.

4. Synthesis of Intermediate I:

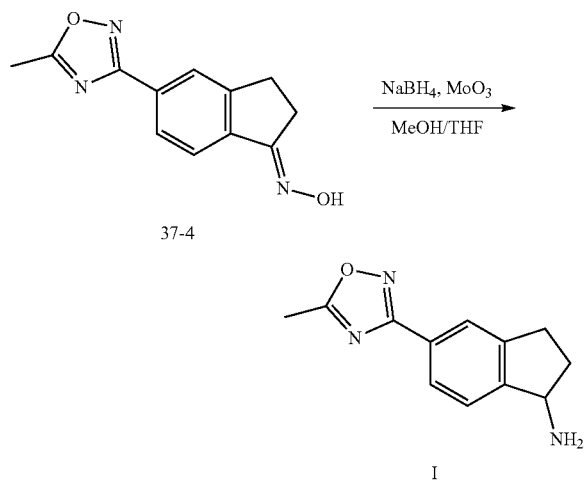

To a solution of N-[(1E)-5-(5-methyl-1,2,4-oxadiazol-3-yl)-2,3-dihydro-1H-inden-1-ylidene] hydroxylamine (15.6 g, 68.1 mmol, 1.00 equiv) in a mixture of MeOH and THF (300/300 mL) were added MoO$_3$ (19.8 g, 138 mmol, 2.00 equiv) and NaBH$_4$ (10.4 g, 273.68 mmol, 4.00 equiv) in portions. After stirring overnight at RT, the reaction was quenched by addition of NH$_4$Cl (aq) (50 mL) and concentrated under reduced pressure. The residue was purified by silica gel chromatography (DCM/MeOH) to give a product. This product was triturated with EA:PE (1/10) to give 11 g (75%) of 5-(5-methyl-1,2,4-oxadiazol-3-yl)-2,3-dihydro-1H-inden-1-amine (Intermediate I) as an off-white solid. LRMS (ES) m/z 199 (M-17). $^1$H-NMR: (DMSO, 300 MHz, ppm): δ 7.99 (2H, s), 7.66 (1H, m), 6.49 (2H, s), 4.56-4.51 (1H, t, J=7.2), 3.16-3.00 (1H, m), 2.92-2.82 (1H, m), 2.66 (3H, s), 2.44-2.43 (1H, m), 1.99-1.80 (1H, m)

Example 38

Intermediate II

1. Synthesis of Intermediate 38-2:

To a solution of 5-bromo-2,3-dihydro-1H-inden-1-one (50 g, 237 mmol, 1.00 equiv) in THF (400 mL) was added (3R)-1-methyl-3,3-diphenyl-hexahydropyrrolo[1,2-c][1,3,2]oxazaborole (1 M in PhMe) (37 mL, 0.15 equiv) under nitrogen. This was followed by the addition of Borane-methylsulfide (10 M in THF) (32.2 g, 1.4 equiv) dropwise with stirring at −10° C. over 1 h. After stirring for 3 hours at −10° C., the reaction was quenched by slow addition of water (200 mL). The resulting solution was extracted with EA (200 mL) three times. The combined organic layers were washed with brine (300 mL), dried over anhydrous sodium sulfate, and concentrated under reduced pressure. The residue was purified by silica gel (packed with 1% TEA in PE) chromatography (EA/PE, 1/3) to give a product. This product was triturated with hexane (300 mL) to afford 38 g (75%) of (1S)-5-bromo-2,3-dihydro-1H-inden-1-ol as a light yellow solid. LRMS (ES) m/z 339 (M-17).

2. Synthesis of Intermediate 38-3:

To a solution of (1S)-5-bromo-2,3-dihydro-1H-inden-1-ol (42 g, 197 mmol, 1.00 equiv) in toluene (500 mL) was added DPPA (74.29 g, 269.95 mmol, 1.37 equiv) under nitrogen. To this mixture was added DBU (45 g, 295 mmol, 1.50 equiv) dropwise with stirring at 0° C. over 1 h. After stirring for 3 h at 0 to 15° C., the mixture was diluted with EA (400 mL), washed with water (400 mL) three times, dried over anhydrous sodium sulfate, and concentrated under reduced pressure. The residue was purified by silica gel (packed with 1% TEA in PE) chromatography (PE) to give 44.4 g (95%) of (1R)-1-azido-5-bromo-2,3-dihydro-1H-indene as dark brown oil. The dark brown oil was used for next step without further purification. LRMS (ES) m/z 195, 197 (M-42).

3. Synthesis of Intermediate 38-4:

To a solution of (1R)-1-azido-5-bromo-2,3-dihydro-1H-indane (44.3 g, 186 mmol, 1.00 equiv) in MeOH (600 mL) was added SnCl$_2$.2H$_2$O (76 g, 337 mmol, 1.81 equiv) carefully. After stirring overnight at room temperature, the mixture was diluted with EA (500 mL) and NaOH (2 N, 700 mL), stirred at room temperature for 1 h, and filtered. The filtrate was separated and the aqueous layer was extracted with EA (300 mL). The combined organic layers were extracted with HCl (1 N, 500 mL) twice and the aqueous layers were combined. The pH of the aqueous layers was adjusted to 11 with sodium hydroxide (sat.) and extracted with EA (300 mL) three times. The combined organic layers were dried over anhydrous sodium sulfate and concentrated under reduced pressure to give 31.8 g (80%) of (1R)-5-bromo-2,3-dihydro-1H-inden-1-amine as yellow oil. LRMS (ES) m/z 195, 197 (M-16).

4. Synthesis of Intermediate 38-5:

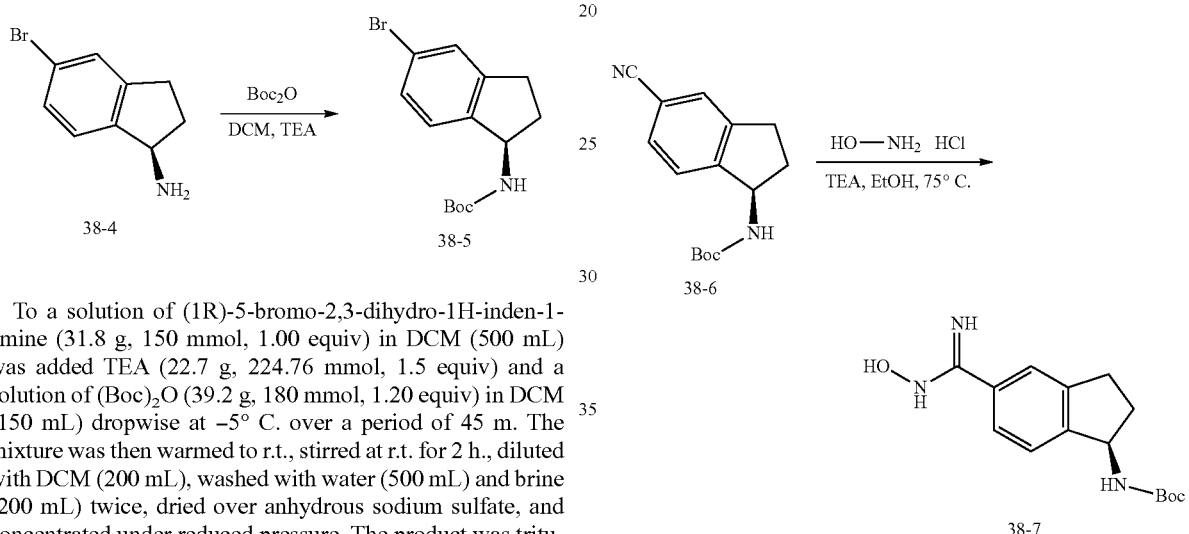

To a solution of (1R)-5-bromo-2,3-dihydro-1H-inden-1-amine (31.8 g, 150 mmol, 1.00 equiv) in DCM (500 mL) was added TEA (22.7 g, 224.76 mmol, 1.5 equiv) and a solution of (Boc)$_2$O (39.2 g, 180 mmol, 1.20 equiv) in DCM (150 mL) dropwise at –5° C. over a period of 45 m. The mixture was then warmed to r.t., stirred at r.t. for 2 h., diluted with DCM (200 mL), washed with water (500 mL) and brine (200 mL) twice, dried over anhydrous sodium sulfate, and concentrated under reduced pressure. The product was triturated with hexanes (300 mL) to give 38.7 g (83%) of tert-butyl N-[(1R)-5-bromo-2,3-dihydro-1H-inden-1-yl]carbamate as a white solid. LRMS (ES) m/z 256, 258 (M+H-56).

5. Synthesis of Intermediate 38-6:

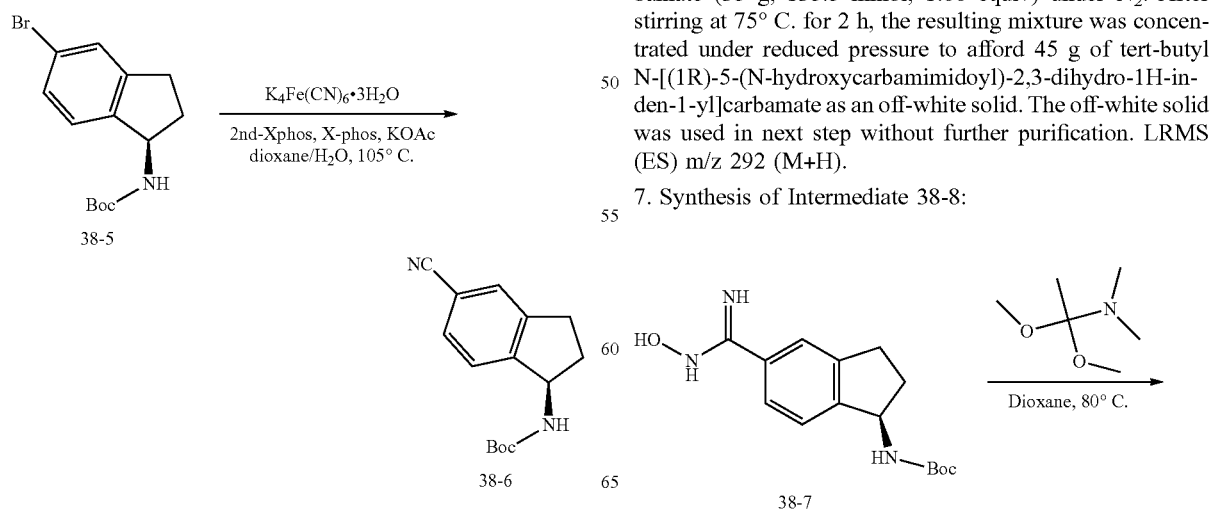

To a solution of tert-butyl N-[(1R)-5-bromo-2,3-dihydro-1H-inden-1-yl]carbamate (25.5 g, 81.7 mmol, 1.00 equiv) in dioxane (270 mL) were added K$_4$Fe(CN)$_6$.3H$_2$O (17.3 g, 41 mmol, 0.50 equiv), 2nd Generation XPhos precatalyst (965 mg, 1.23 mmol, 0.02 equiv), X-phos (584 mg, 1.22 mmol, 0.01 equiv), and a solution of KOAc (16.0 g, 163 mmol, 2.00 equiv) in water (270 mL) under nitrogen. After stirring at 105° C. for 5 h, the resulting solution was diluted with EA (500 mL). The solids were removed by filtration. The filtrate was separated and the aqueous layer was extracted with EA (300 mL) twice. The combined organic layers were washed with brine (300 mL), dried over anhydrous sodium sulfate, and concentrated under reduced pressure. The residue was purified by silica gel chromatography (EA/PE, 15/85) to give 20 g (94%) of tert-butyl N-[(1R)-5-cyano-2,3-dihydro-1H-inden-1-yl]carbamate as a white solid. LRMS (ES) m/z 259 (M+H).

6. Synthesis of Intermediate 38-7:

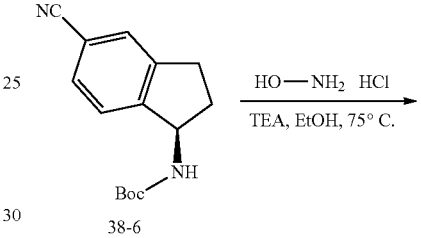

To a solution of hydroxylamine hydrochloride (18.7 g, 269 mmol, 2.0 equiv) in EtOH (600 g, 13.0 mol, 96 equiv) were added TEA (27.4 g, 271 mmol, 2.00 equiv) and tert-butyl N-[(1R)-5-cyano-2,3-dihydro-1H-inden-1-yl]carbamate (35 g, 135.5 mmol, 1.00 equiv) under N$_2$. After stirring at 75° C. for 2 h, the resulting mixture was concentrated under reduced pressure to afford 45 g of tert-butyl N-[(1R)-5-(N-hydroxycarbamimidoyl)-2,3-dihydro-1H-inden-1-yl]carbamate as an off-white solid. The off-white solid was used in next step without further purification. LRMS (ES) m/z 292 (M+H).

7. Synthesis of Intermediate 38-8:

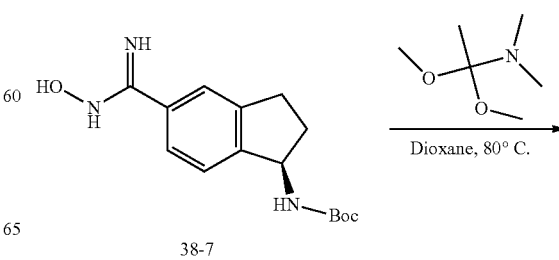

-continued

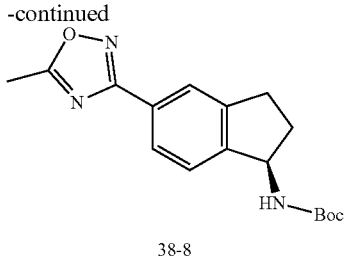

38-8

To a solution of tert-butyl N-[(1R)-5-(N-hydroxycarbamimidoyl)-2,3-dihydro-1H-inden-1-yl]carbamate (5 g, 17.2 mmol, 1.00 equiv) in dioxane (30 mL) was added (1,1-dimethoxyethyl)dimethylamine (4.6 g, 34.2 mmol, 2.00 equiv) under nitrogen. After stirring at 80° C. for 2 h, the mixture was diluted with water (30 mL) and extracted with EA (50 mL) three times. The combined organic layers were washed with brine (30 mL) three times, dried over anhydrous sodium sulfate, and concentrated under reduced pressure. The product was triturated with a mixture of EA and hexanes to afford 2.8 g (52%) of tert-butyl N-[(1R)-5-(5-methyl-1,2,4-oxadiazol-3-yl)-2,3-dihydro-1H-inden-1-yl]carbamate as a light yellow solid. LRMS (ES) m/z 316 (M+H).

8. Synthesis of Intermediate II:

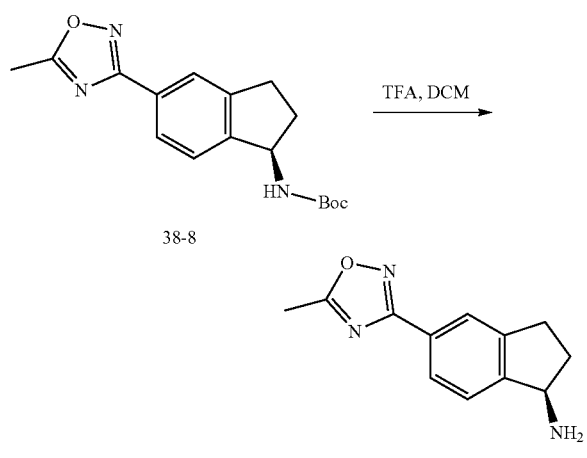

To a solution of tert-butyl N-[(1R)-5-(5-methyl-1,2,4-oxadiazol-3-yl)-2,3-dihydro-1H-inden-1-yl]carbamate (2.8 g, 9.0 mmol, 1.00 equiv) in DCM (30 mL) was added trifluoroacetic acid (5 mL). After stirring for 4 h at room temperature, the resulting mixture was concentrated under reduced pressure. The residue was dissolved in a mixture of EA (20 mL) and water (5 mL). The pH of the solution was adjusted to 10 with sodium carbonate (sat.) and concentrated under reduced pressure. The residue was purified by a silica gel column with DCM/MeOH (10/1) as eluent to afford 1.1 g (56%) of (1R)-5-(5-methyl-1,2,4-oxadiazol-3-yl)-2,3-dihydro-1H-inden-1-amine (Intermediate II) as a white solid. LRMS (ES) m/z 199 (M-16). $^1$H-NMR: (400 MHz, DMSO-d$_6$, ppm) δ 7.85-7.76 (m, 2H), 7.49 (d, J=7.8 Hz, 1H), 4.22 (t, J=7.8 Hz, 1H), 2.91 (ddd, J=16.0, 8.7, 2.8 Hz, 1H), 2.75 (dt, J=16.4, 8.7 Hz, 1H), 2.63 (s, 3H), 2.36 (dtd, J=12.3, 7.5, 2.8 Hz, 1H), 2.17 (s, 2H), 1.62 (ddt, J=12.3, 9.4, 8.6 Hz, 1H).

Example 39

Intermediate III

1. Synthesis of Intermediate 39-2:

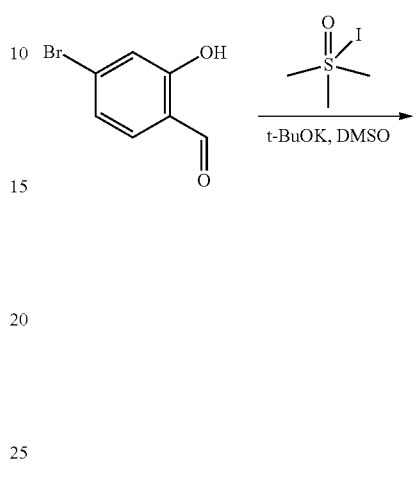

39-2

To a solution of 4-bromo-2-hydroxybenzaldehyde (31.5 g, 156 mmol, 1.00 equiv) in DMSO (500 mL) was added S,S-dimethylmethanesulfinyl iodide (41.3 g, 188 mmol, 1.20 equiv). The mixture was cooled to 0° C. and t-BuOK (21.0 g, 187 mmol, 1.20 equiv) was added in portions at 0° C. over a period of 15 min. The mixture was then warmed to r.t. After stirring for 1.5 h at room temperature, the resulting solution was diluted with water (500 mL) and extracted with EA (400 mL) four times. The combined organic layers were washed with brine (400 mL), dried over anhydrous sodium sulfate, and concentrated under reduced pressure to give a material. This material was combined with a previous batch (same scale) and purified by silica gel chromatography (EA/PE, 1/4) to give 51.7 g of 6-bromo-2,3-dihydro-1-benzofuran-3-ol as a white solid. The product was kept under N$_2$.

2. Synthesis of Intermediate 39-3:

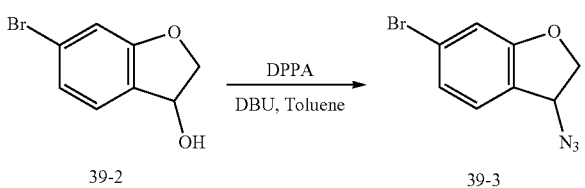 [SMILES: OC1COc2cc(Br)ccc21 ; "DPPA" ; [N-]=[N+]=NC1COc2cc(Br)ccc21]

To a solution of 6-bromo-2,3-dihydro-1-benzofuran-3-ol (30 g, 140 mmol, 1.00 equiv) in toluene (480 mL) under N$_2$ were added DPPA (42.2 g, 153 mmol, 1.10 equiv) and a solution of DBU (23.3 g, 153 mmol, 1.10 equiv) in toluene (20 mL) dropwise at 0° C. over a period of 30 min. After stirring at 15° C. for 3.5 h, the resulting solution was diluted with EA (500 mL), washed with brine (300 mL), dried over anhydrous sodium sulfate, concentrated under reduced pressure, and purified by silica gel chromatography (EA/PE, 1/9) to give 30 g (90%) of 3-azido-6-bromo-2,3-dihydro-1-benzofuran as light yellow oil.

3. Synthesis of Intermediate 39-4:

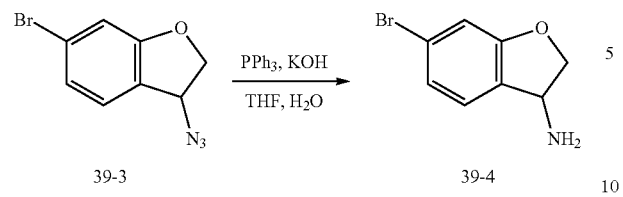

To a solution of 3-azido-6-bromo-2,3-dihydro-1-benzofuran (28 g, 117 mmol, 1.00 equiv) in THF (400 mL) was added PPh₃ (45.8 g, 175 mmol, 1.50 equiv) at r.t. After stirring for 1 h, the mixture was poured into a solution of potassium hydroxide (16.3 g, 291 mmol, 2.49 equiv) in water (100 mL) and stirred for an additional 3 h. The mixture was then heated to 55° C. for 2 h, cooled to RT, and diluted with EA (500 mL) and brine (200 mL). The aqueous layer was extracted with EA (300 mL) twice. The combined organic layers were washed with brine (300 mL), dried over anhydrous sodium sulfate, concentrated under reduced pressure, and purified by silica gel chromatography (MeOH/EA, 1/9) to give 18 g of 6-bromo-2,3-dihydro-1-benzofuran-3-amine as yellow oil.

4. Synthesis of Intermediate 39-5:

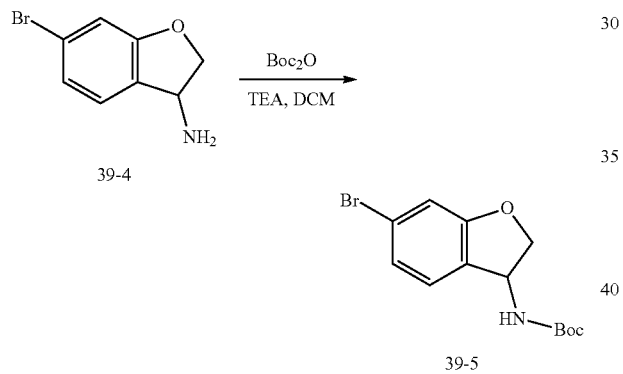

To a solution of 6-bromo-2,3-dihydro-1-benzofuran-3-amine (18.1 g, 84.6 mmol, 1.00 equiv) in DCM (200 mL) cooled to 0° C. under N₂ were added TEA (17.1 g, 169 mmol, 2.00 equiv) and a solution of (Boc)₂O (18.4 g, 84.3 mmol, 1.00 equiv) in DCM (200 mL) dropwise. The mixture was then stirred at r.t. for 4 h, diluted with DCM (400 mL), washed with water (400 mL) and brine (400 mL), dried over anhydrous sodium sulfate, concentrated under reduced pressure, and purified by silica gel chromatography (EA/PE, 6/94) to give 18.4 g (69%) of tert-butyl N-(6-bromo-2,3-dihydro-1-benzofuran-3-yl)carbamate as an off-white solid.

5. Synthesis of Intermediate 39-6:

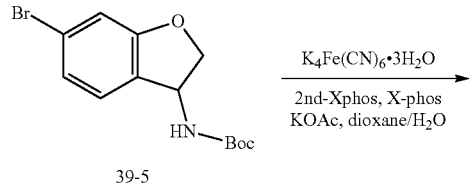

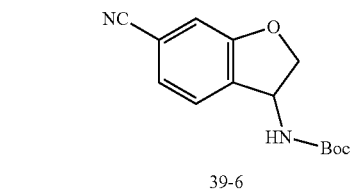

To a solution of tert-butyl N-(6-bromo-2,3-dihydro-1-benzofuran-3-yl)carbamate (17.4 g, 55.3 mmol, 1.00 equiv) in dioxane (260 mL) were added FeK₄(CN)₆·3H₂O (11.7 g, 27.7 mmol, 0.50 equiv), X-phos (400 mg, 0.84 mmol, 0.02 equiv), 2G-Xphos precatalyst (650 mg, 0.83 mmol, 0.01 equiv), and a solution of KOAc (11 g, 112 mmol, 2.03 equiv) in water (260 mL) under nitrogen. After stirring at 80° C. for 4 h, the resulting solution was diluted with EA (500 mL) and was filtered to remove solids. The aqueous layer was extracted with EA (300 mL) three times. The combined organic layers were washed with brine (300 mL), dried over anhydrous sodium sulfate, concentrated under reduced pressure, and purified by silica gel chromatography (EA/PE, 19/81) to give 14.3 g (99%) of tert-butyl N-(6-cyano-2,3-dihydro-1-benzofuran-3-yl)carbamate as an off-white solid.

6. Synthesis of Intermediate III:

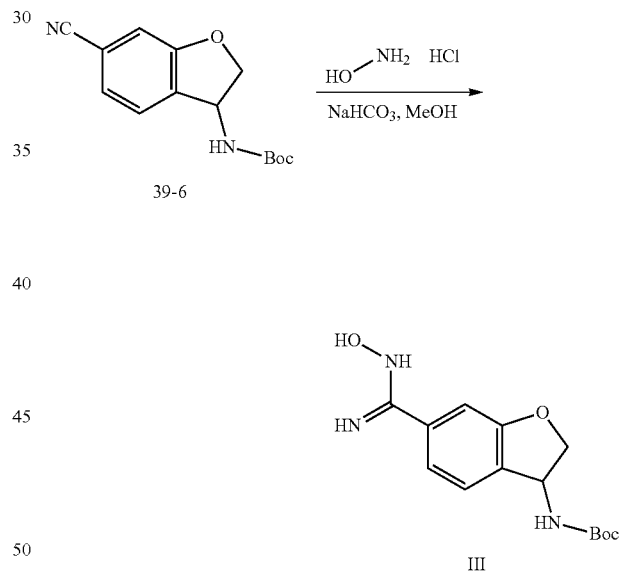

To a solution of tert-butyl N-(6-cyano-2,3-dihydro-1-benzofuran-3-yl)carbamate (13.3 g, 51.1 mmol, 1.00 equiv) in MeOH (270 mL) were added HONH₂·HCl (7.06 g, 102 mmol, 2.00 equiv) and sodium bicarbonate (13 g, 155 mmol, 3.03 equiv). After stirring for 80° C. for 4 h, the solids were filtered off and the filtrate was concentrated under reduced pressure to give 14.3 g (95%) of tert-butyl N-[6-(N-hydroxycarbamimidoyl)-2,3-dihydro-1-benzofuran-3-yl]carbamate (Intermediate III) as a white solid.

Example 40

Intermediate IV

1. Synthesis of Intermediate 40-2:

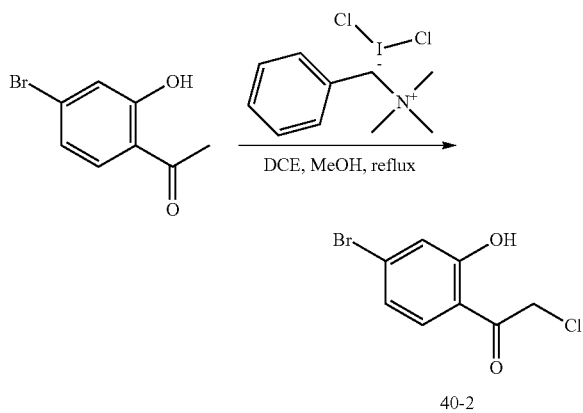

40-2

To a solution of 1-(4-bromo-2-hydroxyphenyl)ethan-1-one (35 g, 163 mmol, 1.0 equiv) in a mixture of DCE (800 mL) and MeOH (320 mL) was added benzyltrimethylazanium dichloroiodanuide (113 g, 325 mmol, 2.0 equiv) under nitrogen. The mixture was stirred at 70° C. for 4 h; cooled to r.t.; concentrated under reduced pressure; dissolved in DCM (800 mL); washed with water (400 mL), brine (400 mL), and NaHSO₃ (5%, 500 mL); dried over Na₂SO₄; and concentrated under reduced pressure to afford 45.3 g of 1-(4-bromo-2-hydroxyphenyl)-2-chloroethan-1-one as a brown solid.

2. Synthesis of Intermediate 40-3:

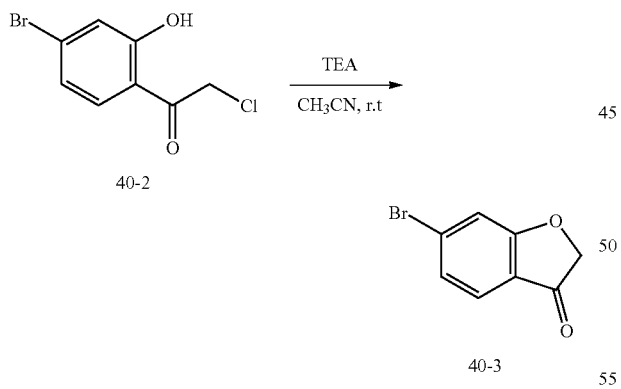

To a solution of 1-(4-bromo-2-hydroxyphenyl)-2-chloroethan-1-one (43.1 g, 173 mmol, 1.0 equiv) in ACN (1.2 L) was added a solution of TEA (26.2 g, 259 mmol, 1.0 equiv) in ACN (15 mL). The mixture was stirred for 2 h, concentrated under reduced pressure, re-dissolved in EA (800 mL), washed with water (400 mL) and brine (400 mL), dried over anhydrous sodium sulfate, concentrated under reduced pressure, and purified by silica gel chromatography (DCM/PE, 3/7) to afford 15 g (41%) of 6-bromo-2,3-dihydro-1-benzofuran-3-one as a yellow solid.

3. Synthesis of Intermediate 40-4:

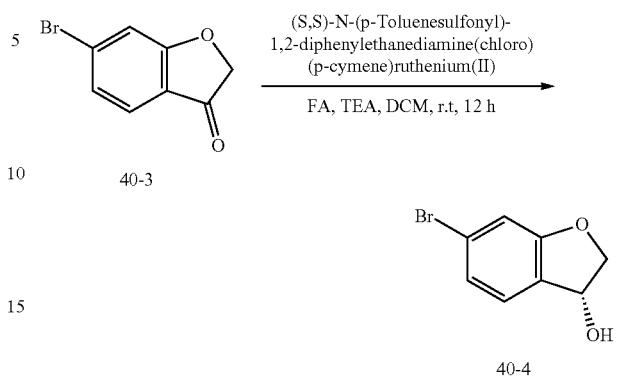

To FA (14.6 g, 318 mmol, 3.5 equiv) cooled to 0° C. was added TEA (27.5 g, 272 mmol, 3.0 equiv) dropwise with stirring under nitrogen. To this mixture were added a solution of 6-bromo-2,3-dihydro-1-benzofuran-3-one (19.4 g, 90.9 mmol, 1.0 equiv) in DCM (500 mL) and (S,S)—N-(p-toluenesulfonyl)-1-2-diphenylethanediamine(chloro)(p-cymene)ruthenium(II) (1.65 g, 2.6 mmol, 0.03 equiv). The mixture was stirred overnight at room temperature and poured into water (500 mL). The resulting solution was extracted with DCM (500 mL) three times. The combined organic layers were washed with brine (500 mL), dried over anhydrous sodium sulfate, concentrated under reduced pressure, and purified by silica gel chromatography (EA/PE, 1/9) to afford 13.4 g (69%) of (3R)-6-bromo-2,3-dihydro-1-benzofuran-3-ol as a yellow solid with 96% ee. (Chiral_SFC, CHIRALPAK AD-H 4.6*100 mm, 5 μm).

4. Synthesis of Intermediate 40-5:

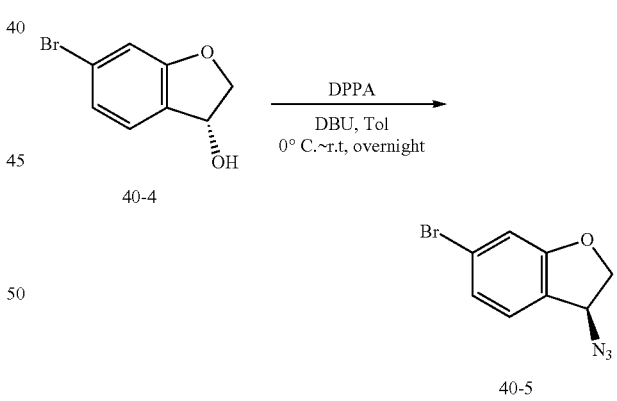

To a solution of (3R)-6-bromo-2,3-dihydro-1-benzofuran-3-ol (13.4 g, 62.3 mmol, 1.0 equiv) in toluene (250 mL) cooled to 0° C. were added DPPA (20.6 g, 74.8 mmol, 1.2 equiv) and a solution of DBU (14.2 g, 93.3 mmol, 1.50 equiv) in toluene (50 mL) dropwise. The mixture was stirred overnight, poured into EA (500 mL), washed with water (250 mL) twice and brine (250 mL), dried over anhydrous sodium sulfate, concentrated under reduced pressure, and purified by silica gel chromatography (EA/PE, 5/95) to give 10.4 g of (3S)-3-azido-6-bromo-2,3-dihydro-1-benzofuran as yellow oil.

5. Synthesis of Intermediate 40-6:

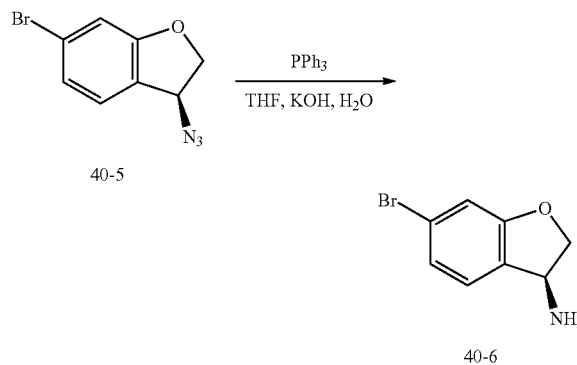

To a solution of (3S)-3-azido-6-bromo-2,3-dihydro-1-benzofuran (10.4 g, 43.5 mmol, 1.0 equiv) in THF (150 mL) were added PPh₃ (22.8 g, 86.8 mmol, 2.0 equiv) and a solution of potassium hydroxide (6.1 g, 108 mmol, 2.5 equiv) in water (40 mL). The mixture was stirred at 50° C. for 1 h and r.t. overnight. The aqueous layer was extracted with EA (100 mL) three times. The combined organic layers were washed with brine (100 mL), dried over anhydrous sodium sulfate, concentrated under reduced pressure, and purified by silica gel chromatography (EA) to give 10.6 g of (3S)-6-bromo-2,3-dihydro-1-benzofuran-3-amine as yellow oil.

6. Synthesis of Intermediate IV:

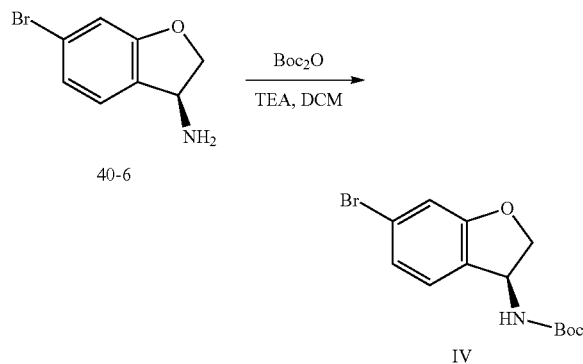

To a solution of (3S)-6-bromo-2,3-dihydro-1-benzofuran-3-amine (10.6 g, 49.7 mmol, 1.0 equiv) in DCM (200 mL) cooled to 0° C. were added TEA (10.0 g, 99.2 mmol, 2.0 equiv) and a solution of Boc₂O (11.9 g, 54.6 mmol, 1.1 equiv) in DCM (50 mL) dropwise for a period of 30 min. The mixture was stirred at r.t. overnight, poured into water (300 mL), and extracted with DCM (300 mL) three times. The combined organic layers were washed with brine (500 mL), dried over anhydrous sodium sulfate, concentrated under reduced pressure, and purified by silica gel chromatography (EA/PE, 60/40) to give an intermediate product, which was titrated from ethanol/water (5/4) to afford 9.2 g (97% ee) of tert-butyl N-[(3S)-6-bromo-2,3-dihydro-1-benzofuran-3-yl]carbamate (Intermediate IV) as a white solid. LRMS (ES) m/z 258, 260 (M+H-56). ¹H-NMR: (300 MHz, DMSO-d6, ppm) δ 7.53 (d, J=7.6 Hz, 1H), 7.25-7.16 (m, 1H), 7.05 (d, J=1.7 Hz, 1H), 7.03 (d, J=1.7 Hz, 1H), 5.21 (d, J=7.7 Hz, 1H), 4.66 (t, J=9.2 Hz, 1H), 4.23 (dd, J=9.6, 5.4 Hz, 1H), 1.38 (s, 9H).

Example 41

Intermediate V

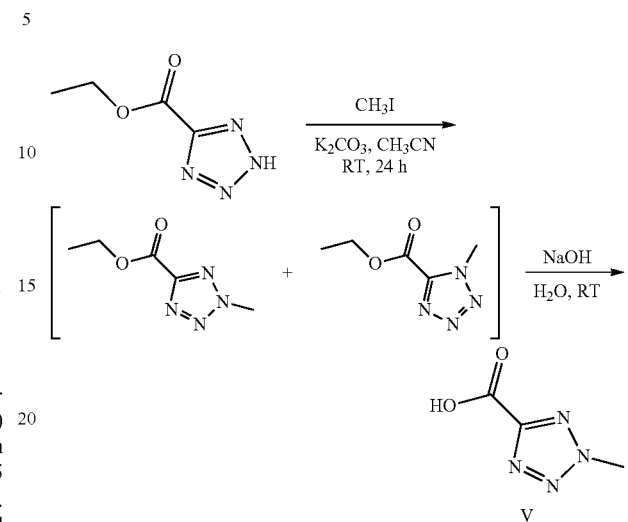

To a stirred solution of ethyl 2H-1,2,3,4-tetrazole-5-carboxylate (100 g, 704 mmol, 1.0 equiv) in ACN (750 mL) was added K₂CO₃ (214 g, 1.5 mol, 2.2 equiv). After the mixture was stirred for 15 min, MeI (210 g, 1.47 mol, 2.1 equiv) was added and the mixture was stirred for 14 h. The mixture was then filtered and the filter cake was washed with ACN (300 mL) three times. The combined filtrate was combined with aqueous NaOH (4 N, 220 mL, 845 mmol, 1.2 equiv) at r.t. and stirred for 1 h. The ACN was then removed by rotary evaporation and the pH of the aqueous solution was adjusted to 1-2 with HCl (6 N). To this mixture was added enough EA to dissolve the precipitate. The phases were separated and the aqueous layer were extracted with EA (1 L) four times. The combined organic layers were dried over anhydrous Na₂SO₄ and concentrated under reduced pressure. The material was suspended in DCM (165 mL) and stirred for 1 h. The solids were collected by filtration, washed with DCM (30 mL) three times, and dried under vacuum to afford 2-methyl-2H-1,2,3,4-tetrazole-5-carboxylic acid (27 g, 30%) (Intermediate V) as a white solid.

Example 41

Intermediate VI

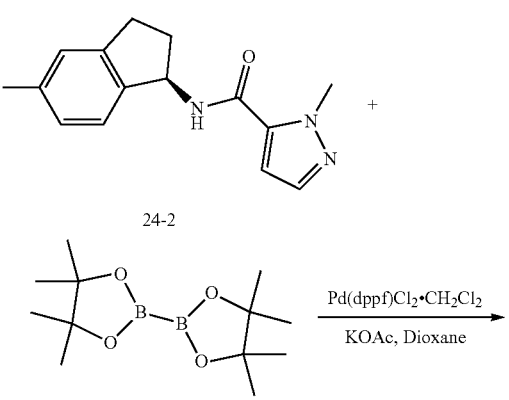

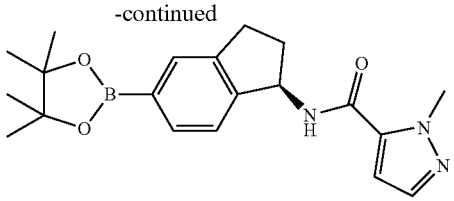

VI

To a solution of N-[(1R)-5-bromo-2,3-dihydro-1H-inden-1-yl]-1-methyl-1H-pyrazole-5-carboxamide (1.6 g, 5.00 mmol, 1.00 equiv) in dioxane (40 mL) were added Pd(dppf)Cl$_2$·CH$_2$Cl$_2$ (200 mg, 0.61 mmol, 0.05 equiv), KOAc (1.2 g, 12.2 mmol, 2.50 equiv), and 4,4,5,5-tetramethyl-2-(tetramethyl-1,3,2-dioxaborolan-2-yl)-1,3,2-dioxaborolane (1.52 g, 5.99 mmol, 1.20 equiv) under nitrogen. The mixture was stirred at 70° C. for 2 h, cooled to r.t., filtered to remove solids, diluted with EA (50 mL), washed with water (50 mL), dried over anhydrous sodium sulfate, concentrated under reduced pressure, and purified by a silica gel chromatography (EA/PE, 13/87) to afford 2.05 g of 1-methyl-N-[(1R)-5-(tetramethyl-1,3,2-dioxaborolan-2-yl)-2,3-dihydro-1H-inden-1-yl]-1H-pyrazole-5-carboxamide (Intermediate VI) as an off-white solid.

Example 42

Synthesis of Compound 295

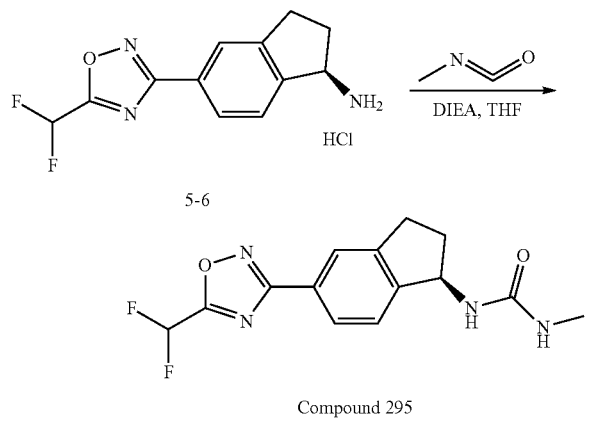

Compound 295

To a suspension of intermediate 5-6 (40 mg, 0.14 mmol, 1.0 equiv.) in THF (1.0 mL) was added DIEA (46 μL, 0.28 mmol, 2.0 equiv.) and isocyanatomethane (15.9 mg, 0.28 mmol, 2.0 equiv.) at rt. The mixture was stirred at 40° C. for 3 h, concentrated, and triturated with MeOH to afford 14.4 mg of (R)-1-(5-(5-(difluoromethyl)-1,2,4-oxadiazol-3-yl)-2,3-dihydro-1H-inden-1-yl)-3-methylurea (Compound 295) as a solid. LRMS (ES) m/z 309.1 (M+H). $^1$H NMR (400 MHz, DMSO-d$_6$) δ 7.94-7.87 (m, 2H), 7.55 (t, J=52 Hz, 1H), 7.42-7.38 (m, 1H), 6.37 (d, J=8.4 Hz, 1H), 5.75 (d, J=4.8 Hz, 1H), 5.18 (q, J=8.2 Hz, 1H), 3.03-2.95 (m, 1H), 2.90-2.80 (m, J=16.4, 1H), 2.62 (d, J=4.7 Hz, 3H), 2.48-2.39 (m, 1H), 1.83-1.71 (m, 1H).

The following compounds were prepared by methods analogous to the method described for Compound 295:

| Compound No. | LRMS (ES) m/z |
|---|---|
| 289 | M + H = 335.1 |
| 292 | M + H = 337.1 |
| 295 | M + H = 309.1 |
| 296 | M + H = 323.1 |
| 297 | M + H = 349.1 |
| 298 | M + H = 363.1 |

Example 43

Synthesis of Compound 304

Compound 304

To a suspension of intermediate 31-2 (1.04 g, 3.9 mmol, 1.0 equiv.) in DCM (10.0 mL) was added pyridine (6.2 g, 78.3 mmol, 20.0 equiv.) and methyl chloroformate (0.44 g, 4.7 mmol, 1.2 equiv.) at 0° C. The mixture was stirred at rt for 3 h, diluted with EA, washed with water, aqueous NH$_4$Cl solution, and brine, dried over Na$_2$SO$_4$, concentrated, and purified on silica gel using EA/HE (20-100%) as eluent to give a solid. The solid was triturated with acetonitrile to afford 1.03 g of methyl (R)-(5-(5-ethyl-1,2,4-oxadiazol-3-yl)-2,3-dihydro-1H-inden-1-yl)carbamate (Compound 304) as a solid. LRMS (ES) m/z 288.2 (M+H). $^1$H NMR (400 MHz, Methylene Chloride-d$_2$) δ 8.00-7.92 (m, 2H), 7.45 (d, J=7.8 Hz, 1H), 5.33-5.24 (m, 1H), 5.03 (br, 1H), 3.74 (s, 3H), 3.13-2.88 (m, 4H), 2.72-2.59 (m, 1H), 1.94-1.84 (m, 1H), 1.46 (t, J=7.6 Hz, 3H).

The following compounds were prepared by methods analogous to the method described for Compound 305:

| Compound No. | LRMS (ES) m/z |
|---|---|
| 278 | M + H = 324 |
| 279 | M + H = 338.1 |
| 280 | M + H = 352.1 |
| 282 | M + H = 310.1 |
| 291 | M + H = 351.1 |
| 303 | M + H = 274.1 |
| 304 | M + H = 288.1 |
| 305 | M + H = 300.1 |
| 306 | M + H = 304.1 |
| 307 | M + H = 302.1 |
| 319 | M + H = 314.1 |
| 320 | M + H = 316.1 |
| 321 | M + H = 328.1 |
| 322 | M + H = 330.1 |
| 323 | M + H = 328.2 |
| 324 | M + H = 332.1 |
| 325 | M + H = 342.2 |
| 326 | M + H = 340.2 |

417
-continued

| Compound No. | LRMS (ES) m/z |
|---|---|
| 327 | M + H = 344.2 |
| 328 | M + H = 354.2 |
| 333 | M + H = 338.1 |
| 334 | M + H = 350.1 |
| 345 | M + H = 341.1 |
| 348 | M + H = 302 |
| 349 | M + H = 290 |
| 350 | M + H = 300 |
| 358 | M + H = 344.1 |
| 359 | M + H = 360.2 |
| 360 | M + H = 385.2 |
| 361 | M + H = 401.1 |
| 362 | M + H = 386.1 |
| 363 | M + H = 400.1 |

Example 44

Synthesis of Compound 551

1. Synthesis of Intermediate 44-3:

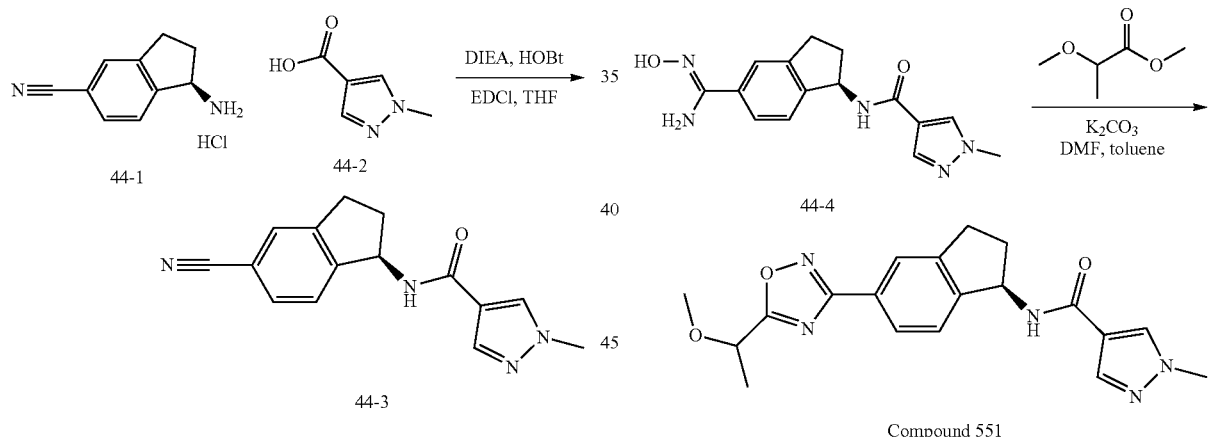

To a mixture of 1-methyl-1H-pyrazole-4-carboxylic acid (2.3 g, 18.2 mmol, 1.2 equiv), HOBt (2.1 g, 15.1 mmol, 1.0 equiv), and EDCI (5.8 g, 30.3 mmol, 2.0 equiv) in DMF (10 mL) was added DIEA (7.5 mL, 45.4 mmol, 3.0 equiv). The mixture was stirred for 10 min, followed by addition of (R)-1-amino-2,3-dihydro-1H-indene-5-carbonitrile 4-methylbenzenesulfonate (5.0 g, 15.1 mmol, 1.0 equiv), and continue to stir overnight. To this mixture was added water (60.0 mL). The solid was collected, washed with more water (20.0 mL), and dried to give 3.5 g (86%) of (R)—N-(5-cyano-2,3-dihydro-1H-inden-1-yl)-1-methyl-1H-pyrazole-4-carboxamide (44-3) as an off-white solid. LRMS (ES) 267.1 (M+H). $^1$H NMR (400 MHz, methylene chloride-d$_2$) δ 7.86 (s, 1H), 7.74 (d, J=0.8 Hz, 1H), 7.60-7.48 (m, 2H), 7.48-7.42 (m, 1H), 6.06 (d, J=8.4 Hz, 1H), 5.69 (q, J=8.3 Hz, 1H), 3.94 (s, 3H), 3.15-2.90 (m, 2H), 2.74-2.64 (m, 1H), 2.03-1.90 (m, 1H).

2. Synthesis of Intermediate 44-4:

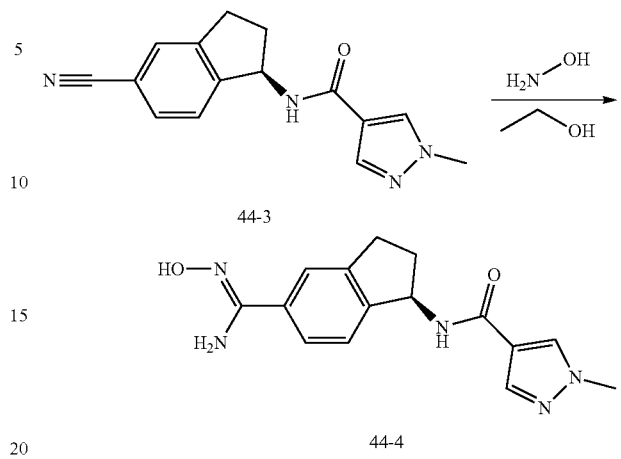

To a suspension of (R)—N-(5-cyano-2,3-dihydro-1H-inden-1-yl)-1-methyl-1H-pyrazole-4-carboxamide (3.0 g, 11.3 mmol, 1.0 equiv) in EtOH (20.0 mL) was added hydroxylamine (50% w/w, 4.0 mL). The mixture was heated to 80° C. for 3 h and concentrated to dryness to afford 3.3 g (98%) of (R,Z)—N-(5-(N'-hydroxycarbamimidoyl)-2,3-dihydro-1H-inden-1-yl)-1-methyl-1H-pyrazole-4-carboxamide (44-4) as an off-white solid. LRMS (ES) m/z 300.1 (M+H).

3. Synthesis of Compound 551:

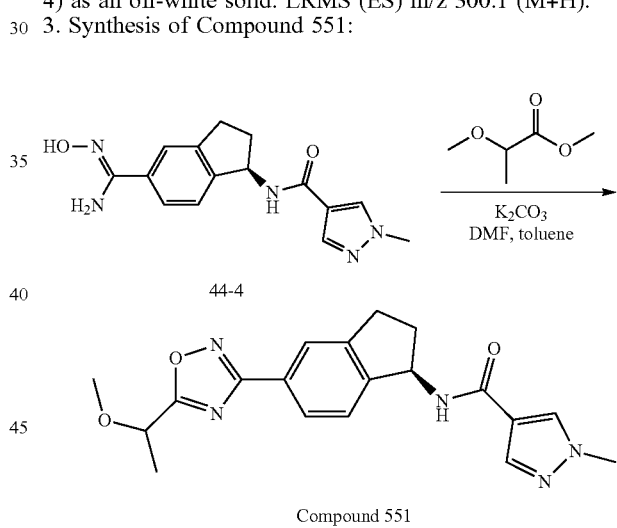

To a suspension of (R,Z)—N-(5-(N'-hydroxycarbamimidoyl)-2,3-dihydro-1H-inden-1-yl)-1-methyl-1H-pyrazole-4-carboxamide (140 mg, 0.47 mmol, 1.0 equiv) in a mixture of toluene and DMF (5.0 mL, 9/1) was added methyl 2-methoxypropanoate (165.8 mg, 1.4 mmol, 3.0 equiv). The mixture was sealed, heated to 120° C. overnight, cooled to rt, and filtered off the solid. The filtrate was concentrated and purified with Prep-HPLC with the following conditions: (Agilent 1100 series) Column, Phenomex Genmuni, 5 μm, 21.5*150 mm; mobile phase, water (0.1 HCOOH) and ACN (35.0% ACN up to 55.0% in 8 min). This purification afforded 85 mg (49%) of N-((1R)-5-(5-(1-methoxyethyl)-1,2,4-oxadiazol-3-yl)-2,3-dihydro-1H-inden-1-yl)-1-methyl-1H-pyrazole-4-carboxamide (Compound 551). LRMS (ES) m/z 368.1 (M+H). $^1$H NMR (400 MHz, Methylene Chloride-d$_2$) δ 8.01 (s, 1H), 7.96 (d, J=8.0 Hz, 1H), 7.86 (s, 1H), 7.75 (s, 1H), 7.46 (d, J=8.0 Hz, 1H), 6.20 (d, J=8.6 Hz, 1H), 5.68 (q, J=8.1 Hz, 1H), 4.73 (q, J=6.7 Hz, 1H), 3.92 (s, 3H), 3.47 (s, 3H), 3.15-3.04 (m, 1H), 3.04-2.92 (m, 1H), 2.76-2.62 (m, 1H), 2.05-1.89 (m, 1H), 1.66 (d, J=6.7 Hz, 3H).

The following compounds were prepared by methods analogous to the method described for Compound 551:

| Compound No. | LRMS (ES) m/z |
|---|---|
| 543 | M + H = 396.1 |
| 544 | M + H = 382.1 |
| 545 | M + H = 352.1 |
| 546 | M + H = 368.1 |
| 547 | M + H = 336.1 |
| 548 | M + H = 396.1 |
| 549 | M + H = 354.1 |
| 550 | M + H = 354.1 |
| 551 | M + H = 368.1 |
| 552 | M + H = 354.1 |

Example 45

Synthesis of Compound 609

1. Synthesis of Intermediate 45-2:

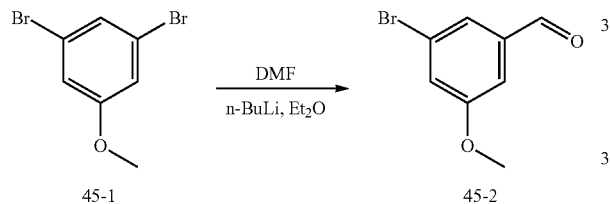

A solution of 1,3-dibromo-5-methoxybenzene (24.5 g, 92.13 mmol, 1 equiv) in Et$_2$O (400 mL) under nitrogen, cooled to -78° C. and stirred for 20 min was added n-BuLi (2.5 mol/L in THF, 44 mL, 1.20 equiv) dropwised at -78° C. The reaction mixture was continued to stir for 1 h at -78° C. followed by addition of DMF (8.1 g, 110.55 mmol, 1.2 equiv) dropwise. After stirring for 45 min at -78° C., the reaction was quenched with water (200 ml) carefully and extracted with EtOAc (500 mL) twice. The combined organic layers were concentrated under reduced pressure to give a mixture, which was further triturated with hexane (200 mL) to afford 3-bromo-5-methoxybenzaldehyde (45-2) (14.5 g, 73.2%) as a white solid.

2. Synthesis of Intermediate 45-3:

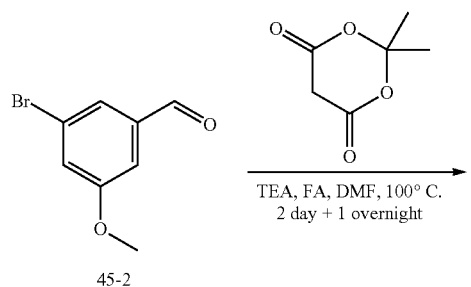

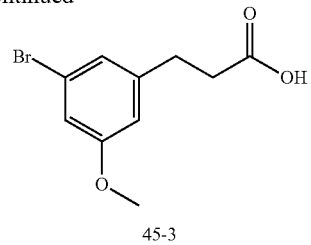

To formic acid (10.8 g, 233.95 mmol, 3 equiv) at 0° C. was added TEA (9.5 g, 93.58 mmol, 1.2 equiv) dropwise. After stirring for 30 min. at rt, to this mixture were added 3-bromo-5-methoxybenzaldehyde (16.77 g, 77.98 mmol, 1 equiv) and 2,2-dimethyl-1,3-dioxane-4,6-dione (11.2 g, 77.71 mmol, 1.00 equiv) in DMF (75 mL) dropwise. The reaction mixture was stirred at 100° C. for 50 h, cooled to 0° C., quenched with conc. HCl (20 mL), and diluted with water (500 mL). The mixture was extracted with DCM (300 mL) three times. The combined organic layers were washed with NaOH (1 N, 500 mL) twice. The aqueous phase was combined, acidified to pH 2 with conc. HCl, and extracted with EtOAc (300 mL) twice. The combined organic layers were washed with brine (500 mL) twice, dried over anhydrous Na$_2$SO$_4$, and concentrated under reduced pressure to give 3-(3-bromo-5-methoxyphenyl) propanoic acid (45-3) (13 g, 64.34%) as a yellow oil.

3. Synthesis of Intermediate 45-4:

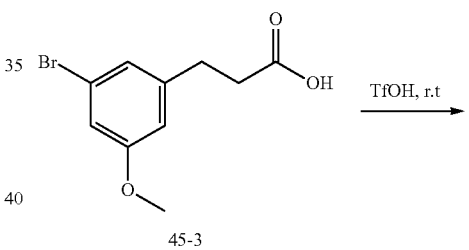

A solution of 3-(3-bromo-5-methoxyphenyl)propanoic acid (30 g, 115.79 mmol, 1 equiv) in triflic acid (90 mL) was stirred for 2 h at room temperature. The reaction was quenched by the addition of ice water (1000 mL) at 0° C., and extracted with EtOAc (500 mL) three times. The combined organic layers were washed with NaHCO$_3$ (500 mL) twice, dried over anhydrous Na$_2$SO$_4$, concentrated under reduced pressure, and purified by reverse flash chromatography with the following conditions: column, C18 silica gel; mobile phase, ACN in water, 35% to 65% gradient in 40 min; detector, UV 254 nm, to give 1.6 g of 5-bromo-7-methoxy-2,3-dihydro-1H-inden-1-one (45-4) as a white solid.

4. Synthesis of Intermediate 45-5:

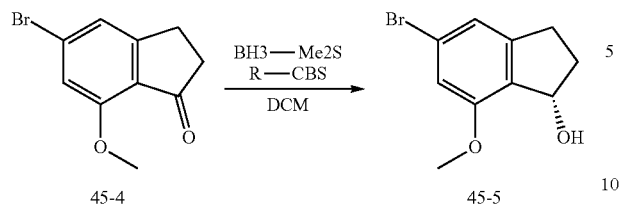

To a solution of 5-bromo-7-methoxy-2,3-dihydro-1H-inden-1-one (1.68 g, 6.97 mmol, 1 equiv) in THF (60 mL) at −10° C. was added R-CBS (1 mol/L in toluene, 1.185 mL, 1.19 mmol, 0.17 equiv). To this solution stirred 10 min at −10° C. was added BH$_3$-Me$_2$S (10 mol/L, 1.18 mL, 11.8 mmol, 1.70 equiv). The mixture was stirred at rt for 1 h, quenched with ice water (10 mL), and extracted with EA (100 mL) twice. The combined organic layers were washed with brine (100 mL) dried over Na$_2$SO$_4$, concentrated under reduced pressure and purified by reverse phase flash chromatography using ACN and water as eluent to afford 680 mg (40%) of (1S)-5-bromo-7-methoxy-2,3-dihydro-1H-inden-1-ol (45-5) as a white solid.

5. Synthesis of Intermediate 45-6:

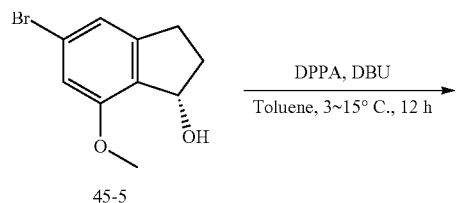

To a solution of (1S)-5-bromo-7-methoxy-2,3-dihydro-1H-inden-1-ol (650 mg, 2.67 mmol, 1.0 equiv) in toluene (10 mL) at 0° C. were added DBU (1221.2 mg, 8.02 mmol, 3 equiv) and DPPA (1471.7 mg, 5.35 mmol, 2.0 equiv) dropwise. After stirring for 10 h, the reaction was quenched with water (10 mL) and extracted with EtOAc (30 mL) three times. The combined organic layers were washed with brine (20 mL), dried over anhydrous Na$_2$SO$_4$, concentrated under reduced pressure, and purified by silica gel column chromatography eluting with PE/EtOAc (3:1) to afford 530 mg (74%) of (1R)-1-azido-5-bromo-7-methoxy-2,3-dihydro-1H-indene (45-6) as a pale-yellow oil.

6. Synthesis of Intermediate 45-7:

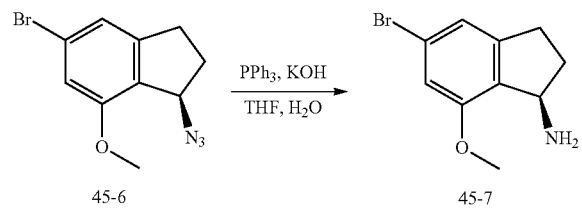

To a solution of (1R)-1-azido-5-bromo-7-methoxy-2,3-dihydro-1H-indene (550 mg, 2.05 mmol, 1.0 equiv) in THF (6 mL) were added PPh$_3$ (645.7 mg, 1.2 eq) and KOH (287.7 mg, 5.13 mmol, 2.5 equiv) in waster (1.5 mL) dropwise. The mixture was stirred at rt for 1 h and at 50° C. overnight. The resulting mixture was concentrated under reduced pressure to give 1.5 g of mixture containing (1R)-5-bromo-7-methoxy-2,3-dihydro-1H-inden-1-amine (45-7).

7. Synthesis of Intermediate 45-8:

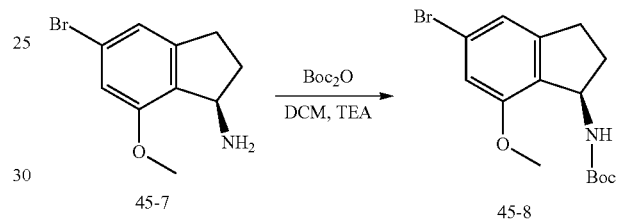

To a solution of (1R)-5-bromo-7-methoxy-2,3-dihydro-1H-inden-1-amine (1.5 g mixture from previously step) in DCM (6 mL), was added TEA (601.8 mg, 5.95 mmol, 3.0 equiv) and Boc$_2$O (649.0 mg, 2.97 mmol, 1.50 equiv). After stirring at rt for 2 h. The mixture was concentrated under reduced pressure and purified by reverse flash chromatography with the following conditions: column, C18 silica gel; mobile phase, ACN in water, 30% to 70% gradient in 30 min; detector, UV 254 nm to afford 330 mg of tert-butyl N-[(1R)-5-bromo-7-methoxy-2,3-dihydro-1H-inden-1-yl]carbamate (45-8) as an off-white solid.

8. Synthesis of Intermediate 45-9:

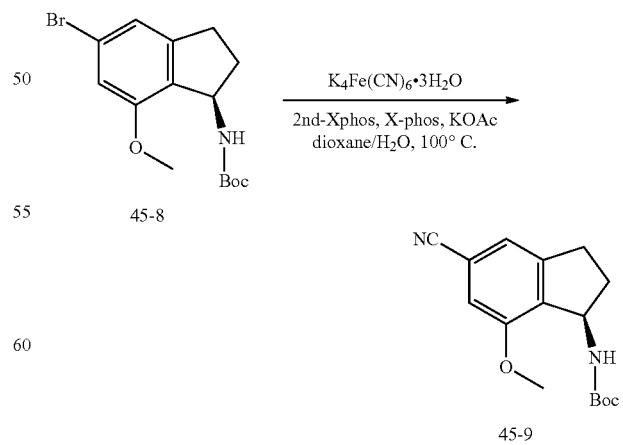

To a solution of tert-butyl N-[(1R)-5-bromo-7-methoxy-2,3-dihydro-1H-inden-1-yl]carbamate (320 mg, 0.94 mmol, 1 equiv) in dioxane (4 mL) and water (1 mL) were added K₄Fe(CN)₆·3H₂O (197.5 mg, 0.47 mmol, 0.50 equiv), 2nd X-PHOS (14.7 mg, 0.02 mmol, 0.02 equiv), and X-Phos (8.9 mg, 0.02 mmol, 0.02 equiv) under nitrogen atmosphere. The mixture was stirred at 100° C. for 8 h, cooled to rt, diluted with water (20 mL), and extracted with EA (20 mL) three times. The combined organic layers were washed with brine (20 mL) dried over sodium sulfate, concentrated, and purified by silica gel eluting with PE/EA (10/1) to afforded 190 mg (74%) of tert-butyl (R)-(5-cyano-7-methoxy-2,3-dihydro-1H-inden-1-yl)carbamate (45-9) as a white solid.

9. Synthesis of Intermediate 45-10:

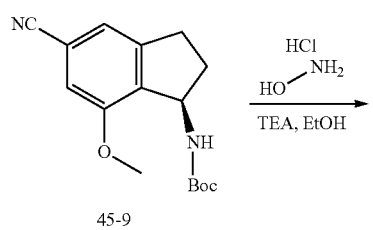

45-9

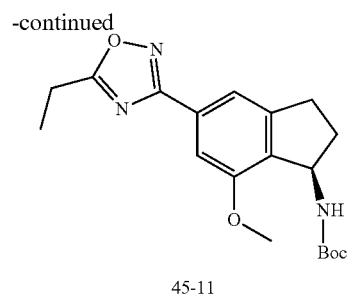

45-11

To a solution of tert-butyl N-[(1R)-5-(N-hydroxycarbamimidoyl)-7-methoxy-2,3-dihydro-1H-inden-1-yl]carbamate (270 mg, 0.84 mmol, 1.0 equiv) in dioxane (3 mL) was added propanoyl propanoate (108.2 mg, 0.83 mmol, 1.0 equiv). The mixture was stirred at 50° C. for 1 h and at 100° C. for 7 h, cooled to rt, concentrated under reduced pressure, and purified by silica gel column chromatography, eluting with PE/EtOAc (9:1) to afford 170 mg (56%) of tert-butyl N-[(1R)-5-(5-ethyl-1,2,4-oxadiazol-3-yl)-7-methoxy-2,3-dihydro-1H-inden-1-yl]carbamate (45-11) as a white solid.

11. Synthesis of Intermediate 45-12:

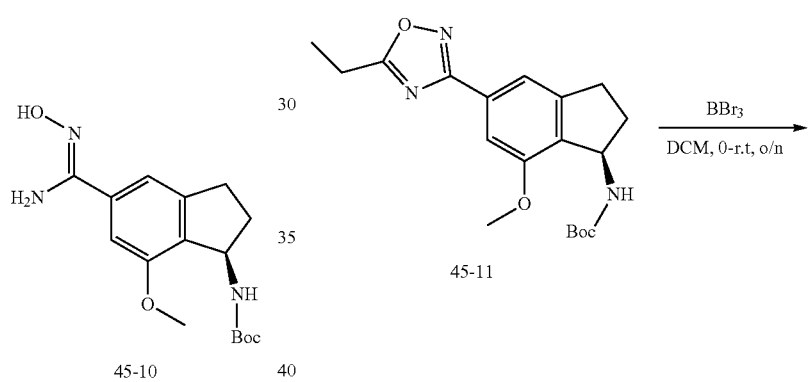

45-11

45-10

To a solution of tert-butyl N-[(1R)-5-cyano-7-methoxy-2,3-dihydro-1H-inden-1-yl]carbamate (180 mg, 0.62 mmol, 1.0 equiv) in EtOH (3 mL) was added TEA (126.3 mg, 1.25 mmol, 2.0 equiv) and hydroxylamine hydrochloride (86.3 mg, 1.24 mmol, 2.0 equiv). The mixture was stirred at 60° C. overnight and concentrated under reduced pressure to give 300 mg of tert-butyl N-[(1R)-5-(N-hydroxycarbamimidoyl)-7-methoxy-2,3-dihydro-1H-inden-1-yl]carbamate (45-10) as an off-white solid.

10. Synthesis of Intermediate 45-11:

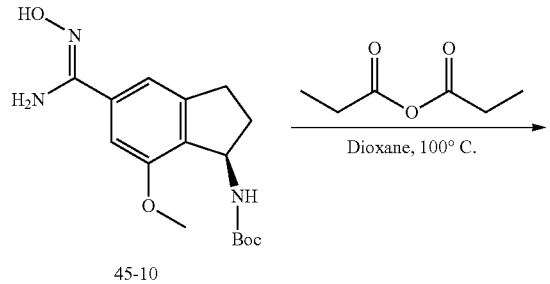

45-10

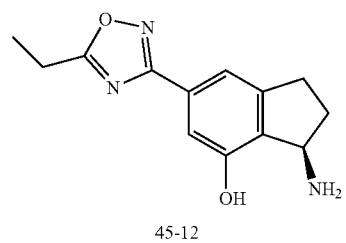

45-12

To a solution of tert-butyl N-[(1R)-5-(5-ethyl-1,2,4-oxadiazol-3-yl)-7-methoxy-2,3-dihydro-1H-inden-1-yl]carbamate (160 mg, 0.45 mmol, 1.0 equiv) in DCM (3.0 mL) at 0° C. was added tribromoborane (2.23 mL, 2.23 mmol, 5.01 equiv) dropwise. The mixture was stirred at rt for 80 h, cooled to 0° C., quenched with MeOH (1 mL), concentrated under reduced pressure, and purified by Prep-HPLC with the following conditions (2#SHIMADZU (HPLC-01)): Column, X Bridge Prep OBD C-18 Column, 30*150 mm 5 um; mobile phase, Water (10 MMOL/L NH4HCO3) and ACN (34% Phase B up to 52% in 8 min); Detector 254 nm, to afford 30 mg (20%) of tert-butyl N-[(1R)-5-(5-ethyl-1,2,4-oxadiazol-3-yl)-7-hydroxy-2,3-dihydro-1H-inden-1-yl]carbamate (45-12) as a white solid.

12. Synthesis of Compound 609:

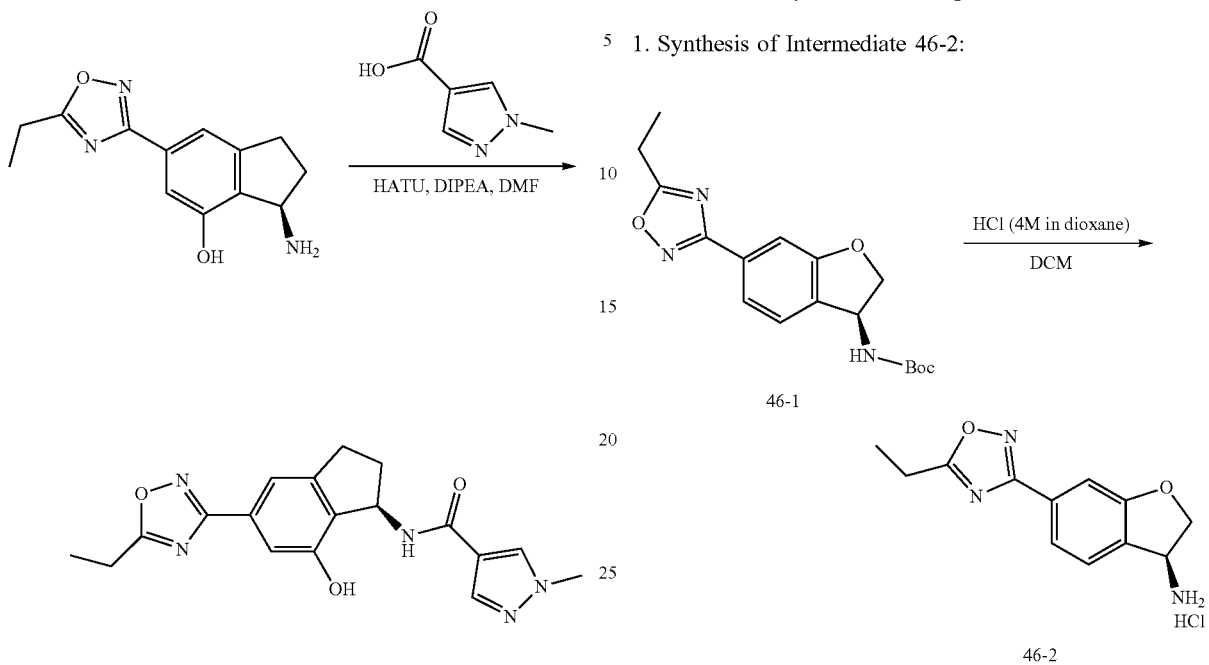

To a solution of 1-methyl-1H-pyrazole-4-carboxylic acid (21.9 mg, 0.17 mmol, 2.0 equiv) in DCM (0.5 mL) were added HOAt (13.0 mg, 0.10 mmol, 1.1 equiv), EDCI (18.3 mg, 0.10 mmol, 1.1 equiv), and DIEA (22.5 mg, 0.17 mmol, 2 equiv). The mixture was stirred at rt for 5 min, followed by addition of tert-butyl N-[(1R)-5-(5-ethyl-1,2,4-oxadiazol-3-yl)-7-hydroxy-2,3-dihydro-1H-inden-1-yl]carbamate (30 mg, 0.09 mmol, 1.0 equiv). The mixture was stirred at rt for 2 h and purified by Prep-HPLC with the following conditions (2#SHIMADZU (HPLC-01)): Column, X Bridge Prep OBD C18 Column, 30*150 mm 5 um; mobile phase, Water (10 MMOL/L $NH_4HCO_3$) and ACN (26% Phase B up to 45% in 8 min); Detector, UV. 25 mg product was obtained. The crude product was purified by Chiral-Prep-HPLC with the following conditions (Prep-HPLC): Column, CHIRALPAK IE, 2*25 cm, 5 um; mobile phase, Hex: DCM=3:1 (10 mM $NH_3$ in MeOH) and EtOH (hold 50% EtOH/HE for 16 min) to afford 11.1 mg (36%) of N-[(1R)-5-(5-ethyl-1,2,4-oxadiazol-3-yl)-7-hydroxy-2,3-dihydro-1H-inden-1-yl]-1-methyl-1H-pyrazole-4-carboxamide (Compound 609) as a white solid. LRMS (ES) m/z 354 (M+H). $^1$H NMR (300 MHz, Chloroform-d) δ 9.62 (br, 1H), 7.90 (br, 1H), 7.75 (br, 1H), 7.50 (br, 2H), 6.30 (br, 1H), 5.49 br, 1H), 3.95 (s, 3H), 3.27-3.19 (m, 1H), 2.99 (m, 3H), 2.72 (s, 1H), 2.15 (s, 1H), 1.46 (br, 3H).

The following compounds were prepared by methods analogous to the method described for Compound 609:

| Compound No. | LRMS (ES) m/z |
|---|---|
| 562 | M + H = 356 |
| 588 | M + H = 372 |
| 699 | M + H = 356 |

Example 46

Synthesis of Compound 744

1. Synthesis of Intermediate 46-2:

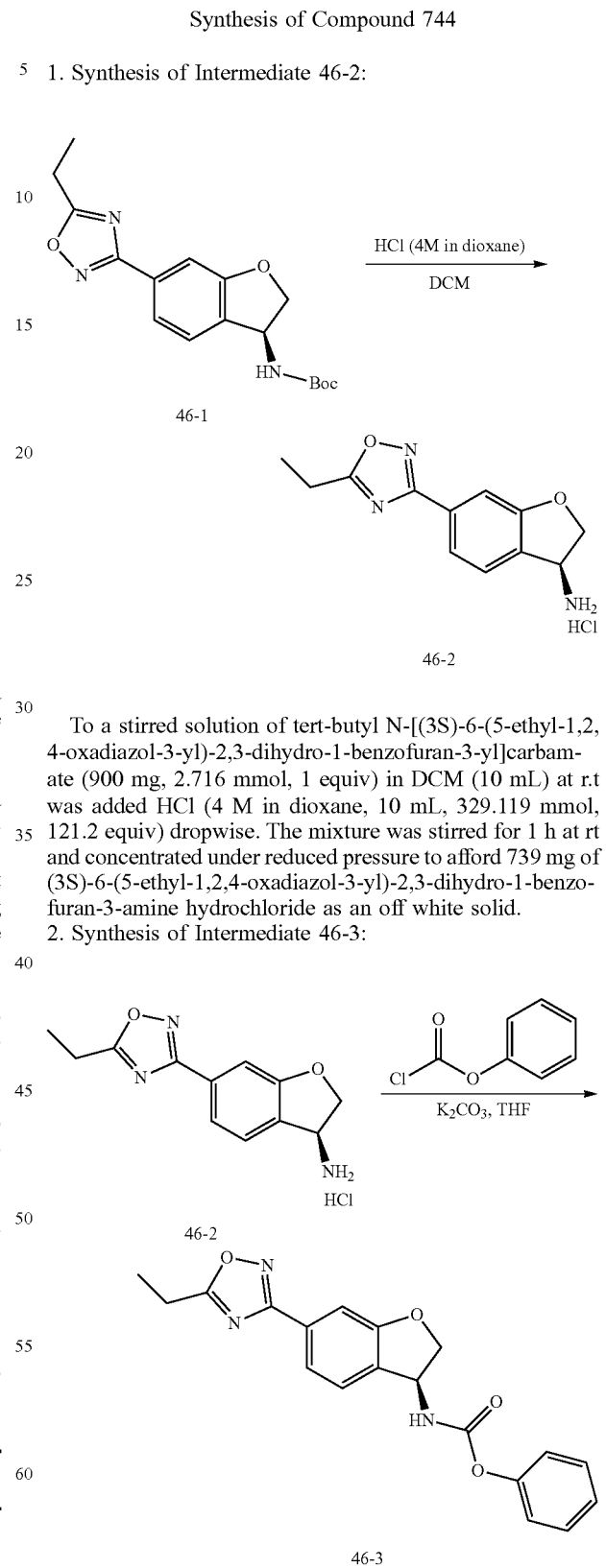

To a stirred solution of tert-butyl N-[(3S)-6-(5-ethyl-1,2,4-oxadiazol-3-yl)-2,3-dihydro-1-benzofuran-3-yl]carbamate (900 mg, 2.716 mmol, 1 equiv) in DCM (10 mL) at r.t was added HCl (4 M in dioxane, 10 mL, 329.119 mmol, 121.2 equiv) dropwise. The mixture was stirred for 1 h at rt and concentrated under reduced pressure to afford 739 mg of (3S)-6-(5-ethyl-1,2,4-oxadiazol-3-yl)-2,3-dihydro-1-benzofuran-3-amine hydrochloride as an off white solid.

2. Synthesis of Intermediate 46-3:

To a stirred solution of (3S)-6-(5-ethyl-1,2,4-oxadiazol-3-yl)-2,3-dihydro-1-benzofuran-3-amine hydrochloride (700.0 mg, 2.62 mmol, 1.0 equiv) in THF (50.0 mL) at 0° C. were added K$_2$CO$_3$ (722.8 mg, 5.2 mmol, 2.0 equiv) and phenyl chloroformate (450.33 mg, 2.876 mmol, 1.10 equiv) dropwise. The resulting mixture was stirred at rt for 4 h and diluted with water. The precipitates were filtered off, washed with EtOAc (10 mL) three times. The aqueous layer was extracted with EtOAc (50 mL) twice. The combined organic layers were washed with brine, (50 mL), dried over anhydrous Na$_2$SO$_4$, concentrated, and purified on silica gel eluting with PE/EA (4/1) to afford 0.88 g (96%) of phenyl N-[(3S)-6-(5-ethyl-1,2,4-oxadiazol-3-yl)-2,3-dihydro-1-benzofuran-3-yl]carbamate as a white solid. LRMS (ES) m/z 352 (M+H).

3. Synthesis of Compound 744:

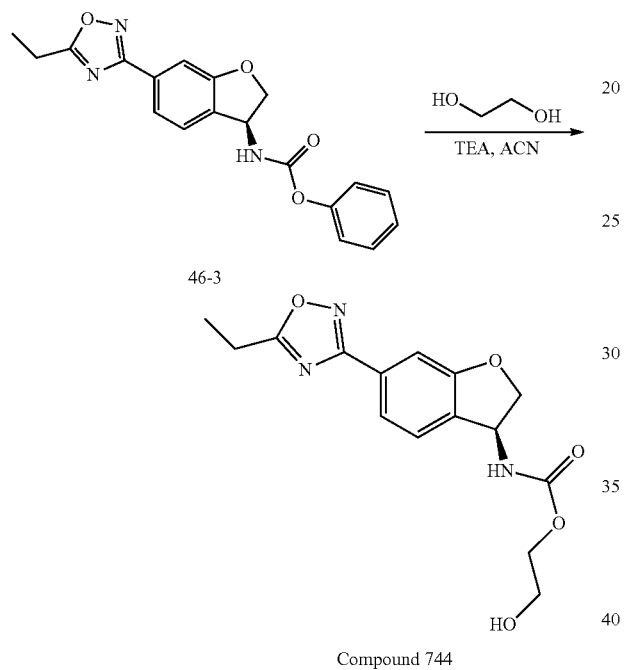

Compound 744

To a stirred solution of phenyl N-[(3S)-6-(5-ethyl-1,2,4-oxadiazol-3-yl)-2,3-dihydro-1-benzofuran-3-yl]carbamate (80.0 mg, 0.23 mmol, 1.0 equiv) in ACN (4.0 mL) at r.t were added ethylene glycol (17.0 mg, 0.27 mmol, 1.2 equiv) and TEA (46.1 mg, 0.456 mmol, 2.0 equiv) dropwise. The resulting mixture was stirred at 65° C. for 4 h, cooled to r.t, and purified by Prep-HPLC with the following conditions (Column: Xselect CSH OBD Column 30*150 mm Sum, n; Mobile Phase A:Water (10 MMOL/L NH4HCO3+0.1% NH3.H$_2$O), Mobile Phase B:ACN; Flow rate: 60 mL/min; Gradient: 18 B to 38 B in 9 min) to afford 2-hydroxyethyl 26.5 mg (36%) of N-[(3S)-6-(5-ethyl-1,2,4-oxadiazol-3-yl)-2,3-dihydro-1-benzofuran-3-yl]carbamate (Compound 744) (26.5 mg, 36.45%) as a white solid. LRMS (ES) m/z 320 (M+H). $^1$H NMR ((300 MHz, DMSO) δ 7.94 (s, 1H), 7.56 (d, J=7.4 Hz, 1H), 7.48 (s, 1H), 7.35 (s, 1H), 5.38 (d, J=6.5 Hz, 1H), 4.74 (s, 1H), 4.31 (d, J=9.8 Hz, 1H), 4.02 (s, 2H), 3.55 (s, 2H), 3.00 (q, J=7.5 Hz, 2H), 1.33 (t, J=7.6 Hz, 3H).

The following compounds were prepared by methods analogous to the method described for Compound 744:

| Compound No. | LRMS (ES) m/z |
|---|---|
| 299 | M + H = 323.1 |
| 300 | M + H = 349.1 |
| 301 | M + H = 365.1 |
| 302 | M + H = 378.1 |
| 723 | M + H = 343.1 |
| 724 | M + H = 343.1 |
| 739 | M + H = 345 |
| 740 | M + H = 345 |
| 741 | M + H = 331 |
| 742 | M + H = 347 |
| 743 | M + H = 347 |
| 744 | M + H = 320 |
| 745 | M + H = 319 |
| 746 | M + H = 333 |

Biological Example B-1

Myofibril Assays

To evaluate the effect of compounds on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in an Ca$^{2+}$ regulated manner. ATPase activities of such myofibril preparations in the presence and absence of compounds were assayed at Ca$^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% (pCa$_{50}$) or 75% (pCa$_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 μM ATP, 0.1 mg/mL BSA (bovine serum albumin), 10 ppm antifoam, 1 mM DTT, 0.5 mM NADH, 1.5 mM PEP, 0.6 mM EGTA, and an amount of CaCl$_2$) sufficient to achieve either 50% or 75% activation of the myofibril ATPase activity. Results for compounds tested are provided in Table A. Compounds tested were prepared in accordance with the synthetic procedures described herein.

TABLE A

| Cmpd No. | CDMF75 IC$_{15}$ (μM) | CDMF75 IC$_{50}$ (μM) |
|---|---|---|
| 1 | 4.5 | 21.7 |
| 2 | 0.6 | 2.0 |
| 3 | 1.8 | 7.0 |
| 4 | 0.43 | 1.6 |

TABLE A-continued

| Cmpd No. | CDMF75 IC$_{15}$ (μM) | CDMF75 IC$_{50}$ (μM) |
|---|---|---|
| 5 | 1.14 | 5.1 |
| 6 | 0.7 | 3.4 |
| 7 | 1.1 | 4.8 |
| 8 | 0.4 | 1.4 |
| 9 | 1.4 | 6.7 |
| 10 | 1.0 | 3.4 |
| 11 | 0.8 | 3.4 |
| 12 | 0.6 | 2.0 |
| 13 | 0.5 | 22.1 |
| 14 | 39.2 | >39.2 |
| 15 | 0.6 | 2.0 |
| 16 | 8.9 | >39.2 |
| 17 | 2.3 | 11.3 |
| 18 | 1.1 | 6.8 |
| 19 | 1.3 | 4.6 |
| 20 | 2.3 | >39.2 |
| 21 | 0.7 | 2.9 |
| 22 | 5.5 | 28.2 |
| 23 | 5.8 | 31.4 |
| 24 | 2.1 | 8.0 |
| 25 | 3.9 | 16.5 |
| 26 | 7.8 | 30.5 |
| 27 | 0.8 | 3.3 |
| 28 | 0.8 | 3.4 |
| 29 | 1.2 | 5.3 |
| 30 | 0.8 | 2.3 |
| 31 | 1.0 | 3.6 |
| 32 | 0.6 | 2.3 |
| 33 | 1.3 | 4.3 |
| 34 | 2.1 | 8.1 |
| 35 | 0.5 | 1.6 |
| 36 | 0.9 | 4.7 |
| 37 | 2.1 | 9.7 |
| 38 | 2.2 | 9.5 |
| 39 | 31.0 | >39.2 |
| 40 | 3.9 | 16.2 |
| 41 | 6.6 | >39.2 |
| 42 | 7.2 | 31.6 |
| 43 | 4.3 | 14.1 |
| 44 | 3.3 | 12.3 |
| 45 | 2.1 | 7.6 |
| 46 | 1.2 | 4.2 |
| 47 | 1.4 | 5.0 |
| 48 | 1.4 | 4.9 |
| 49 | 9.8 | >39.2 |
| 50 | 1.5 | 5.2 |
| 51 | 1.2 | 3.6 |
| 52 | 1.6 | 4.9 |
| 53 | 2.5 | 8.8 |
| 54 | 2.2 | 7.8 |
| 55 | 2.0 | 6.8 |
| 56 | 2.5 | 8.5 |
| 57 | 2.8 | 8.9 |
| 58 | 4.8 | 21.0 |
| 59 | 5.7 | 28.2 |
| 60 | 2.3 | 8.3 |
| 61 | 1.1 | 3.5 |
| 62 | 1.5 | 8.7 |
| 63 | 2.3 | 10.1 |
| 64 | 1.2 | 5.1 |
| 65 | 0.8 | 3.0 |
| 66 | 1.2 | 4.5 |
| 67 | 0.9 | 4.7 |
| 68 | 1.6 | 6.1 |
| 69 | 0.6 | 2.3 |
| 70 | 1.4 | 4.8 |
| 71 | 0.4 | 1.2 |
| 72 | 0.3 | 1.0 |
| 73 | 0.7 | 2.5 |
| 74 | 22.3 | >39.2 |
| 75 | 0.9 | 3.1 |
| 76 | 1.7 | 6.1 |
| 77 | 4.9 | 26.0 |
| 78 | 2.6 | 13.6 |
| 79 | 4.6 | 22.7 |
| 80 | 27.5 | >39.2 |
| 81 | 1.1 | 3.7 |
| 82 | 0.5 | 2.0 |
| 83 | 1.9 | 7.8 |
| 84 | 2.7 | 10.8 |
| 85 | 5.5 | 24.1 |
| 86 | 4.1 | 14.9 |
| 87 | 3.7 | 15.7 |
| 88 | 0.7 | 2.5 |
| 89 | 1.0 | 3.3 |
| 90 | 0.4 | 1.9 |
| 91 | 0.5 | 1.8 |
| 92 | 0.3 | 0.8 |
| 93 | 0.2 | 0.9 |
| 94 | 5.2 | 26.6 |
| 95 | 1.9 | 8.0 |
| 96 | 3.0 | 13.4 |
| 97 | 2.0 | 7.8 |
| 98 | 13.1 | >39.2 |
| 99 | 0.6 | 2.6 |
| 100 | 0.7 | 3.0 |
| 101 | 0.3 | 1.1 |
| 102 | 1.6 | 5.8 |
| 103 | 0.7 | 2.2 |
| 104 | 1.7 | 6.3 |
| 105 | 2.2 | 8.9 |
| 106 | 0.8 | 2.8 |
| 107 | 0.5 | 1.7 |
| 108 | 5.2 | 24 |
| 109 | 1.9 | 7.1 |
| 110 | 39.2 | >39.2 |
| 111 | 1.1 | 3.7 |
| 112 | 1.5 | 5.2 |
| 113 | 0.3 | 1.3 |
| 114 | 0.5 | 2.0 |
| 115 | 0.3 | 0.9 |
| 116 | 0.3 | 1.5 |
| 117 | 1.9 | 10.1 |
| 118 | 19.3 | >39.2 |
| 119 | 39.2 | >39.2 |
| 120 | 2.4 | 9.8 |
| 121 | 1.0 | 3.1 |
| 122 | 0.5 | 1.8 |
| 123 | 0.5 | 1.7 |
| 124 | 0.3 | 0.9 |
| 125 | 1.6 | 6.2 |
| 126 | 1.6 | 5.7 |
| 127 | 1.7 | 7.7 |
| 128 | 2.6 | 12.2 |
| 129 | 0.5 | 1.5 |
| 130 | 2.5 | 10.3 |
| 131 | 1.4 | 5.4 |
| 132 | 4.3 | 17.7 |
| 133 | 1.5 | 5.7 |
| 134 | 39.2 | >39.2 |
| 135 | 39.2 | >39.2 |
| 136 | 0.8 | 2.8 |
| 137 | 1.2 | 4.9 |
| 138 | 0.8 | 2.9 |
| 139 | 3.6 | 17.3 |
| 140 | 7.6 | >39.2 |
| 141 | 0.3 | 0.9 |
| 142 | 0.5 | 2.4 |
| 143 | 0.3 | 1.0 |
| 144 | 0.6 | 2.3 |
| 145 | 39.2 | >39.2 |
| 146 | 21.2 | >39.2 |
| 147 | 1.3 | 6.2 |
| 148 | 2.9 | 13.5 |
| 149 | 39.2 | >39.2 |
| 150 | 0.3 | 1.2 |
| 151 | 0.5 | 2.0 |
| 152 | 0.6 | 2.2 |
| 153 | 0.5 | 1.9 |
| 154 | 0.4 | 1.5 |
| 155 | 1.0 | 4.1 |
| 156 | 1.1 | 4.7 |
| 157 | 1.4 | 5.9 |
| 158 | 0.7 | 2.8 |

TABLE A-continued

| Cmpd No. | CDMF75 IC$_{15}$ (µM) | CDMF75 IC$_{50}$ (µM) |
|---|---|---|
| 159 | 1.9 | 8.4 |
| 160 | 6.5 | 31.3 |
| 161 | 1.1 | 4.4 |
| 162 | 1.6 | 6.4 |
| 163 | 0.8 | 3.1 |
| 164 | 8.2 | >39.2 |
| 165 | 4.6 | 23.5 |
| 166 | 2.0 | 7.0 |
| 167 | 1.0 | 3.8 |
| 168 | 1.1 | 3.8 |
| 169 | 0.5 | 1.8 |
| 170 | 3.8 | 15.9 |
| 171 | 1.7 | 6.9 |
| 172 | 8.1 | >39.2 |
| 173 | 39.2 | >39.2 |
| 174 | 1.1 | 3.8 |
| 175 | 0.4 | 1.4 |
| 176 | 1.2 | 4.5 |
| 177 | 0.5 | 1.8 |
| 178 | 1.9 | 6.8 |
| 179 | 0.7 | 2.2 |
| 180 | 1.7 | 5.8 |
| 181 | 1.1 | 4.0 |
| 182 | 1.0 | 4.1 |
| 183 | 0.3 | 0.9 |
| 184 | 0.4 | 1.4 |
| 185 | 0.8 | 2.7 |
| 186 | 0.7 | 2.4 |
| 187 | 11.5 | >39.2 |
| 188 | 5.3 | 23.6 |
| 189 | 1.4 | 5.1 |
| 190 | 0.6 | 2.0 |
| 191 | 0.3 | 0.9 |
| 192 | 1.0 | 3.8 |
| 193 | 0.5 | 2.1 |
| 194 | 0.7 | 2.6 |
| 195 | 10.1 | >39.2 |
| 196 | 4.5 | 17.4 |
| 197 | 3.2 | 12.4 |
| 198 | 2.0 | 7.2 |
| 199 | 6.0 | 24.1 |
| 200 | 2.6 | 11.3 |
| 201 | 1.4 | 5.4 |
| 202 | 2.6 | 10.5 |
| 203 | 1.0 | 3.6 |
| 204 | 0.5 | 1.8 |
| 205 | 1.1 | 4.0 |
| 206 | 0.7 | 2.3 |
| 207 | 1.0 | 3.6 |
| 208 | 0.5 | 1.6 |
| 209 | 0.9 | 3.3 |
| 210 | 0.5 | 1.6 |
| 211 | 0.8 | 2.8 |
| 212 | 1.7 | 6.0 |
| 213 | 1.2 | 4.7 |
| 214 | 1.3 | 4.9 |
| 215 | 3.0 | 12.4 |
| 216 | 1.3 | 4.9 |
| 217 | 0.6 | 1.9 |
| 218 | 0.5 | 1.6 |
| 219 | 0.7 | 2.5 |
| 220 | 38.3 | >39.2 |
| 221 | 0.6 | 2.0 |
| 222 | 0.3 | 1.0 |
| 223 | 1.3 | 4.2 |
| 224 | 0.6 | 2.1 |
| 225 | 39.2 | 39.2 |
| 226 | 1.2 | 4.0 |
| 227 | 0.7 | 2.2 |
| 228 | 0.3 | 0.8 |
| 229 | 0.5 | 1.4 |
| 230 | 0.6 | 1.8 |
| 231 | 0.3 | 1.0 |
| 232 | 0.7 | 2.4 |
| 233 | 0.3 | 1.1 |
| 234 | 1.9 | 8.0 |
| 235 | 1.2 | 4.8 |

TABLE A-continued

| Cmpd No. | CDMF75 IC$_{15}$ (µM) | CDMF75 IC$_{50}$ (µM) |
|---|---|---|
| 236 | 0.5 | 1.8 |
| 237 | 1.1 | 3.6 |
| 238 | 0.3 | 1.0 |
| 239 | 0.7 | 2.1 |
| 240 | 0.3 | 0.8 |
| 241 | 0.2 | 0.8 |
| 242 | 0.5 | 1.5 |
| 243 | 1.3 | 4.7 |
| 244 | 1.6 | 5.4 |
| 245 | 1.0 | 3.4 |
| 246 | 1.1 | 3.5 |
| 247 | 0.8 | 2.6 |
| 248 | 0.4 | 1.5 |
| 249 | 1.4 | 5.2 |
| 250 | 1.0 | 3.6 |
| 251 | 0.5 | 1.5 |
| 252 | 0.4 | 1.5 |
| 253 | 0.3 | 0.8 |
| 254 | 1.3 | 4.9 |
| 255 | 0.8 | 2.6 |
| 256 | 0.5 | 1.7 |
| 257 | 0.4 | 1.0 |
| 258 | 1.5 | 5.7 |
| 259 | 0.8 | 3.0 |
| 260 | 0.4 | 1.4 |
| 261 | 0.4 | 1.2 |
| 262 | 0.7 | 1.9 |
| 263 | 2.8 | 10.5 |
| 264 | 1.8 | 6.6 |
| 265 | 1.0 | 3.4 |
| 266 | 0.9 | 2.7 |
| 267 | 1.2 | 4.4 |
| 268 | 1.9 | 5.1 |
| 269 | 1.1 | 3.5 |
| 270 | 0.9 | 3.1 |
| 271 | 4.3 | 17.1 |
| 272 | 1.2 | 4.3 |
| 273 | 0.7 | 2.4 |
| 274 | 4.0 | 15.0 |
| 275 | 0.8 | 2.9 |
| 276 | 2.6 | 10.1 |
| 277 | 1.4 | 5.4 |
| 278 | 1.3 | 5.2 |
| 279 | 22.4 | >39.2 |
| 280 | 0.7 | 2.7 |
| 281 | 0.9 | >39.2 |
| 282 | 0.5 | 1.9 |
| 283 | 9.6 | >39.2 |
| 284 | 38.5 | >39.2 |
| 285 | 9.3 | >39.2 |
| 286 | 2.1 | 10.2 |
| 287 | 39.2 | >39.2 |
| 288 | 10.6 | >39.2 |
| 289 | 39.2 | >39.2 |
| 290 | 39.2 | >39.2 |
| 291 | 17.3 | >39.2 |
| 292 | 39.2 | >39.2 |
| 293 | 20.4 | >39.2 |
| 294 | 15.6 | >39.2 |
| 295 | 4.9 | >39.2 |
| 296 | 5.8 | >39.2 |
| 297 | 39.2 | >39.2 |
| 298 | 39.2 | >39.2 |
| 299 | 6.7 | 30.9 |
| 300 | 12.3 | >39.2 |
| 301 | 9.5 | >39.2 |
| 302 | 39.2 | >39.2 |
| 303 | 0.6 | 2.7 |
| 304 | 0.2 | 0.7 |
| 305 | 0.3 | 1.2 |
| 306 | 0.9 | 3.7 |
| 307 | 0.6 | 2.9 |
| 308 | 0.7 | 2.8 |
| 309 | 39.2 | >39.2 |
| 310 | 2.9 | 11.3 |
| 311 | 1.8 | 6.3 |
| 312 | 0.7 | 2.4 |

TABLE A-continued

| Cmpd No. | CDMF75 IC$_{15}$ (μM) | CDMF75 IC$_{50}$ (μM) |
|---|---|---|
| 313 | 1.6 | 6.5 |
| 314 | 0.7 | 2.4 |
| 315 | 6.1 | 26.4 |
| 316 | 15.6 | >39.2 |
| 317 | 2.7 | 12.1 |
| 318 | 2.2 | 9.3 |
| 319 | 1.3 | 5.3 |
| 320 | 0.7 | 3.1 |
| 321 | 0.4 | 1.3 |
| 322 | 0.3 | 0.9 |
| 323 | 0.3 | 0.9 |
| 324 | 0.8 | 3.2 |
| 325 | 0.5 | 1.9 |
| 326 | 0.6 | 2.4 |
| 327 | 1.8 | 8.2 |
| 328 | 1.2 | >39.2 |
| 329 | 1.7 | 7.0 |
| 330 | 3.8 | 17.7 |
| 331 | 20.0 | >39.2 |
| 332 | 39.2 | >39.2 |
| 333 | 0.3 | 0.9 |
| 334 | 0.6 | 1.9 |
| 335 | 19.1 | >39.2 |
| 336 | 30.9 | >39.2 |
| 337 | 24.7 | >39.2 |
| 338 | 39.2 | >39.2 |
| 339 | 0.4 | 1.2 |
| 340 | 0.3 | 0.7 |
| 341 | 1.9 | 7.3 |
| 342 | 8.0 | >39.2 |
| 343 | 1.8 | 6.6 |
| 344 | 8.6 | >39.2 |
| 345 | 0.2 | 0.8 |
| 346 | 0.9 | 3.2 |
| 347 | 0.5 | 1.6 |
| 348 | 0.5 | 1.8 |
| 349 | 0.3 | 0.9 |
| 350 | 0.5 | 2.1 |
| 351 | 18.8 | >39.2 |
| 352 | 13.0 | >39.2 |
| 353 | 29.0 | >39.2 |
| 354 | 34.1 | >39.2 |
| 355 | 2.9 | 10.9 |
| 356 | 13.4 | >39.2 |
| 357 | 0.5 | 1.7 |
| 358 | 0.6 | 2.2 |
| 359 | 2.3 | 9.5 |
| 360 | 21.6 | >39.2 |
| 361 | 23.7 | >39.2 |
| 362 | 1.9 | 6.6 |
| 363 | 4.7 | 21.1 |
| 364 | 1.6 | 6.8 |
| 365 | 0.6 | 2.2 |
| 366 | 8.6 | >39.2 |
| 367 | 13.9 | >39.2 |
| 368 | 17.6 | >39.2 |
| 369 | 39.2 | >39.2 |
| 370 | 3.8 | 19.1 |
| 371 | 0.7 | 2.9 |
| 372 | 3.5 | 15.7 |
| 373 | 0.9 | 3.2 |
| 374 | 1.7 | 6.4 |
| 375 | 10.6 | >39.2 |
| 376 | 3.9 | 18.5 |
| 377 | 4.5 | 17.8 |
| 378 | 2.1 | 12.2 |
| 379 | 39.2 | >39.2 |
| 380 | 2.2 | 10.3 |
| 381 | 39.2 | >39.2 |
| 382 | 2.7 | 10.1 |
| 383 | 3.4 | 11.6 |
| 384 | 39.2 | >39.2 |
| 385 | 0.5 | 1.7 |
| 386 | 0.3 | 0.8 |
| 387 | 0.5 | 1.3 |
| 388 | 0.9 | 2.8 |
| 389 | 0.6 | 1.9 |
| 390 | 0.4 | 1 |
| 391 | 1.3 | 4.6 |
| 392 | 0.9 | 2.7 |
| 393 | 0.4 | 1.2 |
| 394 | 1.2 | 4.1 |
| 395 | 3.1 | 13.5 |
| 396 | 0.4 | 1.6 |
| 397 | 0.9 | 3.2 |
| 398 | 0.4 | 1.2 |
| 399 | 0.3 | 1 |
| 400 | 0.8 | 2.8 |
| 401 | 0.9 | 3.0 |
| 402 | 1 | 3.8 |
| 403 | 0.4 | 1.2 |
| 404 | 0.4 | 1.2 |
| 405 | 0.6 | 2.3 |
| 406 | 1.9 | 7.7 |
| 407 | 3.2 | 13.8 |
| 408 | 2.8 | 12.8 |
| 409 | 0.2 | 0.7 |
| 410 | 0.9 | 3.5 |
| 411 | 0.7 | 3.2 |
| 412 | 0.5 | 1.8 |
| 413 | 0.4 | 1.5 |
| 414 | 0.2 | 0.6 |
| 415 | 0.5 | 1.7 |
| 416 | 1.2 | 4.2 |
| 417 | 0.2 | 0.6 |
| 418 | 0.3 | 1.2 |
| 419 | 1.2 | 4.7 |
| 420 | 0.4 | 1.4 |
| 421 | 0.3 | 0.8 |
| 422 | 0.4 | 1.5 |
| 423 | 0.3 | 1.2 |
| 424 | 0.2 | 0.6 |
| 425 | 0.3 | 1.2 |
| 426 | 0.8 | 2.6 |
| 427 | 0.5 | 1.6 |
| 428 | 1.0 | 3.4 |
| 429 | 0.5 | 1.5 |
| 430 | 1.0 | 3.2 |
| 431 | 0.3 | 0.9 |
| 432 | 0.8 | 2.5 |
| 433 | 0.3 | 0.9 |
| 434 | 0.7 | 2.4 |
| 435 | 2.6 | 11.3 |
| 436 | 0.6 | 2.1 |
| 437 | 8.8 | 34.4 |
| 438 | 3.7 | 15.8 |
| 439 | 1.1 | 4.8 |
| 440 | 2.7 | 10.7 |
| 441 | 3.4 | 13.9 |
| 442 | 2.5 | 12.6 |
| 443 | 0.7 | 2.6 |
| 444 | 1.6 | 7.9 |
| 445 | 0.8 | 3.0 |
| 446 | 0.7 | 2.6 |
| 447 | 1.8 | 9.3 |
| 448 | 0.3 | 0.9 |
| 449 | 0.5 | 1.5 |
| 450 | 3.2 | 12.4 |
| 451 | 2.3 | 7.7 |
| 452 | 4.3 | 20.3 |
| 453 | 0.2 | 0.7 |
| 454 | 0.5 | 1.8 |
| 455 | 0.2 | 0.7 |
| 456 | 0.3 | 1.1 |
| 457 | 1.2 | 5.3 |
| 458 | 2.0 | 9.2 |
| 459 | 0.4 | 1.2 |
| 460 | 1.3 | 5.5 |
| 461 | 1.3 | 6.5 |
| 462 | 0.4 | 1.4 |
| 463 | 0.7 | 2.4 |
| 464 | 0.4 | 1.4 |
| 465 | 0.7 | 2.6 |
| 466 | 0.8 | 2.9 |

TABLE A-continued

| Cmpd No. | CDMF75 IC$_{15}$ (μM) | CDMF75 IC$_{50}$ (μM) |
|---|---|---|
| 467 | 2.1 | 8.4 |
| 468 | 6.6 | 39.2 |
| 469 | 0.3 | 1.1 |
| 470 | 4.4 | 16.8 |
| 471 | 1.9 | 7.1 |
| 472 | 0.8 | 3.1 |
| 473 | 1.1 | 3.8 |
| 474 | 0.6 | 2.2 |
| 475 | 0.9 | 3.8 |
| 476 | 4.2 | 19.5 |
| 477 | 8.5 | 39.2 |
| 478 | 2.9 | 11.9 |
| 479 | 4.5 | 23.1 |
| 480 | 6.6 | 39.2 |
| 481 | 1.9 | 7.8 |
| 482 | 3.9 | 15.9 |
| 483 | 2.0 | 6.8 |
| 484 | 39.2 | 39.2 |
| 485 | 1.2 | 4.1 |
| 486 | 4.1 | 24.3 |
| 487 | 0.9 | 3.4 |
| 488 | 1.1 | 4.3 |
| 489 | 0.6 | 2.2 |
| 490 | 1.6 | 6.9 |
| 491 | 1.0 | 3.7 |
| 492 | 1.1 | 4.0 |
| 493 | 5.6 | 21.4 |
| 494 | 2.4 | 10.0 |
| 495 | 10.0 | 39.2 |
| 496 | 7.1 | 34.3 |
| 497 | 7.4 | 39.2 |
| 498 | 7.9 | 34.7 |
| 499 | 2.4 | 39.2 |
| 500 | 1.0 | 6.5 |
| 501 | 0.3 | 1.1 |
| 502 | 2.0 | 8.0 |
| 503 | 0.8 | 3.4 |
| 504 | 4.4 | 16.6 |
| 505 | 6.5 | 29.2 |
| 506 | 4.5 | 20.0 |
| 507 | 32.6 | 39.2 |
| 508 | 2.6 | 11.3 |
| 509 | 3.2 | 12.8 |
| 510 | 1.9 | 7.9 |
| 511 | 3.0 | 14.0 |
| 512 | 4.5 | 18.2 |
| 513 | 2.2 | 10.9 |
| 514 | 2.7 | 11.0 |
| 515 | 4.3 | 19.5 |
| 516 | 39.2 | 39.2 |
| 517 | 2.2 | 9.7 |
| 518 | 27.8 | 39.2 |
| 519 | 1.9 | 8.7 |
| 520 | 1.8 | 8.1 |
| 521 | 1.2 | 5.0 |
| 522 | 2.0 | 9.1 |
| 523 | 2.9 | 13.3 |
| 524 | 1.7 | 7.3 |
| 525 | 0.7 | 2.5 |
| 526 | 0.4 | 1.3 |
| 527 | 0.3 | 1.1 |
| 528 | 1.1 | 4.9 |
| 529 | 1.8 | 6.8 |
| 530 | 2.6 | 8.9 |
| 531 | 4.1 | 25.1 |
| 532 | 1.1 | 5.5 |
| 533 | 1.5 | 8.7 |
| 534 | 2.2 | 13.5 |
| 535 | 1.0 | 5.8 |
| 536 | 1.1 | 3.5 |
| 537 | 0.4 | 1.8 |
| 538 | 0.7 | 3.3 |
| 539 | 1.3 | 6.0 |
| 540 | 0.7 | 2.9 |
| 541 | 1.2 | 5.2 |
| 542 | 0.9 | 3.5 |
| 543 | 4.6 | 17.3 |
| 544 | 34.9 | 39.2 |
| 545 | 3.2 | 13.1 |
| 546 | 15.5 | 39.2 |
| 547 | 0.4 | 1.5 |
| 548 | 11.8 | 39.2 |
| 549 | 39.2 | 39.2 |
| 550 | 13.1 | 39.2 |
| 551 | 3.6 | 14.6 |
| 552 | 13.7 | 39.2 |
| 553 | 1.2 | 5.1 |
| 554 | 0.4 | 1.5 |
| 555 | 1.0 | 3.5 |
| 556 | 1.4 | 7.6 |
| 557 | 0.4 | 1.4 |
| 558 | 2.0 | 8.3 |
| 559 | 1.4 | 5.7 |
| 560 | 1.3 | 4.7 |
| 561 | 1.4 | 7.0 |
| 562 | 0.3 | 1.0 |
| 563 | 0.4 | 1.2 |
| 564 | 0.2 | 0.6 |
| 565 | 0.3 | 1.1 |
| 566 | 0.2 | 0.8 |
| 567 | 0.3 | 1.0 |
| 568 | 0.4 | 1.6 |
| 569 | 0.7 | 2.8 |
| 570 | 0.4 | 1.4 |
| 571 | 0.4 | 1.3 |
| 572 | 0.5 | 1.8 |
| 573 | 0.9 | 4.1 |
| 574 | 1.0 | 4.2 |
| 575 | 1.1 | 4.2 |
| 576 | 3.5 | 15.2 |
| 577 | 0.4 | 1.3 |
| 578 | 0.4 | 1.2 |
| 579 | 1.2 | 5.1 |
| 580 | 3.1 | 17.6 |
| 581 | 0.4 | 1.4 |
| 582 | 0.4 | 1.3 |
| 583 | 0.4 | 1.3 |
| 584 | 0.3 | 1.2 |
| 585 | 0.5 | 2.5 |
| 586 | 0.5 | 2.3 |
| 587 | 2.5 | 12.9 |
| 588 | 1.2 | 4.3 |
| 589 | 0.7 | 2.3 |
| 590 | 1.4 | 6.8 |
| 591 | 4.4 | 9.8 |
| 592 | 2.7 | 10.9 |
| 593 | 0.5 | 2.1 |
| 594 | 1.4 | 5.8 |
| 595 | 0.3 | 1.0 |
| 596 | 0.8 | 2.5 |
| 597 | 0.5 | 1.9 |
| 598 | 3.9 | 15.7 |
| 599 | 0.9 | 3.2 |
| 600 | 3.5 | 16.5 |
| 601 | 1.6 | 7.3 |
| 602 | 4.1 | 16.9 |
| 603 | 0.3 | 1.0 |
| 604 | 0.3 | 0.9 |
| 605 | 0.8 | 3.4 |
| 606 | 4.6 | 22.6 |
| 607 | 2.9 | 15.4 |
| 608 | 1.2 | 4.6 |
| 609 | 0.3 | 0.9 |
| 610 | 2.0 | 8.6 |
| 611 | 0.7 | 2.5 |
| 612 | 0.7 | 2.1 |
| 613 | 0.4 | 1.4 |
| 614 | 3.4 | 14.7 |
| 615 | 0.4 | 1.4 |
| 616 | 4.5 | 22.9 |
| 617 | 0.3 | 1.2 |
| 618 | 0.3 | 1.1 |
| 619 | 0.6 | 2.5 |
| 620 | 0.2 | 0.6 |

TABLE A-continued

| Cmpd No. | CDMF75 IC$_{15}$ (µM) | CDMF75 IC$_{50}$ (µM) |
|---|---|---|
| 621 | 1.6 | 6.1 |
| 622 | 0.9 | 3.6 |
| 623 | 0.4 | 1.6 |
| 624 | 0.4 | 1.5 |
| 625 | 0.8 | 3.0 |
| 626 | 0.5 | 1.6 |
| 627 | 3.5 | 15.0 |
| 628 | 0.3 | 1.0 |
| 629 | 2.1 | 9.4 |
| 630 | 0.5 | 1.8 |
| 631 | 0.5 | 1.8 |
| 632 | 0.5 | 1.5 |
| 633 | 0.2 | 0.8 |
| 634 | 0.5 | 2.1 |
| 635 | 0.3 | 1.1 |
| 636 | 0.6 | 2.2 |
| 637 | 3.1 | 11.6 |
| 638 | 1.0 | 3.9 |
| 639 | 0.3 | 1.1 |
| 640 | 0.5 | 2.1 |
| 641 | 1.4 | 5.7 |
| 642 | 1.4 | 5.8 |
| 643 | 0.6 | 2.1 |
| 644 | 1.5 | 5.9 |
| 645 | 1.6 | 7.0 |
| 646 | 2.2 | 9.0 |
| 647 | 0.3 | 0.9 |
| 648 | 0.4 | 1.3 |
| 649 | 0.9 | 3.4 |
| 650 | 0.6 | 2.2 |
| 651 | 4.6 | 22.6 |
| 652 | 0.5 | 1.5 |
| 653 | 0.2 | 0.7 |
| 654 | 0.6 | 2.2 |
| 655 | 0.6 | 1.9 |
| 656 | 1.9 | 8.1 |
| 657 | 0.3 | 0.7 |
| 658 | 0.3 | 0.9 |
| 659 | 0.5 | 1.7 |
| 660 | 0.6 | 2.0 |
| 661 | 0.3 | 1.1 |
| 662 | 1.6 | 7.2 |
| 663 | 2.3 | 19.6 |
| 664 | 0.5 | 1.9 |
| 665 | 0.4 | 1.8 |
| 666 | 0.8 | 3.4 |
| 667 | 0.9 | 3.7 |
| 668 | 0.6 | 2.2 |
| 669 | 0.5 | 2.3 |
| 670 | 5.8 | 26.6 |
| 671 | 6.5 | 30.2 |
| 672 | 3.2 | 13.7 |
| 673 | 2.8 | 13.0 |
| 674 | 1.9 | 7.4 |
| 675 | 0.8 | 2.7 |
| 676 | 0.5 | 1.8 |
| 677 | 0.3 | 0.9 |
| 678 | 0.7 | 2.3 |
| 679 | 0.8 | 3.0 |
| 680 | 0.5 | 1.7 |
| 681 | 1.3 | 5.9 |
| 682 | 0.4 | 1.6 |
| 683 | 1.1 | 4.6 |
| 684 | 1.1 | 5.0 |
| 685 | 0.7 | 2.6 |
| 686 | 0.9 | 3.1 |
| 687 | 1.0 | 4.4 |
| 688 | 1.7 | 6.8 |
| 689 | 0.6 | 2.1 |
| 690 | 4.4 | 21.3 |
| 691 | 1.5 | 5.8 |
| 692 | 1.0 | 4.6 |
| 693 | 0.9 | 3.7 |
| 694 | 1.8 | 7.0 |
| 695 | 2.1 | 7.8 |
| 696 | 1.1 | 4.2 |
| 697 | 0.9 | 3.7 |
| 698 | 0.9 | 3.5 |
| 699 | 1.7 | 7.5 |
| 700 | 0.7 | 2.6 |
| 701 | 0.3 | 1.1 |
| 702 | 2.6 | 11.7 |
| 703 | 1.7 | 6.2 |
| 704 | 2.6 | 11.4 |
| 705 | 4.9 | 28.1 |
| 706 | 0.6 | 2.5 |
| 707 | 0.9 | 3.6 |
| 708 | 0.6 | 2.8 |
| 709 | 0.6 | 2.3 |
| 710 | 0.4 | 1.9 |
| 711 | 0.8 | 2.8 |
| 712 | 0.5 | 2.4 |
| 713 | 2.7 | 11.0 |
| 714 | 1.4 | 5.5 |
| 715 | 0.4 | 1.5 |
| 716 | 1.4 | 5.9 |
| 717 | 0.4 | 1.8 |
| 718 | 1.1 | 5.2 |
| 719 | 0.8 | 3.7 |
| 720 | 2.3 | 10.4 |
| 721 | 1.5 | 6.7 |
| 722 | 1.4 | 5.6 |
| 723 | 4.4 | 20.3 |
| 724 | 1.7 | 6.8 |
| 725 | 0.6 | 2.9 |
| 726 | 1.2 | 6.0 |
| 727 | 1.2 | 4.1 |
| 728 | 0.8 | 3.8 |
| 729 | 2.6 | 13.2 |
| 730 | 0.7 | 3.2 |
| 731 | 1.1 | 5.3 |
| 732 | 0.7 | 3.4 |
| 733 | 1.5 | 8.9 |
| 734 | 0.8 | 4.1 |
| 735 | 1.6 | 8.5 |
| 736 | 1.2 | 5.4 |
| 737 | 2.4 | 14.9 |
| 738 | 2.1 | 9.5 |
| 739 | 5.4 | 24.2 |
| 740 | 1.9 | 6.9 |
| 741 | 1.9 | 10.5 |
| 742 | 3.4 | 16.6 |
| 743 | 7.4 | 36.7 |
| 744 | 0.3 | 1.3 |
| 745 | 0.8 | 3.8 |
| 746 | 4.6 | 21.3 |

Biological Example B-2

Myocyte Assays (i) Preparation of Adult Cardiac Ventricular Rat Myocytes.
Adult male Sprague-Dawley rats were anesthetized and the hearts were quickly excised, rinsed and the ascending aorta was cannulated. Continuous retrograde perfusion was initiated on the hearts at a perfusion pressure of 60 cm H$_2$O. Hearts were first perfused with a nominally Ca$^{2+}$-free modified Krebs solution of the following composition: 113 mM NaCl, 4.7 mM KCl, 0.6 mM KH$_2$PO$_4$, 0.6 mM Na$_2$HPO$_4$, 1.2 mM MgSO$_4$, 12 mM NaHCO$_3$, 10 mM KHCO$_3$, 30 mM taurine, 5.5 mM glucose and 10 mM Hepes (all Sigma). This medium is not recirculated and is continually aerated with a 95% O$_2$/5% CO$_2$ mixture. After approximately 3 minutes the heart was perfused with a modified Krebs buffer supplemented with collagenase (Worthington) and 12.5 µM final calcium concentration. The heart was removed from the cannulae after the heart appeared blanched and soft in appearance. The atria and vessels were removed and the ventricles were gently dissected into smaller pieces with forceps. The tissue was homogenized by repeated pipette trituration and the collagenase reaction was stopped by 10% bovine calf serum (BCS), sedimentation and resuspension in perfusion buffer containing 5% BCS and 12.5 uM $CaCl_2$). Myocytes were made calcium tolerant by stepwise addition of a $CaCl_2$) solution to a final concentration of 1.2 mM. Cells were then washed and resuspended in Tyrode's buffer (137 mM NaCl, 3.7 mM KCl, 0.5 mM $MgCl_2$, 11 mM glucose, 4 mM Hepes, and 1.2 mM $CaCl_2$), pH 7.4). Cells were kept for 60 min at 37° C. prior to initiating experiments and used within 5 hrs of isolation. Preparations of cells were used only if cells first passed QC criteria by demonstrating a contractile response to standard (>150% of basal) and isoproterenol (ISO; >250% of basal) treatment. Additionally, only cells whose basal contractility was between 3 and 8% were used in subsequent experiments with compounds.

(II) Adult Ventricular Myocyte Contractility Experiments.

Aliquots of myocytes in Tyrode's buffer were placed in perfusion chambers (series 20 RC-27NE; Warner Instruments) complete with heating platforms. Myocytes were allowed to attach, the chambers were heated to 37° C., and the cells were perfused with 37° C. Tyrode's buffer. Myocytes were field stimulated at 1 Hz in with platinum electrodes (20% above threshold). Only cells that had clear striations and were quiescent prior to pacing were used for contractility experiments. To determine basal contractility, myocytes were imaged through a 40× objective. Using a variable frame rate (60-240 Hz) charge-coupled device camera, the images were digitized and displayed on a computer screen at a sampling speed of 240 Hz (IonOptix Milton, MA). Once cell contraction was stable over time, test compounds (0.01-15 μM) were perfused into the chambers on the myocytes for 5 minutes. Contractility of the myocytes and contraction and relaxation velocities were then recorded using edge detection.

(III) Contractility Analysis.

Five or more individual myocytes were tested per compound from two or more different myocyte preparations. For each cell, twenty or more contractility transients at basal (defined as 1 min prior to compound infusion) and after compound addition (defined as 5 min after starting compound perfusion), were averaged and compared. These average transients were analyzed using the IonWizard software (IonOptix) to determine changes in diastolic length and fractional shortening. Fractional shortening was calculated as: ((resting length–length at peak contraction) divided by the resting length). The percent change in fractional shortening from baseline was calculated as: ((post-dose fractional shortening/basal fractional shortening)*100). The percent reduction in fractional shortening from baseline was calculated as: (100–percent change in fractional shortening from baseline). Maximum contraction and relaxation velocities (um/sec) was also determined. Results from individual cells are averaged and the SEM calculated.

The effect of the compounds on the fractional shortening (FS) of the myocytes is shown in Table B.

TABLE B

| Compound No. | Concentration (μM) | % FS (% reduction from baseline) ± SEM | # of cells tested |
|---|---|---|---|
| 5 | 10 | 73.2 ± 7.1 | 5 |
| 31 | 10 | 23.3 ± 18.9 | 15 |
| 82 | 10 | 89.6 ± −5.7 | 5 |
| 100 | 5 | 54.7 ± −9.8 | 5 |
| 116 | 10 | 72.5 ± −9.5 | 8 |
| 124 | 10 | 84.6 ± −9.8 | 6 |
| 142 | 5 | 67.8 ± −5.4 | 5 |
| 184 | 5 | 67.4 ± −5.8 | 5 |
| 474 | 10 | 75.2 ± −3.7 | 5 |
| 542 | 10 | 68.4 ± −8.5 | 5 |

% FS = Average of each cell's (post baseline percent peak height/pre-baseline percent peak height) × 100

Biological Example B-3

Echocardiography Assessment of Acute Pharmacodynamic Effect in Rat Cardiac Contractility Assessment of in vivo cardiac function by echocardiography was performed in male Sprague Dawley rats under isoflurane (1-3%) anesthesia. 2-D M-mode images of the left ventricle were acquired in the parasternal long-axis view before, during, and after administration of compounds by continuous IV infusion or oral gavage. In vivo fractional shortening was determined by M-mode image analysis with the following calculation: ((End diastolic diameter–end systolic diameter)/end diastolic diameter×100). For continuous IV infusion experiments, three pre-dose baseline M-mode images were taken at 1 minute intervals prior to infusion of compound. Compounds were formulated in 50% Propylene Glycol (PG): 16% Captisol: 10% dimethylacetamide (DMA) and delivered via a jugular vein catheter at the rate of 1 mL/kg/h. During infusion, M-mode images were taken at 5 minute intervals. The infusion stopped when fractional shortening reached up to a 60% reduction from baseline. Blood samples were taken to determine the plasma concentration of the compounds. Data was reported as an estimated $IC_{50}$ value, which is the concentration at which fractional shortening is 50% of the pre-dose baseline contractility. The $IC_{50}$ results are summarized in Table C.

TABLE C

| Compound No. | $IC_{50}$ (Mean ± S.D., μM) |
|---|---|
| 124 | 0.7 ± 0.02 |
| 141 | 1.5 ± 0.05 |
| 144 | 3.4 ± 0.12 |
| 142 | 2.7 ± 0.12 |
| 238 | 5.7 ± 0.31 |
| 184 | 7.2 ± 0.20 |
| 183 | 1.2 ± 0.02 |
| 253 | 1.7 ± 0.08 |
| 304 | 1.7 ± 0.06 |
| 222 | 1.1 ± 0.03 |
| 236 | 11.4 ± 0.6 |
| 211 | 5.4 ± 0.25 |
| 365 | 4.6 ± 0.17 |
| 387 | 2.4 ± 0.08 |
| 100 | 8.1 ± 0.26 |
| 420 | 2.1 ± 0.05 |
| 388 | 5.4 ± 0.10 |
| 434 | 9.3 ± 0.15 |
| 433 | 4.3 ± 0.11 |
| 158 | 1.1 ± 0.03 |
| 538 | 10.9 ± 0.37 |

For oral dosing studies, three pre-dose baseline M-Mode images were taken at 1 minute intervals prior to compound administration. Compounds were formulated in a 0.5% hydroxypropyl methylcellulose 2910 (HPMC 2910): 0.1% Tween 80 suspension and delivered as a single dose (5 mL/kg) by oral gavage. Rats were lightly anesthetized for M-Mode echocardiography measurements at select time points over a 24 hour period. Different dose levels were evaluated for each compound. The compound effect on cardiac fractional shortening at the highest dose evaluated is presented in Table D as a percent reduction of baseline fractional shortening (=100%).

TABLE D

| Compound No. | Dose (mg/kg) | FS (% reduction from baseline) at 1-2 h post dose (Mean ± S.D.) | FS (% reduction from baseline) at 4 h post dose (Mean ± S.D.) |
| --- | --- | --- | --- |
| 238 | 2 | 52 ± 10 | 59 ± 6 |
| 183 | 2 | 42 ± 16 | 15 ± 13 |
| 184 | 2 | 43 ± 9 | 31 ± 9 |
| 253 | 6 | 56 ± 9 | 33 ± 7 |
| 142 | 6 | 40 ± 9 | 18 ± 11 |
| 100 | 6 | 60 ± 4 | 40 ± 3 |
| 387 | 6 | 59 ± 24 | 50 ± 18 |
| 82 | 10 | 65 ± 6 | 55 ± 8 |
| 474 | 6 | 64 ± 8 | 27 ± 6 |
| 542 | 4.5 | 71 ± 1 | 54 ± 7 |
| 489 | 6 | 65 ± 6 | 35 ± 6 |
| 565 | 8 | 55 ± 13 | 43 ± 13 |
| 577 | 4 | 67 ± 6 | 34 ± 11 |
| 589 | 6 | 73 ± 12 | 46 ± 3 |
| 617 | 6 | 64 ± 4 | 37 ± 7 |
| 664 | 6 | 65 ± 4 | 38 ± 5 |
| 697 | 10 | 70 ± 2 | 45 ± 3 |
| 709 | 8 | 68 ± 2 | 31 ± 3 |
| 727 | 8 | 63 ± 1 | 33 ± 1 |

Concurrent with echocardiography measurements, blood samples were taken to determine the corresponding compound plasma concentration. The data in Table E summarizes the estimated $IC_{50}$ and $IC_{10}$ values, which is the concentration at which fractional shortening is 50% and 10% of the pre-dose baseline contractility, respectively.

TABLE E

| Compound No. | $IC_{50}$ (μM) | $IC_{10}$ (μM) |
| --- | --- | --- |
| 238 | 4.9 | 0.9 |
| 183 | 0.9 | 0.2 |
| 184 | 7.9 | 0.8 |
| 253 | 1.3 | 0.3 |
| 142 | 2.9 | 0.7 |
| 100 | 9.1 | 2.3 |
| 387 | 1.6 | 0.4 |
| 82 | 4.9 | 1.5 |
| 474 | 1.4 | 0.2 |
| 542 | 3.5 | 0.9 |
| 489 | 2.4 | 0.7 |
| 565 | 37 | 11 |
| 577 | 0.7 | 0.1 |
| 589 | 1.6 | 0.3 |
| 617 | 1.2 | 0.3 |
| 664 | 3.3 | 1.2 |
| 697 | 8.3 | 3.3 |
| 709 | 4.3 | 1.5 |
| 727 | 4.7 | 1.2 |

Biological Example B-4

Longitudinal Echocardiography Assessment of Mouse Model of HCM

Assessment over time of in vivo cardiac function by echocardiography was performed using a previously reported mouse model of familial hypertrophic cardiomyopathy, which was generated by an arginine to glutamine mutation at residue 403 (R403Q) of the alpha cardiac myosin heavy chain (MHC) gene (Geisterfer-Lowrance et al., Science. 1996 May 3; 272(5262):731-4). Cardiac dysfunction, fibrosis, and measures of cardiac hypertrophy (including ventricular wall thickness) increase with age in this mouse model (Geisterfer-Lowrance, supra; Jiang et al., Science. 2013, 342(6154):111-4).

R403Q mice received vehicle or Compound 142 formulated in chow for 24 weeks. Longitudinal echocardiography measurements were performed every 4 weeks. Echocardiography measurements were taken with mice under isoflurane (1-3%) anesthesia. 2-D M-mode images of the left ventricle were acquired in short-axis view. In vivo fractional shortening was determined by M-mode image analysis with the following calculation: ((End diastolic diameter−end systolic diameter)/end diastolic diameter×100). Treatment with Compound 142 attenuated increases in septal and left ventricular posterior wall thickness that were observed with age in untreated R403Q mice.

Biological Example B-5

Fibrosis Reduction in a Rat Model of Cardiac Hypertrophy

Assessment of fibrosis reduction was performed using Dahl Salt Sensitive (DSS) rats, a previously reported hypertension-induced rat model of heart failure with preserved ejection fraction (Fillmore et al., Mol Med. 2018, 24(1):3; Dahl et al., J Exp Med. 1962, 115:1173-90). DSS rats fed a high salt diet demonstrate progressive cardiovascular dysfunction, including increased systolic blood pressure, diastolic dysfunction, cardiac hypertrophy, and cardiac fibrosis (Fillmore, supra; Dahl, supra, Sakata et al., J Am Coll Cardiol. 2001 January; 37(1):293-9; Kim-Mitsuyama et al., Hypertens Res. 2004 October; 27(10):771-9).

DSS rats received vehicle or Compound 142 formulated in low or high salt chow for 6 weeks. Perivascular and interstitial cardiac tissue samples were imaged and assayed for % cardiac fibrosis. Treatment with Compound 142 attenuated increases in fibrosis in high-salt diet fed DSS rats.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:

1. A method of preparing a compound of formula (A)

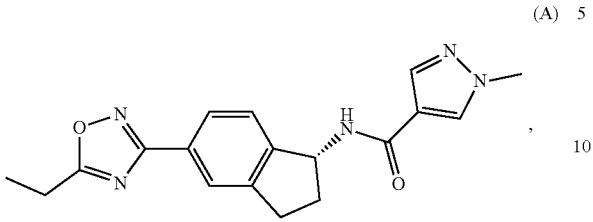
(A)

or a salt thereof, comprising converting a compound of formula (15-3):

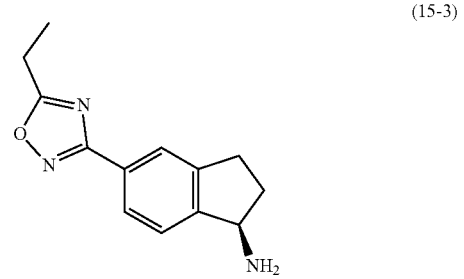 [SMILES: CCc1nc(-c2ccc3c(c2)CC[C@H]3N)no1]
(15-3)

or a salt thereof to the compound of formula (A) or salt thereof.

2. The method of claim 1, wherein converting the compound of formula (15-3) or salt thereof to the compound of formula (A) or salt thereof comprises reacting the compound of formula (15-3) or salt thereof with 1-methyl-1H-pyrazole-4-carboxylic acid or a salt thereof.

3. The method of claim 2, wherein reacting the compound of formula (15-3) or salt thereof with 1-methyl-1H-pyrazole-4-carboxylic acid or a salt thereof is performed in the presence of 1-hydroxy-7-azabenzotriazole (HOAt) and 1-ethyl-3-(3-dimethylaminopropyl)carbodiimide (EDCI).

4. The method of claim 2, wherein reacting the compound of formula (15-3) or salt thereof with 1-methyl-1H-pyrazole-4-carboxylic acid or a salt thereof is performed in the presence of diisopropylethylamine.

5. The method of claim 1, further comprising obtaining the compound of formula (15-3) by converting a compound of formula (15-2):

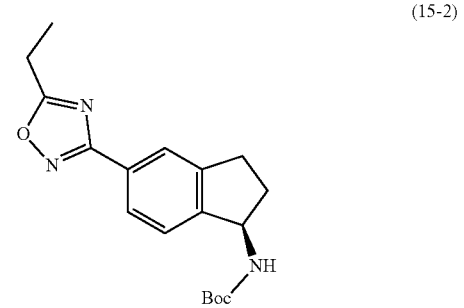 [SMILES: CCc1nc(-c2ccc3c(c2)CC[C@H]3NC(=O)OC(C)(C)C)no1]
(15-2)

or a salt thereof to the compound of formula (15-3) or salt thereof.

6. The method of claim 5, wherein converting the compound of formula (15-2) or salt thereof to the compound of formula (15-3) or salt thereof comprises reacting the compound of formula (15-2) or salt thereof with trifluoroacetic acid.

7. The method of claim 5, further comprising obtaining the compound of formula (15-2) by converting a compound of formula (5-4):

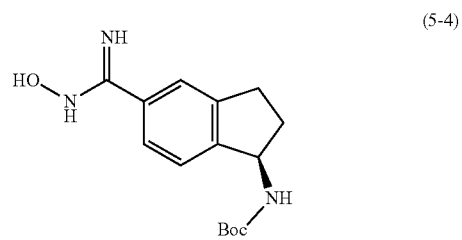 [SMILES: CC(C)(C)OC(=O)N[C@@H]1CCc2cc(C(=N)NO)ccc21]
(5-4)

or a salt thereof to the compound of formula (15-2) or salt thereof.

8. The method of claim 7, wherein converting the compound of formula (5-4) or salt thereof to the compound of formula (15-2) or salt thereof comprises reacting the compound of formula (5-4) with propanoyl propanoate.

9. The method of claim 8, wherein reacting the compound of formula (5-4) or salt thereof with propanoyl propanoate is performed in the presence of dioxane.

10. The method of claim 8, wherein reacting the compound of formula (5-4) or salt thereof with propanoyl propanoate is performed at a temperature of about 105° C.

11. The method of claim 7, further comprising obtaining the compound of formula (5-4) or salt thereof by converting a compound of formula (5-3):

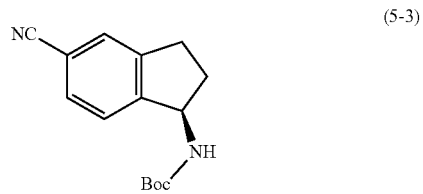 [SMILES: CC(C)(C)OC(=O)N[C@@H]1CCc2cc(C#N)ccc21]
(5-3)

or salt thereof to the compound of formula (5-4) or salt thereof.

12. The method of claim 11, wherein converting the compound of formula (5-3) or salt thereof to the compound of formula (5-4) or salt thereof comprises reacting the compound of formula (5-3) or salt thereof with hydroxylamine.

13. The method of claim 11, further comprising obtaining the compound of formula (5-3) or salt thereof by converting a compound of formula (5-2):

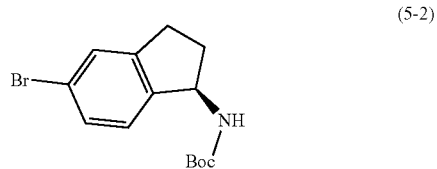 [SMILES: CC(C)(C)OC(=O)N[C@@H]1CCc2cc(Br)ccc21]
(5-2)

or salt thereof to the compound of formula (5-3) or salt thereof.

14. The method of claim 13, wherein converting the compound of formula (5-2) or salt thereof to the compound of formula (5-3) or salt thereof comprises reacting the compound of formula (5-2) or salt thereof with $K_4Fe(CN)_6 \cdot 3H_2O$.

15. The method of claim 14, wherein reacting the compound of formula (5-2) or salt thereof with $K_4Fe(CN)_6 \cdot 3H_2O$ is performed in the presence of potassium acetate, XPhos, and 2nd Generation XPhos pre-catalyst.

16. The method of claim 15, wherein the reaction is performed at a temperature of about 100° C.

17. The method of claim 13, further comprising obtaining the compound of formula (5-2) or salt thereof by converting (1R)-5-bromo-2,3-dihydro-1H-inden-1-amine or a salt thereof to the compound of formula (5-2) or salt thereof.

18. The method of claim 17, wherein converting (1R)-5-bromo-2,3-dihydro-1H-inden-1-amine hydrochloride or salt thereof to the compound of formula (5-2) or salt thereof comprises reacting (1R)-5-bromo-2,3-dihydro-1H-inden-1-amine or salt thereof with di-tert-butyl dicarbonate.

19. The method of claim 17, wherein (1R)-5-bromo-2,3-dihydro-1H-inden-1-amine is provided as a hydrochloride salt.

* * * * *